(12) United States Patent
Logtenberg et al.

(10) Patent No.: US 10,966,411 B2
(45) Date of Patent: *Apr. 6, 2021

(54) ANTIBODY PRODUCING NON-HUMAN MAMMALS

(75) Inventors: Ton Logtenberg, Driebergen (NL); Mark Throsby, Utrecht (NL); Robert A. Kramer, Utrecht (NL); Rui Daniel Pinto, Utrecht (NL); Cornelis A. de Kruif, De Bilt (NL); Erwin Houtzager, Zeist (NL)

(73) Assignee: Merus N.V., Utrecht (NL)

( * ) Notice: Subject to any disclaimer, the term of this patent is extended or adjusted under 35 U.S.C. 154(b) by 671 days.

This patent is subject to a terminal disclaimer.

(21) Appl. No.: 12/589,181

(22) Filed: Oct. 19, 2009

(65) Prior Publication Data

US 2010/0146647 A1 Jun. 10, 2010

Related U.S. Application Data

(63) Continuation of application No. 12/459,285, filed on Jun. 29, 2009, now abandoned.

(60) Provisional application No. 61/133,274, filed on Jun. 27, 2008.

(51) Int. Cl.
| | | |
|---|---|---|
| A01K 67/027 | (2006.01) | |
| C12N 15/85 | (2006.01) | |
| C07K 16/46 | (2006.01) | |
| C07K 14/47 | (2006.01) | |
| C07K 16/24 | (2006.01) | |
| C12P 21/00 | (2006.01) | |
| C07K 16/12 | (2006.01) | |

(52) U.S. Cl.
CPC ........ *A01K 67/0275* (2013.01); *A01K 67/027* (2013.01); *A01K 67/0278* (2013.01); *C07K 16/462* (2013.01); *C12N 15/8509* (2013.01); *A01K 2207/15* (2013.01); *A01K 2217/052* (2013.01); *A01K 2217/075* (2013.01); *A01K 2217/15* (2013.01); *A01K 2217/206* (2013.01); *A01K 2227/105* (2013.01); *A01K 2267/01* (2013.01); *C07K 14/47* (2013.01); *C07K 16/1282* (2013.01); *C07K 16/248* (2013.01); *C07K 2317/24* (2013.01); *C12P 21/00* (2013.01)

(58) Field of Classification Search
CPC ........... A01K 67/0278; A01K 2207/15; A01K 67/0275; A01K 2227/105; A01K 2267/01; A01K 2217/072; C07K 16/462; C07K 2317/515
USPC .............................. 800/18, 13, 6; 530/387.3
See application file for complete search history.

(56) References Cited

U.S. PATENT DOCUMENTS

| | | |
|---|---|---|
| 5,565,332 A | 10/1996 | Hoogenboom et al. |
| 5,614,396 A | 3/1997 | Bradley et al. |
| 5,770,429 A | 6/1998 | Lonberg et al. |
| 5,789,215 A | 8/1998 | Berns et al. |
| 5,885,827 A | 3/1999 | Wabl |
| 5,939,598 A | 8/1999 | Kycherlapati et al. |
| 6,069,010 A | 5/2000 | Choi |
| 6,114,598 A | 9/2000 | Kucherlapati et al. |
| 6,596,541 B2 | 7/2003 | Murphy et al. |
| 7,105,348 B2 * | 9/2006 | Murphy et al. ............... 435/463 |
| 7,262,028 B2 | 8/2007 | Van |
| 7,329,530 B2 | 2/2008 | Houtzager et al. |
| 7,429,486 B2 * | 9/2008 | Van Berkel et al. ......... 435/325 |
| 7,579,446 B2 | 8/2009 | Bakker |
| 7,696,330 B2 | 4/2010 | Meulen |
| 7,740,852 B2 | 6/2010 | Bakker |
| 7,777,010 B2 | 8/2010 | Logtenberg |
| 7,858,086 B2 | 12/2010 | Geuijen |
| 7,901,919 B2 | 3/2011 | Houtzager |
| 7,919,257 B2 | 4/2011 | Hoogenboom et al. |
| 7,927,834 B2 | 4/2011 | Van |
| 7,932,360 B2 | 4/2011 | Van |
| 7,960,518 B2 | 6/2011 | Throsby |
| 7,968,092 B2 | 6/2011 | Throsby |
| 8,052,974 B2 | 11/2011 | Throsby et al. |
| 8,106,170 B2 | 1/2012 | Ter Meulen et al. |
| 8,148,497 B2 | 4/2012 | Bakker |
| 8,192,927 B2 | 6/2012 | Van Den Brink et al. |
| 8,211,431 B2 | 7/2012 | Throsby et al. |
| 8,241,631 B2 | 8/2012 | Throsby |

(Continued)

FOREIGN PATENT DOCUMENTS

| | | |
|---|---|---|
| EP | 0 814 159 | 8/1991 |
| EP | 0469025 | 2/1992 |

(Continued)

OTHER PUBLICATIONS

Storb et al, J. Exp. Med. 164:627-641, 1986.*

(Continued)

*Primary Examiner* — Anne Marie S Wehbe
(74) *Attorney, Agent, or Firm* — Morrison & Foerster LLP

(57) ABSTRACT

Described are transgenic, non-human animals comprising a nucleic acid encoding an immunoglobulin light chain, whereby the immunoglobulin light chain is human, human-like, or humanized. The nucleic acid is provided with a means that renders it resistant to DNA rearrangements and/or somatic hypermutations. In one embodiment, the nucleic acid comprises an expression cassette for the expression of a desired molecule in cells during a certain stage of development in cells developing into mature B cells. Further provided is methods for producing an immunoglobulin from the transgenic, non-human animal.

14 Claims, 82 Drawing Sheets
(3 of 82 Drawing Sheet(s) Filed in Color)
Specification includes a Sequence Listing.

(56) References Cited

U.S. PATENT DOCUMENTS

| | | |
|---|---|---|
| 8,268,756 B2 | 9/2012 | Logtenberg et al. |
| 8,470,327 B2 | 6/2013 | Throsby et al. |
| 8,502,018 B2 | 8/2013 | Murphy et al. |
| 8,642,513 B2 | 2/2014 | Throsby et al. |
| 8,911,738 B2 | 12/2014 | Throsby et al. |
| 9,012,371 B2 | 4/2015 | Logtenberg et al. |
| 9,145,588 B2 | 9/2015 | Throsby et al. |
| 9,248,182 B2 | 2/2016 | De Kruif et al. |
| 9,738,701 B2 | 8/2017 | Hogenboom et al. |
| 9,765,133 B2 * | 9/2017 | Logtenberg ........ A01K 67/0278 |
| 9,908,946 B2 | 3/2018 | Throsby et al. |
| 9,944,695 B2 * | 4/2018 | Logtenberg ........ A01K 67/0278 |
| 9,951,124 B2 * | 4/2018 | Logtenberg ........ A01K 67/0278 |
| 10,605,808 B2 | 3/2020 | Logtenberg et al. |
| 10,647,781 B2 | 5/2020 | Throsby et al. |
| 10,670,599 B2 | 6/2020 | Hoogenboom et al. |
| 2002/0138857 A1* | 9/2002 | Ghayur .............................. 800/6 |
| 2003/0093820 A1* | 5/2003 | Green et al. ...................... 800/8 |
| 2003/0096225 A1 | 5/2003 | Logtenberg |
| 2003/0096226 A1 | 5/2003 | Logtenberg |
| 2005/0170398 A1* | 8/2005 | Van Berkel et al. ............. 435/6 |
| 2006/0015949 A1* | 1/2006 | Lonberg et al. .................. 800/6 |
| 2006/0015957 A1* | 1/2006 | Lonberg et al. ................ 800/18 |
| 2006/0121580 A1 | 6/2006 | Ter Meulen et al. |
| 2006/0160184 A1 | 7/2006 | Hoogenboom et al. |
| 2006/0205077 A1 | 9/2006 | Schwenk et al. |
| 2006/0257397 A1* | 11/2006 | Throsby et al. .......... 424/141.1 |
| 2007/0054362 A1 | 3/2007 | Van Berkel et al. |
| 2007/0059766 A1 | 3/2007 | Logtenberg et al. |
| 2007/0280945 A1 | 12/2007 | Stevens et al. |
| 2008/0014204 A1 | 1/2008 | Ter Meulen et al. |
| 2008/0070799 A1 | 3/2008 | Bakker |
| 2008/0095780 A1 | 4/2008 | Geuijen et al. |
| 2008/0226652 A1 | 9/2008 | Bakker et al. |
| 2009/0017521 A1 | 1/2009 | Houtzager et al. |
| 2009/0054254 A1 | 2/2009 | Throsby et al. |
| 2009/0104204 A1 | 4/2009 | Throsby et al. |
| 2009/0130652 A1 | 5/2009 | Throsby et al. |
| 2009/0169562 A1 | 7/2009 | Throsby et al. |
| 2009/0181855 A1* | 7/2009 | Vasquez et al. ................... 506/9 |
| 2009/0263864 A1 | 10/2009 | Van Berkel et al. |
| 2009/0311265 A1 | 12/2009 | van den Brink et al. |
| 2010/0069614 A1 | 3/2010 | Houtzager |
| 2010/0146647 A1 | 6/2010 | Logtenberg |
| 2010/0172917 A1 | 7/2010 | ter Meulen et al. |
| 2010/0272724 A1 | 10/2010 | Bakker et al. |
| 2010/0297153 A1 | 11/2010 | Geuijen et al. |
| 2010/0303801 A1 | 12/2010 | Throsby et al. |
| 2010/0310572 A1 | 12/2010 | Bakker et al. |
| 2010/0310586 A1 | 12/2010 | Dolcetti et al. |
| 2010/0331527 A1 | 12/2010 | Davis et al. |
| 2011/0177073 A1 | 7/2011 | Van Berkel et al. |
| 2011/0195454 A1 | 8/2011 | McWhirter |
| 2011/0268739 A1 | 11/2011 | Throsby et al. |
| 2012/0021409 A1 | 1/2012 | McWhirter |
| 2012/0039898 A1 | 2/2012 | Throsby |
| 2012/0058907 A1 | 3/2012 | Logtenberg |
| 2012/0076794 A1 | 3/2012 | Throsby |
| 2012/0093823 A1 | 4/2012 | Van |
| 2012/0141493 A1 | 6/2012 | Throsby |
| 2012/0177637 A1 | 7/2012 | Hoogenboom |
| 2012/0192300 A1 | 7/2012 | Babb |
| 2012/0276115 A1 | 11/2012 | Van Den Brink |
| 2012/0315278 A1 | 12/2012 | Throsby |
| 2013/0096020 A1 | 4/2013 | Throsby et al. |
| 2013/0145484 A1 | 6/2013 | Logtenberg et al. |
| 2014/0245468 A1 | 8/2014 | McWhirter et al. |
| 2014/0314755 A1 | 10/2014 | Logtenberg et al. |
| 2014/0317766 A1 | 10/2014 | Logtenberg et al. |
| 2016/0130367 A1 | 5/2016 | Throsby et al. |
| 2016/0238600 A1 | 8/2016 | Hoogenboom et al. |
| 2018/0002404 A1 | 1/2018 | Hoogenboom et al. |
| 2018/0002405 A1 | 1/2018 | Hoogenboom et al. |
| 2018/0031555 A1 | 2/2018 | Hoogenboom et al. |
| 2018/0134770 A1 | 5/2018 | Logtenberg et al. |
| 2018/0142002 A1 | 5/2018 | Logtenberg et al. |
| 2018/0142003 A1 | 5/2018 | Logtenberg et al. |
| 2018/0142004 A1 | 5/2018 | Logtenberg et al. |
| 2018/0142005 A1 | 5/2018 | Logtenberg et al. |
| 2018/0142006 A1 | 5/2018 | Logtenberg et al. |
| 2018/0179300 A1 | 6/2018 | Throsby et al. |

FOREIGN PATENT DOCUMENTS

| | | | |
|---|---|---|---|
| EP | 0814159 A2 | 12/1997 | |
| EP | 1 399 575 | 3/2004 | |
| EP | 1 439 234 | 7/2004 | |
| EP | 1 439 234 A1 | 7/2004 | |
| EP | 1204740 | 9/2005 | |
| EP | 2 147 594 | 1/2010 | |
| JP | 2004-008218 | 1/2004 | |
| JP | 2006-109711 | 4/2006 | |
| RU | 2236127 | 9/2004 | |
| WO | WO-90/04036 | 4/1990 | |
| WO | WO 199012878 | 11/1990 | |
| WO | WO-91/00906 | 1/1991 | |
| WO | WO-92/03918 | 3/1992 | |
| WO | WO-94/02602 | 2/1994 | |
| WO | WO 94/02602 * | 2/1994 | ............ C12N 15/00 |
| WO | WO-94/04667 | 3/1994 | |
| WO | WO-96/30498 | 10/1996 | |
| WO | WO-98/24893 | 6/1998 | |
| WO | WO-98/50431 | 11/1998 | |
| WO | WO 98 50431 | 11/1998 | |
| WO | WO 98/52976 | 11/1998 | |
| WO | WO-99/45962 | 9/1999 | |
| WO | WO 199950657 | 10/1999 | |
| WO | WO-02/36789 | 5/2002 | |
| WO | 02/066630 A1 | 8/2002 | |
| WO | WO-02/66630 | 8/2002 | |
| WO | WO 02/066630 * | 8/2002 | |
| WO | WO-03/47336 | 6/2003 | |
| WO | WO 2003052416 | 6/2003 | |
| WO | 20041009618 A2 | 1/2004 | |
| WO | 20041106375 A1 | 12/2004 | |
| WO | WO-04/106375 | 12/2004 | |
| WO | WO-2004/106375 | 12/2004 | |
| WO | WO 2004/106375 A1 | 12/2004 | |
| WO | WO 2005/068622 A2 | 7/2005 | |
| WO | WO-06/68953 | 6/2006 | |
| WO | 20061117699 A2 | 11/2006 | |
| WO | WO-06/117699 | 11/2006 | |
| WO | 20081054606 A2 | 5/2008 | |
| WO | WO-08/54606 | 5/2008 | |
| WO | WO 2008/054606 | 5/2008 | |
| WO | 20081076379 A2 | 6/2008 | |
| WO | WO-08/76379 | 6/2008 | |
| WO | WO 2008/076379 | 6/2008 | |
| WO | WO 2007/117410 | 9/2008 | |
| WO | WO-09/18411 | 2/2009 | |
| WO | WO-09/23540 | 2/2009 | |
| WO | WO 2009/018411 | 2/2009 | |
| WO | WO 2009/023540 | 2/2009 | |
| WO | WO 2009/100896 | 8/2009 | |
| WO | WO 2009/157771 A2 | 12/2009 | |
| WO | WO 2010136598 | 12/2010 | |
| WO | WO-11/014469 | 2/2011 | |
| WO | WO 2011/097603 A1 | 8/2011 | |
| WO | WO-12/141798 | 10/2012 | |
| WO | WO 2011146514 | 11/2012 | |
| WO | WO-2013/184761 | 12/2013 | |
| WO | WO2016/081923 | 5/2016 | |
| WO | WO 2016081926 | 7/2016 | |

OTHER PUBLICATIONS

Hochedlinger et al, Nature 415:1035-1038, 2002.*
Meyer et al, N.A.R. 18(19):5609-5615, 1990.*
Popov et al, J. Exp. Med. 189(10):1611-1619, 1999.*
Taylor et al, Int. Immunol. 6(4):579-591, 1994.*
Taylor et al, Nuc. Acid Res. 20(23):6287-6295, 1992.*
Davies et al, Biotechnology 11:911-914, 1993.*
Lonberg et al, Nature 368:856-859, 1994.*

(56) References Cited

OTHER PUBLICATIONS

De Wildt et al. (1999) J. Mol. Biol., vol. 285, 895-901.*
O'Brien et al. (1987) Nature, vol. 326, 405-409.*
Peled et al. (2008) Annu. Rev. Immunol., vol. 26, 481-511.*
U.S. Appl. No. 10/184,508, filed Jun. 27, 2002 Inventor: Ton Logtenberg Title: Use of a Native Epitope for Selecting Evolved Binding Members From a Library of Mutants of a Protein Capable of Binding to Said Epitope.
U.S. Appl. No. 10/186,186, filed Jun. 28, 2002, Inventor: Ton Logtenberg Title: Use of a Native Epitope for Selecting Evolved Binding Members From a Library of Mutants of a Protein Capable of Binding to Said Epitope.
U.S. Appl. No. 11/292,414, filed Nov. 30, 2005, Inventor: Hoogenboom et al. Title: FAB Library for the Preparation of Anti VEGF and Anti Rabies Virus FABS.
U.S. Appl. No. 11/337,300, filed Jan. 20, 2006 Inventor: ter Meulen et al. Title: Binding Molecules Against SARS-Coronavirus and Uses Thereof.
U.S. Appl. No. 11/387,997, filed Mar. 23, 2006 Inventor: Throsby et al. Title: Human Binding Molecule Against CD1A.
U.S. Appl. No. 11/593,280, filed Nov. 6, 2006, Inventor: Van Berkel et al. Title: Recombinant Production of Mixtures of Antibodies.
U.S. Appl. No. 11/490,545, filed Jul. 20, 2006 Inventor: Logtenberg et al. Title: Mixture of Binding Proteins.
U.S. Appl. No. 11/665,102, filed Apr. 10, 2007 Inventor: Geuijen et al. Title: Binding Molecules for Treatment and Detection of Cancer.
U.S. Appl. No. 11/667,640, filed May 11, 2007 Inventor: ter Meulen et al. Title: Compositions Against SARS-Coronavirus and Uses Thereof.
U.S. Appl. No. 11/919,265, filed Oct. 24, 2007 Inventor: Throsby et al. Title: Host Cell Specific Binding Molecules Capable of Neutralizing Viruses and Uses Thereof.
U.S. Appl. No. 11/922,405, filed Dec. 13, 2007 Inventor: Throsby et al. Title: Optimization of West Nile Virus Antibodies.
U.S. Appl. No. 11/977,954, filed Oct. 26, 2007 Inventor: Houtzager et al. Title: Chimaeric Phages.
U.S. Appl. No. 11/978.742, filed Oct. 29, 2007 Inventor: Bakker et al. Title: Binding Molecules Capable of Neutralizing Rabies Virus and Uses Thereof.
U.S. Appl. No. 11/980,237, filed Oct. 29, 2007 Inventor: Bakker et al. Title: Binding Molecules Capable of Neutralizing Rabies Virus and Uses Thereof.
U.S. Appl. No. 11/990,974, filed Feb. 21, 2008 Inventor: Throsby et al. Title: Method for Preparing Immunoglobulin Libraries.
U.S. Appl. No. 12/221,021, filed Jul. 29, 2008 Inventor: Van Berkel et al. Title: Recombinant Production of Mixtures of Antibodies.
U.S. Appl. No. 12/227,029, filed Nov. 5, 2008 Inventor: Throsby et al. Title: Human Binding Molecules Having Killing Activity Against Staphylococci and Uses Thereof.
U.S. Appl. No. 12/227,116, filed Nov. 7, 2008 Inventor: Throsby et al. Title: Human Binding Molecules Having Killing Activity Against Enterococci and Uses Thereof.
U.S. Appl. No. 12/310,812, filed Mar. 6, 2009 Inventor: van den Brink et al. Title: Human Binding Molecules Capable of Neutralizing Influenza Virus H5N1 and Uses Thereof.
U.S. Appl. No. 12/459,661, filed Jul. 6, 2009 Inventor: Bakker et al. Title: Binding Molecules Capable of Neutralizing Rabies Virus and Uses Thereof.
U.S. Appl. No. 61/199,906, filed Nov. 21, 2008 Inventor: de Kruif et al. Title: Antibody Producing Non-Human Mammals.
U.S. Appl. No. 61/215,890, filed May 11, 2009 Inventor: Throsby et al. Title: Human Binding Molecules Capable of Neutralizing Influenza Virus H3N2 and Uses Thereof.
Nissim et al., Antibody fragments from a 'single pot' phage display library as immunochemical reagents, The EMBO Journal, 1994, pp. 692-698, vol. 13. No. 3.
PCT International Search Report, PCT/NL2009/050381 dated Dec. 7, 2009.
PCT International Preliminary Report on Patentability, PCT/NL2009/050381 dated Jan. 5, 2011.

Jakobovits et al., From XenoMouse technology to panitumumab, the first fully human antibody product from transgenic mice, Nature Biotechnology, Oct. 2007, pp. 1134-1143, vol. 25, No. 10.
De Kruif et al., Human Immunoglobulin Repertoires against Tetanus Toxoid Contain a Large and Diverse Fraction of High-Affinity Promiscuous $V_H$ Genes, J. Mol. Biol., 2009, pp. 548-558, vol. 387.
Homig-Holzel et al., Constitutive CD40 signaling in B cells selectively activates the noncanonical NF-κB pathway and promotes lymphomagenesis, J. Exp. Med., 2008, pp. 1317-1329, vol. 205, No. 6.
Pelanda et al., A prematurely expressed Ig(kappa) transgene, but not V(kappa)J(kappa) gene segment targeted into the Ig(kappa) locus, can rescue B cell development in lambda5-deficient mice, Immunity, Sep. 1996, pp. 229-239, vol. 5, No. 3.
Lonberg et al., Human antibodies from transgenic animals, Nature Biotechnology, Sep. 1, 2005, pp. 1117-1125, vol. 23, No. 9, Nature Publishing Group, New York, NY, US.
Winter et al., Insertion of 2 kb of bacteriophage DNA between an immunoglobulin promoter and leader exon stops somatic hypermutation in a kappa transgene, Molecular Immunology, Apr. 1997, pp. 359-366, vol. 34, No. 5.
Odegard et al., Targeting of somatic hypermutation, Nature Reviews, Immunology, Aug. 2006, pp. 573-583, vol. 6, No. 8.
Kwaks et al., Employing epigenetics to augment the expression of therapeutic proteins in mammalian cells, Trends in Biotechnology, Mar. 1, 2006, pp. 137-42, vol. 24, No. 3, Elsevier Publications, Cambridge, GB.
Xiang et al., The Downstream Transcriptional Enhancer, Ed, positively regulates mouse Ig kappa gene expression and somatic hypermutation, Journal of Immunology, May 15, 2008, pp. 6725-6732, vol. 180, No. 10, Baltimore, MD.
Presta et al., Engineering of therapeutic antibodies to minimize immunogenicity and optimize function, Advanced Drug Delivery Reviews, Aug. 7, 2006, pp. 640-656, vol. 58, No. 5-6, Elsevier BV, Amsterdam, NL.
Weiner, et al., Abstract, Fully human therapeutic monoclonal antibodies, Journal of Immunotherapy, Jan. 1, 2006, pp. 1-9, vol. 29, No. 1, Lippincott Williams & Wilkins, Hagerstown, MD, US.
Smith-Gill et al., Contributions of immunoglobulin heavy and light chains to antibody specificity for lysozyme and two haptens, Journal of Immunology, Dec. 15, 1987, pp. 4135-4144, vol. 139, No. 12., Baltimore, MD, US.
U.S. Appl. No. 13/199,348, filed Aug. 25, 2011 Inventor: Throsby et al. Title: Host Cell Specific Binding Molecules Capable of Neutralizing Viruses and Uses Thereof.
U.S. Appl. No. 13/138,941, filed Oct. 27, 2011 Inventor: Throsby et al. Title: Human Binding Molecules Capable of Neutralizing Influenza Virus H3N2 and Uses Thereof.
U.S. Appl. No. 12/931,955, filed Feb. 14, 2011 Inventor: Hoogenboom et al. Title: A Method for Selecting a Single Cell Expressing a Heterogeneous Combination of Antibodies.
U.S. Appl. No. 13/200,972, filed Oct. 5, 2011 Inventor: Logtenberg et al. Title: Mixture of Binding Proteins.
Bruggemann et al., A Repertoire of Monoclonal Antibodies with Human Heavy Chains from Transgenic Mice, Proc. Natl. Acad. Sci., Sep. 1989, pp. 6709-6713, vol. 86, USA.
Aucouturier et al., Monoclonal Ig L Chain and L Chain V Domain Fragment Crystallization in Myeloma-Associated Fanconi's Syndrome, The Journal of Immunology, Apr. 15, 1993, pp. 3561-3568, vol. 150, No. 8.
De Wildt et al., Analysis of Heavy and Light Chain Pairings Indicates that Receptor Editing Shapes the Human Antibody Repertoire, J. Mol. Biol., 1999, pp. 895-901, vol. 285.
Gonzales-Fernandez et al., Analysis of somatic hypennutation in mouse Peyer's patches using immunoglobulin κ light-chain transgenes, Proc. Natl. Acad. Sci., Nov. 1993, pp. 9862-9866, vol. 90.
Goyenechea et al., Modifying the sequence of an immunoglobulin V-gene alters the resulting pattern of hypermutation, Proc. Natl. Acad. Sci. 1996, pp. 13979-13984, vol. 93.
Hengstschlager et al., A λ1 transgene under the control of a heavy chain promoter and enhancer does not undergo somatic hypennutation, Eur. J. Immunol. 1994, pp. 1649-1656, vol. 24.

(56) References Cited

OTHER PUBLICATIONS

Jolly et al., Rapid methods for the analysis of immunoglobulin gene hypermutation: application to transgenic and gene targeted mice, Nucleic Acids Research, 1997, pp. 1913-1919, vol. 25, No. 10.
Klotz et al., Somatic Hypermutation of a $\lambda_2$ Transgene Under the Control of the $\lambda$ Enhancer or the Heavy Chain Intron Enhancer, The Journal of Immunology, 1996, pp. 4458-4463, vol. 157.
Kong et al., A $\lambda$ 3' Enhancer Drives Active and Untemplated Somatic Hypermutation of a $\lambda_1$ Transgene, The Journal of Immunology, 1998, pp. 294-301, vol. 161.
Mendez et al., Functional transplant of megabase human inununoglobulin loci recapitulates human antibody response in mice, Nature Genetics, 1997, pp. 146-156, vol. 15.
Sharpe et al., Somatic hypermutation of immunoglobulin κ may depend on sequences 3' of $C_\kappa$ and occurs on passenger transgenes, The EMBO Journal, 1991, pp. 2139-2145, vol. 10, No. 8.
Sirac et al., Role of the monoclonal κ chain V domain and reversibility of renal damage in a transgenic model of acquired Fanconi syndrome, Blood, Jul. 15, 2006, pp. 536-543, vol. 108, No. 2.
ImMunoGeneTics Information System, for analysed sequence CHEB VK, http://www.imgt.org/IMGT_vquest/vquest, at least as early as Apr. 25, 2012.
NCBI, Aucouturier et al., Monoclonal IgL Claim and L chain V domain fragment crystallization in myeloma-associated Fanconi's syndrome, <http://www.ncbi.nlm.nib/gov/nuccore/M87478, at least as early as Apr. 25, 2012.
Third Party Observations Under Article 115 EPC Against European Parent Application No. 09075279.1 in the name of Merus B.V., dated Oct. 25, 2012.
Third Party Observations Under Article 115 EPC Against European Parent Application No. 09075279.1 in the name of Merus B.V., dated Apr. 25, 2012.
European Patent Office Communication for Application No. 09075279.1 dated Nov. 5, 2012.
European Patent Office Communication for Application No. 09075279.1 dated May 8, 2012.
Esposito, Gloria et al., "Phage display of a human antibody against Clostridium tetani toxin," Gene, vol. 148:167-168 (1994).
Goyenechea, Beatriz et al., "Cells strongly expressing Igk transgenes show clonal recruitment of hypermutation: a role for both MAR and the enhancers," The EMBO Journal, vol. 16(13):3987-3994 (1997).
Klohn, Peter-Christian et al., "IBC's 23rd Annual Antibody Engineering, 10th Annual Antibody Therapeutics International Conferences and the 2012 Annual Meeting of the Antibody Society," mAbs, vol. 5(2):178-201 (2013).
Third Party Observation for Application No. EP20090075279, 16 pages, Jun. 14, 2013.
Third Party Observations for Application No. 09075279.1, 8 pages, May 16, 2013.
Bogen, Bjarne et al., "A rearranged lambda 2 light gene chain retards but does not exclude kappa and lambda 1 expression," Eur. J. Immunol., vol. 21:2391-2395 (1991).
Mao, Xiaohong et al., "Activation of EGFP expression by Cre-mediated excision in a new ROSA26 reporter mouse strain," Blood, vol. 97(1):324-326 (2001).
Neuberger, M.S. et al., "Isotype exclusion and transgene down-regulation in immunoglobulin-lambda transgenic mice," Nature, vol. 338:350-352 (1989).
Peled, Jonathan U. et al., "The Biochemistry of Somatic Hypermutation," Annu. Rev. Immunol., vol. 26:481-511 (2008).
Rickert, Robert C. et al., "B lymphocyte-specific, Cre-mediated mutagenesis in mice," Nucleic Acids Research, vol. 25(6):1317-1318 (1997).
Singer, Maxine et al., "Transcription: The Transfer of DNA Sequence Information to RNA," Genes & Genomes, University Science Books, CA, Chapter 3.2, pp. 134-145 (1991).
Yarilin, A.A., Osnovy Immunologii, [Fundamentals of Immunology], Meditsina, Moscow, p. 195 (1999).

Carter, Paul, "Bispecific human IgG by design," Journal of Immunological Methods, vol. 248:7-15 (2001).
Dechiara, Thomas M. et al., "VelociMouse: Fully ES Cell-Derived F0-Generation Mice Obtained from the Injection of ES Cells into Eight-Cell-Stage Embryos," Gene Knockout Protocols: Second Edition, Ralf Kuhn (Ed.), Humana Press, vol. 530, Chapter 16, pp. 311-324 (2009).
GenBank Accession No. DQ187586-1, Protein ID ABA26122.1, Rabquer, B.J. et al., "Differential variable gene usage between pneumococcal polysaccharide specific B cells isolated 5-10 days and 4-6 weeks post-vaccination," 1 page (2005).
GenBank Accession No. M87478, "Human rearranged IgK mRNA VJC region," 1 page (1994).
Murphy, Kenneth, "The Development and Survival of Lymphocytes," Janeway's Immunobioloby, 8th Edition, Taylor & Francis, Chapter 8, pp. 275-290 (2011).
Logtenberg, Ton, "Antibody cocktails: next-generation biopharmaceuticals with improved potency," Trends in Biotechnology, vol. 25(9):390-394 (2007).
Merus, "MeMo—the ingenious mouse, for improved antibody therapeutics," www.merus.nl, 3 pages (2011).
Nemazee, David, "Receptor editing in lymphocyte development and central tolerance," Nature, vol. 6(10):728-740 (2006).
Sasaki, Yoshiteru et al., "Canonical NF-kB Activity, Dispensable for B Cell Development, Replaces BAFF-Receptor Signals and Promotes B Cell Proliferation upon Activation," Immunity, vol. 24:729-739 (2006).
Stevens, Sean, "Human Antibody Discovery, VelocImmune—A novel platform," Pharma Focus Asia, Issue 8, pp. 72-74 (2008).
Torres, Raul M. et al., Laboratory Protocols for Conditional Gene Targeting, Oxford University Press, Oxford, Chapters 10-11, pp. 42-53 (1997).
Van Doorn, S.T., Additional post-filing data and letter filed by the patentee, 1 page, dated Jun. 13, 2013.
Statement of Facts and Arguments in Support of Opposition, Patent No. EP2147594 B1, 46 pages, dated Aug. 11, 2014.
Attaelmannan, Mohammed et al., "Understanding and Identifying Monoclonal Gammopathies," Clinical Chemistry, vol. 46(8B):1230-1238 (2000).
Lie, Y.S. et al., "Advances in quantitative PCR technology: 5' nuclease assays," Curr. Opin. Biotechnol., vol. 9(1):43-48 (1998).
Yang, X.W. et al., "Homologous recombination based modification in *Escherichia coli* and germline transmission in transgenic mice of a bacterial artificial chromosome," Nat. Biotechnol., vol. 15(9):859-865 (1997).
Third Party Observation for Application No. 2009263082, 25 pages, dated Oct. 28, 2013.
Third Party Observation for Application No. 09075279.1, 12 pages, dated Sep. 12, 2013.
Third Party Observation for Application No. 09075279.1, 4 pages, dated Oct. 10, 2013.
Fecteau, Jessie F. et al., "A New Memory CD27 IgG+ B Cell Population in Peripheral Blood Expressing VH Genes with Low Frequency of Somatic Mutation," The Journal of Immunology, vol. 177:3728-3736 (2006).
Kling, Jim, "Big Pharma vies for mice," Nature Biotechnology, vol. 25 (6):613 (2007).
Nagle, Mike, "Regeneron helps make Sanofi VelocImmune to its 'weak' pipeline," Outsourceing-Pharma.com, 2 pages (2007).
Retter, Marc W. et al., "Receptor Editing Occurs Frequently during Normal B Cell Development," J. Exp. Med., vol. 188(7):1231-1238 (1998).
Scott, Christopher Thomas, "Mice with a human touch," Nature Biotechnology, vol. 25:1075-1077 (2007).
Australian Office Action for Application No. 2009263082, 8 pages, dated Mar. 18, 2014.
Canadian Protest and Submission of Prior Art for Application No. 2,729,095, 16 pages, dated Apr. 8, 2014.
Aggarwal and Wah, Novel site-specific DNA endonucleases., Curr Opin Struct Biol., Feb. 1998, 8 (1), pp. 19-25.
Anderson and Potter, Induction of plasma cell tumours in BALB-c mice with 2,6,10,14-tetramethylpentadecane (pristane)., Nature, Jun. 1969, 222 (5197), pp. 994-995.

(56) References Cited

OTHER PUBLICATIONS

Andrew Murphy, Recombinant Antibodies for Immunotherapy, New York: Cambridge University Press, 2009, chapter 8, pp. 100-107.
Angrand et al., Simplified generation of targeting constructs using ET recombination, NAR, Sep. 1999, 27(17):e16 i-iv.
Bethke and Sauer, Segmental genomic replacement by Cre-mediated recombination: genotoxic stress activation of the p53 promoter in single-copy transformants, NAR, Jul. 1997, 25 (14), pp. 2828-2834.
Blankenstein & Krawinkel, Immunoglobulin VH region genes of the mouse are organized in overlapping clusters., Eur J Immunol., Sep. 1987, 17(9), pp. 1351-1357.
Borén et al., A Simple and Efficient Method for Making Site-directed Mutants, Deletions, and Fusions of Large DNA Such as P1 and BAC Clones, Genome Research, Nov. 1996, 6 (11), pp. 1123-1130.
Brüggemann and Neuberger, Strategies for expressing human antibody repertoires in transgenic mice., Immunology Today, Aug. 1996, vol. 17, No. 8, pp. 391-397.
Brüggemann et al., Human antibody production in transgenic mice: expression from 100 kb of the human IgH locus., Eur J Immunol., May 1991, 21 (5), pp. 1323-1326.
Brüggemann M., Molecular Biology of B Cells, Elsevier Science, 2004, Chapter 34: Human Monoclonal Antibodies from Translocus Mice, pp. 547-561.
Brüggemann, Human Antibody Expression in Transgenic Mice., Archivum Immunologiae et Therapiae Experimentalis, 2001, 49 (3), pp. 203-208.
Call et al., A Cre-lox recombination system for the targeted integration of circular yeast artificial chromosomes into embryonic stem cells, HMG, Jul. 2000, 9 (12), pp. 1745-1751).
Carson and Wu, A linkage map of the mouse immunoglobulin lambda light chain locus, Immunogenetics, Mar. 1989, 29(3), pp. 173-179.
Catalano et al., Virus DNA packaging: the strategy used by phage lambda., Mol Microbiol., Jun. 1995, 16(6), pp. 1075-1086.
Cohn et al., Characterization of the antibody to the C-carbohydrate produced by a transplantable mouse plasmacytoma.,Immunochemistry, Jan. 1969, 6 (1), pp. 111-114.
Crescendo's cash fragments, Biocentury, Dec. 2013, vol. 21, No. 48, p. A3.
Decision of the UK Court of Appeal dated Mar. 28, 2018.
D'Eustachio P. and Riblet R., Mouse Chromosome 12, Mammalian Genome, 1998, 8, pp. S241-S257.
Dietrich et al., A comprehensive genetic map of the mouse genome, Nature, Mar. 1996, 380 (6570), pp. 149-152.
Eggan et al., Hybrid vigor, fetal overgrowth, and viability of mice derived by nuclear cloning and tetraploid embryo complementation, PNAS, May 2001, 98 (11), pp. 6209-6214.
Eppig et al., Mouse Genome Informatics (MGI): reflecting on 25 years, Mamm Genome, Aug. 2015, 26 (7-8), pp. 272-284.
Eppig J., Mouse Genetics and Transgenics a practical approach, New York: Oxford University Press, 2000, chapter 7, pp. 170-183.
Extract from: Paul, W.E., Fundamental Immunology, Philadelphia: Lippincott-Raven, 1999, 4th edition, chapter 5, p. 140, figure 16.
Feeney, A. J. and Riblet R., DST4: a new, and probably the last, functional DH gene in the BALB/c mouse, Immunogenetics, Jan. 1993 ,37 (3), pp. 217-221.
Fox and Povey, Mouse Genetics and Transgenics a practical approach, New York: Oxford University Press, 2000, chapter: Fluorescent in situ hybridization (FISH) to mouse chromosomes, pp. 154-169.
Frengen et al., A modular, positive selection bacterial artificial chromosome vector with multiple cloning sites, Genomics, Jun. 1999, 58 (3), pp. 250-253.
Fukita et al., Somatic Hypermutation in the Heavy Chain Locus correlates with transcription., Immunity, Jul. 1998, 9 (1), 105-114.
Giraldo and Montoliu, Size matters: use of YACs, BACs and PACs in transgenic animals,Transgenic Research, Apr. 2001, 10 (2), pp. 83-103.
Glanville et al., Naive antibody gene-segment frequencies are heritable and unaltered by chronic lymphocyte ablation., PNAS, Dec. 2011, 108 (50), pp. 20066-20071.
Glaser et al., Current issues in mouse genome engineering, Nat Genetics, Nov. 2005, 37 (11), 1187-1193.
Green and Jakobovits, Regulation of B Cell Development by Variable Gene Complexity in Mice Reconstituted with Human Immunoglobulin Yeast Artificial Chromosomes, JEM, Aug. 1998, 188 (3), pp. 483-495.
Green et al, Antigen-specific human monoclonal antibodies from mice engineered with human Ig heavy and light chain YACs., Nature Genetics, May 1994, 7 (1), pp. 13-21.
Green, Antibody engineering via genetic engineering of the mouse: XenoMouse strains are a vehicle for the facile generation of therapeutic human monoclonal antibodies., Journal of Immunological Methods, Dec. 1999, 231 (1-2), pp. 11-23.
Gu et al., Most Peripheral B Cells in Mice Are Ligand Selected, J Exp Med. Jun. 1991, 173(6), pp. 1357-1371.
Herring et al., Vector-Hexamer PCR Isolation of All Insert Ends from a YAC Contig of the Mouse Igh Locus, Genome Research, Jun. 1998, 8 (6), pp. 673-681.
Hill et al., BAC Trimming: Minimizing Clone Overlaps, Genomics, Feb. 2000, 64 (1), pp. 111-113.
Huetz et al., Targeted disruption of the VH 81X gene: influence on the B cell repertoire., Eur J Immunol., Jan. 1997, 27 (1), pp. 307-314.
Jessen et. al., Modification of bacterial artificial chromosomes through chi-stimulated homologous recombination and its application in zebrafish transgenesis., PNAS USA, Apr. 1998, vol. 95, issue 9, pp. 5121-5126.
Jonathan Knight, Mouse genome effort 'on course', Nature, May 2001, vol. 411, p. 121.
Kawasaki et al., Evolutionary dynamics of the human immunoglobulin k locus and the germline repertoire of the Vk genes, Eur J Immunol, Apr. 2001, 31 (4), pp. 1017-1028.
Kawasaki et al., One-megabase sequence analysis of the human immunoglobulin lambda gene locus, Genome research, Mar. 1997, 7(3), pp. 250-261.
Kirschbaum et al., the 3' part of the Ig kappa locus of the mouse, Eur J Immunol., May 1998, 28 (5), pp. 1458-1466.
Kirschbaum et al., The central part of the mouse immunoglobulin kappa locus, Eur J Immunol., Jul. 1999, 29 (7), pp. 2057-2064.
Kymab: More mAb diversity, Biocentury, Feb. 2012.
Lee et al., A Highly Efficient *Escherichia coli*-Based Chromosome Engineering System Adapted for Recombinogenic Targeting and Subcloning of BAC DNA, Genomics, Apr. 2001, 73 (1), pp. 56-65.
Lefranc and Lefranc, The Immunoglobulin FactsBook, London: Academic Press, 2001, pp. 52-58.
Lefranc M P, Nomenclature of the Human Immunoglobulin Lambda (IGL) Genes, Exp Clin Immunogenetics, 2001 18 (4), pp. 242-254.
Lonberg, Human antibodies from transgenic animals, nature biotechnology, Sep. 2005, 23 (9), pp. 1117-1125.
Lonberg, Human Monoclonal Antibodies from Transgenic Mice, Therapeutic Antibodies. Handb Exp Pharmacol., 2008, 181, pp. 69-97.
Mainville et al., Deletional Mapping of Fifteen Mouse VH Gene Families Reveals a Common Organization for Three Igh Haplotypes, Journal of Immunology, Feb. 1996, 156 (3), pp. 1038-1046.
Mansour et al., Disruption of the proto-oncogene int-2 in mouse embryo-derived stem cells: a general strategy for targeting mutations to non-selectable genes, Nature, Nov. 1988, 336 (6197), pp. 348-352.
Matsuda et al., The complete nucleotide sequence of the human immunoglobulin heavy chain variable region locus., J. Exp. Med., Dec. 1998, 188 (11), pp. 2151-2162.
McMurry et al., Enhancer control of local accessibility to V(D)J recombinase., Mol Cell Biol, Aug. 1997, 17 (8), pp. 4553-4561.
Mejía and Lakrin, The Assembly of Large BACs by in Vivo Recombination, Genomics, Dec. 2000, 70 (2), pp. 165-170.
Mejia and Monaco, Retrofitting Vectors for *Escherichia coli*-Based Artificial Chromosomes (PACs and BACs) with Markers for Transfection Studies, Genome Research, Feb. 1997, 7 (2), pp. 179-186.

(56) References Cited

OTHER PUBLICATIONS

Mouse Genome Sequencing Consortium, Waterston, et al., Initial sequencing and comparative analysis of the mouse genome, Nature, Dec. 2002, 420(6915), pp. 520-562.
Murphy, Use of Bacteriophage Lambda Recombination Functions to Promote Gene Replacement in *Escherichia coli*, Journal of Bacteriology, Apr. 1998, 180 (8), pp. 2063-2071.
Muyrers et al., ET -Cloning: Think Recombination First, Genetic Engineering, 2000, pp. 77-98.
Muyrers et al., Point mutation of bacterial artificial chromosomes by ET recombination, EMBO Reports, Sep. 2000, 1 (3), pp. 239-243.
Muyrers et al., Rapid modification of bacterial artificial chromosomes by ET-recombination, NAR, Mar. 1999, 27 (6), pp. 1555-1557.
Nagy, A., Cre Recombinase: The Universal Reagent for Genome Tailoring, Genesis, Feb. 2000, 26 (2), pp. 99-109.
Naryanan et al., Efficient and precise engineering of a 200 kb beta-globin human/bacterial artificial chromosome in *E. coli* DH10B using an inducible homologous recombination system., Gene Ther., Mar. 1999, 6 (3), pp. 442-447.
Nefedov et al., Insertion of disease-causing mutations in BACs by homologous recombination in *Ecoli*, NAR, Sep. 2000, 28 (17):e79.
News in brief, Nature Biotechnology, Jun. 2007, vol. 25, No. 6, pp. 613-614.
Nusbaum et al., A YAC-based physical map of the mouse genome, Nature Genetics, Aug. 1999, 22 (4), pp. 388-393.
O'Connor et al., Construction of Large DNA Segments in *E coli*, Science, Jun. 1989, 244 (4910), pp. 1307-1312.
Orford et al., Engineering EGFP reporter constructs into a 200 kb human beta-globin BAC clone using GET Recombination, NAR, Sep. 2000, 28 (18):e84.
Osoegawa et al., Bacterial Artificial Chromosome Libraries for Mouse Sequencing and Functional Analysis, Genome Research, Jan. 2000, 10 (1), pp. 116-128.
Perlmutter et al., The generation of diversity in phosphorylcholine-binding antibodies., Adv Immunol., 1984, vol. 35, pp. 1-37.
Potter and Heller, Transfection by Electroporation, Curr Prot Mol Biol, May 2010, vol. 92, issue 1, chapter: unit-9.3.
Potter et al., Enhancer-dependent expression of human Kc immunoglobulin genes introduced into mouse pre-B lymphocytes by electroporation., PNAS, Nov. 1984, 81 (22), pp. 7161-7165.
Rakesh Anand, DNA Cloning 3 a Practical Approach 2nd Ed, New York: Oxford University Press, 1995, 2nd edition, pp. 112-114.
Ramirez-Solis et al., Gene Targeting in Embryonic Stem Cells, Meth. in Enzymology, 1993, vol. 225, pp. 855-878.
Rathbun et al., Immunoglobulin Genes, London: Academic Press Limited, 1990, 2nd ed., pp. 71-76.
Reyrat et al., Counterselectable Markers: Untapped Tools for Bacterial Genetics and Pathogenesis, Infection and Immunity, Sep. 1998, 66 (9), pp. 4011-4017.
Riblet R., Tutter A. and Brodeur P.,Polymorphism and evolution of Igh-V gene families., Curr. Top. Microbiol. Immunol., 1986, vol. 127, pp. 167-172.
Richards-Smith et al., Deletion mapping of the mouse ornithine decarboxylase-related locus Odc-rs8 within Igh-V, Mammalian Genome, Oct. 1992, 3 (10), pp. 568-574.
Rideout et al., Generation of mice from wild-type and targeted ES cells by nuclear cloning, Nat Genetics, Feb. 2000, 24 (2), pp. 109-110.
Robertson E.J. and Bradley A., Teratocarcinomas and embryonic stem cells: a practical approach, Oxford: IRL Press Limited, 1987, chapters 4 and 5, pp. 71 to 151.
Roschenthaler et al., The 5' part of the mouse Ig k locus as a continuously cloned structure, Eur J Immunol., Dec. 2000, 30(12), pp. 3349-3354.
Röschenthaler et al., The 5 part of the mouse immunoglobulin kappa locus, Eur J Immunol., Jul. 1999, 29(7), pp. 2065-2071.
Sambrook and Russell, Molecular Cloning: A Laboratory Manual, New York: Cold Spring Harbor Laboratory Press, 2001, 3rd edition, vol. 1, pp. 2.110-2.111.
Sambrook and Russell, Molecular Cloning: A Laboratory Manual, New York: Cold Spring Harbor Laboratory Press, 2001, 3rd edition, vol. 1, chapter 5, protocols 15 and 19, pp. 5.68-5.70 and 5.83-5.85.
Sambrook and Russell, Molecular Cloning: A Laboratory Manual, New York: Cold Spring Harbor Laboratory Press, 2001, 3rd edition, vol. 1, p. 6.3.
Sambrook and Russell, Molecular Cloning: A Laboratory Manual, New York: Cold Spring Harbor Laboratory Press, 2001, 3rd edition, vol. 1, chapter 5, protocol 13, pp. 5.61-5.64.
Sambrook and Russell, Molecular Cloning: A Laboratory Manual, New York: Cold Spring Harbor Laboratory Press, 2001, 3rd edition, vol. 1, chapter 6, protocol 2, pp. 6.13-6.15.
Sambrook and Russell, Molecular Cloning: A Laboratory Manual, New York: Cold Spring Harbor Laboratory Press, 2001, 3rd edition, vol. 3, protocol 5, pp. 16.33-16.36.
Sambrook and Russell, Molecular Cloning: A Laboratory Manual, New York: Cold Spring Harbor Laboratory Press, 2001, 3rd edition, vol. 1, chapter 5, pp. 5.2-5.3.
Sambrook and Russell, Molecular Cloning: A Laboratory Manual, New York: Cold Spring Harbor Laboratory Press, 2001, 3rd edition, vol. 1, protocol 7, pp. 4.48-4.52.
Sambrook and Russell, Molecular Cloning: A Laboratory Manual, New York: Cold Spring Harbor Laboratory Press, 2001, 3rd edition, vol. 1, pp. 1.18-1.25.
Sambrook and Russell, Molecular Cloning: A Laboratory Manual, New York: Cold Spring Harbor Laboratory Press, 2001, 3rd edition, vol. 3, chapter 16, pp. 16.54-16.57.
Sambrook and Russell, Molecular Cloning: A Laboratory Manual, New York: Cold Spring Harbor Laboratory Press, 2001, 3rd edition, vol. 1, pp. 4.82-4.85.
Sambrook and Russell, Molecular Cloning: A Laboratory Manual, New York: Cold Spring Harbor Laboratory Press, 2001, 3rd edition, vol. 2, pp. 12.10-12.13.
Sambrook and Russell, Molecular Cloning: A Laboratory Manual, New York: Cold Spring Harbor Laboratory Press, 2001, 3rd edition, vol. 2, pp. 8.94-8.95.
Sambrook and Russell, Molecular Cloning: A Laboratory Manual, New York: Cold Spring Harbor Laboratory Press, 2001, 3rd edition, vol. 1, pp. 4.1-4.8.
Sambrook and Russell, Molecular Cloning: A Laboratory Manual, New York: Cold Spring Harbor Laboratory Press, 2001, 3rd edition, vol. 1, pp. 1.2-1.16.
Sauer, B., Inducible gene targeting in mice using the Cre/loxSystem, Methods, Apr. 1998, 14 (4), pp. 381-392.
Schedl et al., Transgenic mice generated by pronuclear injection of a yeast artificial chromosome, NAR, Jun. 1992, vol. 20, Issue 12, pp. 3073-3077.
Schindelhauer and Cooke, Efficient combination of large DNA in vitro: in gel site specific recombination (IGSSR) of PAC fragments containing alpha satellite DNA and the human HPRTgene locus., NAR, Jun. 1997, 25 (11), pp. 2241-2243.
Sheng et al., Transformation of *Escherichia coli* with large DNA molecules by electroporation, NAR, Jun. 1995, 23 (11), pp. 1990-1996.
Shizuya et al., Cloning and stable maintenance of 300-kilobase-pair fragments of human DNA in *Escherichia coli* using an F-factor-based vector, PNAS, Sep. 2012, 89 (18), pp. 8794-8797.
Soukharev et al., Segmental genomic replacement in embryonic stem cells by double lox targeting, NAR, Sep. 1999, 27 (18):e21 i-viii.
Stevens, Human Antibody Discovery—VelocImmune—A novel platform, Pharma Focus Asia, 2008, issue 8, pp. 72-74.
Supporting information of Murphy et al., Mice with megabase humanization of their immunoglobulin genes generate antibodies as efficiently as normal mice., PNAS, Apr. 2014, 111( 14), pp. 5153-5158.
The life history of the mouse in genetics, Nature, Dec. 2002, vol. 120, pp. 510-511.
Thiebe et al., The variable genes and gene families of the mouse immunoglobulin kappa locus., Eur J Immunol., Jul. 1999, 29(7), pp. 2072-2081.

(56) References Cited

OTHER PUBLICATIONS

Tomizuka et al., Double trans-chromosomic mice: maintenance of two individual human chromosome fragments containing Ig heavy and kappa loci and expression of fuly human antibodies., PNAS, Jan. 2000, 97 (2), pp. 722-727.
Trucksis M et al., The Vibrio cholerae genome contains two unique circular chromosomes.,PNAS, Nov. 1998, 95 (24), pp. 14464-14469.
Van Etten et al., Radiation hybrid map of the mouse genome, Nature Genetics, Aug. 1999, 22 (4), pp. 384-387.
Vasicek et al., B-less: a Strain of Profoundly B Cell-deficient Mice Expressing a Human lambda Transgene, JEM, May 1992, 175 (5), pp. 1169-1180.
Wade-Martins et al., Long-term stability of large insert genomic DNA episomal shuttle vectors in human cells, NAR, Apr. 1999, 27 (7), pp. 1674-1682.
Weigert M. and Riblet R.,The genetic control of antibody variable regions in the mouse, Springer Seminars in Immunopathology, Jun. 1978, 1 (2), pp. 133-169.
Xu and Feiss, Structure of the bacteriophage lambda cohesive end site. Genetic analysis of the site (cosN) at which nicks are introduced by terminase., J Mol Biol., Jul. 1991, 220(2), pp. 281-292.
Yang and Seed, Site-specific gene targeting in mouse embryonic stem cells with intact bacterial artificial chromosomes, Nature Biotechnol, Apr. 2003, 21 (4), pp. 447-451.
Yang. X. W., et al., Homologous recombination based modification in *Esherichia coli* and germline transmission in transgenic mice of a bacterial artificial chromosome, Nat. Biotechnol.,Sep. 1997, vol. 15, issue 9, pp. 859-865.
Yu et al., An efficient recombination system for chromosome engineering in *Escherichia coli*, PNAS, May 2000, 97 (11), pp. 5978-5983.
Zhang et al., A new logic for DNA engineering using recombination in *Escherichia coli*, Nature Genetics, Oct. 1998, 20 (2), pp. 123-128.
Zhang et al., DNA cloning by homologous recombination in *Escherichia coli*, Nature Biotech, Dec. 2000, 18 (12), pp. 1314-1317.
Zhao S., A Comprehensive BAC Resource, Nucleic Acids Research, Jan. 2001, vol. 29, No. 1, pp. 141-143.
Zheng et al., Engineering Mouse Chromosomes with Cre-loxP: Range, Efficiency, and Somatic Applications, Mol Cell Biol., Jan. 2000, 20 (2), pp. 648-655.
Tarlinton, David, Declaration filed Against Australian Application No. 2009263082 in the name of Merus B.V., executed Dec. 21, 2014.
DeFranco, Anthony L., Declaration filed Against Australian Application No. 2009263082 in the name of Merus B.V., executed Dec. 21, 2014.
Murphy, Andrew, Declaration filed Against Australian Application No. 2009263082 in the name of Merus B.V., executed Dec. 19, 2014.
Adderson et al., "Restricted immunoglobulin VH Usage and VDJ combinations in the human response to haermophilus influenza type b capsular polysaccharide," J Clin Invest (1993) 91(6):2734-2743.
Gallo et al., "The human immunoglobulin loci introduced into mice: V (D) and J gene segment usage similar to that of adult humans," Eur J Immunol (2000) 30:534-540.
Wang et al., "Ab-origin: an enhanced tool to identify the sourcing gene segments in germline for rearranged antibodies," BMC Bioinformatics (2008) 9(Suppl 12):S20.
Zhang et al., "Discrimination of germline V genes at different sequencing lengths and mutational burdens: A new tool for identifying and evaluating the reliability of V gene assignment," Journal of Immunological Methods (2015) 427:105-116.
O'Brien et al., "Somatic hypermutation of an immunoglobulin transgene in κ transgenic mice," Nature (1987) 326:405-409.
Protest under 37 CFR § 1.291 in Re-issue U.S. Appl. No. 15/158,543, filed Oct. 14, 2016, 45 pages.
Amendment for U.S. Appl. 12/932,719, filed Oct. 8, 2013, 12 pages.
Amendment under AFCP 2.0 for U.S. Appl. No. 12/932,719, filed Jun. 11, 2014, 12 pages.
Amendment for U.S. Appl. No. 12/932,719, filed Feb. 27, 2012, 10 pages.
Teaching of U.S. Appl. No. 12/589,181, presented May 24, 2012, 30 pages.
Notice of Opposition to a European Patent in EP 1360287 from Kymab Limited, filed Jun. 12, 2013, 8 pages.
Notice of Opposition to a European Patent in EP 1360287 from Merus B.V, filed Jun. 12, 2013, 8 pages.
Notice of Opposition to a European Patent in EP 1360287 from Merus B.V, filed Jun. 12, 2013, 4 pages.
Communication of a notice of opposition in EP 02709544.7, dated Jun. 12, 2013, 1 page.
Payment of fees and expenses in EP 02709544.7, filed Jun. 12, 2013, 1 page.
Authorisation for filing an opposition in EP 02709544.7, filed Jun. 11, 2013, 1 page.
Third party observations filed during prosecution (D12) in EP 02709544.7, filed Jun. 12, 2013, 20 pages.
Thykjaer et al., "Gene targeting approaches using positive-negative selection and large flanking regions," Plant Molecular Biology (1997) 35:523-530.
Deng et al., "Reexamination of gene targeting frequency as a function of the extent of homology between the targeting vector and the target locus," Mol Cell Biol (1992) 12(8):3365-3371.
Taki et al., "Targeted insertion of a variable region gene into the immunoglobulin heavy chain locus," Science (1993) 262:1268.
Zhang et al., "A new logic for DNA engineering using recombination in *Escherichia coli*," Nature Genetics (1998) (20):123-128.
Houldsworth et al., "Comparative genomic hybridization: an overview," AJP (1994) 145(6):1253-1260.
Shi et al., "The mapping of transgenes by fluorescence in situ hybridization on G-branded mouse chromosomes," Mammalian Genome (1994) 5:337-341.
Wilke et al., "Diagnosis of haploidy and triploidy based on measurement of gene copy number by real-time PCR," Human Mutation (2000) 16:431-436.
Bruggemann et al., "Strategies for expressing human antibody repertoires in transgenic mice," Immunol Today (1996) 17(8):391-397.
Zou et al., "Cre-loxP-mediated gene replacement: a mouse strain producing humanized antibodies," Current Biology (1994) 4:1099-1103.
Jessen et al., "Modification of bacterial artificial chromosomes through Chi-stimulated homologous recombination and its application in zebrafish transgenesis," Proc Natl Acad Sci USA (1998) 95:5121-5126.
IMGT Repertoire (IG and TR) Locus representation: Human (*Homo sapiens*) IGH, retrieved from http://www.imgtorg/IMGTrepertoire/index.php?section=LocusGenes&repertoire=locus&species=human&group=IGH on Apr. 2, 2012, 6 pages.
IMGT Repertoire (IG and TR) Locus representation: Human (*Homo sapiens*) IGL, retrieved from http://www.imgt.org/IMGTrepertoire/index.php?section=LocusGenes&repertoire=locus&species=human&group=IGL on Apr. 4, 2012, 3 pages.
Narayanan et al., "Efficient and precise engineering of a 200kb β-globin human/bacterial artificial chromosome in *E. coli* DH10b using an inducible homologous recombination system," Gene Therapy (1999) 6:442-447.
Muyrers et al., "Rapid modification of bacterial artificial chromosomes by ET-recombination," Nucleic Acids Research (1999) 27(6):1555-1557.
Schlake et al., "Use of mutated FLP recognition target (FRT) sites for the exchange of expression cassettes at defined chromosomal loci," Biochemistry (1994) 33:12746-12751.
Waterhouse et al., "Combinatorial infection and in vivo recombination: a strategy for making large phage antibody repertoires," Nucleic Acids Research (1993) 21(9):2265-2266.
Gu et al., "Independent control of immunoglobulin switch recombination at individual switch regions evidenced through Cre-loxP-Mediated gene targeting," Cell (1993) 73:1155-1164.
Mendez et al., "Functional transplant of megabase human immunoglobulin loci recapitulates human antibody response in mice," Nature Genetics (1997) 15:146-156.

(56) References Cited

OTHER PUBLICATIONS

Neuberger et al., "Isotype exclusion and transgene down-regulation in immunoglobulin-λ transgenic mice," Nature (1989) 338:350-352.
Bogen et al., "A rearranged λ2 light gene chain retards but does not exclude κ and λ1 expression," Eur J Immunol (1991) 24:2391-2395.
Davies et al., "Creation of mice expressing human antibody light chains by introduction of a yeast artificial chromosome containing the core region of the human immunoglobulin κ locus," Biotechnology.
Takeda et al., "Construction of chimaeric processed immunoglobulin genes containing mouse variable and human constant region sequences," Nature (1985) 314(4):452-454.
Taylor et al., "Human immunoglobulin transgenes undergo rearrangement, somatic mutation and class switching in mice that lack endogenous IgM," Int Immunol (1994) 6(4):579-591.
Bruggemann, "Human antibody expression in transgenic mice," Archivum Immunologiae et Therapiae Experimentalis (2001) 49:203-208.
Statement of Sean Stevens, PHD in EP 02709544.7, filed Aug. 7, 2009, 14 pages.
U.S. Appl. No. 09/732,234, filed Dec. 7, 2000, 57 pages.
U.S. Appl. No. 60/244,665, filed Oct. 31, 2000, 51 pages.
Appendix 1: The claims of the patent, dated Jun. 12, 2013, 5 pages.
List of evidence, dated Jun. 12, 2013, 2 pages.
Opposition against EP 1360287, dated Jun. 12, 2013, 2 pages.
Statement of facts and arguments, dated Jun. 12, 2013, 22 pages.
Statement of facts and arguments against EP 1360287, dated Jun. 12, 2013, 40 pages.
Acknowledgment of receipt for EP 1360287, dated Jun. 12, 2013, 2 pages.
Acknowledgment of receipt for EP 1360287, dated Jun. 12, 2013, 3 pages.
Submission in opposition proceedings in EP 1360287, dated Jun. 20, 2013, 2 pages.
Brief communication in EP1360287, dated Jun. 20, 2013, 1 page.
Smith et al., "Genomic analysis of transgenic animals," Methods in Molecular Biology (1993) 18:323-327.
Letter regarding the opposition procedure in EP 02709544.7, filed Jun. 14, 2013, 1 page.
Acknowledgment of receipt for EP 1360287, dated Jun. 20, 2013, 2 pages.
Communication of notices of opposition in EP 1360287, dated Jul. 18, 2013, 1 page.
Communication of further notices of opposition pursuant to Rule 79(2) EPC in EP 1360287, dated Jul. 18, 2013, 1 page (Stephen, Robert John).
Communication of further notices of opposition pursuant to Rule 79(2) EPC in EP 1360287, dated Jul. 18, 2013, 1 page (EP&C).
Letter accompanying subsequently filed items in EP 02709544.7, dated Sep. 16, 2013, 1 page.
Acknowledgment of receipt in EP 02709544.7, dated Sep. 16, 2013, 1 page.
Request for extension of time limit in EP 02709544.7, dated Sep. 16, 2013, 1 page.
Brief communication for EP 02709544.7, dated Sep. 17, 2013, 1 page (Stephen, Robert John).
Brief communication for EP 02709544.7, dated Sep. 17, 2013, 1 page (EP&C).
Grant of extension of time limit pursuant to Rule 132 EPC, dated Sep. 17, 2013, 1 page.
Submission in opposition proceedings in EP 02709544.7, dated Oct. 11, 2013, 2 pages.
Opposition proceedings for EP 1360287, dated Oct. 11, 2013, 1 page.
Acknowledgment of receipt in EP 02709544.7, dated Oct. 11, 2013, 1 page.
Brief communication for Ep 02709544.7, dated Oct. 14, 2013, 1 page (Bentham, Andrew).
Brief communication for EP 02709544.7, dated Oct. 14, 2013, 1 page (Ep&C).
Submission in opposition proceedings for EP 02709544.7, dated Jan. 28, 2014, 2 pages.
Letter accompanying subsequently filed items in EP 02709544.7, dated Jan. 28, 2014, 2 pages.
Brief communication for EP 02709544.7, dated Jan. 28, 2014, 1 page (Bentham, Andrew).
Brief communication for EP 02709544.7, dated Jan. 28, 2014, 1 page (Stephen, Robert John).
Bruggemann, "Human monoclonal antibodies from translocus mice," Molecular Biology of B Cells (2004) Chapter 34 pp. 547-561.
Honjo et al., "Molecular Biology of B Cells," $1^{st}$ Edition (2004) 1 page.
Open Monoclonal Technology, Inc, "OmniRat, OmniMouse and OmniFlic, Natually optimized human antibodies," (2013) 3 pages.
Ma et al., "Human antibody expression in transgenic rats: Comparison of chimeric IgH loci with human VH, D and JN but bearing different rat C-gene regions," J Immunol Methods (2013) 400-401:78-86.
Green et al., "Antigen-specific human monoclonal antibodies from mice engineered with human Ig heavy and light chain YACs," Nature Genetics (1994) 7:13-21.
Green et al., "Regulation of B cell development by variable gene complexity in mice reconstituted with human immunoglobulin yeast artificial chromosomes," J Exp Med (1998) 188(3):483-495.
Hansen, "Kymab: More mAb diversity," BioCentury (2012) 2 pages.
McCallister, "Still on the lookout," (2013) 21(48) pp. A1 and A13.
News in Brief , "Big Pharma vies for mice," Nature Biotechnology (2007) 25(6):613-614.
Nagle, "Regeneron helps make Sanofi VelocImmune to its "weak" pipeline," (2007) Retrieved on http://www.outsourcing-pharma.com/Preclinical-Research/Regeneron-helps-make-Sanofi-VelocImmune-to-its-weak-pipeline. Retrieved on Oct. 11, 2013.
"AstraZeneca licenses Regeneron's VelocImmune technology for discovering human monoclonal antibodies," (2007) Retrieved on https://www.drugs.com/news/astrazeneca-licenses-regeneron-s-velocimmune-technology-discovering-human-monoclonal-antibodies-5221.html. Retrieved on Jan. 23, 2014.
The Barnes Report, "A new target and technology have Regeneron's future looking bright," (2007) 1(4):1-2.
Business Wire, "Astellas licenses Regeneron's VelocImmune technology for discovering human monoclonal antibodies," (2007) Retrieved on http://www.businesswire.com/news/home/20070329006182/en/Astellas-Licenses-Regenerons-Velocimmune-Technology-Discovering-Human. Retrieved on Dec. 16, 2016.
Business Wire, "Regeneron and Columbia University enter into a strategic VelocImmune agreement to discover human monoclonal antibodies," (2008) Retrieved on http://www.businesswire.com/news/home/20080916005336/en/Regeneron-Columbia-University-Enter-Strategic-VelocImmune-Agreement. Retrieved on Jan. 23, 2014.
"Regeneron partners VelocImmune with University of Texas," Elsevier Business Intelligence (2009) 1 page.
Statement of Sue Klapholz, M.D., Ph.D, dated Jan. 27, 2014, 14 pages.
Jakobovits, "Production of fully human antibodies by transgenic mice," Current Opinion in Biotechnology (1995) 6:561-566.
Glanville et al., "Niave antibody gene-segment frequencies are heritable and unaltered by chronic lymphocyte ablation," PNAS (2011) 108(50):20066-20071.
Tomizuka et al., "Double trans-chromosomic mice: Maintenance of two individual human chromosome fragments containing Ig heavy and κ loci and expression of fully human antibodies," PNAS (2000) 97(2):722-727.
Green, "Antibody engineering via genetic engineering of the mouse: XenoMouse strains are a vehicle for the facile generation of therapeutic human monoclonal antibodies," Journal of Immunological Methods (1999) 231:11-23.
Statement of Andrew Murphy, dated Jan. 27, 2014, 33 pages.
First auxiliary request, dated Jan. 28, 2014, 8 pages.
Second auxiliary request, dated Jan. 28, 2014, 8 pages.

(56) References Cited

OTHER PUBLICATIONS

Amended claims (First auxiliary request), dated Jan. 28, 2014, 8 pages.
Amended claims (Second auxiliary request), dated Jan. 28, 2014, 8 pages.
Patentee's response to Oppositions in EP 1360287, dated Jan. 28, 2014, 1 page.
Patentee's response to Opposition in EP 1360287, dated Jan. 28, 2014, 47 pages.
Letter regarding Opposition proceedings in EP 1360287, dated Jan. 28, 2014, 1 page.
Acknowledgment of receipt in EP 02709544.7, dated Jan. 28, 2014, 1 page.
Acknowledgment of receipt in EP 02709544.7 by Andrew Bentham, dated Jan. 28, 2014, 2 pages.
Brief Communication in EP 027099544.7, dated Jan. 29, 2014, 1 page (Stephen, Robert & John).
Brief Communication in EP 027099544.7, dated Jan. 29, 2014, 1 page (EP&C).
Submission in opposition proceedings in EP 02709544.7, dated Feb. 10, 2014, 2 pages.
Tan et al., "A human-mouse chimeric immunoglobulin gene with a human variable region is expressed in mouse myeloma cell," The Journal of Immunology (1985) 135(5):3564-3567.
Kouskoff et al., "Cassette vectors directing expression of T cell receptor genes in transgenic mice," J Immunological Methods (1995) 180:273-280.
Fleischer et al., "Reactivity of mouse T-cell hybridomas expressing human Vbeta gene segments with staphylococcal and streptococcal superantigens," Infect Immun (1996) 64(3):987.
Vollmer et al., "Antigen contacts by Ni-reactive TCR: typical $\alpha\beta$ chain cooperation versus $\alpha$ chain-dominated specificity," International Immunology (2000) 12(12):1723-1731.
Opposition against EP 1360287, dated Feb. 10, 2014, 6 pages.
Acknowledgment of receipt in EP 02709544.7, dated Feb. 10, 2014, 2 pages.
Brief Communication in EP 02709544.7, dated Feb. 11, 2014, 1 page (Bentham, Andrew).
Brief Communication in EP 02709544.7, dated Feb. 13, 2014, 1 page (EP&C).
Submission in opposition proceedings in EP 1360287, dated Feb. 11, 2014, 2 pages.
Letter accompanying subsequently filed items in EP 02709544.7, dated Feb. 12, 2014, 1 page.
Baker et al., "Adaptation of TCR expression vectors for the construction of mouse-human chimeric MBP-Specific TCR transgenes," Journal of Neuroscience Research (1996) 45:487-491.
Opposition against EP 1360287, dated Feb. 11, 2014, 1 page.
Request for acceleration of the opposition procedure in EP 1360287, dated Feb. 12, 2014, 2 pages.
Acknowledgement of receipt in EP 02709544.7, dated Feb. 12, 2014, 2 pages.
Acknowledgement of receipt in EP 02709544.7, dated Feb. 12, 2014, 1 page (James Nicholls).
Designation of inventor in EP 02709544.7, dated Feb. 24, 2014, 2 pages (Margaret Karow).
Designation of inventor in EP 02709544.7, dated Feb. 24, 2014, 2 pages (Lynn Macdonald).
Designation of inventor in EP 02709544.7, dated Feb. 24, 2014, 2 pages (Aris Economides).
Designation of inventor in EP 02709544.7, dated Feb. 24, 2014, 2 pages (Sean Stevens).
Designation of inventor in EP 02709544.7, dated Feb. 24, 2014, 2 pages (David Valenzuela).
Letter accompanying subsequently filed items in EP 02709544.7, dated Feb. 26, 2014, 1 page.
Letter concerning the inventors in EP 02709544.7, dated Feb. 26, 2014, 1 page.
Acknowledgement of receipt in EP 02709544.7, dated Feb. 26, 2014, 2 pages.
Preparation for oral proceedings in EP 02709544.7, dated Feb. 18, 2014, 2 pages.
Information concerning oral proceedings in EP 02709544.7, dated Apr. 30, 2014, 3 pages.
Summons to attend oral proceedings pursuant to Rule 115(1) in EP 02709544.7, dated Feb. 28, 2014, 1 page (Stephen, Robert John).
Summons to attend oral proceedings pursuant to Rule 115(1) in EP 02709544.7, dated Feb. 28, 2014, 1 page (EP&C).
Summons to attend oral proceedings pursuant to Rule 115(1) in EP 02709544.7, dated Feb. 28, 2014, 1 page (Bentham, Andrew).
Facts and Submissions in EP 02709544.7, dated Feb. 28, 2014, 7 pages.
Acknowledgement of receipt in EP 02709544.7, dated Feb. 28, 2014, 1 page (Stephen, Robert John).
Acknowledgement of receipt in EP 02709544.7, dated Feb. 28, 2014, 1 page (Andrew Bentham).
Acknowledgement of receipt in EP 02709544.7, dated Feb. 28, 2014, 1 page (EP&C).
Notification of the data mentioned in Rule 19(3) EPC in EP 02709544.7, dated Mar. 5, 2014, 1 page (Sean Stevens).
Notification of the data mentioned in Rule 19(3) EPC in EP 02709544.7, dated Mar. 5, 2014, 1 pages (Margaret Karow).
Notification of the data mentioned in Rule 19(3) EPC in EP 02709544.7, dated Mar. 5, 2014, 1 page (David Valenzuela).
Notification of the data mentioned in Rule 19(3) EPC in EP 02709544.7, dated Mar. 5, 2014, 1 page (Lynn Macdonald).
Notification of the data mentioned in Rule 19(3) EPC in EP 02709544.7, dated Mar. 5, 2014, 1 page (Aris Economides).
Bibliographical data of European patent application No. 02709544.7, dated Feb. 28, 2014, 1 page.
Brief Communication in EP 02709544.7, dated Mar. 5, 2014, 1 page (Stephens, Robert John).
Brief Communication in EP 02709544.7, dated Mar. 5, 2014, 1 page (EP&C).
Brief Communication in EP 02709544.7, dated Mar. 5, 2014, 1 page (Andrew Bentham).
Acknowledgement of receipt of the document 2310 in EP 02709544.7, dated Feb. 28, 2014, 1 page (Stephen, Robert John).
Acknowledgement of receipt of the document 2310 in EP 02709544.7, dated Feb. 28, 2014, 1 page (EPC).
Letter accompanying subsequently filed items in EP 02709544.7, dated Mar. 10, 2014, 1 page.
Letter concerning inventor's name in EP 02709544.7, dated Mar. 10, 2014, 1 page.
Acknowledgement of receipt in EP 02709544.7, dated Mar. 10, 2014, 1 page.
Bibliographical data of European patent application No. 02709544.7, dated Mar. 11, 2014, 1 page.
Brief Communication in EP 02709544.7, dated Mar. 14, 2014, 1 page (Andrew Bentham).
Brief Communication in EP 02709544.7, dated Mar. 14, 2014, 1 page (EP&C).
Brief Communication in EP 02709544.7, dated Mar. 14, 2014, 1 page (Stephens, Robert John).
Letter accompanying subsequently filed items in EP 02709544.7, dated Mar. 18, 2014, 1 page.
Letter concerning inventor's address in EP 02709544.7, dated Mar. 18, 2014, 1 page.
Advice of delivery in EP 02709544.7, dated Feb. 28, 2014, 2 pages.
Acknowledgement of receipt in EP 02709544.7, dated Mar. 18, 2014, 1 page.
Bibliographical data of European patent application No. 02709544.7, dated Mar. 19, 2014, 1 page.
Acknowledgement of receipt of the document 2310 in EP 02709544.7, dated Feb. 28, 2014, 1 page (Andrew Bentham).
Brief Communication in EP 02709544.7, dated Mar. 24, 2014, 1 page (Andrew Bentham).
Brief Communication in EP 02709544.7, dated Mar. 24, 2014, 1 page (Stephen, Robert John).
Brief Communication in EP 02709544.7, dated Mar. 24, 2014, 1 page (EPC).
Notice of Opposition to a European patent in EP 02709544.7, dated Apr. 3, 2014, 4 pages.

(56) References Cited

OTHER PUBLICATIONS

Cover sheet for fax transmission in EP 02709544.7, dated Apr. 3, 2014, 1 page.
Online fee payment in EP 02709544.7, dated Apr. 2, 2014, 1 page.
Notice of Intervention by Novo Nordisk in EP 02709544.7, dated Apr. 3, 2014, 13 pages.
Particulars of Infringement in EP 02709544.7, dated Apr. 3, 2014, 8 pages.
Soukharev et al., "Segmental genomic replacement in embryonic stem cells by double lox targeting," (1999) 27(18):e21.
Letter regarding Notice of Intervention in EP 02709544.7, dated Apr. 3, 2014, 1 page.
Notice of opposition to a European patent in EP 02709544.7, dated Apr. 4, 2014, 4 pages.
Brief Communication in EP 02709544.7, dated Apr. 10, 2014, 1 page (Andrew Bentham).
Brief Communication in EP 02709544.7, dated Apr. 10, 2014, 1 page (Stephen, Robert John).
Brief Communication in EP 02709544.7, dated Apr. 10, 2014, 1 page (EP&C).
Maintenance of oral proceedings in EP 02709544.7, dated Apr. 7, 2014, 2 pages.
Brief Communication in EP 02709544.7, dated Apr. 22, 2014, 1 page (Stephen, Robert John).
Brief Communication in EP 02709544.7, dated Apr. 22, 2014, 1 page (EP&C).
Brief Communication in EP 02709544.7, dated Apr. 22, 2014, 1 page (Andrew Bentham).
Preparation for oral proceedings in EP 02709544.7, dated Apr. 17, 2014, 2 pages.
Information concerning oral proceedings in EP 02709544.7, dated Jul. 16, 2014, 3 pages.
Summons to attend oral proceedings pursuant to Rule 115(1) in EP 02709544.7, dated Apr. 24, 2014, 1 page (Stephen, Robert John).
Summons to attend oral proceedings pursuant to Rule 115(1) in EP 02709544.7, dated Apr. 24, 2014, 1 page (EP&C).
Summons to attend oral proceedings pursuant to Rule 115(1) in EP 02709544.7, dated Apr. 24, 2014, 1 page (Bentham, Andrew).
Summons to attend oral proceedings pursuant to Rule 115(1) in EP 02709544.7, dated Apr. 24, 2014, 1 page (Thomas, Philip John Duval).
Facts and Submissions in EP 02709544.7, dated Apr. 24, 2014, 3 pages.
Acknowledgement of receipt of the document 2310 in EP 02709544.7, dated Apr. 24, 2014, 1 page (Andrew Bentham).
Acknowledgement of receipt of the document 2310 in EP 02709544.7, dated Apr. 24, 2014, 1 page (Stephen, Robert John).
Acknowledgement of receipt of the document 2310 in EP 02709544.7, dated Apr. 24, 2014, 1 page (EP&C).
Acknowledgement of receipt of the document 2310 in EP 02709544.7, dated Apr. 24, 2014, 1 page (Thomas, Philip John Duval).
Advice of delivery in EP 02709544.7, dated Apr. 24, 2014, 2 pages (Thomas, Philip John Duval).
Letter accompanying subsequently filed items in EP 02709544.7, dated May 2, 2014, 1 page.
Acknowledgement of receipt of the document 2310 in EP 02709544.7, dated May 2, 2014, 1 page.
Opposition to EP 1360287, dated Jul. 15, 2014, 3 pages.
Authorisation of representative in EP 1360287, dated Jul. 15, 2014, 1 page.
Letter accompanying subsequently filed items in EP 02709544.7, dated Jul. 16, 2014, 1 page.
First auxiliary request in EP 1360287, dated Jul. 16, 2014, 7 pages.
Second auxiliary request in EP 1360287, dated Jul. 16, 2014, 7 pages.
Third auxiliary request in EP 1360287, dated Jul. 16, 2014, 7 pages.
Fourth auxiliary request in EP 1360287, dated Jul. 16, 2014, 7 pages.
Fifth auxiliary request in EP 1360287, dated Jul. 16, 2014, 7 pages.
Sixth auxiliary request in EP 1360287, dated Jul. 16, 2014, 7 pages.
Seventh auxiliary request in EP 1360287, dated Jul. 16, 2014, 7 pages.
Eighth auxiliary request in EP 1360287, dated Jul. 16, 2014, 7 pages.
Ninth auxiliary request in EP 1360287, dated Jul. 16, 2014, 7 pages.
Tenth auxiliary request in EP 1360287, dated Jul. 16, 2014, 7 pages.
Eleventh auxiliary request in EP 1360287, dated Jul. 16, 2014, 7 pages.
Twelfth auxiliary request in EP 1360287, dated Jul. 16, 2014, 7 pages.
Thirteenth auxiliary request in EP 1360287, dated Jul. 16, 2014, 7 pages.
Fourteenth auxiliary request in EP 1360287, dated Jul. 16, 2014, 7 pages.
McMurry et al., "Enhancer control of local accessibility to V(D)J recombinase," Molecular and Cellular Biology (1997) 17(8):4553-4561.
Johnston et al., "Complete sequence assembly and characterization of the C57BL/6 mouse Ig heavy chain V region," J Immunol (2006) 176:4221-4234.
Xu et al., "Deletion of the Igκ light chain intronic enhancer/matrix attachment region impaires but does not abolish VκJκ Rearrangement," Immunity (1996) 4:377-385.
Meier et al., "Short DNA sequences inserted for gene targeting can accidentally interfere with off-target gene expression," The FASEB Journal (2010) 24:1714-1724.
Ren et al., "Targeted insertion results in a rhombomere 2-specific Hoxa2 knockdown and ectopic activation of Hoxa1 expression," Developmental Dynamics (2002) 225:305-315.
Tucker et al., "Mouse IgA heavy chain gene sequence: Implications for evolution of immunoglobulin hinge exons," Proc Natl Acad Sci USA (1981) 78(12):7684-7688.
Blankenstein et al., "Immunoglobulin $V_H$ region genes of the mouse are organized in overlapping clusters," Eur. J. Immunol. 1987.17:1351-1357.
Rathbun et al., "Organization and expression of the mammalian heavy-chain variable-region locus," (1989) Chapter 4, 9 pages.
Amended claims (First auxiliary request), dated Jul. 16, 2014, 8 pages.
Amended claims (Second auxiliary request), dated Jul. 16, 2014, 8 pages.
Amended claims (Third auxiliary request), dated Jul. 16, 2014, 8 pages.
Amended claims (Fourth auxiliary request), dated Jul. 16, 2014, 8 pages.
Amended claims (Fifth auxiliary request), dated Jul. 16, 2014, 8 pages.
Amended claims (Sixth auxiliary request), dated Jul. 16, 2014, 8 pages.
Amended claims (Seventh auxiliary request), dated Jul. 16, 2014, 8 pages.
Amended claims (Eighth auxiliary request), dated Jul. 16, 2014, 8 pages.
Amended claims (Ninth auxiliary request), dated Jul. 16, 2014, 8 pages.
Amended claims (Tenth auxiliary request), dated Jul. 16, 2014, 8 pages.
Amended claims (Eleventh auxiliary request), dated Jul. 16, 2014, 8 pages.
Amended claims (Twelfth auxiliary request), dated Jul. 16, 2014, 8 pages.
Amended claims (Thirteenth auxiliary request), dated Jul. 16, 2014, 8 pages.
Amended claims (Fourteenth auxiliary request), dated Jul. 16, 2014, 8 pages.
Witness statement of Nicole Helen Dagg, dated Jan. 31, 2014, 5 pages.
Office action (third-party submission), dated Apr. 3, 2014, 17 pages.
Statement of Victor L J Tybulewicz, dated Jul. 15, 2014, 26 pages.
Statement of Daniel J. Capon, dated Jul. 7, 2014, 4 pages.
Documents list (D78-D107), dated Jul. 16, 2014, 1 page.
Curriculum Vitae Hidde L. Ploegh, dated Jul. 16, 2014, 33 pages.
Statement of Craig H. Bassing, dated Jul. 16, 2014, 34 pages.

(56) References Cited

OTHER PUBLICATIONS

Document 89, dated Jul. 16, 2014, 1 page.
Document 93 (ANNEX—MOA), dated Jul. 16, 2014, 6 pages.
Document 95a (Statement of Prof. Dr. Hendriks), dated Jul. 16, 2014, 21 pages.
Curriculum Vitae Prof. Dr. Rudi W. Hendriks, dated Jul. 16, 2014, 24 pages.
Response to substantive Examination Report in EP 02709544.7, dated Dec. 22, 2008, 6 pages.
D80 (Examination in EP 02709544.7), dated Jul. 16, 2014, 2 pages.
Kingzette et al., "Trans-chromosomal recombination within the Ig heavy chain switch region in B lymphocytes," Proc Natl Acad Sci USA (1998) 95:11840-11845.
Karu et al., "Recombinant antibody technology," ILAR Journal (1995) 37(3):132-141.
Giusti et al., "Hypermutation is observed only in antibody H chain V region transgenes that have recombined with endogenous immunoglobulin H DNA: Implications for the location of cis-acting elements required for somatic mutation," J Exp Med (1993) 177:797-809.
Bruggemann et al., "The immunogenicity of chimeric antibodies," J Exp Med (1989) 170:2153-2157.
Seidl et al., "Position-dependent inhibition of class-switch recombination by PGK-neor cassettes inserted into the immunoglobulin heavy chain constant region locus," Proc. Natl. Acad. Sci. USA (1999) 96:3000-3005.
Jakobovits, "The long-awaited magic bullets: therapeutic human monoclonal antibodies from transgenic mice," Exp Opin Invest Drugs (1998) 7(4):607-614.
Jakobovits et al., "From XenoMouse technology to panitumumab, the first fully human antibody product from transgenic mice," Nature Biotechnology (2007) 25(10):1134-1143.
Gavilondo et al., "Antibody engineering at the millennium," BioTechniques (2000) 29:128-145.
Clark, "IgG effector mechanisms," Chem Immunol Basel Karger (1997) 65:88-110.
Yang et al., "Homologous recombination based modification in *Esherichia coli* and germline transmission in transgenic mice of a bacterial artificial chromosome," Nature Biotechnology (1997) 15:859-865.
Thomas et al., "Site-directed mutagenesis by gene targeting in mouse embryo-derived stem cells," Cell (1987) 51:503-512.
Spanopoulou et al., "Functional immunoglobulin transgenes guide ordered B-cell differentiation in Rag-1-deficient mice," Genes & Development (1994) 8:1030-1042.
Monaco et al., "YACs, BACs, PACs and MACs: artificial chromosomes as research tools," TIB Tech (1994) 12:280-286.
Giraldo et al., "Size matters: use of YACs, BACs and PACs in transgenic animals," Transgenic Research (2001) 10:83-103.
Clark, "Antibody humanization: a case of the 'Emperor's new clothes'?" Immunology Today (2000) 21(8):397-402.
D82 (Summary of product characteristics), dated Jul. 16, 2014, 39 pages.
D83 (Summary of product characteristics), dated Jul. 16, 2014, 29 pages.
D84 (Summary of product characteristics), dated Jul. 16, 2014, 63 pages.
Muller et al., "Ten years of gene targeting: targeted mouse mutants, from vector design to phenotype analysis," Mechanisms of Development (1999) 82:3-21.
D86 (Gene Targeting), dated Jul. 16, 2014, 98 pages.
D78 (Datasheet for the decision of the Enlarged Board of Appeal of Apr. 6, 2009 for EP 94115175.5), dated Jul. 16, 2014, 25 pages.
U.S. Appl. No. 09/784,859, filed Feb. 16, 2001, 69 pages.
D91 (Datasheet for the decision of Sep. 12, 2012), dated Jul. 16, 2014, 28 pages.
D92 (European patent specification for EP 1 399 575), dated Jul. 16, 2014, 26 pages.
Opposition against EP 1360287, dated Jul. 16, 2014, 34 pages.
Letter regarding references part 1 dated Jul. 16, 2014, 1 page.
Letter regarding references part 2, dated Jul. 16, 2014, 1 page.
Letter regarding references part 3, dated Jul. 16, 2014, 1 page.
Submission in opposition proceedings in EP 1360287, dated Jul. 16, 2014, 2 pages (Olswang).
Submission in opposition proceedings in EP 1360287, dated Jul. 16, 2014, 2 pages (EPC).
Letter regarding Merus' written submission, dated Jul. 16, 2014, 2 pages, 2 pages.
The alleged invention, dated Jul. 16, 2016, 79 pages.
Response to the Summons to oral proceedings, dated Jul. 16, 2014, 24 pages.
Acknowledgement of receipt in EP 1360287, dated Jul. 16, 2014, 2 pages (Jane Hollywood).
Acknowledgement of receipt in EP 1360287, dated Jul. 16, 2014, 2 pages (Groeneveld).
Acknowledgement of receipt in EP 1360287, dated Jul. 16, 2014, 3 pages (Andrew Bentham).
Joyner, "Gene targeting", dated Jul. 17, 2014, 196 pages.
Letter regarding references part 4, dated Jul. 17, 2014, 1 page.
Letter regarding references part 5, dated Jul. 17, 2014, 1 page.
Brief Communication in EP 02709544.7, dated Jul. 21, 2014, 1 page (Andrew Bentham).
Brief Communication in EP 02709544.7, dated Jul. 21, 2014, 1 page (Stephen, Robert John).
Brief Communication in EP 02709544.7, dated Jul. 21, 2014, 1 page (EP&C).
Brief Communication in EP 02709544.7 (Letter from the opponent 01 of Jul. 16, 2014 with non patent literature only), dated Jul. 21, 2014, 1 page (Andrew Bentham).
Brief Communication in EP 02709544.7, dated Jul. 25, 2014, 1 page (Thomas, Philip John Duval).
Brief Communication in EP 02709544.7, dated Jul. 25, 2014, 1 page (Stephen, Robert John).
Brief Communication in EP 02709544.7, dated Jul. 25, 2014, 1 page (EP&C).
Brief Communication in EP 02709544.7, dated Jul. 28, 2014, 1 page (Andrew Bentham).
Brief Communication in EP 02709544.7, dated Jul. 28, 2014, 1 page (Thomas, Philip John Duval).
Brief Communication in EP 02709544.7, dated Jul. 28, 2014, 1 page (Stephen, Robert John).
Submission in opposition proceedings in EP 1360287, dated Aug. 12, 2014, 2 pages.
Consolidated document list for EP 1360287, dated Aug. 12, 2014, 11 pages.
Letter regarding consolidated document list for EP 1360287, dated Aug. 12, 2014, 1 page.
Acknowledgement of receipt for EP 1360287, dated Aug. 12, 2014, 2 pages.
Brief Communication in EP 02709544.7, dated Aug. 19, 2014, 1 page (Stephen, Robert John).
Brief Communication in EP 02709544.7, dated Aug. 19, 2014, 1 page (EP&C).
Brief Communication in EP 02709544.7, dated Aug. 19, 2014, 1 page (Thomas, Philip John Duval).
Authorisation in EP 1360287, dated Aug. 12, 2014, 1 page.
Submission in opposition proceedings in EP 1360287, dated Aug. 20, 2014, 2 pages.
Acknowledgement of receipt for EP 1360287, dated Aug. 20, 2014, 1 page (Jane Hollywood).
Letter accompanying subsequently filed items in EP 02709544.7, dated Aug. 22, 2014, 1 page.
Murphy et al., "Mice with megabase humanization of their immunoglobulin genes generate antibodies as efficiently as normal mice," PNAS (2014) 111(14):5153-5158.
MacDonald et al., "Precise and in situ genetic humanization of 6 Mb of mouse immunoglobulin genes," 111(14):5147-5152.
Letter with scientific publications, dated Aug. 22, 2014, 2 pages (Olswang).
Acknowledgement of receipt for EP 1360287, dated Aug. 22, 2014, 1 page (Jane Hollywood).
Brief Communication in EP 02709544.7, dated Aug. 28, 2014, 1 page (EP&C).

(56) References Cited

OTHER PUBLICATIONS

Brief Communication in EP 02709544.7, dated Aug. 28, 2014, 1 page (Thomas, Philip John Duval).
Brief Communication in EP 02709544.7, dated Aug. 28, 2014, 1 page (Andrew Bentham).
Letter accompanying subsequently filed items in EP 02709544.7, dated Sep. 2, 2014, 1 page.
Submission in opposition proceedings in EP 1360287, dated Sep. 2, 2014, 2 pages.
Practising Certificate (Dr James Richard Cleland Whyte), dated Apr. 1, 2014, 1 page.
Letter regarding practicing certificate, dated Sep. 2, 2014, 1 page.
Wuerffel et al., "S—S synapsis during class switch recombination is promoted by distantly located transcriptional elements and activation-induced deaminase," Immunity (2007) 27:711-722.
Seidl et al., "An expressed neo$^r$ cassette provides required functions of the ly2b exon for class switching," International Immunology (1998) 10(11):1683-1692.
Kenter et al., "Three-dimensional architecture of the IgH locus facilitates class switch recombination," Ann N.Y. Acad Sci (2012) 1267:86-94.
Kitamura et al., "A B cell-deficient mouse by targeted disruption of the membrane exon of the immunoglobulinμ chain gene," Nature (1991) 350:423-426.
Scapini et al., "Myeloid cells, BAFF, and IFN-$_\gamma$ establish an inflammatory loop that exacerbates autoimmunity in Lyn-deficient mice," J Exp Med (2010) 207(8):1757-1773.
Geuijen, "Full length human IgG bispecific antibodies for cancer therapy," Merus-RABs and Bispecific Antibodies (2013) 33 pages.
Merus, "MeMo—the ingenious mouse for improved antibody therapeutics," Retrieved on Oct. 2011. Retrieved on www.merus.nl.
Merus, "MeMo transgenic mouse for improved antibody therapeutics," Retrieved on Sep. 2012. Retrieved on www.merus.nl.
Lee et al., "Complete humanization of the mouse immunoglobulin loci enables efficient therapeutic antibody discovery," Nature Biotechnology (2014) 32:356-363.
Second statement of Craig H. Bassing Ph.D., dated Sep. 2, 2014, 5 pages.
Written submissions in response to the summons to attend oral proceedings, dated Apr. 23, 2013, 24 pages.
Statement of Prof. Dr. Anthony Defranco, dated Sep. 2, 2014, 19 pages.
Letter regarding submissions made by opponents, dated Sep. 2, 2014, 8 pages.
Acknowledgement of receipt for EP 1360287, dated Sep. 2, 2014, 1 page (Jane Hollywood).
Acknowledgement of receipt for EP 1360287, dated Sep. 2, 2014, 1 page (Andrew Bentham).
Submission in opposition proceedings, dated Sep. 5, 2014, 2 pages.
Consolidated documents list for EP 1360287, dated Sep. 3, 2014, 12 pages.
Letter regarding consolidated documents, dated Sep. 5, 2014, 1 page.
Acknowledgement of receipt for EP 1360287, dated Sep. 5, 2014, 2 pages.
Brief Communication in EP 02709544.7, dated Sep. 8, 2014, 1 page (Stephen, Robert John).
Brief Communication in EP 02709544.7, dated Sep. 8, 2014, 1 page (Thomas, Philip John Duval).
Brief Communication in EP 02709544.7, dated Sep. 8, 2014, 1 page (EP&C).
Submission in opposition proceedings, dated Sep. 9, 2014, 2 pages.
Practising Certificate (Justin John Turner QC), dated Apr. 1, 2014, 1 page.
Letter regarding practicing certificate, dated Sep. 9, 2014, 1 page.
Acknowledgement of receipt for EP 1360287, dated Sep. 9, 2014, 2 pages.
Brief Communication in EP 02709544.7, dated Sep. 10, 2014, 1 page (Stephen, Robert John).
Brief Communication in EP 02709544.7, dated Sep. 10, 2014, 1 page (EP&C).
Brief Communication in EP 02709544.7, dated Sep. 10, 2014, 1 page (Thomas, Philip John Duval).
Letter accompanying subsequently filed items in EP 02709544.7, dated Sep. 11, 2014, 1 page.
Letter regarding attending oral proceedings, dated 11 Sep. 2014, 1 page.
Acknowledgement of receipt for EP 1360287, dated Sep. 11, 2014, 1 page.
Letter accompanying subsequently filed items in EP 02709544.7, dated Sep. 12, 2014, 1 page.
Brief Communication in EP 02709544.7, dated Sep. 15, 2014, 1 page (Stephen, Robert John).
Brief Communication in EP 02709544.7, dated Sep. 15, 2014, 1 page (EP&C).
Brief Communication in EP 02709544.7, dated Sep. 15, 2014, 1 page (Thomas, Philip John Duval).
Brief Communication in EP 02709544.7, dated Sep. 18, 2014, 1 page (Stephen, Robert John).
Brief Communication in EP 02709544.7, dated Sep. 18, 2014, 1 page (Bentham, Andrew).
Brief Communication in EP 02709544.7, dated Sep. 18, 2014, 1 page (Thomas, Philip John Duval).
Letter regarding Opposition proceedings, dated Sep. 15, 2014, 2 pages.
Acknowledgement of receipt for EP 1360287, dated Sep. 15, 2014, 1 page.
Information regarding oral proceedings, dated Sep. 18, 2014, 1 page.
Brief Communication in EP 02709544.7, dated Sep. 17, 2014, 1 page (Stephen, Robert John).
Brief Communication in EP 02709544.7, dated Sep. 17, 2014, 1 page (Andrew Bentham).
Brief Communication in EP 02709544.7, dated Sep. 17, 2014, 1 page (Thomas, Philip John Duval).
Letter regarding Notice of Appeal, dated Sep. 18, 2014, 2 pages.
Payment of fees and costs, dated Sep. 18, 2014, 1 page.
The communication for EP 02709544.7, dated Nov. 28, 2014,1 page.
Provision of the minutes in accordance with Rule 124(4) EPC, dated Nov. 28, 2014, 1 page.
Minutes of the oral proceedings before the opposition division, dated Nov. 28, 2014, 1 page.
Minutes of the oral proceedings before the opposition division sheet 2, dated Nov. 28, 2014, 1 page.
Decision revoking the European Patent (Art 101(3)(b) EPC), dated Nov. 28, 2014, 2 pages.
Revocation of the European Patent (Art 101(3)(b) EPC), dated Nov. 21, 2014, 1 page.
Appeal against the decision, dated Nov. 28, 2014, 2 pages.
Annex to the communication in EP 02709544.7, dated Nov. 28, 2014, 17 pages.
Facts and submissions in EP 02709544.7, dated Nov. 28, 2014, 25 pages.
Acknowledgement of receipt of the document 2331 in EP 02709544.7, dated Nov. 28, 2014, 1 page (Thomas, Philip John Duval).
Acknowledgement of receipt of the document 2331 in EP 02709544.7, dated Nov. 28, 2014, 1 page (EP&C).
Acknowledgement of receipt of the document 2331 in EP 02709544.7, dated Nov. 28, 2014, 1 page (Andrew Bentham).
Acknowledgement of receipt of the document 2331 in EP 02709544.7, dated Nov. 28, 2014, 1 page (Stephen, Robert John).
New sixth auxiliary request, dated Sep. 17, 2014, 11 pages.
New sixth auxiliary request (Annex), dated Sep. 17, 2014, 12 pages.
Advice of payment in EP 02709544.7, dated Apr. 12, 2014, 2 pages.
Letter accompanying subsequently filed items, dated Dec. 9, 2014, 1 page.
Acknowledgement of receipt for EP 1360287, dated Dec. 9, 2014, 1 page.
Commencement of proceedings before the Board of Appeal, dated Dec. 10, 2014, 4 pages.

(56) References Cited

OTHER PUBLICATIONS

Advice of payment in EP 02709544.7, dated Mar. 12, 2014, 2 pages (EP&C).
Appeal order for T2220/14-3.3.08, dated Dec. 12, 2014, 1 page.
Letter accompanying subsequently filed items, dated Dec. 23, 2016, 1 page.
Trial for 2015 from the Patents Court, dated Dec. 18, 2014, 15 pages.
Request for accelerated processing, dated Dec. 23, 2014, 5 pages.
Acknowledgement of receipt in EP 02709544.7, dated Dec. 9, 2014, 1 page.
Letter from Boards of Appeal for T2220/14-3.3.08, dated Jan. 9, 2015, 1 page (Stephen, Robert John).
Letter from Boards of Appeal for T2220/14-3.3.08, dated Jan. 9, 2015, 1 page (Thomas, Philip John Duval).
Letter from Boards of Appeal for T2220/14-3.3.08, dated Jan. 9, 2015, 1 page (EP&C).
Letter from Boards of Appeal for T2220/14-3.3.08, dated Jan. 20, 2015, 1 page (Andrew Bentham).
Letter accompanying subsequently filed items, dated Jan. 22, 2015, 1 page (Andrew Bentham).
Letter accompanying subsequently filed items, dated Jan. 22, 2015, 1 page (Jane Hollywood).
Letter in response to Communication, dated Jan. 22, 2015, 1 page (Andrew Bentham).
Letter in response to Communication from the Board of Appeal, dated Jan. 22, 2015, 1 page (Robert Stephen).
Acknowledgement of receipt in EP 02709544.7, dated Jan. 22, 2015, 1 page (Andrew Bentham).
Acknowledgement of receipt in EP 02709544.7, dated Jan. 22, 2015, 1 page (Jane Hollywood).
Letter from Boards of Appeal for T2220/14-3.3.08, dated Jan. 23, 2015, 1 page (Stephen, Robert John).
Letter from Boards of Appeal for T2220/14-3.3.08, dated Jan. 23, 2015, 1 page (Andrew Bentham).
Letter accompanying subsequently filed items, dated Jan. 30, 2015, 1 page (Andrew Bentham).
Letter accompanying subsequently filed items, dated Jan. 30, 2015, 1 page (Robert Stephen).
Explanation regarding documents disclosed in proceedings, dated Jan. 29, 2015, 2 pages.
Letter regarding acceleration of appeal proceedings, dated Jan. 30, 2015, 2 pages (EP&C).
Letter in response to the communication, dated Jan. 30, 2015, 2 pages (Robert Stephen).
Letter in response to the communication, dated Jan. 30, 2015, 2 pages (Philip Thomas).
Submission in opposition proceedings, dated Jan. 30, 2015, 2 pages (Philip Thomas).
Acknowledgement of receipt in EP 02709544.7, dated Jan. 30, 2015, 1 page (Olivier Brake).
Acknowledgement of receipt in EP 02709544.7, dated Jan. 30, 2015, 1 page (Stephen).
Acknowledgement of receipt in EP 02709544.7, dated Jan. 30, 2015, 1 page (Helen Stanbrook).
Letter from Boards of Appeal for T2220/14-3.3.08, dated Feb. 5, 2015, 3 pages.
Letter from Boards of Appeal for T2220/14-3.3.08, dated Feb. 5, 2015, 3 pages (with EP&C).
Letter accompanying subsequently filed items, dated Feb. 9, 2015, 1 page (Andrew Bentham).
Letter regarding acceleration of the proceedings, dated Feb. 9, 2015, 6 pages.
Acknowledgement of receipt in EP 02709544.7, dated Feb. 9, 2015, 1 page (Andrew Bentham).
Letter from Boards of Appeal for T2220/14-3.3.08, dated Feb. 13, 2015, 1 page (Stephen, Robert John).
Letter from Boards of Appeal for T2220/14-3.3.08, dated Feb. 13, 2015, 1 page (Thomas, Philip John Duval).
Letter from Boards of Appeal for T2220/14-3.3.08, dated Feb. 13, 2015, 1 page (EP&C).
Letter accompanying subsequently filed items, dated Feb. 15, 2015, 3 pages (Andrew Bentham).
Consolidated document list (D1-D155), dated Sep. 12, 2014, 12 pages.
Reichert, "Monoclonal antibodies in the clinic," Nature Biotechnology (2001) 19:819-822.
Jones et al., "Replacing the complementarity-determining regions in a human antibody with those from a mouse," Nature (1986) 321:522-525.
Hurle et al., "Protein engineering techniques for antibody humanization," Current Opinion in Biotechnology (1994) 5:428-433.
Xu et al., "Diversity in the CDR3 region of $V_H$ is sufficient for most antibody specificities," Immunity (2000) 13:37-45.
Figini et al., "Panning phage antibody libraries on cells: isolation of human fab fragments against ovarian carcinoma using guided selection[1]," Cancer Research (1998) 58:991-996.
Mortuza et al., "Immunoglobulin heavy-chain gene rearrangement in adult acute lymphoblastic leukemia reveals preferential usage of $J_H$-proximal variable gene segments," Blood (2001) 97(9):2716-2726.
Fujieda et al., "Multiple types of chimeric germ-line Ig heavy chain transcript in human B cells: evidence for trans-splicing of human Ig RNA ," J Immunol (1996) 157(8):3450-3459.
Shimizu et al., "Trans-splicing as a possible molecular mechanism for the multiple isotype expression of the immunoglobulin gene," J. Exp. Med (1991) 173:1385-1393.
Yancopoulos et al., "Preferential utilization of the most $J_H$-proximal $V_H$ gene segments in pre-B-cell lines," Nature (1984) 311:727-733.
Letter regarding grounds of Appeal, dated Feb. 15, 2015, 41 pages.
Main Request, dated Feb. 15, 2015, 5 pages.
Auxiliary Request 1, dated Feb. 15, 2015, 5 pages.
Auxiliary Request 2, dated Feb. 15, 2015, 5 pages.
Auxiliary Request 3, dated Feb. 15, 2015, 5 pages.
Auxiliary Request 4, dated Feb. 15, 2015, 5 pages.
Auxiliary Request 5, dated Feb. 15, 2015, 5 pages.
Auxiliary Request 6, dated Feb. 15, 2015, 5 pages.
Auxiliary Request 7, dated Feb. 15, 2015, 5 pages.
Auxiliary Request 8, dated Feb. 15, 2015, 5 pages.
Auxiliary Request 9, dated Feb. 15, 2015, 5 pages.
Auxiliary Request 10, dated Feb. 15, 2015, 5 pages.
Auxiliary Request 11, dated Feb. 15, 2015, 5 pages.
Auxiliary Request 12, dated Feb. 15, 2015, 5 pages.
Auxiliary Request 13, dated Feb. 15, 2015, 5 pages.
Auxiliary Request 14, dated Feb. 15, 2015, 5 pages.
Auxiliary Request 15, dated Feb. 15, 2015, 5 pages.
Auxiliary Request 16, dated Feb. 15, 2015, 5 pages.
Auxiliary Request 17, dated Feb. 15, 2015, 5 pages.
Auxiliary Request 18, dated Feb. 15, 2015, 6 pages.
Auxiliary Request 19, dated Feb. 15, 2015, 4 pages.
Auxiliary Request 20, dated Feb. 15, 2015, 5 pages.
Auxiliary Request 21, dated Feb. 15, 2015, 5 pages.
Amended claims (main request), dated Feb. 15, 2015, 8 pages.
Amended claims (Auxiliary request 1), dated Feb. 15, 2015, 8 pages.
Amended claims (Auxiliary request 2), dated Feb. 15, 2015, 8 pages.
Amended claims (Auxiliary request 3), dated Feb. 15, 2015, 8 pages.
Amended claims (Auxiliary request 4), dated Feb. 15, 2015, 8 pages.
Amended claims (Auxiliary request 5), dated Feb. 15, 2015, 8 pages.
Amended claims (Auxiliary request 6), dated Feb. 15, 2015, 8 pages.
Amended claims (Auxiliary request 7), dated Feb. 15, 2015, 8 pages.
Amended claims (Auxiliary request 8), dated Feb. 15, 2015, 8 pages.
Amended claims (Auxiliary request 9), dated Feb. 15, 2015, 8 pages.

(56) References Cited

OTHER PUBLICATIONS

Amended claims (Auxiliary request 10), dated Feb. 15, 2015, 8 pages.
Amended claims (Auxiliary request 11), dated Feb. 15, 2015, 8 pages.
Amended claims (Auxiliary request 12), dated Feb. 15, 2015, 12 pages.
Amended claims (Auxiliary request 13), dated Feb. 15, 2015, 13 pages.
Amended claims (Auxiliary request 14), dated Feb. 15, 2015, 11 pages.
Amended claims (Auxiliary request 15), dated Feb. 15, 2015, 12 pages.
Amended claims (Auxiliary request 16), dated Feb. 15, 2015, 12 pages.
Amended claims (Auxiliary request 17), dated Feb. 15, 2015, 12 pages.
Amended claims (Auxiliary request 18), dated Feb. 15, 2015, 13 pages.
Amended claims (Auxiliary request 19), dated Feb. 15, 2015, 11 pages.
Amended claims (Auxiliary request 20), dated Feb. 15, 2015, 11pages.
Amended claims (Auxiliary request 21), dated Feb. 15, 2015, 8 pages.
Acknowledgement of receipt in EP 02709544.7, dated Feb. 15, 2015, 1 page (James Nicholls).
Letter accompanying subsequently filed items, dated Feb. 20, 2015, 1 page (Jane Hollywood).
Letter accompanying subsequently filed items, dated Feb. 20, 2015, 1 page (EP&C).
Letter from Boards of Appeal for T2220/14-3.3.08, dated Feb. 20, 2015, 1 page (Stephen, Robert John).
Letter from Boards of Appeal for T2220/14-3.3.08, dated Feb. 20, 2015, 1 page (Thomas, Philip John Duval).
Letter from Boards of Appeal for T2220/14-3.3.08, dated Feb. 20, 2015, 1 page (EP&C).
Letter regarding prior art documents, dated Feb. 20, 2015, 2 pages (Robert Stephen).
Letter regarding representation of Merus, dated Feb. 20, 2015, 1 page.
Letter regarding representation of Merus, dated Feb. 20, 2015, 3 pages (Raphael Bosl).
Acknowledgement of receipt in EP 02709544.7, dated Feb. 20, 2015, 1 page (Jane Hollywood).
Acknowledgement of receipt in EP 02709544.7, dated Feb. 20, 2015, 1 page (Olivier Ter Brake).
Letter from Boards of Appeal for T2220/14-3.3.08, dated Feb. 24, 2015, 1 page (Thomas, Philip John Duval).
Letter from Boards of Appeal for T2220/14-3.3.08, dated Feb. 24, 2015, 1 page (Fritz Lahrtz).
Letter from Boards of Appeal for T2220/14-3.3.08, dated Feb. 25, 2015, 1 page (Andrew Bentham).
Letter from Boards of Appeal for T2220/14-3.3.08 (Opponent 1), dated Feb. 26, 2015, 1 page (Andrew Bentham).
Letter from Boards of Appeal for T2220/14-3.3.08 (Opponent 1), dated Feb. 26, 2015, 1 page (Thomas, Philip John Duval).
Letter from Boards of Appeal for T2220/14-3.3.08 (Opponent 2), dated Feb. 26, 2015, 1 page (EP&C).
Letter from Boards of Appeal for T2220/14-3.3.08 (Opponent 2), dated Feb. 26, 2015, 1 page (Andrew Bentham).
Letter from Boards of Appeal for T2220/14-3.3.08 (Opponent 2), dated Feb. 26, 2015, 1 page (Thomas, Philip John Duval).
Letter from Boards of Appeal for T2220/14-3.3.08 (Opponent 2), dated Feb. 26, 2015, 1 page (Stephen, Robert John).
Letter from Boards of Appeal for T2220/14-3.3.08 (form 3575), dated Feb. 26, 2015, 1 page (Andrew Bentham).
Letter from Boards of Appeal for T2220/14-3.3.08 (form 3575), dated Feb. 26, 2015, 1 page (Thomas, Philip John Duval).
Letter from Boards of Appeal for T2220/14-3.3.08 (form 3575), dated Feb. 26, 2015, 1 page (Stephen, Robert John).
Communication of amended entries for T2220/14-3.3.08, dated Feb. 26, 2015, 1 page (Fritz Lahrtz).
Letter accompanying subsequently filed items, dated Mar. 2, 2015, 1 page (Fritz Lahrtz).
Letter accompanying subsequently filed items, dated Mar. 2, 2015, 1 page (Andrew Bentham).
Communication of the Board of Appeal for T2220/14-3.3.08, dated Mar. 2, 2015, 10 pages (Andrew Bentham).
Further to the Communication of the Board of Appeal, dated Mar. 2, 2015, 1 page (Fritz Lahrtz).
Letter regarding communication, dated Mar. 2, 2015, 1 page (Andrew Bentham).
Acknowledgement of receipt in EP 02709544.7, dated Mar. 2, 2015, 1 page (Verena Behre).
Acknowledgement of receipt in EP 02709544.7, dated Mar. 2, 2015, 1 page (Andrew Bentham).
Letter confirming proposed dates, dated Mar. 4, 2015, 2 pages (Philip Thomas).
Letter accompanying subsequently filed items, dated Mar. 9, 2015, 1 page (Robert Stephen).
Letter from Boards of Appeal for T2220/14-3.3.08 (Opponent 2), dated Mar. 9, 2015, 1 page (Andrew Bentham).
Letter from Boards of Appeal for T2220/14-3.3.08 (Opponent 2), dated Mar. 9, 2015, 1 page (Thomas, Philip John Duval).
Letter from Boards of Appeal for T2220/14-3.3.08 (Opponent 2), dated Mar. 9, 2015, 1 page (Stephen, Robert John).
Letter from Boards of Appeal for T2220/14-3.3.08 (Patent proprietor), dated Mar. 9, 2015, 1 page (Stephen, Robert John).
Letter from Boards of Appeal for T2220/14-3.3.08 (Patent proprietor), dated Mar. 9, 2015, 1 page (Thomas, Philip John Duval).
Letter from Boards of Appeal for T2220/14-3.3.08 (Patent proprietor), dated Mar. 9, 2015, 1 page (Fritz Lahrtz).
Letter from Boards of Appeal for T2220/14-3.3.08 (Opponent 3), dated Mar. 9, 2015, 1 page (Andrew Bentham).
Letter from Boards of Appeal for T2220/14-3.3.08 (Opponent 3), dated Mar. 9, 2015, 1 page (Fritz Lahrtz).
Letter from Boards of Appeal for T2220/14-3.3.08 (Opponent 3), dated Mar. 9, 2015, 1 page (Stephen, Robert John).
Letter in response to the EPO communication, dated Mar. 9, 2015, 1 page (Robert Stephen).
Acknowledgement of receipt in EP 02709544.7, dated Mar. 9, 2015, 1 page (Stephen).
Letter from Boards of Appeal for T2220/14-3.3.08 (Opponent 1), dated Mar. 16, 2015, 1 page (Andrew Bentham).
Letter from Boards of Appeal for T2220/14-3.3.08 (Opponent 1), dated Mar. 16, 2015, 1 page (Thomas, Philip John Duval).
Letter from Boards of Appeal for T2220/14-3.3.08 (Opponent 1), dated Mar. 16, 2015, 1 page (Fritz Lahrtz).
Authorisation for EP02709544.7, dated Mar. 8, 2015, 1 page.
Letter regarding power of attorney, dated Mar. 19, 2015, 1 page.
Letter accompanying subsequently filed items, dated Mar. 26, 2015, 2 pages (Andrew Bentham).
Letter from Boards of Appeal for T2220/14-3.3.08 (Opponent 2), dated Mar. 26, 2015, 1 page (Andrew Bentham).
Letter from Boards of Appeal for T2220/14-3.3.08 (Opponent 2), dated Mar. 26, 2015, 1 page (Thomas, Philip John Duval).
Letter from Boards of Appeal for T2220/14-3.3.08 (Opponent 2), dated Mar. 26, 2015, 1 page (Stephen, Robert John).
Letter regarding typographical errors, dated Mar. 26, 2015, 2 pages.
Auxiliary Request 15, dated Mar. 26, 2015, 5 pages.
Auxiliary Request 11, dated Mar. 26, 2015, 5 pages.
Auxiliary Request 10, dated Mar. 26, 2015, 5 pages.
Auxiliary Request 6, dated Mar. 26, 2015, 5 pages.
Auxiliary Request 1, dated Mar. 26, 2015, 5 pages.
Amend claims (Auxiliary Request 1), dated Mar. 26, 2015, 8 pages.
Amend claims (Auxiliary Request 6), dated Mar. 26, 2015, 8 pages.
Amend claims (Auxiliary Request 10), dated Mar. 26, 2015, 8 pages.
Amend claims (Auxiliary Request 11), dated Mar. 26, 2015, 8 pages.

(56) References Cited

OTHER PUBLICATIONS

Amend claims (Auxiliary Request 15), dated Mar. 26, 2015, 8 pages.
Acknowledgement of receipt in EP 02709544.7, dated Mar. 26, 2015, 2 pages (Andrew Bentham).
Letter from Boards of Appeal for T2220/14-3.3.08 (Patent proprietor), dated Apr. 1, 2015, 1 page (Stephen, Robert John).
Letter from Boards of Appeal for T2220/14-3.3.08 (Patent proprietor), dated Apr. 1, 2015, 1 page (Thomas, Philip John Duval).
Letter from Boards of Appeal for T2220/14-3.3.08 (Patent proprietor), dated Apr. 1, 2015, 1 page (Fritz Lahrtz).
Letter accompanying subsequently filed items, dated Jul. 2, 2015, 2 pages (Robert Stephen).
Rule 80 EPC document, dated Jul. 2, 2015, 8 pages.
Submission in response to EPO communication, dated Mar. 23, 2015, 3 pages.
Response to the examination report, dated Apr. 2, 2015, 7 pages (Andrew Bentham).
Opinion & Order, dated Nov. 21, 2014, 59 pages.
Document regarding lack of sufficiency, dated Jul. 2, 2015, 1 page.
Document regarding application documents in application 11728509.8, dated Mar. 4, 2015, 6 pages.
Document regarding application documents in application 10010741.6, dated May 30, 2014, 2 pages.
Submission in response to the third party observations, dated Jul. 1, 2014, 5 pages.
Letter regarding response to application, dated Jun. 23, 2015, 4 pages.
Bruggemann, "The preparation of human antibodies from mice harbouring human immunoglobulin loci," Transgenic animals: generation and use (1997) pp. 397-402.
Dougier et al., "Interallelic class switch recombination can reverse allelic exclusion and allow trans-complementation of an IgH locus switching defect," Eur J Immunol (2006) 36:2181-2191.
Gerstein et al., "Isotype switching of an immunoglobulin heavy chain transgene occurs by DNA recombination between different chromosomes," Cell (1990) 63:537-548.
Decision of technical board of appeal, dated Feb. 3, 2015, 21 pages.
Letter regarding grounds of appeal, dated Jul. 2, 2015, 1 page (Robert Stephen).
Acknowledgement of receipt in EP 02709544.7, dated Jul. 2, 2015, 2 pages.
Request and admissibility, dated Jul. 2, 2015, 64 pages.
Letter regarding a response to the grounds of appeal, dated Jul. 2, 2015, 19 pages (Philip Thomas).
Letter in response to Patentee's grounds of appeal, dated Jul. 2, 2015, 85 pages (Fritz Lahrtz).
Letter in response to Patentee's grounds of appeal, dated Jul. 2, 2015, 44 pages (Philip Thomas).
Letter from Boards of Appeal for T2220/14-3.3.08 (Opponent 1), dated Jul. 8, 2015, 1 page (Andrew Bentham).
Letter from Boards of Appeal for T2220/14-3.3.08 (Opponent 1), dated Jul. 8, 2015, 1 page (Thomas, Philip John Duval).
Letter from Boards of Appeal for T2220/14-3.3.08 (Opponent 1), dated Jul. 8, 2015, 1 page (Fritz Lahrtz).
Letter from Boards of Appeal for T2220/14-3.3.08 (Opponent 3), dated Jul. 8, 2015, 1 page (Andrew Bentham).
Letter from Boards of Appeal for T2220/14-3.3.08 (Opponent 3), dated Jul. 8, 2015, 1 page (Fritz Lahrtz).
Letter from Boards of Appeal for T2220/14-3.3.08 (Opponent 3), dated Jul. 8, 2015, 1 page (Stephen, Robert John).
Letter from Boards of Appeal for T2220/14-3.3.08 (Opponent 2), dated Jul. 9, 2015, 1 page (Andrew Bentham).
Letter from Boards of Appeal for T2220/14-3.3.08 (Opponent 2), dated Jul. 9, 2015, 1 page (Thomas, Philip John Duval).
Letter from Boards of Appeal for T2220/14-3.3.08 (Opponent 2), dated Jul. 9, 2015, 1 page (Stephen, Robert John).
Letter from Boards of Appeal for T2220/14-3.3.08 (Patent proprietor), dated Jul. 14, 2015, 1 page (Andrew Bentham).
Letter from Boards of Appeal for T2220/14-3.3.08 (Patent proprietor), dated Jul. 14, 2015, 1 page (Fritz Lahrtz).
Letter from Boards of Appeal for T2220/14-3.3.08 (Patent proprietor), dated Jul. 14, 2015, 1 page (Stephen, Robert John).
Letter accompanying subsequently filed items, dated Aug. 3, 2015, 1 page (Andrew Bentham).
Consolidated document list for appeal (D1-D168), dated Aug. 3, 2015, 14 pages.
Letter in response to grounds of appeal, dated Aug. 3, 2015, 1 page.
Acknowledgement of receipt in EP 02709544.7, dated Aug. 3, 2015, 1 page.
Letter from Boards of Appeal for T2220/14-3.3.08 (Patent proprietor), dated Aug. 7, 2015, 1 page (Stephen, Robert John ).
Letter from Boards of Appeal for T2220/14-3.3.08 (Patent proprietor), dated Aug. 7, 2015, 1 page (Thomas, Philip John Duval).
Letter from Boards of Appeal for T2220/14-3.3.08 (Patent proprietor), dated Aug. 7, 2015, 1 page (Fritz Lahrtz).
Document regarding oral proceedings, dated Aug. 13, 2015, 1 page.
Summons to oral proceedings pursuant to Rule 115(1) EPC, dated Aug. 14, 2015, 26 pages.
Acknowledgement of receipt of the document 3011, dated Aug. 17, 2015, 1 page (Fritz Lahrtz).
Tracking information, dated Aug. 17, 2015, 1 page.
Letter regarding transfer of all cases, dated Aug. 20, 2015, 2 pages.
Advice of delivery, dated Aug. 24, 2015, 2 pages (Thomas).
Letter accompanying subsequently filed items, dated Aug. 27, 2015, 1 page.
Acknowledgement of receipt of the document 3011, dated Aug. 14, 2015, 1 page.
Acknowledgement of receipt in EP 02709544.7, dated Aug. 27, 2015, 1 page.
Letter from Boards of Appeal for T2220/14-3.3.08 (Board's communication), dated Aug. 31, 2015, 1 page (Andrew Bentham).
Letter from Boards of Appeal for T2220/14-3.3.08 (Opponent 3 and Board's communication), dated Aug. 31, 2015, 1 page (Fritz Lahrtz).
Letter from Boards of Appeal for T2220/14-3.3.08 (Opponent 3 and Board's communication), dated Aug. 31, 2015, 1 page (Stephen, Robert John).
Acknowledgement of receipt of the document 3011, dated Aug. 14, 2015, 1 page (Stephen, Robert John).
Letter in relation to appeal proceedings, dated Sep. 8, 2015, 4 pages.
Velocimmune history narrative- from Drew's memory, dated Sep. 8, 2015, 6 pages.
Letter in relation to Appeal proceedings, dated Sep. 16, 2015, 2 pages.
Letter regarding representative of opponent 1, dated Sep. 21, 2015, 1 page.
Communication of the Board of Appeal, dated Sep. 22, 2015, 1 page (Andrew Bentham).
Communication of the Board of Appeal, dated Sep. 22, 2015, 1 page (Potter Clarkson LLP).
Communication of the Board of Appeal, dated Sep. 22, 2015, 1 page (Fritz Lahrtz).
Communication of the Board of Appeal, dated Sep. 22, 2015, 1 page (Stephen, Robert John).
Letter accompanying subsequently filed items, dated Sep. 25, 2015, 2 pages (Andrew Bentham).
Letter from Boards of Appeal for T2220/14-3.3.08 (Opponent 2), dated Sep. 25, 2015, 1 page (Andrew Bentham).
Letter from Boards of Appeal for T2220/14-3.3.08 (Opponent 2), dated Sep. 25, 2015, 1 page (Potter Clarkson LLP).
Letter from Boards of Appeal for T2220/14-3.3.08 (Opponent 2), dated Sep. 25, 2015, 1 page (Stephen, Robert John).
Letter in relation to Appeal Proceedings, dated Sep. 25, 2015, 19 pages.
Letter in response to the summons to oral proceedings pursuant to Rule 115(1) EPC, dated Sep. 25, 2015, 9 pages.
Main Request, dated Sep. 25, 2015, 5 pages.
Auxiliary Request 4, dated Sep. 25, 2015, 5 pages.
Auxiliary Request 5, dated Sep. 25, 2015, 5 pages.
Auxiliary Request 6, dated Sep. 25, 2015, 5 pages.
Auxiliary Request 8, dated Sep. 25, 2015, 5 pages.
Auxiliary Request 9, dated Sep. 25, 2015, 5 pages.

(56) References Cited

OTHER PUBLICATIONS

Auxiliary Request 10, dated Sep. 25, 2015, 5 pages.
Auxiliary Request 11, dated Sep. 25, 2015, 5 pages.
Auxiliary Request 7, dated Sep. 25, 2015, 5 pages.
Auxiliary Request 1, dated Sep. 25, 2015, 5 pages.
Auxiliary Request 2, dated Sep. 25, 2015, 5 pages.
Auxiliary Request 3, dated Sep. 25, 2015, 5 pages.
Amend claims (Main Request), dated Sep. 25, 2015, 8 pages.
Amend claims (Auxiliary Request 1), dated Sep. 25, 2015, 8 pages.
Amend claims (Auxiliary Request 2), dated Sep. 25, 2015, 8 pages.
Amend claims (Auxiliary Request 4), dated Sep. 25, 2015, 8 pages.
Amend claims (Auxiliary Request 5), dated Sep. 25, 2015, 8 pages.
Amend claims (Auxiliary Request 6), dated Sep. 25, 2015, 8 pages.
Amend claims (Auxiliary Request 7), dated Sep. 25, 2015, 8 pages.
Amend claims (Auxiliary Request 8), dated Sep. 25, 2015, 8 pages.
Amend claims (Auxiliary Request 9), dated Sep. 25, 2015, 8 pages.
Amend claims (Auxiliary Request 11), dated Sep. 25, 2015, 8 pages.
Amend claims (Auxiliary Request 10), dated Sep. 25, 2015, 8 pages.
Acknowledgement of receipt in EP 02709544.7, dated Sep. 25, 2015, 2 pages.
Letter from Boards of Appeal for T2220/14-3.3.08 (Patent proprietor), dated Oct. 1, 2015, 1 page (Stephen, Robert John).
Letter from Boards of Appeal for T2220/14-3.3.08 (Patent proprietor), dated Oct. 1, 2015, 1 page (Potter Clarkson Llp).
Letter from Boards of Appeal for T2220/14-3.3.08 (Patent proprietor), dated Oct. 1, 2015, 1 page (Fritz Lahrtz).
Further to the Submission of Sep. 21, 2015, dated Oct. 1, 2015, 3 pages.
Communication of the Board of Appeal, dated Oct. 2, 2015, 5 pages (Andrew Bentham).
Letter in relation to appeal, dated Oct. 5, 2015, 2 pages.
Letter from Boards of Appeal for T2220/14-3.3.08 (Patent proprietor), dated Oct. 9, 2015, 1 page (Stephen, Robert John).
Letter from Boards of Appeal for T2220/14-3.3.08 (Patent proprietor), dated Oct. 9, 2015, 1 page (Potter Clarkson LLP).
Letter from Boards of Appeal for T2220/14-3.3.08 (Patent proprietor), dated Oct. 9, 2015, 1 page (Fritz Lahrtz).
Letter accompanying subsequently filed items, dated Oct. 12, 2015, 1 page.
Letter from Boards of Appeal for T2220/14-3.3.08 (Opponent 2), dated Oct. 12, 2015, 1 page (Andrew Bentham).
Letter from Boards of Appeal for T2220/14-3.3.08 (Opponent 2), dated Oct. 12, 2015, 1 page (Potter Clarkson Llp).
Letter from Boards of Appeal for T2220/14-3.3.08 (Opponent 2), dated Oct. 12, 2015, 1 page (Stephen, Robert John).
Letter regarding issue of insufficiency, dated Oct. 9, 2015, 1 page.
Letter in relation to appeal, dated Oct. 12, 2015, 3 pages (Andrew Bentham).
Consolidated document list, dated Oct. 12, 2015, 13 pages.
Acknowledgement of receipt in EP 02709544.7, dated Oct. 12, 2015, 1 page.
Letter regarding Oral Proceedings, dated Oct. 13, 2015, 1 page (Fritz Lahrtz).
Letter from Boards of Appeal for T2220/14-3.3.08 (Opponent 1), dated Oct. 16, 2015, 6 pages (Andrew Bentham).
Letter from Boards of Appeal for T2220/14-3.3.08 (Patent Proprietor), dated Oct. 16, 2015, 6 pages (Stephen, Robert John).
Letter from Boards of Appeal for T2220/14-3.3.08 (Opponent 2), dated Oct. 16, 2015, 1 page (Andrew Bentham).
Letter from Boards of Appeal for T2220/14-3.3.08 (Opponent 2), dated Oct. 16, 2015, 1 page (Potter Clarkson Llp).
Letter from Boards of Appeal for T2220/14-3.3.08 (Opponent 2), dated Oct. 16, 2015, 1 page (Stephen, Robert John).
Letter in relation to Appeal proceedings, dated Oct. 22, 2015, 5 pages.
Notice of electronic filing, dated Oct. 25, 2015, 1 page.
Memorandum decision and order, dated Oct. 25, 2015, 11 pages.
Letter regarding decision in US proceedings, dated Oct. 25, 2015, 2 pages.
Letter from Boards of Appeal for T2220/14-3.3.08 (Opponent 2), dated Oct. 26, 2015, 5 pages (Andrew Bentham).
Letter enclosing D173 and D174, dated Oct. 26, 2015, 1 page.
Letter from Boards of Appeal for T2220/14-3.3.08 (Opponent 1), dated Oct. 27, 2015, 1 page (Andrew Bentham).
Letter from Boards of Appeal for T2220/14-3.3.08 (Opponent 1), dated Oct. 27, 2015, 1 page (Potter Clarkson LLP).
Letter from Boards of Appeal for T2220/14-3.3.08 (Opponent 1), dated Oct. 27, 2015, 1 page (Fritz Lahrtz).
Letter from Boards of Appeal for T2220/14-3.3.08 (Patent Proprietor), dated Oct. 28, 2015, 6 pages (Stephen, Robert John).
Letter in relation to appeal, dated Oct. 23, 2015, 3 pages (Andrew Bentham).
Oral proceedings notice, dated Oct. 30, 2015, 1 page.
Acknowledgement of receipt of the document 3011, dated Oct. 30, 2015, 1 page (Potter Clarkson LLP).
Acknowledgement of receipt of the document 3011, dated Oct. 30, 2015, 1 page (Fritz Lahrtz).
Acknowledgement of receipt of the document 3011, dated Oct. 30, 2015, 1 page (Stephen, Robert John).
Opinion and order, dated Nov. 2, 2015, 114 pages.
Letter regarding decision of the court (D175), dated Nov. 3, 2015, 41 pages.
Letter accompanying subsequently filed items, dated Nov. 4, 2015, 1 page (Andrew Bentham).
Summons to oral proceedings pursuant to Rule 115(1) EPC, dated Nov. 4, 2015, 12 pages.
Letter in preparation of the fourth day of oral proceedings, dated Nov. 4, 2015, 6 pages.
Letter regarding amendments, dated Nov. 4, 2015, 2 pages.
First Auxiliary Request, dated Nov. 3, 2015, 2 pages.
Main request, dated Oct. 28, 2015, 4 pages.
New first auxiliary request, dated Nov. 3, 2015, 5 pages.
Acknowledgement of receipt of the document 3011, dated Nov. 4, 2015, 2 pages (Andrew Bentham).
Letter from Boards of Appeal for T2220/14-3.3.08 (Opponent 2), dated Nov. 5, 2015, 5 pages (Andrew Bentham).
Letter from Boards of Appeal for T2220/14-3.3.08 (Patent proprietor), dated Nov. 5, 2015, 6 pages (Stephen, Robert John).
Tracking information, dated Nov. 4, 2015, 1 page.
Acknowledgement of receipt of the document 3011, dated Nov. 5, 2015, 1 page (Fritz Lahrtz).
Letter from Boards of Appeal for T2220/14-3.3.08 (Opponent 2), dated Nov. 6, 2015, 3 pages (Andrew Bentham).
Minutes of oral proceedings, dated Nov. 9, 2015, 11 pages.
Main request, dated Nov. 9, 2015, 5 pages.
Description of EP 1360287, date Nov. 9, 2015, 24 pages.
Advice of delivery, dated Nov. 16, 2015, 2 pages.
Minutes of the oral proceedings, dated Nov. 18, 2015, 4 pages.
Request for correction of minutes, dated Nov. 25, 2015, 2 pages.
Letter from Boards of Appeal for T2220/14-3.3.08 (Opponent 2), dated Dec. 3, 2015, 1 pages (Andrew Bentham).
Letter from Boards of Appeal for T2220/14-3.3.08 (Opponent 2), dated Dec. 3, 2015, 1 page (Potter Clarkson LLP).
Letter from Boards of Appeal for T2220/14-3.3.08 (Opponent 2), dated Dec. 3, 2015, 1 page (Stephen, Robert John).
Communication of the Board of Appeal, dated Dec. 4, 2015, 7 pages.
Datasheet for the decision, dated Nov. 9, 2015, 83 pages.
Decision, dated Mar. 11, 2016, 1 page (Andrew Bentham).
Decision, dated Mar. 11, 2016, 1 page (Potter Clarkson LLP).
Decision, dated Mar. 11, 2016, 1 page (Fritz Lahrtz).
Decision, dated Mar. 11, 2016, 1 page (Stephen, Robert John).
Tracking information, dated Mar. 11, 2016, 1 page (Fritz Lahrtz).
Acknowledgement of receipt of the document 3032, dated Mar. 14, 2016, 1 page (Fritz Lahrtz).
Acknowledgement of receipt of the document 3032, dated Mar. 14, 2016, 1 page (Stephen, Robert John).
Advice of delivery, dated Mar. 16, 2016, 2 pages.
Letter accompanying subsequently filed items, dated Mar. 21, 2016, 1 page (James R Nicholls).
Acknowledgement of receipt of the document 3032, dated Mar. 11, 2016, 1 page (Andrew Bentham).

(56) References Cited

OTHER PUBLICATIONS

Acknowledgement of receipt in EP 02709544.7, dated Mar. 21, 2016, 1 page (James Nicholls).
Notification of the communication, dated May 24, 2016, 1 page.
Communication pursuant to Article 101(1) and Rule 81(2) to (3) EPC, dated May 24, 2016, 2 page (Andrew Bentham).
Application documents, dated May 24, 2016, 1 page.
Request for recordal, dated May 30, 2016, 1 page.
Deed of conversion and amendment of the articles of association, dated May 19, 2016, 53 pages.
Payment of fees and expenses, dated May 30, 2016, 1 page.
Communication of amended entries in register of European patents, dated Jun. 20, 2016, 2 pages (Fritz Lahrtz).
Brief Communication, dated Jun. 20, 2016, 3 pages (Andrew Bentham).
Brief Communication, dated Jun. 20, 2016, 3 pages (Potter Clarkson LLP).
Brief Communication, dated Jun. 20, 2016, 3 pages (Stephen, Robert John).
Submission in opposition proceedings, dated Sep. 19, 2016, 2 pages.
Comments on amendments (opponent 1), dated Sep. 19, 2016, 4 pages.
Response to communication, dated May 24, 2016, 1 page (Robert Stephen).
Acknowledgement of receipt in EP 02709544.7, dated Sep. 19, 2016, 2 pages.
Brief communication, dated Sep. 23, 2016, 1 page (Andrew Bentham).
Brief communication, dated Sep. 23, 2016, 1 page (Fritz Lahrtz).
Brief communication, dated Sep. 23, 2016, 1 page (Potter Clarkson LLP).
Submission in opposition proceedings, dated Sep. 30, 2016, 2 pages (James Nicholls).
Description of U.S. Appl. No. 09/784,859, dated Sep. 30, 2016, 21 pages.
Response to the Communication, dated Sep. 30, 2016, 2 pages.
Acknowledgement of receipt in Ep 02709544.7, dated Sep. 30, 2016, 2 pages.
Submission in opposition proceedings, dated Oct. 3, 2016, 1 page (Philip Thomas).
Letter in response to communication, dated Oct. 3, 2016, 1 page (Philip Thomas).
Acknowledgement of receipt in EP 02709544.7, dated Oct. 3, 2016, 1 page (Rebecca Hamilton).
Brief communication, dated Oct. 7, 2016, 1 page (Stephen, Robert John).
Brief communication (enclosed letter from proprietor of the patent), dated Oct. 7, 2016, 1 page (Fritz Lahrtz).
Brief communication, dated Oct. 7, 2016, 1 page (Potter Clarkson LLP).
Brief communication, dated Oct. 7, 2016, 1 page (Andrew Bentham).
Brief communication (enclosed letter from opponent 3), dated Oct. 7, 2016, 1 page (Stephen, Robert John).
Brief communication (enclosed letter from opponent 3), dated Oct. 7, 2016, 1 page (Fritz Lahrtz).
Communication, dated Oct. 14, 2016, 1 page.
Communication pursuant to Article 101(1) and Rule 82(1) EPC, dated Oct. 14, 2016, 2 pages.
Information of the oral proceedings, dated Oct. 28, 2016, 1 page.
Decision on opposition, dated Sep. 7, 2016, 50 pages.
Abedi et al., "Green fluorescent protein as a scaffold for intracellular presentation of peptides," Nucleic Acids Res (1998) 26(2):623-630.
Abidor et al., "Studies of cell pellets: II. Osmotic properties, electroporation, and related phenomena: membrane interactions," Biophysical Joural (1994) 67:427-435.
Akerstrom et al., "On the interaction between single chain Fv antibodies and bacterial immunoglobulin-binding proteins," J Immunol Methods (1994) 177:151-163.
Alber et al., "Nucleotide sequence of the triose phosphate isomerase gene of *Saccharomyces cerevisiae*," J Mol Appl Genet (1982) 1(5):419-434.
Al-Lazikani et al., "Standard conformations for the Canonical structures of immunoglobulins," J Mol Biol (1997) 273:927-948.
Allen, "Ligand-targeted therapeutics in anticancer therapy," Nat Rev Cancer (2002) 2(10):750-763.
Almagro et al., "Humanization of antibodies," Front Biosci (2008) 13:1619-1633.
Ammerer, "Expression of Genes in Yeast Using the ADCI Promoter," Methods in Enzymology (1983) 101:192-201.
Antica et al., "Thymic Stem Cells in Mouse Bone Marrow," Blood (1994) 84(1):111-117.
Appel et al., "A new generation of information retrieval tools for biologists: the example of the ExPASy WWW server," Trends Biochem Sci (1994) 19(6):258-260.
Approved judgment, dated Feb. 1, 2016, 87 pages.
Arai et al., "Antibody responses induced by immunization with a Japanese rabies vaccine determined by neutralization test and enzyme-linked immunosorbent assay," Vaccine (2002) 20(19-20):2448-2453.
Aramda et al., "Nuclear Hormone Receptors and Gene Expression," Physiol Rev (2001) 81(3):1269-1304.
Arnold et al., "Development of B-1 cells: segregation of phosphatidyl choline-specific B cells to the B-1 population occurs after immunoglobulin gene expression," J Exp Med (1994) 179(5): 1585-1595.
Attaelmannan et al., "Understanding and identifying monoclonal gammopathies," Clin Chem (2000) 46(8 Pt 2):1230-1238.
Atwell et al., "Stable Heterodimers from Remodeling the Domain Interface of a Homodimer using a Phage Display Library," J Mol Biol (1997) 270:26-35.
Aucouturier et al., "Monoclonal Ig L chain and L chain V domain fragment crystallization in myeloma-associated Fanconi's syndrome," J Immunol (1993) 150(8) 3561-3568.
Auerbach et al., "Angiogenesis Assays: A Critical Overview," Clin Chem (2003) 49(1):32-40.
Babcook et al., "A novel strategy for generating monoclonal antibodies from single, isolated lymphocytes producing antibodies of defined specificities," Proc Natl Acad Sci USA (1996) 93:7843-7848.
Banchereau et al., "Long-term human B cell lines dependent on interleukin-4 and antibody to CD40," Science (1991) 251(4989):70-72.
Barbas et al., "Assembly of combinatorial antibody libraries on phage surfaces: The gene III site," Proc Natl Acad Sci U S A (1991) 88(18):7978-7982.
Barnes et al., "Characterization of the Stability of Recombinant Protein Production in the GS-NS0 Expression System," Biotechnol Bioeng (2001) 73(4):261-270.
BD Biosciences, "CD Marker Handbook," (2010) 4 pages.
Bebbington et al., "High-level expression of a recombinant antibody from myeloma cells using a glutamine synthetase gene as an amplifiable selectable marker," Biotechnology (N Y) (1992) 10(2):169-175.
Bell et al., "Insulators and boundaries: versatile regulatory elements in the eukaryotic genome," Science (2001) 291(5503):447-450.
Bengig, "The production of foreign proteins in mammalian cells," Genet Eng (1988) 7:91-127.
Bertagnolli et al., "IL-12 augments antigen-dependent proliferation of activation lymphocytes," J Immunol (1992) 149:3778-3783.
Bertagnolli et al., "IL-4-Supported Induction of Cytolytic T Lymphocytes Requires IL-2 and IL-6," Cell Immunol (1991) 133:327-341.
Bertagnolli et al., "IL-7 supports the generation of cytotoxic T lymphocytes from thymocytes. Multiple lymphokines required for proliferation and cytotoxicity," J Immunol (1990) 145:1706-1712.
Betz et al., "Elements regulating somatic hypermutation of an immunoglobulin kappa gene: critical role for the intron enhancer/matrix attachment region," Cell (1994) 77(2):239-248 (Abstract).
Bhardwaj et al., "Influenza virus-infected dendritic cells stimulate strong proliferative and cytolytic responses from human CD8+ T cells," J Clin Invest (1994) 94(2):797-807.
Bins et al., "A rapid and potent DNA vaccination strategy defined by in vivo monitoring of antigen expression," Nature Medicine (2005) 11(8):899-904.

(56) References Cited

OTHER PUBLICATIONS

Binz et al., "Designing Repeat Proteins: Well-expressed, Soluble and Stable Proteins from Combinatorial Libraries of Consensus Ankyrin Repeat Proteins," J Mol Biol (2003) 332:489-503.
Birchmeier et al., "Met, metastasis, motility and more," Nat Rev Mol Cell Biol (2003) 4(12):915-925.
Bitter et al.,"Expression and secretion vectors for yeast," Methods Enzymol (1987) 153:516-544.
Bitter, "Heterologous gene expression in yeast," Methods Enzymol (1987) 152:673-684.
Bode et al., "The Hitchhiking principle: Optimizing episomal vectors for the use in gene therapy and biotechnology," Gene Ther Mol Biol (2001) 6:33-46.
Boder et al., "Yeast surface display for screening combinatorial polypeptide libraries," Nat Biotechnol (1997) 15(6):553-557.
Boel et al., "Functional human monoclonal antibodies of all isotypes constructed from phage display library-derived single-chain Fv antibody fragments," J Immunol Methods (2000) 239(1-2):153-166.
Bowman et al., "The cloning of CD70 and its identification as the ligand for CD27," J Immunol (1994) 152:1756-1761.
Brady et al., "Rapid specific amplification of rat antibody cDNA from nine hybridomas in the presence of myeloma light chains," J Immunol Methods (2006) 315(1-2):61-67.
Brezinsky et al., "A simple method for enriching populations of transfected CHO cells for cells of higher specific productivity," J Immunol Methods (2003) 277(1-2):141-155.
Brink et al., "Developing efficient strategies for the generation of transgenic cattle which produce biopharmaceuticals in milk," Theriogenology (2000) 53(1):139-148.
Broach et al., "Transformation in yeast: development of a hybrid cloning vector and isolation of the CAN1 gene," Gene (1979) 8(1):121-133.
Burger et al., "An integrated strategy for the process development of a recombinant antibody-cytokine fusion protein expressed in BHK cells," Appl Microbiol Biotechnol (1999) 52(3):345-353.
Burioni et al., Nonneutralizing human antibody fragments against hepatitis C virus E2 glycoprotein modulate neutralization of binding activity of human recombinant Fabs, Virology (2001) 288:29-335.
Campbell et al., "Sheep cloned by nuclear transfer from a cultured cell line," Nature (1996) 380(6569):64-66.
Cao et al., "Neutralizing monoclonal antibodies to hepatocyte growth factor/scatter factor (HGF/SF) display antitumor activity in animal models," Proc Natl Acad Sci U S A (2001) 98(13):7443-7448.
Carmack et al. "Influence of a V kappa 8 L chain transgene on endogenous rearrangements and the immune response to the HA(Sb) determinant on influenza virus," J Immunol (1991) 147(6):2024-2033.
Carter et al. "Humanization of an anti-p185HER2 antibody for human cancer therapy," Proc Natl Acad Sci U S A (1992) 89(10)4285-4289.
Carter, "Bispecific human IgG by design" J Immunol Methods (2001 248(1-2):7-15.
Cascalho et al., "A quasi-monoclonal mouse," Science (1996) 272(5268):1649-1652.
Casellas et al., "Contribution of receptor editing to the antibody repertoire" Science (2001) 291(5508):1541-1544.
Castelli et al., "HLA-DP4, the most frequent HLA II molecule, defines a new supertype of peptide-binding specificity," J Immunol (2002) 169(12):6928-6934.
Champion et al., "The development of monoclonal human rabies virus-neutralizing antibodies as a substitute for pooled human immune globulin in the prophylactic treatment of rabies virus exposure," J Immunol Methods (2000) 235(1-2):81-90.
Chan et al., "Genomic Organization of the T Cell Receptor," Cancer Detect Prev (1989) 14(2):261-267.
Chao et al., "Isolating and engineering human antibodies using yeast surface display," Nature Protocols (2006) 1(2):755-769.
Chen et al., "Selection and Analysis of an Optimized Anti-VEGF Antibody: Crystal Structure of an Affinity-matured Fab in Complex with Antigen," J Mol Biol (1999) 293(4):865-881.
Cheong et al., "Affinity enhancement of bispecific antibody against two different epitopes in the same antigen," Biochem Biophys Res Commun (1990) 173(3):795-800.
Cherrington et al., "New paradigms for the treatment of cancer: the role of anti-angiogenesis agents," Adv Cancer Res (2000) 79:1-38.
Chesnut et al., "Selective isolation of transiently transfected cells from a mammalian cell population with vectors expressing a membrane anchored single-chain antibody," J Immunol Methods (1996) 193(1):17-27.
Cheung et al., "A Recombinant Human Fab Expressed in *Escherichia coli* Neutralizes Rabies Virus," J Virol (1992) 66(11):6714-6720.
Chothia et al., "Canonical Structures for the Hypervariable Regions of Immunoglobulins," J Mol Biol (1987) 196:901-917.
Clackson et al., "Making antibody fragments using phage display libraries," Nature (1991) 352(6336):624-628.
Cobaugh et al., "Synthetic antibody libraries focused towards peptide ligands," J Mol Biol (2008) 378(3):622-633.
Cockett et al., "High level expression of tissue inhibitor of metalloproteinases in Chinese hamster ovary cells using glutamine synthetase gene amplification," Biotechnology (N Y) (1990) 8(7):662-667.
Conn et al., "Purification of a glycoprotein vascular endothelial cell mitogen from a rat glioma-derived cell line," Proc Natl Acad Sci U S A (1990) 87(4):1323-1327.
Conrath et al., "Camel Single-domain Antibodies as Modular Building Units in Bispecific and Bivalent Antibody Constructs," J Biol Chem (2001) 276(10):7346-7350.
Conrath et al., "Emergence and evolution of functional heavy-chain antibodies in Camelidae," Dev Comp Immunol (2003) 27(2):87-103.
Corsaro et al., "Enhancing the Efficiency of DNA-Mediated Gene Transfer in Mammalian Cells," Somatic Cell Genetics (1981) 7(5):603-616.
Crowe, "Recent advances in the study of human antibody responses to influenza virus using optimized human hybridoma approaches," Vaccine (2009) 27S:G47-51.
Cvetkovic et al., "Appropriate Tissue- and Cell-specific Expression of a Single Copy Human Angiotensinogen Transgene Specifically Targeted Upstream of the HPRT Locus by Homologous Recombination," J Biol Chem (2000) 275(2):1073-1078.
Dammacco et al., "Immunoglobulin secretion by peripheral blood and bone marrow B cells in patients with multiple myeloma. Studies by the reverse haemolytic plaque assay," Clin exp Immunol (1984) 87:743-751.
Darzynkiewicz et al., "Features of Apoptotic Cells Measured by Flow Cytometry," Cytometry (1992) 13:795-808.
Davies et al., "Antibody VH Domains as Small Recognition Units," Nature (1995) 13:475-479.
De Chiara et al., "Producing fully ES cell-derived mice from eight-cell stage embryo injections," Methods Enzymol (2010) 476:285-294.
Declaration of Andrew Murphy, dated Dec. 19, 2014, 18 pages.
Declaration of Anthony DeFranco, dated Aug. 24, 2016, 22 pages.
Declaration of Anthony DeFranco, dated Oct. 18, 2015, 31 pages.
Declaration of Christopher Goodnow, dated Oct. 16, 2015, 81 pages.
Declaration of David Tarlinton, dated Oct. 15, 2015, 24 pages.
Declaration of Joel Martin, dated May 18, 2016, 13 pages.
Declaration of John McWhirter, dated Aug. 2, 2016, 4 pages.
Declaration of Peter Hudson, dated Jun. 2, 2015, 7 pages.
Declaration of Peter Hudson, dated May 1, 2015, 52 pages.
Declaration of Robert Brink, dated Jun. 2, 2015, 38 pages.
Declaration of Robert Brink, dated Oct. 19, 2016, 19 pages.
Declaration of Robert Brink, dated Apr. 30, 2015, 34 pages.
Declaration of Ton Logtenberg, dated Sep. 15, 2015, 5 pages.
Second declaration of Ton Logtenberg, dated Dec. 18, 2015, 10 pages.
De Graaf et al., "Expression of scFvs and scFv Fusion Proteins in Eukaryotic Cells," Methods Mol Biol (2002) 178:379-387.

(56) References Cited

OTHER PUBLICATIONS

De Kruif et al., "Human immunoglobulin repertoires against tetanus toxoid contain a large and diverse fraction of high-affinity promiscuous V(H) genes," J Mol Biol (2009) 387(3):548-558.
De Kruif et al., "Rapid selection of cell subpopulation-specific human monoclonal antibodies from a synthetic phage antibody library," Proc. Natl. Acad. Sci. USA (1995) 92:3939-3942.
De Kruif et al., "Selection and Application of Human Single Chain Fv Antibody Fragments from a Semi-synthetic Phage Antibody Display Library with Designed CDR3 Regions," J Mol Biol (1995) 248:97-105.
Desmet et al., "Anchor profiles of HLA-specific peptides: analysis by a novel affinity scoring methods and experimental validation," Protein (2005) 58:53-69.
Desmet et al., "Computation of the binding of fully flexible peptides to proteins with flexible side chains," FASEB Journal (2016) 11(2):164-172.
Desmet et al., "Fast and accurate side-chain topology and energy refinement (FASTER) as a new method for protein structure optimization," Protein (2002) 48:31-43.
Desmet et al., "The dead-end elimination theorem and its use in protein side-chain positioning," Nature (1992) 356:539-542.
De Vries et al., "The Effect of Recombinant Mast Cell Growth Factor on Purified Murine Hematopoietic Stem Cells," J Exp Med (1991) 173(5):1205-1211.
De Wildt et al., "Analysis of Heavy and Light Chain Pairings Indicates that Receptor Editing Shapes the Human Antibody Repertoire," J Mol Biol (1999) 285:895-901.
Declaration of Christopher Carl Goodnow, Oct. 4, 2016, 13 pages.
Declaration of Prof Logtenberg, dated May 4, 2016, 7 pages.
Dejong et al., "Mammalian Artificial Chromosome Pilot Production Facility: Large-Scale Isolation of Functional Satellite DNA-Based Artificial Chromosomes," Cytometry (1999) 35:129-133.
Desmyter et al., "Crystal structure of a camel single-domain VH antibody fragment in complex with lysozyme," Nat Struct Biol (1996) 3(9):803-811.
Detailed results for the IMGT/V-QUEST analysed sequences, IMGT, (2016) 7 pages.
Dinnyes et al., "Somatic Cell Nuclear Transfer: Recent Progress and Challenges," Cloning Stem Cells (2002) 4(1):81-90.
Dumoulin et al., "A camelid antibody fragment inhibits the formation of amyloid fibrils by human lysozyme," Nature (2003) 424(6950):783-788.
Dumoulin et al., "Single-domain antibody fragments with high conformational stability," Protein Sci (2002) 11(3):500-515.
Eggan et al., "Hybrid vigor, fetal overgrowth, and viability of mice derived by nuclear cloning and tetraploid embryo complementation," PNAS (2001) 98(11):6209-6214.
Esposito et al., "Phage display of a human antibody against *Clostridium tetani* toxin," Gene (1994) 148:167-168.
Ettinger et al., "IL-21 induces differentiation of human naïve and memory B cells into antibody-secreting plasma cells[1]," The Journal of Immunology (2005) 176:7867-7879.
Ewert et al., "Biophysical Properties of Camelid VHH Domains Compared to Those of Human VH3 Domains," Biochemistry (2002) 41:3628-3636.
Ewert et al., "Biophysical properties of human antibody variable domains," J Mol Biol (2003) 325:531-553.
Ezzell, "Molecular guided missiles called monoclonal antibodies were poised to shoot down cancer and a host of other diseases—until they crashed and burned. Now a new generation is soaring to market," Scientific American (2001) pp. 35-41.
Fasta, Immunoglobulin light chain variable region, partial [*Homo sapiens*] (2014) 1 page.
Fecteau et al., "A new memory CD27 IgG+ B cell population in peripheral blood expressing $V_H$ genes with low frequency of somatic mutation[1]," The Journal of Immunology (2006) 177:3728-3736.
Feldhaus et al., "Flow-cytometric isolation of human antibodies from a nonimmune *Saccharomyces cerevisiae* surface display library," Natura Biotechnology (2003) 21:163-170.

Feige et al., "Anti-interleukin-1 and anti-tumor necrosis factor-alpha synergistically inhibit adjuvant arthritis in Lewis rats," Cell Mol Life Sci (2000) 57(10):1457-1470.
Ferrara, "Vascular endothelial growth factor: molecular and biological aspects," Curr Top Microbiol Immunol (1999) 237:1-30.
Figini et al., "In Vitro Assembly of Repertoires of Antibody Chains on the Surface of Phage by Renaturation," J Mol Biol (1994) 239(1):68-78.
Fine et al., "Interleukin-10 Enhances γδ T Cell Development in the Murine Fetal Thymus," Cellular Immunol (1994) 155:111-122.
Fischer, "Sequencing antibody repertoires: The next generation," mAbs (2011) 3:17-20.
Fishwild et al., "High-avidity human IgG kappa monoclonal antibodies from a novel strain of minilocus transgenic mice," Nat Biotechnol (1996) 14(7):845-851.
Flavell et al., "Systemic therapy with 3BIT, a triple combination cocktail of anti-CD19, -CD22, and -CD38-saporin immunotoxins, is curative of human B-cell lymphoma in severe combined immunodeficient mice," Cancer Res (1997) 57(21):4824-4829.
Flavell et al., "Therapy of human T-cell acute lymphoblastic leukaemia with a combination of anti-CD7 and anti-CD38-SAPORIN immunotoxins is significantly better than therapy with each individual immunotoxin," Br J Cancer (2001) 84(4):571-578.
Folkman, "Angiogenesis in cancer, vascular, rheumatoid and other disease," Nat Med (1995) 1(1):27-31.
Franconi et al., "Functional expression in bacteria and plants of an scFv antibody fragment against tospoviruses," Immunotechnology (1999) 4(3-4):189-201.
Freken et al., "Isolation of antigen specific Llama VHH antibody fragments and their high level secretion by *Saccharomyces cerevisiae*," J Biotechnol (2000) 78(1):11-21.
French et al., "Cooperative Mixtures of Bispecific F(ab')2 Antibodies for Delivering Saporin to Lymphoma in Vitro and in Vivo," Cancer Res (1991) 51:2353-2361.
Friedenson et al., "Immunoglobulin G antibodies from an individual rabbit in which several heavy chain variants are paired with one light chain sequence," J Biol Chem (1973) 248(20):7073-7079.
Frykman et al., "Quantitating secretion rates of individual cells: design of secretion assays," Biotechnol Bioeng (1998) 59(2):214-226.
Fuchs et al., "Targeting recombinant antibodies to the surface of *Escherichia coli*: fusion to a peptidoglycan associated lipoprotein," Biotechnology (N Y) (1991) 9(12):1369-1372.
Fussenegger et al., "Genetic optimization of recombinant glycoprotein production by mammalian cells," Trends Biotechnol (1999) 17(1):35-42.
Garber, "Biotech industry faces new bottleneck," Nat Biotechnol (2001) 19:183-185.
Garnick, "Peptide Mapping for Detecting Variants in Protein Products," Develop biol Standard (1992) 76:117-130.
Garrard et al., "Fab assembly and enrichment in a monovalent phage display system," Biotechnology (N Y) (1991) 9(12):1373-1377.
Gascan et al., "Human B cell clones can be induced to proliferate and to switch to IgE and IgG4 synthesis by interleukin 4 and a signal provided by activated CD4+ T cell clones," J Exp Med (1991) 173:747-750.
Ge et al., "Rapid construction and characterization of synthetic antibody libraries without DNA amplification," Biotechnology and Bioengineering (2010) 106(3):347-357.
Genbank, ABA26122.1, dated Dec. 31, 2005, 1 page.
Genbank, DQ187586.1, dated Jul. 26, 2016, 1 page.
Genbank, M87478.1, dated Oct. 28, 1994, 1 page.
Gerstner et al., "Sequence Plasticity in the Antigen-binding Site of a Therapeutic Anti-HER2 Antibody," J Mol Biol (2002) 321:851-862.
Giddings et al., "Transgenic plants as factories for biopharmaceuticals," Nat Biotechnol (2000) 18(11):1151-1155.
Gluzman, "SV40-Transformed Simian Cells Support the Replication of Early SV40 Mutants," Cell (1981) 23:175-I 82.
Gonzalez-Fernandez et al., "Analysis of somatic hypermutation in mouse Peyer's patches using immunoglobulin κ light-chain transgenes," Proc Natl Acad Sci USA (1993) 90:9862-9866.

(56) References Cited

OTHER PUBLICATIONS

Good et al., "Kinetics of human B cell behavior and amplification of proliferative responses following stimulation with IL-21," J Immunol (2006) 177:5236-5247.
Gorczyca et al., "DNA strand breaks occurring during apoptosis: Their early in situ detection by the terminal deoxynucleotidyl transferase and nick translation assays and prevention by serine protease inhibitors," Int J Oncol (1992) 1(6):639-648.
Gorczyca et al., "Induction of DNA Strand Breaks Associated with Apoptosis during Treatment of Leukemias," Leukemia (1993) 7(5):659-670.
Gorman et al., "Site-specific gene targeting for gene expression in eukaryotes," Curr Opin Biotechnol (2000) 11(5):455-460.
Goyenechea et al., "Modifying the sequence of an immunoglobulin V-gene alters the resulting pattern of hypermutation," Proc Natl Acad Sci USA (1996) 93:13979-13984.
Goyenechea et al., "Cells strongly expressing Igκ transgenes show clonal recruitment of hypermutation: a role for both MAR and the enhancers," The EMBO Journal (1997) 16(13):3987-3994.
Graham et al., "A New Technique for the Assay of Infectivity of Human Adenovirus 5 DNA," Virology (1973) 52:456-467.
Gram et al., "In vitro selection and affinity maturation of antibodies from a naive combinatorial immunoglobulin library," Proc. Natl. Acad. Sci. USA (1992) 89:3576-3580.
Graslund et al., "Integrated strategy for selective expanded bed ion-exchange adsorption and site-specific protein processing using gene fusion technology," J Biotechnol (2002) 96(1):93-102.
Gray et al., "Secretion capture and report web: use of affinity derivatized agarose microdroplets for the selection of hybridoma cells," J Immunol Methods (1995) 182(2):155-63.
Greenberger et al., "Demonstration of permanent factor-dependent multipotential (erythroid/neutrophil/basophil) hematopoietic progenitor cell lines," Proc. Natl Acad. Sci. USA (1983) 80:2931-2935.
Griffiths et al., "Human anti-self antibodies with high specificity from phage display libraries," EMBO J (1993) 12(2):725-734.
Griffiths et al., "Isolation of high affinity human antibodies directly from large synthetic repertoires," EMBO J (1994) 13(14):3245-3260.
Groeneveld et al., "Bone morphogenetic proteins in human bone regeneration," Eur J Endocrinol (2000)142(1):9-21.
Grosveld, "Activation by locus control regions?" Curr Opin Genet Dev (1999) 9(2):152-7.
Guery et al., "Dendritic cells are the most efficient in presenting endogenous naturally processed self-epitopes to class II-restricted T cells," J Immunol (1995) 154(2):536-544.
Guilli et al., "Epidermal growth factor-induced apoptosis in A431 cells can be reversed by reducing the tyrosine kinase activity[1]," Cell Growth and Differentiation (1996) 7:173-178.
Gunasekaran et al., "Enhancing antibody Fc heterodimer formation through electrostatic steering effects," Journal of Biological Chemistry (2010) 285(25):19637-19646 (enclosing supplementary tables and figures).
Hamers-Casterman et al., "Naturally occurring antibodies devoid of light chains," Nature (1993) 363(6428):446-8.
Hanes et al., "Picomolar affinity antibodies from a fully synthetic naive library selected and evolved by ribosome display," Nat Biotechnol (2000) 18(12):1287-92.
Hanes et al., "Selecting and evolving functional proteins in vitro by ribosome display," Methods Enzymol (2000) 328:404-430.
Harding et al., "The immunogenicity of humanize and fully human antibodies," mAbs (2010) 2:3:256-265.
Hardy et al., "B cell development pathways," Annu Rev Immunol (2001) 19:595-621.
Harjunpaa et al., "Rituximab (Anti-CD20) Therapy of B-Cell Lymphomas: Direct Complement Killing is Superior to Cellular Effector Mechanisms," Scand J Immunol (2000) 51(6):634-41.
Harvey et al., "Anchored periplasmic expression, a versatile technology for the isolation of high-affinity antibodies from Escherichia coli-expressed libraries," PNAS (2004) 101(25):9193-9198.

Hawkins et al., "Selection of Phage Antibodies by Binding Affinity Mimicking Affinity Maturation," J Mol Biol (1992) 226:889-896.
Hay et al., "Bacteriophage cloning and Escherichia coli expression of a human IgM Fab," Hum Antibod Hybridomas (1992) 3:81-85.
Heintges et al., "Cloning, bacterial expression and sequencing of human antibody fragments against hepatitis Virus NS3 by Phage display of a combinatorial Phagemid Library," Hepatology (1998) 28(4 Pt 2):227A.
Hengstchlager et al., "A λ1 transgene under the control of a heavy chain promoter and enhancer does not undergo somatic hypermutation," Eur J Immunol (1994) 24:1649-1656.
Hiatt et al., "Production of antibodies in transgenic plants," Nature (1989) 342(6245):76-8.
Hitzeman et al., "Isolation and Characterization of the Yeast 3-Phosphoglycerokinase Gene (PGK) by an Immunological Screening Technique" J Biol Chem (1980) 255(24):12073-12080.
Hochedlinger et al., "Monoclonal mice generated by nuclear transfer from mature B and T donor cells," Nature (2002) 415:1035-1038.
Holliger et al., ""Diabodies": Small bivalent and bispecific antibody fragments," Proc. Natl. Acad. Sci. USA (1993) 90:6444-6448.
Holmes et al., "Improved cell line development by a high throughput affinity capture surface display technique to select for high secretors," J Immunol Methods (1999) 230(1-2):141-147.
Holt et al., "Domain antibodies: proteins for Therapy," Trends Biotechnol (2003) 21(11):484-490.
Homig-Holzel et al., "Constitutive CD40 signaling in B cells selectively activates the noncanonical NF-κB pathway and promotes lymphomagenesis," J Exp Med (2008) 205(6):1317-1329.
Hoogenboom et al., "Antibody phage display technology and its applications," Immunotechnology (1998) 4(1):1-20.
Hoogenboom et al., "By-passing immunisation. Human antibodies from synthetic repertoires of germline VH gene segments rearranged in vitro," J Mol Biol (1992) 227(2):381-388.
Hoogenboom et al., "Multi-subunit proteins on the surface of filamentous phage: methodologies for displaying antibody (Fab) heavy and light chains," Nucleic Acids Research (1991) 19(15):4133-4137.
Hoogenboom et al., "Natural and designer binding sites made by phage display technology," Immunol Today (2000) 21(8):371-378.
Hoogenboom, "Designing and optimizing library selection strategies for generating high-affinity antibodies," Trends Biotechnol (1997) 15(2):62-70.
Hoogenboom, "Selecting and screening recombinant antibody libraries," Nature Biotechnology (2005) 23(9):1105-1116.
Hooper, "Rabies Virus," Manual of Clinical Laboratory Immunology (1997) 5:755-760.
Houshmand et al., "Use of bacteriophage T7 displayed peptides for determination of monoclonal antibody specificity and biosensor analysis of the binding reaction," Anal Biochem (1999) 268(2):363-370.
Houston Jr et al., "Use of a Conformationally Restricted Secondary Structural Element to Display Peptide Libraries: A Two-stranded α-Helical Coiled-coil Stabilized by Lactam Bridges," J Mol Biol (1996) 262:270-282.
Huang et al., "Role of Bone Marrow-Derived Cells in Presenting MHC Class I-Restricted Tumor Antigens," Science (1994) 264:961-965.
Hudziak et al., "p185$^{HER2}$ Monoclonal Antibody Has Antiproliferative Effects In Vitro and Sensitizes Human Breast Tumor Cells to Tumor Necrosis Factor," Mol Cell Biol (1989) 9(3):1165-1172.
Huls et al., "A recombinant, fully human monoclonal antibody with antitumor activity constructed from phage-displayed antibody fragments," Nat Biotechnol (1999) 17(3):276-281.
Huls et al., "Antitumor Immune Effector Mechanisms Recruited by Phage Display-derived Fully Human IgG1 and IgA1 Monoclonal Antibodies," (1999) Cancer Res 59:1778-5784.
Huse et al., "Generation of a Large Combinatorial Library of the Immunoglobulin Repertoire in Phage Lambda," Science (1989) 246(4935):1275-1281.
Huse et al., "Purification of antibodies by affinity chromatography," J Biochem Biophys Methods (2002) 51:217-231.

(56) References Cited

OTHER PUBLICATIONS

Hwang et al., "Immunogenicity of engineered antibodies," Methods (2005) 36:3-10.
Hynes, "Cell adhesion: old and new questions," Trends Cell Biol (1999) 9(12):M33-M37.
Inaba et al., "Dendritic Cells Pulsed with Protein Antigens In Vitro Can Prime Antigen-specific, MHC-restricted T Cells In Situ," J Exp Med (1990) 172:631-640.
Inaba et al., "Distinct Mechanisms of Neonatal Tolerance Induced by Dendritic Cells and Thymic B Cells," J Exp Med (1991) 173:549-559.
Important information regarding oral proceedings, dated Jul. 16, 2014, 3 pages.
Inlay et al., "Essential roles of the κ light chain intronic enhancer and 3' enhancer in κ rearrangement and demethylation," Nature Immunology (2002) 3-5:463-468.
Inlay et al., "Roles of the Ig κ light chain intronic and 3' enhancers in Igκ somatic hypermutation," Journal of Immunology (2006) 177:1146-1151.
Ishii et al., "TANK-binding kinase-1 delineates innate and adaptive immune responses to DNA vaccines," Nature (2008) 451:725-730.
Itoh et al., "The Polypeptide Encoded by the cDNA for Human Cell Surface Antigen Fas Can Mediate Apoptosis," Cell (1991) 66:233-243.
Jacob et al., "Activity of DNA vaccines encoding self or heterologous Her-2/neu in Her-2 or neu transgenic mice," Cellular Immunology (2006) 240:96-106.
Jacob et al., "Combining human and rat sequences in Her-2 DNA vaccines blunts immune tolerance and drives antitumor immunity," Cancer Research (2010) Cancer Res 70(1):119-128.
Jain et al., "Engineering antibodies for clinical applications," TRENDS in Biotechnology (2007) 25(7):309-316.
Jakobovits et al., "Analysis of homozygous mutant chimeric mice: Deletion of the immunoglobulin heavy-chain joining region blocks B-cell development and antibody production," Proc Natl Acad Sci USA (1993) 90:2551-2555.
Jakobovits et al., "From XenoMouse technology to panitumumab, the first fully human antibody product from transgenic mice," Nat Biotechnol (2007) 25(10):1134-1143.
Jakobovits et al., "Germ-line transmission and expression of a human-derived yeast artificial chromosome," Nature (1993) 362(6417):255-258.
Janeway, "Immuno biology the immune system in health and disease," 4th edition (1999) 21 pages.
Janeway, "The development and survival of lymphocytes," pp. 275-290.
Janeway's immunology, "Antigen presentation to T lymphocytes," (2012) 31 pages.
Jechlinger, "Optimization and delivery of plasmid DNA for vaccination," Expert Rev Vaccines (2006) 5(6):803-825.
Jeffers et al., "Enhanced Tumorigenicity and Invasion-Metastasis by Hepatocyte Growth Factor/Scatter Factor-Met Signalling in Human Cells Concomitant with Induction of the Urokinase Proteolysis Network," Mol Cell Biol (1996) 16(3):1115-1125.
Jespers et al., "Guiding the selection of human antibodies from phage display repertoires to a single epitope of an antigen," Bio-technology (N Y) (1994) 12(9):899-903.
Jiang et al., "A novel strategy for generation of monoclonal antibodies from single B cells using RT-RCR technique and in vitro expression," Biotechnol Prog (2006) 22(4):979-988.
Jin et al., "A rapid and efficient single-cell manipulation method for screening antigen-specific antibody-secreting cells from human peripheral blood," Nature Medicine (2009) 15(9):1088-1093.
Johansson et al., "Evidence for Involvement of Activin A and Bone Morphogenetic Protein 4 in Mammalian Mesoderm and Hematopoietic Development," Mol Cell Biol (1995) 15(1):141-151.
Jolly et al., "Rapid methods for the analysis of immunoglobulin gene hypermutation: application to transgenic and gene targeted mice," Nucleic Acids Research (1997) 25(10):1913-1919.

Jonasson et al., "Genetic design for facilitated production and recovery of recombinant proteins in *Escherichia coli*," Biotechnol Appl Biochem (2002) 35:91-105.
Jones et al., "High Level Expression of Recombinant IgG in the Human Cell Line PER.C6," Biotechnol Prog (2003) 19:163-168.
Kang et al., "Linkage of recognition and replication functions by assembling combinatorial antibody Fab libraries along phage surfaces," Proc Natl Acad Sci USA (1991) 88:4363-4366.
Kakitani et al., "A novel transgenic chimaeric mouse system for the rapid functional evaluation of genes encoding secreted proteins," Nucleic Acids Research (2005) 33(9):e85 8 pages.
Kasprzyk et al., "Therapy of an Animal Model of Human Gastric Cancer Using a Combination of Anti-erbB-2 Monoclonal Antibodies," Cancer Res (1992) 52:2771-2776.
Kato et al., "Cell activation by CpG ODN leads to improved electrofusion in hybridoma production," J Immunological Methods (2011) 373:102-110.
Kaufman et al., "Amplification and Expression of Sequences Cotransfected with a Modular Dihydrofolate Reductase Complementary DNA Gene," J Mol Biol (1982) 159:601-621.
Kaufman, "Overview of Vector Design for Mammalian Gene Expression," Mol Biotechnol (2000) 16(2):151-160.
Keller et al., "Hematopoietic Commitment during Embryonic Stem Cell Differentiation in Culture," Mol Cell Biol (1993) 13(1): 473-486.
Kelley et al., "Antigen binding thermodynamics and antiproliferative effects of chimeric and humanized anti-p185HER2 antibody Fab fragments," Biochemistry (1992) 31(24):5434-541.
Kim et al., "Characterization of chimeric antibody producing CHO cells in the course of dihydrofolate reductase-mediated gene amplification and their stability in the absence of selective pressure," Biotechnol Bioeng (1998) 58(1):73-84.
Kim et al., "Comparative analyses of complex formation and binding sites between human tumor necrosis factor-alpha and its three antagonists elucidate their different neutralizing mechanisms," J Mol Biol (2007) 374:1374-1388.
Kim et al., "Subspecialization of CXCR5+ T Cells: B helper activity is focused in a germinal center-localized subset of CXCR5+ T cells," J Exp Med (2001) 193(12):1373-1381.
Klagsbrun et al., "Vascular endothelial growth factor and its receptors," Cytokine Growth Factor Rev (1996) 7(3):259-270.
Kling et al., "Big Pharma vies for mice," Nature Biotechnology (2007) 25:613-614.
Klitz et al., "New HLA haplotype frequency reference standards: High-resolution and large sample typing of HLA DR-DQ haplotypes in a sample of European Americans," Tissue Antigens (2003) 62:296-307.
Klohn et al., "IBC's 23rd annual antibody engineering, 10th annual antibody therapeutics international conferences and the 2012 annual meeting of the antibody society," mAbs (2013) 5(2):178-201.
Klotz et al., "Somatic hypermutation of a λ2 transgene under the control of the λ enhancer or the heavy chain intron enhancer[1]," Journal of Immunology (1996) 157:4458-4463.
Klotz et al., "Somatic hypermutation of an artificial test substrate within an Igκ transgene[1]," The Journal of Immunology (1998) 161:782-790.
Kohler et al., "Continuous cultures of fused cells secreting antibody of predefined specificity," Nature (1975) 256:495-497.
Kong et al., "A λ 3' enhancer drives active and untemplated somatic hypermutation of a $\lambda_1$ transgene[1]," The Journal of Immunology (1998) 161:294-301.
Koide et al., "The Fibronectin Type III Domain as a Scaffold for Novel Binding Proteins," J Mol Biol (1998) 284:1141-1151.
Kontermann, "Dual targeting strategies with bispecific antibodies," MAbs (2012) 4(2):182-97.
Koochekpour et al., "Met and Hepatocyte Growth Factor/Scatter Factor Expression in Human Gliomas," Cancer Res (1997) 57:5391-5398.
Koopman et al., "Annexin V for Flow Cytometric Detection of Phosphatidylserine Expression on B Cells Undergoing Apoptosis," Blood (1994) 84(5):1415-1420.

(56) References Cited

OTHER PUBLICATIONS

Korndorfer et al., "Crystallographic analysis of an "anticalin" with tailored specificity for fluorescein reveals high structural plasticity of the lipocalin loop region," Proteins (2003) 53(1):121-129.
Korndorfer et al., "Structural Mechanism of Specific Ligand Recognition by a Lipocalin Tailored for the Complexation of Digoxigenin," J Mol Biol (2003) 330:385-396.
Kortt et al., "Dimeric and trimeric antibodies: high avidity scFvs for cancer targeting," Biomol Eng (2001) 18(3):95-108.
Kramer et al., "A novel helper phage that improves phage display selection efficiency by preventing the amplification of phages without recombinant protein," Nucleuic Acids Research (2003) 31(11):e59.
Krebs et al., "High-throughput generation and engineering of recombinant human antibodies," J Immunol Methods (2001) 254(1-2):67-84.
Krosen et al., "Bispecific antibodies for treatment of cancer in experimental animal models and man," Advanced Drug Delivery Reviews (1998) 31:105-129.
Kruse et al., "Tissue Culture, Methods and Applications," Academic Press, New York (1973) p. 868.
Ku et al, "Alternate protein frameworks for molecular recognition," Proc Natl Acad Sci USA (1995) 92:6552-6556.
Kuhlman et al., "Design of a Novel Globular Protein Fold with Atomic-Level Accuracy," Science (2003) 302:1364-1368.
Kunkel et al., "Rapid and efficient site-specific mutagenesis without phenotypic selection," Proc Natl Acad Sci USA (1985) 82:488-492.
Kwakkenbos et al., "Generation of stable monoclonal antibody-producing BCR+ human memory B cells by genetic programming," Nat Med (2010) 16(1):123-128.
Kwaks et al., "Employing epigenetics to augment the expression of the therapeutic proteins in mammalian cells," TRENDS in Biotechnology (2006) 24(3):137-142.
Kwaks et al., "Identification of anti-repressor elements that confer high and stable protein production in mammalian cells," Nat Biotechnol (2003) 21(5):553-558.
Lang et al., "Immunotherapy with Human Monoclonal Antibodies," J Immunol (1993) 151(1):466-472.
Larbouret et al., "In vivo therapeutic synergism of anti-epidermal growth factor receptor and anti-HER2 monoclonal antibodies against pancreatic carcinomas," Clin Cancer Res (2007) 13(11):3356-3362.
Larrick et al., "Producing proteins in transgenic plants and animals," Curr Opin Biotechnol (2001) 12(4):411-418.
Lazar et al., "A molecular immunology approach to antibody humanization and functional optimization," Molecular Immunology (2007) 44:1986-1998.
Lefranc et al., "Nomenclature of the human immunoglobulin kappa (IGK) genes," Exp Clin Immunogenet (2001) 18:161-174.
Lekkerkerker et al., "Phage antibodies against human dendritic cell subpopulations obtained by flow cytometry-based selection on freshly isolated cells," J Immunol Methods (1999) 231(1-2):53-63.
Lenz et al., "Expression of heterobispecific antibodies by genes transfected into producer hybridoma cells," Gene (1990) 87(2):213-218.
Li et al., "Stable expression of three genes from a tricistronic retroviral vector containing a picornavirus and 9-nt cellular internal ribosome entry site elements," J Virol Methods (2004) 115(2):137-144.
Lie et al., "Advances in quantitative PCR technology: 5' nuclease assays," Current Opinion in Biotechnology (1998) 9:43-48.
Lindhofer et al., "Preferential species-restricted heavy/light chain pairing in rat/mouse quadromas. Implications for a single-step purification of bispecific antibodies," J Immunol (1995) 55(1):219-225.
Ling et al., "Modulation of the murine immune response to human IgG by complexing with monoclonal antibodies," Immunology (1987) 62:1-6.
Little et al., "Human antibody libraries in *Escherichia coli*," J Biotechnol (1995) 41(2-3):187-195.
Little, "Recombinant Antibodies for Immunotherapy," Cambridge University Press (2009) 1st edition, 21 pages.
Lobato et al., "Intracellular antibodies and challenges facing their use as therapeutic agents," Trends Mol Med (2003) 9(9):390-396.
Lofgren et al., "Comparing ELISA and surface plasmon resonance for assessing clinical immunogenicity of panitumumab," The Journal of Immunology (2007) 178:7467-7472.
Logtenberg, "Antibody cocktails: next-generation biopharmaceuticals with improved potency," Trends Biotechnol (2007) 25(9):390-394.
Lonberg et al., "Antigen-specific human antibodies from mice comprising four distinct genetic modifications," Nature (1994) 368:856-859.
Lonberg, "Human antibodies from transgenic animals," Nature Biotechnology (2005) 23(9):1117-1125.
Lonberg, "Fully human antibodies from transgenic mouse and phage display platforms," Curr Opin Immunol (2008) 20(4):450-459.
Love et al., "A microengraving method for rapid selection of single cells producing antigen-specific antibodies," Nature Biotechnology (2006) 24(6):703-707.
Lu et al., "Acquired antagonistic activity of a bispecific diabody directed against two different epitopes on vascular endothelial growth factor receptor 2," J Immunol Methods (1999) 230(1-2):159-171.
Lu et al., "Complete Inhibition of Vascular Endothelial Growth Factor (VEGF) Activities with a Bifunctional Diabody Directed against Both VEGF Kinase Receptors, fms-like Tyrosine Kinase Receptor and Kinase Insert Domain-containing Receptor," Cancer Res (2001) 61:7002-7008.
Lu et al., "Identification of the Residues in the Extracellular Region of KDR Important for Interaction with Vascular Endothelial Growth Factor and Neutralizing Anti-KDR Antibodies," J Biol Chem (2000) 275(19):14321-14330.
Lu et al., "Selection of High Affinity Human Neutralizing Antibodies to VEGFR2 From a Large Antibody Phage Display Library for Antiangiogenesis Therapy," Int. J. Cancer (2002) 97:393-399.
Lucas et al., "High-level production of recombinant proteins in CHO cells using a dicistronic DHFR intron expression vector," Nucleic Acids Res (1996) 24(9):1774-1779.
Ma et al., "Assembly of monoclonal antibodies with IgGl and IgA heavy chain domains in transgenic tobacco plants," Eur J Immunol (1994) 24:131-138.
Macatonia et al., "Dendritic cells produce IL-12 and direct the development of Th1 cells from naive CD4+ T cells," J Immunol (1995) 154(10):5071-5079.
Macatonia et al., "Primary stimulation by dendritic cells induces antiviral proliferative and cytotoxic T cell responses in vitro," J Exp Med (1989) 169(4):1255-1264.
MacDonald et al., "Precise and in situ genetic humanization of 6 Mb of mouse immunoglobulin genes," Proc Natl Acad Sci U S A (2014) 111(14):5147-5152.
Macejak et al., "Internal initiation of translation mediated by the 5' leader of a cellular mRNA," Nature (1991) 353(6339):90-94.
Manen et al., "A sensitive reporter gene system using bacterial luciferase based on a series of plasmid cloning vectors compatible with derivatives of pBR322," Gene (1997) 186:197-200.
Manz et al., "Maintenance of serum antibody levels," Annu Rev Immunol (2005) 23:367-386.
Mao et al., "Activation of EGFP expression by cre-mediated excision in a new ROSA26 reporter mouse strain," Blood (2001) 97(1):324-326.
Marasco, "Intrabodies as antiviral agents," Curr Top Microbiol Immunol (2001) 260:247-270.
Marks et al., "By-passing Immunization Human Antibodies from V-gene Libraries Displayed on Phage," J Mol Biol (1991) 222:581-597.
Marks, "Deciphering antibody properties that lead to potent botulinum neurotoxin neutralization," Mov Disord (2004) 19(Suppl 8):S101-S108.
Marvin et al., "Recombinant approaches to IgG-like bispecific antibodies," Acta Pharmacol Sin (2005) 26(6):649-658.

(56) References Cited

OTHER PUBLICATIONS

Massengale et al., "CD20-negative relapse of cutaneous B-cell lymphoma after anti-CD20 monoclonal antibody therapy," J Am Acad Dermatol (2002) 46(3):441-443.
Matsuda et al., "The Complete Nucleotide Sequence of the Human Immunoglobulin Heavy Chain Variable Region Locus," J Exp Med (1998) 188(11):2151-2162.
Mattheakis et al., "An in vitro polysome display system for identifying ligands from very large peptide libraries," Proc Natl Acad Sci U S A (1994) 91:9022-9026.
Mayer, "A new set of useful cloning and expression vectors derived from pBlueScript," Gene (1995) 163(1):41-46.
McBurney et al., "Evidence for Repeat-Induced Gene Silencing in Cultured Mammalian Cells: Inactivation of Tandem Repeats of Transfected Genes," Exp Cell Res (2002) 274(1):1-8.
McCafferty et al., "Antibody engineering," (1996) Oxford University Press 178 pages.
McClanahan et al., "Hematopoietic Growth Factor Receptor Genes as Markers of Lineage Commitment During In Vitro Development of Hematopoietic Cells," Blood (1993) 81(11):2903-2915.
McConnell et al., "Tendamistat as a Scaffold for Conformationally Constrained Phage Peptide Libraries," J Mol Biol (1995) 250:460-470.
McGinnes et al., "B-Lineage colonies from normal, human bone marrow are initiated by B cells and their progenitors," Blood (1991) 77(5):961-970.
Meijer et al., "Isolation of human antibody repertoires with preservation of the natural heavy and light chain pairing," J Mol Biol (2006) 358:764-772.
Mendel et al., "The Angiogenesis Inhibitor SU5416 Has Long-lasting Effects on Vascular Endothelial Growth Factor Receptor Phosphorylation and Function," Clin Cancer Res (2000) 6:4848-4858.
Merchant et al., "An efficient route to human bispecific IgG," Nat Biotechnol (1998) 16(7):677-681.
Merus prior art P61090-/P6498-/P67824, dated Jul. 12, 2016, 4 pages.
Merus prior art P61090-/P6498-/P67824, dated Oct. 18, 2016, 39 pages.
Merus prior art P85261, dated Jul. 19, 2016, 4 pages.
Merus prior art P85261, dated Oct. 21, 2016, 17 pages.
Merus prior art P99390, dated Sep. 30, 2016, 9 pages.
Meyer et al., "The importance of the 3'-enhancer region in immunoglobulin κ gene expression," Nucleic Acids Research (1990) 18(19):5609-5615.
Meyer et al., "The Igκ 3'-enhancer triggers gene expression in early B lymphocytes but its activity is enhanced on B cell activation," International Immunology (1996) 8(10):1561-1568.
Middendorp et al., "Cellular maturation defects in Bruton's tyrosine kinase-deficient immature B cells are amplified by premature B cell receptor expression and reduced by receptor editing[1]," The Journal of Immunology (2004) 172:1371-1379.
Middendorp et al., "Impaired precursor cell differentiation in Bruton's tyrosine kinase-deficient mice[1]," The Journal of Immunology (2002) 168:2695-2703.
Mirick et al., A review of human anti-globulin antibody (HAGA, HAMA, HACA, HAHA) responses to monoclonal antibodies not four letter words, QJ Nucl Med Mol Imaging (2004) 48:251-257.
Mohapatra et al., "Designer monoclonal antibodies as drugs: the state of the art," Expert Rev Clin Immunol (2008) 4(3):305-307.
Morimoto et al., "High level expression of a human rabies virus-neutralizing monoclonal antibody by a rhabdovirus-based vector," J Immunol Methods (2001) 252(1-2):199-206 (Abstract).
Morrison, "Transfectomas Provide Novel Chimeric Antibodies," Science (1985) 229(4719):1202-1207.
Mostoslavsky et al., "Asynchronous replication and allelic exclusion in the immune system," Nature (2001) 414:221-225.
Murakami et al., "Splenic CD19 cd35+B220+ cells function as an inducer of follicular dendritic cell network formation," Blood (2007) 110(4):1215-1224.
Muyldermans, "Single domain camel antibodies: current status," J Biotechnol (2001) 74(4):277-302.
Nahta et al., "The HER-2-Targeting Antibodies Trastuzumab and Pertuzumab Synergistically Inhibit the Survival of Breast Cancer Cells," Cancer Res (2004) 64:2343-2346.
Nair et al., "Induction of Primary, Antiviral Cytotoxic, and Proliferative Responses with Antigens Administered via Dendritic Cells," J Virol (1993) 67(7):4062-4069.
Nanbru et al., "Alternative Translation of the Proto-oncogene c-myc by an Internal Ribosome Entry Site," J Biol Chem (1997) 272(51):32061-32066.
Nelson et al., "Development trends for human monoclonal antibody therapeutics," Nat Rev Drug Discov (2010) 9(10):767-774.
Nemazee, "Receptor Editing in B Cells," Advances in Immunology (2000)74:89-126.
Nemazee, "Receptor editing in lymphocyte development and central tolerance," Nat Rev Immunol (2006) 6(10):728-740.
Neufeld et al., "Vascular endothelial growth factor (VEGF) and its receptors," FASEB J (1999) 13(1):9-22.
Ngo et al., "Identification of functional synergism between monoclonal antibodies. Application to the enhancement of plasminogen activator inhibitor-1 neutralizing effects," FEBS (1997) 416:373-376.
Nicholson et al., "Antibody repertoires of four- and five-feature translocus mice carrying human immunoglobulin heavy chain and kappa and lambda light chain yeast artificial chromosomes," J Immunol (1999) 163(12):6898-6906.
Nikolic et al., "A subfraction of B220+ cells in murine bone marrow and spleen does not belong to the B cell lineage but has dendritic cell characteristics," Eur J Immunol (2002) 32:686-692.
Nissim et al., "Antibody fragments from a 'single pot' phage display library as immunochemical reagents," EMBO J (1994) 13(3):692-698.
Nord et al., "A combinatorial library of an a-helical bacterial receptor domain," Protein Engineering (1995) 8(6):601-608.
Nord et al., "Recombinant human factor VIII-specific affinity ligands selected from phage-displayed combinatorial libraries of protein A," Eur J Biochem (2001) 268:4269-4277.
Norderhaug et al., "Balanced expression of single subunits in a multisubunit protein, achieved by cell fusion of individual transfectants," Eur J Biochem (2002) 269:3205-3210.
Novimmune SA, "Therapeutic Bispecific Antibodies, The Fully-Human Kappa-Lambda Body: Simple, Stable, Smart," (2013) 2 pages.
Novobrantseva et al., "Rearrangement and expression of immunoglobulin light chain genes can precede heavy chain expression during normal B cell development in mice," J Exp Med (1999) 189(1):75-87.
Nowakowski et al., "Potent neutralization of botulinum neurotoxin by recombinant oligoclonal antibody," Proc Natl Acad Sci U S A (2002) 99(17):11346-11350.
Nuemann et al., "Gene transfer into mouse lyoma cells by electroporation in high electric fields," EMBO J (1982) 1(7):841-845.
Odegard et al., "Targeting of somatic hypermutation," Nat Rev Immunol (2006) 6(8):573-583.
Ogunniyi et al., "Screening individual hybridomas by microengraving to discover monoclonal antibodies," Nature Protocols (2009) 4(5):767-782.
Oh et al., "Homeotic gene Antennapedia mRNA contains 5'-noncoding sequences that confer translational initiation by internal ribosome binding," Genes Dev (1992) 6(9):1643-1653.
Opposition against European Patent in EP 2314629 from Merus B.V., filed May 18, 2013, 13 pages.
Orban et al., "Tissue- and site-specific DNA recombination in transgenic mice," Proc Natl Acad Sci USA (1992) 89:6861-6865.
Padlan, "A possible procedure for reducing the immunogenicity of antibody variable domains while preserving their ligand-binding properties," Molecular Immunology (1991) 28(4-5):489-498.
Pasqualucci et al., "BCL-6 mutations in normal germinal center B cells: Evidence of somatic hypermutation acting outside Ig loci," Proc Natl Acad Sci USA (1998) 95:11816-11821.

(56) References Cited

OTHER PUBLICATIONS

Patel et al., "An improved assay for antibody dependent cellular cytotoxicity based on time resolved fluorometry," J Immunol Methods (1995)184(1):29-38.
Pau et al., "The human cell line PER.C6 provides a new manufacturing system for the production of influenza vaccines," Vaccines (2001) 19:2716-2721.
Peeters et al., "Production of Antibodies and Antibody Fragments in Plants," Vaccine (2001) 19 (17-19):2756-2761.
Pelanda et al., "A prematurely expressed Igκ transgene, but not a VκJκ gene segment targeted into the Igκ locus, can rescue B cell development in λ5-deficient mice," Immunity (1996) 5:229-239.
Peled et al., "The biochemistry of somatic hypermutation," Annu Rev Immunol (2008) 26:481-511.
Perrin et al., "In vitro rabies vaccine potency appraisal by ELISA: advantages of the immunocapture method with a neutralizing antiglycoprotein monoclonal antibody," Biologicals. (1990) 18(4):321-330.
Persic et al., "An integrated vector system for the eukaryotic expression of antibodies or their fragments after selection from phage display libraries," Gene (1997) 187(1):9-18.
Persson et al., "A focused antibody library for improved hapten recognition," J Mol Biol (2006) 357:607-620.
Phan et al., "High affinity germinal center B cells are actively selected into the plasma cell compartment," J Exp Med (2006) 203(11):2419-2424.
Phelps et al., "Expression and characterization of a chimeric bifunctional antibody with therapeutic applications," J Immunol (1990) 145(4):1200-1204.
Pluckthun et al., "In vitro selection and evolution of proteins," Adv Protein Chem (2000) 55:367-403.
Ponsel et al., "High Affinity, developability and functional size: the holy grail of combinatorial antibody library generation," Molecules (2011) 16:3675-3700.
Pollock et al., "Transgenic milk as a method for the production of recombinant antibodies," J Immunol Methods (1999) 231(1-2):147-157.
Popov et al., "A human immunoglobulin λ locus is similarly well expressed in mice and humans," J Exp Med (1999) 189(10):1611-1619.
Porgador et al., "Bone Marrow-generated Dendritic Cells Pulsed with a Class I-restricted Peptide Are Potent Inducers of Cytotoxic T Lymphocytes," J Exp Med (1995) 182(1): 255-260.
Poulsen et al., "Limits for antibody affinity maturation and repertoire diversification in hypervaccinated humans," The Journal of Immunology (2011) 187:4229-4235.
Prak et al., "Light chain replacement: A new model for antibody gene rearrangement," J Exp Med (1995) 182:541-548.
Presta et al., "Engineering of therapeutic antibodies to minimize immunogenicity and optimize function," Advanced Drug Delivery Reviews (2006) 58:640-656.
Queen et al., "A humanized antibody that binds to the interleukin 2 receptor," Proc Natl Acad Sci USA (1989) 86:10029-10033.
Radic et al., "Ig H and L chain contributions to autoimmune specificities," J Immunol (1991) 146(1):176-182.
Rajewsky et al., "Perspectives series: molecular medicine in genetically engineered animals," J Clin Invest (1996) 98(3):600-603.
Ravn et al., "By-passing in vitro screening-next generation sequencing technologies applied to antibody display and in silico candidate selection," Necleic Acids Research (2010) 38(21):e193.
Rebar et al., "Phage display methods for selecting zinc finger proteins with novel DNA-binding specificities," Methods Enzymol (1996) 267:129-149.
Reddy et al., "Monoclonal antibodies isolated without screening by analyzing the variable-gene repertoire of plasma cells," Nature Biotechnology (2010) 28(9):965-971.
Reddy et al., "Systems analysis of adaptive immunity by utilization of high-throughput technologies," Current Opinion in Biotechnology (2011) 22:584-589.
Rees et al., "Bicistronic Vector for the Creation of Stable Mammalian Cell Lines that Predisposes All Antibiotic-Resistant Cells to Express Recombinant Protein," BioTechniques (1996) 20:102-110.
Reiter et al., "An Antibody Single-domain Phage Display Library of a Native Heavy Chain Variable Region: Isolation of Functional Single-domain VH Molecules with a Unique Interface," J Mol Biol (1999) 290:685-698.
Repp et al., "Phase I clinical trial of the bispecific antibody MDX-H210 (anti-FcgammaRI x anti-HER-2/neu) in combination with Filgrastim (G-CSF) for treatment of advanced breast cancer," Br J Cancer (2003) 89(12):2234-2243.
Retter et al., "Receptor editing occurs frequently during normal B cell development," J Exp Med (1998) 188(7):1231-1238.
Retter et al., "Receptor editing: genetic reprogramming of autoreactive lymphocytes," Cell Biochemistry and Biophysics (1999) 31:81-88.
Riechmann et al., "Novel folded protein domains generated by combinatorial shuffling of polypeptide segments," Proc Natl Acad Sci U S A (2000) 97(18):10068-10073.
Rickert et al., "B lymphocyte-specific, cre-mediated mutagenesis in mice," Nucleic Acids Research (1997) 25(6):1317-1318.
Ritchie et al., "Allelic exclusion and control of endogenous immunoglobulin gene rearrangement in kappa transgenic mice," Nature (1984) 312(5994):517-520.
Roberts et al., "RNA-peptide fusions for the in vitro selection of peptides and proteins," Proc Natl Acad Sci USA (1997) 94:12297-12302.
Roholt et al., "Antibodies of limited heterogeneity: L chains of a single mobility," Immunochemistry (1970) 7(4):329-340.
Roitt et al., "Anti-idiotypes as surrogate antigens: structural considerations," Immunol Today (1985) 6(9):265-267.
Roitt, Immunology translation, (2000) 3 pages.
Rojas et al., "Phage antibody fragments library combining a single human light chain variable region with immune mouse heavy chain variable regions," J Biotechnol (2002) 94(3):287-298.
Rong et al., "Tumorigenesis induced by coexpression of human hepatocyte growth factor and the human met protooncogene leads to high levels of expression of the ligand and receptor," Cell Growth Differ (1993) 4(7):563-569.
Rong et al., "Tumorigenicity of the met Proto-Oncogene and the Gene for Hepatocyte Growth Factor," Mol Cell Biol (1992) 12(11):5152-5158.
Rosenberg et al., "T7Select® Phage Display System: A powerful new protein display system based on bacteriophage T7," (1996) 7 pages.
Rottgen et al., "A human pancreatic secretory trypsin inhibitor presenting a hypervariable highly constrained epitope via monovalent phagemid display," Gene (1995) 164:243-250.
Ruuls et al., "Novel human antibody therapeutics: The age of the Umabs," Biotechnol journal (2008) 3:1157-1171.
Sanger et al., "DNA sequencing with chain-terminating inhibitors," Proc Natl Acad Sci USA (1977) 74(12):5463-5467.
Santini et al., "Efficient Display of an HCV cDNA Expression Library as C-terminal Fusion to the Capsid Protein D of Bacteriophage Lambda," J Mol Biol (1998) 282:125-135.
Sasaki et al., "Canonical NF-κB activity, dispensable for B cell development, replaces BAFF-receptor signals and promotes B cell proliferation upon activation," Immunity (2006) 24:729-739.
Schaffitzel et al., "In Vitro Selection and Evolution of Protein-Ligand Interactions by Ribosome Display" Protein-Ligand Interactions and Ribosome Display (2001) 27:517-548.
Schaffitzel et al., "Ribosome display: an in vitro method for selection and evolution of antibodies from libraries," J Immunol Methods (1999) 231(1-2):119-135.
Schmidlin et al., "New insights in the regulation of human B cell differentiation," Trends Immunol (2009) 30(6):277-285.
Schlehuber et al., "Tuning ligand affinity, specificity, and folding stability of an engineered lipocalin variant—a so-called 'anticalin'—using a molecular random approach," Biophys Chem (2002) 96(2-3):213-328.
Schmitz et al., "Phage Display: A Molecular Tool for the Generation of Antibodies—A Review," Placenta (2000) 21(A):S106-112.

(56) References Cited

OTHER PUBLICATIONS

Schnieke et al., "Human factor IX transgenic sheep produced by transfer of nuclei from transfected fetal fibroblasts," Science (1997) 278(5346):2130-2133.
Schoonjans et al., "A new model for intermediate molecular weight recombinant bispecific and trispecific antibodies by efficient heterodimerization of single chain variable domains through fusion to a Fab-chain," Biomol Eng (2001) 17(6):193-202.
Scott, "Mice with a human touch," Nat Biotechnol (2007) 25(10):1075-1077.
Segal et al., "Introduction: bispecific antibodies," J Immunol Methods (2001) 248(1-2):1-6.
Seibler et al., "Rapid generation of inducible mouse mutants," Nucleic Acids Research (2003) 31(4):e12.
Shaffer et al., "In vivo occupancy of the κ light chain enhancer in primary pro- and pre-B cells: A model for κ locus activation," Immunity (1997) 6:131-143.
Sharpe et al., "Somatic hypermutation of immunoglobulin ϰ may depend on sequences 3' of Cϰ and occurs on passenger transgenes," The EMBO Journal (1991) 10(8):2139-2145.
Shapiro-Shelef et al., "Regulation of plasma-cell development," Nature Review Immunol (2005) 5:230-242.
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem (2001) 276(9):6591-6604.
Shvarts et al., "A senescence rescue screen identifies BCL6 as an inhibitor of anti-proliferative $p19^{ARF}$-P53 signaling," Genes & Development (2002) 16:681-686.
Sidhu et al., "Phage-displayed antibody libraries of synthetic heavy chain complementarity determining regions," J Mol Biol (2004) 338(2):299-310.
Simmons et al., "Expression of full-length immunoglobulins in *Escherichia coli*: rapid and efficient production of aglycosylated antibodies," J Immunol Methods (2002) 263(1-2):133-147.
Singer, "Genes & Genomes: A changing perspective," University Sceince Books (1991) pp. 134-145.
Sirac et al., "Light chain inclusion permits terminal B cell differentiation and does not necessarily result in autoreactivity," PNAS (2006) 103(20):7747-7752.
Sirac et al., "Role of the monoclonal κ chain V domain and reversibility of renal damage in a transgenic model of acquired Fanconi syndrome," Blood (2006) 108:536-543.
Sirac et al., "Toward understanding renal fanconi syndrome: step by step advances through experimental models," Contrib Nephrol (2011) 169:247-261.
Sjolander et al., "Integrated Fluid Handling System for Biomolecular Interaction Analysis," Anal Chem (1991) 63:2338-2345.
Skerra. "'Anticalins': a new class of engineered ligand-binding proteins with antibody-like properties," J Biotechnol (2001) 74(4):257-275.
Smith et al., "A novel, native-format bispecific antibody triggering T-cell killing of B-cells is robustly active in mouse tumor models and cynomolgus monkeys," Sci Rep (2015) 5:17943.
Smith et al., "Characterization of a murine lymphokine distinct from interleukin 2 and interleukin 3 (IL-3) possessing a T-cell growth factor activity and a mast-cell growth factor activity that synergizes with IL-3," Proc Natl Acad Sci USA (1986) 83:1857-1861.
Smith et al., "Small Binding Proteins Selected from a Combinatorial Repertoire of Knottins Displayed on Phage," J Mol Biol (1998) 277:317-332.
Smith et al., "Rapid generation of fully human monoclonal antibodies specific to a vaccinating antigen," Nature Protocols (2009) 4(3):372-385.
Smith-Gill et al., "Contributions of immunoglobulin heavy and light chains to antibody specificity for lysozyme and two haptens[1]," J Immunol (1987) 139:4135-4144.
Soriano, "Generalized lacZ expression with the ROSA26 cre reporter strain," Nature Genetics (1999) 21:70-71.
Spillner et al., "Paratope-based protein identification by antibody and peptide phage display," Anal Biochem (2003) 321(1):96-104.
Spiridon et al., "Targeting multiple Her-2 epitopes with monoclonal antibodies results in improved antigrowth activity of a human breast cancer cell line in vitro and in vivo," Clin Cancer Res (2002) 8(6):1720-1730.
M70120EPEIN opposition documents (P22), dated Jun. 21, 2016, 108 pages.
Srinivas et al., "Cre reporter strains produced by targeted insertion of EYFP and ECFP into the ROSA26 locus," BMC Developmental Biology (2001) 1:4 8 pages.
Stein et al., "Translation of vascular endothelial growth factor mRNA by internal ribosome entry: implications for translation under hypoxia," Mol Cell Biol (1998) 18(6):3112-3119.
Stevens, "Human Antibody Discovery, VelocImmune—A novel platform," Pharma Focus Asia (2008) 8:72-74.
Stevenson et al., "DNA vaccines to attack cancer," PNAS (2004) 101(sup 2):14646-14652.
Stijlemans et al., "Efficient Targeting of Conserved Cryptic Epitopes of Infectious Agents by Single Domain Antibodies," J Biol Chem (2004) 279(2):1256-1261.
Stoneley et al., "C-Myc 5' untranslated region contains an internal ribosome entry segment," Oncogene (1998) 16, 423-428.
Storb et al., "Transgenic mice with μand κ genes encoding antiphosphorylcholine antibodies," J Exp Med (1986) 164:627-641.
Storb et al., "Immunoglobulin transgenes as targets for somatic hypermutation," Int J Dev Biol (1998) 42:977-982.
Story et al., "Profiling antibody responses by multiparametric analysis of primary B cells," PNAS (2008) 105(46):17902-17907.
Strelkauskas et al., "Human monoclonal antibody: 2. Simultaneous expression of IgG and IgM with similar binding specificities by a human hybrid clone," Hybridoma (1987) 6(5):479-487.
Struhl et al., "High-frequency transformation of yeast: Autonomous replication of hybrid DNA molecules," Proc Natl Acad Sci USA (1979) 76( 3):1035-1039.
Szabo et al., "Surface plasmon resonance and its use in biomolecular interaction analysis (BIA)," Curr Opin Struct Biol (1995) 5(5):699-705.
Tada et al., "Expression and characterization of a chimeric bispecific antibody against fibrin and against urokinase-type plasminogen activator," J Biotechnol (1994) 33(2):157-174.
Tajiri et al., "Cell-microarray analysis of antigen-specific B-cells: single cell analysis of antigen receptor expression and specificity," Cytometry (2007) 71A:961-967.
Takahashi et al., "Role of thrombospondin-1 in hypoxia-induced migration of human vascular smooth muscle cells," Yakugaku Zasshi (2008) 128(3):377-383 (English abstract included).
Takai et al., "B cell stimulatory factor-2 is involved in the differentiation of cytotoxic T lymphocytes," J Immunol (1988) 140(2):508-512.
Takai et al., "Requirement for three distinct lymphokines for the induction of cytotoxic T lymphocytes from thymocytes," J Immunol (1986) 137(11):3494-3500.
Tan et al., "Superhumanized" Antibodies: Reduction of immunogenic potential by complementarity-determining region grafting with human germline sequences: Application to anti-CD28[1], The Journal of Immunology (2002) 169:1119-1125.
Tanaka et al., "De novo production of diverse intracellular antibody libraries," Nucleic Acids Res (2003) 31(5):e23.
Tanha et al., "Selection by phage display of llama conventional $V_H$ fragments with heavy chain antibody $V_HH$ properties," J Immunol Methods (2002) 263:97-109.
Taylor et al., "A transgenic mouse that expresses a diversity of human sequence heavy and light chain immunoglobulins," Nucleic Acids Research (1992) 20(23):6287-6295.
Thiebe et al., "The variable genes and gene families of the mouse immunoglobulin ϰ locus," Eur J Immunol (1999) 29:2072-2081.
Thomassen et al., "Large-scale production of $V_{HH}$ antibody fragments by *Saccharomyces cerevisiae*," Enzyme and Microbial Technology (2002) 30:273-278.
Thotakura et al., "Glycoprotein hormones: glycobiology of gonadotrophins, thyrotrophin and free a subunit," Glycoblology (1995) 5(1):3-10.

(56) References Cited

OTHER PUBLICATIONS

Throbsy et al., "Isolation and characterization of human monoclonal antibodies from individuals infected with west nile virus §," Journal of Virology (2006) 80(14):6982-6992.
Tiller et al., "Efficient generation of monoclonal antibodies from single human B cells by single cell RT-PCR and expression vector cloning," Journal of Immunological Methods (2008) 329:112-124.
Toki et al., "Analyses of T-cell differentiation from hemopoietic stem cells in the $G_o$ phase by an in vitro method," Proc Natl Acad Sci USA (1991) 88:7548-7551.
Tokimitsu et al., "Single lymphocyte analysis with a Microwell array chip," Cytometry (2007) 71A:1003-1010.
Torres et al., "Laboratory protocols for conditional gene targeting," Oxford University Press (1997) 15 pages.
Traggai et al., "An efficient method to make human monoclonal antibodies from memory B cells: potent neutralization of SARS coronavirus," Nature Medicine (2004) 10(8):871-875.
Transue et al., "Camel single-domain antibody inhibits enzyme by mimicking carbohydrate substrate," Proteins (1998) 32(4):515-522.
Urlaub et al., "Isolation of Chinese hamster cell mutants deficient in dihydrofolate reductase activity," Proc Natl Acad Sci USA (1980) 77(7): 4216-4220.
Vagner et al., "Alternative Translation of Human Fibroblast Growth Factor 2 mRNA Occurs by Internal Entry of Ribosomes," Mol Cell Biol (1995) 15(1): 35-44.
Vajdos et al., "Comprehensive functional maps of the antigen-binding site of an anti-ErbB2 antibody obtained with shotgun scanning mutagenesis," J Mol Biol (2002) 320(2):415-428.
Valenzuela et al., "High-throughput engineering of the mouse genome coupled with high-resolution expression analysis," Nat Biotechnol (2003) 21(6):652-659.
Van Den Berg, "Formulation and delivery of dermal DNA vaccines," Gildeprint Drukkerijen B.V (2009) 160 pages.
Van Den Beunken et al., "Building Novel Binding Ligands to B7.1 and B7.2 Based on Human Antibody Single Variable Light Chain Domains," J Mol Biol (2001) 310:591-601.
Van Der Heijden et al., "Structural and functional studies on a unique linear neutralizing antigenic site (G5) of the rabies virus glycoprotein," J Gen Virol (1993) 74(Pt 8):1539-1545.
Van Der Vuurst De Vries et al., "Dissecting the human peripheral B-cell compartment with phage display-derived antibodies," Immunology (1999) 98:55-62.
Vaughan et al., "Human antibodies with sub-nanomolar affinities isolated from a large non-immunized phage display library," Nat Biotechnol (1996) 14(3):309-314.
Verma et al., "Antibody engineering: Comparison of bacterial, yeast, insect and mammalian expression systems," J Immunol Methods (1998) 216:165-181.
Wang et al., "A T cell-independent antitumor response in mice with bone marrow cells retrovirally transduced with an antibody/Fc-gamma chain chimeric receptor gene recognizing a human ovarian cancer antigen," Nat Med (1998) 4(2):168-172.
Ward et al., "Binding activities of a repertoire of single immunoglobulin variable domains secreted from *Escherichia coli*," Nature (1989) 341:544-546.
Warnaar et al., "Purification of Bispecific F(ab')2 from Murine Trinoma OC/TR with Specificity for CD3 and Ovarian Cancer," Hybridoma (1994) 13(6):519-526.
Weeratna et al., "CPG ODN allows lower dose of antigen against hepatitis B surface antigen in BALB/c mice," Immunology and Cell Biology (2003) 81:59-62.
Weinberger et al., "Cellular interactions in the generation of cytolytic T lymphocyte responses: Role of Ia-positive splenic adherent cells in presentation of H-2 antigen," Proc Natl Acad Sci USA (1980) 77(10):6091-6095.
Weinberger et al., "Cellular interactions in the generation of cytolytic T lymphocyte responses. Analysis of the helper T cell pathway," Eur J Immunol (1981) 11(5):405-411.
Weiner et al., "Fully human therapeutic monoclonal antibodies," J Immunother (2006) 29(1):1-9.

Wen et al., "Tricistronic viral vectors co-expressing interleukin-12 (IL-12) and CD80 (B7-1) for the immunotherapy of cancer: Preclinical studies in myeloma," Cancer Gene Ther (2001) 8(5):361-370.
Whittington et al., "DNA vaccination controls Her-2$^+$ tumors that are refractory to targeted therapies," Cancer Res (2008) 68(18):7502-7511.
Wigler et al., "Biochemical Transfer of Single-Copy Eucaryotic Genes Using Total Cellular DNA as Donor," Cell (1978) 14:725-731.
Wilmut et al., "Basic techniques for transgenesis," J Reprod Fertil Suppl (1991) 43:265-275.
Wilmut et al., "Viable offspring derived from fetal and adult mammalian cells," Nature (1997) 385(6619):810-813.
Winter et al., "Insertion of 2 KB of bacteriophage DNA between an immunoglobulin promoter and leader exon stops somatic hypermutation in a κ transgene," Molecular Immunology (1997) 34(5):359-366.
Wrammert et al., "Rapid cloning of high-affinity human monoclonal antibodies against influenza virus," Nature (2008) 453:667-672.
Wright et al., "Effect of glycosylation on antibody function: implications for genetic engineering," Trends Biotechnol (1997) 15(1):26-32.
Wu et al., "Simultaneous targeting of multiple disease mediators by a dual-variable-domain immunoglobulin," Nature Biotechnology (2007) 25(11):1290-1297.
Wunderlich et al., "Generation of inducible Cre systems for conditional gene inactivation in mice," der Universitat zu Koln (2004) 413 pages.
X59315 Annotation, "IMGT/LIGM-DB sequence," (2016) 13 pages.
Xiang et al., "The downstream transcriptional enhancer, Ed, positively regulates mouse Igκ gene expression and somatic hypermutation[1]," The Journal of Immunology(2008) 180:6725-6732.
Yang et al., "Control of gene conversion and somatic hypermutation by immunoglobulin promoter and enhancer sequences," J Exp Med (2006) 203(13):2919-2928.
Yarlin, "Fundamentals of Immunology," Meditsina (1999) 2 pages.
Ye et al., "Ultrabithorax and Antennapedia 5' Untranslated Regions Promote Developmentally Regulated Internal Translation Initiation," Mol Cell Biol (1997) 17(3):1714-1721.
Yelverton et al., "Rabies virus glycoprotein analogs: biosynthesis in *Escherichia coli*," Science (1983) 219(4585):614-620.
Yu et al., "An optimized electrofusion-based protocol for generating virus-specific human monoclonal antibodies," Journal of Immunological Methods (2008) 336:142-151.
Yoo et al., "Structural Requirements for Polymeric Immunoglobulin Assembly and Association with J Chain," J Biol Chem (1999) 274(47): 33771-33777.
Yoshio-Hoshino et al., "Establishment of a new interleukin-6 (IL-6) receptor inhibitor applicable to the gene therapy for IL-6-dependent tumor," Cancer Res (2007) 67(3):871-875.
Zacharchuk et al., "Programmed T lymphocyte death. Cell activation- and steroid-induced pathways are mutually antagonistic," J Immunol (1990) 145(12):4037-4045.
Zamai et al., "Optimal Detection of Apoptosis by Flow Cytometry Depends on Cell Morphology," Cytometry (1993)14:891-897.
Zhan-Zabel et al., "Development of stable cell lines for production or regulated expression using matrix attachment regions," J Biotech (2001) 87:29-42.
Zhu et al., "Inhibition of tumor growth and metastasis by targeting tumor-associated angiogenesis with antagonists to the receptors of vascular endothelial growth factor," Invest New Drugs (1999) 17(3):195-212.
Zhu et al., "Inhibition of Vascular Endothelial Growth Factor-induced Receptor Activation with Anti-Kinase Insert Domain-containing Receptor Single-Chain Antibodies from a Phage Display Library," Cancer Res (1998) 58:3209-3214.
Zhu et al., "Remodeling domain interfaces to enhance heterodimer formation," Protein Science (1997) 6:781-788.
Zou et al., "Generation of mouse strain that produces immunoglobulin κ chains with human constant regions," Science (1993) 262:1271-1274.

(56) References Cited

OTHER PUBLICATIONS

Zubler et al., "Theoretical and practical aspects of B-cells activation: murine and human systems," Immunological Reviews (1987) 99:281-299.
Abstract of Japanese patent application 2006109711, dated Apr. 27, 2006, 1 page.
First witness statement of Andrew Joseph Murphy, dated Oct. 2, 2015, 19 pages.
Mazor et al., "Isolation of engineered, full-length antibodies from libraries expressed in *Escherichia coli*," Nature Biotechnology (2007) 25(5):563-565.
Documents cited in opposition to Merus B.V. AU application No. 2009263082 by Regeneron Pharmaceuticals, Inc, dated Oct. 10, 2016, 5 pages.
Opposition against Japanese Patent application 5749161, dated Jan. 15, 2016, 55 pages.
Notice of Reasons for Revocation for JP 5749161, dated Mar. 17, 2016, 8 pages.
Third party observations under article 115 EPC against European Parent Application No. 09075279.1 in the name of Merus BV, dated Apr. 25, 2012, 6 pages.
Third party observation against European Parent Application No. 09075279.1 in the name of Merus BV, dated Aug. 28, 2013, 11 pages.
Patent Oppositions Application No. 2009263082, dated May 4, 2015, 3 pages.
Information sheet for submitted publications for JP Application No. 2011-516168, dated Apr. 25, 2012, 3 pages.
Patent applicant's outline of submissions for Australian patent application 2009263082, dated Sep. 6, 2016, 49 pages.
Australian opposition procedure, dated Jun. 27, 2014, 1 page.
Communication pursuant to Rule 114(2) EPC, dated Nov. 5, 2012, 7 pages.
Notification of material filed under section 27, dated Apr. 1, 2014, 1 page.
Content of Arguments, dated Jun. 21, 2016, 25 pages.
Documents regarding Opposition (Declaration of Peter Hudson and Robert Brink), dated Jun. 2, 2015, 1 page.
Opponent's final supplementary submissions, dated Oct. 19, 2016, 4 pages.
Declaration of Christopher Goodnow, dated Oct. 16, 2016, 13 pages.
Opponent's initial supplementary submissions, dated Oct. 5, 2016, 7 pages.
Letter enclosing written submissions and fee, dated May 18, 2015, 1 page.
M70120EPEIN opposition documents (P1), dated Jun. 21, 2016, 80 pages.
M70120EPEIN opposition documents (P2), dated Jun. 21, 2016, 61 pages.
M70120EPEIN opposition documents (P3), dated Jun. 21, 2016, 71 pages.
M70120EPEIN opposition documents (P4), dated Jun. 21, 2016, 80 pages.
M70120EPEIN opposition documents (P5), dated Jun. 21, 2016, 100 pages.
M70120EPEIN opposition documents (P6), dated Jun. 21, 2016, 100 pages.
M70120EPEIN opposition documents (P7), dated Jun. 21, 2016, 60 pages.
M70120EPEIN opposition documents (P8), dated Jun. 21, 2016, 60 pages.
M70120EPEIN opposition documents (P9), dated Jun. 21, 2016, 60 pages.
M70120EPEIN opposition documents (P10), dated Jun. 21, 2016, 60 pages.
M70120EPEIN opposition documents (P11), dated Jun. 21, 2016, 60 pages.
M70120EPEIN opposition documents (P12), dated Jun. 21, 2016, 100 pages.
M70120EPEIN opposition documents (P13), dated Jun. 21, 2016, 100 pages.
M70120EPEIN opposition documents (P14), dated Jun. 21, 2016, 100 pages.
M70120EPEIN opposition documents (P15), dated Jun. 21, 2016, 100 pages.
M70120EPEIN opposition documents (P16), dated Jun. 21, 2016, 80 pages.
M70120EPEIN opposition documents (P17), dated Jun. 21, 2016, 70 pages.
M70120EPEIN opposition documents (P18), dated Jun. 21, 2016, 70 pages.
M70120EPEIN opposition documents (P19), dated Jun. 21, 2016, 100 pages.
M70120EPEIN opposition documents (P20), dated Jun. 21, 2016, 100 pages.
M70120EPEIN opposition documents (P21), dated Jun. 21, 2016, 80 pages.
M70120EPEIN Proprietor documents (P1), dated Jul. 27, 2016, 100 pages.
M70120EPEIN Proprietor documents (P2), dated Jul. 27, 2016, 100 pages.
M70120EPEIN Proprietor documents (P3), dated Jul. 27, 2016, 80 pages.
M70120EPEIN Proprietor documents (P4), dated Jul. 27, 2016, 57 pages.
M70120EPEIN Proprietor EPA document, dated Jan. 12, 2016, 51 pages.
M70121EPEIN Oppo EPA (P1), dated Jul. 27, 2016, 60 pages.
M70121EPEIN Oppo EPA (P2), dated Jul. 27, 2016, 60 pages.
M70121EPEIN Oppo EPA (P3), dated Jul. 27, 2016, 50 pages.
M70121EPEIN Oppo EPA (P4), dated Jul. 27, 2016, 60 pages.
M70121EPEIN Oppo EPA (P5), dated Jul. 27, 2016, 80 pages.
M70121EPEIN Oppo EPA (P6), dated Jul. 27, 2016, 90 pages.
M70121EPEIN Oppo EPA (P7), dated Jul. 27, 2016, 100 pages.
M70121EPEIN Oppo EPA (P8), dated Jul. 27, 2016, 80 pages.
M70121EPEIN Oppo EPA (P9), dated Jul. 27, 2016, 100 pages.
M70121EPEIN Oppo EPA (P10), dated Jul. 27, 2016, 120 pages.
M70121EPEIN Oppo EPA (P11), dated Jul. 27, 2016, 100 pages.
M70121EPEIN Oppo EPA (P12), dated Jul. 27, 2016, 60 pages.
M70121EPEIN Oppo EPA (P13), dated Jul. 27, 2016, 59 pages.
M70121EPEIN Proprietor document (P1), dated Aug. 31, 2016, 100 pages.
M70121EPEIN Proprietor document (P2), dated Aug. 31, 2016, 80 pages.
M70121EPEIN Proprietor document (P3), dated Aug. 31, 2016, 60 pages.
M70121EPEIN Proprietor document (P4), dated Aug. 31, 2016, 60 pages.
M70121EPEIN Proprietor document (P5), dated Aug. 31, 2016, 100 pages.
M70121EPEIN Proprietor document (P6), dated Aug. 31, 2016, 100 pages.
M70121EPEIN Proprietor document (P7), dated Aug. 31, 2016, 80 pages.
M70121EPEIN Proprietor document (P8), dated Aug. 31, 2016, 80 pages.
M70121EPEIN Proprietor document (P9), dated Aug. 31, 2016, 90 pages.
M70121EPEIN Proprietor document (P10), dated Aug. 31, 2016, 70 pages.
M70121EPEIN Proprietor document (P11), dated Aug. 31, 2016, 58 pages.
Canada Office Action for CA 2,729,095, dated Nov. 10, 2015, 8 pages.
Response to Office Action for CA 2,729,095, dated May 10, 2016, 12 pages.
Documents to CA Patent Office, Sep. 16, 2015, 15 pages.
Voluntary Amendment, dated May 12, 2016, 2 pages.
M70121PCEPT1 documents(P1), dated Aug. 8, 2016, 100 pages.
M70121PCEPT1 documents (P2), dated Aug. 8, 2016, 100 pages.
M70121PCEPT1 documents (P3), dated Aug. 8, 2016, 100 pages.
M70121PCEPT1 documents (P4), dated Aug. 8, 2016, 100 pages.

(56) References Cited

OTHER PUBLICATIONS

M70121PCEPT1 documents (P5), dated Aug. 8, 2016, 100 pages.
M70121PCEPT1 documents (P6), dated Aug. 8, 2016, 90 pages.
Roitt et al., "Really Essential Medical Immunology," Blackwell Science (2000) 17 pages.
Response to Communication, dated Sep. 29, 2014, 7 pages.
Declaration of Peter Hudson, dated Jun. 17, 2016, 15 pages.
Non-final Office Action for JP 2015-097258, dated Apr. 11, 2016, 7 pages.
Communication of notices of opposition (R. 79(1) EPC), dated Sep. 25, 2014, 1 page.
Notice of Opposition, dated Jun. 20, 2014, 1 page.
Notification for JP 2011-516168, dated May 20, 2014, 1 page.
Third Party Observations, dated Jun. 27, 2013, 16 pages.
Third Party Observations, dated May 16, 2013, 82 pages.
Letter regarding Notice of Opposition, dated Jun. 23, 2014, 1 page.
Opponent counter argument, dated Aug. 22, 2016, 19 pages.
Canada Office Action for CA 2,729,095, dated Apr. 16, 2014, 1 page (Protest section 10).
Canada Office Action for CA 2,729,095, dated Apr. 16, 2014, 1 page (Letter).
Correspondence from Canadian Patent Office, dated Apr. 8, 2014, 16 pages.
Correspondence from Canadian Patent Office, dated Sep. 16, 2015, 15 pages.
Statement of Grounds and Particulars, dated Sep. 22, 2014, 35 pages.
Information in EP 09075279.1, dated Oct. 28, 2016, 1 page.
Communication of a notice of opposition, dated Aug. 20, 2014, 1 page.
Response to Communication under Rule 79(1) EPC, dated Apr. 2, 2015, 32 pages.
Opposition against EP 2147594, dated Aug. 11, 2014, 55 pages.
Annexure PH-4 (P1), dated Jul. 13, 2009, 37 pages.
Annexure PH-4 (P2), dated Jul. 13, 2009, 37 pages.
Carrion et al., "Light chain inclusion permits terminal B cell differentiation and does not necessarily result in autoreactivity," PANS (2006) 103(20):7747-7752.
Patent applicant's outline of submissions, dated Sep. 16, 2016, 15 pages.
Letter regarding new prior art documents, dated Mar. 18, 2014, 8 pages.
Notification of Material filed under Section 27, dated Oct. 28, 2013, 25 pages.
Summary of submissions on behalf of Merus B.V, dated May 18, 2015, 6 pages.
Third party observation, dated May 9, 2014, 14 pages.
Communication pursuant to Rule 114(2) EPC, dated Oct. 10, 2013, 4 pages.
Office Action for U.S. Appl. No. 15/140,321, dated Sep. 2, 2016, 58 pages.
Translation of the pertinent portions of the Action, dated 2016, 11 pages.
Payment of fees and expenses, dated Nov. 10, 2016, 1 page.
Notice of Opposition in EP 2701499, dated Nov. 10, 2016, 27 pages.
Extension of time limit pursuant to Rule 132 EPC, dated Jul. 5, 2016, 6 pages.
Communication of further notices of opposition pursuant to Rule 79(2) EPC, dated Jun. 29, 2016, 1 page (Fritz Lahrtz).
Notice of Opposition in EP 2501817, dated May 25, 2016, 28 pages.
Payment of fees and expenses, dated May 25, 2016, 1 page.
Annex in EP 14163642.3, dated Jan. 29, 2016, 3 pages.
Third party observation for application EP 20120783456, dated Jun. 16, 2016, 3 pages.
Joint Stipulation and Proposed order of invalidity and non-infringement of U.S. Pat. No. 8,502,018, dated Feb. 24, 2015, 7 pages.
Documents filed by proprietor during opposition, dated Aug. 26, 2016, 8 pages.
Communication of further notices of opposition pursuant to Rule 79(2) EPC, dated Aug. 23, 2016, 100 pages (P1).
Communication of further notices of opposition pursuant to Rule 79(2) EPC, dated Aug. 23, 2016, 100 pages (P2).
Communication of further notices of opposition pursuant to Rule 79(2) EPC, dated Aug. 23, 2016, 100 pages (P3).
Communication of further notices of opposition pursuant to Rule 79(2) EPC, dated Aug. 23, 2016, 100 pages (P4).
Communication of further notices of opposition pursuant to Rule 79(2) EPC, dated Aug. 23, 2016, 120 pages (P5).
Communication of further notices of opposition pursuant to Rule 79(2) EPC, dated Aug. 23, 2016, 100 pages (P6).
Communication of further notices of opposition pursuant to Rule 79(2) EPC, dated Aug. 23, 2016, 100 pages (P7).
Communication of further notices of opposition pursuant to Rule 79(2) EPC, dated Aug. 23, 2016, 80 pages (P8).
Communication of further notices of opposition pursuant to Rule 79(2) EPC, dated Aug. 23, 2016, 80 pages (P9).
Communication of further notices of opposition pursuant to Rule 79(2) EPC, dated Aug. 23, 2016, 70 pages (P10).
Communication of further notices of opposition pursuant to Rule 79(2) EPC, dated Aug. 23, 2016, 100 pages (P11).
Communication of further notices of opposition pursuant to Rule 79(2) EPC, dated Aug. 23, 2016, 150 pages (P12).
Communication of further notices of opposition pursuant to Rule 79(2) EPC, dated Aug. 23, 2016, 150 pages (P13).
Communication of further notices of opposition pursuant to Rule 79(2) EPC, dated Aug. 23, 2016, 150 pages (P14).
Communication of further notices of opposition pursuant to Rule 79(2) EPC, dated Aug. 23, 2016, 100 pages (P15).
Communication of further notices of opposition pursuant to Rule 79(2) EPC, dated Aug. 23, 2016, 100 pages (P16).
Communication of further notices of opposition pursuant to Rule 79(2) EPC, dated Aug. 23, 2016, 50 pages (P17).
Communication of further notices of opposition pursuant to Rule 79(2) EPC, dated Aug. 23, 2016, 50 pages (P18).
Communication of further notices of opposition pursuant to Rule 79(2) EPC, dated Aug. 23, 2016, 50 pages (P19).
Communication of further notices of opposition pursuant to Rule 79(2) EPC, dated Aug. 23, 2016, 50 pages (P20).
Communication of further notices of opposition pursuant to Rule 79(2) EPC, dated Aug. 23, 2016, 100 pages (P21).
Communication of further notices of opposition pursuant to Rule 79(2) EPC, dated Aug. 23, 2016, 100 pages (P22).
Communication of further notices of opposition pursuant to Rule 79(2) EPC, dated Aug. 23, 2016, 100 pages (P23).
Communication of further notices of opposition pursuant to Rule 79(2) EPC, dated Aug. 23, 2016, 150 pages (P24).
Communication of further notices of opposition pursuant to Rule 79(2) EPC, dated Aug. 23, 2016, 100 pages (P25).
Communication of further notices of opposition pursuant to Rule 79(2) EPC, dated Aug. 23, 2016, 150 pages (P26).
Communication of further notices of opposition pursuant to Rule 79(2) EPC, dated Aug. 23, 2016, 139 pages (P27).
Communication of further notices of opposition pursuant to Rule 79(2) EPC, dated Aug. 23, 2016, 150 pages (Potter Clarkson LLP) (P1).
Communication of further notices of opposition pursuant to Rule 79(2) EPC, dated Aug. 23, 2016, 150 pages (Potter Clarkson LLP) (P2).
Communication of further notices of opposition pursuant to Rule 79(2) EPC, dated Aug. 23, 2016, 140 pages (Potter Clarkson LLP) (P3).
Communication of further notices of opposition pursuant to Rule 79(2) EPC, dated Aug. 23, 2016, 110 pages (Potter Clarkson LLP) (P4).
Communication of further notices of opposition pursuant to Rule 79(2) EPC, dated Aug. 23, 2016, 150 pages (Potter Clarkson LLP) (P5).
Communication of further notices of opposition pursuant to Rule 79(2) EPC, dated Aug. 23, 2016, 150 pages (Potter Clarkson LLP) (P6).

(56) References Cited

OTHER PUBLICATIONS

Communication of further notices of opposition pursuant to Rule 79(2) EPC, dated Aug. 23, 2016, 150 pages (Potter Clarkson LLP) (P7).
Communication of further notices of opposition pursuant to Rule 79(2) EPC, dated Aug. 23, 2016, 150 pages (Potter Clarkson LLP) (P8).
Communication of further notices of opposition pursuant to Rule 79(2) EPC, dated Aug. 23, 2016, 120 pages (Potter Clarkson LLP) (P9).
Communication of further notices of opposition pursuant to Rule 79(2) EPC, dated Aug. 23, 2016, 85 pages (Potter Clarkson LLP) (P10).
Declaration of Robert Brink, Apr. 30, 2015, 34 pages.
Declaration of Anthony L. DeFranco, Dec. 21, 2014, 56 pages.
Declaration of Peter Hudson, May 1, 2015, 52 pages.
Declaration of Andrew Murphy, Dec. 19, 2014, 18 pages.
Declaration of David Tarlinton, Dec. 21, 2014, 40 pages.
Second Declaration of Robert Brink, Jun. 2, 2015, 38 pages.
Second Declaration of Peter Hudson, Jun. 2, 2015, 81 pages.
Friedrich et al., "Promoter traps in embryonic stem cells: a genetic screen to identify, and mutate developmental genes m mice," Genes & Development (1991) 5:1513-1523.
U.S. Appl. No. 16/852,184, filed Apr. 17, 2020, by Throsby et al. (Copy not submitted herewith pursuant to the waiver of 37 C.F. R. § 1.98(a)(2)(iii) issued by the Office on Sep. 21, 2004).
Abstract to 2006 Macdonald poster (1st International Mugen Conference Sep. 2006, Athens).
Abstract to 2006 Stevens poster (1st International Mugen Conference Sep. 2006, Athens).
Betz et al., "Elements regulating somatic hypermutation of an immunoglobulin kappa gene: critical role for the intron enhancer/ matrix attachment region," Cell (1994) 77(2):239-248.
Bio-Rad Cat No. 165-2105—Gene Pulser® II Electroporation System Instruction Manual.
Clark et al. (2003) Nat. Rev. Gen. 4:825-833.
Declaration and CV of Anthony De Franco originally submitted for the EP1360287 Opposition, dated Sep. 2, 2014.
Declaration and CV of Craig Bassing, originally submitted for the EP1360287 Opposition.
Declaration of Andrew Murphy originally submitted for the EP1360287 Opposition (including appendices), dated Jan. 27, 2014.
Declaration of Dr Andrew Murphy dated Dec. 21, 2016 in opposition proceedings EP2264163.
Declaration of Dr Lynn Macdonald dated Dec. 20, 2016 in opposition proceedings EP2264163.
Declaration of Dr Werner Muller dated Dec. 22, 2016 in opposition proceedings EP2264163.
Declaration of Professor Hidde Ploegh dated Dec. 23, 2016 in opposition proceedings EP2264163.
Declaration of Professor Kenan Murphy dated Dec. 29, 2016 in opposition proceedings EP2264163.
Declaration of Sir Martin Evans dated Dec. 23, 2016 in opposition proceedings EP2264163.
Declaration of Sue Klapholz, originally submitted for the EP1360287 Opposition (including appendicies), Jan. 27, 2014.
DNA Cloning 3, A Practical Approach, 2nd Ed, pp. 112-114.
DNA Sequencing Core Website, dated Nov. 21, 2015.
Email relating to Gene Bridges course on RedET recombination.
Factsheet from Opponent1 re MeMo mouse dated 2012.
GeneBridges course invitation, 2003.
Hansen et al., "Crescendo's Cash Fragments," BioCentury, The BernsteinReport on BioBusiness, Dec. 23, 2013, p. A13.
Honjo et al., (Eds), Immunoglobulin Genes, Academic Press: London, 2nd Edition, (1990) pp. 71, 74-76.
International Preliminary Report on Patentability and Written Opinion for Application No. PCT/NL2009/050381, 11 pages, dated Jan. 5, 2011.
Janeway et al., "Immunobiology: the immune system in health and disease," Current Biology Publications, 4th edition, 1999, chapter 3, pp. 79-113.
Macdonald et al., Poster 2006—Velocigene® Technology Extended to Humanization of Several Megabases of Complex.
Materials from examination of a European Patent Application No. 09075279.1 in the name of O1, Apr. 23, 2013.
Mead et al., "Detection of Bence Jones myeloma and monitoring of myeloma chemotherapy using immunoassays specific for free immunoglobulin light chains," Clinical Laboratory (2003) 49(1-2):25-27.
Moldenhauer, "Bispecific antibodies from hybrid hybridoma," Bispecific Antibodies (2011) pp. 29-46.
Mouse Genome Data available in public databases, Feb. 2001, NIH.
"Murine." Merriam-Webster.com. Merriam-Webster, n.d. Web. Apr. 2, 2018.https://www.merriam-webster.com/dictionary/murine.
"Murinae" Encyclopedia of Life 2018 http://eol.org/pages/2847355/hierarchy_entries/57454206/overview.
NEB 1-Ceul datasheet and heat inactivation table.
NEB PI-Scel datasheet.
Niemann et al., (2005) Rev. Sci, Tech. Off. Int. Spiz. 24:285-298.
NIH website—Mouse BAC end sequencing project.
Opinion of in re Chu, United States Court of Appeals for the Federal Circuit, decided on Sep. 14, 1995.
Pokorna et al., "DNA-vaccination via tattooing induces stronger humoral and cellular immune responses than intramuscular delivery supported by molecular adjuvants," Genetic Vaccines and Therapy (2008) 6:4.
Potter et al., "Transfection by Electroporation," Curr Prot Mol Biol (2003) Chapter 9:Unit9.3. doi: 10.1002/0471142727.mb0903s92.
Prelle (2002) Anat. Histol. Embryol. 31:169-186.
Presentation by Cecile Geuijen, May 27, 2013: Full length human IgG bispecific antibodies for cancer therapy.
Presentation by Open Monoclonal Technology, Inc (Nov. 3, 2013), http://www.openmonoclonaltechnology.com/downloads.html.
Red/ET Recombination guide (Gene Bridges).
Reply letter of proprietor in response to the opposition proceedings against EP 2264163 B1, dated Dec. 30, 2016.
Reply letter of proprietor in response to the opposition proceedings against EP 2501817 B1, dated Dec. 23, 2016.
Riblet et al., "Polymorphism and evolution of Igh-V gene families," Curr. Top. Microbial. Immunol. (1986) 127:168.
Rickert et al., "Impairment of T-cell-dependent B-cell responses and B-1 cell development in CD19-deficient mice," Nature (1995) 376(6538):352-355.
Roebroek et al., "Mutant Lrp1 Knock-In mice generated by recombinase-mediated cassette exchange reveal differential importance of the NPXY motifs in the intracellular domain on LRP1 for normal fetal development," Molecular and Cellular Biology (2006) 26(2):605-616.
Sambrook 3rd Ed Chapter 1.21.
Second Declaration of Craig Bassing (Bassing II), originally submitted for the EP1360287 Opposition, dated Sep. 2, 2014.
Shmerling et al., "Strong and ubiquitous expression of transgenes targeted into the beta-actin locus by Cre/lox cassette replacement," Genesis (2005) 42(4):229-235.
Staerz et al., "Hybrid hybridoma producing a bispecific monoclonal antibody that can focus effector T-cell activity," Proc Natl Acad Sci USA (1986) 83(5):1453-1457.
Statement of Dr Yancopoulos, first witness statement in UK litigation (The High Court of Justice, Chancery Division, Patents Court, Case No. HP-2013-000001/HP-2014-000001 dated Oct. 2, 2015, Report relates to a patent owned by Regeneron Pharmaceuticals, Inc., EP 2264163).
Statement of Professor Anthony De Franco, first witness statement in UK litigation (The High Court of Justice, Chancery Division, Patents Court, Case No. HP-2013-000001/HP-2014-000001 dated Oct. 3, 2015, Report relates to a patent owned by Regeneron Pharmaceuticals, Inc., EP 2264163).
Statement of Professor Ishida submitted in the UK High Court, first witness statement in UK litigation (The High Court of Justice, Chancery Division, Patents Court, Case No. HP-2013-000001/HP-2014-000001 dated Sep. 3, 2015, Report relates to a patent owned by Regeneron Pharmaceuticals, Inc., EP 2264163)000001 dated

(56) References Cited

OTHER PUBLICATIONS

Sep. 3, 2015, Report relates to a patent owned by Regeneron Pharmaceuticals, Inc., EP 2264163).
Stevens et al., Poster 2006—VelocImmune™: Humanization of immunoglobulin loci using VelociGene® technology.
Third Party Observation for Application No. EP20090075279, 11 pages (2013).
Third Party Observations against EP 12186010.0, dated Mar. 13, 2017, 8 pages.
Third Party Observations Against European Parent Application No. 09075279.1 in the Name of Merus BV, 3 pages, dated Jul. 1, 2013.
Third party pre-issuance submission in U.S. Appl. No. 15/090,505, dated Feb. 24, 2017, 30 pages.
Third party pre-issuance submission in U.S. Appl. No. 15/140,321, dated Feb. 10, 2017, 19 pages.
Toledo et al., "RMCE-ASAP: a gene targeting method for ES and somatic cells to accelerate phenotype analyses," Nucleic Acids Research (2006) 34(13):e92.
Wheeler (2001) Theriogenology, 56:1345-1369.
Request for exclusion of file inspection, dated Jul. 12, 2016, 3 pages.
Bruggemann et al., "A repertoire of monoclonal antibody with human heavy chains from transgenic mice," PNAS USA (1989) 86:6709-6713.
Smith et al., "Filamentous fusion phage: Novel expression factors that display cloned antigens on the Virion surface," Science (1985) 228:1315-1317.
U.S. Appl. No. 13/750,753, filed Jan. 25, 2013, Ton Logtenberg.
Roitt, A. et al., Immunology, Mir, Moscow, pp. 134, 214 (2000).
Yarilin, A.A. et al., Osnovy Immunologii, [Fundamentals of Immunology], Meditsina, Moscow, p. 194 (1999).

* cited by examiner

Fig. 12 human germline IGKV1-39/J DNA
```
  1  GAC ATC CAG ATG ACC CAG AGC CCC AGC AGC CTG AGC GCC AGC GTG GGC GAC AGA GTG ACC ATC ACC TGC AGA GCC AGC
 79  CAG AGC ATC AGC AGC TAT CTG AAC TGG TAT CAG CAG AAG CCC GGC AAG GCC CCC AAG CTG CTG ATC TAC GCC GCC AGC
157  TCC CTG CAG AGC GGC GTG CCC AGC AGA TTC AGC GGC AGC GGC TCC GGC ACC GAC TTC ACC CTG ACC ATC AGC AGC CTG
235  CAG CCC GAG GAC TTC GCC ACC TAC TGC CAG CAG AGC TAC AGC ACC CCC CCC ACC TTC GGC CAG GGC ACC AAG GTG GTG
313  GAG ATC AAG
``` human germline IGKV1-39/J Protein
```
  1  DIQMTQSPSS LSASVGDRVT ITCRASQSIS SYLNWYQQKP GKAPKLLIYA
 51  ASSLQSGVPS RFSGSGSGTD FTLTISSLQP EDFATYYCQQ SYSTPPTFGQ
101  GTKVEIK
``` human germline IGLV2-14/J DNA
```
  1  CAG TCT GCC CTG ACC CAG CCC GCC TCT GTG TCT GGC AGC CCT GGC CAG AGC ATC ACC ATC AGC TGC ACC GGC ACC AGC
 79  AGC GAC GTG GGC GGC TAC AAC TAC GTG TCC TGG TAT CAG CAG CAC CCC AAG GCC CCC AAG GCC CTG ATG ATC TAC GAG
157  GTG TCC AAC AGA CCC AGC GGC GTG AGC AAC AGA TTC AGC GGC AGC AAG AGC GGC AAC ACC GCC AGC CTG ACC ATC AGC
235  GGC CTC CAG GCT GAG GAC GAG GCC GAC TAC TAC TGC AGC AGC TAC ACC AGC AGC TCC ACC CTG GTG TTT GGC GGC GGA
313  ACA AAG CTG ACC GTG CTG
``` human germline IGLV2-14/J Protein
```
  1  QSALTQPASV SGSPGQSITI SCTGTSSDVG GYNYVSWYQQ HPGKAPKLMI
 51  YEVSNRPSGV SNRFSGSKSG NTASLTISGL QAEDEADYYC SSYTSSSTLV
101  FGGGTKLTVL
```

Rat IGCK allele a DNA
```
  1  AGA GCC GAC GCC GCT CCC ACC GTG TCC ATC TTC CCC CCC AGC ATG GAA CAG CTG ACC TCT GGC GGA GCC ACC GTG GTC
 79  TGC TTC GTG AAC AAC TTC TAC CCC AGA GAC ATC AGC GTG AAG TGG AAG ATC GAC GGC AGC GAG AGC AGG GAC GGC GTG
157  CTG GAC AGC AGG ACC GAC AGC AAG GAC AGC ACC TAC AGC ATG AGC AGC ACC CTG AAG ATG AGC AGC ACC GAG TAC AAC CGG
235  TAC GAG AGG CAC AAC AGC TAC ACC TGC GAG GTG GTG CAC AAG ACC AGC TCC AGC CCC GTC GTC AAG TCC TTC AAC CGG
313  AAC GAG TGT
```

Fig. 12, contd.

Rat IGCK allele a protein
  1 RADAAPTVSI FPPSMEQLTS GGATVVCFVN NFYPRDISVK WKIDGSEQRD
 51 GVLDSVTDQD SKDSTYSMSS TLSLTKVEYE RHNLYTCEVV HKTSSSPVVK
101 SFNRNEC IGKV1-39/J-Ck
  1 GGT ACC GCG GCC ACC ATG GAC ATG AGA GTG CCC GCC CAG CTC CTG GGG CTC CTG CTA CTC TGG CTC CGA GGT AAG
 79 GAT GGA GAA CAC TAG AAT ATT ACT TTT TGT CAG CCA GTG TGC TCA ACT GGA TCA ACT GGG AAG TTC TCT GAT AAC ATG
157 ATT AAT AGT GAG CGC AAG CGT TTT TAT GTT TCC AAT CAT CTC AGG CTG CAG AGC TGA CCA CAT GAC CAG CCA GCC CCC CAG
235 CAG CCT GAG GCA GAA GCC CGA AGT CAA GCT GAC AGT CTG CGC CGG CAG AGC CCT GCA CTC GCA GAG CGG CGT GCC CAC CTG
313 GTA TCA GCA GAA CAG CGG CTC CAG CCC CGA CTT CAC CTT CGG CAT CAG GGA CGA CTT CGC CGA CTA CAG
391 ATT CAG GCA GAG GTC CAT CTT CCC CAG CAT GGA CCA GGG CTC TGG CGG AGC CTT GGA CTG GCT CTT GAA CAA TCC
469 CTG CCA CGT GTC CAG AGA CAA GGA CAT GTG GAA GAT GAG CAT CGA CAG CCT CGA CGG CAC CCT CGT GAG CGT GCA CTT
547 CAC CGT CAG CAG CAG CTC CAC GGA GGT GCT GCA CAA GGT CGG GCA CCT CGT GGA GTA CGA CAG CGT GAC CAA CGT GAC CGA CCT
625 CTA CCC CAT AGA CAA GGA CAT GTG CAG GAT CTA CAG CCT CGT GAG CGT GGA GTA CGA GAG GCA CAA CCT
703 CCA GGA CAG CAG CTC CAC GGA CAA GAC CAC CAG CCT CAA CCC CGT CAA GTG GAA CCG GTG TTG AGC CGA
781 GTA CAC CTG CGA GGT GGT GCA GAC CTC GGT
859 CGA GCT C IGLV2-14/J-Ck
  1 GGT ACC GCG GCC ACC ATG GAC ATG AGA GTG CCC GCC CAG CTC CTG GGG CTC CTG CTA CTC TGG CTC CGA GGT AAG
 79 GAT GGA GAA CAC TAG AAT ATT TGT GGG CCA CCC TGG CAC CAT GAC AGT CTG CGC CGG CAG CGC AGC TCA ACT GGA CAG CAG TCA GTC CTG GGA AAG TTC TCT GAT AAC ATG
157 ATT AAT AGT GAG CCT TGG CAG CCC TGG CAG CCC CGG CAA GAG CAG CTG CCC CGG CAG CGC AGC ATC CGG CTG CCT GGG TGC CTC GAC GCC CGC CTC
235 TGT GTC TGG GTA TCA GCA GCG CGG CAA GAG CGG CAG CAG CTG CCC CGG CAG CGG CAG CGG CAG CAG CGG CAC CAG GGT GTC CGA CGG CAA CAG CGG CGT GAG
313 GTC CTG CTG GTA ATT CAG CGG CAG CAG CTA CGG CAA GGA CTT GCC CAC GAT GAT GCT CAG CCT GAC CAT CAG GCC CAG CGG CAG ACC CAG GGC CGA GGC CGA
391 CAA CAG CTA CTG CGC CAG CGT GCC CAG CGC CCT GGT GTT TGG CGG CGG CAC TGG CAC AAA GCT GAC CGT CCT GGT GCT CCA GCT CTG CTT CGT
469 CGC CGC TCC CAC CGT CTA CCC CAT GGA CAT CTT CCC CAG GAA CAT CGG CCT CGT GAC GCT CGG GCG CTC TGG CGG CAC CGA GGA CAG GCA GCC CAC GAG AGC CGA
547 GAA CAA CTT CTA CCC CAG AGA CAT CAG CGT GAA GTG GAA GAT CGA CGG CTC CGA GCA GAG GGA CGT GCT CGA CAG
625 CGT GAC CGA CCA GGA CAG CAG CTC GGA CAG CGT CAC CGA CCA GGA CAG CAG CTC CGT GAT GCA GAC CTG CTG GAG CGA GGA GAC GTC CTG GAA CGA GTG
703 GCA CAA CCT GTA CAC CTG CGA GGT GCA GAC CTC GGT CAA GGG CCA CAA GAC CTC GGA GAG AGC GGA GGA GCC CGA
781 TTG AGC TAG CGA GCT
859 C

Fig. 12, contd.

VkP-IGKV1-39/J-Ck

```
   1 GGC CGG CCC ACA TGA AAC AAT GGG AAC CAT GTG ACA ATC ACA GAG TTG TTA CTA CAA AAG GGA TTG TTA CTC
  79 TCC ACA TCC CTT TAA GTA ACT TGA AGG CAA ATA CTC CCA GAT AGA AAT CCC ATA TTC GAC TTC ATT AGA CAT CGA ATG GTT
 157 ATA CTC TCC TGT TCA AAA TAT CTC TTG TCA CAA ATT GCC CTC GTG CTG AGA CAT GAA ATA TTA TTC AGG GTA TTA AAG TTT GAC
 235 TTT TTT CCT CTG GTT ACC TGG CCC CCT GGG TTG ATT TGC TAA GAC AGT ACA GCC CCC TCC CTC CCA GCC CTG TGC TGC TCA
 313 GCT GCC TGC CCC ATG TGC CCC ATG CTG TGA TCA GTC TCA AGG AGC CAC CAT GGA CAT GAG AGT GCC CCA GCT CCT GGG GCT CCT
 391 TCG CAC CTG GCT GTG GCT CCT GGA TCA GTC AGG AGA ACA CTA GGA ATT TAC TCA GCC AGT GTG CTC AGT CCT ATG GGC TGG
 469 GCT ACT CTG GCT CCG AGG TAA CAT GAT TAA TAG CCC TGA GCA GTT CTC TGA TAA CAT GAT TTG TTT TTA TGT TTA CAA GTG CCA GAT GTG ACA TTC
 547 AGG GAA GTT CTC TGA TAA CAT GAT TAA TAG CCC TGA GCA GCC TGA GCG CCA GAG TGA CCA TCA CCT TCA TCA TCA TCA CCT GCA GCC ACA
 625 TCC AGA TGA CCA GCA GCT ACC TGT ACT TTC TCA AGC GGT ATC AGC AGA AGC CCC CCA AGC CCC ACT ACT ACT ACT ACT ACT ACT ACT ACT
 703 GCA TCA GCA GCT GCG CCA TGC CCA CCT ACT TTC TCA AGC GGT ATC AGC AGA AGC CCC CCA AAA AAG CCC CTA AGC CTC TCC CCA GCT CCC
 781 GCA TCA GCA GCT GCG CCA TGC CCA ACT CAG GTT TCA AAA GTC TTT ATC AGT CCA AAA GCC AGG AGG CCG GCA TCA CCA AGG TGG AGA
 859 TGC AGA GCG ACT TCG CCA CCT ACT TTC TCA AGC GGT TTT CTG ATC TCT GAG GGC GAG GGC AGG AGA GAT ATC ACA AAA AAG CCC CTA AGC
 937 CCG AGG ACT TCG CCA CCT ACT TTC TCA AGC GGT TAT CTG GAT CTG ACA ATG CCC AAA AAA AAG AGG GCT GTT ATT CTC TAC GCT GCT GAG TCA ATC
1015 TCA AAC GTA AGT ACA CTT TCT CCA AGG ATG GCA CTT CTC AAA ATA AAT ACA CAT GTA GAT CAC TAT GGT GAA GTT CAA GTC AAG GAT TGG GGC CAG AGG AAG AAT AGA AAT CAG AAA CAG TAA AAA CAG
1093 GTG GCA TTA GGG GCA AAA ATG GAG AGA AGG GCT TTT CAT AGT GCT TGA GAG GTC TGA CTG AAG AAG AGG GCT CAG AGG AGA CAG GCT GCG TTG GAG GAG TAG GTC CAG AGT AAA AAC
1171 GTG AGA TTA GGG GCA AAA ATG GAG AGA AGG GCT TTT CAT AGT GCT TGA GAG GTC TGA CTG AAG AAG AGG GCT CAG AGG AGA CAG GCT GCG TTG GAG GAG TAG GTC CAG AGT TGG GGC
1249 GGA GAA GCA TGA GGG GAT GAG GAA ACT TTG CAT CTG TTG AAA GTA GTT ATT GAG AAC TTC AGG AAG GGC TGG GTC TTG TAT CCA CTC CTG GAC CTC TGA GAG AAA
1327 TTT GGA GGG CAA ACT TTG AAG GAT CAT CCG AGT TCT TGT CTC CAA AAT ACA AGT GTC CTA ATG TTA CAC ATC GCT TTT AAA CAG TAA AAT CAG TAA GAG TCA CAG TAG AAA TAA
1405 GAG GAG AAG GAG CGT AGC CAT CTG TTG AAA GTA TGA TGA AAT ACA TGA GTT TCT GCC AAA ATG TAA ATT GGA ACC TCT GTA GTA TGT AAG AGG AGG AGG AGG AGG AGG AGG AGG AGG AGG AGG AGG AGG AGG AGG AGG AGG AGG AGG AGG AGG
1483 GAG GAG AAG GAG ACT TTG GAT CAT CCG AGT TCT CAT CGG AGT TAT GTT TTC CAA CTG GGT GAC CTC GCG GCT GTG GAC CAC TTT TAG AGG TCA TTG CCA GCC
1561 GTG GTG GCA ACT TTG AAG GAT CAT CCG AGT TAT ATA CCA AGA GAC TCT GTA GGA CTT TTC GGT GAC CTG ACA GAT GTG TTA TAT TAG ATG AAA AAT ATG ACT
1639 TCA TTA AGC TGT TTG AAA GTA TCA CAA AAT ACA TGA CGG CCT TGA GTC CGA CTT TTC CTT TTT CTT TAT TAT CTT ATA TTC TAG AGG TCA TTG CCA GCC
1717 TTA TTC TAA GTT CTC ATT TCT ACA TGA GCT TTG TAA GAC ACC TCT GAA CCC CCG GAC AGT GAT GTG TTA TCC CTT ATA ATC AAT TAT CTA GCG GTG CTT CCT
1795 TTT TTT TCT GAA CTA TAT GCC AGC CCT ATG GGA CTG AAA CGG CTG TAA GGG GCA TCC GCG AAA TCT AGT TAT TAT TAT TAT TAT TAT TAT TAT TAT TAT
1873 TTT TAT ATC GCC AGC CCC TGC CGC TGC CAG CAG AGT TGC CAC TAA TTA TAA AGC TCT TAC AAA TCT TAG CAC GTG CTC GAC CAC TTT CCT
1951 TTT TAT ATC GCC AGC CCC TGC CGC TGC CAG CAG AGT TGC CAC TAA TTA TAA AGC TCT TAC AAA TCT TAG CAC GTG CTC GAC CAC TTT CCT
2029 ATT TGG CGT TCA CCC TGC TGA CAG CAG AGT TGC CAC TAA TCT AGA GAT TGC TTT AAT ATT CTT TAA ACT GGT TAG TGT TAG TGT AAA AAT ACT ATA ATC
2107 GAG GCA CAG TGA TGA CTT ATT GGA CTT ATT GGA AAC TGC TTT AAT ATT CTT TAA ACT GGT TAG TGT TGT GAT AGA ATG AAA CAA CTA TTT AAG GAC TTC CCT TTA
2185 AGG AAA GGG TGA CTT ATT GGA AAC TGC TTT AAT ATT CTT TAA ACT GGT TAG TGT TGT GAT AGA ATG AAA CAA CTA TTT AAG GAC TTC CCT TTA
2263 GGA ATT AGA AAG GCA AAA GTC ATG GTA AAT ATT TGT GAC ATG AGC TAT TTC CCA ATA CTT GTT ATT CTT TAA ACT TAA GCT CAT TTT TTC CGA TTG TAA GCC
2341 CTA CAG CCA GTT AAA ATA TAA ATT TGT GAC ATG AGC TAT TTC CCA ATA CTT GTT ATT CTT TAA ACT TAA GCT CAT TTT TTC CGA TTG TAA GCC
2419 CTG GTT AAA AAT TTA GCA CAA CTA TTT ATT AGC CAT CAT TTC TGA CCC TTC TAA CTT AAT TCT AGA GGC CAT CTG TTA AAT GAC TTC CAG TTT CCT
2497 AAT AAT TTT TGA AAA CTA CTT TAG AGT TAG AGG GGG AAG AGT TGC CAA GTT CCT CCC AAG AGT GCA ATT TCA AAA CTA TTT AAG GAC TTC CCT TTA
2575 CCA TAA CTC TTG TAA TTT ATT TCA AGG GGA AAG AGT TGC CAA GTT CCT CCC AAG AGT GCA ATT TCA AAA CTA TGA TGT CAA TGT CAA TCT CAG TTT TCG
2653 AAA CAC TTG TAA TTT ATT TCA AGG GGA AAG AGT TGC CAA GTT CCT CCC AAG AGT GCA ATT TCA AAA CTA TGA TGT CAA TGT CAA TCT CAG TTT TCG
2731 AAC TAT TAA TTT CTA CTG TCA AAC CTG ATA ATT TAA CTC ATA ATT TAA AAC AGG GCC CAT CTC TTC AAG AAC TCT CAG TTT GCT TAA
2809 GAG TTT TTA CTA CCT CTG TCA AAC CTG ATA ATT TAA CTC ATA ATT TAA AAC AGG GCC CAT CTC TTC AAG AAC TCT CAG TTT GCT TAA
2887 GAT CAG AGG TGA AAG CAT CTG ACA AAC CAT TAG CCT CCC AAG GTG GCC CAG ATT GCT ACA GTT TCT GGA CAC CCA AAT ACA GAC
2965 TTG TCC CAT GTG GTT ACA AAC CAT TAG CCT CCC AAG GTG GCC CAG ATT GCT ACA GTT TCT GGA CAC CCA AAT ACA GAC
```

Fig. 12, contd.

```
3043 CCT GGC TTA AGG CCC TGT CCA TAC AGT AGG TTT AGC TTG GCT ACA CCA AAG GAA GCC ATA CAG AGG CTA ATA TCA GAG
3121 TAT TCT TGG AAG AGA CAG AGA ATG AAA ATG GCC AGT TTC TGC CTT ATG AGT TCA GAC TCC CAA ACA
3199 TCA GGA GTG TCA GAT AAA CTG TGA ATC GTC TGA AGC TG GAA CTG AAA TTT ACT TTC TGA AGA TAG TTT CAG GGA AGA AAG
3277 GCA ATA GAA GGA ACA AGA ATA TCT TCA AAG GGT GCA TCC TGG ATA AGA ATG TAA ATC TTC GTA GGG ATA AGC TAG CTA GGG
3355 AAT AAC TTA GAA ACA AGA TTG TAT ATA ACT GTT TGT TAC ACA CCC CAT GAA ATG GAG CCC CTT GTT ACT TCA AGC GTG CTT
3433 TTT TGT CTG TGC TTC GTA TCT CCT CAG GGG ACG CCG ACA CTC ACT TGT CCA GAG TCC CCA GCA TGG AAC AGC TGA CAT
3511 CCT CTG GCG AGC GAG CCA CCG TGG TCT GCT TCG ACA GCG TGA CCT ACA GCA TGA GCA AGA TCG ACG GCA
3589 CTG GCG AGC AGA GGG ACG GCG TGC AGT ACG ACG GGC TGG ACA CCT GCG GAG GCA CCA GCT CCA GCC CCG
3667 GCG AGC TGA GCG AGA GGG ACG GCG TGC AGT ACG ACG GGC TGG ACA CCT GCG GAG GCA CCA GCT CCA GCC CCG
3745 TGA GCC TGA CCA TGG AGT CCT TCA ACC GGA ACG AGT GCT GAA GAC AAA GTT CCA CAA CCA GCT CCC CAT CCT
3823 TGG TCA AGT CCT TCA AGC GTC TTG GAG GCT TCC CCA ACA GAA GGT CTA AAT GCG ACA CTG TGC CCA AAC CTC CCC ACC
3901 ATC TTC TCC TCC CCT CTG GCT TTG CTT ATC ATG CTA ATT CAA AAT CAA AAT ATT CAA AAT CAA AGT GAG TCT TTG
3979 TCC TTC TCC CCT CTG GCT TTG CTT ATC ATG CTA ATT CAA AAT CAA AAT ATT CAA AAT CAA AGT GAG TCT TTG
4057 CAC TTG AGA TCT CTG TCT TTC CTA GTT TGC CTT TTC AAT CAC CAG ATA TTT AAT CTT ATT GGG TTT CCC TTG GCT GAG GAG
4135 AGT TAA ATG GCA GTC CTA GTT ACC CAG ATT CAA GAA ATC GTT TAA CCC TAA ACT TGG CGA AGC GTA GAA ACC ATG TTC TAA ATG TGC
4213 CAC TAC ATG TTC CTA GTT ACC CAG ATT CAA CCT CAG AAT GTG CCT TCA CTA AGT TTT TAA ACA
4291 GCA TAC TTC CTA GTT ACC CAG ATT CAA AAG GCC CAT GCA TTG CCA TGC ATT GCC TGA ACA CCA CCA AAC AAT TAA ATG TGC
4369 CTG ATT CAA CCT CAG AAT GTG GAA GCC CAT GCA TTG CCA TTG GGA CAA ATT CTC GGC ACT ACC CAC CCA TTA GGT GCT TCT CTC TGT
4447 AAG CAA TAG GAA TCC TAT CTG CCA TTG GGA CAA ATT CTC GGC ACT ACC CAC CCA TTA GGT GCT TCT CTC TGT
4525 TGA GCT GGC TCC TAT CTG CCA TTG GGA CAA ATT CTC GGC ACT ACC CAC CCA TTA GGT GCT TCT CTC TGT
4603 ACA CAC ATA CAT CAA AAT TTG GGA AGC AGC GAT CTA CCA ACG TGA GAG ACT TGA TGA ACT CTT AAA ACT TAA AAT GTC
4681 ACA CCA GAA ACC TTA AGC AGC CAT TAT GAC AAC CAG AGA TTC ACA ATT GAG CTT AAT TTT TAA AAG CAG GTA AAA
4759 CAC CAA CAG TTA AGG AAA TCT TAA ACA AGA TAA AGA TTT GGA AAA CTC CCT GTA AAG GTT CTG TCT CTC TGT
4837 CAT AGT TTA AAT AAG AGA TTA AAT AAG AGA TTA TTT GGA AAA CTC CCT GTA AAG GTT CTG TCT CTC TGT
4915 TTT AAA ATT GGA TGT GAA ATA TCT AAT ACC CAG TGC ATA CAG AGA ATC AAA ATC CTT CAA GGC CAG AAA GAC
4993 ATG CCT AAA GAA GTA GGG GAT AAT CCA GGA TCA AAT TGA TCC AAC AGG TCA AAG AAT ATA GGT AGT TGC GCC AAA CTG TAA AAG TAC
5071 CCT AAT AAA ACA CAT AAT AAT CCA GGA TCA AAT TGA TCC AAC AGG TCA AAG AAT ATA GGT AGT TGC GCC AAA CTG TAA TAA
5149 AAT AAA ACA CAT AAT AAT TCA AAC ACC TTC ATC AAC AGG TCA AAG AAT ATA GGT AGT TGC GCC AAA CTG TAA TAA
5227 AAA ACA ATA GGG GAT ACA GAG ACC TTC ATC AAC AGG TCA AAG AAT ATA GGT AGT TGA GCC CAC GCA TGC ATT TAG
5305 AAT ACA ATA GAA GGG GAT ACA GAG ACC TTC ATC AAC AGG TCA AAG AAT ATA GGT AGT TGA GCC CAC GCA TGC ATT TAG
5383 AAG GTT ACA TTA CAC GAG AAG GAA GGA GAC CAC ACA TTT AAG CAT TTC CCT CTT CAC TTC AGC CTA CAC CCT CTT GAA GGA GAA TAA
5461 TCC CTC GTG GGA TCA TCC CCC CAG TTA ATA AGG AGA TTT TTT TTA ATT TGC CTC TCT AAA TAG AAT GCC ATT TTA ACA CTG AGC CTT
5539 TGT TAG TGT CCC TTC CCC CAG AAT TGC CAT TCT AAA AAA AAA AGA ATA TCT TTA TAT TTA GAA CTT GTG GGA ACC
5617 GGG AAA GGA ACT TCT AAT CAG TGC CTC TTA TCT CAA AAA AAA AGA ATA TCT TTT ATA TGT TCG AGT CTT
5695 TTT GAA TTT ATC AAT CAG TGC CTC TTA TCT CAA AAA AAA AGA ATA TCT TTT ATA TGT TCG AGT CTT
5773 AAA ATC TAA AAC AGA ACC ATA ATC GAT CCT AGG ATC TGC AGG AAT AGC ATT TTA ACA CTG TCA CAA GGA
5851 ATC TAA AAC AGA ACC ATA ATC GAT CCT AGG ATC TGC AGG AAT AGC ATT TTA ACA CTG TCA CAA GGA
5929 TGT AAA AAA AAT ATA ACC CAC AAT TGT CAC AGG ATC TAG GGC AAA TTA TAC CAT TAG AAT ATT GTG CTT
6007 AGA GGA TCT TCA AGG TCA CAG ATC CAG CAC TGT TAC AGA TAA TAA GAA CAT CTG TAA AAT ATG TCA CAA GTT GTT
6085 GGA TCT TCA AGG TCA CAG ATC CAG CAC TGT TAC AGA TAA TAA GAA CAT CTG TAA AAT ATG TCA CAA GTT GTT
6163 GAA CTA TAT TCA TAT ATT GTA TCA CCA ATT TGG CTC TAT AGT ATT ATT ATG CAC TAA ATA ACT ATT
```

Fig. 12, contd.

```
6241 TGG ACA AAG AAA ATG ATG TTT ACA TCA AAG GTG AGG CCA TAT TTG TTA GGA ACA TAA CTT AAA AAC CAT TTT GGA TAA
6319 CTA ATG AAA AGC CAT TTT GTG CAG TGC CTT GGC ATA TCA GGC TGC ACA CAG CCA TTT TGT CAC CAG ATA AGA CCT AAG CCT
6397 CAG AAG CAA GCC TCA AGG TGG TGC CAG GCA GCA CCT TAA ACC TGT GAG CCC CAA GAC AGG CCA TGA TAT GCT AAT GAA
6475 CTA CCT TCA AGG TGG TGT TGC TGA ACT TTG GGA ATG GTG TGC AGG ATC TGT GAG AGA TTC CCC ATG TGG AAC GCT ACT GCC CAA
6553 AGA AAT TTT ACA ATA CCA AAC GTC TAG AAG CTT CCT TGT TCT CAC CTG AGA AGA TTC GAG AGA GCT GAC ACA GCT TCT CTA
6631 TGT TTT GTA TGC CCA AAC TGC TGC ATA TTT TAA GGT GTG ATA ATA TCT GTT TTG TGT AAT TGC TAA AAA GTT TAC CCC TAC AGA
6709 CTC TTT TGT GTG AAT AAA CCA CAC AAT GCT CTC CAC AAT ACT GGA TCC CAC AAT TTT ACA GAG AGA AGG AGC TAA
6787 GTT TGT TGT TCC CAT GCT CTC CAC AAT GCA CAT GCT GCA CAT TCA ATT TCA ATG TTG GGC ATC TTT ACA CTG TAG TCA AAG
6865 TAG TCC CAT GCT CTC CAC AAT GCA AGA CAT GGA AGT ACA AGT GCA GAG TCC AAA TAA GTC CTA ATT TCA ATG TTG GGC ATC TTT ACA CTG TAG TCA AAG
6943 TTA AAA ATG AAG AGA TTC CAG AGA CCT TGC TTA AGA CTT GTT AAG GTA GAG TCA AGA AAC TTG AGA AAC AAT GTG AGA GAC AGA CAA AGT GAC CAA AGT ATC CTT CAG AGT GTT CTA AGC CCC
7021 AGG ATT AAG GAC TTC CAG AGA CCT TGC TTA AGA CTT GTT AAG GTA GAG TCA AGA AAC TTG AGA GAC AGA CAA AGT GAC CAA AGT GTT TTA TGT TTC CAG
7099 AAC CAA CCA ATA TGC TGC CAG TCA AGA AAC AAT GTG AGA GAC AGA CAA AGT GAC CAA AGT TTA TGT TTC CAG
7177 AGT ATG TGG CAT TCT GTT AAG GTA GAG TTT TGT TCT AGA CAG ATT GAA AGA ATT TGT CAT TTA TGT TGT TTA TTC CTC ATT
7255 GCC CTT TCT TAT TTT TGG GGT TTT TTT AGA GGG GAT TCT GTT TCT GGG AGA ATT GAA CTC AGT CTG ATA ATG AGT TCT GAG CCA GCA ACT AAT
7333 TGG GGA GTT TTT TTG TTT TTT TTT TTT TTT TTT CAG AGA CAT CTC AGA GGG GAT TCT GTT TCT GGG AGA ATT GAA CTC AGT CTG ATA ATG AGT TCT GAG CCA GCA ACT AAT
7411 TTT TGT TTT CTA CAT CTC AGA GGG GAT TCT GTT TCT GGG AGA ATT GAA CTC AGT CTG ATA ATG AGT TCT GAG CCA GCA ACT AAT
7489 TAA TGT TTA CTT ACT TAC TTA CAT CTC AGA GGG GAT TCT GTT TCT GGG AGA ATT GAA CTC AGT CTG ATA ATG AGT TCT GAG CCA GCA ACT AAT
7567 TAT TTA CTT ACT TAC TTA CAT CTC AGA GGG GAT TCT GTT TCT GGG AGA ATT GAA CTC AGT CTG ATA ATG AGT TCT GAG CCA GCA ACT AAT
7645 GAG GAG CTA CAG ATT GAT GTT TCT GGG AGA ATT GAA CTC AGT CTG AGA GCT TTT GAT ATA GCT AGT TGT TTT AAA AAT AAA
7723 ATG TTC CTG TGG CTG ATG TCA CAC AGA CAA TTA CAA AAA CTG AAA AAT CTG ACA CAA CAG GTA ATG CTC AGT CAG TTA ATG CTG AGA AGA ATT AGT TAT ATA AGT CAC AGT GTA TGA TGA CTC ATG AAG AGG AAT AAA AAC
7801 AAA GGG CAT GAA GCT TGG GAT GCA ATT AGC TAT GCT TCT CTG GAA AAC TTG CTT CTG AGA ACT TCA AAA TTG CTT CTG AGA ACT CAG AAG GAA CAG GAT GGC CCC AGT AGG AAT AAT ATA AGT CAC AGT GTA TGA TGA CTC ATG AAG AGG AAT AAA AAC
7879 ATT TCT TTT TTT GTA GAA AGC AGA ATT GTA GAG GAG AAT GGC TGA CAT CTG TTT TAA CTG GGT TAT AAT GGT TAA ATC CCT GGC TGC CTT TCT GAA ATT TTA ATA AGT CAC CAG GAA CTG GCC CAT TAT TTA ATT ATA ACC TCT GGA AAG GCA CTC CAA GTG CTG GGA ATA AAG TAG ACA TTT AAT AAT
7957 AGT TAT ATT GTA GAA AGC AGA AGT GGC TGA CAT CTG TTT TAA CTG GGT TAT AAT GGT TAA ATC CCT GGC TGC CTT TCT GAA ATT TTA ATA AGT CAC CAG GAA CTG GCC CAT TAT TTA ATT ATA ACC TCT GGA AAG GCA CTC CAA GTG CTG GGA ATA AAG TAG ACA TTT AAT AAT
8035 AGA GGA GAA AGC AGA AGT GGC TGA CAT CTG TTT TAA CTG GGT TAT AAT GGT TAA ATC CCT GGC TGC CTT TCT GAA ATT TTA ATA AGT CAC CAG GAA CTG GCC CAT TAT TTA ATT ATA ACC TCT GGA AAG GCA CTC CAA GTG CTG GGA ATA AAG TAG ACA TTT AAT AAT
8113 GGG TAT TTC AAC AGA GTC TTT TAA CTG GGT TAT AAT GGT TAA ATC CCT GGC TGC CTT TCT GAA ATT TTA ATA AGT CAC CAG GAA CTG GCC CAT TAT TTA ATT ATA ACC TCT GGA AAG GCA CTC CAA GTG CTG GGA ATA AAG TAG ACA TTT AAT AAT
8191 TGC CAA TCC TGT TTA CTG TTT CTT TAA CTG GGT TAT AAT GGT TAA ATC CCT GGC TGC CTT TCT GAA ATT TTA ATA AGT CAC CAG GAA CTG GCC CAT TAT TTA ATT ATA ACC TCT GGA AAG GCA CTC CAA GTG CTG GGA ATA AAG TAG ACA TTT AAT AAT
8269 TTA TAG AAG ATT TTG AAG AGT TTG TAC AAT GTA TGT ATA ATT ATA ACC TCT GGA AAG GCA CTC CAA GTG CTG GGA ATA AAG TAG ACA TTT AAT AAT
8347 TAC AAA GAT ACT AAT TCT ATA ATG AGT TGT ATA ATT ATA ACC TCT GGA AAG GCA CTC CAA GTG CTG GGA ATA AAG TAG ACA TTT AAT AAT
8425 CAA GAT ACT AAT TCT ATA ATG AGT TGT ATA ATT ATA ACC TCT GGA AAG GCA CTC CAA GTG CTG GGA ATA AAG TAG ACA TTT AAT AAT
8503 TTT CGA GAC AGG GTT TCT CTG TAT AGC CCT GGC TGT CCT GGA ACT CAC TTT GTA GAC CAG GCT GGC CTC GAA CTC AGA AAT CTG CCT GCC TCT GCC TCC CAA GTG CTG GGA TTA AAG GCG TGC GCC ACC ACG CCC GGC TAT TTT TCA ACT
8581 AAC CTA CCT TGC CTC TGC CTC TCT CTC TGC CTC TGC CTC TCT CTC TCT GCC TCT GCC TCT GCC TCT GCC AAA TTT TAT TGT GGT
8659 TCT GCC TCT GCC TCT GCC TCT GCC TCT GCC TCT GCC TCT GCC TAG AGG CCA ACT TTT TTT GCT GCC TCT GCC TCT AGA
8737 TCT GCC TCT GCC TCT GCC TCT ATA TAT GTC TCA TTC TGT TGT TTT GCT TTT CTC AGT TGC TTC TGC TTT TTT GCT
8815 AAC TTT AAT CGC AAG TTG CTT GCT TTG TAG AGG CTG TTT GCT TTG TTT TTT GCT GCC TCT AGA AAG TGT CTT TGC TTT CCG
8893 AGT AGT AAT CGC AAG TTG CTT GCT TTG TAG AGG CTG TTT GCT TTG TTT TTT GCT GCC TCT AGA AAG TGT CTT TGC TTT CCG
8971 TTG CTT TGC TTT GCT TTG CTT TGC TTT GCT TTG CTT TGC TTT TCC TGG GCA CTC ACT CTC ACT TAG ATC CCC AGA CTT GAT
9049 GGG GAG GGG TGG GGA GGG ACT CTG AGA GAT CTG AAA GTT ACA GAT CGA TCA AAA TTA ACA GCA AAG TAG TGA CCA AGC AGC AGC TAG TGA
9127 TCA ACT GAG TTT TTA GCA GAT CTG AAA GTT ACA GAT CGA TCA AAA TTA ACA GCA AAG TAG TGA CCA AGC AGC AGC TAG TGA
9205 TCC CAA GTT TAC CCT GAA CTC GGA AAG TCA CAA TTT ACT CAA GAG CCT AAT CCA AGC GTG CCA AAA GCA TAG TGA
9283 GAG TTT ACC TGA ATC CTA TAT ACT AGG CTT AGT GAC TGC ATC AAA TTA ACA GCA AAG TAG TGA CCA AGC AGC AGC TAG TGA
9361 CAT TCA ATG GCA GTG TTT GCC ATC ATG GCA TTG GGG GCA ATA TTA CTC ATT
```

Fig. 12, contd.

```
 9439 ATA CAG ATG AGA AAC TGG GAA AGA CTT ATT GCC TCA GAT TCT CTA CTG AAA GGC TGA GTT TGT GGC TTC TAG AAA ATC TTT
 9517 TAC TTT CAA TAT CAA TTT TAA TGT ATA ATT TTT AAA TTC CCA CTG ATT TTT ATT TTT AAC ATT TAT AAG AAA TAA
 9595 ATG CAA TAA ACC ATG ATG GAC AAA ACA ATA CAA GAA TCA TAT GAT CAC CTC AAT GGA AGG AAA AGG GCT ATC AGA
 9673 AAA AGT CTT TGA TCA AAT CTT TTA TTC ACA CCC AAA CCC TCC ATT TTC CTG GCC ATT TCA TCC TGT ACT
 9751 AAA GCC CCC TAT GAT TTC CCA AAA TGC ACC TGC CAA CCC TCT CAT TGG CCG ACT ATT AGG CCA TTC GCA TTC CTC TGT ACT
 9829 GAG GCA ACT AGA GAC TAC CTT CAA AAG GGT ACT GGT TAG GTC TTA TTG GTC CCA TCT AGA AGT TGC AGA CCC CTT TAG
 9907 GCA ACT AGA GAC TAC CTT GGA TTC CTC CAT CAT ACG AGA AAG AGA GAG CCC TGT CAG AGT AGA CTG AGT GTC AGT CTT CTG GCA
 9985 CTC CTT GGA TTT GCC AGG CAC TGG GGG CAT AGC CTC ACG AGA AAG AGA GAG CCC TGT CAG AGT AGA CTG AGT GTC AGT CTT CTG GCA
10063 GTA TTT GCA ATA GTA TCT CAG CTC CAA ACT TTG TCT CTA TAA CTC CTT CCA TGG GAT GGA TCC CAA GTC TCT GAA GCA GTC TCC TTC CTT
10141 TAT GCA ATA GTA TCT CAG CTC CAA ACT TTG TCT CTA TAA CTC CTT CCA TGG GAT GGA TCC CAA GTC TCC TAA GTG AAG AAT
10219 CCA TCT CAG CTT GGT CAT GCC CAA TTT CCT TCT TGA CTT TCA TAT GTT GCA TCT TGG GGG TTA ATA TCC ACG
10297 CCA ATA TTT CAG TGA GTG CAT ATC ATC ATA AAT ATA AAT CAT TTG CTC ACT CAG GAT ATC CTC CAG ATG CAT TTT CTG
10375 TAT CAG TGA GAA TTC CTC TGT GTC CTT TGA GGG GCA TTT TGT GAA TTT GGG CAT ATA ATC CAT ATA ATG CAT GAG CAT AGC
10453 TTT GCC TAA TTC CTC TGT GTC CTT TGA GGG GCA TTT TGT GAA TTT GGG CAT ATA ATC CAT ATA ATG CAT GAG CAT AGC
10531 TAT CCA TGT GTC CTT TGA GGG GCA TTT TGT GAA TTT GGG CAT CTT AGA ACA AGG AAC ATA TTC CAA CAT AAT AAA GGT TAT
10609 GGA GCA TCA ACA TGC CAT GAC ACT TCT AAT CAA TAT CAT CTT AGA ACA AGG AAC ATA TTC CAA CAT AAT AAA GGT TAT
10687 CCA TCA ACA TGC CAT GAC ACT TCT AAT CAA TAT CAT CTT AGA ACA AGG AAC ATA TTC CAA CAT AAT AAA GGT TAT
10765 GTA TGA TCA ACT ACT GAC TGA AGG GGA AAT TGA AGC ATT AGC TTA TAC ATC CAC AAT CTT CTC CCC AGC TTC TGC TTG CTT
10843 ACT ATC CCT AAA TTG TTT TCA ATT GAA AGT GTT ATG ATG CCT GCA CTC CTT GGA TGA GCC CTT TGT CTT AGA GAC ATT CTA TCT ATG AGG
10921 AAA TAT GTC AAA ATT AGG AAA ATT TTG AGA CCC ACT GTA AGC TCT GTA AGC TTA CAT GAG CAT GAG GAA AAG CCC AAT TTT GGA CCA
10999 TGT GCA GCA TTA GGA ATG TTG AGA CCC ACT GTA AGC TCT GTA AGC TTA CAT GAG CAT GAG GAA AAG CCC AAT TTT GGA CCA
11077 CTC TCT TCT TGC ATT TGC AAC ATG GTC TAT CAC ATC ATG GCC CTT CTT CCC AGC TTG GTT TGT TGC TTG CTT
11155 CTC CTC CTG TGA CTG AGT ACT TCA CAA AAC GTT CTA CCT GCC AAA CCT GGA TGA GCC CTT TGT CTT GAA GCT ATG AGG
11233 CTC TCT ACA TAG ACT CAA GAA AAT ACT TCA GAA GAC CAA ATA GAC AAT GAC GTA AAA GTA AAA GCT TAG GCA TTG CTC
11311 CTG TGT GGC TTA ATT TCT GTT AGA GAA TGA TGA CAG CTG AGG GAC TCA TGG TCA TGA CTC CTT TAT GGG TCA CTA
11389 AGG TTC TCA CCT TAT TTC ACA CAG GTT GCA TAT ATT TAG TAA TCA TTT AGT TGT GAG AAT GAA CTG TAT ATA AGG
11467 AAC TAC CCT AAC AGT AGG AAA ATT ATT TTG AGA CCC ACT GTA ATA AGC TCT GTA AGC TTA TTG GTT TGT GAA TTT TGT AAA TGG GGA CCA
11545 TTT CAC GTT GCA GCA TTA GGA ATG TTG AGA CCC ACT GTA ATA AGC TCT GTA AGC TTA TTG GTT TGT GAA TTT TGT AAA TGG GGA CCA
11623 GTT GCA GCA TTA GGA ATG TTG AGA CCC ACT GTA ATA AGC TCT GTA AGC TTA CAC TTG GTT TGT GAA TTT TGT AAA TGG GGA CCA
11701 TGT GCC AAC ATT TGC CAC ATG GTC TAT CAC CAA TCA TAG AAG ACA CAG GCT TAG TGG CCT GTG AAA AAT AAT TAC
11779 ATA AGG GTC TTC ACT GTC TAT CAC CAA TCA TAG AAG ACA CAG GCT TAG TGG CCT GTG AAA AAT AAT TAC
11857 AAT CCT CAA GCT CAA CCT AAG ACA TAG CAG TGA AAC CAA TAG GAA TGA CAT GAT CTA TCT TCT GAT
11935 GGC TCC ACA GGC GAA CTG CAA ATC TTG CAA ATG GAC CAG ACT ACA CCA CTT TGG CAA ACT GTA AAG TGG GAA TTG
12013 AAT CTT CAG TGC CTG AGA TCA GCT CTT GTG TAT GGT TGC TAT TAG TTC TGA CAA AGA ACG CAA GTA GAT TCC ATG AAG AAT GTT GTT
12091 ATG CCT TCA TCA GCT GTG GCT TTA AAC AGA GTC CTC AAG ACG CAA GTA GAT TCC ATG AAG AAT GTT GTT
12169 CCT TCA GCT GTG TTA AAC AGA GTC CTC AAG ACG CAA GTA GAT TCC ACC GTG AAA AAT CCA TCG
12247 CTA AAT CAG ACT CTG AGG ATG TGC TAT AAC AGA TTA GGA GAT GAA ACG GTA GCT TAG AGA AAC TAT CGA AGC CAG TAT TTT CTA
12325 TGA AGA CTG AGG CTG AGG AGA TTG GAT GTT GCA AGG ATC TAA GTG TAG ATA TAT AAT AAG ATT CTA TTG ATC TCT GCA ACA TAC
12403 TAA CTA CTT AAT AGG AGA TTG GCA AGG ATC TAA GTG TAG ATA TAT AAT AAG ATT CTA TTG ATC TCT GCA ACA TAC
12481 CCT AGT GTT AGA TTT AGA ATT GTT TGG AAA ATA ATA TTA TCA GCC AAC ATT TTC CAT TTC AGT ATA GCA ATA GCA AGT ACC CAC
12559 GAG AGT AGT GTT AGA TTT AGA ATT GTT TGG AAA ATA ATA TTA TCA GCC AAC ATT TTC CAT TTC AGT ATA GCA ATA GCA AGT ACC CAC
```

Fig. 12, contd.

```
12637 CCA TAT CTC CCC ACC CAT CCC CCA TAC CAG ACT GGT TAT TGA TTT TCA TGG TGA CTG GCC TGA GAA GAT TAA AAA AAG
12715 TAA TGC TAC CTT ATT GGG AGT GTC AAA GAA CTG GTC ACA GAA ATA CCA AAG ACT GTC ACC GTC TCC ACA CTT TGA TCA AGA
12793 AGA CCC TTT GAG CAC ACC CTT TCA AGT TTC CCA CCT TAG GCA CAT CTG TTG CTT TCG CCT CTC AAC AGC CTG GGT
12871 GGT GCA CTC GAT GAA AAT GAT AGT CCA AAT CTA TGT CTA CAT ATA CAC CTA TCT TGA ATA ATC CTT GAA GAG TTC AGC GGC TGT CCC ATC
12949 CAG CAC TGG TGC TTT TGC ACA GTC TGT GGA AAA GAT GTT TAG GCA ATA TGG GGC CCA GAC TTC TGA TAT GGT CAC TGG GCC CAG
13027 TCC CAT ATA CCA TGT GCT AAG ACA TAG TTT GGC CAT CTT TAG GCT GAG AGA CTA GGA TTC ACA GCG ATG GAC TAT ATC AGC GCA AAA
13105 AAT AGT TGT CCA GTA AAC ACC CCA ATA GAA GTA TTC TCT TCT CCA TCC ATG GCA ATT GCA
13183 GGA TAG TTG TCA AAC ACC CCA ATA GAA GTA TTC TCT TCT
13261
13339 ATG GCT GTC TTC ATA TTT GTT CTA GAC GGC CC
```

VkP-IGKV1-39/J-Ck-Δ1

```
   1 GGC CGG CCC ACA TGA AAC AAT GGG AAC CAT GTG ACA ATC ACA GAG GTG TTG CTA TTA GAC CAA AAG GGA TTG TTA CTC
  79 TCC ACA TCC CTT TAA GTA ACT CCA ATA CTC TGA AGG CAA AGG CCT CTC CAA AGA ACC CTC TAA GAC TTC ATT AGA CAT TCC CTA CGA ATG GTT
 157 ATA CTC TGT ATA CTC TTG TCA GAC TAT CTC TTG GGG AGG AGG CAA ATA TTA TTC CAG GCA AAT CTA AAG TTT GAC
 235 TTT TTT CCT TCA ACC TGG ACC CTG GGG TTG ATT TGC ATT GCC CCT GTG CAG GCC CTG CAG GAC CCA GAA GCC TTT ATG TGC TGC TCA
 313 GCT GGT GTG ACC ATG CCC TGC TGA GAG TTC CAC CAT GGA AGT ACA GCC TAA GCC GAA GAC GCC CTG GGA GCT CCT
 391 GCC TGC CCT GTG CTG CAG GAG TCA GTC CAG AGG ATT TAC TCA GTC TTT ATG GCA CAT GGA TAT TTG CAG TTA GCC AGT GTG TGG AAC TTC
 469 TCG GCT ACT CTG GCT CTC TGA TAA CAT GGA AGA ACA CTA GGA TAT TTT TTA TCA GCC AGT GTG CTG CAA TCT CAG GTG CCA GAT GTG ACA
 547 AGG GAA GTT TGA CCC AGA GCC CCA AGA GCC GGT ATC GTG ACA TCA CCT TCT ACG CCG CCA GCT
 625 TCC AGA TGA GCA GCT ACC TGA ACT GCA GAT TCA GCC CCT ACT GCC AGA CCC CCG ACT TCA CCT TCG GCC CCG CCG AGC
 703 GCA TCA GCA GCG AGC TCA TCG GCA TCA CCC CCG CTC CCC ACT TCG GCC AGG TGG GCC AGG AGC
 781 TGC AGA GCG ACT CGG CCA CCT ACT ACT GCC AGC AGT ATT TAT TTT ATG TGT CAG CAT AAC AGC CAG GTT TTA GGA GTC AGT TCA
 859 CCG AGG ACT GTA AGT ACA GTT TTC TCA AGG ATG ATA AGG AGA AGA GGC GTT GAT TTA GCG TGG TCA GTG TCA GAT TGG ATC
 937 TCA AAC GTA AGT GAG GAT CTG AGA ACT CAT TGG TCT CAT CCA GTT ACA GTG TGG TCT TGT GCA GTT CAG AGG GCC CTA GTA AGA GAT TGG GAA
1015 GAA AAT ATG ACA AGG GCA TCT GCT TTT GAG TCA GTG TCT AGC AGG AAA ATG AAG GGA TAG GTG GAG TAG CAG CTG AAA TAA
1093 GTG AGA TTA GGG GCA AAA AGA GGC GTT TGA AGT AGT TTT GAT ACC GTG TGA TCA GCG AGT CGA AGA TCA GCC CTA AGA GAT TGG ATC
1171
1249 GGA GAA TAA CTG GGA GTA TGA AAC TGA AGG ATC TGG GTG AGT CTG TGA GCT GGA TCA GCT TTA AGT GGG ATG TGG GAA
1327 TTT TGA GGG GAT TTG AAG GAG GAT TTG ATG AAC AGG AAG CAG GGC CTT TGG CAT CCG CTA AAA TGG GAG CTC TGA AAA TGA
1405 GAG GAG AAG ACT CAT CCG AGT TGT TCT TAT GAG CAG TAG AAA ATC AGG GGA TAG GTG GAG TAG CAG CTG AAA TAA
1483 CAG AAG AGC CGT AGG CTG AAA CGG GTC AAA GAC ACT AGT CTC ACA TGG CTT TAT TAG CCA TGA GTG TCA CTG GTG CTC
1561 GTG AGC TTA AAA TGT GTA GTA CAA AAT GTC AAG GTT TTG AAT TGA ATT TAA AGT ACA GCT AGA AAT ACT CGA TTG TAA
1639 TCA TAA TTC CTT CTC CTT TTG TCA AAT TCT ACA TGA TGA AAG CCT TTG AAT GAT CTT TTT CAA CTG GGT TAG GGG GTT
1717 TTT TTT TAT ATC GCC AAT GGA CTG AAA CGG TCC GCA ACC TCT TTA CAG CCC CCG TCC CAT GTG CTC CGC GTG CCA GCC
1795 TTT TTT GAA ATT TGG CGT TCA CCC TGC TCA TGC TTA GAG CAC CAG GAA TAG GAT GTG AGA AAA ACA
1873
1951
2029
2107 GAG GCA CAG TGA GAA CAG AGC TAG
```

```
5383 CCC ACA ATA AAA AAG AAG AAA GAA TAC ATA TAA GCA TTT ATA TAA TTC TGA GCA ACC TTG TGC TTT GTG AAA AAA ATA
5461 TAA TCT AAT GTC CTA GGA TCT AGG TGC TGT ATT CTT ACA GAT CTT ATT TTT CAC TGG TAT ACC ATT AGA GAG GAT CAA AGA TCA
5539 CTG ATC CTA GGA TCT AGG TTG ATT TCA GTG GTG GTT ACA AAT GTG AAG AGC TGT GAT AAG AGC TTG TTG GAG CTT CAA GGT
5617 CAC AGA ATC ACT GTC TTG ATT TCA GTG GTG GTT GGC TCT ATA GTA TTA TGC ACT AAA ATA TGT GAT AAA ATG TTG AAC TAT ATT CAT
5695 ATA TTG TAC CAA ATG TGA GGC TGA TAT ATT TGT TAG CAT AGA TTA GAA CAT AAA TTA GGA CTA TTT GGA CAA AGA AAA
5773 TGA TGT TTA CAT GCC TTG GCA TAT GCA AGC ATA GAT GTC ACC AGA ATC TTA AAA TAA GAT ATG GAT AGC CTC AGA AGC AAG CCC
5851 ATT TTT GCC AAG CAG GCA GCA CAG GCT AGA GCT GTG AGG ACA CCC AAT AGC AGC CCC AAA GAA TAC CTT CAA ATA CAA GGT
5929 CTG CCC AGC GAC CTA GTG AAC CAG CCC CAA GCT GTG TCG CTC TGC TGT GGA ACA CAG CTT CTC TAT GTT TTG TAT TGA
6007 GGT GTT GCT GAC CTT TGG GAA TGG TGT GGA TCG ACT GAA GAT CTT GGA ACC CCT ACA GAC TCT TTT GCC CAA
6085 AAA TTG GAA CTT TGG GAA AGC TTC CTA GAA CAT CTG GAT TTT ATG TTG GGG ACC TGT ATA GGA ATG TTT GTG TGA CTA
6163 TAC CAG AGT CCT CTC CTG GTG TGA TAT AAA TAT TGT ACA GAT GTT CAC ATG CTA AGT GCT AAT GCT ACA GGA ATA TTT ACA GGA AGA GAA AGA CAT AGA ACC ATG CCC ATG CTC
6241 ACA ACT CTC CTG GTG TGA TAT AAA TAT TGT ACA GAT GTT CAC ATG CTA AGT GCT AAT GCT ACA GGA ATA TTT ACA GGA AGA GAA AGA CAT AGA ACC ATG CCC ATG CTC
6319 AAC CAA ACA TAT TTT AAA AGC CCA AAT CAT AGG CAC AGG TTG ATG GCA TCT TTA CAG ACT GTT CAG AGA ACT GTT CAA CAT AGA GAA ACC TAA AAA TGA AGA ACT
6397 TCC ACA ATA CTG AGA GTG CAG AGC CAC CAA AGG GAG CAT TGG GCA AGT GAC TGA AGT GGT TTC CAG GTA TCC TTG GAA GAC ATA GCT GTT GTT GTT CCA TTC ATT TAT TAT TTA CAC
6475 GAC ATG AGC GCT TAA GAC TTC TTG CCT TCA GGA AGT AGT CTG ATG AGT GGT TTT GTT GTC GGA GTT CCT CTG ATT TAT TCA ATT TAT TAT TTA CAC
6553 TCC AGA AGC CTT GCT TAA GAC TTC TTG CCT TCA GGA ATG ATG GGT GGT TTT GTT GTC GGA GTT CCT CTG ATT TAT TAT TCT AAT GTC TAC ATC
6631 CTT TTT GCT TAA AGG TAG AGT CAA GAA ACC AAT GGT GGT TTT GTT GTC GGA GTT CCT CTG ATT TAT TAT TCT AAT GTC TAC ATC
6709 TTG TTA AGG TAG AGT CAA GAA ACC AAT GGT GGT GGT TTT GTT GTC GGA GTT CCT CTG ATT TAT TAT TCT AAT GTC TAC ATC
6787 ATT TTT GGT TTT GTT GGT TTT GTT GGT TTG GGG GTT TTG TGC ATC ATC TCT AAT GTC TAC ATC TTA TTA CTT CTT CTT
6865 GGG GTT TTT TTG GGT TTT GTT TGA GAC AGT GTT TCT CTG TAT GGT TTT GTT GTC GGA GTT CCT CTG ATT TAT TAT AGG AGC TAC AGA
6943 TTT TTG TTT TTT TTG GAC AGT GTT TCT CTG TAT GCA AGA GCA CAC TGA GAT GTG CTA CAA CTT TGA TTT ATT CAA CTC AGC AGC TAC AGA
7021 TCA GAG GGG ATC CTC TAA TTT CAA GAA TTT GGG ACA GTT TCT TGG GTC ATG AGA GTA TAA GGA GTT TAA GGA GTT TAA GGA GCC ATG TCC AGA
7099 ACT TAT CTG TAG ATG GGG GAG TAT GCA AAC TAC AAT CTT CTT AAA GGA GAG ATA GTT AAG GGC CTT ATA TTG GCC
7177 CAA TTG ATG CTG TAG ATG GGG GAG TAT GCA AAC AAT CTT CTT AAA GAG AGG ACA GTT AAA ACA TTT TTG TAG
7255 TGA TGT CAC ACC AGA ATT AAG GAT AAA GAT ATG GCT ATG GGT GGT GGT GGG GAG ATA TTT TTT GAG GAG AAA ATT ATC TCA
7333 CTT GGG ATA CAT AAT CCA GAA TTA GCT ATG GGG GAG ATA TTT TTT GAG GAG AAA ATT GTA GAT ATG AGA GTG GCC TAT CCA
7411 AAA AAG TAG AGA GGA GAA TTA GCT ATG TGG ATG TGG AAG AGA GGA ATG AGG AGG GAG ATC GGT ATT TCT TTG
7489 AAA AGG TAG GCA ATG GCT GAT AGA CAC ATG GCA ATG GTC GGT GGT GTA GCC CCA GGA GAA GAG ATG GGT ATT TCT CAA ACA
7567 GCA GAA GCA ATG GCT GAT AGA CAC ATG GCA ATG GTC GGT GTT GCA AGA GCA GCT AGT CAG TAT CAG GGC TAT AGG TAC TCT CCT
7645 CCT ATC CCT TTC GAC TTG CAC ATG GCA ATG GTC CCA GGA GAA GCA AGT GCC CTA GGA GGT GCC CCT CAC CAC TTA AAC TCA CCT
7723 GAG TCT TTC ATA ACC TTG TGA GTA ATT AGG GGA GGA AGT GCA AGT AAT ATT ATG TAA CTC TTT AAT GAA GCC CCT CAC TTA ACT
7801 GTT TAT AAC TGG GTA ACT TTG TGA GTA TAA ATA TAT TAA CCC CTG TGA GTG CTA CAA CTA CTA AAT GTG CTT TAA AAA TTT TGA
7879 AGA GTT TAT ATA TGT ACA ATG TAT AAA TAT TCA GCT CTC CCT GCT CTG CTC CAT GTT CAA CTC GTT TCA GAA ACA AAA TTT TGA
7957 CTA TGT CTC TGT ATA TGG GTT AAA TCA GTT TAG CTG GCA CTC CCT CCT CCT TAA AAC TCA TCA GAA ACC CTG CCT CTT ACT ATG
8035 TTT CTG TGT GGG ATA GCC CTG CTG CCT GCT CTG CTC CAT GCC CCT CCT CCT TAA AAC TCA AAA CTG CCT CTT ACT ATG
8113 CTG CTG CTG CTG CTG CCT CTG CTG CCT GCT CTG CTC CAT GCC CCT CCT CCT TAA AAC TCA AAA CTG CCT CTT ACA AGT
8191 CTG CTG CTG CTG CTG CCT ATT CCT CTG CTG CCT GCT CCA CAC TGC CCT CCT CCT TAA AAC TCA AAA CTG CCT CTT ACA AGT
8269 CTG CTG CTG CTG CTG CCT AGT GCT AGT GCA GAC TGT TGC CTT TTG CCT GCA ATA AAT GTG CTT TAA ACT GTA ACT ATG
8347 TCT CAT CTT ATC TCT ATC AGT GCT TAG GAC TGC CTT TGC CTT TGC GTG GGG AGG AGG AGG AGT
8425 TGT ATT GTT GCT CTT TGC CTT TGC CTT TGC CTT TGC GTG GGG AGG AGG AGG AGT
8503 CTT TGC TTT GCT TTT GCT TTG CTT TGC TTT GCT GGG AGG GAG GGT
```

```
11779 CAT TTA ACA GAT TAG GAG ATG AAA CGG TAG ACT CTG TGT AGT TGT ACA CCC CTG TGA TCC CAT CGC TAG GAA GAC TGA
11857 GGC AGG AAG TCC AGC TCG ATG TCA AAC CAG CCT AGG CTA CAC AGA TTG AGA TTC ATC ATA ATT TTC AAC CTG GTA TTA ATA
11935 GGA GAT TGG TTA GGA TCT AAG GGT CAC TAA GAG GCA GAA TAT ATA AGA GAA GCC AGT ATT TAC CTG AGA GTG TGT TTT
12013 AAA TTG CAG TAA TGT AGA TGT AGA CCA ACA TCT TCT CAT TGA TCT CTG CAA GTA CCC CAA CAG GTG TTA GAT
12091 TTG TTT GGA AAA AAA ACC CAT AGA TAT TAT CAG GTT ATT GAT GGT CAT TCA GTA TAG GAG TTC ACC CAT AAT GCT TCC CCA
12169 CCC ATC CCC AGT GTG TCC CAT AAC CTT GGA CCA AGA CTG CCA TCA CCT TCA TGG CCT GAG CAC CCT GTA AAA GAC GTG TTA
12247 TTG GGA GTG AAA CAG GTT CAA GCC CAT AAC CTT AGG CCA CAC TGT TGC CGC CAT CAG ACA TGC TTT GAT CAA GCC GTG TCC CAC TTG AGG
12325 AAC TGA AAA CAG GCC CAT AAC GCC TCA TAC ACC CCA TCC CTA CCC CAG GCT GTA TCC AGC CCT GTA AGC CCC AGT GAC TCC ACA
12403 CCC TTT CAA GTT CCC CAC CTC AAA CTC CAT CTT GTT TGA TAT TAC TCT ATC TCA AGC CCC ACT GGG CCC ATA TAC AGC GGG ATG
12481 AAA ATG ATA CCC AAA ATG TCA AAA CTC AAC CTT AGG TTT CAT GGG GCC TGA TAT TCC AAT GTC ACT GGG CCC ATA TAC CAT GTA
12559 GCA CAG TCA GTG AAG ATG TTT AGG CTG GCC TAA TCA CCA ACA CGT TCT AGA AGT ACC TGA TGG ACT ATA TCA GCA TGG GTT AGA GTT CAG
12637 AGA CAT GTG GCC ATC TTT AGG CTG AGA GAC TAG GCA GAC TAG GCT ATA TCT CTT ATA TCC CAT CTG AGC AGT ATT GTG CTA
12715 AAT AGT TTG GCC ATC TTT AGG CTG AGA GAC TAG GCA GAC TAG GCT ATA TCT CTT CTT ATA TCC CAT CTG AGC AGT ATT GTG CTA
12793 TAA ACA CCC CAC AAC CCA TAA CAG GCC C
12871 TAT TTG TTC TAG ACG GGC
```

VkP-IGKV1-39/J-Ck-Δ2

```
   1 GGC CGG CCC ACA TGA AAC AAT GGG ACA ATC ACA GAG GTG TTG CTA TAG CAA AAG GGA TTG TTA CTC
  79 TCC ACA TCC TCC TGT ATA AAA TAA CAG ATA CTC TTG TCA CAA CTC TAG AGA AAT ATA TTA TTC ATT AGA GAC TTC ATT AGG TTT GTA TTA CGA AAG ATG GTT
 157 ATA CTC TCC CCT CTG ACC GTA AAA ATG GAC CCT CAA CAA CGG CCT TTC TAG CTC GTG AGA CAT GAA GCA AAT CTG CAG GCA CTG TGC GAC
 235 TTT TTT CCT CTG ACC GTA AAA ATG GAC CCT TGA ATT GCC ATG GCC ATG GAT TAC ACC ATA TTA TAA GAT CAT CCA GCC CTG TTT ATG GGC TGC TCA
 313 GCT GGT TGC CCC ATG CCC TGA TCA GTC TCA GTC ATT GCC AGG AGC CAT GGA CAC ATT TTG GCT CCT GAA GCC CGC CCA GCT GTG CCC AGT GCT TGG CCT
 391 GCC TGC CAC CCT CTG GCT CTC CAG GAG TAA CAT GAT TAA TCA GCA GGA TAT TTT TTA TGT TTC CAA TCT CAG GTG CCA GAG CCA GCC AGG GCT AAC TTC
 469 TCG GCT ACT CTG CCC TGA GTT CCC CAG TAA CAT GAT TAA TCA GCA GGA TAT TTT TTA TGT TTC CAA TCT CAG GTG CCA GAG CCA GCC AGG GCT AAC TTC
 547 GCT ACT CTG CCC TGA GTT CCC CAG TAA CAT GAT TAA TCA GCA GGA TAT TTT TTA TGT TTC CAA TCT CAG GTG CCA GAG CCA GCC AGG GCT AAC TTC
 625 AGG GAA GTT CTC TGA TAA CAT GAT TAA TCA GCA GGA TAT TTT TTA TGT TTC CAA TCT CAG GTG CCA GAG CCA GCC AGG GCT AAC TTC
 703 TCC AGA TGA ACC TGA ACT GGT ATC AGC GCA GAT ACT GGT ATC AGC GCA GAT ACT GGT TAT CCA CCC CAC ACT TCG ATG TCA GCC GCA AGG CCA GCC GCC AGC
 781 GCA TCA GCA GCT GCG TCG AGT GCG GCG ACT ACT TTC CTC TCA CCT TTC ATG TCA GTG TAT GGT CTT TCT AGA CGT CTA AAA CGT GGA CAG CTC TGA GAA
 859 TGC AGA GCG ACT GTA CTT GAG ATG AAA AGA GGC ATT GAG GTT TGA GAA GCG CAG AGT CAA GTC ATC ACA AGG GCC CAC GAG CTC TGA GAA
 937 CCG AGG CGC GCG TCG AGT GCG GCG ACT ACT TTC CTC TCA CCT TTC ATG TCA GTG TAT GGT CTT TCT AGA CGT CTA AAA CGT GGA CAG CTC TGA GAA
1015 TCA AAC AAT CTT GAG ATG AAA AGA GGC ATT GAG GTT TGA GAA GCG CAG AGT CAA GTC ATC ACA AGG GCC CAC GAG CTC TGA GAA
1093 GAA GTG AGA TTA GGG GCA TGA GTA GTT ATT GAG AAC ATG ACC ACC GAG GGC GTA TGA CGC CTA AAA CGT TTA AAA CAG CTC TGA GAA
1171 GTG GGA TAA GCA TGA GGG GAT GAG ATA AAC TGA GTT TGA TGA TCT CTC TGT CTT GCC ATA AAT CAG TAA CAG TAA TAA
1249 GGA TTT GGA CAA ACT TTG ACT AGG TGT TTG AAA GTA TGA GGA TAG GTC CTA TAT CAG TAA CAG TAA TAA
1327 GAG AAG CAG CAT CCG AGT TCT CTC TGT CTT GCC ATA AAT CAG TAA CAG TAA TAA CCT GAA TAA TGA
1405 GAG AAG CAG CAT CCG AGT TCT CTC TGT CTT GCC ATA AAT CAG TAA CAG TAA TAA CCT GAA TAA TGA
1483 GAG AAG GAG ACT TTG ACT AGG TGT TTG AAA GTA TGA GGA TAG GTC CTA TAT CAG TAA CAG TAA TAA
1561 GTG AGC CGT AGG CTG TTT GAA AGT ATG AGG ATA TCT CAG CCT AGG TGT TGC TCG ATG AAT AAG CCT AGT GAA
1639 TCA TTA AGC TGT TTG AAA GTA TGA GGA CAA TCA CAG TAA CAG TAA TAA
1717 TTA TTC TAA AAT TTG TCA CAA ATG AGA GAC TCT GTA GTC CCA GTG TGA CAG CAG ACA GCT CAA GGG GTT
```

Fig. 12, contd.

```
1795 TTT TTC CTT CTA ATT TCT ACA TGA AAG TAA ATT TGA AAT GAT CTT TTT TAT AAG AGT AGA AAT ACA GTT GGG
1873 TTT GAA CTA TAT GTT TTA ATG GCC ACG AAA GTT TTG GAC ATT TGG TTC GTT TTC CCA GTT ATT ACT CGA TTG TAA
1951 TTT TAT ATC GCC AGC AAT GGA CTG CGG AAA CGG CCA TGT GAA ACC TCT TCT CGG TAC CTG GAC GCT GCG GTG CCA GCC
2029 ATT TGG CGT TCA CCC TGC TAA GGG CAC AGC CAG TGT GAA GAG ATG TAC ACT ATT TTC CTC CTG CTC GAC CAC TTT CCT
2107 GAG GCA CAG TGA TAG GAA CAG GAT TTC TTT GGA AAT AAA ATG CAT ACA GAT GTG TTA ATA ATC TTT AAT GTG AGA ACA
2185 AGG AAA ATT AGA CCA AAA GGC ATA GTC ATG TGC TTT ATC CAG CTT TGA CTG AAC AGC TAT ATG CCT ATA TTT TAG AGG TCA TAA TAT TAG AAT
2263 GGA CTA CAG GTT AAA ATT GCA TAA ATT TGT GAC ATG GTA TAG ACT GGT TAG GTA GGA TAT TCT TTT AAA AAT ATG ACT
2341 CTG GTT AAA AAT ATT TTA GCA CAA CTA TAT TTC CCA ATA CTT TAA TTC TGT GAT AGA ATG TTT AAC TCA GCT ACT ATA ATC
2419 CCA TAA TTT TGA AAA TTT ATT TGG CTA CAC CAA AGG AAG CCA TAA TAT CAG AGT ATT CTT GGA AGA
2497 AAT AAT ATT TTA GCA CAA CTA TAT TTC CCA ATA CTT TAA TTC TGT GAT AGA ATG TTT AAC TCA GCT ACT ATA ATC
2575 CCA TAA TTT TGA AAA CTA TTT ATT TGG CTA CAC CAA AGG AAG CCA TAA TAT CAG AGT ATT CTT GGA AGA
2653 GAC AGG AGA AAA TGA AAG CCA GTT TCT GCT CTT ACC TTA TGT GCT TTA CAG TGT AGT TTC AGG GAA AAT CCC AAA CAT CAG GAG TGT CAG
2731 ATA AAC TGG TCT GAA TCT CTG TCT GAA GCA TGG ACA CTC AGG GAA GAA TTC AGG GAA ACT AGG AAG GAA
2809 GCC TGA GAA TAT CTT CAA AGG GTC CAT CAT TCC AGA CTC GGC GTC AAT TTA CTT GTT CCT TAT CCT CCC CAG GAA ATA ACT TAG AAA
2887 CAA CAA ATA TGT TTT ATA TAT CTG TTT ACA TAA CTG TTT GTG ACA CAT CAT TCC AGA CCT AAT GTG CAT CCT AAT CAC CGT GTC CAG CAG CTG GTC CAG CAG GAT GAG CAG CCT GAG AGC CAC
2965 TAT ATA ACA TAA CTG TTT ACA CAT CAT TCC AGA CCT AAT CAC CGT GTC CAG CAG CTG GTC CAG CAG GAT GAG CAG CCT GAG AGC CAC
3043 TTC CTC AGG GGC CGA CTC CGT GAA CGT CAG GAC CAA CTA CAA CAG CTG GGT GCA CAG GAC CTC CAG CCC CGT CTA TCT TCC CTT CTA
3121 CGT GGT CTG GGA CAG CGT GGA CAA CTG CGA CCT GTA AAG CAC CTG GGT GCA CAG GAC CTC CAG CCC CGT CTA TCT TCC CTT CTA
3199 CGG CGT GCT GTA GAG GCA CAA CTG CGA CCT GTA AAG CAC CTG GGT GCA CAG GAC CTC CAG CCC CGT CTA TCT TCC CTT CTA
3277 GGT GGA CGA GTG TTG AAG ACA AAG CGC CAC CAC CAC CCA TCT CCC CGT CTA TCT TCC CTT CTA
3355 CAA CAG TCT TGG GGA CCT TGG TAA TAT CAG CTT TTA TCA TGC ATC AGT TGT TTT TAA ATA AAA GGA TAT CTG ACT CTG ACT TGC CCT TGG GAA GTT AAA TGT TTA
3433 AGG TCT CCC TTT CTT CCT CTG CTT TTA TCA TGC ATC AGT TGT TTT TAA ATA AAA GGA TAT CTG ACT CTG ACT TGC CCT TGG GAA GTT AAA TGT TTA
3511 CCT CCC TGT CTT TAC AAA TCC CTG CTA AGT TGT TTT TAA ATA AAA GGA TAT CTG ACT CTG ACT TGC CCT TGG GAA GTT AAA TGT TTA
3589 TGT CTT GCC CTG CTA ATG ACC ACA CTT AAA AGA TAC TCC AAA CCC TCC TGG CCC ATG AGC AGG ATC TTC ACA CCT GTA AGC CAT ACT TCC TAG
3667 GTT GCC CTG CTA ATG ACC ACA CTT AAA AGA TAC TCC AAA CCC TCC TGG CCC ATG AGC AGG ATC TTC ACA CCT GTA AGC CAT ACT TCC TAG
3745 TCC TTT CTA AGG TTC ACG AGT ACT ATT TCC TGA GGG ACA GTC TTT CTC TGG CCC ATG AGC AGG ATC TTC ACA CCT GTA AGC CAT ACT TCC TAG
3823 TTT TCT TCC CTT AAG TCA AAG GCA TAG AAG ACA GTG TTT GCA GTT TTT TGC CTT GTG CAA CCT AAA TGT GCA AGC GAG CTG CTA AAT AGG AAA
3901 CCC AGT CTT GGC GAA GCA ATA GTA CTT GGA CTT GGA GCA CTA GAC AGA AGC CTC TAG TCA CAA CAT GTA AAA CAT GAG CTG GCT CCT
3979 ATG TGG AAG CCC ATC ATA GTA CTT GGA CTT GGA GCA CTA GAC AGA AGC CTC TAG TCA CAA CAT GTA AAA CAT GAC TTA CAC ACA TAC ATC
4057 ATC TGC CAT TGG CAA GTC TGG GCA CTA GCT GGA AGA CTC ATT TAT TTA AAG GAA AAC ATT AAA AGC CCT GTA CAC CAT CTG GAA CAG CAG ACA ACA TAC ATC
4135 AAA ATT TGG GAA AAG TTC TAC TGG AGA CTC ATT TAT TTA AAG GAA AAC ATT AAA AGC CCT GTA CAC CAT CTG GAA CAG CAG ACA CAG AAA CCT TAA
4213 TAA GAA GCA ACA TGT TCA CAA TTG CAA TTG CAA GAT CTA AGA ATG TGG GAT AAA CTG GAT AAT AAG AGC ATG AGC ATA GTT TAA TCT
4291 ATT ATG AAA GAT GTT TTG AGG TAG CAA GAT CTA AGA ATG TGG GAT AAA CTG GAT AAT AAG AGC ATG AGC ATA GTT TAA TCT
4369 CAT AAA ACA TAA GTT TTG AGG TAG CAA GAT CTA AGA ATG TGG GAT AAA CTG GAT AAT AAG AGC ATG AGC ATA GTT TAA TCT AGA
4447 GAG ACA ACT ATT GTG GGA TTG AGG TTC CAA TCT ATA TTG AAT CTC CTG TAT ACT TCA TAA CTT CAC CTA AAG GAT GTG AAA TTA AGA
4525 GTT CTA ATT GTG GGA TTG GAA TTG TAC ATA AAA GAG AAT GAA ATT CTG CCT ATT TGC ATC GAA TTA GTC TCC AGA ATA AAG CAC GGG
4603 CTA ATA CCC GAT GCA ATC TCC CAC AAC CTT TCT CCC TTG TGG TCT TGC ATC GAA TTA GTC TCC AGA ATA AAG CAC GGG
4681 ATC CAG GAT CAT GAT CCC TTG GGG TCT TTG TGG TCT TGC ATC GAA TTA GTC TCC AGA ATA AAG CAC GGG ATT
4759 CAA ACA CCT TCA TCA GGT CAA ATA TAG ACT CTT CCC GCA ATA TTG TCT GGG TAT GAA GCC CAT CAA AGG CAC TTA CAT TAG AAG
4837 AGA CCT TCA TCA GGT CAA ATA TAG ACT CTT CCC GCA ATA TTG TCT GGG TAT GAA GCC CAT CAA AGG TTA CAT TAG
4915 GGA AGG AGG ACA CTA ACA GTG ACA CTA ACA CTA CTG AGC CCT TTT AGT CCC TCG TGG GCT
```

Fig. 12, contd.

```
4993 CAT CCA CTC AGC ACA CAT TTA CTA AGC ATC TTC TCA GCC TAC ACT CTG AAG GCA GTG CAG AAT AAT GTT AGT GTC CCT
5071 TCC CCC AGT TAA TAT GCA GGC TTT CAG GTC TGC TCC TAC CTC TTC CCT TTC TCA GTC TAC ATT ATC CAC TTT AAA GAC AGT
5149 CAC CAA ATA GGA GAG GGC AAC TTT TAA CCT GTC ATT GCT AAA ACA ATG AAT AGC ATG ATA TAT TTC TGG GAA GTC TTA AAT TTA TCA CTT
5227 TTA ATT GCT TTT AAT CTG AAG TGC TCT GCT ATT GAA TAC AAA TGC ATG GCA TTT CAA AAT TTC TGA GCA ATT GTT CGA ATG TCT AAA ACA GAA
5305 AAC AGT GCC ACA ATA GTC ACA TGC AGA TCT AGG GAT GTT TCA GTG GTG ATT TCA CAC TGG TGA AAA TAT AGG AGA GAG GAT CTT CAA GGT
5383 CCC TAA TCT AAT GTC GGA TCT AGG GAT GTT TCA GTG GTG ATT TCA CAC TGG TGA AAA TAT AGG AGA GAG GAT CTT CAA GGT
5461 TAA TCT AAT GTC CTA GA ATC GTC TTG ATT TCA GTG GTG ATT TCA CAC TGG TGA AAA TAT AGG AGA GAG GAT CTT CAA GGT
5539 CTG ATC AGA ATC GTC TTG ATT TCA GTG GTG ATT TCA CAC TGG TGA AAA TAT AGG AGA GAG GAT CTT CAA GGT
5617 CAC AGA ATC GTC TTG ATT TCA GTG GTG ATT ACA AAT GTG ACA AAT ACA AAG AGC TGT AAA ATG TTG TTG GGA CAA CTA TAT ATT CAT
5695 ATA TTG TAC CAA TGT CAA ATG CTT AAT TTT GGC TCT ATA GTA TTA TGC AAA TAA ATA ACT ATT TAA GAT AAC TAA TGA AAA GCC
5773 TGA TGT TTA TGT GCC TTG GCA TAT GAA AGG TGA GGC CAT GTC ACC TGA CTA AGC CTC AGA AGC ATG AGC AGC AAG CCC
5851 ATT TTG TGT AGC AAG CAG GCA CTA GTG AAC CAG GCT GTC ACC AGA CAT AAT TTA AAA ATC TAA TAA AGC CTA AGC CTC AAA GAA ATT TTG TAT TGA
5929 CTG CCC GTT GCT AGC CTT AGA AGC CTT GGA AGC TCG ACT GCA GCT GAA GAT TCC TGT ATG TCC CCA AAA AAC TAC CTC TAT GCC ATA CAA
6007 GGT GTT GCT CAA CAG GCA CTG AAT CTT CCA GAA CCC ACA AAT AGC GGG ACA CAG ACC ACC CTC TAT GAC CTG TTT GCC ATA CAA
6085 AAA TTG GAA AGC TCT CCA GGA TCG ACT GCA GCT GAA GAT TCC TGT ATG TCC CCA AAA AAC TAC CTC TAT GAC CTG TTT GCC ATA CAA
6163 TAC CAG TCT GCT TCC CTG CTG GTG AAA ACA CAG ACC ACC CTC TAT GAC CTG TTT GCC ATA CAA
6241 ACA ACT CCC TTT GAG GAA CTG ACA CTG TAG GCA CAT CTG TTG TCG CTT TCC TCC AAC AGC ATG GCT
6319 AGA CCC TTC ATA TTT GTT CTA GAC GGC CC
6397 GTC TTC ATA TTT GTT CTA GAC GGC CC
```

VkP-IGLV2-14/J-Ck

```
   1 GGC CGG CCC ACA TGA AAC AAT GGG AAC CAT GTG ACA ATC ACA GAG GTG TTG CTA TAG CAA AAG GGA TTG TTA CTC
  79 TCC ACA TCC TCC CTT TAA GTA ACT CCA ATA CTC TGA AGG CCT AGA AGG TTC ATT AGA CAT GTC CTA ATA GTC ATG GTT
 157 ATA CTC TCC TGT ATA AAA TAT CTC TTG GGG GAC CCT TCA CAA CAG CTC CCT GTG CTG AGT TAC AGA GAA TAT ATA TTC CAT ATA TTC GCA AAT CTA TGC GAC
 235 TTT TTT CCT GGT GTT GAC CCT TGA TTA TAT TGC CCT ATG GCC CTG GTG AGT ACA AGC CCC TGC AGT TTT ATG TGC TCA
 313 GCT GCC ATG CCC TGC TGA GTC TCA GTC ATG AGG ACA CTA GGA TAT TTG TTT CAG TCA TCA GCA CAT GGA GGC ACC AGT CCT TTT ATG GGC GCT TTC
 391 TCG CAC ACT CTG GCT CTG CAG GTC TCA GCT GCT CCA GTG CTC TCA TCA GCA TCA GGA TAT TTG TTT CAG TCA TCA GCA CAT GGA GGC ACC AGT CCT TTT ATG GGC GCT TTC
 469 TCG CAC ACT CTG GCT CTG CCG AGG TAA CAT GAC CTC TTA TGT TTA GAA TAT TTG TTT CAG TCA TCA GCA CAT GGA GGC ACC AGT CCT TTT ATG GGC GCT TTC
 547 GCT ACT CTG GCT CTG CCG AGG TAA CAT GAC CTC TTA TGT TTA GAA TAT TTG TTT CAG TCA TCA GCA CAT GGA GGC ACC AGT CCT TTT ATG GGC GCT TTC AAC TTC
 625 AGG GAA GTT CTC TGA TAA CAT CTG CCT CTG CCC AGA GCA TCA CCA TCA CCA GCC CCA GCC CCA GCC CCA GCC CCA GCC CCA GCC CCA GCC CCA GAT GTC AGT
 703 CTG CCC TGA CCC AGC CCT CTG TGT CCT GCT ATC AGC AGC ATC TCA GCA GCG GCA ACA CCG CCC AGC CCA TGG GCA CCG GCA GCA GCG GAA GTT CTG TTT
 781 ACG TGG GCG TCA ACT ACA ATG AGA ATG GGA GCA ACA GAT TCA GCA GGT CTT TTT TCA GCA GGG ACT CCA GCA GCA GCG AAG TCA GCG AGG TGT
 859 CCA ACA GAC GCG CCA GCG AGG ACG AGG TGA GCA ACA GAT TCA GCA GGT CTT TTT TCA GCA GGG ACT CCA GCA GCA GCG AAG TCA GCG AGG TGT
 937 TCC AGG CTG AGT GGC GTA GGA GCT ACT ACT CTT TTC TCA CTA GGA GTT TAT CAG CAT ATA TAC TGG TCT CTT GCG GCG CAA
1015 AGC GTC AGT CTC GAA AAT CTT GAG GAG ATG AAA ATG GGA GCA GTA TGA GAA ACT TTC AGG AAC ATG GTC AGT CTC GAA AAT CTT GAG GAG ATG AAA ATG GGA GCA GTA TGA GAA ACT TTC AGG AAC ATG GTC AGT CTC GAA AAT CTT
1093 GTC AGT TCA GAA GTG AGA GTA GGG GCA TTA GCA GAA AGA GGC TTT ATT GAG AAC TTC ACC AGG ATA TGA AAC AGT CGT TTT
1171 ATC AAG CTG AGA AGA GGG GCA TTA GCA GAA AGA GGC TTT ATT GAG AAC TTC ACC AGG ATA TGA AAC AGT CGT TTT
1249 GAT TGG ATC GGA GAA GAA TAA GCA TGA GTA GAA TTC AGG AAC ATG GTC AGT CTC AGT CAG GTT CAG GTT CCA AGA CGT TTA
1327 AGT GGG AGA TTT GGA GGG GAT TTG CAA ACT CAT TGA GTT GCA GAG ATA GAA GTT CAG GTT CAA AGG GGC CTC CTA AAA
1405 TGG ATG GAG CAA ACT TTG AAG ATA AAC TGA GTT TCC ACA AGT ACT GTC TTG AGT TTT GCA ATA AAA GTG GGA TAG
1483 CTC TGA GAA GAG GAG AAG CAG ACT CAT CCG TGT GTT TCC ACA AGT ACT GTC TTG AGT TTT GCA ATA AAA GTG GGA TAG
```

Fig. 12, contd.

```
1561 CAG AGT TGA GTG AGC CGT AGG CTG AGT TCT CTC TTT TGT CTC CTA AGT TAT GAC TAC AAA AAT CAG TAG TAT GTC
1639 CTG AAA TCA TTA AGC TGT TTG AAA GTA TGA CTG CTT GCC ATG TAG GTC TAG ATA CCA TGG CTT GCT GAA TCA GAA GAG
1717 GTG TGA CTC TTA AAT TTG TCA CAA GAC AAT ATG AGA GAC TCT GTA GGA CAG AGT CCT TGA CAG ACA GCT
1795 CAA GGG GTT TTT TTC CTT TGT CTC ATT TCT ACA TGA AAG GTT TAA AAT TGA GAT CTT TAT TAT AAG AGT AGA AAT
1873 ACA GTT GGG TAA TTT GAA CTA TAT ATC GCC AGC AAT TTA ATG GGA CTG AAA CGG TCC GCA ATT TTC CCA GTT ATT ACT
1951 CGA TTG TAA GCC ATT TGG CGT TCA CCC TGC TAA GGG CAC TGT GAA CCC GGT CTG CAT CCC TTG GAC CTC GCG GTG GAC
2029 GTG CCA TTT GAG GCA CAG TGA CTT ATT GGA GAT TTC AGA AAT AAA ATG CAT TTA TTA TAT TCC CTT ATT TTA ATT
2107 CAC TTT CCT ACA AGG AAA GGG TGA CTT ATT GGA GAT TTC AGA AAT AAA ATG CAT TTA TTA TAT TCC CTT ATT TTA ATT
2185 AGA AAA ACA AGG AAA GGG TGA CTT ATT GGA GAT TTC AGA AAT AAA ATG CAT TTA TTA TAT TCC CTT ATT TTA ATT
2263 TTC TAT TAG GGA ATT AGA AAG GGC ATA AAC TGC TTT ATC CAG TGT TAT ATT AAA AGC TTA ATG TAT ATA ATC TTT TAG
2341 AGG TAA AAT CTA CAG CCA AAA GTC ATG GTA AAT ATT CTT TGA CTG GTA TAA ACT CCT CTA AAT TAT ATG
2419 TCA TAT AAT AAT CGT AAA TTA ATA TAA ATT TGT GAC ATG ACC TTA ACT GGT TAA TTC TCT TCA TTT AAC TGC AAA
2497 AAT ATG ACT AAT AAT TTA GCA CAA CAA TAT TTC TGT GAT AGA AAA ATG TTT AAC AAG CAA CTA TTT AAG
2575 ACT ATA ATC CCA TAA TTT TGA AAA CTA CTT TAG AGT CAT ATT TGT GTT ATT CTC CCT TTA CCA ATT CTA TTG TTT TTC GTA AAA TGA TGT CAA
2653 GAC CCT TTA AAA CTC TAT TAT TTA CTA TAG AGG GGG GAA AGT CTG CAT AGG TGG CAT CTG TTC TGG TGT
2731 TTC CCT TTT AAC TAT TTA CTG TCA CCC CCA GTT CTG AGT CCT CCC AGG CAG GTG GCC ATT ACA GTT ACA AAT ATT CCG AGA GGC CTG TTC GGA CAC CCA
2809 CAG TTT TCG TAA GAT CAG AAG TGA AGT CTG TCA CCC CCA GTT CTG AGT CCT CCC AGG CAG GTC TGA ATT ACA GTT ACA AAT ATT CCG AGA GGC CTG TTC GGA CAC CCA
2887 GTT GCT TAA AAA TTG TCC CAT GTG AGG CCC TTA ACA AAC CAT TAC TAG ACC AGG GTC TGA GCT AGG TTT AGC GAA GCC ATA CAG AGG CTA
2965 GGC TAA AAA TTG TCC CAT GTG AGG CCC TTA ACA AAC CAT TAC TAG ACC AGG GTC TGA GCT AGG TTT AGC GAA GCC ATA CAG AGG CTA
3043 AAT ACA GAC CCT GGC TTA AGG CCC TGT CCA AAG ATG TCA CAC AGT AGG TGC ACT TGT TCA GAC
3121 ATA TCA GGA TAT TCT TGG AAG AGA CAG AGA CTA GAT AAA CTG GTC TGA ATC TCT GTC TGA AGC ATG ATG AGA ATG TAG TTT CAG
3199 TCC CAA ACA TCA GGA GCA ATA GGA AGC CTG AGA AGA TTT ACT TGT TCC CAT GAA ATG CAA CCC TGG GTA AGT AGC TAG
3277 GGA AGA AAG GCA AAT AAC TTA GAA ACA ACA AGA TTG TAT ACT GTT TAC ACA CTC ACC ACT TGT GCA CAC AGG ACA TCT GCG AGG ACA AGA CCA TGG
3355 GAA CTA GGG CTT TTT TGT GTG CCT CTG TGC TTC CCT GTA TAT AAC ATA CCG GGG TGT GCT TTC ACC AGG ACA TCT ACC AGG ACA TCT ACC TGT ACA GCA TGG AAC
3433 AGC GTG TGA CAT CCT CTG GCG AGC GAG AGA GCG TGG CCA CCG ACG AGG TGA GCG AGA GCG TGG ACT CCA GCG ACA CCA GCT CCC CAG
3511 TCA TAC CAT CCT CTG GCG AGC GAG AGA GCG TGG CCA CCG ACG AGG TGA GCG AGA GCG TGG ACT CCA GCG ACA CCA GCT CCC CAG
3589 AGC TGA CCT CTG GCG AGC GAG AGA GCG TGG CCA CCG ACG AGG TGA GCG AGA GCG TGG ACT CCA GCG ACA CCA GCT CCC CAG
3667 TCG ACG GCA GCG TGA GCC AGG GCG TGA AGG AGA GGC TTG CAG GCG TCA AGT CCT TCA AGT CCA GGT TGT GCA TGC AGC CCA GCC TGC ATG
3745 GCA GCA GCG CCC CCG TGG TCA GCA GTT ACC GGA GAC GTT GAA GCT GTA TCA TTA CAG GCA TCA GCA TGG AAG CAC GCA ACC
3823 CCA GCC ATG CCG CCT ATC CTT CCC AAG GTC TTG GAG CTT TCC TTA CTA ATC CTT CTG CAT CTG GAT CAT GGT GTG CCA AAC CTC
3901 CTC CAT CTC CCC ACC TCC TTC TCC TCC TCT AGA TCT GAC ACG GCA ACG CTG GCT TTT GCA GAA AAT ATT CAA TAA AGT
3979 CTC CCC TTG CAC TTT AGA ATG TTT AGT GCT CTT TCT TTC CCT GCA GCT TAC TCA CAC GAG AAA CTG CTG AAG CAC CTC GGC
4057 GAG TTT TAA AGT CAC ATG ACA GTC CAT AGC CTG CTT TGG AAG ATC CTC CTG GGC TAC AAG CTT CCC TGG
4135 TTC TAA AGT CAC ATG ACA GTC CAT AGC CTG CTT TGG AAG ATC CTC CTG GGC TAC AAG CTT CCC TGG
4213 TTG GCT CAC ATG ACA GTC CAT AGC CTG CTT TGG AAG ATC CTC CTG GGC TAC AAG CTT CCC TGG
4291 TTT GAG GAG GTC CAC TAC TTC CTA GTT ACC CCT ACC CAG GTG GAA AAA GTA TCA TTA CAG GAA AAG CAC ATG
4369 TTC TGT GCT ATT CAA CTT CAA CCT TCA AGT GAA GCC TAA ACT TGG CGA AGC AGT ACT GGA ACT TCA CTA AGT
4447 TAA ATG TGC ACA CAA TAG GAA AAT TGC CTT GAA GCC TAA ACT TGG CGA AGC AGT ACT GGA ACT TCA CTA AGT
4525 TTT TAA ACA AGG CAG TTG GAA ATT CAT CAT CAT GGA AGG AGG CAC ACC CAC ACC TGA GAG CTG AGG ATC ACC CCA CCT TCA AGT
4603 CGT GAG ATT ACA CCA ATA CAC CAT CAT GGA AGG AGG CAC ACC CAC ACC TGA GAG CTG AGG ATC ACC CCA CTC TTA GGT GCT
4681 TAT CTC TGT ACA CCA GAA ACC TTA AGA AGC ACT TTA AGA ACC CAT CAG ACT TGA GAG ACT CAT TTA TGA ACT GGA TAC AAC
```

Fig. 12, contd.

```
4759 CAA AAT GTC CAC CAA CAG TTA AAT TAT GAC ATG TTC ACA ATT GAG CTA TTA CTT AAT AAG GAG AAT TAA TAA AAT AAA
4837 ACT TAA GAG CAT AGT TTA ATC TCA TAA ACA AGA TAA TAA ACA AAA AAT TTC TCA TCC ATG TCA TCC ATG TAA GTT TAA AAG
4915 CAG GTA AAA TTT AAG AGA GAC ATA AGT TTT GAG GTA GCA AGA TGG GTA GCA AGA TGG AAA CTC TGG GGC TTG GGG AAT GTT CTG
4993 TCT CTC TGT ATG GGA TGT GAA AGT TAC TAT GGA ATT GGG ATC AAA AGA CCT TAT GTT CTT CCT GTA TAT ATT GTA TAC TTC ATA
5071 ATA ACT TCA CCT AAT GAA ATA GGG GAT TCA AAT CCA GGA TCA AAA CAA CTC CCA TTG GGA TGC ATC TGA ATC TCT GCC ATA CGT TTC CAA GGC
5149 CAG AAG GAC TAC AAA ACA CAT GAA GTA CAT TCA AAC AGG TCA ATC AAC AGG TCA ATC AAC TTC ATG GCC ATT TCT CGA ATT AGA AAT AGC
5227 TCA CAT GTA TAA AAT GAG GTT ACA TTA GGG AAG GAA GAG AAG ACT AGT GAT TCA CAT CCT GTA TGA AGA GCC
5305 CAC GTA TCA AAG TCC CTG GGC TCA TCC CCT CTA CAC TTT CCC CTA CAC TTT CCC CTA CAC TTT CCC CCT CTT CCC CTT GAA GGC AGT
5383 TGC ATT TAG TGT TAG TGT CCC TTC CAG AAT TGC AGT CCA GTT ACT AAG CAT CTT CTC AGT GTA CAT TAT
5461 GCA GAA GAT GGG AAA GGA CAG CAG CTA ATA TGC AGG CAA CCC TTT GCC TTC CTA CCT TTC GAG AAT GTT CAT CCA TTT
5539 AAG GCA CTT TTT GAA ACT TCT TTT AAT TGC TTT TAT TTT CTT TAA AAA TAT CTG AGC AAC
5617 TAT CCA CTT TTT GAA ACT TCT TTT AAT TGC TTT TAT TTT CTT TAA AAA TAT CTG AGC AAC
5695 CTG GGA ACC CTT ATC TAA GAA TTT CAA CAG CAC AAT AGC ATT TAA ATA CAT CTG AGC TAC CAT
5773 TCG AGT CTT ATC TGT GAA AGA ACT TAA AAA AAT CAG TCA TAT TTT AGA GAA ATA CAT TTT AAA ATT CTG TTA TAC CAT
5851 CTT GTG CTT TGT GAA AGA GGA TCT TAT ATT GTA TCA AAT GCT TTA GGA ACA TAA CTT AAA AAC CAT
5929 TAG AGA GAA GGA TCT TCA AGG TCA TAT ATT GTA TCA AAT GCT TTA GGA ACA TAA CTT AAA AAC CAT
6007 TCA CAA GGA TCT TCA TAT CTA TAA AAG AAA AAG ATG CAT TTT GTG GGA AAG GTG CCA TAT AGT GTG ACA TAA CTT AAA AAC CAT
6085 AAT GTT GTT GAA CTA ATT TGG ACA AAG AAA ATG AGC CAT TTT GTG GGA AAG GTG CCA TAT AGT GTG ACA TAA CTT AAA AAC CAT
6163 ATA ACT ATT TGG ACA AAG AAA ATG AGC CAT TTT GTG GGA AAG GTG CCA TAT AGT GTG ACA TAA CTT AAA AAC CAT
6241 TAT TGA TAA CTA ATG AAA AGC CAT TTT GTG CCA GAG ATA TCA TGC GGC AGA GCA GAT AAG AGC TGT GAG CCC CAA TAG CAC AAA ATG GGG
6319 TTT GGA TAA CTA ATG AAA AGC CAT TTT GTG CCA GAG ATA TCA TGC GGC AGA GCA GAT AAG AGC TGT GAG CCC CAA TAG CAC AAA ATG GGG
6397 CCT AAG CCT CAG AGA CCT TCA AGG TGT TGC TGA ACT TTG GGA ATT GGA AAA ATT TAT GTA TCA CCA GTC TAG TTC CCC CTG AGA AGA TTC CTT TAG TGT TAG CAT AAT
6475 GCT AAT GCC CAA CTA CCT TCA AGG TGT TGC TGA ACT TTG GGA ATT GGA AAA ATT TAT GTA TCA CCA GTC TAG TTC CCC CTG AGA AGA TTC CTT TAG TGT TAG CAT AAT
6553 ACT GCT TCT CTA TGT TTT GTA TTA TTG CCA AAC TGC TTC CCT TAG ATT ACT GGA AGT GCA CCA AAG GCA CAT TCA ATT TGG CAT AAT GTT
6631 CCC TAC AGA CTC TTT TGT GTG CAT GCT CTC CAC AAT AAA CCA CAC AAT GCA AGA CAT GCA AGT GCA CAT GGT GAA CTG AGA CTG TTT CTC CCT CAG AGT ATC CAG
6709 ATA AGG AAT GTT TGT GTG CAT GCT CTC CAC AAT AAA CCA CAC AAT GCA AGA CAT GCA AGT GCA CAT GGT GAA CTG AGA CTG TTT CTC CCT CAG AGT ATC CAG
6787 TAC AGC TAA TAG TCC CAT GCT CTC AAG AGA CAT GCA AGA CAT GCA AGT GCA CAT GGA AGT GGA AAG ACT GTG AGG ACT GTG AGG AGT ATC CAG
6865 AGA AAG ACA TTA AAA ATG AAG AGA TTC CAG AAG GCA CAT CCT TTA CAA AGA GTA GAG TCA ATA AAT GTT CAT GAG TCT TAT
6943 TAG TCA AAG AGG ATT AAG GAC TTC TGC CTA TGC CTT TGT GGG GAG TGT TGG GGT TTT TTG CAA CAT TGC TTT TTG CAA CCA
7021 AGG AGA CTA CCA AGT ATG TGG CCT TTT GTT AAG GTA TGG TTT TGT GGG GAG TGT TGG GGT TTT TTG CAA CAT TGC TTT TTG CAA CCA
7099 CTA AGC CCC AGT ATG TGG CCT TTT GTT AAG GTA TGG TTT TGT GGG GAG TGT TGG GGT TTT TTG CAA CAT TGC TTT TTG CAA CCA
7177 TAG TTT TTC CAG GTT TGT CCT CCT TAT CCT TAT TTT GGT TTT TTG CAA CAT TGC TTT TTG CAA CCA
7255 GTT TTC TTT GGA CTT CCT TAT CCT TAT TTT GGT TTT TTG CAA CAT TGC TTT TTG CAA CCA
7333 TGT TTT TTG GGA GTT GTA TTT TTT GGT TTT TTG CAA CAT TGC TTT TTG CAA CCA
7411 TGT TTG CTT TTA AAA AGG ATT TAG TGT CTC AGA GGG GAT CCT CTA ATT GAT GAA AGG AGA ATT TTG GAA TTT CAT GAG GTT TTT TGT GGT TGG AGT TTA ATG TCT GAT TGT
7489 TTC TTC TAT CTC AGA GGG GAT CCT CTA ATT GAT GAA AGG AGA ATT TTG GAA TTT CAT GAG GTT TTT TGT GGT TGG AGT TTA ATG TCT GAT TGT
7567 TTA TTC ATT ACT TAC TTA TTG GTT GTT GTC CTC GTA GAT CCA CAC CCT CCA GGA TAA ATT CAA CAA TTA AAT TCT CCT ATT GTT
7645 GCA ACT AAT GAG GAG TTC CTG ATG TCA CAC CCT CCA GGA TAA ATT CAA CAA TTA AAT TCT CCT ATT GTT
7723 GGG TCA ACC ATG TCA TGG CAT GGG CAT GAA GTA TAA GTA TAA GAT TAA CAA TTA AAT TCT GAA AGT TCT GAT
7801 AAA AAT AAT AAC ATT TCT TTT AAA AAA ATT AGC TAT AGC CTT TCT CTA TCA GGA AAT TCT GAA AGA ATT
7879 AAT AAA AAC ATT TCT TTT AAA AAA ATT AGC TAT AGC CTT TCT CTA TCA GGA AAT TCT GAA AGA ATT
```

Fig. 12, contd.

```
 7957 AGT TAA ATA AGT TAT ATT GTA GAA AAG AGA GTA GAG AGG AGA ATA GTG GAA GAG AGA GAT AAG GAG ACT TCA AAA GGA GTG
 8035 GAG GGA GAT AGA GGA TAT TTC GCC AGA AGC AGC TGA AAT GGC CAG TGA CAT TAG CAG GAT AAG CAG AAA GGA CAA GGT AGA GGA
 8113 AGC CAG GAT TTC GCC TAT CTG TTT GCC AGA GTC TTT TAA TGA CAT CTG GCA CAT CTT GGT GAA AAT TGA GTT CAA GGC TTA ATT
 8191 CTT CAC TTG TGC TTA CAA CTC CAA ATT TAG TTA CTG GGT AAC TTT GTG AAG TGC ACA CTG AGA TAT GCA CTT GTA GGT CCT ACA
 8269 CTT ATC TCC TAA TAC AAA GAT ACT TTG AAG AGT ATA TGT TTA TAT AAT TTA ATA AGT CAC TTT GTA CAT CAG GCT TAG ATT TTT
 8347 ACT ATT TCA ACT CAA CAA TGT GGT TTT CGA GAC AGG GTT TCT CTG TAT CCT GGA ACC CAC TCA GAC TGT GTA GAC CAG GCT GGC CTC
 8425 ATT TCA ACT CAA CAA TGT GGT TTT CGA GAC AGG GTT TCT CTG TAT CCT GGA ACC CAC TCA GAC TGT GTA GAC CAG GCT GGC CTC
 8503 TAT GGT TGT CGA GAC CTA AAC CTC AGA CCT TCT GCC TCT GCC TCT GCC TCT GCC TCT GCC TCT GCC TCT GCC TCT
 8581 AAA CTC AGA AAC CTA GCC TCT GCC TCT GCC TCT GCC TCT GCC TCT GCC TCT GCC TCT GCC TCC CCA CGC CCG GTG
 8659 GCC TCT GCC TCT GCC TCT GCC TCT GCC TCT GCC TAG AAT TAA AGG CTG TGC TAG AGA CTG TGC TAA ACT AAT AAA TGT
 8737 GCC TCT GCC TCT GCC TCT GCC TAG AAT TAA AGG CTG TGC TAG AGA CTG TGC TAA ACT AAT AAA TGT
 8815 AAA TTT TTA AAC AGT AAT TAT GTC TCA TTC TGT TGT TGT CTT TGT CTT TTG CTT TTG CTT TTG CTT
 8893 GCC CTC AAA AGT AAT AAG TTG TAT AAG TTT GCT TTG CTT TGT TTT GCT TTG TTT TTT GCT TTG CTT
 8971 TGC TTT TTT CCG GGG GAG TCA CTG TGG AGA GAT CAT GTT TTA GCA AAG CCT TTG AGA AAG GCA ACA TAC ACC TCC ATG CCC
 9049 TTT TTT CCG GGG GAG TCA CTG TGG AGA GAT CAT GTT TTA GCA AAG CCT TTG AGA AAG GCA ACA TAC ACC TCC ATG CCC
 9127 AGG CTT GAT TGA TCC CAA GTT ACC CAA GTT TTA GCA ATA CTC ATA TCT GCC ATA GAG CTT AGT CTT CTA GAT CTT ATG CGA ATT CCA GTG GGG GCA ATA
 9205 AGA TAG AAT GTG GAG CAT TCA ATG GCA GTG TTT AAG CTT CCT ATA TCT AGT CTT CTA GAT CTT ATG CGA ATT CCA GTG GGG GCA ATA
 9283 ACT AAT AGG CTC ATT ATA CAG ATG ATG AAC TTT CAA TAT TTT CCA CTG ATT TTT ATT TTT AAC ATT TAT
 9361 TAG CTC ATT ATA CAG ATG ATG AAC TTT CAA TAT TTT CCA CTG ATT TTT ATT TTT AAC ATT TAT
 9439 TTA CTC ATT TAC TTT CAA TAT TTT CAA TAC ATG AAA AAA TCA GAA TCA TAT GAT CAC CTC TTC GAT CAC CTC ATT TAC ATT TCA AAT
 9517 AAA ATC ATT TAC TTT CAA TAT TTT CAA TAC ATG AAA AAA TCA GAA TCA TAT GAT CAC CTC TTC GAT CAC CTC ATT TAC ATT TCA AAT
 9595 AAG AAT TAA ATG AAA AGT CTT TGA TAA AAC GCC CCT GCT ACC TGC CCT AAG CCC CAA ACC CTC TTT CTG GCC ATT AGG CCA TAG AGT TGC AGA
 9673 AAA GAA AGA AGA AAA AGT CTT TGA TAA AAC GCC CCT GCT ACC TGC CCT AAG CCC CAA ACC CTC TTT CTG GCC ATT AGG CCA TAG AGT TGC AGA
 9751 GCT ATC CCC AAA GCC GCA TAT GAT GAC CTT CAA GCT CTA GGG AAG GTT CTT CAT GTC ATA TTG TTA GTC TCC AAT AGA TCT CTA TAG AGT TGC AGA
 9829 CTC TGT ACT GAG GCA ACT AGA GAC TAC TTT CTC GGA TAG GGG TTC CTC ACG AGA AAG TGG AGA GAG CTA TGA TCC CAA AGT CCT GTC AGT CTT TAA GAA TGG
 9907 GCT ACA TAG CTC CTT TTT GCC AGG CAC TGG GGG AGA CTG AGC CTC ACG AGA AAG TGG AGA GAG CTA TGA TCC CAA AGT CCT GTC AGT CTT TAA GAA TGG
 9985 CCC CTT TAG CTC CTT TTT GCC AGG CAC TGG GGG TCT GGG CTC CAA ACT TTG TCT CTA GAG CTG GAT GGA GCA GTC GTC TCT GAA TGG
10063 TCC ACT TCT GTA TTT GCA ATA GTA TCT GGG CTC CAA ACT TTG TCT CTA GAG CTG GAT GGA GCA GTC GTC TCT GAA TGG
10141 TTT CTG GCA ATA GTA TCT GGG CTC CAA ACT TTG TCT CTA GAG CTG GAT GGA GCA GTC GTC TCT GAA TGG
10219 TCC TTC CTT CCA TCT CAG CTC CTT CCT TCT GTT TGA GTT TCA GTT TCT GCA TCT GTT TGA TAT TTC TAA GTT TCT GGG TTA
10297 GTG AAG AAT CCA CAC TTT GGT CTC CCT TCT ATC ATG GTG CAT GTT TTT ACT CGT TTC ACA ATC CAG GAT ATC CTC CAG
10375 ATA TCC ACG TAT CAG TGA GTG CAT TTT GCC CAT TTT GGG CAT CTT TGT GTT TGA TAT TGC CCA TAT AAA GGC TGC TAT CTT
10453 ATG ATG CAT TTT CTG CTC TGT CTC ATC CAT TTG ACA CAT CCT CCT AGA CAA TGA AGC TAT ATT AAA GAA ATC AGA
10531 CAT TTT CTG CTC TGT CTC ATC CAT TTG ACA CAT CCT CCT AGA CAA TGA AGC TAT ATT AAA GAA ATC AGA
10609 GAG CAT AGC GTA CCA GCA TCA ACA TGC ATT CTT GAC CAT ATT GTC GGT AGG ACA ATG AGC TAT ATT AAA GAA ATC AGA
10687 CCG GTA TAT GTA TAT GTA CCT CCT AAA TGA ACA TGA AGG ACA ATG AGC TAT ATT AAA GAA ATC AGA
10765 AAA GGT TAT GTA CCC ACT ATC CCT CAT TCT CAT CAC ATC CTT ATT AGC CAC CTC CCC AGA ATC AGA
10843 GGA CTG CCC ACT ATC CCT CAT TCT CAT CAC ATC CTT ATT AGC CAC CTC CCC AGA ATC AGA
10921 CAA ATG GGA AAA TAT TAT GTC AAA TTG TTT TCA ATT CAG AGT GAT TAT AGC ACC AGA TCA AAT TTT GAC
10999 TAG AAA AAT TGT AGA AAT TAT CAA TAA CAA TTG TCT AGA GAT TAT CAT CTT CTC CCC AGC TTC
11077 TGC TTG CTT CTC TCT TCT TGC TCT TCA TCC TTT CTG TTT CAG CTG TCT CAA GAC TGA GTG CAG
```

Fig. 12, contd.

```
11155 CGT GTA ACT CTC CTG TGA CTG AGT ATC TCA CAA AAC GTT CTA CCT GCC AAA CCT GGA TGA GCC CTT TGT CTT TCT GAA
11233 GCT ATG AGG CTC TCT ACA TAG ACT TTA ATT TCT CAA GAA GAT TCA GAG GAG GTA ATA AAG TGG GGA AGG CTG ACA TTA
11311 GCA TTG CTC CTG TGT GGC TCC TAT GGC GTT AGT GTT GCA CAG TGA GAG CAC TGA GAT GTT ATT AAC TGT GAC TCA GTG CTC CTT
11389 CCA GAG CTA AGG TTC TCA TAT CCT TTC ACA CAG GTT GCA GTA GTA GGA TCC TAA TTT TAT ATA AAC TAT GGG TCA TGA CTC CTT
11467 TAT GGG TCA AAC TAC CCT TTC ACA CAG GTT GCA GTA GTA GGA TCC TAA TTT TAT ATA AAC TAT GGG TCA TGA CTC CTT
11545 ATA TAT ATA TTT CAC AGT AGG AAA ATT TTG AGA CCC ATG TCT GTA TAT GAG AAT TAG GGC AGG CAT GAG GAA CTG
11623 TAT AAT GGA CCA TGT GCC TTT GCC AAC ATT GTC TAT CTT GTA AGC TCT GTA TAA ATA CAT AAG GCT TTG GTT TGT AAT
11701 AAT GGA CCA TGT GCC TTT GCC AAC ATT GTC TAT CTT GTA AGC TCT GTA TAA ATA CAT AAG GCT TTG GTT TGT AAT
11779 TTT AAA TGG ATA AGG GTC TTC ACT CCT AAG ACA TAG ACA ATT GAT GAC CAA ATA GGA ATG AAT CCA TGT AGA GAC CTT CTA
11857 AAA TGC AAA AAT CCT TCC ACA GGC TCC ACA GCC TTG CAA AGT TCT ACT TTG CTA CCA CTT CTT AAA GAC GTG TCT AAG CTC
11935 TCT CTT GAT GGC AAT CTT CAG GAC ATG AGC CCT GAA ATG AAC TTG TGC TGA CAG CAA AGT ATC TGT GTG TAC ACC CCT GTA AAA
12013 CTG CCA TTG TAA ATG TCA AGC TCA TGC AGA TCA TGC CTG TGT TGC TCC AAG CAG CAA AGT ATC GAC TCT GTG TAG TTC ACC CCT GTA AAA
12091 AGG GAA TAA ATG GTT GTT CCT TCA CTA GCT GTC TCA TTT AAC AGA GTC GAT CTC CTC AAA GTA GCT CTA AGA AAT ATC TGG TAC CCC TAG TGG GAA
12169 AAT GTT GTT CCT TCA CTA GCT GTC TCA TTT AAC AGA GTC GAT CTC CTC AAA GTA GCT CTA AGA AAT ATC TGG TAC CCC TAG TGG GAA
12247 AAG ACT TGG AAA TCA GGA AGA CTT AAT AGG AGA ATT GTT TAA CCT ATG GTT AGA ATC TGG GTA GCC TAT GCC TGA GAA CTG CTT
12325 ATC CCA TCG CTA TAC CTA CCT GGT AGT GTC TCA AAT AGA CTT ATG GTT AGA ATC TGG GTA GCC TAT GCC TGA GAA CTG CTT
12403 AAT AAT TAC TAA CCT GAG AGT GTT AGA TTT ATG GTT AGA ATT GTT TGG AAA ATA ATA TTA TCA GCC TAT TGA TTT TCA TGG TGA GCC ATA GCA CAG
12481 TAT TTT CTA CCT GGT AGT GTC TCA AAT AGA CTT ATG GTT AGA ATT GTT TGG AAA ATA ATA TTA TCA GCC TAT TGA TTT TCA TGG TGA GCC ATA GCA CAG
12559 GCA ACA ACA CAC CCA TAT CTC CCC ACC CAT GGG AGT GTC CCA TGG ACC TAC CAG ACT GGT TAT TGA TTT TCA TGG TGA GCC ATA GCA CAG
12637 AGT ACC ACC CAC TAT CTC CCC ACC CAT GGG AGT GTC CCA TGG ACC TAC CAG ACT GGT TAT TGA TTT TCA TGG TGA GCC ATA GCA CAG
12715 TAA AAA AAG TAA TGC CTT GAG CAC ATT GAA ACC CTG TAG ACC CTA GAA ACC CTT CAC GCG CCC TAC TCC TCC TCC AAC
12793 TGA TCA AGA AGA CCC TTT GAG GAA CTG GCA CAT ATA CAC CTG ATA CAC CTG ATA CAC CTG ATA CAC CTG ATA CAC CTG ATA CAC CTG ATA CAC CTG ATA CAC CTG AAG
12871 AGC GCG TGT ATC CAG CAC CAG CAC CTG GCA GAA AAT GAT GAA ACT TCA AGC TGT TTG ATA TTA CAC CTG ATA CAC CTG ATA CAC CTG AAG
12949 GGC TGT CCC CAG TCC CAA TGC TTT TGC AAG ACA TGT GCT AAA TAG TTT GGC CAT CAA GAT CTT TAG GTT TCA GCT AGA CCC CAG GTT
13027 AGT CCC CAG TCC CAA TGC TTT TGC AAG ACA TGT GCT AAA TAG TTT GGC CAT CAA GAT CTT TAG GTT TCA GCT AGA CCC CAG GTT
13105 CAC TGG GCA AAA AAT TGT GCT AAA TAG TTT GGC CAT CAA GAT CTT TAG GCT ACA CCC ATA CCC ATG GCG CGG AAT ACA GCG ATG GAC TAT ATC
13183 GTG AGC ATT GCA GGA TAG TGC TTG TCA GTA AAC ACC GTT ACA GAA GTA TTC TCT TAT ATC CCT TTT CCA
13261 AGC ATT GCA GGA TAG TGC TTG TCA GTA AAC ACC GTT ACA GAA GTA TTC TCT TAT ATC CCT TTT CCA
13339 TCC ATG TAG GCT GTC ATA TTT CTA GAC GGC CGG CC
``` pSELECT-IGKV1-39/J-Ck

```
  1 GCG GCC GCA ATA AAA TAT TTT CAT AAC TAC TGT GTG TTT TGT AAT CGT CAG GTG CAA AGT AGG CTG TTG TCC CCA CAT ACG CTC
 79 TCC ATC AAA ACA CGA AAC AAA CGA ATC TAG CCC GTC CCA GAG AAT GTG CAG CAG TCC CCG AGA CAT TTC
157 TCT ATC GAA GGA TCT GCG ATT GAA CGG GTG CCT AGA GAA GCA AGT GGT GGG CAG AGC GTC ATG ACT TTC GCA AGT TGG
235 GGG GAG GGG TCG GCA AGC GGG GTC CCG GCG AAA GTG TCG ATG TTT TTC GCA ACG GGT
313 TCC GCC TTT TTC CCG AGG GTG AGC GTG CAG AAC GTG CAG TAA GTG CAG GGG CCC CCG CTC CCG GTC CTA CCT GCA GCC GCC
391 TTG CCG CAC GCC GGT TGA GTC GGG TTC TGC GCC CTC GAG CTC GTG CTG GTG CCT CCT GGA CTG GAT CCT AGG TAA GTT
469 ATC CAC GCC TCA GTT CGA GAC GCC TTT GTC CGC CGG CCG CTT GGA GCC TCT CCA CGC TTT
547 TAA AGC TCA CCC TGC TTG CTC AAC TCT ACG TCT CGT TTG CGC TCG CTC ACG GCA GCG CGT CAT CCT TGT
625 GCC TGA CCC TGA GGT TTA GTC TGG CCT ACC TGC TCG TAG GAT ACA AGC AGC CCT ACG TCT CCA CGC TTT
```

Fig. 12, contd.

```
 703  CGC CTA GAG ATC ACC GGC GTG TCG ACG CCA TGG ACA TGA GAG TGC CCG CCC AGC TCC TGG GGC TCC TGC TAC
 781  TCT GGC TCC GAG GTA ACA TGA GAG AAC ACT AGA AAT AGG ATA CTC AGC TGT GCT CAG TAC TGA CTT CAG GGA
 859  AGT TCT CTG ATA AGC CCC AGC TGA TTA GTA AGC GCC ATC TTT GTT TTT ATG TCA ATC GCC AGA TGT GAC ATC CAG
 937  ATG ACC AGC AGC CCC AGC TGG TAT CAG CAG AAC GTG GGC AAG GTG ACC ATC ACC GCC ATC TGC AGC AGC ATC
1015  AGC AGC GGC GTG CCC ACC TAT TTC AGC CAG CAG CAG TTC AGC CTG CTG ACC TTC GCC AGC AGC TCC CAG CAG
1093  AGC TTC GCC GAC GCC AGA TAC TGC ACC GTG TCC CAG ATC TTC GGC CTG GGC CTG GGA GCC GAG ATC GTC
1171  GAC TTC GCC GAC GCC TAC CCC AGA CAG GTG TCC CCC AGC ATC AAG GAA CAG ATG GGC CTG GGA GCC GTG GTC
1249  AGA GCC TTC GTG AAC GAC TTC TAC CCC AGA GAC AAG AAG TGG ACC AGC ATC AGC AGG GAC AAG GTG GTG
1327  CTG GAC AGC GTG TAC ACC CTG AAC GAC AAG GAC TAC TGC CGT GAC CTG AAG GTC ACC TTC AAC CGG
1405  TAC GAG AGG TGT GCA CAC AAC TGG AAA GAG ATG GTG GTG CAC AAG GCA CAA CAA ACA ACT AGA ATG CAG GAG
1483  AAC AAC AAA ACC CTG TGA TTT ATT TGT GAA ATT TGT GAT GTA TTT ACC ATT GTA AGC TAA CCT AGA CTT CTT TCT
1561  AAA AAA ATG CAA AAT GGT ATG CAT TTT TAA AAT CAG CAA ATT GCT GTG GAG GTG AAC CTC CAG CAA ATC CTC
1639  AAC TGT GGA TGA ATA AGG CAT TCC CAA GGT TTG AAC TGC TTC ATT TCT AAA TGC ACT GAC CTT CTT TCA TGG
1717  GAG GGA TGA AGA TAT AGT GTA TTT TCC AGA TTT AGT ATA CTC CAA TCA TTG CAA TGA AAA TAA ATG TTT ATT AGG CAG
1795  AGT TTA AGA TAT AGT GTA TTT AGT AGT GCT CAA AAT ATA TTC AGA AAT ACA TTG CAA TGA AAA TAA ATG TTT AAT AGA
1873  CAT TCC CTT AGT GCT CAA GCT CAA GGC CCT TCA TAT AGC GCT TCT ACA CAG GGG AAC AAA GGA GTG CTG GGG CGT CCG
1951  AAT CCA GAT GCT CAA AGA AAG CGA AGA ACG TCG AGA TCT CTT ACG GTC CGG CTT GGA GCG ATT TGT GTA CGC CCG
2029  AAT TGG ACA CGG CAG CTG CAC GAT GTA CAG TAC CGT AAA TGG TCT CAA GCT GTA AGG GGC CGC AGG AGG CTG GAG
2107  TTT CCA GTC GCG AGT ACT TCT ACA CAG CCA TCG GTC CAG CGA TCA CAG CTG ATT TGT GTA CGC CCG
2185  ACA GTC CCG GCT CCG ACG ATT GCG ACG CGG CAA GCT GCA ACA GCT GGA TCG AAA TTG CCG TCA ACC
2263  AAG CTC TGA TAG AGT TGG CGC AGA CCA ATG AGC ATA GCC CGG AAG ATG CCT GCA AGC TCC GGA TGC TAT
2341  CTC CGC TCG AAG TAG CGC ACG ATC GCC TGC CTC CAG ACT GTT CCG CAC CAA ATG ACC GTT TCC GTC AGG GCG ACA TTG TTG GAG
2419  TGG GAA TCC CGG CGG AAC ATC ACG AGG TGC TCC AGG ACT ACA GTT TGC CAG TGA AAT GGG CCG CAG TCC TCG TAC AGC CCG AGA GCC TGC GCG
2497  CCG AAA TCC GCG TGC ACG GTG TCG ATT CCT TGC CGG GGT TGC AGA ACA CCG AGT TCC AAT GCG CTG AGT TCA AAC CGT CCG
2575  ACG GAC GCA CTG GTA GTG TAT TGA TCC GCG AGC TCC ATG AGC CGG CGG CAA TAG ACC GCG TTC CAA ATG ACG CTA AGA CGC TGG AGG GCT ATG AAA TCA
2653  CGC CAT GCA GTA GTG TAT TGA TCC GCG ATC CTT TGC CGG GGT TGC AGA ACA CCG AGT TCC AAT GCG CTG AGT TCA AAC CGT CCG
2731  ATC GCA CGG AGC ATG AGC TCC ATG AGC CGG CGG CAA TAG ACC GCG TTC CAA ATG ACG CTA AGA CGC TGG AGG GCT ATG AAA TCA
2809  CGC CAT GCA GTA GTG TAT TGA TCC GCG ATC CTT TGC CGG GGT TGC AGA ACA CCG AGT TCC AAT GCG CTG AGT TCA AAC CGT CCG
2887  ATC GCA CAT GTA GTG TAT TGA TCC GCG ATC CTT TGC CGG GGT TGC AGA ACA CCG AGT TCC AAT GCG CTG AGT TCA AAC CGT CCG
2965  TGT GCA CGG CGG GAG ATG CAA TAG CGG AGT AGT CCA ATG CCT GAT CAG TCA ATG CGA CTA ATG CGG AGC ACG AGC CCG
3043  GCC GAT GCA GTA TGC GGA GAT CGA TAA ACA TAA GCA GAC GCA GAC CGG AGT CTT TTG TAG AAA TCG ATG CAG GCG ACA TAT CCA
3121  CGC CCT GCA CCT ACA TCG AAG CTG AAA GCA GAC TCT TCG CCC GTG AGT TCA AGA GAT CCT CTC GGC CCT GAG TTT TCA AAC
3199  TTT TCG ATC AGA AAC TTC TCG ACA GAC TCG TCG CGG GCC CTA ATG CAC GTA TAG TGA CTG CAT GCC TAT CTG ACG GTT
3277  TTA TAC GCC GAT ATA TCT GCT ATA TGC CGA TGA TTA ATT GTC TAG CCA CGG CAT TGG CAC CGT TCG CCA CAC GTT TAC TGA CGT GGC
3355  CAC TAA ACG AGC TCC CGG CTA GTC ATC CCG TTG ATT TAC CCC ATT GAT GTA AAA CCG TCA AAA CAA CAA CAG GGG GTG GAG ACT TGG AAA
3433  ACG ACA TTT TGG AAA GTC GAG AAT ACG AAA GTC CGA TAG ATT GAT GTA CTG CAT GTA ATG CAT CCA TGC GAT AGC GAT TGG ACA CCC
3511  TCC CCG TGA GTC AAA CCG CTA TCC ACG AAA ATG GCC ATT AGG GCA TAG GTT AGC CCA TGA CTT TAC CTA GGG GAT AGC GAT TGG ACA CCC
3589  TAC GTA GAT GTA CTG CCA GGG GCG AGT AGT GTT CAT ATG TAA AAC CGC AGT GTG GGC AGT TTA CCG TAA ATA CTC
3667  ATT GAC GTC AAT AAT GAC GGG ACT AGG AGT CGT GAA AGT CCC TAT TGG CCC TAT TAT GAC AAC ATG GCG GGG
3745  CAC CCA TTG ACG TCA ATG GGA AGT CCA ATA CGT TAC CAT CAG TGT AGG CGG TAC ACT TGA TGT AAG CGG GGG
3823  GTC GTT GGG CGG TCA GCC AGG CGG GCC ATT TAC CGT AAG TTA ATG AAC GGG TAA ATT AAG AAC ATG TGA GCA
```

Fig. 12, contd.

```
3901 AAA GGC CAG CAA AAG GCC AGG AAC CGT AAA AAG GCC TTG CTG TTT CAT AGG CTC CGC CCC CCT GAC GAG
3979 CAT CAC AAA AAT CGA CGC TCA CGT CTT CCG AGT TGG CGA AAC CCG ACA GGA TAA AGA TAC CAG GCG TTT CCC GGA
4057 AGC TCC CTC GTG CGC TCT GTT CCG ACC CTG CGC CTT ACC GGA TAC CTG CTC CCT TCG GGA AGC GTG
4135 GCG CTT TCT CAT AGC TCA CGC TGT AGG TAT CTC AGT TCG GTG TAG GTC AGC TGT GTG CAC GAA
4213 CCC CCC GTT CAG GCA GCC CCC TGC GCC TTA TCC GGT ACT TAT CTT GAG CGT CTT GTA GAC TTA TCG
4291 CCA CTG GCA GCA GCC ACT GGT AAC AGA ATT AGC AGA GCG AGG TAT GCT ACA GAG TTC TTG AAG TGG TGG
4369 CCT AAC TAC GGC TGA CTT AGA AGG ACA ACC ACC TTT GGT ATC TGC GCT CTG CTG AAG AAA AGA GTT
4447 GGT AGC TCT TGA TCC GGC AAA CAA ACC GCT TTT GTT TGC AAG CAG CAG ATT ACG CGC AGA
4525 AAA AAA GGA TCT CAA GAA GAT CCT TTG ATC TTT TCT ACG GGG TCT GAC GCT CAG TGG AAC GAA AAC TCA CGT TAA GGG
4603 ATT TTG GTC ATG AGA TTA TCA AAA AGG TTT ACA AGG TTT ACA TTT AAA TCA pSelect-IGLV2-14/J-Ck
   1 GCG GCC GCA ATA AAA TAT CTT TAT TTT CAT ATC TGT GTT GTT TGT AAT CGT AAC TAA CAT ACG CTC
  79 TCC ATC AAA ACA AGA TCT GCA ATT CGA AAC ACA CGA AAA ACA CCG TAG CCC GTG CAA CTG TCC CCA GTG CCA GAA CAT TTC
 157 TCT ATC GAA GGG TCG GCA ATT GAA CGG GGG ATC CCT AGA GAA AGT GGG GCG CAG AGC TCC CCG AGA AGT TGG
 235 GGG GAG GAG TTT TTC CCG AGG GTG AGC AAC CGT ATA TAA GTG TCG ACG TTT TTC GCA ACG GGT
 313 TCC GCC TTT TTC CCG AGG GTG AGC AGC TTC GAG TTC TGC GCA TCT CTC CCT GAA CTG CGT CCT GAG GCC
 391 TTG CCG CCA GAA CAC GCC GGT TGA GAC GTT GCG TGC TGC CCG CGC TTT GTC CGC CCG TCT CCA CGC TTT
 469 ATC ACC GCC GGA GAC TCA GGT GCG CCG GCC CTT TCT GCC CCG CGG CCG TTT CGT TGC GCC GTT CCC CAG TGC GAC CGG
 547 TAA AGC TCA GGT TGC CTC GAG ATC ACC GTG TCG AAC GGC ATG TGC CCG CAG TAC GGC GAA CTT CAG GGA
 625 GCC TGA CCT TCC CTG GAG ATA ACA CCC GCC TCT GTG TCC TGG TAT TTC GTT TTT CCA ATC ATG AGC CAG TTT GCC CCG CAG TAC GGC GAA CTT CAG TCT GCC
 703 CGC CTA CCT CTG GAG ATA ACA CCC GCC TCT GTG TCC TGG TAT TTC GTT TTT CCA ATC ATG AGC CAG TTT GCC CCG CAG TAC GGC GAA CTT CAG TCT GCC
 781 TCT GGC TCC CTG GAG ATA ACA CCC GCC TCT GTG TCC TGG TAT TTC GTT TTT CCA ATC ATG AGC CAG TTT GCC CCG CAG TAC GGC GAA CTT CAG TCT GCC
 859 AGT TCT CTG GAG ATA ACA CCC GCC TCT GTG TCC TGG TAT TTC GTT TTT CCA ATC ATG AGC CAG TTT GCC CCG CAG TAC GGC GAA CTT CAG TCT GCC
 937 CTG ACC CAG CAG CCC GCC TCT GTG TCC TGG TAT TTC GTT TTT CCA ATC ATG AGC CAG TTT GCC CCG CAG TAC GGC GAA CTT CAG TCT GCC
1015 GGC GGC TAC AAC GGC GTG AGC GCC GAC TAC GTG TCC TGG TAT CAG CAG CAC CCC GGC AAG GCC CCC GTG CTG ATC TAC GAG GTG TCC AAC
1093 AGA CCC AGC AGC GAC GAG CGG AGC GCC GAC AGA TTC AGC GGC AGC AAG TCC GGC AAC ACC GCC AGC CTC
1171 GCT GAG GTG CTG ACC ATC AGC GGA CTG CAG AGC GAG GAC GAG GCC GAC TAC TAC TGC AGC AGC TAC ACA AGC
1249 ACC GTG GTG TTC GGA GGA GCC GGG ACC AAG CTG ACC GTG CTA GAA CAG CCA TTC ACA TCC ATG ATG GAA GCC ACT GA
1327 ACC GTG GCC GCC CCA TCT GTC TTC ATC TTC CCG CCA TCT GAT GAG CAG TTG AAA TCT GGA ACT AGT
1405 GAC GCC CTG CTG GAC GAG AGC GTG AAG ATG AGC TGG AAG ATG AGC ACC AGC TTA TGG ATT TAT GAG GTC AGT AAT
1483 AAG GTG GAG GAG TAC CAC AGA TAT CGC AAA ATC TAC CTG AGG TCT GCC GAC ACT CCT GGG CTC AAG
1561 TTC AAC CGG AAC TGT GAT GCT TTT ATA GCA ACT ACA CCA GAG CCA CAA GAA CTC TCA GAA GGT GCC ACC AAG CTG
 937 CTG ACT CAG CCT GCC TCC GTG TCT GGG TCT CCT GGA CAG TCG ATC ACC ATC TCC TGC ACT GGA ACC AGC AGT GAT
1015 GGT GGT TAT AAC TAT GTC TCC TGG TAC CAA CAG CAC CCA GGC AAA GCC CCC AAA CTC ATG ATT TAT GAG GTC AGT AAT
1093 CGG CCC TCA GGG GTT TCT AAT CGC TTC TCT GGC TCC AAG TCT GGC AAC ACG GCC TCC CTG ACC ATC TCT GGG CTC CAG
1171 GCT GAG GAC GAG GCT GAT TAT TAC TGC AGC TCA TAT ACA AGC AGC AGC ACT CGT ATC ACA GAA GAT ACT TTT GAT GAG GGT
1249 ACC GTC GTG CGG GCT GAT TTC GGC ACC ATG AAG CTC GTA AAA AGC TGC ACT GCA GAG CGA
1327 ACA GTC GTG TGC TTC TTG AAC AAC TTC TAT CCC AGA GCC AGT GTC ATG TCC TTG GAA ATG GTG
1405 GAT GGT GTC GTC GAC AGT GTT ACT CAG CAG CAG CAG AGC GAG AGC AAA AGC AGT AAA CAA GCA CGA AAT ACG ACC
```

Fig. 12, contd.

```
1483 AAG GTT GAA TAT GAA AGG CAT AAC CTC TAT ACC TGT GAG GTT CAT AAG ACA TCA CCC GTC AAG AGC
1561 TTC AAC AGG TGA AAT GAG TGT TAG GCT AGC TTT ATT TGG GAA ATT TGT GAC ATG ATA AGA TAT GAT TTT GGA CAA TTT GGA CAA ACA ACT AGA
1639 ATG CAG TGA AAA AAA TGC TTT ATT TGT GAA ATT GCT ATT GAT CAG GTT CAG GGG GAG GTG ACC ATT GTA ACC ATA AGC TGC AAT AAA
1717 CAA GTT AAC AAC AAT TGT ATG TTC ATT TAT ATG AAT CAT TTC ACA GCA GTT CAA AAC CTG TGG CTC ATT AGC TTT TAA AGC CTT AAG TAA
1795 AAC CTC TTT TCT GAG GGA TGA AGG TTA AGG CAT GTA TTT TCC CAA GGG TTG AAC ATG CTC TTG TGT TTA TGT TTT AAA ATG TTT ACT
1873 TCC TTT TCT GAG AGT TTA AGA TAT TTT AGT AAA GGC CCT TCA GTT TAA TAT CCC AGA AAT TTA AAT CCA GTT TAG TTG GAC TTA TGA AAA GGA ACC
1951 CTT TCA TGG CCA CAT TCC CTT CAA GAT GCT CAA AGA AAG AGA AAG CGA GCT TCT CAT TCC TTT GCC CTC GGA CGA GTG CTG
2029 GAC CTC AGT CAT TCC CTT CAA GAT GCT CAA AGA AAG AGA AAG CGA GCT TCT ACT GAA TTC TCG CAT TCC TTT GCC CTC GGA CGA GTG CTG
2107 ATT AGG CAG AAT CCA GAT GCT CAA AGA AAG AGA AAG CGA GCT TCT ACT GAA TTC TCG CAT TCC TTT GCC CTC GGA CGA GTG CTG
2185 TTT AAT AGA AAT TGG ACA CTA TCG GCG AGT ACT TCT ACA CAG CCA TTC GTC CAG ACC CGC TCG GCG GCG ATT TGT
2263 GGG CGT CGG TTT CCA GTC CCG GCT CCG GAT TGG TCA AGT GGC CCG GAT TGG GCC AGG GAT CCT GCA TCG AAA TTG
2341 GTA CGC ACA GTC CGG GCT CCG GAT TGG TCA AGT GGC CCG GAT TGG GCC AGG GAT CCT GCA TCG AAA TTG
2419 CCG TCA ACC AAG CTC CGC TCG TAG AGT TGG TCA AGA CCA ATA CGG AGC ATA TAC GCC AAC AGC CGC CAG AAG ATG TTG AGG ACA
2497 TCC GGA TGC CTC CGC TCG TAG AGT TGG TCA AGA CCA ATA CGG AGC ATA TAC GCC AAC AGC CGC CAG AAG ATG TTG AGG ACA
2575 ACC TCG TAT TGG GAA TCC CCG GCG AAC TCC GCG TGC ACG GTG TCG TCC ATC ACA GTT TGC CAG TGA CCG AAT AGC GCG CAT
2653 TTG TTG GAG GCG ACG GAC GCA CTG GTA TGA CCG TAT TGA GCC ATT CCT TGC GGT TGC AGA ACA GCG GGC CCG CTC GTC TGG CTA AGA TCG
2731 GCC TGC GCG ACA TCA CGC ATC GCA TCC ATG AGC TCC CGG ATG CAA TAG GTC CTG AGA ACA GCG GGC AAT TCG GCC AGG TCT TGC AAC
2809 ATG AAA TCA CGC ATC GCA TCC ATG AGC TCC CGG ATG CAA TAG GTC CTG AGA ACA GCG GGC AAT TCG GCC AGG TCT TGC AAC
2887 GCC GCA GCG ATC GCA TCC TGT GCA CGG CGG ATG CGG AAG TGC CGA TAA ACA TCT TTG TAG AGG GCC TTC AAT TCA TCA CTA TTT ACC CGA ATC
2965 GTG ACA CCC TGT GCA CGG CGG ATG CGG AAG TGC CGA TAA ACA TCT TTG TAG AGG GCC TTC AAT TCA TCA CTA TTT ACC CGA ATC
3043 GGG AGC GCG GAT GCG CCT GTT GGG CAA AGC TCT ACA CGC CCT ACA CGC CCT ATC ACA CGA AAG CTG AAA GCA CGA AAG CTG CGA TGC ATC CGA AGC TGC ATG GGG CTG TAG CAC TAG CTG CAA GAG TCG GAG ACG
3121 ACA TAT CCA CGC CCT ACA CGC CCT ATC ACA CGA AAG CTG AAA GCA CGA AAG CTG CGA TGC ATC CGA AGC TGC ATG GGG CTG TAG CAC TAG CTG CAA GAG TCG GAG ACG
3199 CTG TCG AAC TTT TTA TCG ATC AGA AAC TTC ACA GAC GTC GTG AGT TCA AAA GCG TGG ATG GCC TCT CCA GCT TAT
3277 TGA GTC GTA GTT TTA TAC TAT GCC GAT ATA CTA GCT ATA TGC CGA TGA ATT GTC TAC AAA ACG CAA CCG TAC AAA ACG CAA CCT ACT CCC CAT GAC CTG GTT GAG GTC CGT AAT GGG GTG GAG
3355 CTG ACG GTT GTT ACG ACA TTT TGG AAA GTC CCG CTA TAC AAG CGT AGT ACT AGT GAC CGT AAT GGG GTG GAG
3433 GGA GTT GTT ACG ACA TTT TGG AAA GTC CCG CTA TAC AAG CGT AGT ACT AGT GAT CAT GAT CAT GGT AAT AGC
3511 ACT TGG AAA TCC CCG TGA GTC GTA GAT GTA CCG CCA GTC CTG AAT AGG GGG ACT TGG ATG GTG GGC AGT TGA CGT CAA
3589 GAT GAC TAC ATT GAC GTC AAT GGG GTG GAA ATG GCG CAT CAT ATG GTG GGC AGT TGA CGT CAA
3667 TTT ACC GTC ATT GAC GTC AAT GGG AGT TTG TTT TGG CAC CAA AAA TCA ACG GGA CTT TCC AAA ATG TCG TAA CAA
3745 TAA ATA CTC CAC CCA TTG ACG TCA ATG GGA GTT TGT TTT GGC ACC AAA ATC AAC GGG ACT TTC CAA AAT GTC GTA ACA ACT CCG CCC CAT TGA CGC AAA
3823 TGG GCG GTA GTT TAC TCA GCC GAA TGG GAC CCG CCC GCT CGG GCG ATG CGG AAT TAC CAA CAT GGT AAG AAC
3901 ATG TGA GCA GAG CAT CCG CAG CAA AAT CGA CGC TCT TAA AAG CGC GGG CGA CTC CGT TTT CAT AGA TAC CGC GCG TTT CCA
3979 CCT GAC GTC TCC CTG GGA AGT CCC CTT GTG GGC GCG GCC ACA AAA TCA ACG GAA AAC CCC TCC AAC CCC AAC ATG ATG GGC GCC ATG CTA TAG
4057 CCC CCT GTA AGC GGG CCC CTT CAT TCG CAT AAC GGA CTC CCA TAT GGC TCC ATA GCT
4135 GGA AGC GTG GCG CTT TCT CAT GAG GCC CCT AGG GAC TGT ATA AAC GCG CGG GCG TGC TTT AGG CAA AAA GCC CTG AAC TTT CGT GAG TCA ACG GCA TCA TTT
4213 GTG CAC GAA CCC GTT GCA GCA CCC TTA ACC TAT GAC CGC TCC GCC GGA ACG TCC AAC CCG GTA AGC ACG GCC GCC GCC AGT CTT GCC CGG CGG TAA CGA GAG
4291 GAC TTA TCG CCA CTG GCA GCA GCC ACT GGT AAC AGG ATT AGC AGA GCG AGG TAT GTA GGC GGT GCT ACA GAG TTC TTG
4369 AAG TGG CCT AAC TAC GGC TAC ACT AGA AGA ACA GTA TTT GGT ATC TGC GCT CTG CTG TTT GCA AGC AGC AGA TTA CGC GCA GAG TCT AAG CAG CAG AAC TCA AAG AAC
4447 AAA AGA GTT GGT AGC TCT TGA TCC GGC AAA CAA ACC ACC GCT GGT AGC GGT GGT TTT TTT GTT TGC AAG CAG CAG ATT ACG CGC AGA AAA AAG ATC CTT TGA TCT TTT CTA CGG GGT CTG ACG CTC AGT GGA ACG AAA ACT CAC GTT AAG GGA TTT TGG TCA TGA
4525 ACG CGC AGA AAA AAG ATC CTT TGA TCT TTT CTA CGG GGT CTG ACG CTC AGT GGA ACG AAA ACT CAC GTT AAG GGA TTT TGG TCA TGA
4603 CGT TAA GGG ATT TTG GTC ATG A
```

```
   1 CTT GAT TTG GGT GAT GGT TCA CGT AGT GGG CCA TCG CCC TGA TAG ACG GTT TTT CGC CCT TTG GAG TCC ACG
  79 TTC TTT AAT AGT GGA CTC TTG TTC CAA ACT AAA ATA GGA ACA CTC ATT CAA AAC TCT TTT GAT TTA GGG
 157 ATT TTG CCG GTC ATT TCG GTC TAT TGG TTA TTA AAA AAT ACA GAG ATT TAA AAC GCG AAT AAC AAA ATA TTA
 235 ACG TTT ACA ATT TTA TGC AGT CTC AGT GGA TAG ATC TGC GCA TAG GCC CAG CCC CGA GTC TCC GGG CCA
 313 ACA CCC GCT GAC GCG CCC TGT CGG GCT TCA CCG CCG CTG AAA ATC CTC CCG GCT TAC AAG GTC ACC TCC AGC
 391 TGC ATG TGT CAG AGG TTT TCA CCG TCA TAG CGC CAA AGA CGC AGA GGC CTC GTG ATA CGC CTA TTT TTA TAG
 469 GTT AAT GTC ATG ATA ATA CAT TCA ATG TCT ATG TAT CCG GGA AAT GTG CGC CTT CAA TAA TAT CCT ATT TGT
 547 TTA TTC TAA AGT ATT CAA CAT TTC CGT GTC CCG CTC ATG AGA CCC TTT TGC CTT TGC CTT GTT TTT GCT
 625 AGG AAG AGT ATG AGT ATT GTG AAA GAT GTA AAA GAT GCT GAA GAT CCC TTG GGT GCC TAC ATC GAA CTG GAT CTC
 703 CAC CCA GAA ACG CTT GAG ATC CTT GAG CCC GAA GAA GAG CGT TTG CCA ATG AGC ACT TTT AAA GTT CTG CTA TGT
 781 AAC AGC GGT AAG ATC CTT CGT ATT GAC GCC CAA CGT CTC GGT CGC ATA AGC CGA ATA TGC AGT GCT GCC ATA GAC TTG GTT
 859 GGC GCG GTA TTA TCC CGT ATT GAC GCC CAT CTT ACG AAG CAT CTT ACG AGA GTA ACA CCG GGA TTA TGC AGT GCT GCC ATA ACC ATG
 937 GAG TAC TCA CCA GTC ACA GAA AAG CAT CTT ACG ACA GTA ACA CCG AAG GGA ATC GAG CTA CCA ACT CTT TTG CAC AAC ATG
1015 AGT GAT AAC ACT GTA ACT GCG GCC TTA CTT CGT CGT TGG CGA AAT GGC TTA ACT CTA ACT CTA GCT TCC GAT ATC ACG
1093 GGG GAT CAT GTA GCA ATG GAG GCG ATG GCG GAT AAA GTT CAG GCA GTT TAC CTC TTC CAC TGA GCG TCA TTT AAA AGG
1171 ATG CCT GTA GCA ATG GAG GCG GAT AAA GTT CAG GCA GTT TAC CTC TTC CAC TGA GCG TCA GAC
1249 ATA GAC TGG GAG ATG GAG GCG GAT AAA GTT CAG GCA GTT TAC CTC TTC CAC TGA GCG TCA GAC
1327 AAA TCT GGA GCC GGT GAG GGG GCA GTT TAC CTC TTT TGC GTA GAT ATC TGC AAG AAC TTC CAC CCG AGC AGA GCG
1405 GTT ATC TAC ACG ACG CTG TAA CTG TCA GAC CAA GTT TAC CTC TTT TGC GTA GAT ATC TGC AAG AAC TTC CAC CCG AGC AGA GCG
1483 AAG CAT TGG TAA CTG TCA GAC CAA GTT TAC CTC TTT CAT TTC ATT GCC TAA TTT AAA AGG
1561 ATC TAG GTG AAG ATC TTT AAT CTC ATG AGA TCT TTT TTC TGC GTA GCG TCA GCG TCA GAC
1639 CCC GTA GAA AAG ATC AAA AGA TCT TCT TGA GAT CCT TTT TTC TGC GTA ATC TGC AAG AAC TTC CAC CCG AGC AGA GCG
1717 CCG CTA CCA GCG GTG GTT TGT CTT TTA CCG GTG TAG TTA GGC CAC CAC TTC AAG AAC TCG TGC ACA AAA ACC
1795 CAG ATA CCA AAT ACT GTT CTT CTA CCG GTG TAG TTA GGC CAC CAC TTC AAG AAC TCG TGC ACA AAA ACC
1873 CTC GCT CTG CTA ATC CTG TTA CCA GTG GCT GCT GCC AGT GGC GAT AAG TCG TGC CTT CCC AGC TTG GAG CGA ACG ACC TAC
1951 TAG TTA CCG GAT AAG GCG CAG CAG CGG TCG GAG AGC GAG TGA GAA AGC GCC ACA CTT CCC AGC TTG GAG CGA ACG ACC TCG
2029 ACC GAA CTG AGA TAC CTA CAG ACA GGA GAG CGT CCA CGC TTG CAG CGC CAC GCT TCC CGA AGG GAG AAA CGC CTG GTA TCT CTG GTC
2107 GTA AGC GGC AGG GTC GGA ACA GGA GAG CGC ACG AGG GAG CTT CCA GGG GGA AAC GCC TGG TAT CTT CCT GTC
2185 GGG TTT CGC CAC CTC TGA CTT GAG CGT CGA TTT TTG TGA TGC TCG TCA GGG GGC AGC CTA TGG AAA AAC GCC AGC
2263 AAC GCG GCC TTT TTA CGG TTC CTG GCC TTT TGC TGG CAC ATG TTC TTT CCT GCG TTA TCC CCT GAT TCT
2341 GTG GAT AAC GCC TTT ATT ACC GCC TTT GAG TGA GCT GAT ACC GCT CGC CGC AGC CGA ACG ACC GAG CGC AGC GAG TCA GTG
2419 AGC GAG GAA GCG GAA GAG CGC CCA ATA CGC AAA CCG CCT CTC CCC GCG CGT TGG CCG ATT CAT TAA TGC AGC TGG CAC GAC AGG
2497 GAC AGG TTT CCC GAC TGG AAA GCG GGC AGT GAG CGC AAC GCA ATT TAA TGT GAG TTA GCT CAC TCA TTA GGC ACC CCA GGC TTT ACA
2575 GCT TTA CAC TTT ATG CTT CCG GCT CGT ATG TTG TGT GGA ATT GTG AGC GGA TAA CAA TTT CAC ACA GGA AAC AGC TAT
2653 GAC CAT GAT TAC GCC AAG CTT GCA TGC CTG CAG GTC GAC TCT AGA GGA TCC CCG GGT ACC GAG CTC GAA TTC GTA ATC ATG TGT CAG AAG ATC TCC TTT
2731 AGT TGT TCC TTT CTA TTC TCA CTC CGC TGA AAT CGT CCA CAT GGT CTG CAG CTA CCT AAG AAC CTC GAA CTC TGG GTT CGT AGG AGG
2809 CAG CAT CAC TTG CCG AAG TGC CGT AAC TTT GTT GTC CCC CTG TCC AAC TCC TGT CAA AAT CAG GAT AGC CCG AAA TGG GTT CCG CAG CGT CCT CAT ATT
2887 CCC TAA GAC CCT TTC TAA GCC TTT CAC ATC GAT TTG GAT GTG GTT TGC TCA GAA ACC AAG TGG ATG CGC AGC GAG GAA AGC
2965 AGA TTT CAC TCT CAC CAG CAG TGC GCA CAG TCT CAC CAG TGG GAT TTG CAC TCT ACA GAG TTA CAG TAC CCC
3043 TCC AAC GTT CGG CCA AGG GAC CAA AGC GCT CGG GAC GAT CAA CTA CGG GAC TGT CTT CAT CTT CCC GCC ATC
```

Fig. 12, contd.

```
3121 TGA TGA GCA GTT GAA ATC TGG AAC TGC CTC TGT TGT CCT GCT GAA TAA CTT CTA TCC CAG AGA GGC CAA AGT ACA
3199 GTG GAA GGT CAG CCT GAA TAA CGC CCT GAC CGT CAC GCT GAG CCT CAA GAG GGA TAA CTC CCA GGA GAG CAA CAG CAC CTA
3277 CAG CCT CAG CTC GAG CCG CGT ACC CAC GCT GAG CCT CAC AAA GAG CGG CTA TGT AGC CGA GAA ACA CTG GGA AGT CTA CGC AGT CAC CCA TCA
3355 GGG CCT CAC GAG TCA TAA TGA AAT TAT GCC CTA TGC GGA AAA TGG CCT TTC TGG ATT GAT TGT ATT CCC AGC CGG GGG TGT CTT CCT CGT GCT
3433 CAG TCA TAA TGA AAT TAT GCC CTA TGC GGA AAA TGG CGA TAT CGC CGC CTT TTC TGG ATT GAT TGG CGA ACC TGT CTT CCT CGT GCT
3511 CTG CTT GCC GAA CAT CGC GGA TAT AGC GTT TCC CGA TTC GCA GCG CAT CGC CAC CGC CTT TGC TGA AGA GCT TGG CCT CTG AGC GGG ACT CTG
3589 CTA TCA GGA TAT CGC CGC CGA TTC CGA AGA TTT CGA TTC CGA GCG CAT CGC CAC CGC CTT TGC TGA AGA GCT TGG CCT CTG AGC GGG ACT CTG
3667 TTA CGG TTC GGT GCT GAT GAT CCT ACG AGA TTT CGA GCG CGG CAT CAT GCT CAC CGC CAA GTT CGG CTT TAT TGC AGC TTT CCG GGA CGC
3745 GGG TTC GGT GCT GAT GAT CCT ACG AGA TTT CGA GCG CGG CAT CAT GCT GCT GGA TCT CAA GTT CGG CTT TAT TGC AGC TTT CCG GGA CGC
3823 CGG CTG CAA ATA AAG CAA TAG CAT CAC TGT CTG TAT ACC GTC GAC CTC TAG CTA GAG CTT CGG ATC GTC ATG GTC ATA GCT
3901 TGG TTA CAA ACT CAT CAT TGA TTA TCA TCT CTG CAT CAC TGT CTG TAT ACC GTC GAC CTC TAG CTA GAG CTT CGG ATC GTC ATG GTC ATA GCT
3979 CAA ACT GTT TCC TGT GTG AAA TTG TTA TCC GCT CAC AAT TCC ACA CAA CAT ACT GAG CCG AAG CAT GTC CAA GTC CAA TTC ACT GCA TTC TAG AGC TGG TAA AGC CTG GGG CCA
4057 GTT TCC CTA ATG AGT GAG CTA ACT CAC ATT AAT TGC GTT GCG CTC ACT GCC CGC TTT CCA GTC GGG AAA CCT GTC GTG CCA
4135 TGC CTA ATG AGT GAG CTA ACT CAC ATT AAT TGC GTT GCG CTC ACT GCC CGC TTT CCA GTC GGG AAA CCT GTC GTG CCA
4213 GAA TTG CAT GAA GAA TCT GCT TAG GGT TAG GCG TTT TGC GCT TAT TGG GCG CTC TTC CGC TTC CTC GCT CAC TGA CTC GCT GCG CTC GGT CGT
4291 TTA TTC ATT GGT TAT ATA GCA TAA ATC AAT ATT CCG GAG TTC CGC GTT GTT CCC ATA GTA ACA AGG CCA TAA AAT TGG CCA TAT CAT AAT GTG CCA CCT TTC CAT TGA CGT TTG GCC ATA TAC
4369 ATT TAT ATT GGC TCA GTT CAT AGC CGC CCA TTG ACG TAA ATA ATG ACG TTC CGC GTT GTT CCC ATA GTA ACA AGG CCA TAA AAT GGG CCC
4447 GGG AAC GAC CCC CGG GAG TAT TTA CGG TAA ACT GCC CAC TTG GCA GTA CAT CAA GTG TAT TAG CGT CAA TAG GGC TAT GGC TGA CAC CCT GTA TAG
4525 ACG GTA CCC CGG GAG TAT CAA ACC AAG CGC CCT CAC CCC CTC GCC CAA GCT CTC CGC CTA TCC GGA GTC GAC TAT AGC AGC CAC CGC GCC CTG CCT CAG GGT GCT ATC ATA ACC CAA GTC CCT ATT AGC AGC CAC TAT AGC AGC CGG AGG
4603 TGG GTG GAG TAT TTA CGG TGG TGG TGG TGG TGG TGG TGG TGG TGG TGG TGG TGG TGG TGG TGG TGG TGG TGG TGG TGG CCG CGG GGA TAC ACC CGG TAA GTC CGC CTA ATT GAC
4681 GTC AAT GAC CGG GGA TAC ACC CGG TAA GTC CGC CTA ATT GAC CGC CGG TTA TTA CGG ATG CAC CAG CGG TCC CGA CAG GAC TAT CGG GAA CTC AGG
4759 CTC TGG GGC CAC CAG CGG ACC CTG GTT ATC CGG CTA GAA GTC CGA GCG GTT CCG AAC TCA CCA GTC AAG CAA GCA GAG CGC AGG ATA AGC ACG AGG AAA
4837 CGC CCT GCC CTC CAG CAG CGT ACT GCA GGC CTA ACA GCC ACC CCC CTA CAG AGG AAA CAC GAA CTC CAG ACC GTA GCT CAA GCC TTA TGC AGC AGT AGA
4915 CGT GCG CAG GCC TTA ACA GCC ACC CCC CTA CAG AGG AAA CAC GAA CTC CAG ACC GTA GCT CAA GCC TTA TGC AGC AGT AGA
4993 GAA AGT GAT GAG CGG ATA ACG CGG AAA CGC ACC CGT CGG AAA ACC TCA AGA ACA AAA TTC ATT TAC CAT CTC AGA
5071 AGA CTG GAA CGA AGA TCT GGC CAA ATC TTT AGA TCG CCA AAT GTG TTA CTA TGA AAG TTT GGC CGA GAA CGC CGT GTT AGG AGG CGT TGT GGT TTG
5149 CTG TAC TGG GAA CGA AAC TCA GTG TTA CGG TGG TGG TTA ATG GGT TCC TAT CCC TGA AAA TGA TAC AAA ACC TGC TAT TCC
5227 TAC TGG GGT TGG GTG TTC ATA CGG CGG TGG TGG TGG TGG CGC CCA GCT GGG TCC CTA CCC TGG CTC ACT TGG CCG TAT CCC TGA AAA TAG CCC TAT TCC
5305 CTC TGA GGG CTA TAC CTG TCT TAC CGG GAG GGT CAA TAG GGC GCC CGC TCT CGT CCC CGC TCT CGA ACT CCG CGG GGA CAC ACA GCG CGG GCG CTT GAG CTC TCG
5383 GGG CTA TAC CTA CGT TCA GTC TCA GGT GCT ATC ATC TAC TCC CGT CTT CCA TGC AGG CAC CAC GCG TGA CCG CTA TAT TTC TGG AGA ATT TCC CCA TAC TCC TTC
5461 TCT TGA GCC TCA CCT GCA CGG GAA TTC TCA AGG TTT CAT CTC TCA CTC TCC CGT CTT CCA TGC AGG CAC CAC GCG TGA CGG GCG CTT GAG ATT AGC CAT
5539 TTA TAC GGG CAC TTA CGC GAA CTG CCT GGA CCC GAG TTT CCC CGT GTT CAG AGG CAC CAG TTT CAC CGT CAT CCG TCT ATC GTG AGC TCA GGC CAA CGC TGG CAG CTC CCG GGG GAT TTA TTT GGT TCG
5617 GTA TGA CGG TAG TTT GTT AGG CGG CTA GCA CCC ACA AAA TGA CTG ACT TCA GAG TCA AGC ATT GGT TCC TAT ATC GGG CTT AGC TAC GAC AGT TTT TGT CTC TTC AGC ATG TAC CGT CAT ACT GGT TCC CAA CAT CCT ATC ATT TCT GGG AGG CGA TTT CTA
5695 ATA TCA AGG CCA ATC GTC TCG GAC GTC CGC CGC CGG TGA TAA TTC CGC TGG CAA ACT ATT TTC GCC TTC AAT TAT CTC TCT CCC CAT ACC ATT AAT GCT TGA CAA AAT CGT TGG TGG CGG TTC CCC GGT AAA TGC
5773 CTC TGA TGG TGG CGC CTG TGG GTG TGG CGG GCT CGG GCC GGC GCT ACA GTC CGG TAT TGC CGT CAT AAC CGA TAA TCG CTT AGC AGT ATG GTC CGG ATG GTC CTC TTG TGC TCG TCA ACG CAA TCT GGG GAT ACT TGG AAA ATG CGG GAA AAC AGC CTG TGC TGT CGG TGT GGC CAG CTC CTG CTT ACC
5851 GGG CGG ACC GTG TTT AAA AGG TGG TTT CAA ACT TGG TGC TCA ATC AGC GGT CCT CTG GCT CAC TTG CAA TAC GTT GGT TTG CTT CCG TTC TCA AAG ACC TGG AAA ATG CGG GAA AAC AGC CTG TGC TGT CGG TGT GGC CTG CGG CTG CGG CTC TTG TGT AGC CAT GGC
5929 CGA TGA AAA CGC TTC CTT CTT GTT CAT ACC AGT CAG GGT CAT TGC GCC TGA TGT GTA GGG CCT TAT GAC TGC GGA AAA TGC
6007 TTT CAT CTT GCT TGA CGG TAA TTC GGG TGG CTT CAT CCA AAT CAT GGC
6085 TCA AGT CGG CCC TTA TAA TCC TGC GCG TGG GGT CAT CCT TCC TGT TCA ACA TTC AAT CGC CTC CTC GCC CCG CTC CTC GCC CTC TCT CCT GTC GAC CCG GAA AAT CGT GAA TCC GGA AGC CAT GGA GCC TGC CGG AAT CAG CAG ATG GCC CAT CTT CGA AAT GCG CCG TCA GTC GGT CCG TGA
6163 ATG TCG CCC TTA TGT TAC TGG GAC ACA GTC CTT CGG GCT GCC CTC TCC TCA ATA TGA TGA TAT TGA TCT TGA TGA TGA TAA TCC GGC CCT CCG TGG
6241 TGT CTT TGC GTT TCT TCT ATA TGT TGT GAC TTC ATT TTC CAC GAC GTT TTG ATT TGC TAA TAA CAT ACT GCG TAA TAA GGA
```

Fig. 12, contd.

```
6319 GTC TTA ATA AGA ATT CAC TGG CCG TCG TTT TAC AAC GTC GTG ACT GGG AAA ACC CTG GCG TTA CCC AAC TTA ATC GCC
6397 TTG CAG CAC ATC CCC CTT GGC TCG CCA GCT TGC GGT GTA ATT TTC TCC TTA GCG AAG CCG ATC GCC CTT CAC CCC AAC AGT TGC GCA
6475 GCC TGA ATG GCG AAT GCC TGA TGC CTG TAG CGC ATT AAG CGC ATC TGT GGT GGT GCA TTT CAC ACC GCA TAC GTC AAA
6553 GCA ACC ATA GTA CGC GCC AGC GCC TCC TTT CGC TTT CCC TTC TCT CGC CAC GTT CGC CAG CGT GAC CGC TAC ACT
6631 TGC CAG CGC CTT GGG GCT CCC TTT AGG GTT CCG ATT TAG TGC TTT ACG CCT GCA CCC CGA CCC CAA AAA A
6709 TCT AAA TCG GGG GCT CCC TTT AGG GTT CCG ATT TAG TGC TTT ACG
```

MV1057

```
   1 TAC TCT TCC TTT TTC AAT ATT ATT GAA GCA TTT ATC AGG GTT ATT GTC TCA GCG GAT ACA TAT TTG AAT GTA TTT
  79 AGA AAA ATA AAC ATG TAG AAA TAG CTT CGC GCA AAT TAG TTC CCC TGA AAG TGC CTG GAA CAC CTG AAG TCG ACG GAG ATC TCC
 157 CGA TCC CCT ATG CGC ATG GGT CAC GTA TCT CAG CGC GTG TAC AAT CTG CTC TTA AGC GTT GCA GTT GCA CCA TCT GCT CCC TGC TTG GAA TGT
 235 GTT GGA GGT TAG CAC TGA GTA GTG TTT GCG TTT GCT GGT CTA GGT ACG GCA TGG CCA CTT TTA GCC ATG CGA CAA TTA TTC CAT GGT TAT
 313 TCT GCT TAG GGT TAG AAT ATT GGC TAT TGC CCA TGT TGA CAT TTG TTA TCG ACT AGT TAA TCA ATT ACG GGG TCA TTA GTT CAT
 391 ATA GCA TAA ATC CCG CCA TGT CGC GTT ACA CTT ACG GTA AAT GGC CCT TTC CAT TGA CGT CAA TGG GTG GAG TAT TTA
 469 TGT CCA ACA TAT ATG GAG TTC CGC TAT GTT CCC ATA GTA ACG CCA ATA ATG CCC ACT ATT GAC GTC AAT GAC GGT AAA
 547 AGC CCA TAT ATA ACT GCC CAC TTG GCA GTA CAT CAA GTG TAC ATC AAT ATG ACC TTA TGG GAC TTT CCT ACT TGG CAG TAC ATC TAC GTA TTA GTC ATC
 625 TTG ACG TCA ATA ATG GGG TAG CAC ACT ATG CAT ATG ACG CAT CAT ACT CTT GAC TCG GGA TTT CCA AAA TGT CGT AAC AGT
 703 CGG TAA ACT GCC CAC TTG GCA GTA CAT CAA TGG GCG TGG ATA GCG GTT TGA CTC ACG GGG ATT TCC AAG TCT CCA CCC CAT TGA
 781 TGG CCC ATT ACC ATG GTG ATG CGG TTT TGG CAG TAC ATC AAT GGG TCG TTT CCA AAA TGT CGT AAC AGT CCG CCC CCT ATT GAC GTC AAT GGG AGT
 859 GCT ATT TAC CCT ATT GAC GTC AAT GAC GGT AAA TGG CCC GCC TGG CAT TAT GCC CAG TAC ATG ACC TTA TGG GAC TTT CCT ACT TGG CAG TAT AGC CGA TAC AAC TCC
 937 CTC CAC CCC ATT GAC GTC AAT GGG AGT TTG TTT TGG CAC CAA AAT CAA CGG GAC TTT CCA AAA TGT CGT AAC AGT GTG TCC CGG CAG TCC CAG
1015 GCC CCA TTG ACG CAA ATG GGC GGT AGG CGT GTA CGG TGG GAG GTC TAT ATA AGC AGA GCT CGT TTA GTG AAC CGT CAG
1093 ATC GCC TGG AGA CGC CAT CCA CGC TGT TTT GAC CTC CAT AGA AGA CAC CGG GAC CGA TCC AGC CTC CGC GGC CGG GAA
1171 CGG TGC ATT GGA ACG CGA TTG GTA CCG GTG AAT ATG GGG CAC CAG GTC GCC ATC GAT TGG AAA CGG ACC CTG GCC GCG TTC GCG
1249 AGA GGC CGC AAT AGC CGG AGC GCC GGA ACT GGG CAC GGC TGG TAG GGC GAC AAC GCA ATT GTG AGC GGA
1327 ATG GGG CGG AGA ATG GGC GGA ACT GGG CGG AGT TAG GGG CGG GAT GGG CGG AGT TAG GGG CGG ATG CGT CGT ATT CTT TCC GCC TCA GAA GCC
1405 CTA ATT GAG CTC GCC CAT CAT AGG CGC ATC CGC TGG CCC CAG CAG GCC TTA TGC CAA GGG GTC GGT CAC CCT TTG CAT CTG TTG GAC ACA GGC ACA GTC GGG GCG GAT
1483 AGT TAG CTC GCC ACA TTT CAC ACA GGA AAC AGC TAT GAC CAT GAT TAC GCC AAG CTT GGT AGC CCT TCG GCG TTC CCT ACA AGG GGT GGG GTG CCG AAG GCT GCA
1561 TAA CAA GAT GCC CCC ATA CCC CCA TTA CAC CCA CTC AGA CAA TGC GGG GAG GCC CTT CGC CCG GAA TCC ATT AGG ACA ACC ATC CCC GCC TCA GAA CCC
1639 ATA GAG CCC AGA ATA GAA GGT CCC CAG GGT CCC CAG GCC GTC GTG AGG CAA TGG AGG GGG CGG GGT GCC GGG GTC CGG GAA GCC GGG CCA CCA CGC
1717 CCC AGA ATA GAA GGT CCC CAG GGT CCC CAG GCC GTC GTG AGG CAA TGG AGG GGG CGG GGT GCC GGG GCC GAC GAG CAC GCA
1795 CCT CCT AGG GCT CTA GAT CAT CGA TGC ATG CCA CCA GGG CAG CCT TCG GCC CCT CGC CGG GGT GTC GTG CTT GGC CAG GCT GAT
1873 CAG CGA ACC CGA GCT CTA GAT CAT CGA TGC ATG CCA GGG CAG GCT TCG GCC CCT CGC CGG GGT GTC GTG CTT GGC CAG GCT GAT
1951 GGC ACC CTC GGG CTT GAA GGA CAC GTT GCG GCC CTT CAG GCT CTG TTG GAC CTT CAG GCG TTC GAC GCG TTC GAC CCC TCA GTA CCC CCA GTC CAG GCA CCG CCG GCG TCA
2029 CCG CCG CTC GTA GAA GGA GAC GTG GCG CAG CCC GGG CAG CCC CAG CCC CAG CCC CAG CCC CAG CCC GGG GCG GCG GCT CTC CAC
2107 TCC GGG CTC CGG CGT CGC GGA GAC GTG CTG GGT CTG TTG GCT CAT CCC CGC CGG GAA CGC CGC GAC CAA CGC CGC
2185 GGG CTC GGG CCT GGT GAC GCG TAG GAA GAG CCC GGG GGC CCC TCC TAA GCG CCC CGC AAT CTC GGC
2263 CAT GTC GTC GGG GTT GCG GCC CAC GAC GCG CAT GTC TCC CCG GAT GGC GGC GGA CAC GGC GAT GGC CGA AGT GGC GTC GGG
2341 GTC GTC GCG CGG CTT GCC GGC CTG GAG GAA GAC GAG CGG GAA CGC CAC CGT GGC CGG CAG GCG CAC CGC GGG
2419 CAG TGC TAG CAC CAA GGG CCC ATC CTT CTT GGT GCG CCT GGG CAC CTC TGG GGG CAC AGC GGC CGT GGC CCT
```

Fig. 12, contd.

```
2497 GGG CTG CCT GGT CAA GGA CTA CTT CCC CGA ACC GGT GAC GGT GTC CAG GAA CTC AGG CGC CCT GAC CAG CGG CAG CGT GCA
2575 CAC CTT CCC GGC TGT CCT ACA GTC CTC AGG ACT CTC CCT CAG CAG CAA CGT CGT GAC CTC CAG CAG CTT GGG
2653 CAC CCA GAC CTA CAT CTG CAA CGT GAA TCA CAA GCC TCA GGA GTT TGG TGA GAG GCC AGC
2731 ACA GGG AGG GAC GTC TGC TGG AAG CCA TCT GCC AGG CCC CTG CCT GGA CGC GCT ATG AGT CAG TCC CAG TCC
2809 AGG GCA GCA TTT CCC AGG GCC AGG CTC TCA GCC TCA CCC TGC ACA GGC GTG CAC GCA TGC CAC ATG GGG AAG GGG CAA GGG CAG GTG
2887 TCT GGC TCA GAC AGC CCA AGA GCC ATA TCC TCC CTG CCC CAA CCC AAA GCC CTG CAG AGC TCT CAG GGG CAA ACT CTC
2965 CTG GGC TCG CTG GAC CAT GCC TTC TCT CCT GCC CAC CGT TTC CTG GAC CGT TCC TCC CCA AAT CTT
3043 CAC GTG ACA AAA CTC ACA CCC CGT CCC CAC CCC CAG AAC TCC TGG GGG GAC TCT CAG TCT CCC CAA
3121 GTG AAC CCA AGG ACA CCC TCA TGA TCT CCC GGA CCC CTG AGG TGG TGG ACG TGA GCC AGG AGT ACC CTG
3199 AGG TCA AGT TCA ACT GGT ACG TGG ACG GCG TGG AGG TGC ATA ATG GCA AGA ACG AGT GCA AGG ACA
3277 GCA CGT ACC GTG TGG TCA GCG TCC TCA CCG TCC TGC ACC AGG ACT GGC TGA ATG GCA AGG AGT ACA
3355 CCA ACA AGG CCC TCC CAG CCC CCA TCG AGA AAA CCA TCT CCA AAG CCA AAG GGC AGC CCC GAG AAC CAC AGG TGT ACA
3433 CCC TGC CCC CAT CCC GGG AGG AGA TGA CCA AGA ACC AGG TCA GCC TGA CCT GCC TGG TCA AAG GCT TCT ATC CCA GCG
3511 ACA TCG CCG TGG AGT GGG AGA GCA ATG GGC AGC CGG AGA ACA ACT ACA AGA CCA CGC CTC CCG TGC TGG ACT CCG ACG
3589 GCT CCT TCT TCC TCT ATA GCA AGC TCA CCG TGG ACA AGA GCA GGT GGC AGC AGG GGA ACG TCT TCT CAT GCT CCG TGA
3667 TGC ATG AGG CTC TGC ACA ACC ACT ACA CGC AGA AGA GCC TCT CCC TGT CTC CGG GTA AAT GAG TTT GCC AGC ATG TAA
3745 TTA ATC CGA GCT CCT CCC ATT GTC TGC CTT CCT TGA CTC TGA CTC TCC TTT CCT AAT AAA ATG AGG AAA CAT CTG
3823 TTG TTT GCC CTT CCC ATT GTC TGC GTA GGT GTC GGG ATT CTA TTC TGG GGG GTG GGG TGG GGG AGG ACA AGG ATT GGG
3901 TTG CAT CGC ATT GTC TGA GTA ATG CGG ATG GGG CGG TTA GCG CAT TAA GCG CGG CGG GTG TGG TGG CTA GGG
3979 AAG ACA ATA GCA GGC ATG CGC CCT GTA GCG GCG CAT TAA GCG CGG CGG GTG TGG TGG CAC TTG
4057 TGG CGG TTA GCG GCG CTT CAC GCC CTT TAA ACT GGA GTG GGG GCG CTT CCC CGG TTA GGG TCA AGC TCT
4135 CCA GCG CGG CCT TTA AGG GTT CTG GCA AAA ACT GTT CTT ATA GGG AAT ACG CAT TAG CCT GAG TAG TGG ACT
4213 CCA GCG CGG GGT ATC GCC ATC GAC CCC TAT ACA AGT CAA AGT CAT CCA AGA AGC ATC AAG CCA AGG TAG AGG GCC AGG CCC TAT TAG CCT GAC CTA GGG GAT TTC GGC
4291 AAA TCG GGG CGG GCT GCC AAA TGA GCC GCA AGT CAA AGC CCA AGT ATC AGG CCA AGG CAC GTT CTT CTT TTT TTC CAT TCT
4369 TTC ACG TAG TGG CCA GCC ATC GGC TGA CCC ATC CGA CTG GAC CCA GCC ATC GTC TGC GTT GAT TTT GCC GAT TTC GGC
4447 CTT GTT CCA AAC TGG AAC ACT GAT GAA TGT TAA CAA AGC ATG CTC AAT TAG TCA ACC ATA AGT CCC CTA ACT
4525 CTA TTG GTT AAA AAA AGC TCG CCA GCA GCG AGA AGT ATG CAA TCA TCT CCG CAT GGG TGA ATT TTT TAT TCA GCC
4603 GGA AAG TCC CCA GCG TCC CAA GGC AGT ATG CCC AGT TCC GCC CAT TCG GTC ACA TTT TGA CCC CTC ACT GCC CAT TCT CCG CAT CAG
4681 TCC CAG TCC ATC CCG CCG CCC CCT CTC TGA GCC TTC ACA AGT TCT AAG TAG GCT TGA GGA GAT GAG TCA GCA GTA ATT TTT ATT TAT TAT TGC AAA
4759 CCG ATC CCC CCC CGG AGA GCA GCT TGG ATA TCC ATT TTC GGA TGG GCA TGG CAG CTA CAG CTG CTG TTT CTG AAA TCT
4837 GAG CCC CCG GGA CTC CCG GGA TTG CAC GCA GCA GGT TCT CCG CGG CTG TCA GCG GGG CGC TGT GCG AGG CTA TTC CGG CAT GGA CCA TTC GAC
4915 AAG CTC GGG CAC GCC CGG GCC ACA ATT GAG CGA ACT CGG TTT AGT CCA ATG CAG AGC TGC TGC TCC GGT CTC GAC
4993 GAT GGA TTG CAC GCA GGT TCT CCG CGG CCG TCA CAG CTA TTC GCC GCT CAG CTA ATG ACA CAG ACC CGG GCC CCA TTC GCT
5071 TGC TCT GAT GCC GGG GTG TTC CTG TCA GCG CGG GGG CCG CAG GAC CGG CTG GTT GTC TGT AAG CCT CTC GCA
5149 CTG AAT GAA CTG CAA GAC GAG GCA GCG TGG CGG CTG CCC CGT GGA GCT CTC GAA GGC ATG GCG GAT GCG TCC CCA TTC TGC CAG CCA GCA CAT CTC CTT GCT CGA
5227 GTT GTC ACT GAA GCG GGA AGG GAC TGG CTG CTA TTG GGC GAA GCT CAT ACG CGG GAT TGA TTT CCG ATC ACG CAT ATT
5305 CCT GCC ATC ATC CGC TGG GAT GCA CGA GGA CAT CGC GCT ATC CAC CTT GCT
5383 CAC CAA CAT GGG TGC AAA CAT CGC ATC GAG CCT ACT GCG GCT GAC ATC AAG CGC CAG GCC GCG ATG ACA CAG CGG CTC
5461 GAG CAT CAG GCT CGC GGA GCA CCC CTT GGA GAA GCC AGG CAG CTC ATG GGC CAA ATC ACA CGC TTT CTA ATC AAA AAT ATA GCG TTG GCT ACC CGT GAT ATT
5539 ACC CAT GCA GGC CAG GCA ATT CTT CCA AAT GAA CGT GAT GTG GCC GAG CGT GGC
5617 GGT GTG GCG CGC CGC TAT CAG GAC CTA GTC TGG GGA GGC TGC CAG CGC AGC TCC AGT CCT GAG CAC CCA AGG CCG CAG GAC GGT GCA TGG AAT CCA CAG CCT CGT GCT
```

Fig. 12, contd.

```
5695 CGC TTC CTC CTT TAC GGT ATC GCC GCT CCC GAT TCG CAG CGC ACC ATC GCC TTC TAT CGC CTT GAC GAG TTC TTC
5773 TGA GCG GGA CTC TGG GGT TCG GTG ATG GAT TTC GAT TCC CAG GAT TCC ACC GCC TAT TAT GAA AGG TTG GGC TTC GGA ATC
5851 GTT TTC CGG GAC GCC TGG ATC CTC AGC TAA AAT AGC CTC CGC ATG CTC GAG ATC ACA CTC ACC AAT TTC GCC CCC AAC TTG TTT
5929 ATT GCA GCT GGT TAC AAA ATC AAT GTA TCT TGT AGC ATC TCT TTT TCA CTG CAT TCT
6007 AGT TGT GCT GTG TCC CTG TTT CCT GTG TGA AAT TGT TAA ATT CCA CAC AAC CCG GAA GCC TTG GCG TAA
6085 TCA TGG AAA GCC TGG GGT CAG AAT TGC ATG AAG CTG GTT ATA TAG CTT AGG CCC GCT TTC CAG AGC TCG GGA
6163 TGT AAC CTG TCG TAG CAT TAG CCA TAT TTG GCT TTG GCT ATT GAC ATT GGC CAT GAT TAT TGA CGT TGT GTC AAT ATT
6241 GGC ATC ATA ATA TGT ACA TTA CGG GGT CAT TAG TTC ATA TGC CAA CAT ATA TGC AGT ATT GAC TTA CGG TAA ATG GCC CGC
6319 AGT AAT CAA TTA CGG GGT CAT TAG TTC ATA GCC CCC GCC CAT TGA CGT CAA TGA CGG TTA CAA TAG GGA CTT
6397 ATC ATA ATA TGT ACA TTA CGG GGT CAT TAG TTC ATA GCC CCC GCC CAT TGA CGT CAA TGA CGG TTA CAA TAG GGA CTT
6475 AGT AAT CAA TTA CGG GGT CAT TAG TTC ATA GCC CCC GCC CAT TGA CGT CAA TGA CGG TTA CAA TAG GGA CTT
6553 CTG ACC GTC AAT GAC GGT AAA TGG CCC GCC TGG CAT TAT GCC CAG TAC ATG ACC TTA TGG GAC TTT CCT ATT GGC AGT ATG TAT AGT GTT GGA GTA TTT TAC GGT ACC TTT GGC AGT ATG TAT AGT GTT GGA GTA
6631 TCC ATT GAC GTC AAT GGG AGT TTT GTT TTG GCA CCA AAA TCA ACG GGA CTT TCC AAA ATG TCG TAA TAA CCC CGC CCC GTT GAC GCA AAT GGG CGG TAG GCG TGT ACG GTG GGA GGT CTA TAT AAG CAG AGC TCG TTT AGT GAA CCG TCA GAT CGC CTG GAG ACG CCA TCC ACG CTG TTT TGA CCT CCA TAG AAG ACA CCG GGA CCG ATC CAG CCT CCG CGG CCG GGA ACG GTG CAT TGG AAC GCG GAT TCC CCG TGC CAA GAG TCT GGA TCT GCG CTC ACC GTC CAG CAC CCA GCT CCA CCA GTG TAT TGA GGT TCC ACT AGT GGA CCC ATC TTT CAT TTT CAA AAT CAA TGT TCA CGC TCT TAA GCG GCA TTT GGC CAT GCC CCT GAA CCG TCG CTT GAT TTC TTT ACG TTT AAT TTC GTT CAG GTG CCA AGT TGG CCG AAG CAT GCT TAC CCA TGC TCT CCA ATC CTG TTC GGA TAA TTC TGG AAC TGA TGA ACT GAC TGA GGT TCC ACT AGT GGA CCC CGG TAT TGA GGC CAG GCT TAA CCT CAG CAG CCC CTG AGG AGT AGA TCT GCA CCC CTG GCT CCA TGG TTT TCA CTG GAT CAA AAG CAG TCA TTC CGG CAG ACA AAG TGT CAA ACC CAG TTC AAT CTC CGC CAG TTC CGC TGT GGT GAG GTT CCT CGT GAG GCT
```

Fig. 12, contd.

```
8893  GTT CGG TGT AGG TCG TTC GCT CCA AGC TGG GCT GTG TGC ACG AAC CCC CAC TTC AGC CCG ACC GCT GCG CCT TAT CCG
8971  GTA ACT ATC GTC TTG AGT CCA ACC CGG CAG AGT TCT TGA ACG ACT TAT CGC GGC CTA ACT CGC CAG CCA CTG GTA GAA CAG TTA GCA
9049  GAG CGA GGT ATG GCG TAG GCG GTG CTA CAG AGT TCT TCG GAA AAA GAG TTG GTA GAA TTG CCG GCA AAC ATC CCG TAT TTG
9127  GTA TCT GCG CTC TGC TGA AGC CAG TTA GCA GAA TTA CGC GTA GAA AAA GAT CTC CTT TGA TCT TTT
9205  GTA GCG GTG TTT TTG TTT GCA AGC ACG CTC AAA ACT GGA ACG GAT AAG GAT TGG TCA TGA TAT CAA AAA GGA TCT TCA
9283  CTA CGG GGT CTG ACG CTC AGT GGA ACG AAA GTT TAA ATT GAA TCT AAA GTA TTT GTA TGA TAT CTT GGT CTG ACA GTT ACC
9361  CCT AGA TCC TTT TAA ATT AAA AAT CTA TCT CAG CAC CGA TCT GTC TAT TTC CAT CCA TAG TTG CCT GAC TCC CCG TCG TGT
9439  AAT GCT TAA TCA GTG AGG CAC CTA TCT CAG CAC CAT CTG GCC CCA GTG CTG CAA TGA TAC CGC GAG ACC CAC GCT CAC CGG CTC
9517  AGA TAA CTA CGA TAC GGG AGG GCT TAC CAT CCG GAA GGG CCG AGC GCA GAA GTG GTC CAA CTT TAT CCG CCT CCA TCC
9595  CAG ATT TAT CAG CAA TAA ACC AGC CAG CTA GAG TTG GTA GTT CGT TCG CTT CAT TCA GCT CAG GTT TGC GCA ACG TTG CCA TTG CTA
9673  AGT CTA TTA ATT GTT GCC GGG AAG GCT CGT AAG CGG TTA GCT CCT TCG GTC CGA TCA GAT CAA GTA AGT TGG CCG GAG TTA CAT
9751  CAG GCA TCG TGG TGT CAC GCT GTT GCA AAA AAG CGG TTA GCT CTC AAG GAT CTT TCA GAA GTA AGT CCG TTT CTG TGA CTG GTG
9829  GAT CCC CCA TGT TGT TGC AAA AAA GCG GTT AGC TCT GAC CAT GAT TAC AAA GTT GCT TGT GTA ACC GCT GTT CTG TGA CTG GTG
9907  TAT CAC TCA TGG TTA TGG CAG CAC TGC ATA ATT CTC TTA CTG TCA TGC CAT CCG TCA TGC CGT CAA TAC GGG ATA ATA
9985  AGT ACT CAA CCA AGT CAT TCT GAG AAT AGT GTA TGC GGC CGA GTT GCT CTT CGG CGT CAA AAC TCT CAA GGA TCT TAC
10063 CCG CGC CAC ATA GCA GAA CTT TAA AAG TGC TCA TCA TTG GAA AAC GTT CTT CGG CAG CAT CTT CAA GGA TCT TAC
10141 CGC TGT TGA GAT CCA GTT CGA TGT AAC CCA GTG CAC CCA AAA CCA ACT GAT CTT TTA CTT TCA CCA GCG TTT
10219 CTG GAG CAA AAA CAG GAA GGC AAA ATG CCG CAA AGG GGA TAA CAC CGA AAT GTT GAA TAC TCA
```

Fig. 13B

```
   1 atccaggcgc ggatcaataa aagatcatta tttttcaatag atctgtgtgt tggtttttttg
  61 tgtgccttgg gggaggggga ggccagaatg aggcgcggcc aaggggagg gggaggccag
 121 aatgaccttg ggggaggggg aggccagaat gaccttgggg gaggggagg ccagaatgag
 181 gcgcggatcc ggagaagttc ctattccgaa gttcctattc ttcaaatagt ataggaactt
 241 cgctcgaggg atcggccatt gaacaagatg gattgcacgc aggttctccg gccgcttggg
 301 tggagaggct attcggctat gactgggcac aacagacaat cggctgctct gatgccgccg
 361 tgttccggct gtcagcgcag gggcgcccgg ttctttttgt caagaccgac ctgtccggtg
 421 ccctgaatga actgcaggac gaggcagcgc ggctatcgtg gctggccacg acgggcgttc
 481 cttgcgcagc tgtgctcgac gttgtcactg aagcgggaag ggactggctg ctattgggcg
 541 aagtgccggg gcaggatctc ctgtcatctc accttgctcc tgccgagaaa gtatccatca
 601 tggctgatgc aatgcggcgg ctgcatacgc ttgatccggc tacctgccca ttcgaccacc
 661 aagcgaaaca tcgcatcgag cgagcacgta ctcggatgga agccggtctt gtcgatcagg
 721 atgatctgga cgaagagcat caggggctcg cgccagccga actgttcgcc aggctcaagg
 781 cgcgcatgcc cgacggcgag gatctcgtcg tgacccatgg cgatgcctgc ttgccgaata
 841 tcatggtgga aaatggccgc ttttctggat tcatcgactg tggccggctg ggtgtggcgg
 901 accgctatca ggacatagcg ttggctaccc gtgatattgc tgaagagctt ggcggcgaat
 961 gggctgaccg cttcctcgtg ctttacggta tcgccgctcc cgattcgcag cgcatcgcct
1021 tctatcgcct tcttgacgag ttcttctgag gggatcgatc cgctgtaagt ctgcagaaat
1081 tgatgatcta ttaaacaata aagatgtcca ctaaaatgga agttttcct gtcatacttt
1141 gttaagaagg gtgagaacag agtacctaca ttttgaatgg aaggattgga gctacggggg
1201 tgggggtggg gtgggattag ataaatgcct gctctttact gaaggctctt tactattgct
1261 ttatgataat gtttcatagt tggatatcat aatttaaaca agcaaaacca aattaagggc
1321 cagctcattc ctcccactca tgatctatag atctatagat ctctcgtggg atcattgttt
1381 ttctcttgat tcccactttg tggttctaag tactgtggtt tccaaatgtg tcagtttcat
1441 agcctgaaga acgagatcag cagcctctgt tccacataca cttcattctc agtattgttt
1501 tgccaagttc taattccatc agaagctgac tctagatggc gcgtatgcag gttttcgaca
1561 ttgattattg actagttatt aatagtaatc aattacgggg tcattagttc atagcccata
1621 tatggagttc cgcgttacat aacttacggt aaatggcccg cctggctgac cgcccaacga
1681 cccccgccca ttgacgtcaa taatgacgta tgttcccata gtaacgccaa tagggacttt
1741 ccattgacgt caatgggtgg agtatttacg gtaaactgcc cacttggcag tacatcaagt
1801 gtatcatatg ccaagtacgc cccctattga cgtcaatgac ggtaaatggc ccgcctggca
1861 ttatgcccag tacatgacct tatgggactt tcctacttgg cagtacatct acgtattagt
1921 catcgctatt accatggtcg aggtgagccc cacgttctgc ttcactctcc ccatctcccc
1981 cccctcccca ccccaatttt gtatttatt tatttttttaa ttattttgtg cagcgatggg
2041 ggcgggggggg gggggggcgc gcgccaggcg gggcggggcg gggcgagggg cggggcgggg
2101 cgaggcggag aggtgcggcg gcagccaatc agagcggcgc gctccgaaag tttccttta
2161 tggcgaggcg gcggcggcgg cggccctata aaaagcgaag cgcgcggcgg gcgggagtcg
2221 ctgcgttgcc ttcgccccgt gccccgctcc gcgccgcctc gcgccgcccg ccccggctct
```

Fig. 13B, contd.

```
2281 gactgaccgc gttactccca caggtgagcg ggcgggacgg cccttctcct ccgggctgta
2341 attagcgctt ggtttaatga cggctcgttt cttttctgtg gctgcgtgaa agccttaaag
2401 ggctccggga gggccctttg tgcgggggggg agcggctcgg ggggtgcgtg cgtgtgtgtg
2461 tgcgtgggga gcgccgcgtg cggcccgcgc tgcccggcgg ctgtgagcgc tgcggcgcg
2521 gcgcggggct ttgtgcgctc cgcgtgtgcg cgaggggagc gcggccgggg gcggtgcccc
2581 gcggtgcggg ggggctgcga ggggaacaaa ggctgcgtgc ggggtgtgtg cgtgggggggg
2641 tgagcagggg gtgtgggcgc ggcggtcggg ctgtaacccc ccctgcacc ccctccccg
2701 agttgctgag cacggcccgg cttcgggtgc ggggctccgt gcggggcgtg gcgcggggct
2761 cgccgtgccg ggcgggggt ggcggcaggt ggggtgccg ggcggggcgg ggccgcctcg
2821 ggccggggag ggctcggggg aggggcgcgg cggccccgga gcgccggcgg ctgtcgaggc
2881 gcggcgagcc gcagccattg ccttttatgg taatcgtgcg agagggcgca gggacttcct
2941 ttgtcccaaa tctgtgcgga gccgaaatct gggaggcgcc gccgcacccc ctctagcggg
3001 cgcggggcga agcggtgcgg cgccggcagg aaggaaatgg gcggggaggg ccttcgtgcg
3061 tcgccgcgcc gccgtccctt tctccctctc cagcctcggg gctgtccgcg gggggacggc
3121 tgccttcggg ggggacgggg cagggcgggg ttcggcttct ggcgtgtgac cggcggctct
3181 agaagcgttg gggtgagtac tccctctcaa aagcgggcat gacttctgcg ctaagattgt
3241 cagtttccaa aaacgaggag gatttgatat tcacctggcc cgcggtgatg cctttgaggg
3301 tggccgcgtc catctggtca gaaaagacaa tcttttttgtt gtcaagcttg aggtgtggca
3361 ggcttgagat ctggccatac acttgagtga cattgacatc cactttgcct ttctctccac
3421 aggtgtccac tcccagggcg gcctccggag cgatcgccga tccgcctagg caattgttta
3481 aatcggccgg ccataacttc gtataatgta tgctatacga agttatggat cctcacagta
3541 ggtggcatcg ttcctttctg actgcccgcc ccccgcatgc cgtcccgcga tattgagctc
3601 cgaacctctc gccctgccgc cgccggtgct ccgtcgccgc cgcgccgcca tggaatcgaa
3661 gccaccatgg atcttaccgg aaaactcgac gcaagaaaaa tcagagagat cctcataaag
3721 gtcaagaagg gcggaaagat cgccgtgtaa ttctagaccg gttcgagatc caggcgcgga
3781 tcaataaaag atcattattt tcaatagatc tgtgtgttgg tttttttgtgt gccttggggg
3841 agggggaggc cagaatgagg cgcggccaag ggggaggggg aggccagaat gaccttgggg
3901 gaggggggagg ccagaatgac cttggggggag ggggaggcca gaatgaggcg cgccctccgt
3961 cgacctataa cttcgtataa tgtatgctat acgaagttat ggcggccgcc accatggaca
4021 tgagagtgcc cgcccagctc ctgggcctcc tgctactctg gctccgaggt aaggatggag
4081 aacactagga atttactcag ccagtgtgct cagtactgac tggaacttca gggaagttct
4141 ctgataacat gattaatagt aagaatattt gtttttatgt ttccaatctc aggtgccaga
4201 tgtgacatcc agatgaccca gagccccagc agcctgagcg ccagcgtggg cgacagagtg
4261 accatcacct gcagagccag ccagagcatc agcagctacc tgaactggta tcagcagaag
4321 cccggcaagg cccccaagct gctgatctac gccgccagct ccctgcagag cggcgtgccc
4381 agcagattca gcggcagcgg ctccggcacc gacttcaccc tgaccatcag cagcctgcag
4441 cccgaggact tcgccaccta ctactgccag cagagctaca gcaccccccc caccttcggc
```

Fig. 13B, contd.

```
4501 cagggcacca aggtggagat caagagagcc gacgccgctc ccaccgtgtc catcttcccc
4561 cccagcatgg aacagctgac ctctggcgga gccaccgtgg tctgcttcgt gaacaacttc
4621 taccccagag acatcagcgt gaagtggaag atcgacggca gcgagcagag ggacggcgtg
4681 ctggacagcg tgaccgacca ggacagcaag gactccacct acagcatgag cagcaccctg
4741 agcctgacca aggtggagta cgagaggcac aacctgtaca cctgcgaggt ggtgcacaag
4801 accagctcca gccccgtggt caagtccttc aaccggaacg agtgttgagc tagcttaaga
4861 tttaaatagg ccggccgcgt cgacctcgag atccaggcgc ggatcaataa aagatcatta
4921 ttttcaatag atctgtgtgt tggttttttg tgtgccttgg gggaggggga ggccagaatg
4981 aggcgcggcc aaggggagg gggaggccag aatgaccttg ggggagggg aggccagaat
5041 gaccttgggg gaggggagg ccagaatgag gcgcgccccc gggtaccgag ctcgaattag
5101 tggatcctca cagtaggtgg catcgttcct ttctgactgc ccgcccccg catgccgtcc
5161 cgcgatattg agctccgaac ctctcgccct gccgccgccg tgctccgtc gccgccgcgc
5221 cgccatggaa tcgcgccggt aaccgaagtt cctatacttt ctagagaata ggaacttcgg
5281 aataggaact tcaagccggt acccagcttt tgttcccttt agtgagggtt aatttcgagc
5341 ttggcgtaat catggtcata gctgtttcct gtgtgaaatt gttatccgct cacaattcca
5401 cacaacatac gagccgggag cataaagtgt aaagcctggg gtgcctaatg agtgagctaa
5461 ctcacattaa ttgcgttgcg ctcactgccc gctttccagt cgggaaacct gtcgtgccag
5521 ctgcattaat gaatcggcca acgcgcgggg agaggcggtt tgcgtattgg gcgctcttcc
5581 gcttcctcgc tcactgactc gctgcgctcg gtcgttcggc tgcggcgagc ggtatcagct
5641 cactcaaagg cggtaatacg gttatccaca gaatcagggg ataacgcagg aaagaacatg
5701 tgagcaaaag gccagcaaaa ggccaggaac cgtaaaaagg ccgcgttgct ggcgtttttc
5761 cataggctcc gcccccctga cgagcatcac aaaaatcgac gctcaagtca gaggtggcga
5821 aacccgacag gactataaag ataccaggcg tttccccctg gaagctccct cgtgcgctct
5881 cctgttccga ccctgccgct taccggatac ctgtccgcct ttctcccttc gggaagcgtg
5941 gcgctttctc atagctcacg ctgtaggtat ctcagttcgg tgtaggtcgt tcgctccaag
6001 ctgggctgtg tgcacgaacc ccccgttcag cccgaccgct gcgccttatc cggtaactat
6061 cgtcttgagt ccaacccggt aagacacgac ttatcgccac tggcagcagc cactggtaac
6121 aggattagca gagcgaggta tgtaggcggt gctacagagt tcttgaagtg gtggcctaac
6181 tacggctaca ctagaaggac agtatttggt atctgcgctc tgctgaagcc agttaccttc
6241 ggaaaaagag ttggtagctc ttgatccggc aaacaaacca ccgctggtag cggtggtttt
6301 tttgtttgca agcagcagat tacgcgcaga aaaaaggat ctcaagaaga tcctttgatc
6361 ttttctacgg ggtctgacgc tcagtggaac gaaaactcac gttaagggat tttggtcatg
6421 agattatcaa aaaggatctt cacctagatc cttttaaatt aaaaatgaag ttttaaatca
6481 atctaaagta tatatgagta aacttggtct gacagttacc aatgcttaat cagtgaggca
6541 cctatctcag cgatctgtct atttcgttca tccatagttg cctgactccc cgtcgtgtag
6601 ataactacga tacgggaggg cttaccatct ggccccagtg ctgcaatgat accgcgagac
6661 ccacgctcac cggctccaga tttatcagca ataaaccagc cagccggaag ggccgagcgc
```

Fig. 13B, contd.

```
6721 agaagtggtc ctgcaacttt atccgcctcc atccagtcta ttaattgttg ccgggaagct
6781 agagtaagta gttcgccagt taatagtttg cgcaacgttg ttgccattgc tacaggcatc
6841 gtggtgtcac gctcgtcgtt tggtatggct tcattcagct ccggttccca acgatcaagg
6901 cgagttacat gatcccccat gttgtgcaaa aaagcggtta gctccttcgg tcctccgatc
6961 gttgtcagaa gtaagttggc cgcagtgtta tcactcatgg ttatggcagc actgcataat
7021 tctcttactg tcatgccatc cgtaagatgc ttttctgtga ctggtgagta ctcaaccaag
7081 tcattctgag aatagtgtat gcggcgaccg agttgctctt gcccggcgtc aatacgggat
7141 aataccgcgc cacatagcag aactttaaaa gtgctcatca ttggaaaacg ttcttcgggg
7201 cgaaaactct caaggatctt accgctgttg agatccagtt cgatgtaacc cactcgtgca
7261 cccaactgat cttcagcatc ttttactttc accagcgttt ctgggtgagc aaaaacagga
7321 aggcaaaatg ccgcaaaaaa gggaataagg gcgacacgga atgttgaat actcatactc
7381 ttcctttttc aatattattg aagcatttat cagggttatt gtctcatgag cggatacata
7441 tttgaatgta tttagaaaaa taaacaaata ggggttccgc gcacatttcc ccgaaaagtg
7501 ccacctaaat tgtaagcgtt aatattttgt taaaattcgc gttaaatttt tgttaaatca
7561 gctcattttt taaccaatag gccgaaatcg gcaaaatccc ttataaatca aaagaataga
7621 ccgagatagg gttgagtgtt gttccagttt ggaacaagag tccactatta agaacgtgg
7681 actccaacgt caaagggcga aaaaccgtct atcagggcga tggcccacta cgtgaaccat
7741 caccctaatc aagttttttg gggtcgaggt gccgtaaagc actaaatcgg aaccctaaag
7801 ggagccccg atttagagct tgacgggaa agccggcgaa cgtggcgaga aaggaaggga
7861 agaaagcgaa aggagcgggc gctagggcgc tggcaagtgt agcggtcacg ctgcgcgtaa
7921 ccaccacacc cgccgcgctt aatgcgccgc tacagggcgc gtcccattcg ccattcaggc
7981 tgcgcaactg ttgggaaggg cgatcggtgc gggcctcttc gctattacgc cagctggcga
8041 aaggggggatg tgctgcaagg cgattaagtt gggtaacgcc agggttttcc cagtcacgac
8101 gttgtaaaac gacggccagt gagcgcgcgt aatacgactc actataggc gaattggggg
8161 taactaagta aggatcgag
```

Fig. 15B

```
   1 atccaggcgc ggatcaataa aagatcatta ttttcaatag atctgtgtgt tggtttttg
  61 tgtgccttgg gggaggggga ggccagaatg aggcgcggcc aaggggagg gggaggccag
 121 aatgaccttg ggggagggg aggccagaat gaccttgggg gaggggagg ccagaatgag
 181 gcgcggatcc ggagaagttc ctattccgaa gttcctattc ttcaaatagt ataggaactt
 241 cgctcgaggg atcggccatt gaacaagatg gattgcacgc aggttctccg gccgcttggg
 301 tggagaggct attcggctat gactgggcac aacagacaat cggctgctct gatgccgccg
 361 tgttccggct gtcagcgcag gggcgcccgg ttcttttgt caagaccgac ctgtccggtg
 421 ccctgaatga actgcaggac gaggcagcgc ggctatcgtg ctggccacg acgggcgttc
 481 cttgcgcagc tgtgctcgac gttgtcactg aagcgggaag ggactggctg ctattgggcg
 541 aagtgccggg gcaggatctc ctgtcatctc accttgctcc tgccgagaaa gtatccatca
 601 tggctgatgc aatgcggcgg ctgcatacgc ttgatccggc tacctgccca ttcgaccacc
 661 aagcgaaaca tcgcatcgag cgagcacgta ctcggatgga agccggtctt gtcgatcagg
 721 atgatctgga cgaagagcat caggggctcg cgccagccga actgttcgcc aggctcaagg
 781 cgcgcatgcc cgacggcgag gatctcgtcg tgacccatgg cgatgcctgc ttgccgaata
 841 tcatggtgga aaatggccgc ttttctggat tcatcgactg tggccggctg ggtgtggcgg
 901 accgctatca ggacatagcg ttggctaccc gtgatattgc tgaagagctt ggcggcgaat
 961 gggctgaccg cttcctcgtg ctttacggta tcgccgctcc cgattcgcag cgcatcgcct
1021 tctatcgcct tcttgacgag ttcttctgag gggatcgatc cgctgtaagt ctgcagaaat
1081 tgatgatcta ttaaacaata aagatgtcca ctaaaatgga gttttttcct gtcatacttt
1141 gttaagaagg gtgagaacag agtacctaca ttttgaatgg aaggattgga gctacggggg
1201 tgggggtggg gtgggattag ataaatgcct gctctttact gaaggctctt tactattgct
1261 ttatgataat gtttcatagt tggatatcat aatttaaaca agcaaaacca aattaagggc
1321 cagctcattc ctcccactca tgatctatag atctatagat ctctcgtggg atcattgttt
1381 ttctcttgat tcccactttg tggttctaag tactgtggtt tccaaatgtg tcagtttcat
1441 agcctgaaga acgagatcag cagcctctgt tccacataca cttcattctc agtattgttt
1501 tgccaagttc taattccatc agaagctgac tctagatggc gcgtatgcag gttttcgaca
1561 ttgattattg actagttatt aatagtaatc aattacgggg tcattagttc atagcccata
1621 tatggagttc cgcgttacat aacttacggt aaatggcccg cctggctgac cgcccaacga
1681 cccccgccca ttgacgtcaa taatgacgta tgttcccata gtaacgccaa tagggacttt
1741 ccattgacgt caatgggtgg agtatttacg gtaaactgcc cacttggcag tacatcaagt
1801 gtatcatatg ccaagtacgc ccctattga cgtcaatgac ggtaaatggc ccgcctggca
1861 ttatgcccag tacatgacct tatgggactt tcctacttgg cagtacatct acgtattagt
1921 catcgctatt accatggtcg aggtgagccc cacgttctgc ttcactctcc ccatctcccc
1981 cccctcccca ccccaatttt gtatttatt tatttttaa ttattttgtg cagcgatggg
2041 ggcggggggg gggggggcgc gcgccaggcg gggcggggcg gggcgagggg cggggcgggg
2101 cgaggcggag aggtgcggcg gcagccaatc agagcggcgc gctccgaaag tttccttta
```

Fig. 15B, contd.

```
2161 tggcgaggcg gcggcggcgg cggccctata aaaagcgaag cgcgcggcgg gcgggagtcg
2221 ctgcgttgcc ttcgccccgt gccccgctcc gcgccgcctc gcgccgcccg ccccggctct
2281 gactgaccgc gttactccca caggtgagcg ggcgggacgg cccttctcct ccgggctgta
2341 attagcgctt ggtttaatga cggctcgttt cttttctgtg gctgcgtgaa agccttaaag
2401 ggctccggga gggccctttg tgcgggggg agcggctcgg ggggtgcgtg cgtgtgtgtg
2461 tgcgtgggga gcgccgcgtg cggcccgcgc tgcccggcgg ctgtgagcgc tgcgggcgcg
2521 gcgcggggct ttgtgcgctc cgcgtgtgcg cgaggggagc gcggccgggg gcggtgcccc
2581 gcggtgcggg ggggctgcga ggggaacaaa ggctgcgtgc ggggtgtgtg cgtgggggg
2641 tgagcagggg gtgtgggcgc ggcggtcggg ctgtaacccc ccctgcacc ccctccccg
2701 agttgctgag cacggcccgg cttcgggtgc ggggctccgt gcggggcgtg gcgcggggct
2761 cgccgtgccg ggcgggggt ggcggcaggt ggggtgccg ggcggggcgg ggccgcctcg
2821 ggccggggag ggctcggggg aggggcgcgg cggccccgga gcgccggcgg ctgtcgaggc
2881 gcggcgagcc gcagccattg ccttttatgg taatcgtgcg agagggcgca gggacttcct
2941 ttgtcccaaa tctgtgcgga gccgaaatct gggaggcgcc gccgcacccc ctctagcggg
3001 cgcggggcga agcggtgcgg cgccggcagg aaggaaatgg gcggggaggg ccttcgtgcg
3061 tcgccgcgcc gccgtcccct tctccctctc cagcctcggg gctgtccgcg gggggacggc
3121 tgccttcggg ggggacgggg cagggcgggg ttcggcttct ggcgtgtgac cggcggctct
3181 agaagcgttg gggtgagtac tccctctcaa aagcgggcat gacttctgcg ctaagattgt
3241 cagtttccaa aaacgaggag gatttgatat tcacctggcc cgcggtgatg cctttgaggg
3301 tggccgcgtc catctggtca gaaaagacaa tcttttttgtt gtcaagcttg aggtgtggca
3361 ggcttgagat ctggccatac acttgagtga cattgacatc cactttgcct ttctctccac
3421 aggtgtccac tcccagggcg gcctccggag cgatcgccga tccgcctagg caattgttta
3481 aatcggccgg ccataacttc gtataatgta tgctatacga agttatggat cctcacagta
3541 ggtggcatcg ttcctttctg actgcccgcc ccccgcatgc cgtcccgcga tattgagctc
3601 cgaacctctc gccctgccgc cgccggtgct ccgtcgccgc cgcgccgcca tggaatcgaa
3661 gccaccatgg atcttaccgg aaaactcgac gcaagaaaaa tcagagagat cctcataaag
3721 gtcaagaagg gcggaaagat cgccgtgtaa ttctagaccg gttcgagatc caggcgcgga
3781 tcaataaaag atcattattt tcaatagatc tgtgtgttgg ttttttgtgt gccttggggg
3841 aggggaggc cagaatgagg cgcggccaag ggggagggg aggccagaat gaccttgggg
3901 gaggggagg ccagaatgac cttggggag ggggaggcca gaatgaggcg cgccctccgt
3961 cgacctataa cttcgtataa tgtatgctat acgaagttat ggcggccgcc accatggaca
4021 tgagagtgcc cgcccagctc ctggggctcc tgctactctg gctccgaggt aaggatggag
4081 aacactagga atttactcag ccagtgtgct cagtactgac tggaacttca gggaagttct
4141 ctgataacat gattaatagt aagaatattt gttttatgt ttccaatctc aggtgccaga
4201 tgtcagtctg ccctgaccca gcccgcctct gtgtctggca gccctggcca gagcatcacc
4261 atcagctgca ccggcaccag cagcgacgtg ggcggctaca actacgtgtc ctggtatcag
4321 cagcaccccg gcaaggcccc caagctgatg atctacgagg tgtccaacag acccagcggc
```

Fig. 15B, contd.

```
4381 gtgagcaaca gattcagcgg cagcaagagc ggcaacaccg ccagcctgac catcagcggc
4441 ctccaggctg aggacgaggc cgactactac tgcagcagct acaccagcag ctccaccctg
4501 gtgtttggcg gcggaacaaa gctgaccgtg ctgagagccg acgccgctcc caccgtgtcc
4561 atcttccccc ccagcatgga acagctgacc tctggcggag ccaccgtggt ctgcttcgtg
4621 aacaacttct accccagaga catcagcgtg aagtggaaga tcgacggcag cgagcagagg
4681 gacggcgtgc tggacagcgt gaccgaccag acagcaagg actccaccta cagcatgagc
4741 agcaccctga gcctgaccaa ggtggagtac gagaggcaca acctgtacac ctgcgaggtg
4801 gtgcacaaga ccagctccag ccccgtggtc aagtccttca accggaacga gtgttgagct
4861 agcttaagat ttaataggc cggccgcgtc gacctcgaga tccaggcgcg gatcaataaa
4921 agatcattat tttcaataga tctgtgtgtt ggttttttgt gtgccttggg ggagggggag
4981 gccagaatga ggcgcggcca aggggagggg ggaggccaga atgaccttgg gggaggggga
5041 ggccagaatg accttggggg aggggaggc cagaatgagg cgcgccccg ggtaccgagc
5101 tcgaattagt ggatcctcac agtaggtggc atcgttcctt tctgactgcc cgccccccgc
5161 atgccgtccc gcgatattga gctccgaacc tctcgccctg ccgccgccgg tgctccgtcg
5221 ccgccgcgcc gccatggaat cgcgccggta accgaagttc ctatactttc tagagaatag
5281 gaacttcgga ataggaactt caagccggta cccagctttt gttcccttta gtgagggtta
5341 atttcgagct tggcgtaatc atggtcatag ctgtttcctg tgtgaaattg ttatccgctc
5401 acaattccac acaacatacg agccgggagc ataaagtgta aagcctgggg tgcctaatga
5461 gtgagctaac tcacattaat tgcgttgcgc tcactgcccg ctttccagtc gggaaacctg
5521 tcgtgccagc tgcattaatg aatcggccaa cgcgcgggga gaggcggttt gcgtattggg
5581 cgctcttccg cttcctcgct cactgactcg ctgcgctcgg tcgttcggct gcggcgagcg
5641 gtatcagctc actcaaaggc ggtaatacgg ttatccacag aatcagggga taacgcagga
5701 aagaacatgt gagcaaaagg ccagcaaaag gccaggaacc gtaaaaaggc cgcgttgctg
5761 gcgtttttcc ataggctccg ccccctgac gagcatcaca aaatcgacg ctcaagtcag
5821 aggtggcgaa acccgacagg actataaaga taccaggcgt ttcccctgg aagctccctc
5881 gtgcgctctc ctgttccgac cctgccgctt accggatacc tgtccgcctt tctccttcg
5941 ggaagcgtgg cgctttctca tagctcacgc tgtaggtatc tcagttcggt gtaggtcgtt
6001 cgctccaagc tgggctgtgt gcacgaaccc ccgttcagc ccgaccgctg cgccttatcc
6061 ggtaactatc gtcttgagtc aacccggta agacacgact tatcgccact ggcagcagcc
6121 actggtaaca ggattagcag agcgaggtat gtaggcggtg ctacagagtt cttgaagtgg
6181 tggcctaact acggctacac tagaaggaca gtatttggta tctgcgctct gctgaagcca
6241 gttaccttcg gaaaaagagt tggtagctct tgatccggca acaaaccac cgctggtagc
6301 ggtggttttt ttgtttgcaa gcagcagatt acgcgcagaa aaaaggatc tcaagaagat
6361 cctttgatct tttctacggg gtctgacgct cagtggaacg aaaactcacg ttaagggatt
6421 ttggtcatga gattatcaaa aaggatcttc acctagatcc ttttaaatta aaaatgaagt
6481 tttaaatcaa tctaaagtat atatgagtaa acttggtctg acagttacca atgcttaatc
6541 agtgaggcac ctatctcagc gatctgtcta tttcgttcat ccatagttgc ctgactcccc
```

Fig. 15B, contd.

```
6601 gtcgtgtaga taactacgat acgggagggc ttaccatctg gccccagtgc tgcaatgata
6661 ccgcgagacc cacgctcacc ggctccagat ttatcagcaa taaaccagcc agccggaagg
6721 gccgagcgca gaagtggtcc tgcaacttta tccgcctcca tccagtctat taattgttgc
6781 cgggaagcta gagtaagtag ttcgccagtt aatagtttgc gcaacgttgt tgccattgct
6841 acaggcatcg tggtgtcacg ctcgtcgttt ggtatggctt cattcagctc cggttcccaa
6901 cgatcaaggc gagttacatg atcccccatg ttgtgcaaaa aagcggttag ctccttcggt
6961 cctccgatcg ttgtcagaag taagttggcc gcagtgttat cactcatggt tatggcagca
7021 ctgcataatt ctcttactgt catgccatcc gtaagatgct tttctgtgac tggtgagtac
7081 tcaaccaagt cattctgaga atagtgtatg cggcgaccga gttgctcttg cccggcgtca
7141 atacgggata taccgcgcc acatagcaga actttaaaag tgctcatcat tggaaaacgt
7201 tcttcggggc gaaaactctc aaggatctta ccgctgttga tccagttc gatgtaaccc
7261 actcgtgcac ccaactgatc ttcagcatct tttactttca ccagcgtttc tgggtgagca
7321 aaaacaggaa ggcaaaatgc cgcaaaaaag gaataaggg cgacacggaa atgttgaata
7381 ctcatactct tcctttttca atattattga agcatttatc agggttattg tctcatgagc
7441 ggatacatat ttgaatgtat ttagaaaaat aaacaaatag gggttccgcg cacatttccc
7501 cgaaaagtgc cacctaaatt gtaagcgtta atattttgtt aaaattcgcg ttaaattttt
7561 gttaaatcag ctcattttt aaccaatagg ccgaaatcgg caaaatccct tataaatcaa
7621 aagaatagac cgagataggg ttgagtgttg ttccagtttg gaacaagagt ccactattaa
7681 agaacgtgga ctccaacgtc aaagggcgaa aaaccgtcta tcagggcgat ggcccactac
7741 gtgaaccatc accctaatca agttttttgg ggtcgaggtg ccgtaaagca ctaaatcgga
7801 accctaaagg gagcccccga tttagagctt gacggggaaa gccggcgaac gtggcgagaa
7861 aggaagggaa gaaagcgaaa ggagcgggcg ctagggcgct ggcaagtgta gcggtcacgc
7921 tgcgcgtaac caccacccc gccgcgctta atgcgccgct acagggcgcg tcccattcgc
7981 cattcaggct gcgcaactgt tgggaagggc gatcggtgcg ggcctcttcg ctattacgcc
8041 agctggcgaa agggggatgt gctgcaaggc gattaagttg ggtaacgcca gggttttccc
8101 agtcacgacg ttgtaaaacg acggccagtg agcgcgcgta atacgactca ctatagggcg
8161 aattggggt aactaagtaa ggatcgag
``` pVkP-O12-del2_Final(ML104)

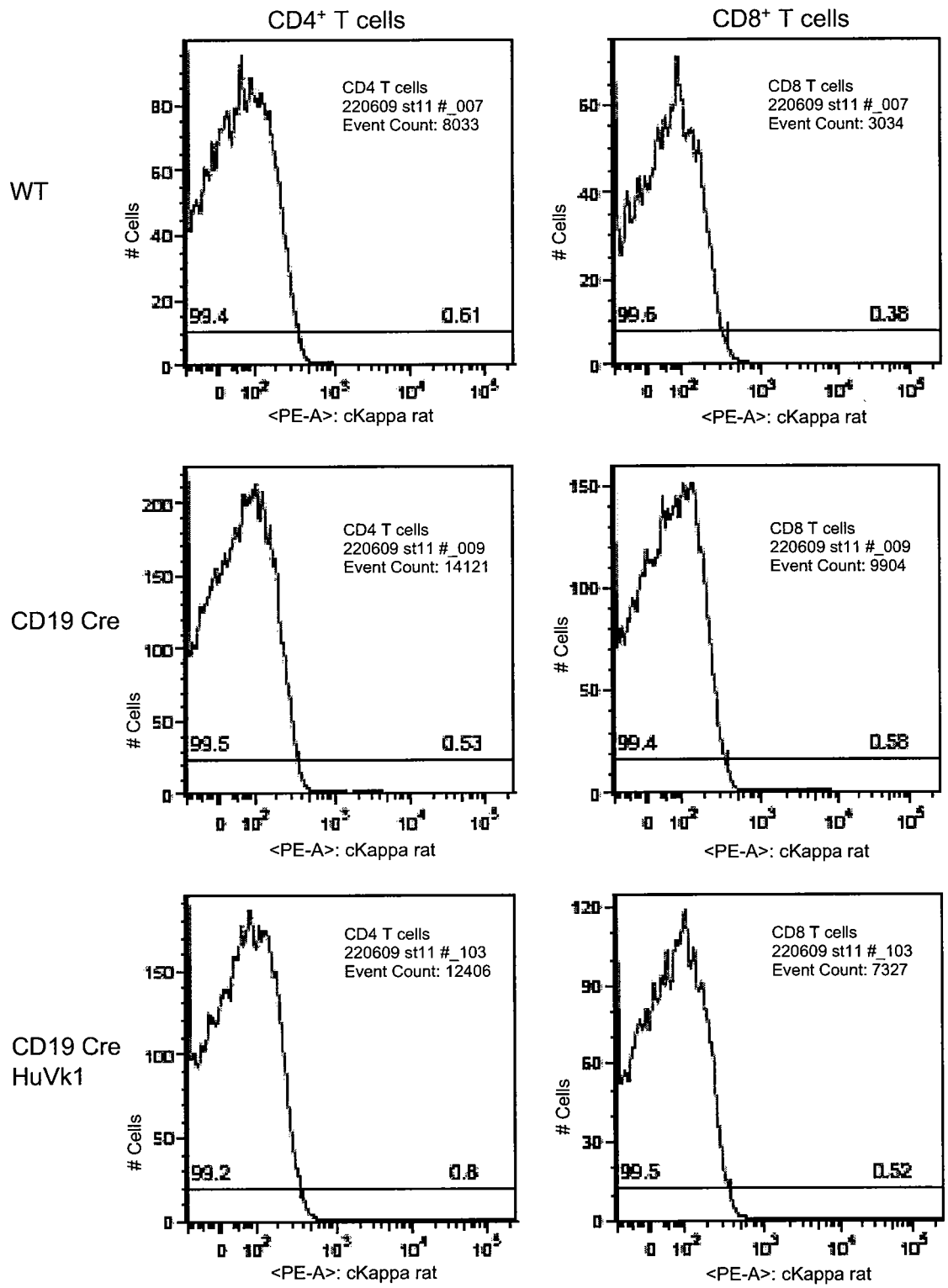
Fig. 23, contd.

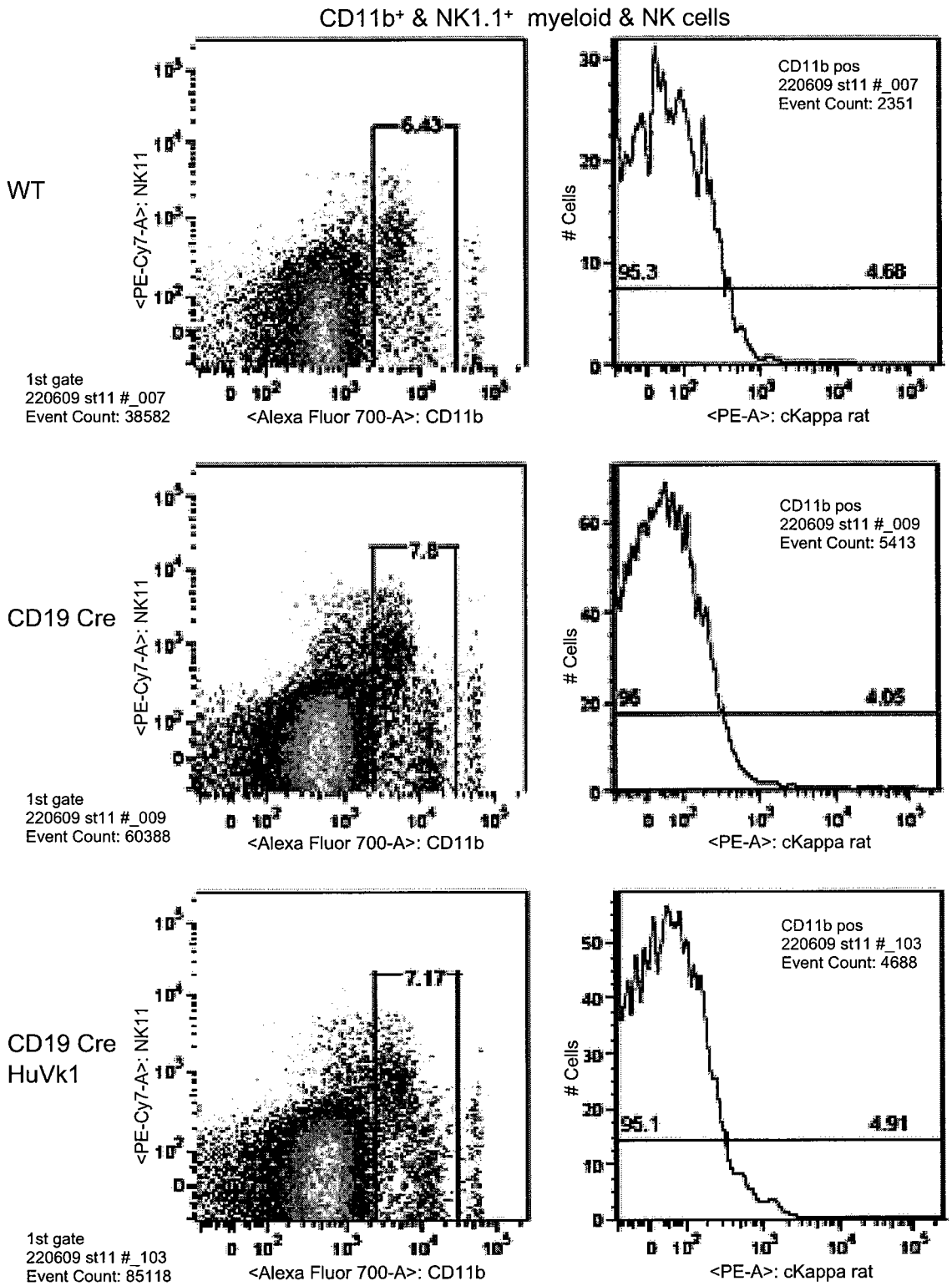
Fig. 23, contd.

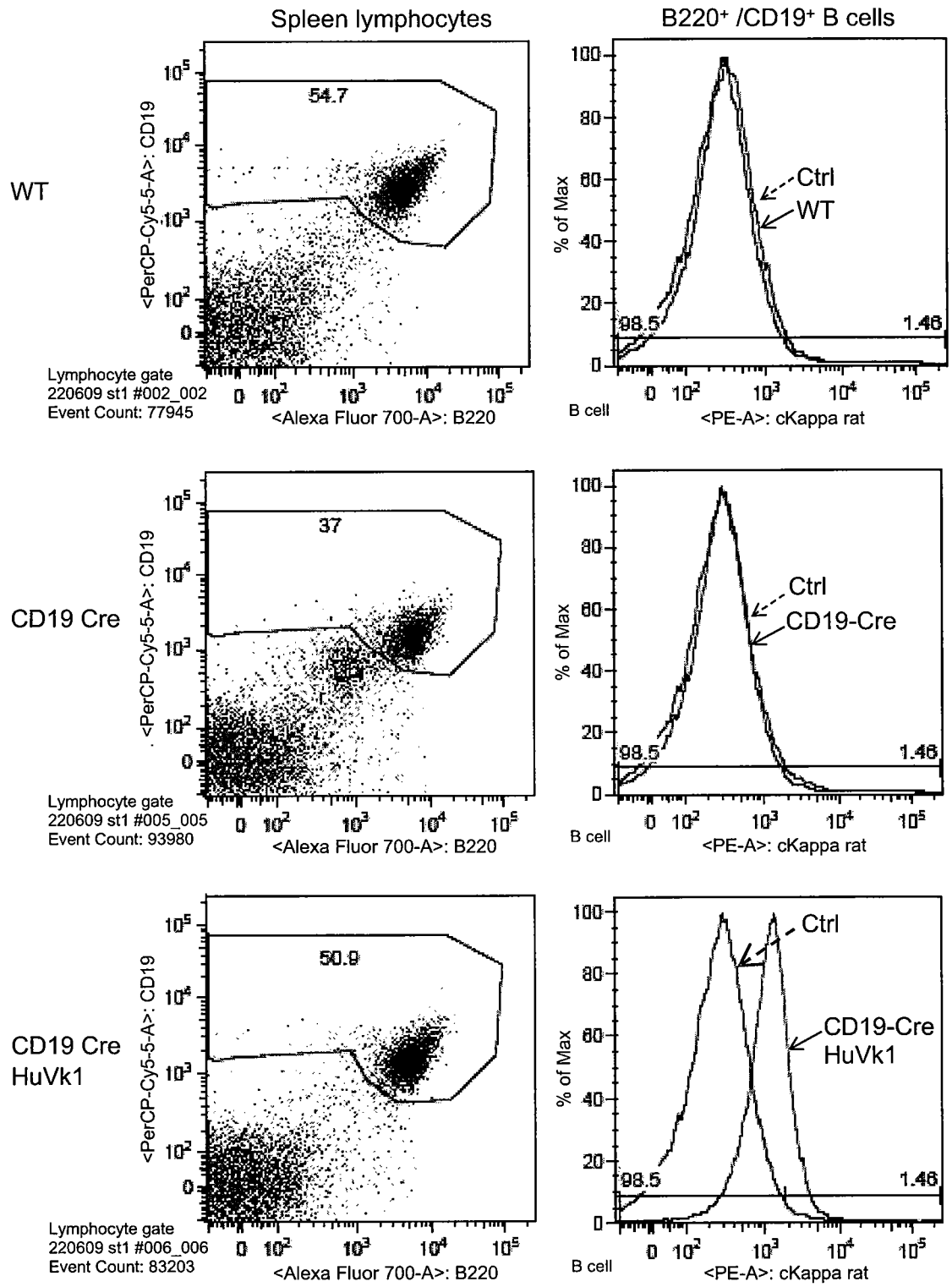
Fig. 24, contd.

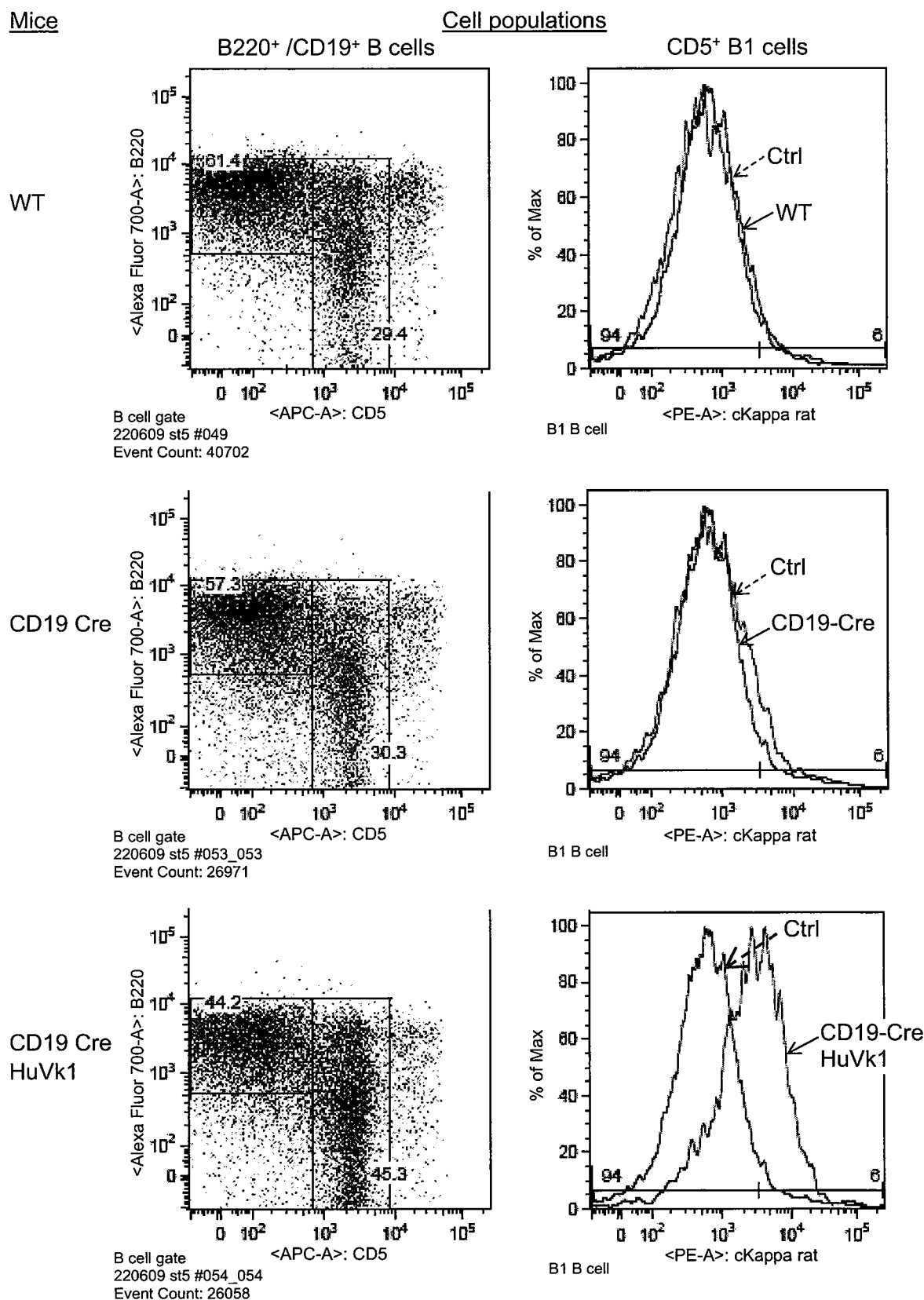
Fig. 25, contd.

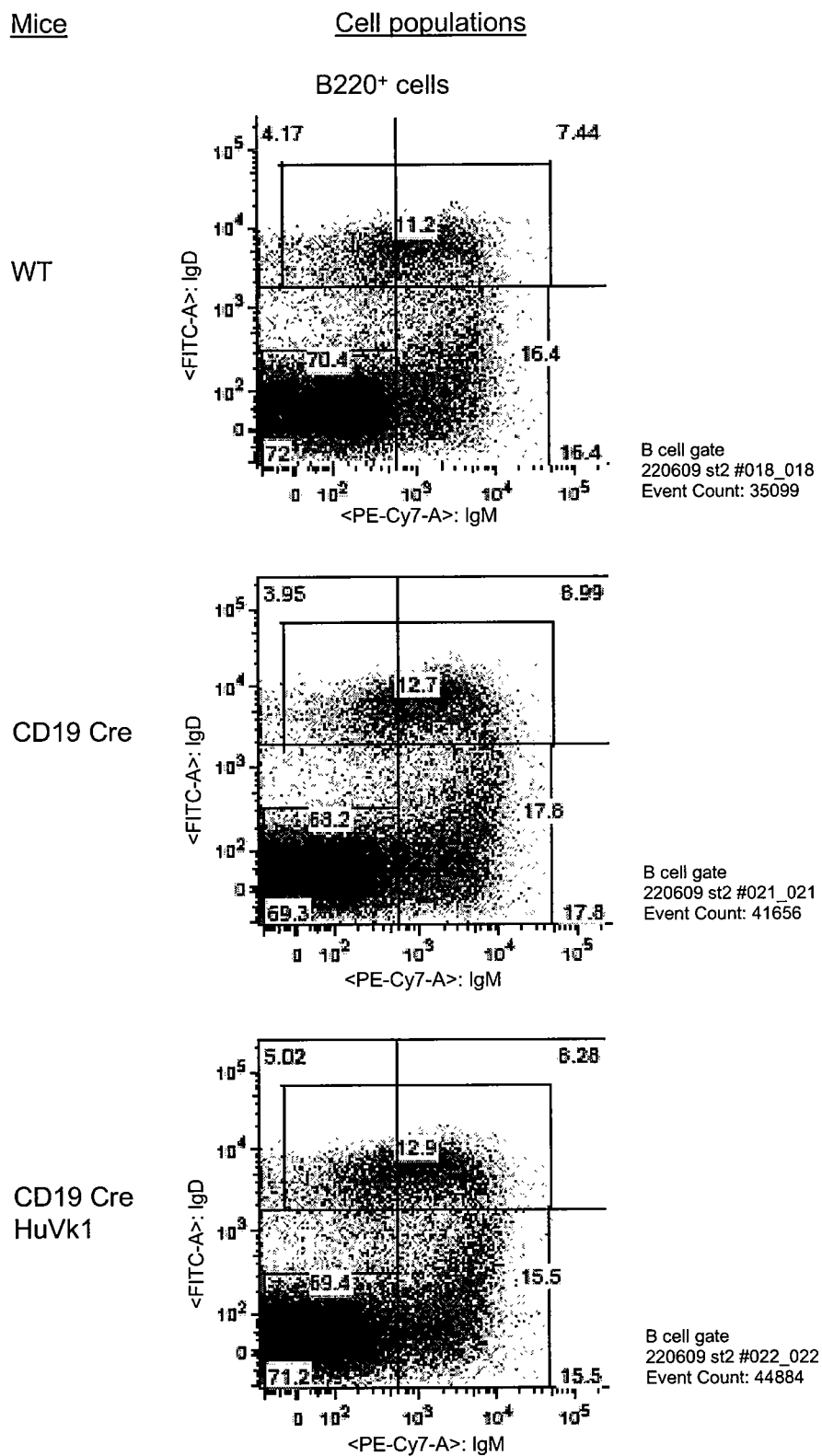
Fig. 26A, contd.

| Mice | Cell populations |
|---|---|
| | Recirculating B cells |
| WT | 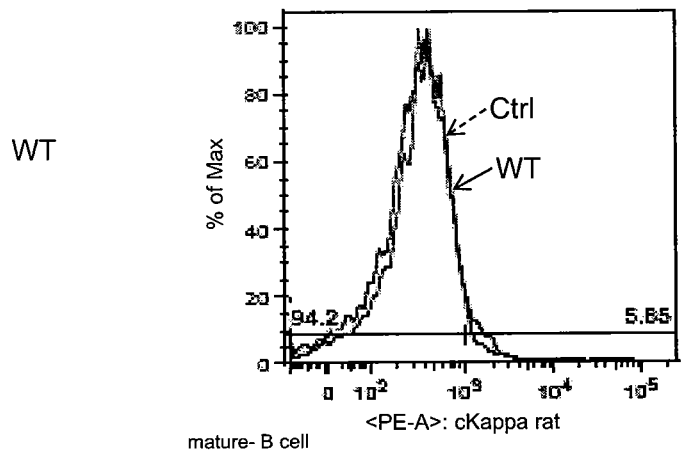 mature- B cell |
| CD19 Cre | 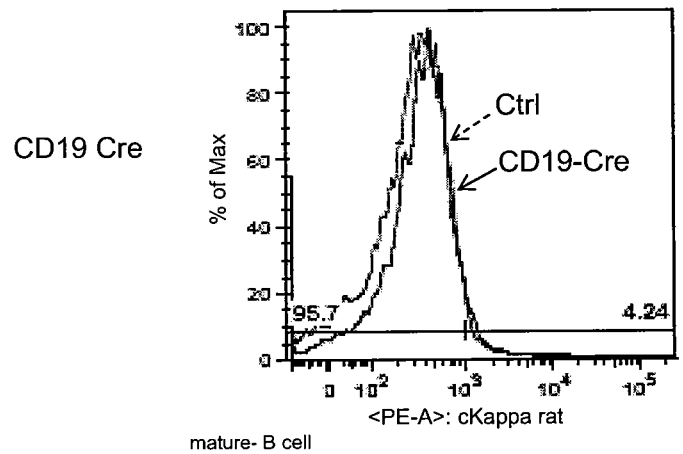 mature- B cell |
| CD19 Cre HuVk1 | 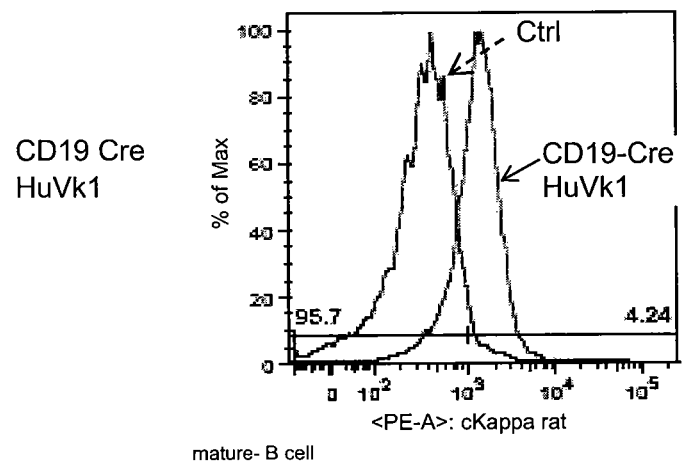 mature- B cell |
Fig. 26B, contd.

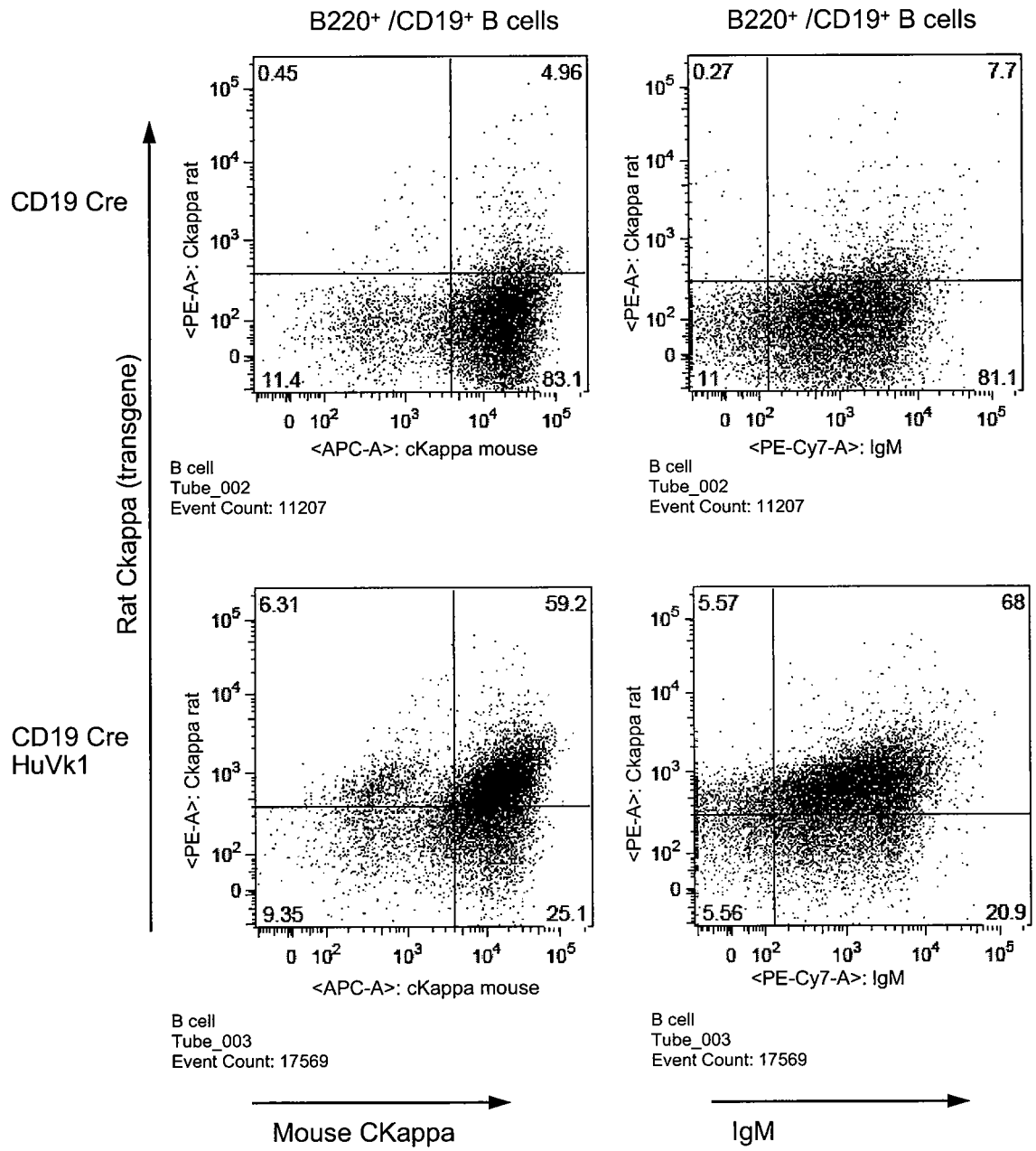
Fig. 27, contd.

FIG. 28

|  | Stainings | | | | Mixtures | | | | |
|---|---|---|---|---|---|---|---|---|---|
|  | # | Facs tubes # | Monoclonal | Work dilution | volume | 1st step | 2nd step | 3rd step | Final dilution |
| A | | | | | | | | | |
| Spleen | 1 | 1-8 | CD21$^{FITC}$ | 640 | 320 | | 0.50 | | |
|  | | | Ckappa rat$^{PE}$ | 160 | | 2.00 | | | |
|  | | | CD19$^{PerCP-Cy5.5}$ | 640 | | | 0.50 | | |
|  | | | CD23$^{PE-Cy7}$ | 50 | 1:20 | | 6.40 | | 1000 |
|  | | | DAPI | | | | | | |
|  | | | Ckappa mouse$^{BIO-APC}$ | 100 | 1:50 | | | 3.20 APC | 5000 |
|  | | | Clambda mouse$^{BIO-APC}$ | 100 | 1:30 | | | 3.20 APC | 3000 |
|  | | | B220$^{Alex-700}$ | 160 | | | 2.00 | | |
|  | | | FC block | 400 | | | 0.80 | | |
| Spleen | 2 | 9-16 | IgD$^{FITC}$ | 640 | 640 | | 1.00 | | |
| BM | | 17-24 | Ckappa rat$^{PE}$ | 160 | | 4.00 | | | |
|  | | | CD19$^{PerCP-Cy5.5}$ | 500 | | | 1.28 | | |
|  | | | IgM$^{PE-Cy7}$ | 640 | | | 1.00 | | |
|  | | | DAPI | | | | | | |
|  | | | Ckappa mouse$^{BIO-APC}$ | 100 | 1:50 | | | 6.40 APC | 5000 |
|  | | | Clambda mouse$^{BIO-APC}$ | 100 | 1:30 | | | 6.40 APC | 3000 |
|  | | | B220$^{Alex-700}$ | 160 | | | 4.00 | | |
|  | | | FC block | 400 | | | 1.60 | | |
| Spleen | 3 | 25-32 | Ckappa mouse$^{FITC}$ | 400 | 320 | | 0.80 | | |
|  | | | Ckappa rat$^{PE}$ | 160 | | 2.00 | | | |
|  | | | CD19$^{PerCP-Cy5.5}$ | 500 | | | 0.64 | | |
|  | | | IgM$^{PE-Cy7}$ | 640 | | | 0.50 | | |
|  | | | DAPI | | | | | | |
|  | | | Clambda mouse$^{BIO-APC}$ | 100 | 1:30 | | | 3.20 APC | 3000 |
|  | | | B220$^{Alex-700}$ | 160 | | | 2.00 | | |
|  | | | FC block | 400 | | | 0.80 | | |
| Spleen | 4 | 33-40 | Ckappa mouse$^{FITC}$ | 400 | 640 | | 1.60 | | |
|  | | 41-46 | lambda$^{FITC}$ | 600 | | | 1.07 | | |
| PP | | | Ckappa rat$^{PE}$ | 160 | | 4.00 | | | |
|  | | | CD19$^{PerCP-Cy5.5}$ | 500 | | | 1.28 | | |

FIG. 29A

| Tissue | # | Range | Marker | Val1 | Val2 | Val3 | Val4 | Label | Val5 |
|---|---|---|---|---|---|---|---|---|---|
| | | | IgM$^{PE-Cy7}$ | 640 | | | 1.00 | | |
| | | | DAPI | | | | | | |
| | | | IgD$^{A647}$ | 1280 | | | 0.50 | | |
| | | | B220$^{Alex-700}$ | 160 | | | 4.00 | | |
| | | | PNA$^{BIO-SAV-APC-Cy7}$ | 300 | | | 2.13 | APC-Cy7 | |
| | | | FC block | 400 | | | 1.60 | | |
| PC | 5 | 49-56 | IgM$^{FITC}$ | 160 | | 320 | 2.00 | | |
| | | | Ckappa rat$^{PE}$ | 160 | | | 2.00 | | |
| | | | CD19$^{PerCP-Cy5.5}$ | 500 | | | 0.64 | | |
| | | | Ckappa mouse$^{BIO-PE-Cy7}$ | 100 | 1:50 | | 3.20 | PE-Cy7 | 5000 |
| | | | Clambda mouse$^{BIO-PE-Cy7}$ | 100 | 1:30 | | 3.20 | PE-Cy7 | 3000 |
| | | | DAPI | | | | | | |
| | | | CD5$^{APC}$ | 320 | | | 1.00 | | |
| | | | B220$^{Alex-700}$ | 160 | | | 2.00 | | |
| | | | FC block | 400 | | | 0.80 | | |
| BM | 6 | 57-64 | IgM$^{FITC}$ | 160 | | 640 | 4.00 | | |
| | | | Ckappa rat$^{PE}$ | 160 | | | 4.00 | | |
| | | | CD19$^{PerCP-Cy5.5}$ | 500 | | | 1.28 | | |
| | | | Ckappa mouse$^{BIO-PE-Cy7}$ | 100 | 1:50 | | 6.40 | PE-Cy7 | 5000 |
| | | | Clambda mouse$^{BIO-PE-Cy7}$ | 100 | 1:30 | | 6.40 | PE-Cy7 | 3000 |
| | | | DAPI | | | | | | |
| | | | CD25$^{APC}$ | 80 | | | 8.00 | | |
| | | | B220$^{Alex-700}$ | 160 | | | 4.00 | | |
| | | | FC block | 400 | | | 1.60 | | |
| RAT spleen | | | | | | | | | |
| | 7 | 144 | Ckappa rat$^{PE}$ | 160 | | 80 | 0.5 | | |
| | | | rat B220$^{FITC}$ | 160 | | | 0.5 | | |
| Spleen | 8 | 97-104 | cyt CD3$^{FITC}$ | 320 | | 320 | 1 | | |
| | | | cyt Ckappa rat$^{PE}$ | 80 | | | 4.00 | | |
| | | | cyt CD11c$^{PE-TexasRED}$ | 75 | | | 4.27 | | |
| | | | cyt NK1.1$^{BIO-PE-Cy7}$ | 200 | | | 1.6 | PE-Cy7 | |
| | | | cyt CD19$^{PerCP-Cy5.5}$ | 320 | | | 1 | | |
| | | | cyt CD4$^{APC}$ | 500 | | | 0.64 | | |
| | | | cyt CD11b$^{Alex-700}$ | 50 | | | 6.40 | | |

FIG. 29B

SEQUENCE LISTING

<160> NUMBER OF SEQ ID NOS: 102

<210> SEQ ID NO 1
<211> LENGTH: 20
<212> TYPE: DNA

-continued

```
<213> ORGANISM: Artificial Sequence
<220> FEATURE:
<223> OTHER INFORMATION: primer

<400> SEQUENCE: 1
ccctttccaa tctttatggg                                              20

<210> SEQ ID NO 2
<211> LENGTH: 23
<212> TYPE: DNA
<213> ORGANISM: Artificial Sequence
<220> FEATURE:
<223> OTHER INFORMATION: primer

<400> SEQUENCE: 2
aggtggattg gtgtctttt ctc                                           23

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3
gtcatgtcgg cgaccctacg cc                                           22

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
tgccaggggg aagaccgatg                                              20

<210> SEQ ID NO 5
<211> LENGTH: 38
<212> TYPE: DNA
<213> ORGANISM: Artificial Sequence
<220> FEATURE:
<223> OTHER INFORMATION: primer

<400> SEQUENCE: 5
gccggccatg gccgaggtrm agcttcagga gtcaggac                          38

<210> SEQ ID NO 6
<211> LENGTH: 38
<212> TYPE: DNA
<213> ORGANISM: Artificial Sequence
<220> FEATURE:
<223> OTHER INFORMATION: primer

<400> SEQUENCE: 6
gccggccatg gccgaggtsc agctkcagca gtcaggac                          38

<210> SEQ ID NO 7
<211> LENGTH: 36
<212> TYPE: DNA
<213> ORGANISM: Artificial Sequence
<220> FEATURE:
<223> OTHER INFORMATION: primer

<400> SEQUENCE: 7
gccggccatg gcccaggtgc agctgaagsa stcagg                            36
```

<210> SEQ ID NO 8
<211> LENGTH: 38
<212> TYPE: DNA
<213> ORGANISM: Artificial Sequence
<220> FEATURE:
<223> OTHER INFORMATION: primer

<400> SEQUENCE: 8
gccggccatg gccgaggtgc agcttcagga gtcsggac         38

<210> SEQ ID NO 9
<211> LENGTH: 38
<212> TYPE: DNA
<213> ORGANISM: Artificial Sequence
<220> FEATURE:
<223> OTHER INFORMATION: primer

<400> SEQUENCE: 9
gccggccatg gccgargtcc agctgcaaca gtcyggac         38

<210> SEQ ID NO 10
<211> LENGTH: 36
<212> TYPE: DNA
<213> ORGANISM: Artificial Sequence
<220> FEATURE:
<223> OTHER INFORMATION: primer

<400> SEQUENCE: 10
gccggccatg gcccaggtcc agctkcagca atctgg         36

<210> SEQ ID NO 11
<211> LENGTH: 36
<212> TYPE: DNA
<213> ORGANISM: Artificial Sequence
<220> FEATURE:
<223> OTHER INFORMATION: primer

<400> SEQUENCE: 11
gccggccatg gcccagstbc agctgcagca gtctgg         36

<210> SEQ ID NO 12
<211> LENGTH: 38
<212> TYPE: DNA
<213> ORGANISM: Artificial Sequence
<220> FEATURE:
<223> OTHER INFORMATION: primer

<400> SEQUENCE: 12
gccggccatg gcccaggtyc agctgcagca gtctggrc         38

<210> SEQ ID NO 13
<211> LENGTH: 36
<212> TYPE: DNA
<213> ORGANISM: Artificial Sequence
<220> FEATURE:
<223> OTHER INFORMATION: primer

<400> SEQUENCE: 13
gccggccatg gcccaggtyc agctycagca gtctgg         36

<210> SEQ ID NO 14
<211> LENGTH: 39
<212> TYPE: DNA
<213> ORGANISM: Artificial Sequence
<220> FEATURE:

<223> OTHER INFORMATION: primer

<400> SEQUENCE: 14
gccggccatg gccgaggtcc arctgcaaca atctggacc                         39

<210> SEQ ID NO 15
<211> LENGTH: 37
<212> TYPE: DNA
<213> ORGANISM: Artificial Sequence
<220> FEATURE:
<223> OTHER INFORMATION: primer

<400> SEQUENCE: 15
gccggccatg gcccaggtcc acgtgaagca gtctggg                           37

<210> SEQ ID NO 16
<211> LENGTH: 35
<212> TYPE: DNA
<213> ORGANISM: Artificial Sequence
<220> FEATURE:
<223> OTHER INFORMATION: primer

<400> SEQUENCE: 16
gccggccatg gccgaggtga asstggtgga atctg                             35

<210> SEQ ID NO 17
<211> LENGTH: 35
<212> TYPE: DNA
<213> ORGANISM: Artificial Sequence
<220> FEATURE:
<223> OTHER INFORMATION: primer

<400> SEQUENCE: 17
gccggccatg gccgavgtga agytggtgga gtctg                             35

<210> SEQ ID NO 18
<211> LENGTH: 38
<212> TYPE: DNA
<213> ORGANISM: Artificial Sequence
<220> FEATURE:
<223> OTHER INFORMATION: primer

<400> SEQUENCE: 18
gccggccatg gccgaggtgc agskggtgga gtctgggg                          38

<210> SEQ ID NO 19
<211> LENGTH: 37
<212> TYPE: DNA
<213> ORGANISM: Artificial Sequence
<220> FEATURE:
<223> OTHER INFORMATION: primer

<400> SEQUENCE: 19
gccggccatg gccgakgtgc amctggtgga gtctggg                           37

<210> SEQ ID NO 20
<211> LENGTH: 36
<212> TYPE: DNA
<213> ORGANISM: Artificial Sequence
<220> FEATURE:
<223> OTHER INFORMATION: primer

<400> SEQUENCE: 20
gccggccatg gccgaggtga agctgatgga rtctgg                            36

<210> SEQ ID NO 21
<211> LENGTH: 38
<212> TYPE: DNA
<213> ORGANISM: Artificial Sequence
<220> FEATURE:
<223> OTHER INFORMATION: primer

<400> SEQUENCE: 21
gccggccatg gccgaggtgc arcttgttga gtctggtg         38

<210> SEQ ID NO 22
<211> LENGTH: 37
<212> TYPE: DNA
<213> ORGANISM: Artificial Sequence
<220> FEATURE:
<223> OTHER INFORMATION: primer

<400> SEQUENCE: 22
gccggccatg gccgargtra agcttctcga gtctgga         37

<210> SEQ ID NO 23
<211> LENGTH: 36
<212> TYPE: DNA
<213> ORGANISM: Artificial Sequence
<220> FEATURE:
<223> OTHER INFORMATION: primer

<400> SEQUENCE: 23
gccggccatg gccgaagtga arsttgagga gtctgg         36

<210> SEQ ID NO 24
<211> LENGTH: 37
<212> TYPE: DNA
<213> ORGANISM: Artificial Sequence
<220> FEATURE:
<223> OTHER INFORMATION: primer

<400> SEQUENCE: 24
gccggccatg gccgaagtga tgctggtgga gtctggg         37

<210> SEQ ID NO 25
<211> LENGTH: 38
<212> TYPE: DNA
<213> ORGANISM: Artificial Sequence
<220> FEATURE:
<223> OTHER INFORMATION: primer

<400> SEQUENCE: 25
gccggccatg gcccaggtta ctctraaagw gtstggcc         38

<210> SEQ ID NO 26
<211> LENGTH: 36
<212> TYPE: DNA
<213> ORGANISM: Artificial Sequence
<220> FEATURE:
<223> OTHER INFORMATION: primer

<400> SEQUENCE: 26
gccggccatg gcccaggtcc aactvcagca rcctgg         36

<210> SEQ ID NO 27
<211> LENGTH: 35
<212> TYPE: DNA
<213> ORGANISM: Artificial Sequence
<220> FEATURE:
<223> OTHER INFORMATION: primer

<400> SEQUENCE: 27
gccggccatg gcccaggtyc arctgcagca gtctg                                35

<210> SEQ ID NO 28
<211> LENGTH: 36
<212> TYPE: DNA
<213> ORGANISM: Artificial Sequence
<220> FEATURE:
<223> OTHER INFORMATION: primer

<400> SEQUENCE: 28
gccggccatg gccgatgtga acttggaagt gtctgg                               36

<210> SEQ ID NO 29
<211> LENGTH: 36
<212> TYPE: DNA
<213> ORGANISM: Artificial Sequence
<220> FEATURE:
<223> OTHER INFORMATION: primer

<400> SEQUENCE: 29
gccggccatg gccgaggtga aggtcatcga gtctgg                               36

<210> SEQ ID NO 30
<211> LENGTH: 45
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (44)..(44)
<223> OTHER INFORMATION: n is a, c, g, or t

<400> SEQUENCE: 30
cagtcacaga tcctcgcgaa ttggcccagc cggccatggc csang                     45

<210> SEQ ID NO 31
<211> LENGTH: 45
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (44)..(44)
<223> OTHER INFORMATION: n is a, c, g, or t

<400> SEQUENCE: 31
cagtcacaga tcctcgcgaa ttggcccagc cggccatggc csanc                     45

<210> SEQ ID NO 32
<211> LENGTH: 37
<212> TYPE: DNA
<213> ORGANISM: Artificial Sequence
<220> FEATURE:
<223> OTHER INFORMATION: primer

<400> SEQUENCE: 32
gggggtgtcg ttttggctga ggagacggtg accgtgg                              37

<210> SEQ ID NO 33
<211> LENGTH: 37
<212> TYPE: DNA
<213> ORGANISM: Artificial Sequence
<220> FEATURE:
<223> OTHER INFORMATION: primer

```
<400> SEQUENCE: 33
gggggtgtcg ttttggctga ggagactgtg agagtgg                              37

<210> SEQ ID NO 34
<211> LENGTH: 37
<212> TYPE: DNA
<213> ORGANISM: Artificial Sequence
<220> FEATURE:
<223> OTHER INFORMATION: primer

<400> SEQUENCE: 34
gggggtgtcg ttttggctgc agagacagtg accagag                              37

<210> SEQ ID NO 35
<211> LENGTH: 37
<212> TYPE: DNA
<213> ORGANISM: Artificial Sequence
<220> FEATURE:
<223> OTHER INFORMATION: primer

<400> SEQUENCE: 35
gggggtgtcg ttttggctga ggagacggtg actgagg                              37

<210> SEQ ID NO 36
<211> LENGTH: 37
<212> TYPE: DNA
<213> ORGANISM: Artificial Sequence
<220> FEATURE:
<223> OTHER INFORMATION: primer

<400> SEQUENCE: 36
gggggtgtcg ttttggctga ggagacggtg accgtgg                              37

<210> SEQ ID NO 37
<211> LENGTH: 37
<212> TYPE: DNA
<213> ORGANISM: Artificial Sequence
<220> FEATURE:
<223> OTHER INFORMATION: primer

<400> SEQUENCE: 37
gggggtgtcg ttttggctga ggagacggtg acagtgg                              37

<210> SEQ ID NO 38
<211> LENGTH: 37
<212> TYPE: DNA
<213> ORGANISM: Artificial Sequence
<220> FEATURE:
<223> OTHER INFORMATION: primer

<400> SEQUENCE: 38
gggggtgtcg ttttggctga ggagacggtg accagag                              37

<210> SEQ ID NO 39
<211> LENGTH: 37
<212> TYPE: DNA
<213> ORGANISM: Artificial Sequence
<220> FEATURE:
<223> OTHER INFORMATION: primer

<400> SEQUENCE: 39
gggggtgtcg ttttggctga ggagacggtg accgagg                              37

<210> SEQ ID NO 40
```

```
<211> LENGTH: 15
<212> TYPE: PRT
<213> ORGANISM: Artificial Sequence
<220> FEATURE:
<223> OTHER INFORMATION: CDR3

<400> SEQUENCE: 40

His Gly Ala Tyr Tyr Thr Tyr Asp Glu Lys Ala Trp Phe Ala Tyr
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: CDR3

<400> SEQUENCE: 41

His Gly Ala Phe Tyr Thr Tyr Asp Glu Lys Pro Trp Phe Ala Tyr
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: CDR3

<400> SEQUENCE: 42

His Ile Ser Tyr Tyr Arg Tyr Asp Glu Glu Val Ser Phe Ala Tyr
1               5                   10                  15

<210> SEQ ID NO 43
<211> LENGTH: 7
<212> TYPE: PRT
<213> ORGANISM: Artificial Sequence
<220> FEATURE:
<223> OTHER INFORMATION: CDR3

<400> SEQUENCE: 43

Gly Trp Arg Ala Phe Ala Tyr
1               5

<210> SEQ ID NO 44
<211> LENGTH: 10
<212> TYPE: PRT
<213> ORGANISM: Artificial Sequence
<220> FEATURE:
<223> OTHER INFORMATION: CDR3

<400> SEQUENCE: 44

Asp Arg Gly Asn Tyr Tyr Gly Met Asp Tyr
1               5                   10

<210> SEQ ID NO 45
<211> LENGTH: 12
<212> TYPE: PRT
<213> ORGANISM: Artificial Sequence
<220> FEATURE:
<223> OTHER INFORMATION: CDR3

<400> SEQUENCE: 45

Leu Gly Asp Tyr Tyr Val Asp Trp Phe Phe Ala Val
1               5                   10

<210> SEQ ID NO 46
<211> LENGTH: 8
```

```
<212> TYPE: PRT
<213> ORGANISM: Artificial Sequence
<220> FEATURE:
<223> OTHER INFORMATION: CDR3

<400> SEQUENCE: 46

Asn Phe Pro Ala Trp Phe Ala Phe
1               5

<210> SEQ ID NO 47
<211> LENGTH: 17
<212> TYPE: PRT
<213> ORGANISM: Artificial Sequence
<220> FEATURE:
<223> OTHER INFORMATION: CDR3

<400> SEQUENCE: 47

Ser Phe Thr Pro Val Pro Phe Tyr Tyr Gly Tyr Asp Trp Tyr Phe Asp
1               5                   10                  15

Val

<210> SEQ ID NO 48
<211> LENGTH: 9
<212> TYPE: PRT
<213> ORGANISM: Artificial Sequence
<220> FEATURE:
<223> OTHER INFORMATION: CDR3

<400> SEQUENCE: 48

Ser Asp Tyr Asp Trp Tyr Phe Asp Val
1               5

<210> SEQ ID NO 49
<211> LENGTH: 10
<212> TYPE: PRT
<213> ORGANISM: Artificial Sequence
<220> FEATURE:
<223> OTHER INFORMATION: CDR3

<400> SEQUENCE: 49

Asp Ser Lys Trp Ala Tyr Tyr Phe Asp Tyr
1               5                   10

<210> SEQ ID NO 50
<211> LENGTH: 10
<212> TYPE: PRT
<213> ORGANISM: Artificial Sequence
<220> FEATURE:
<223> OTHER INFORMATION: CDR3

<400> SEQUENCE: 50

Gly Asp Tyr Thr Gly Tyr Gly Met Asp Tyr
1               5                   10

<210> SEQ ID NO 51
<211> LENGTH: 10
<212> TYPE: PRT
<213> ORGANISM: Artificial Sequence
<220> FEATURE:
<223> OTHER INFORMATION: CDR3

<400> SEQUENCE: 51

Gly Gly Tyr Asp Gly Tyr Trp Phe Pro Tyr
1               5                   10

<210> SEQ ID NO 52
```

```
<211> LENGTH: 15
<212> TYPE: PRT
<213> ORGANISM: Artificial Sequence
<220> FEATURE:
<223> OTHER INFORMATION: epitope IGKV1-39

<400> SEQUENCE: 52

Asp Ile Gln Met Thr Gln Ser Pro Ser Ser Leu Ser Ala Ser Val
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: epitope IGKV1-39

<400> SEQUENCE: 53

Met Thr Gln Ser Pro Ser Ser Leu Ser Ala Ser Val Gly Asp Arg
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: epitope IGKV1-39

<400> SEQUENCE: 54

Ser Pro Ser Ser Leu Ser Ala Ser Val Gly Asp Arg Val Thr Ile
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: epitope IGKV1-39

<400> SEQUENCE: 55

Ser Leu Ser Ala Ser Val Gly Asp Arg Val Thr Ile Thr Cys Arg
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 56

Ala Ser Val Gly Asp Arg Val Thr Ile Thr Cys Arg Ala Ser Gln
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 57

Gly Asp Arg Val Thr Ile Thr Cys Arg Ala Ser Gln Ser Ile Ser
1               5                   10                  15

<210> SEQ ID NO 58
<211> LENGTH: 15
```

```
<212> TYPE: PRT
<213> ORGANISM: Artificial Sequence
<220> FEATURE:
<223> OTHER INFORMATION: Epitope IGKV1-39

<400> SEQUENCE: 58

Val Thr Ile Thr Cys Arg Ala Ser Gln Ser Ile Ser Ser Tyr Leu
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 59

Thr Cys Arg Ala Ser Gln Ser Ile Ser Ser Tyr Leu Asn Trp Tyr
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 60

Ala Ser Gln Ser Ile Ser Ser Tyr Leu Asn Trp Tyr Gln Gln Lys
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 61

Ser Ile Ser Ser Tyr Leu Asn Trp Tyr Gln Gln Lys Pro Gly Lys
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 62

Ser Tyr Leu Asn Trp Tyr Gln Gln Lys Pro Gly Lys Ala Pro Lys
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 63

Asn Trp Tyr Gln Gln Lys Pro Gly Lys Ala Pro Lys Leu Leu Ile
1               5                   10                  15

<210> SEQ ID NO 64
<211> LENGTH: 15
<212> TYPE: PRT
```

<213> ORGANISM: Artificial Sequence
<220> FEATURE:
<223> OTHER INFORMATION: Epitope IGKV1-39

<400> SEQUENCE: 64

```
Gln Gln Lys Pro Gly Lys Ala Pro Lys Leu Leu Ile Tyr Ala Ala
1               5                   10                  15
```

<210> SEQ ID NO 65
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 65

```
Pro Gly Lys Ala Pro Lys Leu Leu Ile Tyr Ala Ala Ser Ser Leu
1               5                   10                  15
```

<210> SEQ ID NO 66
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 66

```
Ala Pro Lys Leu Leu Ile Tyr Ala Ala Ser Ser Leu Gln Ser Gly
1               5                   10                  15
```

<210> SEQ ID NO 67
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 67

```
Leu Leu Ile Tyr Ala Ala Ser Ser Leu Gln Ser Gly Val Pro Ser
1               5                   10                  15
```

<210> SEQ ID NO 68
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 68

```
Tyr Ala Ala Ser Ser Leu Gln Ser Gly Val Pro Ser Arg Phe Ser
1               5                   10                  15
```

<210> SEQ ID NO 69
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 69

```
Ser Ser Leu Gln Ser Gly Val Pro Ser Arg Phe Ser Gly Ser Gly
1               5                   10                  15
```

<210> SEQ ID NO 70
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 70

Gln Ser Gly Val Pro Ser Arg Phe Ser Gly Ser Gly Ser Gly Thr
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 71

Val Pro Ser Arg Phe Ser Gly Ser Gly Ser Gly Thr Asp Phe Thr
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 72

Arg Phe Ser Gly Ser Gly Ser Gly Thr Asp Phe Thr Leu Thr Ile
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 73

Gly Ser Gly Ser Gly Thr Asp Phe Thr Leu Thr Ile Ser Ser Leu
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 74

Ser Gly Thr Asp Phe Thr Leu Thr Ile Ser Ser Leu Gln Pro Glu
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 75

Asp Phe Thr Leu Thr Ile Ser Ser Leu Gln Pro Glu Asp Phe Ala
1               5                   10                  15

<210> SEQ ID NO 76
<211> LENGTH: 15
<212> TYPE: PRT
<213> ORGANISM: Artificial Sequence
<220> FEATURE:

```
<223> OTHER INFORMATION: Epitope IGKV1-39

<400> SEQUENCE: 76

Leu Thr Ile Ser Ser Leu Gln Pro Glu Asp Phe Ala Thr Tyr Tyr
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 77

Ser Ser Leu Gln Pro Glu Asp Phe Ala Thr Tyr Tyr Cys Gln Gln
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 78

Gln Pro Glu Asp Phe Ala Thr Tyr Tyr Cys Gln Gln Ser Tyr Ser
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 79

Asp Phe Ala Thr Tyr Tyr Cys Gln Gln Ser Tyr Ser Thr Pro Pro
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 80

Thr Tyr Tyr Cys Gln Gln Ser Tyr Ser Thr Pro Pro Thr Phe Gly
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 81

Cys Gln Gln Ser Tyr Ser Thr Pro Pro Thr Phe Gly Gln Gly Thr
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Epitope IGKV1-39
```

-continued

```
<400> SEQUENCE: 82

Ser Tyr Ser Thr Pro Pro Thr Phe Gly Gln Gly Thr Lys Val Glu
1               5                   10                  15

<210> SEQ ID NO 83
<211> LENGTH: 14
<212> TYPE: PRT
<213> ORGANISM: Artificial Sequence
<220> FEATURE:
<223> OTHER INFORMATION: Epitope IGKV1-39

<400> SEQUENCE: 83

Thr Pro Pro Thr Phe Gly Gln Gly Thr Lys Val Glu Ile Lys
1               5                   10

<210> SEQ ID NO 84
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 84 gac atc cag atg acc cag agc ccc agc agc ctg agc gcc agc gtg ggc      48
Asp Ile Gln Met Thr Gln Ser Pro Ser Ser Leu Ser Ala Ser Val Gly
1               5                   10                  15 gac aga gtg acc atc acc tgc aga gcc agc cag agc atc agc agc tac      96
Asp Arg Val Thr Ile Thr Cys Arg Ala Ser Gln Ser Ile Ser Ser Tyr
            20                  25                  30 ctg aac tgg tat cag cag aag ccc ggc aag gcc ccc aag ctg ctg atc     144
Leu Asn Trp Tyr Gln Gln Lys Pro Gly Lys Ala Pro Lys Leu Leu Ile
        35                  40                  45 tac gcc gcc agc tcc ctg cag agc ggc gtg ccc agc aga ttc agc ggc     192
Tyr Ala Ala Ser Ser Leu Gln Ser Gly Val Pro Ser Arg Phe Ser Gly
    50                  55                  60 agc ggc tcc ggc acc gac ttc acc ctg acc atc agc agc ctg cag ccc     240
Ser Gly Ser Gly Thr Asp Phe Thr Leu Thr Ile Ser Ser Leu Gln Pro
65                  70                  75                  80 gag gac ttc gcc acc tac tac tgc cag cag agc tac agc acc ccc ccc     288
Glu Asp Phe Ala Thr Tyr Tyr Cys Gln Gln Ser Tyr Ser Thr Pro Pro
                85                  90                  95 acc ttc ggc cag ggc acc aag gtg gag atc aag                         321
Thr Phe Gly Gln Gly Thr Lys Val Glu Ile Lys
            100                 105

<210> SEQ ID NO 85
<211> LENGTH: 107
<212> TYPE: PRT
<213> ORGANISM: Homo sapiens

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
```

|   |   |   |   | 65 |   |   |   |   | 70 |   |   |   |   | 75 |   |   |   |   | 80 |
|---|---|---|---|---|---|---|---|---|---|---|---|---|---|---|---|---|---|---|---|

Glu Asp Phe Ala Thr Tyr Tyr Cys Gln Gln Ser Tyr Ser Thr Pro Pro
        85        90        95

Thr Phe Gly Gln Gly Thr Lys Val Glu Ile Lys
       100        105

```
<210> SEQ ID NO 86
<211> LENGTH: 330
<212> TYPE: DNA
<213> ORGANISM: Homo sapiens
<220> FEATURE:
<221> NAME/KEY: CDS
<222> LOCATION: (1)..(330)

<400> SEQUENCE: 86
```

| cag | tct | gcc | ctg | acc | cag | ccc | gcc | tct | gtg | tct | ggc | agc | cct | ggc | cag | 48 |
|---|---|---|---|---|---|---|---|---|---|---|---|---|---|---|---|---|
| Gln | Ser | Ala | Leu | Thr | Gln | Pro | Ala | Ser | Val | Ser | Gly | Ser | Pro | Gly | Gln | |
| 1 | | | | 5 | | | | | 10 | | | | | 15 | | |

| agc | atc | acc | atc | agc | tgc | acc | ggc | acc | agc | agc | gac | gtg | ggc | ggc | tac | 96 |
|---|---|---|---|---|---|---|---|---|---|---|---|---|---|---|---|---|
| Ser | Ile | Thr | Ile | Ser | Cys | Thr | Gly | Thr | Ser | Ser | Asp | Val | Gly | Gly | Tyr | |
| | | | 20 | | | | | 25 | | | | | 30 | | | |

| aac | tac | gtg | tcc | tgg | tat | cag | cag | cac | ccc | ggc | aag | gcc | ccc | aag | ctg | 144 |
|---|---|---|---|---|---|---|---|---|---|---|---|---|---|---|---|---|
| Asn | Tyr | Val | Ser | Trp | Tyr | Gln | Gln | His | Pro | Gly | Lys | Ala | Pro | Lys | Leu | |
| | | 35 | | | | | 40 | | | | | 45 | | | | |

| atg | atc | tac | gag | gtg | tcc | aac | aga | ccc | agc | ggc | gtg | agc | aac | aga | ttc | 192 |
|---|---|---|---|---|---|---|---|---|---|---|---|---|---|---|---|---|
| Met | Ile | Tyr | Glu | Val | Ser | Asn | Arg | Pro | Ser | Gly | Val | Ser | Asn | Arg | Phe | |
| 50 | | | | | 55 | | | | | 60 | | | | | | |

| agc | ggc | agc | aag | agc | ggc | aac | acc | gcc | agc | ctg | acc | atc | agc | ggc | ctc | 240 |
|---|---|---|---|---|---|---|---|---|---|---|---|---|---|---|---|---|
| Ser | Gly | Ser | Lys | Ser | Gly | Asn | Thr | Ala | Ser | Leu | Thr | Ile | Ser | Gly | Leu | |
| 65 | | | | | 70 | | | | | 75 | | | | | 80 | |

| cag | gct | gag | gac | gag | gcc | gac | tac | tac | tgc | agc | agc | tac | acc | agc | agc | 288 |
|---|---|---|---|---|---|---|---|---|---|---|---|---|---|---|---|---|
| Gln | Ala | Glu | Asp | Glu | Ala | Asp | Tyr | Tyr | Cys | Ser | Ser | Tyr | Thr | Ser | Ser | |
| | | | | 85 | | | | | 90 | | | | | 95 | | |

| tcc | acc | ctg | gtg | ttt | ggc | ggc | gga | aca | aag | ctg | acc | gtg | ctg | | | 330 |
|---|---|---|---|---|---|---|---|---|---|---|---|---|---|---|---|---|
| Ser | Thr | Leu | Val | Phe | Gly | Gly | Gly | Thr | Lys | Leu | Thr | Val | Leu | | | |
| | | | 100 | | | | | 105 | | | | | 110 | | | |

```
<210> SEQ ID NO 87
<211> LENGTH: 110
<212> TYPE: PRT
<213> ORGANISM: Homo sapiens

<400> SEQUENCE: 87
```

Gln Ser Ala Leu Thr Gln Pro Ala Ser Val Ser Gly Ser Pro Gly Gln
1        5        10        15

Ser Ile Thr Ile Ser Cys Thr Gly Thr Ser Ser Asp Val Gly Gly Tyr
     20        25        30

Asn Tyr Val Ser Trp Tyr Gln Gln His Pro Gly Lys Ala Pro Lys Leu
    35        40        45

Met Ile Tyr Glu Val Ser Asn Arg Pro Ser Gly Val Ser Asn Arg Phe
50        55        60

Ser Gly Ser Lys Ser Gly Asn Thr Ala Ser Leu Thr Ile Ser Gly Leu
65        70        75        80

Gln Ala Glu Asp Glu Ala Asp Tyr Tyr Cys Ser Ser Tyr Thr Ser Ser
       85        90        95

Ser Thr Leu Val Phe Gly Gly Gly Thr Lys Leu Thr Val Leu
      100        105        110

```
<210> SEQ ID NO 88
<211> LENGTH: 321
```

```
<212> TYPE: DNA
<213> ORGANISM: Rattus norvegicus
<220> FEATURE:
<221> NAME/KEY: CDS
<222> LOCATION: (1)..(321)

<400> SEQUENCE: 88 aga gcc gac gcc gct ccc acc gtg tcc atc ttc ccc ccc agc atg gaa      48
Arg Ala Asp Ala Ala Pro Thr Val Ser Ile Phe Pro Pro Ser Met Glu
1               5                   10                  15 cag ctg acc tct ggc gga gcc acc gtg gtc tgc ttc gtg aac aac ttc      96
Gln Leu Thr Ser Gly Gly Ala Thr Val Val Cys Phe Val Asn Asn Phe
            20                  25                  30 tac ccc aga gac atc agc gtg aag tgg aag atc gac ggc agc gag cag     144
Tyr Pro Arg Asp Ile Ser Val Lys Trp Lys Ile Asp Gly Ser Glu Gln
        35                  40                  45 agg gac ggc gtg ctg gac agc gtg acc gac cag gac agc aag gac tcc     192
Arg Asp Gly Val Leu Asp Ser Val Thr Asp Gln Asp Ser Lys Asp Ser
    50                  55                  60 acc tac agc atg agc agc acc ctg agc ctg acc aag gtg gag tac gag     240
Thr Tyr Ser Met Ser Ser Thr Leu Ser Leu Thr Lys Val Glu Tyr Glu
65                  70                  75                  80 agg cac aac ctg tac acc tgc gag gtg gtg cac aag acc agc tcc agc     288
Arg His Asn Leu Tyr Thr Cys Glu Val Val His Lys Thr Ser Ser Ser
                85                  90                  95 ccc gtg gtc aag tcc ttc aac cgg aac gag tgt                         321
Pro Val Val Lys Ser Phe Asn Arg Asn Glu Cys
            100                 105

<210> SEQ ID NO 89
<211> LENGTH: 107
<212> TYPE: PRT
<213> ORGANISM: Rattus norvegicus

<400> SEQUENCE: 89

Arg Ala Asp Ala Ala Pro Thr Val Ser Ile Phe Pro Pro Ser Met Glu
1               5                   10                  15

Gln Leu Thr Ser Gly Gly Ala Thr Val Val Cys Phe Val Asn Asn Phe
            20                  25                  30

Tyr Pro Arg Asp Ile Ser Val Lys Trp Lys Ile Asp Gly Ser Glu Gln
        35                  40                  45

Arg Asp Gly Val Leu Asp Ser Val Thr Asp Gln Asp Ser Lys Asp Ser
    50                  55                  60

Thr Tyr Ser Met Ser Ser Thr Leu Ser Leu Thr Lys Val Glu Tyr Glu
65                  70                  75                  80

Arg His Asn Leu Tyr Thr Cys Glu Val Val His Lys Thr Ser Ser Ser
                85                  90                  95

Pro Val Val Lys Ser Phe Asn Arg Asn Glu Cys
            100                 105

<210> SEQ ID NO 90
<211> LENGTH: 865
<212> TYPE: DNA
<213> ORGANISM: Artificial Sequence
<220> FEATURE:
<223> OTHER INFORMATION: IGKV1-39/J-Ck

<400> SEQUENCE: 90
ggtaccgcgg ccgccaccat ggacatgaga gtgcccgccc agctcctggg gctcctgcta      60
ctctggctcc gaggtaagga tgagaacac taggaattta ctcagccagt gtgctcagta     120
```

```
ctgactggaa cttcagggaa gttctctgat aacatgatta atagtaagaa tatttgtttt    180
tatgtttcca atctcaggtg ccagatgtga catccagatg acccagagcc ccagcagcct    240
gagcgccagc gtgggcgaca gagtgaccat cacctgcaga gccagccaga gcatcagcag    300
ctacctgaac tggtatcagc agaagcccgg caaggccccc aagctgctga tctacgccgc    360
cagctccctg cagagcggcg tgcccagcag attcagcggc agcggctccg gcaccgactt    420
caccctgacc atcagcagcc tgcagcccga ggacttcgcc acctactact gccagcagag    480
ctacagcacc ccccccacct tcggccaggg caccaaggtg gagatcaaga gagccgacgc    540
cgctcccacc gtgtccatct ccccccagat catggaacag ctgacctctg gcggagccac    600
cgtggtctgc ttcgtgaaca acttctaccc cagagacatc agcgtgaagt ggaagatcga    660
cggcagcgag cagagggacg gcgtgctgga cagcgtgacc gaccaggaca gcaaggactc    720
cacctacagc atgagcagca ccctgagcct gaccaaggtg gagtacgaga ggcacaacct    780
gtacacctgc gaggtggtgc acaagaccag ctccagcccc gtggtcaagt ccttcaaccg    840
gaacgagtgt tgagctagcg agctc                                         865

<210> SEQ ID NO 91
<211> LENGTH: 874
<212> TYPE: DNA
<213> ORGANISM: Artificial Sequence
<220> FEATURE:
<223> OTHER INFORMATION: IGLV2-14/J-Ck

<400> SEQUENCE: 91
ggtaccgcgg ccgccaccat ggacatgaga gtgcccgccc agctcctggg gctcctgcta     60
ctctggctcc gaggtaagga tggagaacac taggaattta ctcagccagt gtgctcagta    120
ctgactggaa cttcagggaa gttctctgat aacatgatta atagtaagaa tatttgtttt    180
tatgtttcca atctcaggtg ccagatgtca gtctgccctg acccagcccg cctctgtgtc    240
tggcagccct ggccagagca tcaccatcag ctgcaccggc accagcagcg acgtgggcgg    300
ctacaactac gtgtcctggt atcagcagca ccccggcaag gcccccaagc tgatgatcta    360
cgaggtgtcc aacagaccca gcggcgtgag caacagattc agcggcagca agagcggcaa    420
caccgccagc ctgaccatca gcggcctcca ggctgaggac gaggccgact actactgcag    480
cagctacacc agcagctcca cctggtgtt tggcggcgga acaaagctga ccgtgctgag    540
agccgacgcc gctcccaccg tgtccatctt ccccccagc atggaacagc tgacctctgg    600
cggagccacc gtggtctgct tcgtgaacaa cttctacccc agagacatca gcgtgaagtg    660
gaagatcgac ggcagcgagc agagggacgg cgtgctggac agcgtgaccg accaggacag    720
caaggactcc acctacagca tgagcagcac cctgagcctg accaaggtgg agtacgagag    780
gcacaacctg tacacctgcg aggtggtgca caagaccagc tccagccccg tggtcaagtc    840
cttcaaccgg aacgagtgtt gagctagcga gctc                               874

<210> SEQ ID NO 92
<211> LENGTH: 13373
<212> TYPE: DNA
<213> ORGANISM: Artificial Sequence
<220> FEATURE:
<223> OTHER INFORMATION: VkP-IGKV1-39/J-Ck

<400> SEQUENCE: 92
ggccggccca catgaaacaa tgggaaccat gtgacaatca cagaggtgtt gttactatag     60
caaaagggat tgttactctc cacatccctt taagtaactt gaaggcctga tagacccacc    120
```

```
ctctaagact tcattagaca ttccctacga atggttatac tctcctgtat actcccaata      180
caactctaaa atatattatt ccatatagtc cttaggtttg tattaaagtt tgactttttt      240
ccttcaaaat atctcttgtc acaacagcgg ctctagagag aaatacattc cctccaggca      300
aatctatgct gcgctggtct gacctgggac cctggggaca ttgcccctgt gctgagttac      360
taagatgagc cagccctgca gctgtgctca gcctgcccca tgccctgctg attgatttgc      420
atgttccaga gcacagcccc ctgccctgaa gacttttta tgggctggtc gcaccctgtg       480
caggagtcag tctcagtcag gagccaccat ggacatgaga gtgcccgccc agctcctggg      540
gctcctgcta ctctggctcc gaggtaagga tggagaacac taggaattta ctcagccagt      600
gtgctcagta ctgactggaa cttcagggaa gttctctgat aacatgatta atagtaagaa      660
tatttgtttt tatgtttcca atctcaggtg ccagatgtga catccagatg acccagagcc      720
ccagcagcct gagcgccagc gtgggcgaca gagtgaccat cacctgcaga gccagccaga      780
gcatcagcag ctacctgaac tggtatcagc agaagcccgg caaggccccc aagctgctga      840
tctacgccgc cagctccctg cagagcggcg tgcccagcag attcagcggc agcggctccg      900
gcaccgactt caccctgacc atcagcagcc tgcagcccga ggacttcgcc acctactact      960
gccagcagag ctacagcacc ccccccacct tcggccaggg caccaaggtg gagatcaaac     1020
gtaagtacac ttttctcatc tttttttatg tgtaagacac aggttttcat gttaggagtt     1080
aaagtcagtt cagaaaatct tgagaaaatg gagagggctc attatcagtt gacgtggcat     1140
acagtgtcag attttctgtt tatcaagcta gtgagattag gggcaaaaag aggctttagt     1200
tgagaggaaa gtaattaata ctatggtcac catccaagag attggatcgg agaataagca     1260
tgagtagtta ttgagatctg ggtctgactg caggtagcgt ggtcttctag acgtttaagt     1320
gggagatttg gaggggatga ggaatgaagg aacttcagga tagaaaaggg ctgaagtcaa     1380
gttcagctcc taaaatggat gtgggagcaa actttgaaga taaactgaat gacccagagg     1440
atgaaacagc gcagatcaaa gaggggcctg gagctctgag aagagaagga gactcatccg     1500
tgttgagttt ccacaagtac tgtcttgagt tttgcaataa aagtgggata gcagagttga     1560
gtgagccgta ggctgagttc tctcttttgt ctcctaagtt tttatgacta caaaaatcag     1620
tagtatgtcc tgaaataatc attaagctgt ttgaaagtat gactgcttgc catgtagata     1680
ccatggcttg ctgaataatc agaagaggtg tgactcttat tctaaaattt gtcacaaaat     1740
gtcaaaatga gagactctgt aggaacgagt ccttgacaga cagctcaagg ggttttttc      1800 ctttgtctca tttctacatg aaagtaaatt tgaaatgatc ttttttatta taagagtaga     1860
aatacagttg ggtttgaact atatgtttta atggccacgg ttttgtaaga catttggtcc     1920
tttgttttcc cagttattac tcgattgtaa tttatatcg ccagcaatgg actgaaacgg      1980
tccgcaacct cttctttaca actgggtgac ctcgcggctg tgccagccat ttggcgttca     2040
ccctgccgct aagggccatg tgaaccccg cggtagcatc ccttgctccg cgtggaccac      2100
tttcctgagg cacagtgata ggaacagagc cactaatctg aagagaacag agatgtgaca     2160
gactacacta atgtgagaaa aacaaggaaa gggtgactta ttggagattt cagaaataaa     2220
atgcatttat tattatattc ccttatttta attttctatt agggaattag aaagggcata     2280
aactgcttta tccagtgtta tattaaaagc ttaatgtata taatctttta gaggtaaaat     2340
ctacagccag caaagtcat ggtaaatatt ctttgactga actctcacta aactcctcta      2400
aattatatgt catattaact ggttaaatta atataaattt gtgacatgac cttaactggt     2460
```

```
taggtaggat attttcttc atgcaaaaat atgactaata ataatttagc acaaaaatat    2520
ttcccaatac tttaattctg tgatagaaaa atgtttaact cagctactat aatcccataa    2580
ttttgaaaac tatttattag cttttgtgtt tgacccttcc ctagccaaag gcaactattt    2640 aaggacccctt taaaactctt gaaactactt tagagtcatt aagttattta accactttta    2700
attactttaa aatgatgtca attcccttt aactattaat ttatttaag gggggaaagg      2760 ctgctcataa ttctattgtt tttcttggta aagaactctc agttttcgtt tttactacct    2820
ctgtcaccca agagttggca tctcaacaga ggggactttc cgagaggcca tctggcagtt    2880
gcttaagatc agaagtgaag tctgccagtt cctcccaggc aggtggccca gattacagtt    2940
gacctgttct ggtgtggcta aaaattgtcc catgtggtta caaaccatta gaccagggtc    3000
tgatgaattg ctcagaatat ttctggacac ccaaatacag accctggctt aaggccctgt    3060
ccatacagta ggtttagctt ggctacacca aaggaagcca tacagaggct aatatcagag    3120
tattcttgga agagacagga gaaaatgaaa gccagtttct gctcttacct tatgtgcttg    3180
tgttcagact cccaaacatc aggagtgtca gataaactgg tctgaatctc tgtctgaagc    3240
atggaactga aaagaatgta gtttcaggga agaaaggcaa tagaaggaag cctgagaata    3300
tcttcaaagg gtcagactca atttactttc taaagaagta gctaggaact agggaataac    3360
ttagaaacaa caagattgta tatatgtgca tcctggcccc attgttcctt atctgtaggg    3420
ataagcgtgc ttttttgtgt gtctgtatat aacataactg tttacacata atacactgaa    3480
atggagccct tccttgttac ttcataccat cctctgtgct tccttcctca ggggccgacg    3540
ccgctcccac cgtgtccatc ttccccccca gcatggaaca gctgacctct ggcggagcca    3600
ccgtggtctg cttcgtgaac aacttctacc ccagagacat cagcgtgaag tggaagatcg    3660
acggcagcga gcagagggac ggcgtgctgg acagcgtgac cgaccaggac agcaaggact    3720
ccacctacag catgagcagc accctgagcc tgaccaaggt ggagtacgag aggcacaacc    3780
tgtacacctg cgaggtggtg cacaagacca gctccagccc cgtggtcaag tccttcaacc    3840
ggaacgagtg ttgaagacaa aggtcctgag acgccaccac cagctcccca gctccatcct    3900
atcttccctt ctaaggtctt ggaggcttcc ccacaagcga cctaccactg ttgcggtgct    3960
ccaaacctcc tccccacctc cttctcctcc tcctcccttt ccttggcttt tatcatgcta    4020
atatttgcag aaaatattca ataaagtgag tcttgcact tgagatctct gtctttctta     4080
ctaaatggta gtaatcagtt gttttccag ttacctgggt ttctcttcta aagaagttaa     4140
atgtttagtt gccctgaaat ccaccacact taaaggataa ataaaaccct ccacttgccc    4200
tggttggctg tccactacat ggcagtcctt tctaaggttc acgagtacta ttcatggctt    4260 attctctgg gccatggtag gtttgaggag gcatacttcc tagttttctt ccctaagtc     4320 gtcaaagtcc tgaagggga cagtctttac aagcacatgt tctgtaatct gattcaacct    4380
acccagtaaa cttggcgaag caaagtagaa tcattatcac aggaagcaaa ggcaacctaa    4440
atgtgcaagc aataggaaaa tgtggaagcc catcatagta cttggacttc atctgctttt    4500
gtgccttcac taagttttta aacatgagct ggctcctatc tgccattggc aaggctgggc    4560
actacccaca acctacttca aggacctcta taccgtgaga ttacacacat acatcaaaat    4620
ttgggaaaag ttctaccaag ctgagagctg atcacccccac tcttaggtgc ttatctctgt    4680
acaccagaaa ccttaagaag caaccagtat tgagagactc atttatgaaa gtctaaaact    4740
ggatacaacc aaaatgtcca ccaacagtta aattatgaca tgttcacaat tgagctatta    4800
cttaataagg agaattaata aaataaaact taagagcata gtttaatctc ataaacaaga    4860
```

```
taataagcaa acaaaaacat tttttcatcc atgtaagttt aaaagcaggt aaaatttaaa      4920
attaagagag acataagttt tgaggtagca agatggaaac tctggggctt ggggaatgtt      4980
ctgtctctct gtatgggatg tgaaagttac tattgtggaa ttgggatcta tgttcttcct      5040
gtatatattg tatacttcat aataacttca cctaaagaaa tatctaatac ccagtgcata      5100
cataaaagag gatacaagga atgaatcata cgtcaaggcc agaaagacaa taaagtaggg      5160
gatccaggat caaatctccc acaaccttga gccttctact attctgcctt ccagagctca      5220
aagtacaaaa cacataattc aaacacatga tccctccttg gggtctcttc cttcatgcat      5280
cgaattagaa atagccatgt ataaaatgag atagaagaga ccttcatcaa caggtcaaag      5340
aatataggta attttgtctg ggtatgaaga gcccacgtat caaaggttac attagggaag      5400
gaagaggaca ctaacagtga ctttcattct cccctcttc ctggaggccc ctgcatttag       5460
tccctcgtgg gctcatccac tcagcacaca tttactaagc atcttctcag cctacactct      5520
gaaggcagtg cagaataatg ttagtgtccc ttcccccagt taatatgcag tccagtttcc      5580
ctgctccttc cctttctcag tccacataag gatgatggga aaggacagtc accaaatagg      5640
agagggcaac cctttgcctt cctacctctt gagaatgtac attattatcc acttttttgaa     5700 acttctttta attgcttttt tttaatttgt cttttcaaat agcataacct tgttcatcca      5760
tttctgggaa ccaaatttat caatcaacag tgcctctaat ctggctatta atacaaaaat      5820
gcctcctcaa aatatatatg ttcgagtctt atctaaaaca gaacccacaa taaaaaagaa      5880
gaaagaatac atataagcat ttatataatt ctgagcaacc ttgtgctttg tgaaaaaaat      5940
ataatctaat gtcacatgct gtattctttt tatttaacac tggtgaaatt ataccattag      6000
agagaaagag gacagatcac tgatcctagg atctagggat gttacagata agaaaacaaa      6060
tgtgacaaag agctgtcaca aggaggatct tcaaggtcac agaatcactg tcttgatttc      6120
agtggtggtt acatacattt aaatatgtga taaaatgttg ttgaactata ttcatatatt      6180
gtaccaatgt caaatgctta attttggctc tatagtataa ttatgcacta ataactatt      6240 tggacaaaga aaatgatgtt tacatcaaag gtgaggccat atttgttagg aacataactt      6300
aaaaaccatt ttggataact aatgaaaagc cattttgtgt gccttggcat atcatgccta      6360
agctgtcacc agatagatct aataagacct aagcctcaga agcaagcccc tgcccagcaa      6420
gcaggcagca cagataagag ctaaacccag gacaggccat gatatgctaa tgaactacct      6480
tcaaggtggt gttgctgacc tagtgaacca gccccaagct gtgagcccca atagcacaaa      6540
gctactgccc aaagaaatta tacaaaaatt ggaactttgg gaatggtgtg caggatcgct      6600
ctgctgtatg cctggaacac agcttctcta tgttttgtat tgataccagt ctagaagctt      6660
ccaaaacttt ctcactgaag aagattcccc atgtgggacc cctacagact cttttgccca      6720
aacaactgct tccctcctgg tgtgatatct gttttgcttt tatgttagca taatattata      6780
aggaatgttt gtgtgaataa accaaacata ttttaaaagc aaatattgta tgcacatcct      6840
aattgctaaa aagtttacag ctaatagtcc catgctctcc acaatactgg atccaaataa      6900
gtcctaattt caatgttggg catctttaca gagagaaaga cattaaaaat gaagagacat      6960
gcagagagtg caccatgcca tcgtggagac agactgaagt gacacaactg ttagtcaaag      7020
aggattaagg acttccagaa gccaccaaag gaaggaggta tgaagtggtt tctccctcag      7080
agtatccaga ggagactaaa ccaaccaaca ccttttttgct taagacttct tgccttcagg      7140
actgtgagaa ggtagcttcc tattgttcta agccccagta tgtggcattt tgttaaggta      7200
```

```
gagtcaagaa accaataaaa tgcagacaga caaaaggata gctgagtttt ccaggccctt   7260
ccttcttatt tttggttttg ttggtggtgg tggtggtggt ggtgatggtg gtggttttgt   7320
ttatgttttg tttggggagt ttttgggt tttttgggt tttgttttg ttgttgtttt       7380
ggggtttttt gttgttgttg ttgtttgctt ttttgttttt tgtttttgt ttttttgaga    7440
cagtgtttct ctgtatagcc ctggctgtcc tggagttcct tctatctcta atgtctacat   7500
ctcagagggg atcctctaat ttcaaatgag cagtagctct ccatttttag ctcttattta   7560
ttcatttatt tacttactta cttattgtct gtagatgaaa gaattttgga gtgggaaagg   7620
gttcatgagc ccccagcaac taatgaggag ctacagacaa ttgatgtttc tggggaaagg   7680
agactcagtt tctttgagag tatagcttct gatgggtcaa ccatgttcct gtggctgatg   7740
tcacacccag gagtatgcag acaacagaaa ctggagttaa tgagttgttt taaaaataaa   7800
aaagggcatg aagcttggga tagaaattaa ggataaatac aattaaatac aggaaattct   7860
gaaagaatta ataaaaacat ttcttttttt aaaaaaaaat ccagaattag ctatgcttct   7920
tcaaaattgc ttctggagaa ctttacaagt taaataagtt atattgtaga aaaggtagag   7980
aggagaatag tggaagagag agataaggag acttcaaaag gagtggaggg agatagagga   8040
ggagaaagca gaagcaatgg ctgatagaca caggataaga gggaacagaa aggagaaaga   8100
ggaagccagg atgggtattt ctttgcctat ctgtgacttg cacatggtct tggcaattat   8160
tgatgagttc aaggcttaat tcttcacttg tgccaactca acagagtctt tctttcttat   8220
aaccaggccc ccagtatgct catgtatgta tcaggtcctc ttatctcctt atagcaatcc   8280
tgtttataac tgggtaactt tgtgaaggga aggaagtgca cactgagatg tgctacaact   8340
ttttaataca aaattttgaa gagtttgtac aatgtatgta taattaataa ttatatattat   8400
gcactttaga ttttgatttc aactcaagat actaattcta tatatatggg ttaaatcaat   8460
atattaataa gtttaatttc acatgcttat ttttattgtg gttttcgaga cagggtttct   8520
ctgtatagcc ctggctgtcc tggaacccac tttgtagacc aggctggcct caaactcaga   8580
aacctacctg cctctgcctc tgcctctgcc tctgcctctg cctctgcctc tgcctctgcc   8640
tctgcctctg cctctgcctc tgcctctgcc tctgcctctg cctctgcctc tgcctctgcc   8700
tctgcctctg cctctgcctc tgcctctgcc tctgcctctg cctctgcctc tgcctctgcc   8760
tctgcctagt gctggaatta aaggtttgcg ccaccacgcc cggtgaaatt tttaaacttt   8820
atatatgtct cattctattt ctatcagata ggactgtgta gactgtgcta aactaataaa   8880
tgtgccctca aaagtaatcg caagttgtat tgttgttgtt ttgctttgct ttgctttgct   8940
ttgctttgct ttgctttgct ttgctttgct ttgctttgct ttgctttgct ttgctttgct   9000
ttgctttgct ttgctttgct ttgctttttt gttttgggtt tttttccggg ggagggaggg   9060
tggagaaaga atcttactat gaagctctga ctgtcctggg aactcactat atagatcagg   9120
cttgattcaa ctcatagaga tctgccttct tctgcctccc aagtgctggg aataaaggca   9180
tacacctcca tgcccagata gtgatcccaa gttttagcaa aagtttctag acttgacatt   9240
aatcgatgga gatagacatg aattacacaa agaactaatg tggagtttac ctgaatcata   9300
ctctatactt tatcagagat taaattaaca tttaataatc cagtgccagg ctagaggcac   9360
cattcaatgg cagtgtttgc catcatgcat aggcttagtc ttcagtgctg aaaggcattg   9420
ggggcaatat tactcattat acagatgaga aactgggaaa gacttgcctc agattctcta   9480
ctgaaaggct gagtttgtgg cttctagaaa atctttact ttcaatatttt ttaatgtata   9540
attttttat ttccactgat tttattttttt attttaaca tttataagaa ataaatgcaa    9600
```

```
taaaccaaat acatggacaa aaaaatacaa gaatcatatg atcacctcaa tggaaggaaa    9660
aaaaaagaaa gaaaaagtct ttgataagat tcaacattca ttcttttttt attagatatt    9720
ttcttcattt acatttcaaa tgctatcccc aaagcccccct ataccttccc ctgccctgct    9780
ccccaaccca cccactcctg ctttctggcc ctggcattcc tctgtactga ggcatatgat    9840
cttcaaaaaa ccaagggcct ctcctctcat tggtggccga ctattaggcc atcttttgct    9900
acatatgcaa ctagagacac agctctgggg gttactggtt agttcatatt gttagtcctc    9960
ctatagagtt gcagacccct ttagctcctt ggatactttc tctagttcct tcattagggg   10020
ccctgtgtcc catccaatag atgactgtga gcatccactt ctgtatttgc caggcactgg   10080
catagcctca cgagaaagag agagctatgt caggatcctg tcagtaaaat ctttctggca   10140
tatgcaatag tatctgggtt tggtggttgt atatgggatg gatccccaag tggagcagtc   10200
tctgaatggt ccttccttcc atctcagctc caaactttgt ctctataact ccttccatgg   10260
gtattttgtt ccccattcta agaaggagtg aagaatccac actttggtct tccttcttct   10320
tgagtttcat atgttgcatc ttggatattc taagtttctg ggttaatatc cacgtatcag   10380
tgagtgcata tcatgcgtgt tattttgtga ttagtttacc tcactcagga tgatatcctc   10440
cagatgcatc catttgccta agaatttcat taattcactg ttttttaattg ctgaatagta   10500 ctccattgtg taaatgtacc acattttctg tatccattcc tctgttgagg ggcatctggg   10560 ttcttttccag cttctggcta ttataaataa ggctgctatg agcatagcgg agcatgtgtc   10620
cttatcaagt tggaacatct tctaggtata tgcccaggag aggaattgct ggatcttccg   10680
gtagtaccat caacatgcat tcttaataaa agccctagaa caaggaggac tgtaggaaac   10740
atattccaac ataataaagg ttatgtatga caaactcatg accaatatca tcctaaatga   10800
atgaaaccat taataagctc cattaaaatc agaggactgc ccactatccc tacttctcat   10860
ccataatgag attgaagcat tagctggagc aataaggcaa gagaagggat acaaatggga   10920
aaatattaag tcaaattgtt ttcaattgaa gattatatta tcttataccc aatgacctca   10980
aattttgact agaaaaattg tagaaattat caataaattc agcaaagtgt tatgatgcac   11040
cacatcctta ttcttctccc cagcttctgc ttgcttctct cttcttgctc ttcatccttt   11100
ctgtccttcc atctgcctgc actcttgtct caagactgag tgcagcgtgt aactctcctg   11160
tgactgagta tctcacaaaa cgttctacct gccaaacctg gatgagccct ttgtctttct   11220
gaagctatga ggctctctac atagactcaa gaaggaaatg acagggagga ggtaataatg   11280
aagtggggaa ggctgacatt agcattgctc ctgtgtggct ccttaatttc tcatacttca   11340
cactgagatg ttattaactg tgactcatag gtgaagaagc cagagctaag gttctcatat   11400
ttgagtgtta tagaatgagt agagcagtag ttctcaaact atgggtcatg actccttat    11460 gggtcaaact acccctttcac acaggttgca tatcagatat cctaatttta tatacatata   11520
tatatgcata tgtatatata tatatttcac aacagtagga aaattattta gtaatcattt   11580
tatagttgtg ggtcatggca acatgaggaa ctgtattaaa gggttgcagc attaggaatg   11640
ttgagaccca ctgtaataga gaatgaggct taaggcaggg ctataaagcc caatggacca   11700 tgtgccttt ccaacatttg ccacatggta agctctgtat agacttttta aagaacattg   11760
gtttgtaatt ttaaatggat aagggtcttc actgtctatc acccatctat ataataaata   11820
cataagtttt gattccacca tggattcaaa tgcaaaaatc ctcaacctaa gacatagcag   11880
tgaaacattg atgaccaaat aggaaatcca tgtagagacc ttctatcttc tgatggctcc   11940
```

```
acaggcacca tcttgcaaca gagttctact ttgctaccag taatgaatac agtgtctcaa    12000
ctcctgccat tgaatcttca ggaagcccct gaaatgactt gtactacacc atttcttaaa    12060
gacagaaaag ctaagactta gagggaataa atgtcatgcc tgagatcatg caaccaatta    12120
agtccaactt ggcctgatca agaggcacaa ttcaaaagca atgttgttcc ttcactagct    12180
cttgtgtatg gttgctgatt ccggaagcaa agtatcagtg aatatcccta gtgggaaaag    12240
acttggaaat caaatgtctc atttaacaga ttaggagatg aaacggtaga ctctgtgtag    12300
ttgtacaccc ctgtgatccc atcgctagga agactgaggc aggaagtcct cgagctcaaa    12360
ccagcttagg ctacacagag aaactatcta aaaataatt actaactact taataggaga    12420
ttggatgtta agatctggtc actaagaggc agaattgaga ttcgaagcca gtattttcta    12480
cctggtatgt tttaaattgc agtaaggatc taagtgtaga tatataataa taagattcta    12540
ttgatctctg caacaacaga gagtgttaga tttgtttgga aaaaaatatt atcagccaac    12600
atcttctacc atttcagtat agcacagagt acccacccat atctcccac ccatccccca     12660 taccagactg gttattgatt tcatggtga ctggcctgag aagattaaaa aaagtaatgc     12720
taccttattg ggagtgtccc atggaccaag atagcaactg tcatagctac cgtcacactg    12780 cttttgatcaa gaagaccctt tgaggaactg aaaacagaaac cttaggcaca tctgttgctt    12840
tcgctcccat cctcctccaa cagcctgggt ggtgcactcc acccctttc aagtttccaa     12900 agcctcatac acctgctccc taccccagca cctggccaag gctgtatcca gcactgggat    12960
gaaaatgata ccccacctcc atcttgtttg atattactct atctcaagcc ccaggttagt    13020
ccccagtccc aatgcttttg cacagtcaaa actcaacttg gaataatcag tatccttgaa    13080
gagttctgat atggtcactg ggcccatata ccatgtaaga catgtggaaa agatgtttca    13140
tggggcccag acacgttcta gaagtacctg agagtggcaa aaaatagttg tgctaaatag    13200
tttggccatc tttaggctga gagactagga aatacagcga tggactatat cagcattgca    13260
ggatagttgt cagtaaacac cccacaaccc ataacgaaag tattctcttc tttctatatc    13320
ccttttccat ccatgtagat ggctgtcttc atatttgttc tagacggccg gcc           13373
```

<210> SEQ ID NO 93
<211> LENGTH: 12892
<212> TYPE: DNA
<213> ORGANISM: Artificial Sequence
<220> FEATURE:
<223> OTHER INFORMATION: VkP-IGKV1-39/J-Ck-delta1

<400> SEQUENCE: 93

```
ggccggccca catgaaacaa tgggaaccat gtgacaatca cagaggtgtt gttactatag      60
caaaagggat tgttactctc cacatccctt taagtaactt gaaggcctga tagacccacc    120
ctctaagact tcattagaca ttccctacga atggttatac tctcctgtat actcccaata    180
caactctaaa atatattatt ccatatagtc cttaggtttg tattaaagtt tgactttttt    240
ccttcaaaat atctcttgtc acaacagcgg ctctagagag aaatacattc cctccaggca    300
aatctatgct gcgctggtct gacctgggac cctggggaca ttgcccctgt gctgagttac    360
taagatgagc cagccctgca gctgtgctca gcctgcccca tgccctgctg attgatttgc    420
atgttccaga gcacagcccc ctgccctgaa gactttttta tgggctggtc gcaccctgtg    480
caggagtcag tctcagtcag gagccaccat ggacatgaga gtgccgccc agctcctggg    540 gctcctgcta ctctggctcc gaggtaagga tggagaacac taggaattta tcagccagt     600 gtgctcagta ctgactggaa cttcagggaa gttctctgat aacatgatta atagtaagaa    660
```

```
tatttgtttt tatgtttcca atctcaggtg ccagatgtga catccagatg acccagagcc    720
ccagcagcct gagcgccagc gtgggcgaca gagtgaccat cacctgcaga gccagccaga    780
gcatcagcag ctacctgaac tggtatcagc agaagcccgg caaggccccc aagctgctga    840
tctacgccgc cagctccctg cagagcggcg tgcccagcag attcagcggc agcggctccg    900
gcaccgactt caccctgacc atcagcagcc tgcagcccga ggacttcgcc acctactact    960
gccagcagag ctacagcacc ccccccacct tcggccaggg caccaaggtg gagatcaaac   1020
gtaagtacac ttttctcatc tttttttatg tgtaagacac aggttttcat gttaggagtt   1080
aaagtcagtt cagaaaatct tgagaaaatg gagagggctc attatcagtt gacgtggcat   1140
acagtgtcag attttctgtt tatcaagcta gtgagattag gggcaaaaag aggctttagt   1200
tgagaggaaa gtaattaata ctatggtcac catccaagag attggatcgg agaataagca   1260
tgagtagtta ttgagatctg ggtctgactg caggtagcgt ggtcttctag acgtttaagt   1320
gggagatttg gagggatga ggaatgaagg aacttcagga tagaaagggg ctgaagtcaa   1380
gttcagctcc taaaatggat gtgggagcaa actttgaaga taaactgaat gacccagagg   1440
atgaaacagc gcagatcaaa gaggggcctg gagctctgag aagagaagga gactcatccg   1500
tgttgagttt ccacaagtac tgtcttgagt tttgcaataa aagtgggata gcagagttga   1560
gtgagccgta ggctgagttc tctcttttgt ctcctaagtt tttatgacta caaaaatcag   1620
tagtatgtcc tgaaataatc attaagctgt ttgaaagtat gactgcttgc catgtagata   1680
ccatggcttg ctgaataatc agaagaggtg tgactcttat tctaaaattt gtcacaaaat   1740
gtcaaaatga gagactctgt aggaacgagt ccttgacaga cagctcaagg ggttttttc    1800
ctttgtctca tttctacatg aaagtaaatt tgaaatgatc tttttttatta taagagtaga   1860
aatacagttg ggtttgaact atatgtttta atggccacgg ttttgtaaga catttggtcc   1920
tttgttttcc cagttattac tcgattgtaa ttttatatcg ccagcaatgg actgaaacgg   1980
tccgcaacct cttctttaca actgggtgac ctcgcggctg tgccagccat ttggcgttca   2040
ccctgccgct aagggccatg tgaaccccccg cggtagcatc ccttgctccg cgtggaccac   2100
tttcctgagg cacagtgata ggaacagagc cactaatctg aagagaacag agatgtgaca   2160
gactacacta atgtgagaaa aacaaggaaa gggtgactta ttggagattt cagaaataaa   2220
atgcatttat tattatattc ccttatttta attttctatt agggaattag aaagggcata   2280
aactgctta tccagtgtta tattaaaagc ttaatgtata taatctttta gaggtaaaat   2340
ctacagccag caaaagtcat ggtaaatatt ctttgactga actctcacta aactcctcta   2400
aattatatgt catattaact ggttaaatta atataaattt gtgacatgac cttaactggt   2460
taggtaggat attttcttc atgcaaaaat atgactaata ataatttagc acaaaaatat   2520
ttcccaatac tttaattctg tgatagaaaa atgtttaact cagctactat aatcccataa   2580
ttttgaaaac tatttatttg gctacaccaa aggaagccat acagaggcta atatcagagt   2640
attcttggaa gagacaggag aaaatgaaag ccagtttctg ctcttacctt atgtgcttgt   2700
gttcagactc ccaaacatca ggagtgtcag ataaactggt ctgaatctct gtctgaagca   2760
tggaactgaa aagaatgtag tttcagggaa gaaaggcaat agaaggaagc ctgagaatat   2820
cttcaaaggg tcagactcaa tttactttct aaagaagtag ctaggaacta gggaataact   2880
tagaaacaac aagattgtat atatgtgcat cctggcccca ttgttcctta tctgtaggga   2940
taagcgtgct tttttgtgtg tctgtatata acataactgt ttacacataa tacactgaaa   3000
```

```
tggagccctt ccttgttact tcataccatc ctctgtgctt ccttcctcag gggccgacgc    3060
cgctcccacc gtgtccatct tcccccccag catggaacag ctgacctctg gcggagccac    3120
cgtggtctgc ttcgtgaaca acttctaccc cagagacatc agcgtgaagt ggaagatcga    3180
cggcagcgag cagagggacg gcgtgctgga cagcgtgacc gaccaggaca gcaaggactc    3240
cacctacagc atgagcagca ccctgagcct gaccaaggtg gagtacgaga ggcacaacct    3300
gtacacctgc gaggtggtgc acaagaccag ctccagcccc gtggtcaagt ccttcaaccg    3360
gaacgagtgt tgaagacaaa ggtcctgaga cgccaccacc agctcccag ctccatccta    3420 tcttcccttc taaggtcttg gaggcttccc cacaagcgac ctaccactgt tgcggtgctc    3480
caaacctcct ccccacctcc ttctcctcct cctccctttc cttggctttt atcatgctaa    3540
tatttgcaga aaatattcaa taaagtgagt ctttgcactt gagatctctg tctttcttac    3600
taaatggtag taatcagttg tttttccagt tacctgggtt tctcttctaa agaagttaaa    3660
tgtttagttg ccctgaaatc caccacactt aaaggataaa taaaaccctc cacttgccct    3720
ggttggctgt ccactacatg gcagtccttt ctaaggttca cgagtactat tcatggctta    3780
tttctctggg ccatggtagg tttgaggagg catacttcct agttttcttc ccctaagtcg    3840
tcaaagtcct gaaggggac agtctttaca agcacatgtt ctgtaatctg attcaaccta    3900
cccagtaaac ttggcgaagc aaagtagaat cattatcaca ggaagcaaag gcaacctaaa    3960
tgtgcaagca ataggaaaat gtggaagccc atcatagtac ttggacttca tctgcttttg    4020
tgccttcact aagttttta acatgagctg gctcctatct gccattggca aggctgggca    4080
ctacccacaa cctacttcaa ggacctctat accgtgagat tacacacata catcaaaatt    4140
tgggaaaagt tctaccaagc tgagagctga tcaccccact cttaggtgct tatctctgta    4200
caccagaaac cttaagaagc aaccagtatt gagagactca tttatgaaag tctaaaactg    4260
gatacaacca aaatgtccac caacagttaa attatgacat gttcacaatt gagctattac    4320
ttaataagga gaattaataa aataaaactt aagagcatag tttaatctca taaacaagat    4380
aataagcaaa acaaaacatt ttttcatcca tgtaagttta aaagcaggta aaatttaaaa    4440
ttaagagaga cataagtttt gaggtagcaa gatggaaact ctggggcttg gggaatgttc    4500
tgtctctctg tatgggatgt gaaagttact attgtggaat tgggatctat gttcttcctg    4560
tatatattgt atacttcata ataacttcac ctaaagaaat atctaatacc cagtgcatac    4620
ataaaagagg atacaaggaa tgaatcatac gtcaaggcca gaaagacaat aaagtagggg    4680
atccaggatc aaatctccca caaccttgag ccttctacta ttctgccttc cagagctcaa    4740
agtacaaaac acataattca aacacatgat ccctccttgg ggtctcttcc ttcatgcatc    4800
gaattagaaa tagccatgta taaaatgaga tagaagagac cttcatcaac aggtcaaaga    4860
atataggtaa ttttgtctgg gtatgaagag cccacgtatc aaaggttaca ttagggaagg    4920
aagaggacac taacagtgac tttcattctc cccctcttcc tggaggcccc tgcatttagt    4980
ccctcgtggg ctcatccact cagcacacat ttactaagca tcttctcagc ctacactctg    5040
aaggcagtgc agaataatgt tagtgtccct tcccccagtt aatatgcagt ccagtttccc    5100
tgctccttcc ctttctcagt ccacataagg atgatgggaa aggacagtca ccaaatagga    5160
gagggcaacc ctttgccttc ctacctcttg agaatgtaca ttattatcca cttttgaaa    5220 cttcttttaa ttgctttttt ttaatttgtc ttttcaaata gcataacctt gttcatccat    5280
ttctgggaac caaattatc aatcaacagt gcctctaatc tggctattaa tacaaaaatg    5340
cctcctcaaa atatatatgt tcgagtctta tctaaaacag aacccacaat aaaaaagaag    5400
```

```
aaagaataca tataagcatt tatataattc tgagcaacct tgtgctttgt gaaaaaaata   5460
taatctaatg tcacatgctg tattcttttt atttaacact ggtgaaatta taccattaga   5520
gagaaagagg acagatcact gatcctagga tctagggatg ttacagataa gaaaacaaat   5580
gtgacaaaga gctgtcacaa ggaggatctt caaggtcaca gaatcactgt cttgatttca   5640
gtggtggtta catacattta aatatgtgat aaaatgttgt tgaactatat tcatatattg   5700
taccaatgtc aaatgcttaa ttttggctct atagtataat tatgcactaa ataactattt   5760
ggacaaagaa aatgatgttt acatcaaagg tgaggccata tttgttagga acataactta   5820
aaaaccattt tggataacta atgaaaagcc attttgtgtg ccttggcata tcatgcctaa   5880
gctgtcacca gatagatcta ataagaccta agcctcagaa gcaagcccct gcccagcaag   5940
caggcagcac agataagagc taaacccagg acaggccatg atatgctaat gaactacctt   6000
caaggtggtg ttgctgacct agtgaaccag ccccaagctg tgagccccaa tagcacaaag   6060
ctactgccca agaaattat acaaaaattg gaactttggg aatggtgtgc aggatcgctc   6120
tgctgtatgc ctgaacacac gcttctctat gttttgtatt gataccagtc tagaagcttc   6180
caaaactttc tcactgaaga agattcccca tgtgggaccc ctacagactc ttttgcccaa   6240
acaactgctt ccctcctggt gtgatatctg ttttgctttt atgttagcat aatattataa   6300
ggaatgtttg tgtgaataaa ccaaacatat tttaaaagca aatattgtat gcacatccta   6360
attgctaaaa agtttacagc taatagtccc atgctctcca caatactgga tccaaataag   6420
tcctaatttc aatgttgggc atctttacag agagaaagac attaaaaatg aagagacatg   6480
cagagagtgc accatgccat cgtggagaca gactgaagtg acacaactgt tagtcaaaga   6540
ggattaagga cttccagaag ccaccaaagg aaggaggtat gaagtggttt ctccctcaga   6600
gtatccagag gagactaaac caaccaacac cttttttgctt aagacttctt gccttcagga   6660
ctgtgagaag gtagcttcct attgttctaa gccccagtat gtggcatttt gttaaggtag   6720
agtcaagaaa ccaataaaat gcagacagac aaaaggatag ctgagttttc caggcccttc   6780
cttcttattt ttggttttgt tggtggtggt ggtggtggtg gtgatggtgg tggttttgtt   6840
tatgttttgt ttggggagtt ttttgggggtt ttttggggtt ttgttttttgt tgttgttttg   6900 ggggttttttg ttgttgttgt tgtttgcttt ttttgttttttt gttttttgtt tttttgagac   6960
agtgtttctc tgtatagccc tggctgtcct ggagttcctt ctatctctaa tgtctacatc   7020 tcaggggga tcctctaatt tcaaatgagc agtagctctc cattttttagc tcttatttat   7080 tcatttattt acttacttac ttattgtctg tagatgaaag aattttggag tgggaagggg   7140
ttcatgagcc cccagcaact aatgaggagc tacagacaat tgatgtttct ggggaaagga   7200
gactcagttt ctttgagagt atagcttctg atgggtcaac catgttcctg tggctgatgt   7260
cacacccagg agtatgcaga caacagaaac tggagttaat gagttgtttt aaaaataaaa   7320
aagggcatga agcttgggat agaaattaag gataaataca attaaataca ggaaattctg   7380
aaagaattaa taaaaacatt tcttttttta aaaaaaatc cagaattagc tatgcttctt   7440
caaaattgct tctggagaac tttacaagtt aaataagtta tattgtagaa aaggtagaga   7500
ggagaatagt ggaagagaga gataaggaga cttcaaaagg agtggaggga gatagaggag   7560
gagaaagcag aagcaatggc tgatagacac aggataagag ggaacagaaa ggagaaagag   7620
gaagccagga tgggtatttc tttgcctatc tgtgacttgc acatggtctt ggcaattatt   7680
gatgagttca aggcttaatt cttcacttgt gccaactcaa cagagtcttt ctttcttata   7740
```

```
accaggcccc cagtatgctc atgtatgtat caggtcctct tatctcctta tagcaatcct    7800
gtttataact gggtaacttt gtgaagggaa ggaagtgcac actgagatgt gctacaactt    7860
tttaatacaa aattttgaag agtttgtaca atgtatgtat aattaataat taatattatg    7920
cactttagat tttgatttca actcaagata ctaattctat atatatgggt taaatcaata    7980
tattaataag tttaatttca catgcttatt tttattgtgg ttttcgagac agggtttctc    8040
tgtatagccc tggctgtcct ggaacccact ttgtagacca ggctggcctc aaactcagaa    8100
acctacctgc ctctgcctct gcctctgcct ctgcctctgc ctctgcctct gcctctgcct    8160
ctgcctctgc ctctgcctct gcctctgcct ctgcctctgc ctctgcctct gcctctgcct    8220
ctgcctctgc ctctgcctct gcctctgcct ctgcctctgc ctctgcctct gcctctgcct    8280
ctgcctagtg ctggaattaa aggtttgcgc caccacgccc ggtgaaattt ttaaacttta    8340
tatatgtctc attctatttc tatcagatag gactgtgtag actgtgctaa actaataaat    8400
gtgccctcaa aagtaatcgc aagttgtatt gttgttgttt tgctttgctt tgctttgctt    8460
tgctttgctt tgctttgctt tgctttgctt tgctttgctt tgctttgctt tgctttgctt    8520
tgctttgctt tgctttgctt tgcttttttg ttttgggttt ttttccgggg gagggagggt    8580
ggagaaagaa tcttactatg aagctctgac tgtcctggga actcactata tagatcaggc    8640
ttgattcaac tcatagagat ctgccttctt ctgcctccca agtgctggga ataaaggcat    8700
acacctccat gcccagatag tgatcccaag ttttagcaaa agtttctaga cttgacatta    8760
atcgatggag atagacatga attacacaaa gaactaatgt ggagtttacc tgaatcatac    8820
tctatacttt atcagagatt aaattaacat ttaataatcc agtgccaggc tagaggcacc    8880
attcaatggc agtgtttgcc atcatgcata ggcttagtct tcagtgctga aaggcattgg    8940
gggcaatatt actcattata cagatgagaa actgggaaag acttgcctca gattctctac    9000
tgaaaggctg agtttgtggc ttctagaaaa tcttttactt tcaatatttt taatgtataa    9060 ttttttttatt tccactgatt ttatttttta ttttttaacat ttataagaaa taaatgcaat    9120
aaaccaaata catggacaaa aaaatacaag aatcatatga tcacctcaat ggaaggaaaa    9180
aaaaagaaag aaaaagtctt tgataagatt caacattcat tcttttttta ttagatattt    9240
tcttcattta catttcaaat gctatcccca aagccccta taccttcccc tgccctgctc    9300
cccaacccac ccactcctgc tttctggccc tggcattcct ctgtactgag gcatatgatc    9360
ttcaaaaaac caagggcctc tcctctcatt ggtggccgac tattaggcca tcttttgcta    9420
catatgcaac tagagacaca gctctggggg ttactggtta gttcatattg ttagtcctcc    9480
tatagagttg cagaccccctt tagctccttg gatactttct ctagttcctt cattaggggc    9540
cctgtgtccc atccaataga tgactgtgag catccacttc tgtatttgcc aggcactggc    9600
atagcctcac gagaaagaga gagctatgtc aggatcctgt cagtaaaatc tttctggcat    9660
atgcaatagt atctgggttt ggtggttgta tatgggatgg atccccaagt ggagcagtct    9720
ctgaatggtc cttccttcca tctcagctcc aaactttgtc tctataactc cttccatggg    9780
tattttgttc cccattctaa gaaggagtga agaatccaca cttggtctt ccttcttctt    9840 gagtttcata tgttgcatct tggatattct aagtttctgg gttaatatcc acgtatcagt    9900
gagtgcatat catgcgtgtt attttgtgat tagtttacct cactcaggat gatatcctcc    9960
agatgcatcc atttgcctaa gaatttcatt aattcactgt ttttaattgc tgaatagtac   10020
tccattgtgt aaatgtacca catttctgt atccattcct ctgttgaggg gcatctgggt   10080 tcttttccagc ttctggctat tataaataag gctgctatga gcatagcgga gcatgtgtcc   10140
```

```
ttatcaagtt ggaacatctt ctaggtatat gcccaggaga ggaattgctg gatcttccgg    10200
tagtaccatc aacatgcatt cttaataaaa gccctagaac aaggaggact gtaggaaaca    10260
tattccaaca taataaaggt tatgtatgac aaactcatga ccaatatcat cctaaatgaa    10320
tgaaaccatt aataagctcc attaaaatca gaggactgcc cactatccct acttctcatc    10380
cataatgaga ttgaagcatt agctggagca ataaggcaag agaagggata caaatgggaa    10440
aatattaagt caaattgttt tcaattgaag attatattat cttatactca atgacctcaa    10500
attttgacta gaaaaattgt agaaattatc aataatttca gcaaagtgtt atgatgcacc    10560
acatccttat tcttctcccc agcttctgct tgcttctctc ttcttgctct tcatccttc    10620 tgtccttcca tctgcctgca ctcttgtctc aagactgagt gcagcgtgta actctcctgt    10680
gactgagtat ctcacaaaac gttctacctg ccaaacctgg atgagccctt tgtctttctg    10740
aagctatgag gctctctaca tagactcaag aaggaaatga cagggaggag gtaataatga    10800
agtggggaag gctgacatta gcattgctcc tgtgtggctc cttaatttct catacttcac    10860
actgagatgt tattaactgt gactcatagg tgaagaagcc agagctaagg ttctcatatt    10920
tgagtgttat agaatgagta gagcagtagt tctcaaacta tgggtcatga ctcctttatg    10980
ggtcaaacta cccttttcaca caggttgcat atcagatatc ctaattttat atacatatat    11040
atatgcatat gtatatatat atatttcaca acagtaggaa aattatttag taatcatttt    11100
atagttgtgg gtcatggcaa catgaggaac tgtattaaag ggttgcagca ttaggaatgt    11160
tgagacccac tgtaatagag aatgaggctt aaggcagggc tataaagccc aatggaccat    11220
gtgccttttc caacatttgc cacatggtaa gctctgtata gacttttaa agaacattgg    11280 tttgtaattt taaatggata agggtcttca ctgtctatca cccatctata taataaatac    11340
ataagttttg attccaccat ggattcaaat gcaaaaatcc tcaacctaag acatagcagt    11400
gaaacattga tgaccaaata ggaaatccat gtagagacct tctatcttct gatggctcca    11460
caggcaccat cttgcaacag agttctactt tgctaccagt aatgaataca gtgtctcaac    11520
tcctgccatt gaatcttcag gaagcccctg aaatgacttg tactacacca tttcttaaag    11580
acagaaaagc taagacttag agggaataaa tgtcatgcct gagatcatgc aaccaattaa    11640
gtccaacttg gcctgatcaa gaggcacaat tcaaaagcaa tgttgttcct tcactagctc    11700
ttgtgtatgg ttgctgattc cggaagcaaa gtatcagtga atatcccag tgggaaaaga    11760 cttggaaatc aaatgtctca tttaacagat taggagatga aacggtagac tctgtgtagt    11820
tgtacacccc tgtgatccca tcgctaggaa gactgaggca ggaagtcctc gagctcaaac    11880
cagcttaggc tacacagaga aactatctaa aaaataatta ctaactactt aataggagat    11940
tggatgttaa gatctggtca ctaagaggca gaattgagat tcgaagccag tattttctac    12000
ctggtatgtt ttaaattgca gtaaggatct aagtgtagat atataataat aagattctat    12060
tgatctctgc aacaacagag agtgttagat ttgtttggaa aaaatatta tcagccaaca    12120 tcttctacca tttcagtata gcacagagta cccacccata tctccccacc catccccat    12180 accagactgg ttattgattt tcatggtgac tggcctgaga agattaaaaa aagtaatgct    12240
accttattgg gagtgtccca tggaccaaga tagcaactgt catagctacc gtcacactgc    12300
tttgatcaag aagaccttt gaggaactga aaacagaacc ttaggcacat ctgttgcttt    12360
cgctcccatc ctcctccaac agcctgggtg gtgcactcca cacccttca agtttccaaa    12420 gcctcataca cctgctccct accccagcac ctggccaagg ctgtatccag cactgggatg    12480
```

| | | | | | |
|---|---|---|---|---|---|
| aaaatgatac | cccacctcca | tcttgtttga | tattactcta | tctcaagccc | caggttagtc | 12540 |
| cccagtccca | atgcttttgc | acagtcaaaa | ctcaacttgg | aataatcagt | atccttgaag | 12600 |
| agttctgata | tggtcactgg | gcccatatac | catgtaagac | atgtggaaaa | gatgtttcat | 12660 |
| ggggcccaga | cacgttctag | aagtacctga | gagtggcaaa | aaatagttgt | gctaaatagt | 12720 |
| ttggccatct | ttaggctgag | agactaggaa | atacagcgat | ggactatatc | agcattgcag | 12780 |
| gatagttgtc | agtaaacacc | ccacaaccca | taacagaagt | attctcttct | ttctatatcc | 12840 |
| cttttccatc | catgtagatg | gctgtcttca | tatttgttct | agacggccgg | cc | 12892 |

<210> SEQ ID NO 94
<211> LENGTH: 6425
<212> TYPE: DNA
<213> ORGANISM: Artificial Sequence
<220> FEATURE:
<223> OTHER INFORMATION: VkP-IGKV1-39/J-Ck-delta2

<400> SEQUENCE: 94

| | | | | | |
|---|---|---|---|---|---|
| ggccggccca | catgaaacaa | tgggaaccat | gtgacaatca | cagaggtgtt | gttactatag | 60 |
| caaaagggat | tgttactctc | cacatcccctt | taagtaactt | gaaggcctga | tagacccacc | 120 |
| ctctaagact | tcattagaca | ttccctacga | atggttatac | tctcctgtat | actcccaata | 180 |
| caactctaaa | atatattatt | ccatatagtc | cttaggtttg | tattaaagtt | tgactttttt | 240 |
| ccttcaaaat | atctcttgtc | acaacagcgg | ctctagagaa | aaatacattc | cctccaggca | 300 |
| aatctatgct | gcgctggtct | gacctgggac | cctggggaca | ttgcccctgt | gctgagttac | 360 |
| taagatgagc | cagccctgca | gctgtgctca | gcctgcccca | tgccctgctg | attgatttgc | 420 |
| atgttccaga | gcacagcccc | ctgccctgaa | gactttttta | tgggctggtc | gcaccctgtg | 480 |
| caggagtcag | tctcagtcag | gagccaccat | ggacatgaga | gtgcccgccc | agctcctggg | 540 |
| gctcctgcta | ctctggctcc | gaggtaagga | tggagaacac | taggaattta | ctcagccagt | 600 |
| gtgctcagta | ctgactggaa | cttcaggaa | gttctctgat | aacatgatta | atagtaagaa | 660 |
| tatttgtttt | tatgtttcca | atctcaggtg | ccagatgtga | catccagatg | acccagagcc | 720 |
| ccagcagcct | gagcgccagc | gtgggcgaca | gagtgaccat | cacctgcaga | gccagccaga | 780 |
| gcatcagcag | ctacctgaac | tggtatcagc | agaagcccgg | caaggccccc | aagctgctga | 840 |
| tctacgccgc | cagctccctg | cagagcggcg | tgcccagcag | attcagcggc | agcggctccg | 900 |
| gcaccgactt | caccctgacc | atcagcagcc | tgcagcccga | ggacttcgcc | acctactact | 960 |
| gccagcagag | ctacagcacc | cccccccacct | tcggccaggg | caccaaggtg | gagatcaaac | 1020 |
| gtaagtacac | ttttctcatc | tttttttatg | tgtaagacac | aggttttcat | gttaggagtt | 1080 |
| aaagtcagtt | cagaaaatct | tgagaaaatg | gagagggctc | attatcagtt | gacgtggcat | 1140 |
| acagtgtcag | attttctgtt | tatcaagcta | gtgagattag | gggcaaaaag | aggctttagt | 1200 |
| tgagaggaaa | gtaattaata | ctatggtcac | catccaagag | attggatcgg | agaataagca | 1260 |
| tgagtagtta | ttgagatctg | ggtctgactg | caggtagcgt | ggtcttctag | acgtttaagt | 1320 |
| gggagatttg | gagggatga | ggaatgaagg | aacttcagga | tagaaaaggg | ctgaagtcaa | 1380 |
| gttcagctcc | taaatggat | gtgggagcaa | actttgaaga | taaactgaat | gacccagagg | 1440 |
| atgaaacagc | gcagatcaaa | gagggggcctg | gagctctgag | aagagaagga | gactcatccg | 1500 |
| tgttgagttt | ccacaagtac | tgtccttgagt | tttgcaataa | aagtgggata | gcagagttga | 1560 |
| gtgagccgta | ggctgagttc | tctcttttgt | ctccctaagtt | tttatgacta | caaaaatcag | 1620 |
| tagtatgtcc | tgaaataatc | attaagctgt | ttgaaagtat | gactgcttgc | catgtagata | 1680 |

```
ccatggcttg ctgaataatc agaagaggtg tgactcttat tctaaaattt gtcacaaaat    1740
gtcaaaatga gagactctgt aggaacgagt ccttgacaga cagctcaagg ggttttttc     1800 ctttgtctca tttctacatg aaagtaaatt tgaaatgatc ttttttatta taagagtaga    1860
aatacagttg ggtttgaact atatgtttta atggccacgg ttttgtaaga catttggtcc    1920
tttgttttcc cagttattac tcgattgtaa ttttatatcg ccagcaatgg actgaaacgg    1980
tccgcaacct cttctttaca actgggtgac ctcgcggctg tgccagccat ttggcgttca    2040
ccctgccgct aagggccatg tgaaccccg cggtagcatc ccttgctccg cgtggaccac     2100
tttcctgagg cacagtgata ggaacagagc cactaatctg aagagaacag agatgtgaca    2160
gactacacta atgtgagaaa acaaggaaa gggtgactta ttggagattt cagaaataaa     2220
atgcatttat tattatattc ccttatttta attttctatt agggaattag aaagggcata    2280
aactgcttta tccagtgtta tattaaaagc ttaatgtata taatcttta gaggtaaaat     2340 ctacagccag caaagtcat ggtaaatatt ctttgactga actctcacta aactcctcta     2400
aattatatgt catattaact ggttaaatta atataaattt gtgacatgac cttaactggt    2460
taggtaggat attttcttc atgcaaaaat atgactaata ataatttagc acaaaaatat     2520
ttcccaatac tttaattctg tgatagaaaa atgtttaact cagctactat aatcccataa    2580
ttttgaaaac tatttatttg gctacaccaa aggaagccat acagaggcta atatcagagt    2640
attcttggaa gagacaggag aaaatgaaag ccagtttctg ctcttacctt atgtgcttgt    2700
gttcagactc ccaaacatca ggagtgtcag ataaactggt ctgaatctct gtctgaagca    2760
tggaactgaa aagaatgtag tttcagggaa gaaaggcaat agaaggaagc ctgagaatat    2820
cttcaagggg tcagactcaa tttactttct aaagaagtag ctaggaacta gggaataact    2880
tagaaacaac aagattgtat atatgtgcat cctggcccca ttgttcctta tctgtaggga    2940
taagcgtgct ttttgtgtg tctgtatata acataactgt ttacacataa tacactgaaa     3000 tggagcccttccttgttact tcataccatc ctctgtgctt ccttcctcag gggccgacgc     3060
cgctcccacc gtgtccatct tcccccccag catggaacag ctgacctctg gcggagccac    3120
cgtggtctgc ttcgtgaaca acttctaccc cagagacatc agcgtgaagt ggaagatcga    3180
cggcagcgag cagagggacg gcgtgctgga cagcgtgacc gaccaggaca gcaaggactc    3240
cacctacagc atgagcagca ccctgagcct gaccaaggtg gagtacgaga ggcacaacct    3300
gtacacctgc gaggtggtgc acaagaccag ctccagcccc gtggtcaagt ccttcaaccg    3360
gaacgagtgt tgaagacaaa ggtcctgaga cgccaccacc agctccccag ctccatccta    3420
tcttcccttc taaggtcttg gaggcttccc cacaagcgac ctaccactgt tgcggtgctc    3480
caaacctcct ccccacctcc ttctcctcct cctcccttc cttggctttt atcatgctaa     3540
tatttgcaga aaatattcaa taaagtgagt ctttgcactt gagatctctg tctttcttac    3600
taaatggtag taatcagttg tttttccagt tacctgggtt tctcttctaa agaagttaaa    3660
tgtttagttg ccctgaaatc caccacactt aaaggataaa taaaaccctc cacttgccct    3720
ggttggctgt ccactacatg gcagtccttt ctaaggttca cgagtactat tcatggctta    3780
tttctctggg ccatggtagg tttgaggagg catacttcct agtttcttc ccctaagtcg     3840 tcaaagtcct gaaggggac agtctttaca agcacatgtt ctgtaatctg attcaaccta     3900
cccagtaaac ttggcgaagc aaagtagaat cattatcaca ggaagcaaag gcaacctaaa    3960
tgtgcaagca ataggaaaat gtggaagccc atcatagtac ttggacttca tctgcttttg    4020
```

-continued

```
tgccttcact aagtttttaa acatgagctg gctcctatct gccattggca aggctgggca    4080
ctacccacaa cctacttcaa ggacctctat accgtgagat acacacata catcaaaatt    4140 tgggaaaagt tctaccaagc tgagagctga tcaccccact cttaggtgct tatctctgta    4200
caccagaaac cttaagaagc aaccagtatt gagagactca tttatgaaag tctaaaactg    4260
gatacaacca aaatgtccac caacagttaa attatgacat gttcacaatt gagctattac    4320
ttaataagga gaattaataa aataaaactt aagagcatag tttaatctca taaacaagat    4380
aataagcaaa acaaaacatt tttcatcca tgtaagttta aaagcaggta aaatttaaaa    4440
ttaagagaga cataagtttt gaggtagcaa gatggaaact ctggggcttg ggaatgttc    4500 tgtctctctg tatgggatgt gaaagttact attgtggaat tgggatctat gttcttcctg    4560
tatatattgt atacttcata ataacttcac ctaaagaaat atctaatacc cagtgcatac    4620
ataaaagagg atacaaggaa tgaatcatac gtcaaggcca gaaagacaat aaagtagggg    4680
atccaggatc aaatctccca caaccttgag ccttctacta ttctgccttc cagagctcaa    4740
agtacaaaac acataattca aacacatgat ccctccttgg ggtctcttcc ttcatgcatc    4800
gaattagaaa tagccatgta taaaatgaga tagaagagac cttcatcaac aggtcaaaga    4860
atataggtaa ttttgtctgg gtatgaagag cccacgtatc aaaggttaca ttagggaagg    4920
aagaggacac taacagtgac tttcattctc cccctcttcc tggaggcccc tgcatttagt    4980
ccctcgtggg ctcatccact cagcacacat ttactaagca tcttctcagc ctacactctg    5040
aaggcagtgc agaataatgt tagtgtccct tcccccagtt aatatgcagt ccagtttccc    5100
tgctccttcc ctttctcagt ccacataagg atgatgggaa aggacagtca ccaaatagga    5160
gagggcaacc ctttgccttc ctacctcttg agaatgtaca ttattatcca cttttgaaa    5220 cttcttttaa ttgctttttt ttaatttgtc ttttcaaata gcataacctt gttcatccat    5280
ttctgggaac caaatttatc aatcaacagt gcctctaatc tggctattaa tacaaaaatg    5340
cctcctcaaa atatatatgt tcgagtctta tctaaaacag aacccacaat aaaaaagaag    5400
aaagaataca tataagcatt tatataattc tgagcaacct tgtgctttgt gaaaaaaata    5460
taatctaatg tcacatgctg tattctttt atttaacact ggtgaaatta taccattaga    5520
gagaaagagg acagatcact gatcctagga tctagggatg ttacagataa gaaaacaaat    5580
gtgacaaaga gctgtcacaa ggaggatctt caaggtcaca gaatcactgt cttgatttca    5640
gtggtggtta catacattta aatatgtgat aaaatgttgt tgaactatat tcatatattg    5700
taccaatgtc aaatgcttaa ttttggctct atagtataat tatgcactaa ataactattt    5760
ggacaaagaa aatgatgttt acatcaaagg tgaggccata tttgttagga acataactta    5820
aaaaccattt tggataacta atgaaaagcc attttgtgtg ccttggcata tcatgcctaa    5880
gctgtcacca gatagatcta ataagaccta agcctcagaa gcaagcccct gcccagcaag    5940
caggcagcac agataagagc taaacccagg acaggccatg atatgctaat gaactacctt    6000
caaggtggtg ttgctgacct agtgaaccag ccccaagctg tgagcccaa tagcacaaag    6060 ctactgccca agaaattat acaaaaattg gaactttggg aatggtgtgc aggatcgctc    6120
tgctgtatgc ctggaacaca gcttctctat gttttgtatt gataccagtc tagaagcttc    6180
caaaactttc tcactgaaga agattcccca tgtgggaccc ctacagactc ttttgcccaa    6240
acaactgctt ccctcctggt gtgatcatgg accaagatag caactgtcat agctaccgtc    6300
acactgcttt gatcaagaag acccttgag gaactgaaaa cagaaccta ggcacatctg    6360 ttgctttcgc tcccatcctc ctccaacagc atggctgtct tcatatttgt tctagacggc    6420
``` cggcc 6425

<210> SEQ ID NO 95
<211> LENGTH: 13382
<212> TYPE: DNA
<213> ORGANISM: Artificial Sequence
<220> FEATURE:
<223> OTHER INFORMATION: VkP-IGLV2-14/J-Ck

<400> SEQUENCE: 95

```
ggccggccca catgaaacaa tgggaaccat gtgacaatca cagaggtgtt gttactatag      60
caaaagggat tgttactctc cacatccctt taagtaactt gaaggcctga tagacccacc     120
ctctaagact tcattagaca ttccctacga atggttatac tctcctgtat actcccaata     180
caactctaaa atatattatt ccatatagtc cttaggtttg tattaaagtt tgactttttt     240
ccttcaaaat atctcttgtc acaacagcgg ctctagagag aaatacattc cctccaggca     300
aatctatgct gcgctggtct gacctgggac cctggggaca ttgcccctgt gctgagttac     360
taagatgagc cagccctgca gctgtgctca gcctgcccca tgccctgctg attgatttgc     420
atgttccaga gcacagcccc ctgccctgaa gactttttta tgggctggtc gcaccctgtg     480
caggagtcag tctcagtcag gagccaccat ggacatgaga gtgcccgccc agctcctggg     540
gctcctgcta ctctggctcc gaggtaagga tggagaacac taggaattta ctcagccagt     600
gtgctcagta ctgactggaa cttcagggaa gttctctgat aacatgatta atagtaagaa     660
tatttgtttt tatgtttcca atctcaggtg ccagatgtca gtctgccctg acccagcccg     720
cctctgtgtc tggcagccct ggccagagca tcaccatcag ctgcaccggc accagcagcg     780
acgtgggcgg ctacaactac gtgtcctggt atcagcagca ccccggcaag gcccccaagc     840
tgatgatcta cgaggtgtcc aacagaccca gcggcgtgag caacagattc agcggcagca     900
agagcggcaa caccgccagc ctgaccatca gcggcctcca ggctgaggac gaggccgact     960
actactgcag cagctacacc agcagctcca ccctggtgtt tggcggcgga acaaagctga    1020
ccgtgctgcg taagtacact tttctcatct tttttatgt gtaagacaca ggttttcatg    1080
ttaggagtta aagtcagttc agaaaatctt gagaaaatgg agagggctca ttatcagttg    1140
acgtggcata cagtgtcaga ttttctgttt atcaagctag tgagattagg ggcaaaaaga    1200
ggctttagtt gagaggaaag taattaatac tatggtcacc atccaagaga ttggatcgga    1260
gaataagcat gagtagttat tgagatctgg gtctgactgc aggtagcgtg gtcttctaga    1320
cgtttaagtg ggagatttgg aggggatgag gaatgaagga acttcaggat agaaaagggc    1380
tgaagtcaag ttcagctcct aaaatggatg tgggagcaaa ctttgaagat aaactgaatg    1440
acccagagga tgaaacagcg cagatcaaag aggggcctgg agctctgaga agagaaggag    1500
actcatccgt gttgagtttc cacaagtact gtcttgagtt ttgcaataaa agtgggatag    1560
cagagttgag tgagccgtag gctgagttct ctcttttgtc tcctaagttt ttatgactac    1620
aaaaatcagt agtatgtcct gaaataatca ttaagctgtt gaaagtatg actgcttgcc     1680
atgtagatac catggcttgc tgaataatca gaagaggtgt gactcttatt ctaaaatttg    1740
tcacaaaatg tcaaatgag agactctgta ggaacgagtc cttgacagac agctcaaggg    1800
gttttttcc tttgtctcat ttctacatga aagtaaattt gaatgatct ttttttattat     1860
aagagtagaa atacagttgg gtttgaacta tatgttttaa tggccacggt tttgtaagac    1920
atttggtcct ttgttttccc agttattact cgattgtaat tttatatcgc cagcaatgga    1980
```

```
ctgaaacggt ccgcaacctc ttctttacaa ctgggtgacc tcgcggctgt gccagccatt    2040
tggcgttcac cctgccgcta agggccatgt gaaccccgc ggtagcatcc cttgctccgc     2100
gtggaccact ttcctgaggc acagtgatag gaacagagcc actaatctga agagaacaga    2160
gatgtgacag actacactaa tgtgagaaaa acaaggaaag ggtgacttat tggagatttc    2220
agaaataaaa tgcatttatt attatattcc cttatttaa ttttctatta gggaattaga     2280
aagggcataa actgctttat ccagtgttat attaaaagct taatgtatat aatcttttag    2340
aggtaaaatc tacagccagc aaaagtcatg gtaaatattc tttgactgaa ctctcactaa    2400
actcctctaa attatatgtc atattaactg gttaaattaa tataaatttg tgacatgacc    2460
ttaactggtt aggtaggata ttttcttca tgcaaaaata tgactaataa taatttagca     2520 caaaatatt tcccaatact ttaattctgt gatagaaaaa tgtttaactc agctactata     2580
atcccataat tttgaaaact atttattagc ttttgtgttt gacccttccc tagccaaagg    2640
caactattta aggaccctt aaactcttg aaactacttt agagtcatta agttatttaa       2700
ccacttttaa ttactttaaa atgatgtcaa ttccctttta actattaatt tattttaagg    2760
ggggaaaggc tgctcataat tctattgttt ttcttggtaa agaactctca gttttcgttt    2820
ttactacctc tgtcacccaa gagttggcat ctcaacagag gggactttcc gagaggccat    2880
ctggcagttg cttaagatca gaagtgaagt ctgccagttc ctcccaggca ggtggcccag    2940
attacagttg acctgttctg gtgtggctaa aaattgtccc atgtggttac aaaccattag    3000
accagggtct gatgaattgc tcagaatatt tctggacacc caaatacaga ccctggctta    3060
aggccctgtc catacagtag gtttagcttg gctacaccaa aggaagccat acagaggcta    3120
atatcagagt attcttggaa gagacaggag aaaatgaaag ccagtttctg ctcttacctt    3180
atgtgcttgt gttcagactc ccaaacatca ggagtgtcag ataaactggt ctgaatctct    3240
gtctgaagca tggaactgaa agaatgtag tttcagggaa gaaaggcaat agaaggaagc     3300
ctgagaatat cttcaaaggg tcagactcaa tttactttct aaagaagtag ctaggaacta    3360
gggaataact tagaaacaac aagattgtat atatgtgcat cctggcccca ttgttcctta    3420
tctgtaggga taagcgtgct ttttttgtgtg tctgtatata acataactgt ttacacataa   3480
tacactgaaa tggagcccctt ccttgttact tcataccatc ctctgtgctt ccttcctcag   3540
gggccgacgc cgctcccacc gtgtccatct tccccccag catggaacag ctgacctctg     3600
gcggagccac cgtggtctgc ttcgtgaaca acttctaccc cagagacatc agcgtgaagt    3660
ggaagatcga cggcagcgag cagagggacg gcgtgctgga cagcgtgacc gaccaggaca    3720
gcaaggactc cacctacagc atgagcagca ccctgagcct gaccaaggtg gagtacgaga    3780
ggcacaacct gtacacctgc gaggtggtgc acaagaccag ctccagcccc gtggtcaagt    3840
ccttcaaccg gaacgagtgt tgaagacaaa ggtcctgaga cgccaccacc agctccccag    3900
ctccatccta tcttcccttc taaggtcttg gaggcttccc cacaagcgac ctaccactgt    3960
tgcggtgctc caaacctcct ccccacctcc ttctcctcct cctcccttc cttggctttt     4020 atcatgctaa tatttgcaga aaatattcaa taaagtgagt ctttgcactt gagatctctg    4080
tctttcttac taaatggtag taatcagttg ttttccagt tacctgggtt tctcttctaa     4140
agaagttaaa tgtttagttg ccctgaaatc caccacactt aaaggataaa taaaaccctc    4200
cacttgccct ggttggctgt ccactacatg gcagtccttt ctaaggttca cgagtactat    4260
tcatggctta tttctctggg ccatggtagg tttgaggagg catacttcct agttttcttc    4320
ccctaagtcg tcaaagtcct gaaggggggac agtctttaca agcacatgtt ctgtaatctg    4380
```

```
attcaaccta cccagtaaac ttggcgaagc aaagtagaat cattatcaca ggaagcaaag    4440
gcaacctaaa tgtgcaagca ataggaaaat gtggaagccc atcatagtac ttggacttca    4500
tctgcttttg tgccttcact aagttttaa acatgagctg gctcctatct gccattggca     4560
aggctgggca ctaccacaa cctacttcaa ggacctctat accgtgagat tacacacata     4620
catcaaaatt tgggaaaagt tctaccaagc tgagagctga tcaccccact cttaggtgct    4680
tatctctgta caccgaaaac cttaagaagc aaccagtatt gagagactca tttatgaaag    4740
tctaaaactg gatacaacca aaatgtccac caacagttaa attatgacat gttcacaatt    4800
gagctattac ttaataagga gaattaataa aataaaactt aagagcatag tttaatctca    4860
taaacaagat aataagcaaa acaaaacatt ttttcatcca tgtaagttta aaagcaggta    4920
aaatttaaaa ttaagagaga cataagtttt gaggtagcaa gatggaaact ctggggcttg    4980
gggaatgttc tgtctctctg tatgggatgt gaaagttact attgtggaat tgggatctat    5040
gttcttcctg tatatattgt atacttcata ataacttcac ctaaagaaat atctaatacc    5100
cagtgcatac ataaaagagg atacaaggaa tgaatcatac gtcaaggcca gaaagacaat    5160
aaagtagggg atccaggatc aaatctccca caaccttgag ccttctacta ttctgccttc    5220
cagagctcaa agtacaaaac acataattca aacacatgat ccctccttgg ggtctcttcc    5280
ttcatgcatc gaattagaaa tagccatgta taaaatgaga tagaagagac cttcatcaac    5340
aggtcaaaga atataggtaa ttttgtctgg gtatgaagag cccacgtatc aaaggttaca    5400
ttagggaagg aagaggacac taacagtgac tttcattctc ccctcttcc tggaggcccc     5460 tgcatttagt ccctcgtggg ctcatccact cagcacacat ttactaagca tcttctcagc    5520
ctacactctg aaggcagtgc agaataatgt tagtgtccct tcccccagtt aatatgcagt    5580
ccagtttccc tgctccttcc ctttctcagt ccacataagg atgatgggaa aggacagtca    5640
ccaaatagga gagggcaacc ctttgccttc ctacctcttg agaatgtaca ttattatcca    5700 cttttgaaa cttcttttaa ttgcttttt ttaatttgtc ttttcaaata gcataacctt      5760
gttcatccat ttctgggaac caaatttatc aatcaacagt gcctctaatc tggctattaa    5820
tacaaaaatg cctcctcaaa atatatatgt tcgagtctta tctaaaacag aacccacaat    5880
aaaaaagaag aaagaataca tataagcatt tatataattc tgagcaacct tgtgctttgt    5940
gaaaaaaata taatctaatg tcacatgctg tattctttt atttaacact ggtgaaatta     6000
taccattaga gagaaagagg acagatcact gatcctagga tctagggatg ttacagataa    6060
gaaaacaaat gtgacaaaga gctgtcacaa ggaggatctt caaggtcaca gaatcactgt    6120
cttgatttca gtggtggtta catacattta aatatgtgat aaaatgttgt tgaactatat    6180
tcatatattg taccaatgtc aaatgcttaa ttttggctct atagtataat tatgcactaa    6240
ataactattt ggacaaagaa aatgatgttt acatcaaagg tgaggccata tttgttagga    6300
acataactta aaaaccattt tggataacta atgaaaagcc attttgtgtg ccttggcata    6360
tcatgcctaa gctgtcacca gatagatcta ataagaccta agcctcagaa gcaagcccct    6420
gcccagcaag caggcagcac agataagagc taaacccagg acaggccatg atatgctaat    6480
gaactacctt caaggtggtg ttgctgacct agtgaaccag ccccaagctg tgagcccaa     6540 tagcacaaag ctactgccca agaaattat acaaaaattg gaactttggg aatggtgtgc     6600
aggatcgctc tgctgtatgc ctggaacaca gcttctctat gttttgtatt gataccagtc    6660
tagaagcttc caaaactttc tcactgaaga agattcccca tgtgggaccc ctacagactc    6720
```

```
ttttgcccaa caactgctt ccctcctggt gtgatatctg ttttgctttt atgttagcat    6780
aatattataa ggaatgtttg tgtgaataaa ccaaacatat tttaaaagca aatattgtat    6840
gcacatccta attgctaaaa agtttacagc taatagtccc atgctctcca caatactgga   6900
tccaaataag tcctaatttc aatgttgggc atctttacag agagaaagac attaaaaatg   6960
aagagacatg cagagagtgc accatgccat cgtggagaca gactgaagtg acacaactgt   7020
tagtcaaaga ggattaagga cttccagaag ccaccaaagg aaggaggtat gaagtggttt   7080
ctccctcaga gtatccagag gagactaaac caaccaacac cttttttgctt aagacttctt  7140
gccttcagga ctgtgagaag gtagcttcct attgttctaa gcccagtat gtggcatttt    7200
gttaaggtag agtcaagaaa ccaataaaat gcagacagac aaaaggatag ctgagttttc   7260
caggcccttc cttcttattt ttggttttgt tggtggtggt ggtggtggtg gtgatggtgg   7320
tggttttgtt tatgttttgt ttgggagtt ttttggggtt ttttgggtt ttgttttttgt    7380
tgttgttttg ggggttttg ttgttgttgt tgtttgctttt tttgtttttt gttttttgtt   7440
tttttgagac agtgtttctc tgtatagccc tggctgtcct ggagttcctt ctatctctaa   7500
tgtctacatc tcagagggga tcctctaatt tcaaatgagc agtagctctc cattttagc    7560
tcttatttat tcatttattt acttacttac ttattgtctg tagatgaaag aattttggag   7620
tgggaagggg ttcatgagcc cccagcaact aatgaggagc tacagacaat tgatgtttct   7680
ggggaaagga gactcagttt ctttgagagt atagcttctg atgggtcaac catgttcctg   7740
tggctgatgt cacacccagg agtatgcaga caacagaaac tggagttaat gagttgtttt   7800
aaaaataaaa aagggcatga agcttgggat agaaattaag gataaataca attaaataca   7860
ggaaattctg aaagaattaa taaaaacatt tcttttttta aaaaaaatc cagaattagc    7920
tatgcttctt caaaattgct tctggagaac tttacaagtt aaataagtta tattgtagaa   7980
aaggtagaga ggagaatagt ggaagagaga gataaggaga cttcaaaagg agtggaggga   8040
gatagaggag gagaaagcag aagcaatggc tgatagacac aggataagag ggaacagaaa   8100
ggagaaagag gaagccagga tgggtatttc tttgcctatc tgtgacttgc acatggtctt   8160
ggcaattatt gatgagttca aggcttaatt cttcacttgt gccaactcaa cagagtcttt   8220
ctttcttata accaggcccc cagtatgctc atgtatgtat caggtcctct tatctcctta   8280
tagcaatcct gtttataact gggtaacttt gtgaagggaa ggaagtgcac actgagatgt   8340
gctacaactt tttaatacaa aattttgaag agtttgtaca atgtatgtat aattaataat   8400
taatattatg cactttagat tttgatttca actcaagata ctaattctat atatatgggt   8460
taaatcaata tattaataag tttaatttca catgcttatt tttattgtgg ttttcgagac   8520
agggtttctc tgtatagccc tggctgtcct ggaacccact tgtagacca ggctggcctc    8580
aaactcagaa acctacctgc ctctgcctct gcctctgcct ctgcctctgc ctctgcctct   8640
gcctctgcct ctgcctctgc ctctgcctct gcctctgcct ctgcctctgc ctctgcctct   8700
gcctctgcct ctgcctctgc ctctgcctct gcctctgcct ctgcctctgc ctctgcctct   8760
gcctctgcct ctgcctagtg ctggaattaa aggtttgcgc caccacgccc ggtgaaattt   8820
ttaaacttta tatgtctc attctatttc tatcagatag gactgtgtag actgtgctaa    8880
actaataaat gtgccctcaa agtaatcgc aagttgtatt gttgttgttt tgctttgctt    8940
tgctttgctt tgctttgctt tgctttgctt tgctttgctt tgctttgctt tgctttgctt   9000
tgctttgctt tgctttgctt tgctttgctt tgcttttttg ttttgggttt ttttccgggg   9060
gagggagggt ggagaaagaa tcttactatg aagctctgac tgtcctggga actcactata   9120
```

```
tagatcaggc ttgattcaac tcatagagat ctgccttctt ctgcctccca agtgctggga    9180
ataaaggcat acacctccat gcccagatag tgatcccaag ttttagcaaa agtttctaga    9240
cttgacatta atcgatggag atagacatga attacacaaa gaactaatgt ggagtttacc    9300
tgaatcatac tctatacttt atcagagatt aaattaacat ttaataatcc agtgccaggc    9360
tagaggcacc attcaatggc agtgtttgcc atcatgcata ggcttagtct tcagtgctga    9420
aaggcattgg gggcaatatt actcattata cagatgagaa actgggaaag acttgcctca    9480
gattctctac tgaaaggctg agtttgtggc ttctagaaaa tcttttactt tcaatatttt    9540
taatgtataa ttttttttatt tccactgatt ttatttttta ttttttaacat ttataagaaa    9600 taaatgcaat aaaccaaata catggacaaa aaaatacaag aatcatatga tcacctcaat    9660
ggaaggaaaa aaaaagaaag aaaaagtctt tgataagatt caacattcat tcttttttta    9720
ttagatattt tcttcattta catttcaaat gctatcccca aagcccccta taccttcccc    9780
tgccctgctc cccaacccac ccactcctgc tttctggccc tggcattcct ctgtactgag    9840
gcatatgatc ttcaaaaaac caagggcctc tcctctcatt ggtggccgac tattaggcca    9900
tcttttgcta catatgcaac tagagacaca gctctggggg ttactggtta gttcatattg    9960
ttagtcctcc tatagagttg cagaccccctt tagctccttg gatactttct ctagttcctt   10020
cattaggggc cctgtgtccc atccaataga tgactgtgag catccacttc tgtatttgcc   10080
aggcactggc atagcctcac gagaaagaga gagctatgtc aggatcctgt cagtaaaatc   10140
tttctggcat atgcaatagt atctgggttt ggtggttgta tatgggatgg atccccaagt   10200
ggagcagtct ctgaatggtc cttccttcca tctcagctcc aaactttgtc tctataactc   10260
cttccatggg tattttgttc cccattctaa gaaggagtga agaatccaca ctttggtctt   10320
ccttcttctt gagtttcata tgttgcatct tggatattct aagtttctgg gttaatatcc   10380
acgtatcagt gagtgcatat catgcgtgtt attttgtgat tagtttacct cactcaggat   10440
gatatcctcc agatgcatcc atttgcctaa gaatttcatt aattcactgt ttttaattgc   10500
tgaatagtac tccattgtgt aaatgtacca cattttctgt atccattcct ctgttgaggg   10560
gcatctgggt tctttccagc ttctggctat tataaataag gctgctatga gcatagcgga   10620
gcatgtgtcc ttatcaagtt ggaacatctt ctaggtatat gcccaggaga ggaattgctg   10680
gatcttccgg tagtaccatc aacatgcatt cttaataaaa gccctagaac aaggaggact   10740
gtaggaaaca tattccaaca taataaaggt tatgtatgac aaactcatga ccaatatcat   10800
cctaaatgaa tgaaaccatt aataagctcc attaaaatca gaggactgcc cactatccct   10860
acttctcatc cataatgaga ttgaagcatt agctggagca ataaggcaag agaagggata   10920
caaatgggaa aatattaagt caaattgttt tcaattgaag attatattat cttatatccca   10980 atgacctcaa attttgacta gaaaaattgt agaaattatc ataatttttca gcaaagtgtt   11040 atgatgcacc acatccttat tcttctcccc agcttctgct tgcttctctc ttcttgctct   11100
tcatcctttc tgtccttcca tctgcctgca ctcttgtctc aagactgagt gcagcgtgta   11160
actctcctgt gactgagtat ctcacaaaac gttctacctg ccaaacctgg atgagccctt   11220
tgtctttctg aagctatgag gctctctaca tagactcaag aaggaaatga cagggaggag   11280
gtaataatga agtggggaag gctgacatta gcattgctcc tgtgtggctc cttaatttct   11340
catacttcac actgagatgt tattaactgt gactcatagg tgaagaagcc agagctaagg   11400
ttctcatatt tgagtgttat agaatgagta gagcagtagt tctcaaacta tgggtcatga   11460
```

```
ctcctttatg ggtcaaacta cccttcaca caggttgcat atcagatatc ctaatttat    11520 atacatatat atatgcatat gtatatatat atatttcaca acagtaggaa aattatttag    11580
taatcatttt atagttgtgg gtcatggcaa catgaggaac tgtattaaag ggttgcagca    11640
ttaggaatgt tgagacccac tgtaatagag aatgaggctt aaggcagggc tataaagccc    11700
aatggaccat gtgccttttc caacatttgc cacatggtaa gctctgtata gacttttaa    11760 agaacattgg tttgtaattt taaatggata agggtcttca ctgtctatca cccatctata    11820
taataaatac ataagttttg attccaccat ggattcaaat gcaaaaatcc tcaacctaag    11880
acatagcagt gaaacattga tgaccaaata ggaaatccat gtagagacct tctatcttct    11940
gatggctcca caggcaccat cttgcaacag agttctactt tgctaccagt aatgaataca    12000
gtgtctcaac tcctgccatt gaatcttcag gaagcccctg aaatgacttg tactacacca    12060
tttcttaaag acagaaaagc taagacttag agggaataaa tgtcatgcct gagatcatgc    12120
aaccaattaa gtccaacttg gcctgatcaa gaggcacaat tcaaaagcaa tgttgttcct    12180
tcactagctc ttgtgtatgg ttgctgattc cggaagcaaa gtatcagtga atatccctag    12240
tgggaaaaga cttggaaatc aaatgtctca tttaacagat taggagatga aacggtagac    12300
tctgtgtagt tgtacacccc tgtgatccca tcgctaggaa gactgaggca ggaagtcctc    12360
gagctcaaac cagcttaggc tacacagaga aactatctaa aaaataatta ctaactactt    12420
aataggagat tggatgttaa gatctggtca ctaagaggca gaattgagat tcgaagccag    12480 tatttctac ctggtatgtt ttaaattgca gtaaggatct aagtgtagat atataataat    12540
aagattctat tgatctctgc aacaacagag agtgttagat ttgtttggaa aaaaatatta    12600
tcagccaaca tcttctacca tttcagtata gcacagagta cccacccata tctccccacc    12660 catccccat accagactgg ttattgattt tcatggtgac tggcctgaga agattaaaaa    12720
aagtaatgct accttattgg gagtgtccca tggaccaaga tagcaactgt catagctacc    12780
gtcacactgc tttgatcaag aagacccttt gaggaactga aaacagaacc ttaggcacat    12840
ctgttgcttt cgctcccatc ctcctccaac agcctgggtg gtgcactcca cacccttca    12900 agtttccaaa gcctcataca cctgctccct accccagcac ctggccaagg ctgtatccag    12960
cactgggatg aaaatgatac cccacctcca tcttgtttga tattactcta tctcaagccc    13020
caggttagtc cccagtccca atgcttttgc acagtcaaaa ctcaacttgg aataatcagt    13080
atccttgaag agttctgata tggtcactgg gcccatatac catgtaagac atgtggaaaa    13140
gatgtttcat ggggcccaga cacgttctag aagtacctga gagtggcaaa aaatagttgt    13200
gctaaatagt ttggccatct ttaggctgag agactaggaa atacagcgat ggactatatc    13260
agcattgcag gatagttgtc agtaaacacc ccacaaccca taacagaagt attctcttct    13320
ttctatatcc cttttccatc catgtagatg gctgtcttca tatttgttct agacggccgg    13380
cc                                                                   13382

<210> SEQ ID NO 96
<211> LENGTH: 4638
<212> TYPE: DNA
<213> ORGANISM: Artificial Sequence
<220> FEATURE:
<223> OTHER INFORMATION: pSELECT-IGKV1-39/J-Ck

<400> SEQUENCE: 96
gcggccgcaa taaatatct ttattttcat tacatctgtg tgttggtttt ttgtgtgaat    60
cgtaactaac atacgctctc catcaaaaca aaacgaaaca aaacaaacta gcaaaatagg    120
```

```
ctgtccccag tgcaagtgca ggtgccagaa catttctcta tcgaaggatc tgcgatcgct    180
ccggtgcccg tcagtgggca gagcgcacat cgcccacagt ccccgagaag ttgggggggag   240
gggtcggcaa ttgaacgggt gcctagagaa ggtggcgcgg ggtaaactgg gaaagtgatg    300
tcgtgtactg gctccgcctt tttcccgagg gtggggggaga accgtatata agtgcagtag   360
tcgccgtgaa cgttcttttt cgcaacgggt ttgccgccag aacacagctg aagcttcgag    420
gggctcgcat ctctccttca cgcgcccgcc gccctacctg aggccgccat ccacgccggt    480
tgagtcgcgt tctgccgcct cccgcctgtg gtgcctcctg aactgcgtcc gccgtctagg    540
taagtttaaa gctcaggtcg agaccgggcc tttgtccggc gctcccttgg agcctaccta    600
gactcagccg gctctccacg cttttgcctga ccctgcttgc tcaactctac gtctttgttt   660
cgttttctgt tctgcgccgt tacagatcca agctgtgacc ggcgcctacc tgagatcacc    720
ggcgtgtcga cgccaccatg gacatgagag tgcccgccca gctcctgggg ctcctgctac    780
tctggctccg aggtaaggat ggagaacact aggaatttac tcagccagtg tgctcagtac    840
tgactggaac ttcagggaag ttctctgata acatgattaa tagtaagaat atttgttttt    900
atgtttccaa tctcaggtgc cagatgtgac atccagatga cccagagccc cagcagcctg    960
agcgccagcg tgggcgacag agtgaccatc acctgcagag ccagccagag catcagcagc   1020
tacctgaact ggtatcagca gaagcccggc aaggccccca agctgctgat ctacgccgcc   1080
agctccctgc agagcggcgt gcccagcaga ttcagcggca gcggctccgg caccgacttc   1140
accctgacca tcagcagcct gcagcccgag gacttcgcca cctactactg ccagcagagc   1200
tacagcaccc cccccacctt cggccagggc accaaggtgg agatcaagag agccgacgcc   1260
gctcccaccg tgtccatctt ccccccagc atggaacagc tgacctctgg cggagccacc   1320
gtggtctgct tcgtgaacaa cttctacccc agagacatca gcgtgaagtg gaagatcgac   1380
ggcagcgagc agagggacgg cgtgctggac agcgtgaccg accaggacag caaggactcc   1440
acctacagca tgagcagcac cctgagcctg accaaggtgg agtacgagag gcacaacctg   1500
tacacctgcg aggtggtgca aagaccagc tccagccccg tggtcaagtc cttcaaccgg    1560
aacgagtgtt gagctagctg gccagacatg ataagataca ttgatgagtt tggacaaacc   1620
acaactagaa tgcagtgaaa aaaatgcttt atttgtgaaa tttgtgatgc tattgcttta   1680
tttgtaacca ttataagctg caataaacaa gttaacaaca caattgcat tcattttatg    1740
tttcaggttc agggggaggt gtgggaggtt ttttaaagca agtaaaacct ctacaaatgt   1800
ggtatgaat tctaaaatac agcatagcaa aactttaacc tccaaatcaa gcctctactt    1860
gaatccttt ctgagggatg aataaggcat aggcatcagg ggctgttgcc aatgtgcatt    1920
agctgtttgc agcctcacct tctttcatgg agtttaagat atagtgtatt ttcccaaggt   1980
ttgaactagc tcttcatttc tttatgtttt aaatgcactg acctcccaca ttccctttttt   2040
agtaaaatat tcagaaataa tttaaataca tcattgcaat gaaaataaat gttttttatt   2100
aggcagaatc cagatgctca aggcccttca taatatcccc cagtttagta gttggactta   2160
gggaacaaag gaacctttaa tagaaattgg acagcaagaa agcgagcttc tagcgaattc   2220
tcgactcatt cctttgccct cggacgagtg ctggggcgtc ggtttccact atcggcgagt   2280
acttctacac agccatcggt ccagacggcc gcgcttctgc gggcgatttg tgtacgcccg   2340
acagtcccgg ctccggatcg gacgattgcg tcgcatcgac cctgcgccca agctgcatca   2400
tcgaaattgc cgtcaaccaa gctctgatag agttggtcaa gaccaatgcg gagcatatac   2460
```

```
gcccggagcc gcggcgatcc tgcaagctcc ggatgcctcc gctcgaagta gcgcgtctgc    2520
tgctccatac aagccaacca cggcctccag aagaagatgt tggcgacctc gtattgggaa    2580
tccccgaaca tcgcctcgct ccagtcaatg accgctgtta tgcggccatt gtccgtcagg    2640
acattgttgg agccgaaatc cgcgtgcacg aggtgccgga cttcggggca gtcctcggcc    2700
caaagcatca gctcatcgag agcctgcgcg acggacgcac tgacggtgtc gtccatcaca    2760
gtttgccagt gatacacatg gggatcagca atcgcgcata tgaaatcacg ccatgtagtg    2820
tattgaccga ttccttgcgg tccgaatggg ccgaacccgc tcgtctggct aagatcggcc    2880
gcagcgatcg catccatgag ctccgcgacg ggttgcagaa cagcgggcag ttcggtttca    2940
ggcaggtctt gcaacgtgac accctgtgca cggcgggaga tgcaataggt caggctctcg    3000
ctgaattccc caatgtcaag cacttccgga atcgggagcg cggccgatgc aaagtgccga    3060
taaacataac gatctttgta gaaaccatcg gcgcagctat ttacccgcag acatatccca    3120
cgccctccta catcgaagct gaaagcacga gattcttcgc cctccgagag ctgcatcagg    3180
tcggagacgc tgtcgaactt ttcgatcaga aacttctcga cagacgtcgc ggtgagttca    3240
ggcttttttca tgatggccct cctatagtga gtcgtattat actatgccga tatactatgc    3300
cgatgattaa ttgtcaaaac agcgtggatg gcgtctccag cttatctgac ggttcactaa    3360
acgagctctg cttatataga cctcccaccg tacacgccta ccgcccattt gcgtcaatgg    3420
ggcggagttg ttacgacatt ttggaaagtc ccgttgattt actagtcaaa acaaactccc    3480
attgacgtca atggggtgga gacttggaaa tccccgtgag tcaaaccgct atccacgccc    3540
attgatgtac tgccaaaacc gcatcatcat ggtaatagcg atgactaata cgtagatgta    3600
ctgccaagta ggaaagtccc ataaggtcat gtactgggca taatgccagg cgggccattt    3660
accgtcattg acgtcaatag ggggcgtact tggcatatga tacacttgat gtactgccaa    3720
gtgggcagtt taccgtaaat actccaccca ttgacgtcaa tggaaagtcc ctattggcgt    3780
tactatggga acatacgtca ttattgacgt caatgggcgg gggtcgttgg gcggtcagcc    3840
aggcgggcca tttaccgtaa gttatgtaac gcctgcaggt taattaagaa catgtgagca    3900
aaaggccagc aaaaggccag gaaccgtaaa aaggccgcgt tgctggcgtt tttccatagg    3960
ctccgccccc ctgacgagca tcacaaaaat cgacgctcaa gtcagaggtg gcgaaacccg    4020
acaggactat aaagatacca ggcgtttccc cctggaagct ccctcgtgcg ctctcctgtt    4080
ccgaccctgc cgcttaccgg atacctgtcc gcctttctcc cttcgggaag cgtggcgctt    4140
tctcatagct cacgctgtag gtatctcagt tcggtgtagg tcgttcgctc caagctgggc    4200
tgtgtgcacg aaccccccgt tcagcccgac cgctgcgcct tatccggtaa ctatcgtctt    4260
gagtccaacc cggtaagaca cgacttatcg ccactggcag cagccactgg taacaggatt    4320
agcagagcga ggtatgtagg cggtgctaca gagttcttga agtggtggcc taactacggc    4380
tacactagaa gaacagtatt tggtatctgc gctctgctga gccagttac cttcggaaaa    4440
agagttggta gctcttgatc cggcaaacaa accaccgctg gtagcggtgg ttttttttgtt    4500
tgcaagcagc agattacgcg cagaaaaaaa ggatctcaag aagatccttt gatcttttct    4560
acggggtctg acgctcagtg gaacgaaaac tcacgttaag ggattttggt catggctagt    4620
taattaacat ttaaatca                                                 4638
```

<210> SEQ ID NO 97
<211> LENGTH: 5349
<212> TYPE: DNA
<213> ORGANISM: Artificial Sequence
<220> FEATURE:
<223> OTHER INFORMATION: pSelect-IGVL2-14/J-Ck

<400> SEQUENCE: 97

```
gcggccgcaa taaaatatct ttattttcat tacatctgtg tgttggtttt ttgtgtgaat      60
cgtaactaac atacgctctc catcaaaaca aaacgaaaca aaacaaacta gcaaaatagg     120
ctgtccccag tgcaagtgca ggtgccagaa catttctcta tcgaaggatc tgcgatcgct     180
ccggtgcccg tcagtgggca gagcgcacat cgcccacagt ccccgagaag ttgggggag      240
gggtcggcaa ttgaacgggt gcctagagaa ggtggcgcgg ggtaaactgg aaagtgatg      300
tcgtgtactg gctccgcctt tttcccgagg gtgggggaga accgtatata agtgcagtag     360
tcgccgtgaa cgttcttttt cgcaacgggt ttgccgccag aacacagctg aagcttcgag     420
gggctcgcat ctctccttca cgcgcccgcc gccctacctg aggccgccat ccacgccggt     480
tgagtcgcgt tctgccgcct cccgcctgtg gtgcctcctg aactgcgtcc gccgtctagg     540
taagtttaaa gctcaggtcg agaccggcc  tttgtccggc gctcccttgg agcctaccta     600
gactcagccg gctctccacg ctttgcctga ccctgcttgc tcaactctac gtctttgttt     660
cgttttctgt tctgcgccgt tacagatcca agctgtgacc ggcgcctacc tgagatcacc     720
ggcgtgtcga cgccaccatg gacatgagag tgcccgccca gctcctgggg ctcctgctac     780
tctggctccg aggtaaggat ggagaacact aggaatttac tcagccagtg tgctcagtac     840
tgactggaac ttcagggaag ttctctgata acatgattaa tagtaagaat atttgttttt     900
atgtttccaa tctcaggtgc cagatgtcag tctgccctga cccagcccgc ctctgtgtct     960
ggcagccctg gccagagcat caccatcagc tgcaccggca ccagcagcga cgtgggcggc    1020
tacaactacg tgtcctggta tcagcagcac cccggcaagg cccccaagct gatgatctac    1080
gaggtgtcca acagacccag cggcgtgagc aacagattca gcggcagcaa gagcggcaac    1140
accgccagcc tgaccatcag cggcctccag gctgaggacg aggccgacta ctactgcagc    1200
agctacacca gcagctccac cctggtgttt ggcggcggaa caaagctgac cgtgctgaga    1260
gccgacgccg ctcccaccgt gtccatcttc cccccagca tggaacagct gacctctggc    1320
ggagccaccg tggtctgctt cgtgaacaac ttctaccca gagacatcag cgtgaagtgg    1380
aagatcgacg gcagcgagca gagggacggc gtgctggaca gcgtgaccga ccaggacagc    1440
aaggactcca cctacagcat gagcagcacc ctgagcctga ccaaggtgga gtacgagagg    1500
cacaacctgt acacctgcga ggtggtgcac aagaccagct ccagccccgt ggtcaagtcc    1560
ttcaaccgga acgagtgttg agctagctgg ccagacatga taagatacat tgatgagttt    1620
ggacaaacca caactagact gactcagcct gcctccgtgt ctgggtctcc tggacagtcg    1680
atcaccatct cctgcactgg aaccagcagt gacgttggtg gttataacta tgtctcctgg    1740
taccaacagc acccaggcaa agcccccaaa ctcatgattt atgaggtcag taatcggccc    1800
tcagggggttt ctaatcgctt ctctggctcc aagtctggca acacggcctc cctgaccatc    1860
tctgggctcc aggctgagga cgaggctgat tattactgca gctcatatac aagcagcagc    1920
actctcgtat tcggcggagg gaccaagctg accgtcctac gggctgatgc tgcaccaact    1980
gtatccatct tcccaccatc catgaacag  ttaaacatctg gaggtgccac agtcgtgtgc    2040
ttcgtgaaca acttctatcc cagagacatc agtgtcaagt ggaagattga tggcagtgaa    2100
caacgagatg gtgtcctgga cagtgttact gatcaggaca gcaaagacag cacgtacagc    2160
atgagcagca ccctctcgtt gaccaaggtt gaatatgaaa ggcataacct ctatacctgt    2220
```

```
gaggttgttc ataagacatc atcctcaccc gtcgtcaaga gcttcaacag gaatgagtgt    2280
taggctagct ggccagacat gataagatac attgatgagt ttggacaaac cacaactaga    2340
atgcagtgaa aaaaatgctt tatttgtgaa atttgtgatg ctattgcttt atttgtaacc    2400
attataagct gcaataaaca agttaacaac aacaattgca ttcattttat gtttcaggtt    2460
caggggagg tgtgggaggt ttttaaagc aagtaaaacc tctacaaatg tggtatggaa     2520
ttctaaaata cagcatagca aaactttaac ctccaaatca agcctctact tgaatccttt    2580
tctgagggat gaataaggca taggcatcag ggctgttgc caatgtgcat tagctgtttg     2640
cagcctcacc ttctttcatg gagtttaaga tatagtgtat tttcccaagg tttgaactag    2700
ctcttcattt ctttatgttt taaatgcact gacctcccac attccttttt tagtaaaata    2760
ttcagaaata atttaaatac atcattgcaa tgaaaataaa tgttttttat taggcagaat    2820
ccagatgctc aaggcccttc ataatatccc ccagtttagt agttggactt agggaacaaa    2880
ggaaccttta atagaaattg gacagcaaga aagcgagctt ctagcgaatt ctcgactcat    2940
tcctttgccc tcggacgagt gctggggcgt cggtttccac tatcggcgag tacttctaca    3000
cagccatcgg tccagacggc cgcgcttctg cgggcgattt gtgtacgccc gacagtcccg    3060
gctccggatc ggacgattgc gtcgcatcga ccctgcgccc aagctgcatc atcgaaattg    3120
ccgtcaacca agctctgata gagttggtca agaccaatgc ggagcatata cgcccggagc    3180
cgcggcgatc ctgcaagctc cggatgcctc cgctcgaagt agcgcgtctg ctgctccata    3240
caagccaacc acggcctcca gaagaagatg ttggcgacct cgtattggga atccccgaac    3300
atcgcctcgc tccagtcaat gaccgctgtt atgcggccat tgtccgtcag gacattgttg    3360
gagccgaaat ccgcgtgcac gaggtgccgg acttcggggc agtcctcggc ccaaagcatc    3420
agctcatcga gagcctgcgc gacggacgca ctgacggtgt cgtccatcac agtttgccag    3480
tgatacacat ggggatcagc aatcgcgcat atgaaatcac gccatgtagt gtattgaccg    3540
attccttgcg gtccgaatgg gccgaacccg ctcgtctggc taagatcggc cgcagcgatc    3600
gcatccatga gctccgcgac gggttgcaga acagcgggca gttcggtttc aggcaggtct    3660
tgcaacgtga caccctgtgc acggcgggag atgcaatagg tcaggctctc gctgaattcc    3720
ccaatgtcaa gcacttccgg aatcgggagc gcggccgatg caaagtgccg ataaacataa    3780
cgatctttgt agaaaccatc ggcgcagcta tttacccgca ggacatatcc acgcctcct    3840
acatcgaagc tgaaagcacg agattcttcg ccctccgaga gctgcatcag gtcggagacg    3900
ctgtcgaact tttcgatcag aaacttctcg acagacgtcg cggtgagttc aggctttttc    3960
atgatggccc tcctatagtg agtcgtatta tactatgccg atatactatg ccgatgatta    4020
attgtcaaaa cagcgtggat ggcgtctcca gcttatctga cggttcacta aacgagctct    4080
gcttatatag acctcccacc gtacacgcct accgcccatt tgcgtcaatg gggcggagtt    4140
gttacgacat tttggaaagt cccgttgatt tactagtcaa acaaactcc cattgacgtc     4200
aatggggtgg agacttggaa atccccgtga gtcaaaccgc tatccacgcc cattgatgta    4260
ctgccaaaac cgcatcatca tggtaatagc gatgactaat acgtagatgt actgccaagt    4320
aggaaagtcc cataaggtca tgtactgggc ataatgccag gcgggccatt taccgtcatt    4380
gacgtcaata gggggcgtac ttggcatatg atacacttga tgtactgcca gtgggcagt     4440
ttaccgtaaa tactccaccc attgacgtca atggaaagtc cctattggcg ttactatggg    4500
aacatacgtc attattgacg tcaatgggcg gggtcgttg gcggtcagc caggcgggcc      4560
atttaccgta agttatgtaa cgcctgcagg ttaattaaga acatgtgagc aaaaggccag    4620
```

| | |
|---|---|
| caaaaggcca ggaaccgtaa aaaggccgcg ttgctggcgt ttttccatag gctccgcccc | 4680 |
| cctgacgagc atcacaaaaa tcgacgctca agtcagaggg ggcgaaaccc gacaggacta | 4740 |
| taaagatacc aggcgtttcc ccctggaagc tccctcgtgc gctctcctgt tccgaccctg | 4800 |
| ccgcttaccg gatacctgtc cgcctttctc ccttcgggaa gcgtggcgct ttctcatagc | 4860 |
| tcacgctgta ggtatctcag ttcggtgtag tcgttcgct ccaagctggg ctgtgtgcac | 4920 |
| gaaccccccg ttcagcccga ccgctgcgcc ttatccggta actatcgtct gagtccaac | 4980 |
| ccggtaagac acgacttatc gccactggca gcagccactg gtaacaggat tagcagagcg | 5040 |
| aggtatgtag gcggtgctac agagttcttg aagtggtggc ctaactacgg ctacactaga | 5100 |
| agaacagtat ttggtatctg cgctctgctg aagccagtta ccttcggaaa aagagttggt | 5160 |
| agctcttgat ccggcaaaca aaccaccgct ggtagcggtg gtttttttgt ttgcaagcag | 5220 |
| cagattacgc gcagaaaaaa aggatctcaa gaagatcctt tgatcttttc tacggggtct | 5280 |
| gacgctcagt ggaacgaaaa ctcacgttaa gggattttgg tcatgctag ttaattaaca | 5340 |
| tttaaatca | 5349 |

<210> SEQ ID NO 98
<211> LENGTH: 6772
<212> TYPE: DNA
<213> ORGANISM: Artificial Sequence
<220> FEATURE:
<223> OTHER INFORMATION: MV1043

<400> SEQUENCE: 98

| | |
|---|---|
| cttgatttgg gtgatggttc acgtagtggg ccatcgccct gatagacggt ttttcgccct | 60 |
| ttgacgttgg agtccacgtt ctttaatagt ggactcttgt tccaaactgg aacaacactc | 120 |
| aactctatct cgggctattc ttttgattta agggatttt gccgatttc ggtctattgg | 180 |
| ttaaaaatg agctgattta caaaaattt aacgcgaatt ttaacaaaat attaacgttt | 240 |
| acaatttat ggtgcagtct cagtacaatc tgctctgatg ccgcatagtt aagccagccc | 300 |
| cgacacccgc caacacccgc tgacgcgccc tgacgggctt gtctgctccc ggcatccgct | 360 |
| tacagacaag ctgtgaccgt ctccgggagc tgcatgtgtc agaggttttc accgtcatca | 420 |
| ccgaaacgcg cgagacgaaa gggcctcgtg atacgcctat ttttataggt taatgtcatg | 480 |
| ataataatgg tttcttagac gtcaggtggc acttttcggg gaaatgtgcg cggaaccct | 540 |
| atttgtttat ttttctaaat acattcaaat atgtatccgc tcatgagaca ataaccctga | 600 |
| taaatgcttc aataatattg aaaaggaag agtatgagta ttcaacattt ccgtgtcgcc | 660 |
| cttattccct tttttgcggc attttgcctt cctgtttttg ctcacccaga aacgctggtg | 720 |
| aaagtaaaag atgctgaaga tcagttgggt gcccgagtgg gttacatcga actggatctc | 780 |
| aacagcggta agatccttga gttttcgc cccgaagaac gttttccaat gatgagcact | 840 |
| tttaaagttc tgctatgtgg cgcggtatta tcccgtattg acgccgggca agagcaactc | 900 |
| ggtcgccgca tacactattc tcagaatgac ttggttgagt actcaccagt cacagaaaag | 960 |
| catcttacgg atggcatgac agtaagagaa ttatgcagtg ctgccataac catgagtgat | 1020 |
| aacactgcgg ccaacttact tctgacaacg atcggaggac cgaaggagct aaccgctttt | 1080 |
| ttgcacaaca tgggggatca tgtaactcgc cttgatcgtt gggaaccgga gctgaatgaa | 1140 |
| gccataccaa acgacgagcg tgacaccacg atgcctgtag caatggcaac aacgttgcgc | 1200 |
| aaactattaa ctggcgaact acttactcta gcttcccggc aacaattaat agactggatg | 1260 |

```
gaggcggata aagttgcagg accacttctg cgctcggccc ttccggctgg ctggtttatt    1320
gctgataaat ctggagccgg tgagcgtggg tctcgcggta tcattgcagc actggggcca    1380
gatggtaagc cctcccgtat cgtagttatc tacacgacgg ggagtcaggc aactatggat    1440
gaacgaaata gacagatcgc tgagataggt gcctcactga ttaagcattg gtaactgtca    1500
gaccaagttt actcatatat actttagatt gatttaaaac ttcattttta atttaaaagg    1560
atctaggtga agatccttt tgataatctc atgaccaaaa tcccttaacg tgagttttcg    1620
ttccactgag cgtcagaccc cgtagaaaag atcaaaggat cttcttgaga tcctttttt    1680 ctgcgcgtaa tctgctgctt gcaaacaaaa aaaccaccgc taccagcggt ggtttgtttg    1740
ccggatcaag agctaccaac tcttttccg aaggtaactg gcttcagcag agcgcagata    1800
ccaaatactg ttcttctagt gtagccgtag ttaggccacc acttcaagaa ctctgtagca    1860
ccgcctacat acctcgctct gctaatcctg ttaccagtgg ctgctgccag tggcgataag    1920
tcgtgtctta ccgggttgga ctcaagacga tagttaccgg ataaggcgca gcggtcgggc    1980
tgaacggggg gttcgtgcat acagcccagc ttggagcgaa cgacctacac cgaactgaga    2040
tacctacagc gtgagctatg agaaagcgcc acgcttcccg aagggagaaa ggcggacagg    2100
tatccggtaa gcggcaggt cggaacagga gagcgcacga gggagcttcc agggggaaac    2160
gcctggtatc tttatagtcc tgtcgggttt cgccacctct gacttgagcg tcgatttttg    2220
tgatgctcgt cagggggggcg gagcctatgg aaaaacgcca gcaacgcggc cttttacgg    2280 ttcctggcct tttgctggcc ttttgctcac atgttcttc ctgcgttatc ccctgattct    2340
gtggataacc gtattaccgc ctttgagtga gctgataccg ctcgccgcag ccgaacgacc    2400
gagcgcagcg agtcagtgag cgaggaagcg gaagagcgcc caatacgcaa accgcctctc    2460
cccgcgcgtt ggccgattca ttaatgcagc tggcacgaca ggtttcccga ctggaaagcg    2520
ggcagtgagc gcaacgcaat taatgtgagt tagctcactc attaggcacc ccaggcttta    2580
cactttatgc ttccggctcg tatgttgtgt ggaattgtga gcggataaca atttcacaca    2640
ggaaacagct atgaccatga ttacgccaag ctttggagcc tttttttgg agattttcaa    2700 cgtgaaaaaa ttattattcg caattccttt agttgttcct ttctattctc acagtgcaca    2760
gatccaaatg acccagtctc catcctccct gtctgcatct gtaggagaca gagtcaccat    2820
cacttgccgg gcaagtcaga gcattagcag ctacttaaat tggtatcagc agaaaccagg    2880
gaaagcccct aagctcctga tctatgctgc atccagtttg caaagtgggg tcccatcaag    2940
gttcagtggc agtggatctg ggacagattt cactctcacc atcagcagtc tgcaacctga    3000
agattttgca acttactact gtcaacagag ttacagtacc cctccaacgt tcggccaagg    3060
gaccaagctc gagatcaaac gtactgtggc tgcaccatct gtcttcatct tcccgccatc    3120
tgatgagcag ttgaaatctg gaactgcctc tgttgtgtgc ctgctgaata acttctatcc    3180
cagagaggcc aaagtacagt ggaaggtgga taacgccctc caatcgggta actcccagga    3240
gagtgtcaca gagcaggaca gcaaggacag cacctacagc ctcagcagca ccctgacgct    3300
gagcaaagca gactacgaga aacacaaagt ctacgcctgc gaagtcaccc atcagggcct    3360
gagctcgccc gtcacaaaga gcttcaacag gggagagtgt tagtaaggcg cgccaattct    3420
atttcaagga gacagtcata atgaaatacc tattgcctac ggcagccgct ggattgttat    3480
tactcgcggc ccagccggcc atggcgatgc ctgcttgccg aatatcatgg tggaaaatgg    3540
ccgcttttct ggattcatcg actgtggccg gctgggtgtg gcggaccgct atcaggacat    3600
agcgttggct acccgtgata ttgctgaaga gcttggcggc gaatgggctg accgcttcct    3660
```

```
cgtgctttac ggtatcgccg ctcccgattc gcagcgcatc gccttctatc gccttcttga    3720
cgagttcttc tgagcgggac tctggggttc ggtgctacga gatttcgatt ccaccgccgc    3780
cttctatgaa aggttgggct tcggaatcgt tttccgggac gccggctgga tgatcctcca    3840
gcgcggggat ctcatgctgg agttcttcgc ccaccccaac ttgtttattg cagcttataa    3900
tggttacaaa taaagcaata gcatcacaaa tttcacaaat aaagcatttt tttcactgca    3960
ttctagttgt ggtttgtcca aactcatcaa tgtatcttat catgtctgta taccgtcgac    4020
ctctagctag agcttggcgt aatcatggtc atagctgttt cctgtgtgaa attgttatcc    4080
gctcacaatt ccacacaaca tacgagccgg aagcataaag tgtaaagcct ggggtgccta    4140
atgagtgagc taactcacat taattgcgtt gcgctcactg cccgctttcc agtcgggaaa    4200
cctgtcgtgc cagaattgca tgaagaatct gcttagggtt aggcgttttg cgctgcttcg    4260
ctaggtggtc aatattggcc attagccata ttattcattg gttatatagc ataaatcaat    4320
attggctatt ggccattgca tacgttgtat ccatatcata atatgtacat ttatattggc    4380
tcatgtccaa cattaccgcc atgttgacat tgattattga ctagttatta atagtaatca    4440 attacgggt cattagttca tagcccatat atggagttcc gcgttacata acttacggta    4500
aatggcccgc ctggctgacc gcccaacgac ccccgcccat tgacgtcaat aatgacgtat    4560
gttcccatag taacgccaat agggactttc cattgacgtc aatgggtgga gtatttacgg    4620
taaactgccc acttggcagt acatcaagtg tatcatatgc caagtacgcc ccctattgac    4680
gtcaatgacg gtcaccgtct caagcgcctc caccaagggc ccatcggtct tcccctggc    4740 accctcctcc aagagcacct ctgggggcac agcggccctg ggctgcctgg tcaaggacta    4800
cttccccgaa ccggtgacgg tgtcgtggaa ctcaggcgcc ctgaccagcg gcgtccacac    4860
cttcccggct gtcctacagt cctcaggact ctactccctc agcagcgtag tgaccgtgcc    4920
ctccagcagc ttgggcaccc agacctacat ctgcaacgtg aatcacaagc ccagcaacac    4980
caaggtggac aagaaagttg agcccaaatc ttgtgcggcc gcacatcatc atcaccatca    5040
cggggccgca gaacaaaaac tcatctcaga agaggatctg aatggggccg catagactgt    5100
tgaaagttgt ttagcaaaac ctcatacaga aaattcattt actaacgtct ggaaagacga    5160
caaaacttta gatcgttacg ctaactatga gggctgtctg tggaatgcta caggcgttgt    5220
ggtttgtact ggtgacgaaa ctcagtgtta cggtacatgg gttcctattg gcttgctat    5280 ccctgaaaat gagggtggtg gctctgaggg tggcggttct gagggtggcg gttctgaggg    5340
tggcggtact aaacctcctg agtacggtga tacacctatt ccgggctata cttatatcaa    5400
ccctctcgac ggcacttatc cgcctggtac tgagcaaaac cccgctaatc ctaatccttc    5460
tcttgaggag tctcagcctc ttaatacttt catgtttcag aataataggt tccgaaatag    5520
gcagggtgca ttaactgttt atacgggcac tgttactcaa ggcactgacc ccgttaaaac    5580
ttattaccag tacactcctg tatcatcaaa agccatgtat gacgcttact ggaacgtaa    5640 attcagagac tgcgctttcc attctggctt taatgaggat ccattcgttt gtgaatatca    5700
aggccaatcg tctgacctgc ctcaacctcc tgtcaatgct ggcggcggct ctggtggtgg    5760
ttctggtggc ggctctgagg gtggcggctc tgagggtggc ggctctgagg gtggcggttc    5820
tgagggtggc ggctctgagg gtggcggttc cggtggcggc tccggttccg gtgattttga    5880
ttatgaaaaa atggcaaacg ctaataaggg ggctatgacc gaaaatgccg atgaaaacgc    5940
gctacagtct gacgctaaag gcaaacttga ttctgtcgct actgattacg gtgctgctat    6000
```

| | |
|---|---:|
| cgatggtttc attggtgacg tttccggcct tgctaatggt aatggtgcta ctggtgattt | 6060 |
| tgctggctct aattcccaaa tggctcaagt cggtgacggt gataattcac ctttaatgaa | 6120 |
| taatttccgt caatatttac cttctttgcc tcagtcggtt gaatgtcgcc cttatgtctt | 6180 |
| tggcgctggg aaaccatatg aattttctat tgattgtgac aaaataaact tattccgtgg | 6240 |
| tgtctttgcg tttcttttat atgttgccac ctttatgtat gtattttcga cgtttgctaa | 6300 |
| catactgcgt aataaggagt cttaataaga attcactggc cgtcgtttta caacgtcgtg | 6360 |
| actgggaaaa ccctggcgtt acccaactta atcgccttgc agcacatccc cctttcgcca | 6420 |
| gctggcgtaa tagcgaagag gcccgcaccg atcgcccttc ccaacagttg cgcagcctga | 6480 |
| atggcgaatg gcgcctgatg cggtattttc tccttacgca tctgtgcggt atttcacacc | 6540 |
| gcatacgtca aagcaaccat agtacgcgcc ctgtagcggc gcattaagcg cggcgggtgt | 6600 |
| ggtggttacg cgcagcgtga ccgctacact tgccagcgcc ttagcgcccg ctcctttcgc | 6660 |
| tttcttccct cctttctcg ccacgttcgc cggctttccc cgtcaagctc taaatcgggg | 6720 |
| gctcccttta gggttccgat ttagtgcttt acggcacctc gaccccaaaa aa | 6772 |

<210> SEQ ID NO 99
<211> LENGTH: 10293
<212> TYPE: DNA
<213> ORGANISM: Artificial Sequence
<220> FEATURE:
<223> OTHER INFORMATION: MV1057

<400> SEQUENCE: 99

| | |
|---|---:|
| tactcttcct ttttcaatat tattgaagca tttatcaggg ttattgtctc atgagcggat | 60 |
| acatatttga atgtatttag aaaaataaac aatagggt tccgcgcaca tttccccgaa | 120 |
| aagtgccacc tgacgtcgac ggatcgggag atctcccgat cccctatggt gcactctcag | 180 |
| tacaatctgc tctgatgccg catagttaag ccagtatctg ctccctgctt gtgtgttgga | 240 |
| ggtcgctgag tagtgcgcga gcaaaattta agctacaaca aggcaaggct tgaccgacaa | 300 |
| ttgcatgaag aatctgctta gggttaggcg ttttgcgctg cttcgctagg tggtcaatat | 360 |
| tggccattag ccatattatt cattggttat atagcataaa tcaatattgg ctattggcca | 420 |
| ttgcatacgt tgtatccata tcataatatg tacatttata ttggctcatg tccaacatta | 480 |
| ccgccatgtt gacattgatt attgactagt tattaatagt aatcaattac ggggtcatta | 540 |
| gttcatagcc catatatgga gttccgcgtt acataactta cggtaaatgg cccgcctggc | 600 |
| tgaccgccca acgacccccg cccattgacg tcaataatga cgtatgttcc catagtaacg | 660 |
| ccaataggga ctttccattg acgtcaatgg gtggagtatt tacggtaaac tgcccacttg | 720 |
| gcagtacatc aagtgtatca tatgccaagt acgccccta ttgacgtcaa tgacggtaaa | 780 |
| tggcccgcct ggcattatgc ccagtacatg accttatggg actttcctac ttggcagtac | 840 |
| atctacgtat tagtcatcgc tattaccatg gtgatgcggt tttggcagta catcaatggg | 900 |
| cgtggatagc ggtttgactc acggggattt ccaagtctcc accccattga cgtcaatggg | 960 |
| agtttgtttt ggcaccaaaa tcaacgggac tttccaaaat gtcgtaacaa ctccgcccca | 1020 |
| ttgacgcaaa tgggcggtag gcgtgtacgg tgggaggtct atataagcag agctcgttta | 1080 |
| gtgaaccgtc agatcgcctg gagacgccat ccacgctgtt tgacctcca tagaagacac | 1140 |
| cgggaccgat ccagcctccg cggccgggaa cggtgcattg gaagcttggt accggtgaat | 1200 |
| tggccggccc gcgccgtcga ggttatcgat ccgaccgacg cgttcgcgag aggccgcaat | 1260 |
| tccctagcca ccatgggatg gagctgtatc atcctcttct tggtactgct gctggcccag | 1320 |

```
ccggccatgg ggcggagaat gggcggaact gggcggagtt aggggcggga tgggcggagt    1380
taggggcggg actatggttg ctgactaatt gagatgcgga tccgctggca cgacaggttt    1440
cccgactgga aagcgggcag tgagcgcaac gcaattaatg tgagttagct cactcattag    1500
gcaccccagg ctttacactt tatgcttccg gctcgtatgt tgtgtggaat tgtgagcgga    1560
taacaatttc acacaggaaa cagctatgac catgattacg ccaagcttgg gctgcaggtt    1620
ctttccgcct cagaagccat agagcccacc gcatcccag catgcctgct attgtcttcc     1680
caatcctccc ccttgctgtc ctgccccacc ccacccccca gaatagaatg acacctactc    1740
agacaatgcg atgcaatttc ctcattttat taggaaagga cagtgggagt ggcaccttcc    1800
agggtcaagg aaggcacggg ggaggggcaa acaacagatg gctggcaact agaaggcaca    1860
gtcgaggctg atcagcgagc tctagatcat cgatgcatgg ggtcgtgcgc tcctttcggt    1920
cgggcgctgc gggtcgtggg gcgggcgtca ggcaccgggc ttgcgggtca tgcaccaggt    1980
gcgcggtcct tcgggcacct cgacgtcggg ggtgacggtg aagccgagcc gctcgtagaa    2040
ggggaggttg cggggcgcgg aggtctccag gaaggcgggc accccggcgc gctcggccgc    2100
ctccactccg gggagcacga cggcgctgcc cagacccttg ccctggtggt cgggcgagac    2160
gccgacggtg gccaggaacc acgcgggctc cttgggccgg tgcggcgcca ggaggccttc    2220
catctgttgc tgcgcggcca gcgggaacc gctcaactcg gccatgcgcg ggccgatctc     2280
ggcgaacacc gccccgctt cgacgctctc cggcgtggtc cagaccgcca ccgcggcgcc     2340
gtcgtccgcg acccacacct tgccgatgtc gagcccgacg cgcgtgagga agagttcttg    2400
cagctcggtc accgtctcca gtgctagcac caagggccca tcggtcttcc ccctggcacc    2460
ctcctccaag agcacctctg ggggcacagc ggccctgggc tgcctggtca aggactactt    2520
ccccgaaccg gtgacggtgt cgtggaactc aggcgccctg accagcggcg tgcacacctt    2580
cccggctgtc ctacagtcct caggactcta ctccctcagc agcgtcgtga ccgtgccctc    2640
cagcagcttg ggcacccaga cctacatctg caacgtgaat cacaagccca gcaacaccaa    2700
ggtggacaag agagttggtg agaggccagc acagggaggg agggtgtctg ctggaagcca    2760
ggctcagcgc tcctgcctgg acgcatcccg gctatgcagt cccagtccag ggcagcaagg    2820
caggccccgt ctgcctcttc acccggaggc ctctgcccgc ccactcatg ctcagggaga     2880 gggtcttctg gctttttccc caggctctgg gcaggcacag gctaggtgcc cctaacccag    2940
gccctgcaca caaggggca ggtgctgggc tcagacctgc caagagccat atccgggagg     3000
accctgcccc tgacctaagc ccaccccaaa ggccaaactc tccactccct cagctcggac    3060
accttctctc ctcccagatt ccagtaactc ccaatcttct ctctgcagag cccaaatctt    3120
gtgacaaaac tcacacatgc ccaccgtgcc cagcacctga actcctgggg ggaccgtcag    3180
tcttcctctt ccccccaaaa cccaaggaca cctcatgat ctcccggacc cctgaggtca     3240
catgcgtggt ggtggacgtg agccacgaag accctgaggt caagttcaac tggtacgtgg    3300
acggcgtgga ggtgcataat gccaagacaa agccgcggga ggagcagtac aacagcacgt    3360
accgtgtggt cagcgtcctc accgtcctgc accaggactg gctgaatggc aaggagtaca    3420
agtgcaaggt ctccaacaaa gccctcccag cccccatcga gaaaaccatc tccaaagcca    3480
aagggcagcc ccgagaacca caggtgtaca ccctgccccc atcccgggag gagatgacca    3540
agaaccaggt cagcctgacc tgcctggtca aaggcttcta tcccagcgac atcgccgtgg    3600
agtgggagag caatgggcag ccggagaaca actacaagac cacgcctccc gtgctggact    3660
```

```
ccgacggctc cttcttcctc tatagcaagc tcaccgtgga caagagcagg tggcagcagg    3720
ggaacgtctt ctcatgctcc gtgatgcatg aggctctgca caaccactac acgcagaaga    3780
gcctctccct gtctccgggt aaatgagttt aacggatctt aattaatccg agctcggtac    3840
caagcttaag tttaaaccgc tgatcagcct cgactgtgcc ttctagttgc cagccatctg    3900
ttgtttgccc ctccccgtg ccttccttga ccctggaagg tgccactccc actgtccttt    3960
cctaataaaa tgaggaaatt gcatcgcatt gtctgagtag tgtcattct attctggggg     4020 gtggggtggg gcaggacagc aagggggagg attgggaaga caatagcagg catgctgggg    4080
atgcggtggg ctctatggct tctgaggcgg aaagaaccag ctggggctct aggggggtatc   4140 cccacgcgcc ctgtagcggc gcattaagcg cggcgggtgt ggtggttacg cgcagcgtga    4200
ccgctacact tgccagcgcc tagcgcccgc tcctttcgct ttcttccctt cctttctcgc    4260
cacgttcgcc ggctttcccc gtcaagctct aaatcggggg ctccctttag ggttccgatt    4320
tagtgcttta cggcacctcg accccaaaaa acttgattag ggtgatggtt cacgtagtgg    4380
gccatcgccc tgatagacgg ttttcgccc tttgacgttg gagtccacgt tctttaatag    4440
tggactcttg ttccaaactg gaacaacact caacccctatc tcggtctatt cttttgattt    4500
ataagggatt ttgccgattt cggcctattg gttaaaaaat gagctgattt aacaaaaatt    4560
taacgcgaat taattctgtg aatgtgtgt cagttagggt gtggaaagtc cccaggctcc     4620
ccagcaggca gaagtatgca aagcatgcat ctcaattagt cagcaaccag gtgtggaaag    4680
tccccaggct ccccagcagg cagaagtatg caaagcatgc atctcaatta gtcagcaacc    4740
atagtcccgc ccctaactcc gcccatcccg cccctaactc cgcccagttc cgcccattct    4800
ccgccccatg gctgactaat ttttttatt tatgcagagg ccgaggccgc ctctgcctct    4860
gagctattcc agaagtagtg aggaggcttt tttggaggcc taggcttttg caaaaagctc    4920
ccgggagctt ggatatccat tttcggatct gatcaagaga caggatgagg atcgtttcgc    4980
atgattgaac aagatggatt gcacgcaggt tctccggccg cttgggtgga gaggctattc    5040
ggctatgact gggcacaaca gacaatcggc tgctctgatg ccgccgtgtt ccggctgtca    5100
gcgcaggggc gcccggttct ttttgtcaag accgacctgt ccggtgccct gaatgaactg    5160
caggacgagg cagcgcggct atcgtggctg gccacgacgg cgttccttg cgcagctgtg    5220 ctcgacgttg tcactgaagc gggaagggac tggctgctat tgggcgaagt gccggggcag    5280
gatctcctgt catctcacct tgctcctgcc gagaaagtat ccatcatggc tgatgcaatg    5340
cggcggctgc atacgcttga tccggctacc tgcccattcg accaccaagc gaaacatcgc    5400
atcgagcgag cacgtactcg gatggaagcc ggtcttgtcg atcaggatga tctggacgaa    5460
gagcatcagg ggctcgcgcc agccgaactg ttcgccaggc tcaaggcgcg catgcccgac    5520
ggcgaggatc tcgtcgtgac ccatggcgat gcctgcttgc cgaatatcat ggtggaaaat    5580
ggccgctttt ctggattcat cgactgtggc cggctgggtg tggcggaccg ctatcaggac    5640
atagcgttgg ctacccgtga tattgctgaa gagcttggcg gcgaatgggc tgaccgcttc    5700
ctcgtgcttt acggtatcgc cgctcccgat tcgcagcgca tcgccttcta tcgccttctt    5760
gacgagttct tctgagcggg actctgggt tcggtgctac gagatttcga ttccaccgcc    5820
gccttctatg aaaggttggg cttcggaatc gttttccggg acgccggctg atgatcctc     5880 cagcgcgggg atctcatgct ggagttcttc gcccacccca acttgtttat tgcagcttat    5940
aatggttaca aataaagcaa tagcatcaca aatttcacaa ataaagcatt ttttcactg     6000 cattctagtt gtggtttgtc caaactcatc aatgtatctt atcatgtctg tataccgtcg    6060
```

```
acctctagct agagcttggc gtaatcatgg tcatagctgt ttcctgtgtg aaattgttat    6120
ccgctcacaa ttccacacaa catacgagcc ggaagcataa agtgtaaagc ctggggtgcc    6180
taatgagtga gctaactcac attaattgcg ttgcgctcac tgcccgcttt ccagtcggga    6240
aacctgtcgt gccagaattg catgaagaat ctgcttaggg ttaggcgttt tgcgctgctt    6300
cgctaggtgg tcaatattgg ccattagcca tattattcat tggttatata gcataaatca    6360
atattggcta ttggccattg catacgttgt atccatatca taatatgtac atttatattg    6420
gctcatgtcc aacattaccg ccatgttgac attgattatt gactagttat taatagtaat    6480
caattacggg gtcattagtt catagcccat atatggagtt ccgcgttaca taacttacgg    6540
taaatggccc gcctggctga ccgcccaacg accccgccc attgacgtca ataatgacgt    6600
atgttcccat agtaacgcca ataggggactt tccattgacg tcaatgggtg gagtatttac    6660
ggtaaactgc ccacttggca gtacatcaag tgtatcatat gccaagtacg cccctattg    6720
acgtcaatga cggtaaatgg cccgcctggc attatgccca gtacatgacc ttatgggact    6780
ttcctacttg gcagtacatc tacgtattag tcatcgctat taccatggtg atgcggtttt    6840
ggcagtacat caatgggcgt ggatagcggt ttgactcacg gggatttcca agtctccacc    6900
ccattgacgt caatgggagt ttgttttggc accaaaatca acgggacttt ccaaaatgtc    6960
gtaacaactc cgccccattg acgcaaatgg gcggtaggcg tgtacggtgg gaggtctata    7020
taagcagagc tcgtttagtg aaccgtcaga tcgcctggag acgccatcca cgctgttttg    7080
acctccatag aagacaccgg gaccgatcca gcctccgcgg ccgggaacgg tgcattggaa    7140
gcttggtacc ggtgaattag cgcgccgtc gaggttatcg atccgaccga cgcgttcgcg    7200
agaggccgca attccctagc caccatggca tgccctggct tcctgtgggc acttgtgatc    7260
tccacctgtc ttgaattctc catggctgac atccagatga cccagtctcc atcctccctg    7320
tctgcatctg taggagacag agtcaccatc acttgccggg caagtcagag cattagcagc    7380
tacttaaatt ggtatcagca gaaaccaggg aaagccccta agctcctgat ctatgctgca    7440
tccagtttgc aaagtggggt cccatcaagg ttcagtggca gtggatctgg gacagatttc    7500
actctcacca tcagcagtct gcaacctgaa gattttgcaa cttactactg tcaacagagt    7560
tacagtaccc ctccaacgtt cggccaaggg accaaggtgg agatcaaacg taagtgcact    7620
ttgcggccgc taggaagaaa ctcaaaacat caagatttta aatacgcttc ttggtctcct    7680
tgctataatt atctgggata agcatgctgt tttctgtctg tccctaacat gccctgtgat    7740
tatccgcaaa caacacaccc aagggcagaa cttttgttact aaacaccat cctgtttgct    7800
tctttcctca ggaactgtgg ctgcaccatc tgtcttcatc ttcccgccat ctgatgagca    7860
gttgaaatct ggaactgcct ctgttgtgtg cctgctgaat aacttctatc ccagagaggc    7920
caaagtacag tggaaggtgg ataacgccct ccaatcgggt aactcccagg agagtgtcac    7980
agagcaggac agcaaggaca gcacctacag cctcagcagc accctgacgc tgagcaaagc    8040
agactacgag aaacacaaag tctacgcctg cgaagtcacc catcagggcc tgagctcgcc    8100
cgtcacaaag agcttcaaca ggggagagtg ttaggtttaa cggatccgag ctcggtacca    8160
agctcaagtt taaaccgctg atcagcctcg actgtgcctt ctagttgcca gccatctgtt    8220
gtttgcccct cccccgtgcc ttccttgacc ctggaaggtg ccactcccac tgtcctttcc    8280
taataaaatg aggaaattgc atcgcattgt ctgagtaggt gtcattctat tctggggggt    8340
ggggtggggc aggacagcaa gggggaggat tgggaagaca atagcaggca tgctggggat    8400
```

```
gcggtgggct ctatggcttc tgaggcggaa agaaccagct gcattaatga atcggccaac    8460
gcgcggggag aggcggtttg cgtattgggc gctcttccgc ttcctcgctc actgactcgc    8520
tgcgctcggt cgttcggctg cggcgagcgg tatcagctca ctcaaaggcg gtaatacggt    8580
tatccacaga atcaggggat aacgcaggaa agaacatgtg agcaaaaggc cagcaaaagg    8640
ccaggaaccg taaaaaggcc gcgttgctgg cgttttttcca taggctccgc cccctgacg    8700
agcatcacaa aaatcgacgc tcaagtcaga ggtggcgaaa cccgacagga ctataaagat    8760
accaggcgtt tccccctgga agctccctcg tgcgctctcc tgttccgacc ctgccgctta    8820
ccggatacct gtccgccttt ctcccttcgg aagcgtggc gctttctcat agctcacgct    8880
gtaggtatct cagttcggtg taggtcgttc gctccaagct gggctgtgtg cacgaacccc    8940
ccgttcagcc cgaccgctgc gccttatccg gtaactatcg tcttgagtcc aacccggtaa    9000
gacacgactt atcgccactg gcagcagcca ctggtaacag gattagcaga gcgaggtatg    9060
taggcggtgc tacagagttc ttgaagtggt ggcctaacta cggctacact agaagaacag    9120
tatttggtat ctgcgctctg ctgaagccag ttaccttcgg aaaaagagtt ggtagctctt    9180
gatccggcaa acaaaccacc gctggtagcg gtggtttttt tgtttgcaag cagcagatta    9240
cgcgcagaaa aaaaggatct caagaagatc ctttgatctt ttctacgggg tctgacgctc    9300
agtggaacga aaactcacgt taagggattt tggtcatgag attatcaaaa aggatcttca    9360
cctagatcct tttaaattaa aaatgaagtt ttaaatcaat ctaaagtata tatgagtaaa    9420
cttggtctga cagttaccaa tgcttaatca gtgaggcacc tatctcagcg atctgtctat    9480
ttcgttcatc catagttgcc tgactccccg tcgtgtagat aactacgata cgggagggct    9540
taccatctgg ccccagtgct gcaatgatac cgcgagaccc acgctcaccg gctccagatt    9600
tatcagcaat aaaccagcca gccggaaggg ccgagcgcag aagtggtcct gcaactttat    9660
ccgcctccat ccagtctatt aattgttgcc gggaagctag agtaagtagt tcgccagtta    9720
atagtttgcg caacgttgtt gccattgcta caggcatcgt ggtgtcacgc tcgtcgtttg    9780
gtatggcttc attcagctcc ggttcccaac gatcaaggcg agttacatga tcccccatgt    9840
tgtgcaaaaa agcggttagc tccttcggtc ctccgatcgt tgtcagaagt aagttggccg    9900
cagtgttatc actcatggtt atggcagcac tgcataattc tcttactgtc atgccatccg    9960
taagatgctt ttctgtgact ggtgagtact caaccaagtc attctgagaa tagtgtatgc   10020
ggcgaccgag ttgctcttgc ccggcgtcaa tacgggataa taccgcgcca catagcagaa   10080
ctttaaaagt gctcatcatt ggaaaacgtt cttcggggcg aaaactctca aggatcttac   10140
cgctgttgag atccagttcg atgtaaccca ctcgtgcacc caactgatct tcagcatctt   10200
ttactttcac cagcgtttct gggtgagcaa aaacaggaag gcaaaatgcc gcaaaaaagg   10260
gaataagggc gacacggaaa tgttgaatac tca                                10293
```

<210> SEQ ID NO 100  
<211> LENGTH: 8179  
<212> TYPE: DNA  
<213> ORGANISM: Artificial Sequence  
<220> FEATURE:  
<223> OTHER INFORMATION: pCAGGS-IgVK1-39 targeting vector

<400> SEQUENCE: 100

```
atccaggcgc ggatcaataa aagatcatta ttttcaatag atctgtgtgt tggttttttg      60
tgtgccttgg gggaggggga ggccagaatg aggcgcggcc aaggggagg gggaggccag     120
aatgaccttg ggggagggggg aggccagaat gaccttgggg gaggggagg ccagaatgag    180
```

```
gcgcggatcc ggagaagttc ctattccgaa gttcctattc ttcaaatagt ataggaactt      240
cgctcgaggg atcggccatt gaacaagatg gattgcacgc aggttctccg gccgcttggg      300
tggagaggct attcggctat gactgggcac aacagacaat cggctgctct gatgccgccg      360
tgttccggct gtcagcgcag gggcgcccgg ttcttttttgt caagaccgac ctgtccggtg     420
ccctgaatga actgcaggac gaggcagcgc ggctatcgtg gctggccacg acgggcgttc      480
cttgcgcagc tgtgctcgac gttgtcactg aagcgggaag ggactggctg ctattgggcg      540
aagtgccggg gcaggatctc ctgtcatctc accttgctcc tgccgagaaa gtatccatca      600
tggctgatgc aatgcggcgg ctgcatacgc ttgatccggc tacctgccca ttcgaccacc      660
aagcgaaaca tcgcatcgag cgagcacgta ctcggatgga agccggtctt gtcgatcagg      720
atgatctgga cgaagagcat caggggctcg cgccagccga actgttcgcc aggctcaagg      780
cgcgcatgcc cgacggcgag gatctcgtcg tgacccatgg cgatgcctgc ttgccgaata      840
tcatggtgga aaatggccgc ttttctggat tcatcgactg tggccggctg ggtgtggcgg      900
accgctatca ggacatagcg ttggctaccc gtgatattgc tgaagagctt ggcggcgaat      960
gggctgaccg cttcctcgtg ctttacggta tcgccgctcc cgattcgcag cgcatcgcct     1020
tctatcgcct tcttgacgag ttcttctgag gggatcgatc cgctgtaagt ctgcagaaat     1080
tgatgatcta ttaaacaata aagatgtcca ctaaaatgga agttttcct gtcatacttt      1140 gttaagaagg gtgagaacag agtacctaca ttttgaatgg aaggattgga gctacgggggg    1200 tgggggtggg gtgggattag ataaatgcct gctctttact gaaggctctt tactattgct     1260
ttatgataat gtttcatagt tggatatcat aatttaaaca agcaaaacca aattaagggc     1320
cagctcattc ctcccactca tgatctatag atctatagat ctctcgtggg atcattgttt     1380
ttctcttgat tcccactttg tggttctaag tactgtggtt tccaaatgtg tcagtttcat     1440
agcctgaaga acgagatcag cagcctctgt tccacataca cttcattctc agtattgttt     1500
tgccaagttc taattccatc agaagctgac tctagatggc gcgtatgcag gttttcgaca     1560
ttgattattg actagttatt aatagtaatc aattacgggg tcattagttc atagcccata     1620
tatggagttc cgcgttacat aacttacggt aaatggcccg cctggctgac cgcccaacga     1680
cccccgccca ttgacgtcaa taatgacgta tgttcccata gtaacgccaa tagggacttt     1740
ccattgacgt caatgggtgg agtatttacg gtaaactgcc cacttggcag tacatcaagt     1800
gtatcatatg ccaagtacgc ccctattga cgtcaatgac ggtaaatggc ccgcctggca      1860
ttatgcccag tacatgacct tatgggactt tcctacttgg cagtacatct acgtattagt     1920
catcgctatt accatggtcg aggtgagccc cacgttctgc ttcactctcc ccatctcccc     1980
cccctcccca cccccaattt tgtatttatt tattttttaa ttattttgtg cagcgatggg     2040
ggcggggggg gggggggcgc gcgccaggcg gggcggggcg gggcgagggg cggggcgggg     2100
cgaggcggag aggtgcggcg gcagccaatc agagcggcgc gctccgaaag tttccttttta    2160 tggcgaggcg gcggcggcgg cggccctata aaaagcgaag cgcgcggcgg gcgggagtcg     2220
ctgcgttgcc ttcgccccgt gccccgctcc gcgccgcctc gcgccgcccg cccggctct      2280 gactgaccgc gttactccca caggtgagcg ggcgggacgg cccttctcct ccgggctgta     2340
attagcgctt ggtttaatga cggctcgttt cttttctgtg gctgcgtgaa agccttaaag     2400
ggctccggga gggccctttg tgcgggggggg agcggctcgg ggggtgcgtg cgtgtgtgtg    2460
tgcgtgggga gcgccgcgtg cggcccgcgc tgcccggcgg ctgtgagcgc tgcgggcgcg     2520
```

```
gcgcggggct tgtgcgctc cgcgtgtgcg cgaggggagc gcggccgggg gcggtgcccc    2580
gcggtgcggg ggggctgcga ggggaacaaa ggctgcgtgc ggggtgtgtg cgtgggggg    2640
tgagcagggg gtgtgggcgc ggcggtcggg ctgtaacccc ccctgcacc ccctccccg     2700
agttgctgag cacggcccgg cttcgggtgc ggggctccgt gcggggcgtg gcgcggggct   2760
cgccgtgccg ggcgggggt ggcggcaggt ggggtgccg ggcggggcgg ggccgcctcg    2820
ggccggggag ggctcggggg aggggcgcgg cggccccgga gcgccggcgg ctgtcgaggc   2880
gcggcgagcc gcagccattg cctttatgg taatcgtgcg agagggcgca gggacttcct    2940
ttgtcccaaa tctgtgcgga gccgaaatct gggaggcgcc gccgcacccc ctctagcggg   3000
cgcggggcga agcggtgcgg cgccggcagg aaggaaatgg gcggggaggg ccttcgtgcg   3060
tcgccgcgcc gccgtcccct tctccctctc cagcctcggg gctgtccgcg ggggacggc    3120
tgccttcggg ggggacgggg cagggcgggg ttcggcttct ggcgtgtgac cggcggctct   3180
agaagcgttg gggtgagtac tccctctcaa aagcggcat gacttctgcg ctaagattgt   3240
cagtttccaa aaacgaggag gatttgatat tcacctggcc cgcggtgatg cctttgaggg   3300
tggccgcgtc catctggtca gaaaagacaa tctttttgtt gtcaagcttg aggtgtggca   3360
ggcttgagat ctggccatac acttgagtga cattgacatc cactttgcct ttctctccac   3420
aggtgtccac tcccagggcg gcctccggag cgatcgccga tccgcctagg caattgttta   3480
aatcggccgg ccataacttc gtataatgta tgctatacga agttatggat cctcacagta   3540
ggtggcatcg ttcctttctg actgcccgcc ccccgcatgc cgtcccgcga tattgagctc   3600
cgaacctctc gccctgccgc cgccggtgct ccgtcgccgc cgcgccgcca tggaatcgaa   3660
gccaccatgg atcttaccgg aaaactcgac gcaagaaaaa tcagagagat cctcataaag   3720
gtcaagaagg gcgaaagat cgccgtgtaa ttctagaccg gttcgagatc caggcgcgga   3780
tcaataaaag atcattattt tcaatagatc tgtgtgttgg ttttttgtgt gccttggggg   3840
aggggagggc cagaatgagg cgcggccaag gggagggg aggccagaat gaccttgggg    3900
gaggggagg ccagaatgac cttggggag ggggaggcca gaatgaggcg cgccctccgt    3960
cgacctataa cttcgtataa tgtatgctat acgaagttat ggcggccgcc accatggaca   4020
tgagagtgcc cgcccagctc ctggggctcc tgctactctg gctccgaggt aaggatggag   4080
aacactagga atttactcag ccagtgtgct cagtactgac tggaacttca gggaagttct   4140
ctgataacat gattaatagt aagaatattt gttttatgt ttccaatctc aggtgccaga    4200
tgtgacatcc agatgaccca gagccccagc agcctgagcg ccagcgtggg cgacagagtg   4260
accatcacct gcagagccag ccagagcatc agcagctacc tgaactggta tcagcagaag   4320
cccggcaagg ccccccaagct gctgatctac gccgccagct ccctgcagag cggcgtgccc   4380
agcagattca gcggcagcgg ctccggcacc gacttcaccc tgaccatcag cagcctgcag   4440
cccgaggact tcgccaccta ctactgccag cagagctaca gcaccccccc caccttcggc   4500
cagggcacca aggtggagat caagagagcc gacgccgctc ccaccgtgtc catcttcccc   4560
cccagcatgg aacagctgac ctctggcgga gccaccgtgg tctgcttcgt gaacaacttc   4620
taccccagag acatcagcgt gaagtggaag atcgacggca gcgagcagag ggacggcgtg   4680
ctggacagcg tgaccgacca ggacagcaag gactccacct acagcatgag cagcaccctg   4740
agcctgacca aggtggagta cgagaggcac aacctgtaca cctgcgaggt ggtgcacaag   4800
accagctcca gccccgtggt caagtccttc aaccggaacg agtgttgagc tagcttaaga   4860
tttaaatagg ccggccgcgt cgacctcgag atccaggcgc ggatcaataa aagatcatta   4920
```

```
ttttcaatag atctgtgtgt tggttttttg tgtgccttgg gggaggggga ggccagaatg    4980
aggcgcggcc aaggggagg gggaggccag aatgaccttg ggggagggg aggccagaat      5040 gaccttgggg gaggggagg ccagaatgag gcgcgccccc gggtaccgag ctcgaattag     5100
tggatcctca cagtaggtgg catcgttcct ttctgactgc ccgcccccg catgccgtcc     5160 cgcgatattg agctccgaac ctctcgccct gccgccgccg gtgctccgtc gccgccgcgc    5220
cgccatggaa tcgcgccggt aaccgaagtt cctatacttt ctagagaata ggaacttcgg    5280
aataggaact tcaagccggt acccagcttt tgttcccttt agtgagggtt aatttcgagc    5340
ttggcgtaat catggtcata gctgttcct gtgtgaaatt gttatccgct cacaattcca    5400
cacaacatac gagccggag cataaagtgt aaagcctggg gtgcctaatg agtgagctaa    5460
ctcacattaa ttgcgttgcg ctcactgccc gctttccagt cgggaaacct gtcgtgccag    5520
ctgcattaat gaatcggcca acgcgcgggg agaggcggtt tgcgtattgg gcgctcttcc    5580
gcttcctcgc tcactgactc gctgcgctcg gtcgttcggc tgcggcgagc ggtatcagct    5640
cactcaaagg cggtaatacg gttatccaca gaatcagggg ataacgcagg aaagaacatg    5700
tgagcaaaag gccagcaaaa ggccaggaac cgtaaaaagg ccgcgttgct ggcgttttc     5760 cataggctcc gcccccctga cgagcatcac aaaaatcgac gctcaagtca gaggtggcga    5820
aacccgacag gactataaag ataccaggcg tttccccctg gaagctccct cgtgcgctct    5880
cctgttccga ccctgccgct taccggatac ctgtccgcct ttctcccttc gggaagcgtg    5940
gcgctttctc atagctcacg ctgtaggtat ctcagttcgg tgtaggtcgt tcgctccaag    6000
ctgggctgtg tgcacgaacc ccccgttcag cccgaccgct gcgccttatc cggtaactat    6060
cgtcttgagt ccaacccggt aagacacgac ttatcgccac tggcagcagc cactggtaac    6120
aggattagca gagcgaggta tgtaggcggt gctacagagt tcttgaagtg gtggcctaac    6180
tacggctaca ctagaaggac agtatttggt atctgcgctc tgctgaagcc agttaccttc    6240
ggaaaaagag ttggtagctc ttgatccggc aaacaaacca ccgctggtag cggtggtttt    6300
tttgtttgca agcagcagat tacgcgcaga aaaaaaggat ctcaagaaga tcctttgatc    6360
ttttctacgg ggtctgacgc tcagtggaac gaaaactcac gttaagggat tttggtcatg    6420
agattatcaa aaaggatctt cacctagatc cttttaaatt aaaaatgaag ttttaaatca    6480
atctaaagta tatatgagta aacttggtct gacagttacc aatgcttaat cagtgaggca    6540
cctatctcag cgatctgtct atttcgttca tccatagttg cctgactccc cgtcgtgtag    6600
ataactacga tacgggaggg cttaccatct ggccccagtg ctgcaatgat accgcgagac    6660
ccacgctcac cggctccaga tttatcagca ataaaccagc cagccggaag ggccgagcgc    6720
agaagtggtc ctgcaacttt atccgcctcc atccagtcta ttaattgttg ccgggaagct    6780
agagtaagta gttcgccagt taatagtttg cgcaacgttg ttgccattgc tacaggcatc    6840
gtggtgtcac gctcgtcgtt tggtatggct tcattcagct ccggttccca acgatcaagg    6900
cgagttacat gatcccccat gttgtgcaaa aaagcggtta gctccttcgg tcctccgatc    6960
gttgtcagaa gtaagttggc cgcagtgtta tcactcatgg ttatggcagc actgcataat    7020
tctcttactg tcatgccatc cgtaagatgc ttttctgtga ctggtgagta ctcaaccaag    7080
tcattctgag aatagtgtat gcggcgaccg agttgctctt gcccggcgtc aatacgggat    7140
aataccgcgc cacatagcag aactttaaaa gtgctcatca ttggaaaacg ttcttcgggg    7200
cgaaaactct caaggatctt accgctgttg agatccagtt cgatgtaacc cactcgtgca    7260
```

| | |
|---|---|
| cccaactgat cttcagcatc tttactttc accagcgttt ctgggtgagc aaaaacagga | 7320 |
| aggcaaaatg ccgcaaaaaa gggaataagg gcgacacgga aatgttgaat actcatactc | 7380 |
| ttcctttttc aatattattg aagcatttat cagggttatt gtctcatgag cggatacata | 7440 |
| tttgaatgta tttagaaaaa taaacaaata ggggttccgc gcacatttcc ccgaaaagtg | 7500 |
| ccacctaaat tgtaagcgtt aatattttgt taaaattcgc gttaaatttt tgttaaatca | 7560 |
| gctcattttt taaccaatag gccgaaatcg gcaaaatccc ttataaatca aagaataga | 7620 |
| ccgagatagg gttgagtgtt gttccagttt ggaacaagag tccactatta agaacgtgg | 7680 |
| actccaacgt caaagggcga aaaccgtct atcagggcga tggcccacta cgtgaaccat | 7740 |
| caccctaatc aagttttttg gggtcgaggt gccgtaaagc actaaatcgg aaccctaaag | 7800 |
| ggagccccg atttagagct tgacggggaa agccggcgaa cgtggcgaga aggaaggga | 7860 |
| agaaagcgaa aggagcgggc gctagggcgc tggcaagtgt agcggtcacg ctgcgcgtaa | 7920 |
| ccaccacacc cgccgcgctt aatgcgccgc tacagggcgc gtcccattcg ccattcaggc | 7980 |
| tgcgcaactg ttgggaaggg cgatcggtgc gggcctcttc gctattacgc cagctggcga | 8040 |
| aaggggatg tgctgcaagg cgattaagtt gggtaacgcc agggttttcc cagtcacgac | 8100 |
| gttgtaaaac gacggccagt gagcgcgcgt aatacgactc actatagggc gaattggggg | 8160 |
| taactaagta aggatcgag | 8179 |

<210> SEQ ID NO 101
<211> LENGTH: 8188
<212> TYPE: DNA
<213> ORGANISM: Artificial Sequence
<220> FEATURE:
<223> OTHER INFORMATION: pCAGGS-IgVL2-14 targeting vector

<400> SEQUENCE: 101

| | |
|---|---|
| atccaggcgc ggatcaataa aagatcatta ttttcaatag atctgtgtgt tggttttttg | 60 |
| tgtgccttgg gggaggggga ggccagaatg aggcgcggcc aaggggagg gggaggccag | 120 |
| aatgaccttg ggggagggg aggccagaat gaccttgggg gaggggagg ccagaatgag | 180 |
| gcgcggatcc ggagaagttc ctattccgaa gttcctattc tcaaatagt ataggaactt | 240 |
| cgctcgaggg atcggccatt gaacaagatg gattgcacgc aggttctccg gccgcttggg | 300 |
| tggagaggct attcggctat gactgggcac aacagacaat cggctgctct gatgccgccg | 360 |
| tgttccggct gtcagcgcag gggcgcccgg ttcttttgt caagaccgac ctgtccggtg | 420 |
| ccctgaatga actgcaggac gaggcagcgc ggctatcgtg gctggccacg acgggcgttc | 480 |
| cttgcgcagc tgtgctcgac gttgtcactg aagcgggaag ggactggctg ctattgggcg | 540 |
| aagtgccggg gcaggatctc ctgtcatctc accttgctcc tgccgagaaa gtatccatca | 600 |
| tggctgatgc aatgcggcgg ctgcatacgc ttgatccggc tacctgccca ttcgaccacc | 660 |
| aagcgaaaca tcgcatcgag cgagcacgta ctcggatgga agccggtctt gtcgatcagg | 720 |
| atgatctgga cgaagagcat caggggctcg cgccagccga actgttcgcc aggctcaagg | 780 |
| cgcgcatgcc cgacggcgag gatctcgtcg tgacccatgg cgatgcctgc ttgccgaata | 840 |
| tcatggtgga aaatggccgc ttttctggat tcatcgactg tggccggctg ggtgtggcgg | 900 |
| accgctatca ggacatagcg ttggctaccc gtgatattgc tgaagagctt ggcggcgaat | 960 |
| gggctgaccg cttcctcgtg ctttacggta tcgccgctcc cgattcgcag cgcatcgcct | 1020 |
| tctatcgcct tcttgacgag ttcttctgag gggatcgatc cgctgtaagt ctgcagaaat | 1080 |
| tgatgatcta ttaaacaata aagatgtcca ctaaaatgga agtttttcct gtcatacttt | 1140 |

```
gttaagaagg gtgagaacag agtacctaca ttttgaatgg aaggattgga gctacggggg    1200
tgggggtggg gtgggattag ataaatgcct gctctttact gaaggctctt tactattgct    1260
ttatgataat gtttcatagt tggatatcat aatttaaaca agcaaaacca aattaagggc    1320
cagctcattc ctcccactca tgatctatag atctatagat ctctcgtggg atcattgttt    1380
ttctcttgat tcccactttg tggttctaag tactgtggtt tccaaatgtg tcagtttcat    1440
agcctgaaga acgagatcag cagcctctgt tccacataca cttcattctc agtattgttt    1500
tgccaagttc taattccatc agaagctgac tctagatggc gcgtatgcag gttttcgaca    1560
ttgattattg actagttatt aatagtaatc aattacgggg tcattagttc atagcccata    1620
tatggagttc cgcgttacat aacttacggt aaatggcccg cctggctgac cgcccaacga    1680
cccccgccca ttgacgtcaa taatgacgta tgttcccata gtaacgccaa tagggacttt    1740
ccattgacgt caatgggtgg agtatttacg gtaaactgcc cacttggcag tacatcaagt    1800
gtatcatatg ccaagtacgc ccctattga cgtcaatgac ggtaaatggc ccgcctggca    1860
ttatgcccag tacatgacct tatgggactt tcctacttgg cagtacatct acgtattagt    1920
catcgctatt accatggtcg aggtgagccc cacgttctgc ttcactctcc ccatctcccc    1980
cccctcccca cccccaattt tgtatttatt tattttttaa ttattttgtg cagcgatggg    2040
ggcggggggg ggggggcgc gcgccaggcg gggcggggcg gggcgagggg cggggcgggg    2100
cgaggcggag aggtgcggcg gcagccaatc agagcggcgc gctccgaaag tttccttta    2160 tggcgaggcg gcggcggcgg cggccctata aaaagcgaag cgcgcggcgg gcgggagtcg    2220
ctgcgttgcc ttcgccccgt gccccgctcc gcgccgcctc gcgccgcccg cccggctct    2280 gactgaccgc gttactccca caggtgagcg ggcgggacgg cccttctcct ccgggctgta    2340
attagcgctt ggtttaatga cggctcgttt cttttctgtg gctgcgtgaa agccttaaag    2400
ggctccggga gggcccttg tgcgggggg agcggctcgg ggggtgcgtg cgtgtgtgtg    2460
tgcgtgggga gcgccgcgtg cggcccgcgc tgcccggcgg ctgtgagcgc tgcgggcgcg    2520
gcgcggggct ttgtgcgctc cgcgtgtgcg cgaggggagc gcggccgggg gcggtgcccc    2580
gcggtgcggg ggggctgcga ggggaacaaa ggctgcgtgc ggggtgtgtg cgtgggggg    2640 tgagcagggg gtgtgggcgc ggcggtcggg ctgtaacccc cccctgcacc cccctccccg    2700
agttgctgag cacggcccgg cttcgggtgc ggggctccgt gcggggcgtg gcgcggggct    2760
cgccgtgccg ggcggggggt ggcggcaggt gggggtgccg ggcggggcgg ggccgcctcg    2820
ggccggggag ggctcgggg aggggcgcgg cggcccgga gcgccggcgg ctgtcgaggc    2880
gcggcgagcc gcagccattg ccttttatgg taatcgtgcg agagggcgca gggacttcct    2940
ttgtcccaaa tctgtgcgga gccgaaatct gggaggcgcc gccgcacccc ctctagcggg    3000
cgcggggcga agcggtgcgg cgccggcagg aaggaaatgg gcgggagggg ccttcgtgcg    3060
tcgccgcgcc gccgtcccct tctccctctc cagcctcggg gctgtccgcg ggggacggc    3120 tgccttcggg gggacgggg cagggcgggg ttcggcttct ggcgtgtgac cggcggctct    3180
agaagcgttg gggtgagtac tccctctcaa aagcgggcat gacttctgcg ctaagattgt    3240
cagtttccaa aaacgaggag gatttgatat tcacctggcc cgcggtgatg cctttgaggg    3300
tggccgcgtc catctggtca gaaaagacaa tctttttgtt gtcaagcttg aggtgtggca    3360
ggcttgagat ctggccatac acttgagtga cattgacatc cactttgcct ttctctccac    3420
aggtgtccac tcccagggcg gcctccggag cgatcgccga tccgcctagg caattgttta    3480
```

-continued

```
aatcggccgg ccataacttc gtataatgta tgctatacga agttatggat cctcacagta    3540
ggtggcatcg ttcctttctg actgcccgcc ccccgcatgc cgtcccgcga tattgagctc    3600
cgaacctctc gccctgccgc cgccggtgct ccgtcgccgc cgcgccgcca tggaatcgaa    3660
gccaccatga tcttaccgg aaaactcgac gcaagaaaaa tcagagagat cctcataaag     3720
gtcaagaagg gcggaaagat cgccgtgtaa ttctagaccg gttcgagatc caggcgcgga    3780
tcaataaaag atcattattt tcaatagatc tgtgtgttgg ttttttgtgt gccttggggg    3840 aggggggaggc cagaatgagg cgcggccaag gggaggggg aggccagaat gaccttgggg     3900 gaggggggagg ccagaatgac cttgggggag gggaggcca gaatgaggcg cgccctccgt    3960
cgacctataa cttcgtataa tgtatgctat acgaagttat ggcggccgcc accatggaca    4020
tgagagtgcc cgcccagctc ctggggctcc tgctactctg gctccgaggt aaggatggag    4080
aacactagga atttactcag ccagtgtgct cagtactgac tggaacttca gggaagttct    4140
ctgataacat gattaatagt aagaatattt gttttatgt ttccaatctc aggtgccaga     4200
tgtcagtctg ccctgaccca gccgcctct gtgtctggca gccctggcca gagcatcacc     4260
atcagctgca ccggcaccag cagcgacgtg ggcggctaca actacgtgtc ctggtatcag    4320 cagcacccg gcaaggcccc caagctgatg atctacgagg tgtccaacag acccagcggc    4380
gtgagcaaca gattcagcgg cagcaagagc ggcaacaccg ccagcctgac catcagcggc    4440
ctccaggctg aggacgaggc cgactactac tgcagcagct acaccagcag ctccaccctg    4500
gtgtttggcg gcggaacaaa gctgaccgtg ctgagagccg acgccgctcc caccgtgtcc    4560 atcttcccc ccagcatgga acagctgacc tctggcggag ccaccgtggt ctgcttcgtg     4620
aacaacttct accccagaga catcagcgtg aagtggaaga tcgacggcag cgagcagagg    4680
gacggcgtgc tggacagcgt gaccgaccag gacagcaagg actccaccta cagcatgagc    4740
agcaccctga gcctgaccaa ggtggagtac gagaggcaca acctgtacac ctgcgaggtg    4800
gtgcacaaga ccagctccag ccccgtggtc aagtccttca accggaacga gtgttgagct    4860
agcttaagat ttaaataggc cggccgcgtc gacctcgaga tccaggcgcg gatcaataaa    4920
agatcattat tttcaataga tctgtgtgtt ggttttttgt gtgccttggg ggagggggag    4980
gccagaatga ggcgcggcca agggggaggg ggaggccaga atgaccttgg gggaggggga    5040
ggccagaatg accttggggg aggggaggc cagaatgagg cgcgccccg ggtaccgagc      5100 tcgaattagt ggatcctcac agtaggtggc atcgttcctt tctgactgcc cgccccccgc    5160
atgccgtccc gcgatattga gctccgaacc tctcgccctg ccgccgccgg tgctccgtcg    5220
ccgccgcgcc gccatggaat cgcgccggta accgaagttc ctatactttc tagagaatag    5280
gaacttcgga ataggaactt caagccggta cccagctttt gttcccttta gtgagggtta    5340
atttcgagct tggcgtaatc atggtcatag ctgtttcctg tgtgaaattg ttatccgctc    5400
acaattccac acaacatacg agccgggagc ataaagtgta aagcctgggg tgcctaatga    5460
gtgagctaac tcacattaat tgcgttgcgc tcactgcccg ctttccagtc gggaaacctg    5520
tcgtgccagc tgcattaatg aatcggccaa cgcgcgggga ggcggttt gcgtattggg      5580 cgctcttccg cttcctcgct cactgactcg ctgcgctcgg tcgttcggct gcggcgagcg    5640
gtatcagctc actcaaaggc ggtaatacgg ttatccacag aatcagggga taacgcagga    5700
aagaacatgt gagcaaaagg ccagcaaaag gccaggaacc gtaaaaaggc cgcgttgctg    5760 gcgttttcc ataggctccg ccccctgac gagcatcaca aaaatcgacg ctcaagtcag      5820
aggtggcgaa acccgacagg actataaaga taccaggcgt ttccccctgg aagctccctc    5880
```

-continued

```
gtgcgctctc ctgttccgac cctgccgctt accggatacc tgtccgcctt tctcccttcg   5940
ggaagcgtgg cgctttctca tagctcacgc tgtaggtatc tcagttcggt gtaggtcgtt   6000
cgctccaagc tgggctgtgt gcacgaaccc cccgttcagc ccgaccgctg cgccttatcc   6060
ggtaactatc gtcttgagtc caacccggta agacacgact tatcgccact ggcagcagcc   6120
actggtaaca ggattagcag agcgaggtat gtaggcggtg ctacagagtt cttgaagtgg   6180
tggcctaact acggctacac tagaaggaca gtatttggta tctgcgctct gctgaagcca   6240
gttaccttcg gaaaaagagt tggtagctct tgatccggca aacaaaccac cgctggtagc   6300
ggtggttttt ttgtttgcaa gcagcagatt acgcgcagaa aaaaggatc tcaagaagat   6360 cctttgatct tttctacggg gtctgacgct cagtggaacg aaaactcacg ttaagggatt   6420
ttggtcatga gattatcaaa aaggatcttc acctagatcc ttttaaatta aaatgaagt    6480 tttaaatcaa tctaaagtat atatgagtaa acttggtctg acagttacca atgcttaatc   6540
agtgaggcac ctatctcagc gatctgtcta tttcgttcat ccatagttgc ctgactcccc   6600
gtcgtgtaga taactacgat acgggagggc ttaccatctg gccccagtgc tgcaatgata   6660
ccgcgagacc cacgctcacc ggctccagat ttatcagcaa taaaccagcc agccggaagg   6720
gccgagcgca gaagtggtcc tgcaacttta tccgcctcca tccagtctat taattgttgc   6780
cgggaagcta gagtaagtag ttcgccagtt aatagtttgc gcaacgttgt tgccattgct   6840
acaggcatcg tggtgtcacg ctcgtcgttt ggtatggctt cattcagctc cggttcccaa   6900
cgatcaaggc gagttacatg atcccccatg ttgtgcaaaa aagcggttag ctccttcggt   6960
cctccgatcg ttgtcagaag taagttggcc gcagtgttat cactcatggt tatggcagca   7020
ctgcataatt ctcttactgt catgccatcc gtaagatgct tttctgtgac tggtgagtac   7080
tcaaccaagt cattctgaga atagtgtatg cggcgaccga gttgctcttg cccggcgtca   7140
atacgggata taccgcgcc acatagcaga actttaaaag tgctcatcat tggaaaacgt    7200 tcttcgggc gaaaactctc aaggatctta ccgctgttga tccagttc gatgtaaccc      7260 actcgtgcac ccaactgatc ttcagcatct tttactttca ccagcgtttc tgggtgagca   7320
aaaacaggaa ggcaaaatgc cgcaaaaaag gaataaggg cgacacggaa atgttgaata    7380
ctcatactct cctttttca atattattga agcatttatc agggttattg tctcatgagc    7440
ggatacatat ttgaatgtat ttagaaaaat aaacaaatag gggttccgcg cacatttccc   7500
cgaaaagtgc cacctaaatt gtaagcgtta atattttgtt aaaattcgcg ttaaatttt    7560 gttaaatcag ctcatttttt aaccaatagg ccgaaatcgg caaaatccct tataaatcaa   7620
aagaatagac cgagataggg ttgagtgttg ttccagtttg gaacaagagt ccactattaa   7680
agaacgtgga ctccaacgtc aaagggcgaa aaaccgtcta tcagggcgat ggcccactac   7740
gtgaaccatc accctaatca agttttttgg ggtcgaggtg ccgtaaagca ctaaatcgga   7800
accctaaagg gagcccccga tttagagctt gacggggaaa gccggcgaac gtggcgagaa   7860
aggaagggaa gaaagcgaaa ggagcgggcg ctagggcgct ggcaagtgta gcggtcacgc   7920
tgcgcgtaac caccaccc gccgcgctta atgcgccgct acaggcgcg tcccattcgc     7980 cattcaggct gcgcaactgt tgggaagggc gatcggtgcg ggcctcttcg ctattacgcc   8040
agctggcgaa agggggatgt gctgcaaggc gattaagttg ggtaacgcca gggttttccc   8100
agtcacgacg ttgtaaaacg acggccagtg agcgcgcgta atacgactca ctatagggcg   8160
aattgggggt aactaagtaa ggatcgag                                      8188
```

```
<210> SEQ ID NO 102
<211> LENGTH: 10
<212> TYPE: DNA
<213> ORGANISM: Artificial Sequence
<220> FEATURE:
<223> OTHER INFORMATION: Kozak sequence

<400> SEQUENCE: 102
gccaccatgg                                                          10
```

ANTIBODY PRODUCING NON-HUMAN MAMMALS

CROSS-REFERENCE TO RELATED APPLICATION

This application is a continuation of U.S. patent application Ser. No. 12/459,285, filed Jun. 29, 2009, which application claims the benefit, under 35 U.S.C. § 119(e), to U.S. Provisional Patent Application Ser. No. 61/133,274, filed Jun. 27, 2008, for "Antibody Producing Non-Human Mammals," the entire contents of each of which are hereby incorporated herein by this reference.

STATEMENT ACCORDING TO 37 C.F.R. § 1.821(C) OR (E)—SEQUENCE LISTING SUBMITTED AS ASCII TEXT FILE

Pursuant to 37 C.F.R. § 1.52(e)(1)(ii), a compact disc containing an electronic version of the Sequence Listing has been submitted concomitant with this application, the contents of which are hereby incorporated by reference. A second compact disc is submitted and is an identical copy of the first compact disc. The discs are labeled "copy 1" and "copy 2," respectively, and each disc contains one file entitled "sequence listing 10192009.txt" which is 140 KB and created on Oct. 19, 2009.

TECHNICAL FIELD

The invention relates to the production and use of non-human animals capable of producing antibodies or derivatives thereof, which are expressed from at least partially exogenous nucleic acids (transgenes). Transgenes to produce such transgenic animals and methods to produce such heterologous antibodies; methods and vectors for producing such transgenic animals are disclosed.

BACKGROUND

B cells mediate humoral immunity by producing specific antibodies. The basic structural subunit of an antibody (Ab) is an immunoglobulin (Ig) molecule. Ig molecules consist of a complex of two identical heavy (H) and two identical light (L) polypeptide chains. At the amino terminus of each H chain and L chain is a region that varies in amino acid sequence named the variable (V) region. The remaining portion of the H and L chains is relatively constant in amino acid sequence and is named the constant (C) region. In an Ig molecule, the H and L chain V regions (VH and VL) are juxtaposed to form the potential antigen-binding site. The genes that encode H and L chain V regions are assembled somatically from segments of germline DNA during precursor B (pre-B) cell differentiation: V, D and J gene segments for the H chain and V and J gene segments for the L chain. Within Ig V regions are three regions of greatest amino acid sequence variability that interact to form the antigen-recognition site and are thus referred to as complementarity determining regions (CDRs).

The V gene segment encodes the bulk of the V region domain, including CDR1 and CDR2. Diversity in CDR1 and CDR2 derives from sequence heterogeneity among multiple different germline-encoded V segments. CDR3 is encoded by sequences that are formed by the joining of H chain V, D, and J gene segments and L chain V and J segments and by mechanisms that create nucleotide sequence heterogeneity where these segments are combined. Additional diversity may be derived from pairing of different H and L chain V regions. Collectively these processes yield a primary repertoire of antibodies encoded by germline gene segments and expressed by newly formed B cells.

An additional source of antibody diversity is imposed on top of the diversity generated by recombination of Ig gene segments. B cells are able to introduce mutations into the antibody V regions that they express, a process called somatic hypermutation. Thus, when an animal first encounters an antigen, the antigen binds to a specific B cell which happens to carry antibodies which have a V domain which binds the antigen. This primary response may activate this B cell to go on to secrete the cognate antibody. These activated B cells can also now target a somatic mutation process to their rearranged antibody gene segments and thus allow the production of daughter cells which make variants of the antibodies of the primary response. A selection process amplifies those variant B cell descendants which make an antibody of improved affinity of the antigen. In B cells, somatic hypermutations are targeted to a restricted genomic region including both the rearranged VH and VL genes. Thus somatic mutation allows affinity maturation—the production and selection of high affinity antibodies. Therefore, somatic mutation is important for the generation of high affinity antibodies.

The exquisite specificity and high affinity of antibodies and the discovery of hybridoma technology allowing the generation of monoclonal antibodies (mAbs) has generated great expectations for their utilization as targeted therapeutics for human diseases. MAbs are identical because they are produced by a single B cell and its progeny. MAbs are made by fusing the spleen cells from a mouse that has been immunized with the desired antigen with myeloma cells to generate immortalized hybridomas. One of the major impediments facing the development of in vivo applications for mAbs in humans is the intrinsic immunogenicity of non-human Igs. Patients respond to therapeutic doses of mouse mAbs by making antibodies against the mouse Ig sequences (Human Anti Mouse Antibodies; HAMA), causing acute toxicity, alter their biodistribution and accelerate clearance, thus reducing the efficacy of subsequent administrations (Mirick et al. (2004), *Q. Nucl. Med. Mol. Imaging* 48:251-257).

To circumvent the generation of HAMA, antibody humanization methods have been developed in an attempt to produce mAbs with decreased immunogenicity when applied to humans. These endeavors have yielded various recombinant DNA-based approaches aimed at increasing the content of human amino acid sequences in mAbs while retaining the specificity and affinity of the parental non-human antibody. Humanization began with the construction of mouse-human chimeric mAbs (S. L. Morrison et al. (1984), *Proc. Natl. Acad Sci. USA* 81:6851-5), in which the Ig C regions in murine mAbs were replaced by human C regions. Chimeric mAbs contain 60-70% of human amino acid sequences and are considerably less immunogenic than their murine counterparts when injected into humans, albeit that a human anti-chimeric antibody response was still observed (W. Y. Hwang et al. (2005), *Methods* 36:3-10).

In attempts to further humanize murine mAbs, CDR grafting was developed. In CDR grafting, murine antibodies are humanized by grafting their CDRs onto the VL and VH frameworks of human Ig molecules, while retaining those murine framework residues deemed essential for specificity and affinity (P. T. Jones et al. (1986), *Nature* 321:522). Overall, CDR-grafted antibodies consist of more than 80% human amino acid sequences (C. Queen et al. (1989), *Proc.*

*Natl. Acad Sci. U.S.A.* 86:10029; P. Carter et al. (1992), *Proc. Natl. Acad Sci. U.S.A.* 89:4285). Despite these efforts, CDR-grafted, humanized antibodies were shown to still evoke an antibody response against the grafted V region (W. Y. Hwang et al. (2005), *Methods* 36:3).

Subsequently to CDR grafting, humanization methods based on different paradigms such as resurfacing (E. A. Padlan et al. (1991), *Mol. Immunol.* 28:489), superhumanization (P. Tan D. A. et al. (2002), *J. Immunol.* 169:1119), human string content optimization (G. A. Lazar et al. (2007), *Mol. Immunol.* 44:1986) and humaneering have been developed in an attempt to further decrease the content of non-human sequences in therapeutic mAbs (J. C. Almagro et al. (2008), *Frontiers in Bioscience* 13:1619). As in CDR grafting approaches, these methods rely on analyses of the antibody structure and sequence comparison of the non-human and human mAbs in order to evaluate the impact of the humanization process into immunogenicity of the final product. When comparing the immunogenicity of chimeric and humanized antibodies, humanization of variable regions appears to decrease immunogenicity further (W. Y. Hwang et al. (2005), *Methods* 36:3-10).

De-immunization is another approach developed to reduce the immunogenicity of chimeric or mouse antibodies. It involves the identification of linear T-cell epitopes in the antibody of interest, using bioinformatics, and their subsequent replacement by site-directed mutagenesis to human or non-immunogenic sequences (WO 9852976 A1, the contents of which are incorporated by this reference). Although de-immunized antibodies exhibited reduced immunogenicity in primates, compared with their chimeric counterparts, some loss of binding affinity was observed (M. Jain et al. (2007), *Trends in Biotechnol.* 25:307).

The development of phage display technology complemented and extended humanization approaches in attempts to obtain less immunogenic mAbs for therapy in humans. In phage display, large collections ("libraries") of human antibody VH and VL regions are expressed on the surface of filamentous bacteriophage particles. From these libraries, rare phages are selected through binding interaction with antigen; soluble antibody fragments are expressed from infected bacteria and the affinity of binding of selected antibodies is improved by mutation (G. Winter et al. (1994), *Annu. Rev. Immunol.* 12:433). The process mimics immune selection, and antibodies with many different bindings specificities have been isolated using this approach (H. R. Hoogenboom et al. (2005), *Nat. Biotechnol.* 23:1105). Various sources of H and L chain V regions have been used to construct phage display libraries including those isolated from non-immune or immune donors. In addition, phage display libraries have been constructed of V regions that contain artificially randomized synthetic CDR regions in order to create additional diversity. Often, antibodies obtained from phage display libraries are subjected to in vitro affinity maturation to obtain high affinity antibodies (H. R. Hoogenboom et al. (2005), *Nat. Biotechnol.* 23:1105).

The creation of transgenic mouse strains producing human antibodies in the absence of mouse antibodies has provided another technology platform for the generation of specific and high affinity human mAbs for application in humans. In these transgenic animals, the endogenous mouse antibody machinery is inactivated and replaced by human Ig loci to substantially reproduce the human humoral immune system in mice (A. Jakobovits et al. (2007), *Nat. Biotechnol.* 25:1134; N. Lonberg (2005), *Nat. Biotechnol.* 23:1117). B cell development as well as Ig diversification by recombination of gene segments is faithfully reproduced in these mice, leading to a diverse repertoire of murine B cells expressing human Igs. By immunizing these mice with antigens, it was further demonstrated that these transgenic animals accumulated somatic mutations in the V regions of both heavy and light chains to produce a wide diversity of high-affinity human mAbs (N. Lonberg (2005), *Nat. Biotechnol.* 23:1117).

The question, whether "fully human" mAbs such as derived from phage display libraries or transgenic mice are less immunogenic than humanized mAbs cannot be answered yet, because full immunogenicity data are available for just two human mAbs. An anti-tumor necrosis factor mAb, developed from phage-displayed human libraries induced antibody responses in 12% of patients—at the higher end of the incidence of anti-antibody responses of the humanized antibodies (W. Y. Hwang et al. (2005), *Methods* 36:3-10).

Evaluation of the immunogenicity of the first registered human mAb generated by the transgenic approach demonstrated that mAb treatment resulted in the generation of antibodies in approximately 5.5% of treated cancer patients (A. Jakobovits et al. (2007), *Nat. Biotechnol.* 25:1134; J. A. Lofgren et al. (2007), *J. Immunol.* 178:7467).

DISCLOSURE OF THE INVENTION

Disclosed are a method and means for producing antibodies that are specific for their targets, but are less immunogenic. Described herein, the reduction of immunogenicity is at least partially achieved by providing a transgenic non-human mammal comprising, at least in its B cell lineage, a nucleic acid encoding at least an immunoglobulin light chain or heavy chain, wherein the heavy- or light chain encoding sequence is provided with a means that renders it resistant to DNA rearrangements and/or somatic hypermutations, preferably such a non-human animal is a rodent, more specifically a mouse. In certain embodiments, the nucleic acid encodes a human, human-like, or humanized immunoglobulin chain.

In the remainder of this specification, mice are typically used as examples of the non-human mammals. The transgenic, non-human, mammalian hosts are capable of mounting an immune response to an antigen, where the response produces antibodies having primate, particularly human, variable regions. Various transgenic hosts may be employed, particularly murine, lagomorpha, ovine, avine, porcine, equine, canine, feline, or the like. Mice have been used for the production of B-lymphocytes for immortalization for the production of antibodies. Since mice are easy to handle, can be bred in large numbers, and are known to have an extensive immune repertoire, mice will usually be the animal of choice. Therefore, in the following discussion, the discussion will refer to mice, but it should be understood that other animals, particularly non-primate mammals, may be readily substituted for the mice, following the same procedures.

The reason for preventing rearrangements and hypermutation is that in this manner a non-immunogenic polypeptide can be chosen beforehand knowing that this polypeptide chain will remain non-immunogenic. At least one of the chains of the resulting immunoglobulin is thus less immunogenic. The resulting antibody needs to have (usually) both a light- and a heavy chain. The non-immunogenic chain must therefore be capable of pairing with the other chain. The other chain may be an endogenous chain, an exogenous chain or a hybrid of both. For human therapy, the non-immunogenic chain should be as close to human as possible.

A means for rendering a gene encoding an immunoglobulin chain (or chains) resistant to DNA rearrangement and/or mutation is of course removal of all genetic elements responsible for the rearrangement and/or mutation. The drawback thereof is that the variability of the two chains is eliminated, whereas the invention preferably retains the variability in one chain (preferably the heavy chain) and inhibits and/or prevents the rearrangement-mutation of the other chain (preferably the light chain).

The elements for rearrangement and/or hypermutation characterized so far are located within the loci for immunoglobulins. Therefore the means for rendering the immunoglobulin encoding sequence resistant to DNA rearrangement and/or mutation is inserting the gene in a locus outside the immunoglobulin loci.

Thus, described herein, a transgenic non-human mammal is provided wherein the light/heavy chain encoding sequence is integrated in the genome of the non-human mammal in a locus outside the immunoglobulin loci. Preferably the insertion is in a locus that is resistant to gene silencing. Described herein, the integration is in the Rosa-locus or a comparable locus.

In certain embodiments, provided is an expression cassette that can be inserted into a Rosa locus or comparable locus with a means that allows expression of the immunoglobulin chain(s) essentially limited to cells of B cell lineage, preferably with a means that allows expression of the light chain encoding nucleic acid during a certain stage of the development of B cells. The term "essentially limited expression" indicates that expression is predominantly in cells of the B-cell lineage, but that lower levels of expression in other cells, as compared to the level of expression in B-cells, is possible. In certain embodiments, the term "essentially limited expression" indicates that the expression is exclusively present in cells of the B-cell lineage. Such means typically and preferably include B cell (developmental stage) specific promoters such as CD19, CD20, pHC (all V-genes), VpreB1, VpreB2, VpreB3, λ5, Igα, Igβ, κLC (all genes), λLC (all genes), BSAP (Pax5). Although it is very well possible to direct the expression of the DNA rearrangement and/or mutation resistant chain by such promoters, they are relatively weak. A strong promoter will typically be required to ensure adequate surface expression of the B cell receptor (made up of the membrane attached Ig H and L chain) and to compete with the expression and pairing of endogenous chains (if present) through allelic exclusion. Such a promoter, however is usually not tissue specific. To confer tissue specificity, an indirect system employing Cre/lox or the like is preferred. The desired chain is put under control of a strong promoter inhibited by an element that can be removed by the action of a Cre-protein, leading to activation of the desired immunoglobulin encoding gene. This system is described in detail in F. T. Wunderlich (2004), "Generation of inducible Cre systems for conditional gene inactivation in mice," Inauguraldissertation zur Erlangung des Doktorgrades der Mathematisch-Naturwissenschaftlichen Fakultät der Universität zu Köln; on the internet at deposit.ddb.de/cgi-bin/dokserv?idn=97557230x&dok_var=d1&dok_ext=pdf&filename=97557230x.pdf.

Preferably the immunoglobulin chain produced in a manner resistant to rearrangements and hypermutation is a light chain capable of pairing with different heavy chains encoded by the non-human mammal. The light chain will then be the same (and less immunogenic) in all antibodies, but variety in specificity is retained through rearrangements and hypermutations in the heavy chains. It may in that case be preferable to silence at least one of the endogenous loci encoding a light chain, although allelic exclusion may render this unnecessary.

According to this embodiment, preferably the endogenous kappa (κ) light chain locus is functionally silenced.

If the endogenous κ light chain locus is silenced, but also for other reasons, it is preferred that the resistant light chain is a κ light chain, preferably a light chain that has a germline-like sequence. Described herein such a light chain would lead to an antibody with reduced immunogenicity. The preferred germline sequence is based on the human IGKV1-39 (O12) as this light chain is very frequently observed in the human repertoire (de Wildt et al. 1999, *J. Mol. Bot.* 285(3):895) and has superior thermodynamic stability, yield and solubility (Ewert et al. 2003, *J. Mol. Biol.* 325(3):531).

The following gives more specific embodiments of the expression cassette with which the non-human animal can be provided described herein. Although this is typically advantageous for immunoglobulins, other genes of interest are also contemplated.

Thus, provided in a specific embodiment, is a transgenic non-human mammal wherein the light chain encoding nucleic acid comprises in 5'-3' direction: a B cell specific promoter, a leader, a rearranged human V gene, optionally a mouse κ-intron enhancer (MoEκi), a constant region (κ) and optionally a (truncated) mouse κ-3' enhancer (MoEκ3'). Neuberger identified and examined a novel B-cell specific enhancer located downstream of the kappa constant region (Neuberger, EP 00469025 B1, the contents of which are incorporated herein by this reference). This enhancer has been shown to play a crucial role in the expression of kappa genes as removal of the 808 bp enhancer strongly reduced expression. Deletion of the 3' kappa enhancer also strongly reduced the level of somatic hypermutations (SHM). In transgenic and cell expression studies, it has been revealed that reduced, mutated or deleted 3' kappa enhancers not only lowered expression levels, but also decreased the level of somatic hypermutations. Currently, it cannot be determined whether the 3' kappa enhancer is involved in SHM processes, expression regulation or both (review V. H. Odegard et al. (2006), *Nat. Rev. Immunol.* 6:573; M. Inlay et al. (2002), *Nat Immunol.* 3:463).

Detailed expression studies using engineered variants of the 3' kappa enhancer indicated that a 50 nucleotide region is sufficient to drive expression. However for proper expression a reduced sequence of 145 nucleotides is preferred (EP04690251; K. B. Meyer et al. (1990), *Nucleic Acids Res.* 18(19):5609-15).

Thus, the invention in one aspect provides a nucleic acid for insertion into the genome of a non human animal that is an expression cassette for the expression of a desired proteinaceous molecule in cells developing into mature B cells during a certain stage of development, the cassette comprising means for preventing silencing of expression of the desired proteinaceous molecule after introduction into a host cell, and means for timing expression of the desired proteinaceous molecule with the desired developmental stage of the host cell.

An expression cassette is defined as a nucleic acid that has been provided with means for introduction into the genome of a host cell, such as sequences which allow for homologous recombination with a certain site in the genome. Usually the nucleic acid will be DNA, typically double stranded. Typically the expression cassette will be provided to the cell in a vector from which it is transferred to the genome of the cell. The expression cassette further comprises all elements necessary for expression of the gene in a host cell, although in certain embodiments some of such elements may be present on a second nucleic acid to be introduced, whereby these elements act in trans. Elements necessary for expression in a host cell include promoters, enhancers and other regulatory elements. Only those elements are necessary that are not provided by the host cell.

The expression of the gene of interest should not be silenced in the genome of the host cell, especially not in the development stage where expression is required. This can be done by various means, such as insertion into the endogenous locus or by providing the cassette with nucleic acid elements that prevent silencing (Kwaks et al. (2006), *Trends Biotechnol.* 24(3):137-142, which is incorporated herein by reference). It is preferred that the expression cassette is inserted in a locus that is not silenced in the host cells (EP 01439234; which is incorporated herein by reference).

The means for prevention of silencing comprise STabilizing Anti-Repression-sequences (STAR®-sequences) and Matrix Attachment Regions (MARs). A STAR sequence is a nucleic acid sequence that comprises a capacity to influence transcription of genes in cis. Typically, although not necessarily, a STAR sequence does not code by itself for a functional protein element. In one embodiment more than one STAR element is used. Preferably, however, more than one STAR element is used. In a particularly preferred embodiment an expression cassette described herein is provided with two STAR sequences; one STAR sequence at the 5' side of the coding sequence of the immunoglobulin gene and one STAR sequence at the 3' side of the coding sequence of the immunoglobulin gene. MARs are DNA sequences that are involved in anchoring DNA/chromatin to the nuclear matrix and they have been described in both mammalian and plant species. MARs possess a number of features that facilitate the opening and maintenance of euchromatin. MARs can increase transgene expression and limit position-effects.

Expression from the cassette should only occur during a certain period in the development of a cell, in particular a developing B cell, more in particular a B cell in a transgenic non-human animal, in particular a mouse. In this particular case the developmental period is chosen such that the expression of the gene from the cassette (typically a light- or heavy chain-like polypeptide) does not significantly interfere with the normal differentiation and/or maturation of the cell and when applicable, allows for pairing of the polypeptide chain produced with its counterpart.

This may, in one embodiment, be achieved by providing a nucleic acid described herein, wherein the means for timing expression is a promoter of which the activity is essentially limited to the certain stage of development. In a developing B cell, which, e.g., after immunization is maturing and/or differentiating, the expression of the gene of interest, when it is one of the polypeptide chains of an immunoglobulin, must not interfere (significantly) with the maturation and/or differentiation and it needs to be timed such that the resulting polypeptide can pair with its counterparts. Therefore, provided is a nucleic acid described herein wherein the certain stage starts at a stage immediately preceding or coinciding with the onset of the expression of light chain molecules by the cells at a certain stage of development into a mature B cell. This may be achieved by selecting a promoter which is active only during the suitable period. Such a promoter may be a CD19 promoter, the Ig-α promoter, the Ig-β promoter, the μhc (all genes) promoter, the Vκ promoter or analogues or homologues thereof.

In a specific embodiment, the promoter as disclosed above does not drive the expression of the gene of interest directly. Instead it drives the expression of a gene of which the product activates in trans the expression of the gene of interest. Such an activating gene may be a gene encoding a so-called Cre recombinase or Cre-like protein. The expression cassette for the gene of interest may, e.g., be provided with a sequence that inhibits expression of the gene of interest. The sequence can be removed by the action of the Cre recombinase, which is under control of the desired promoter (active during the proper stage of development). In this embodiment a set of expression cassettes is required.

Therefore, provided is a set of nucleic acids that are expression cassettes, wherein one nucleic acid comprises an expression cassette encoding a Cre-like protein under control of a promoter active during the desired stage of development of the host cell and the second nucleic acid comprises a sequence encoding a desired proteinaceous molecule under control of a constitutive promoter which can be activated by the action of a Cre-like protein. The activation is preferably achieved by removal of a stop sequence flanked by loxP sites. The Cre/lox system is described in detail in Rajewsky et al. (1996), *J. Clin. Invest.* 98:600-603, which is incorporated herein by reference. Such systems are reviewed in F. T. Wunderlich (2004), "Generation of inducible Cre systems for conditional gene inactivation in mice," Inauguraldissertation zur Erlangung des Doktorgrades der Mathematisch-Naturwissenschaftlichen Fakultät der Universität zu Köln; on the World Wide Web at deposit.ddb.de/cgi-bin/dokserv?idn=97557230x&dok_var=dI&dok_ext=pdf&filename=97557230x.pd, which is incorporated herein by reference.

Further provided is a transgenic non-human animal that has been provided with an expression cassette hereof, wherein the desired proteinaceous molecule is a polypeptide chain of an immunoglobulin. A preferred polypeptide chain is a light chain. A more preferred polypeptide is a germline or germline-like light chain. A most preferred polypeptide is encoded by the immunoglobulin kappa variable 1-39 (IGKV1-39, also known as O12) gene segment, preferably the rearranged germline kappa light chain IGKV1-39*01/IGKJ1*01 (nomenclature according to the IMGT database, at [worldwideweb].imgt.org).

In certain embodiments, the polypeptide chain is rendered essentially incapable of rearrangement and/or of excluded of any sequence modification such as normally operating on Ig during the process of B cell affinity maturation. Therefore, provided is a transgenic non-human animal that has been provided with an expression cassette described herein, wherein the rearrangement and/or sequence modifications are prevented by the absence of elements at least partially responsible for somatic hypermutation such as, for example, the MoEκi enhancer.

A preferred expression cassette described herein comprises means for prevention of silencing. In one embodiment, the means for prevention of silencing are means for insertion into a locus in the genome of the host cell that is resistant to silencing. The means for insertion are preferably means for homologous recombination into the site resistant to silencing. A preferred locus when the non-human animal is a mouse is the rosa-locus.

A further preferred expression cassette described herein comprises in 5'-3' direction: a Vκ promoter, a mouse leader, a human V gene, optionally a MoEκi enhancer, a rat constant region (Cκ) and optionally a (truncated) MoEκ3' enhancer.

Yet a further preferred expression cassette described herein comprises in 5'-3' direction: a Vκ promoter, a human leader, a human V gene, optionally a MoEκi enhancer, a rat constant region (Cα) and optionally a (truncated) MoEκ3' enhancer.

Certain antibodies produced as described herein may be be used in human therapeutics and diagnostics. Thus, provided is a method for producing a desired antibody comprising exposing a non-human mammal described herein to an antigen such that an antibody response is induced and isolating the antibodies specific for the antigen.

In certain embodiments, provided are methods for producing a desired antibody comprising exposing a non-human mammal described herein to an antigen such that an antibody response is induced and isolating cells producing such antibodies, culturing and optionally immortalizing the cells and harvesting the antibodies.

In certain embodiments, provided is a method for producing a desired antibody comprising exposing a non-human mammal described herein to an antigen such that an antibody response is induced and isolating a nucleic acid encoding at least part of such an antibody, inserting the nucleic acid or a copy or a derivative thereof in an expression cassette and expressing the antibody in a host cell.

The methods for producing antibodies from transgenic mice are known to a person skilled in the art. Particularly preferred are methods for production of mixtures of antibodies from one cell, whereby the nucleic acids encoding these antibodies have been derived from mice described herein.

These so-called oligoclonics are disclosed in WO04106375 and WO05068622, which are incorporated herein by reference.

Described herein are transgenic non-human mammals, preferably mice, capable of generating specific and high affinity hybrid mouse-human antibodies with preferably human immunoglobulin light chain variable (VL) regions in or near germline configuration and preferably murine immunoglobulin heavy chain variable (VH) regions that may have accumulated somatic mutations during the process of antigen-driven affinity maturation. It is envisaged that the murine VH regions of the hybrid antibodies may be subjected to humanization procedures to yield mAbs that have reduced immunogenicity when applied in humans based on germline or near-germline VL regions and murine VH regions that have been humanized.

In particular, we have shown that transgenic mice that harbor a DNA expression construct that encodes a rearranged human VL region under the control of cis-acting genetic elements that provide timely and regulated expression of the transgene on a significant proportion of B cells during B cell development, yet lack elements that direct the somatic hypermutation machinery to the transgene, are capable of generating specific and high affinity mouse-human hybrid antibodies with essentially unmutated L chains. It is shown that the rearranged human transgene is capable of pairing with a diversity of endogenous murine immunoglobulin H chains to form mouse-human hybrid immunoglobulins expressed on the surface of B cells and to sufficiently facilitate murine B cell development to obtain a sizeable and diverse peripheral B cell compartment.

In certain embodiments, the transgene expression construct harbors the coding sequences of a human rearranged L chain V region under the control of a human VL promoter to direct B-cell specific expression. In addition, the construct harbors the murine 3' Ck enhancer sequence for B cell specific and inducible and high level expression of the transgene. Furthermore, the construct is designed to lack regulatory elements that facilitate the recruitment of the somatic hypermutation machinery to the transgene, such as the intron enhancer and the 3' C-kappa enhancer.

In a related embodiment, the rearranged human VL gene is inserted in the murine Rosa26 locus by site-specific integration. The Rosa26 locus is useful in the context of the "targeted transgenesis" approach for efficient generation of transgenic organisms (such as mice) with a predictable transgene expression pattern.

In certain embodiments, the rearranged human VL region is selected for its capacity to pair with many different murine VH genes so as to ensure the generation of a population of B cells with a diverse VH gene repertoire. A method of obtaining such VL regions comprises amplifying a repertoire of rearranged VH genes from the B cells of mice and a repertoire of human rearranged germline VL regions from the B cells of humans and cloning them into phagemid display vectors to prepare diverse libraries of hybrid immunoglobulins in bacteria. By nucleotide sequence analysis of collections of unselected and antigen-selected VH/VL pairs, human germline VL genes that pair with many different murine VH genes are identified. A collection of human germline VL genes with this capacity is described.

In one embodiment, it is shown that upon immunization with antigen, the B cells are capable of mounting an immune response, leading to the generation of B cells that secrete hybrid antibodies with high specificity and affinity. The V regions encoding these antibodies are characterized by the human transgenic light chain that harbors no or very few mutations and a murine heavy chain that harbors a variable number of mutations introduced by the somatic hypermutation machinery.

In a related embodiment, strategies to obtain high affinity hybrid monoclonal antibodies from the transgenic mice by hybridoma and display technologies are contemplated as well as procedures to humanize the murine VH regions to obtain less immunogenic antibodies for application in humans.

In one embodiment, provided is an immunoglobulin L chain transgene construct comprising DNA sequences that encode a human immunoglobulin VL region in combination with a light chain constant region (CL) of an animal immunoglobulin protein, which sequences are operably linked to transcription regulatory sequences that, when integrated in a non-human transgenic animal, produce an Ig VL-CL polypeptide with a human VL region that is not or marginally subject to somatic hypermutation. The Ig VL is capable of pairing with rearranged VH-CH polypeptides that are generated during B cell development in the non-human transgenic animal, with the VH-CH polypeptides retaining the capacity to undergo somatic hypermutation upon stimulation. The CL region may be of any animal species and is generally capable of pairing with the CH regions of the non-human transgenic animal.

Also included is the use of a transgene construct as above in producing a transgenic non-human animal capable of the production of hybrid antibodies consisting of VL-CL polypeptides and VH-CH polypeptides in which the VL region is of human origin and the CL, VH and CH may be of any animal species, including human. Upon immunization, these transgenic animals are capable of generating high affinity antibodies encoded by somatically hypermutated VH genes and essentially non-mutated VL genes encoded by the transgene.

In another aspect, provided is a process for the production of a transgenic non-human animal capable of the production of hybrid antibodies in response to antigenic challenge, comprising functionally disrupting the endogenous immunoglobulin light chain locus and inserting into the animal genome a transgene construct of the invention.

Included is the use of animals obtainable by this process in the production of B cells that produce immunoglobulin having human VL light chain. In another aspect of the invention there is provided a process for the production of B cells that produce immunoglobulin having human VL and binding to a selected antigen, comprising challenging an animal obtainable by a process as above with the antigen and screening for B cells from the animal that bind the antigen. Further included is B cells obtainable by this process and hybridomas obtainable by immortalizing such B cells, e.g., hybridomas obtained by fusing B cells as above with myeloma cells. Also included is a process for producing monoclonal antibody comprising cultivating such a hybridoma. In yet a further aspect, provided is the use of the above B cells in producing a hybridoma or corresponding monoclonal antibody.

Described herein is a process for the production of immunoglobulin having human VL chain and binding to a selected antigen, comprising challenging an animal obtainable as above with the antigen and obtaining immunoglobulin there from.

In one strategy, as an individual step, a rearranged VL region encoded by human germline V and J gene segments and a light chain constant region of any animal species but preferably a murine constant region is introduced into the mouse germ line. The transgene DNA may be introduced into the pronuclei of fertilized oocytes or embryonic stem cells. The integration may be random or homologous depending on the particular strategy to be employed. For example, the VL transgene may be introduced by random insertion, resulting in mice that bear one or multiple copies of the transgene in the genome. Alternatively, the human VL transgene may be targeted to a specific genomic locus using site-specific recombination as described in the art.

In certain embodiments, the VL transgene is targeted to the murine ROSA26 locus which is a suitable integration site allowing strong and predictable expression of inserted transgenes (European Patent Office document EP 1,439,234 A1, the contents of which are incorporated herein by this reference). The targeting vector allows insertion of a single copy of a gene expression cassette, thus avoiding modulation of transgene expression by the arrangement of multiple copies. By choosing the autosomal Rosa26 locus as insertion site, the expression pattern of the inserted transgene in the non-human animal is predictable. Furthermore, random X inactivation and/or modulation by chromosomal position effects are avoided. This also eliminates the need to generate and analyze multiple transgenic strains for any given transgene. Finally, the Rosa26 targeting vector for the site-specific integration can be used for multiple gene expression cassettes. Thus, it may be envisaged that two or more different rearranged germline human VL regions are inserted into the Rosa26 locus to further increase the diversity of the repertoire of hybrid or human antibodies.

In another embodiment, a rearranged human VL region may be targeted to the murine Ig kappa or lambda light chain locus so as to functionally inactivate the endogenous locus or mice containing the rearranged human VL region may be bred with mice that lack functional kappa or lambda Ig loci or both. Thus, by using transformation, using repetitive steps or in combination with breeding, transgenic animals may be obtained which are able to produce antibodies harboring the human VL transgene in the substantial absence of endogenous host immunoglobulin light chains.

In one embodiment, a human VL transgene is selected for its capacity to pair with a substantial portion of murine VH regions to form a diverse repertoire of functional mouse-human hybrid antibodies expressed on the surface of B cells. By a substantial portion of murine VH regions is meant that the human VL pairs with at least with 0.1% of the murine VH regions generated during B cell development, more preferably with at least 1% and most preferably with at least 10%. Methods to identify human VL genes with this characteristic include randomly pairing a repertoire of human VL regions with a repertoire of murine VH regions, co-expression of VH and VL regions in appropriate eukaryotic or prokaryotic expression vectors and screening for human VL regions that pair with a substantial portion of murine VH regions. In one embodiment, phagemid vectors may be used to direct expression of mouse-human antibody fragments in bacterial cells or to the surface of filamentous phage and analysis of binding capacity of antibody fragments by methods known in the art.

In another embodiment, a human VL transgene is selected for its capacity to pair with a substantial portion of human VH regions to form a diverse repertoire of human antibodies expressed on the surface of B cells. By a substantial portion of human VH regions is meant that the human VL pairs with at least with 0.1% of the human VH regions generated during B cell development, more preferably with at least 1% and most preferably with at least 10%0.

In the latter embodiment, the human VL transgenic mice are crossed with mice that harbor functional rearranged or non-rearranged human H chain immunoglobulin loci and functionally inactivated endogenous H chain Ig loci as described in the art. The functional inactivation of the two copies of each of the three host Ig loci (heavy chain, kappa and lambda light chain), where the host contains the human IgH and the rearranged human VL transgene would allow for the production of purely human antibody molecules without the production of host or host human chimeric antibodies. Such a host strain, by immunization with specific antigens, would respond by the production of mouse B-cells producing specific human antibodies, which B-cells are subsequently fused with mouse myeloma cells or are immortalized in any other manner for the continuous stable production of human monoclonal antibodies. Alternatively, the population of B cells is used as a source of VH regions that can be obtained by constructing cDNA libraries or by PCR amplification using primers for human VH regions as is known in the art.

A human rearranged VL gene is reconstructed in an appropriate eukaryotic or prokaryotic microorganism and the resulting DNA fragments can be introduced into pronuclei of fertilized mouse oocytes or embryonic stem cells. Various constructs that direct B cell specific expression of VL transgenes have been described in the art and have the following general format: a leader sequence and relevant upstream sequences to direct B cell specific expression of the transgene, a coding sequence of a human VL transgene, an enhancer sequence that directs B cell specific and high level expression of the transgene and a murine constant region gene. In a preferred format, the enhancer is the C-kappa 3' enhancer because it directs high level expression in B-lineage cells, but does not recruit somatic hypermutation when used in transgene constructs.

In one embodiment, animals, preferably mice, comprising one or multiple copies of the transgene in the genome are isolated and analyzed for stable expression. Animals are selected that show stable expression of the transgene over longer periods of time, preferably in B-cells. If required, different animal lines comprising independent insertions of one or multiple copies of the transgene, preferably on different chromosomes, are crossed to obtain animals with different insertions of one or multiple copies of the transgene to increase expression of the transgene in animals, preferably in B-cells.

Further provided is progeny of a transgenic non-human animal described herein, the progeny comprising, at least in its B-cell lineage, a heavy- or light chain encoding sequence together with a means that renders the sequence resistant to DNA rearrangements and/or somatic hypermutations.

Further provided is progeny of a transgenic non-human animal described herein, the progeny comprising an expression cassette for the expression of a desired proteinaceous molecule in cells during a certain stage of development in cells developing into mature B cells.

In addition, provided is a cell that is isolated from a transgenic non-human animal described herein, the cell comprising a heavy- or light chain encoding sequence together with a means that renders the sequence resistant to DNA rearrangements and/or somatic hypermutations. In addition, provided is a cell that is isolated from a transgenic non-human animal described herein, the cell comprising an expression cassette for the expression of a desired proteinaceous molecule in cells during a certain stage of development in cells developing into mature B cells. A cell described herein, preferably an antibody-producing B-cell or a cell that is capable of differentiating or maturating into an antibody-producing B-cell, can be used for in vitro production of antibodies, as is known to the skilled person, for example, from Gascan et al. 1991, *J. Exp. Med.* 173:747-750. Methods for immortalization of a cell described herein are known in the art and include the generation of hybridomas, for example, by fusion with a myeloma cell, transformation with Epstein Barr Virus; expression of the signal transducer of activation and transcription (STAT), activation via CD40 and IL4 receptor signaling, and/or expression of Bcl6 (Shvarts et al. 2002, *Genes Dev.* 16: 681-686).

In a separate step, the mouse endogenous Kappa and Lambda light chain loci are rendered essentially non-functional such that at least the majority of B cells in the transgenic mice bear Ig receptors that contain the transgenic human VL region. Inactivation of the endogenous mouse immunoglobulin loci is achieved by targeted disruption of the appropriate loci by homologous recombination in mouse embryonic stem cells. The targeted disruption comprises alteration of the genomic sequence such that substantially no functional endogenous mouse immunoglobulin Kappa and/or Lambda light chain is produced. The term "substantially no functional endogenous mouse immunoglobulin" indicates that the endogenous Kappa and/or Lambda light chain loci are functionally silenced such that the level of functional protein expression of the endogenous Kappa and/or Lambda light chain loci, preferably the endogenous Kappa light chain locus, is reduced to about 20% of the level of expression in a reference mouse, more preferred to about 10%, more preferred to about 5%, more preferred to about 2% and more preferred to about 1%. In a most preferred embodiment, the level of functional protein expression of the endogenous Kappa and/or Lambda light chain loci is reduced to 0%. The level of functional protein expression can be determined by means known to the skilled person, including western blotting and pairing with a mouse heavy chain. The reference mouse is a mouse in which the endogenous Kappa and/or Lambda light chain loci is not disrupted. The alteration comprises mutation and/or deletion of gene sequences that are required for functional expression of the endogenous immunoglobulin genes. Alternatively, the alteration comprises insertion of a nucleic acid into the endogenous mouse immunoglobulin Kappa and/or Lambda light chain loci such that the functional expression of the endogenous immunoglobulin genes is reduced. In one embodiment, the nucleic acid comprises a silencing element resulting in transcriptional silencing of the endogenous immunoglobulin gene. In a further embodiment, or in addition, the nucleic acid comprises a sequence that disrupts splicing and/or translation of the endogenous immunoglobulin gene, for example, by introducing an exon that renders a frame shift in the coding sequence, or that comprises a premature stop codon. In each case chimeric animals are generated which are derived in part from the modified embryonic stem cells and are capable of transmitting the genetic modifications through the germ line. The mating of mouse strains with human immunoglobulin loci to strains with inactivated mouse loci yields animals which produce antibodies comprising essentially only human light chains.

A construct for homologous recombination is prepared by means known in the art and any undesirable sequences are removed, e.g., procaryotic sequences. Any convenient technique for introducing a construct for homologous recombination into a target cell may be employed. These techniques include spheroplast fusion, lipofection, electroporation, calcium phosphate-mediated DNA transfer or direct microinjection. After transformation or transfection of the target cells, target cells are selected by means of positive and/or negative markers, for example, by neomycin resistance and/or acyclovir and/or gancyclovir resistance. Those cells which show the desired phenotype may then be further analyzed by restriction analysis, electrophoresis, Southern analysis, PCR, or the like. By identifying fragments which show the presence of the lesion(s) at the target locus, cells in which homologous recombination has occurred to inactivate a copy of the target locus are identified.

Furthermore, it is shown that upon immunization, the murine and human VH regions in the afore-mentioned transgenic mice but not the VL regions are capable of undergoing somatic hypermutations to generate high affinity antibodies. Advantageously, these antibodies encoded by germline VL regions are predicted to contribute to lower immunogenicity when applied in humans and result in more stable antibodies that are less prone to aggregation and thus safer for therapeutic use in humans.

MAbs derived from the afore-mentioned non-human transgenic animals or cells all share the same identical human VL regions. It has been described that mAbs that share the same identical VL region may be co-expressed in a single clonal cell for the production of mixtures of recombinant antibodies with functional binding sites (see the incorporated WO04106375 and WO05068622). Thus, provided is a platform for the generation of specific and high affinity mAbs that constitute the basis for mixtures of mAbs produced by clonal cells.

It is preferred that mAbs derived from the afore-mentioned non-human transgenic animals or cells are directed against cellular targets. Preferred targets are human surface-expressed or soluble proteins or carbohydrate molecules. Further preferred targets are surface-expressed proteins or carbohydrate molecules that are expressed on the surface of bacteria, viruses, and other pathogens, especially of humans.

More specifically, preferred targets include cytokines and chemokines, including but not limited to InterLeukin 1beta (IL1beta), IL2, IL4, IL5, IL7, IL8, IL12, IL13, IL15, IL18, IL21, IL23 and chemokines such as, for example, CXC chemokines, CC chemokines, C chemokines (or γ chemokines) such as XCL1 (lymphotactin-α) and XCL2 (lymphotactin-ß), and CX3C chemokines. Further included as preferred targets are receptor molecules of the cytokines and chemokines, including type I cytokine receptors such as, for example, the IL-2 receptor, type II cytokine receptors such as, for example, interferon receptors, immunoglobulin (Ig) superfamily receptors, tumor necrosis factor receptor family including receptors for CD40, CD27 and CD30, serine/threonine-protein kinase receptors such as TGF beta receptors, G-protein coupled receptors such as CXCR1-CXCR7, and tyrosine kinase receptors such as fibroblast growth factor receptor (FGFR) family members, EGF receptor family members including erbB1 (EGF-R; HER1), erbB2, (HER2), erbB3 (HER3), and erbB4 (HER4), insulin receptor family members including IGF-R1 and IGF-RII, PDGF receptor family members, Hepatocyte growth factor receptor family members including c-Met (HGF-R), Trk receptor family members, AXL receptor family members, LTK receptor family members, TIE receptor family members, ROR receptor family members, DDR receptor family members, KLG receptor family members, RYK receptor family members, MuSK receptor family members, and vascular endothelial growth factor receptor (VEGFR) family members.

Further preferred targets are targets that are over-expressed or selectively expressed in tumors such as, for example, VEGF, CD20, CD38, CD33, CEA, EpCAM, PSMA, CD54, Lewis Y, CD52, CD40, CD22, CD51/CD61, CD74, MUC-1, CD38, CD19, CD262 (TRAIL-R2), RANKL, CTLA4, and CD30; targets that are involved in chronic inflammation such as, for example, CD25, CD11a, TNF, CD4, CD80, CD23, CD3, CD14, IFNgamma, CD40L, CD50, CD122, TGFbeta and TGFalpha.

Preferred surface-expressed proteins or carbohydrate molecules that are expressed on the surface of bacteria, viruses, and other parasitic pathogens, especially of humans, include surface markers of influenza A and B viruses such as hemagglutinin (HA) and neuraminidase (NA), filoviruses such as Ebola virus, rabies, measles, rubella, mumps, flaviviruses such as Dengue virus types 1-4, tick-borne encephalitis virus, West Nile virus, Japanese encephalitis virus, and Yellow fever virus, Paramyxoviruses including Paramyxovirus such as Parainfluenza 1, 3, Rubulavirus such as Mumpsvirus and Parainfluenza 2, 4, Morbillivirus, and Pneumovirus such as Respiratory syncytial virus, Vaccinia, small pox, coronaviruses, including Severe Acute Respiratory Syndrome (SARS) virus, hepatitis virus A, B and C, Human Immunodeficiency Virus, Herpes viruses, including cytomegalovirus, Epstein Barr virus, Herpes simplex virus, and Varicella zoster virus, parvoviruses such as, for example, B19; *Legionella pneumophila; Listeria monocytogenes; Campylobacter jejuni; Staphylococcus aureus; E. coli* O157:H7; *Borrelia burgdorferi; Helicobacter pylori; Ehrlichia chaffeensis; Clostridium difficile; Vibrio cholera; Salmonella enterica* Serotype *Typhimurium; Bartonella henselae; Streptococcus pyogenes* (Group A Strep); *Streptococcus agalactiae* (Group B Strep); Multiple drug resistant *S. aureus* (e.g., MRSA); *Chlamydia pneumoniae; Clostridium botulinum; Vibrio vulnificus*; Parachlamydia pneumonia; *Corynebacterium amycolatum; Klebsiella pneumonia*; Linezolid-resistant enterococci (*E. faecalis* and *E. faecium*); and Multiple drug resistant *Acinetobacter baumannii*.

Most preferred targets are IL-6 and its receptor, IL-6Ralpha, glycoprotein-denominated gp130, RSV, especially the surface proteins F, G and SH and non-structural proteins such as N and M, and receptor tyrosine kinases, in particular erbB1 (EGF-R; HER1), erbB2, (HER2), erbB3 (HER3), erbB4 (HER4), IGF-R1 and IGF-RII, c-Met (HGF-R).

Therefore, provided is a platform for the generation of specific and high affinity mAbs against the above mentioned targets that constitute the basis for mixtures of mAbs produced by clonal cells. In certain embodiments, the specific and high affinity mAbs comprise mAbs that are directed against different epitopes on at least one of the targets. In a further preferred embodiment, the specific and high affinity mAbs comprise mAbs that are directed against different targets, such as, for example, one or more members of the EGF-receptor family, including erbB1 (EGF-R; HER1), erbB2, (HER2), erbB3 (HER3) and erbB4 (HER4).

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See, e.g., Sambrook et al., *Molecular Cloning: A Laboratory Manual* (3rd edition, Cold Spring Harbor Laboratory Press, Cold Spring Harbor, N.Y. (2001)), which is incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

DESCRIPTION OF THE DRAWINGS

The patent or application file contains at least one drawing executed in color. Copies of this patent or patent application publication with color drawing(s) will be provided by the Office upon request and payment of the necessary fee.

FIG. 12: Overview of the sequences used or referred to in this applicationx: Human germline IGKV1-39/J DNA (SEQ ID NO:84); human germline IGKV1-39/J Protein (SEQ ID NO:85); human germline IGLV2-14/J DNA (SEQ ID NO:86); human germline IGLV2-14/J Protein (SEQ ID NO:87); Rat IGCK allele a DNA (SEQ ID NO:88); Rat IGCK allele a protein (SEQ ID NO:89); IGKV1-39/J-Ck (SEQ ID NO:90); IGLV2-14/J-Ck (SEQ ID NO:91); VkP-IGKV1-39/J-Ck (SEQ ID NO:92); VkP-IGKV1-39/J-Ck-Δ1 (SEQ ID NO:93); VkP-IGKV1-39/J-Ck-Δ2 (SEQ ID NO:94); VkP-IGLV2-14/J-Ck (SEQ ID NO:95); pSELECT-IGKV1-39/J-Ck (SEQ ID NO:96); pSelect-IGLV2-14/J-Ck (SEQ ID NO:97); MV1043 (SEQ ID NO:98); and MV1057 (SEQ ID NO:99).

FIGS. 13A-C: Generation of Rosa26-IgVk1-39 KI allele. FIG. 13A Schematic drawing of the pCAGGS-IgVK1-39 targeting vector. FIG. 13B Nucleotide sequence of the pCAGGS-IgVK1-39 targeting vector (SEQ ID NO:100). FIG. 13C Targeting strategy.

FIG. 14A Southern blot analysis of genomic DNA of ES clones comprising an insertion of the pCAGGS-IgVK1-39 targeting vector. Genomic DNA of four independent clones was digested with AseI and probed with 5e1 indicating the 5'-border of the targeting vector. All clones comprise a correct insertion of the targeting vector at the 5' end. FIG. 14B Southern blot analysis of genomic DNA of ES clones comprising an insertion of the pCAGGS-IgVK1-39 targeting vector. Genomic DNA of four independent clones was digested with MscI and probed with 3e1 indicating the 3'-border of the targeting vector. All clones comprise a correct insertion of the targeting vector at the 3' end. FIG. 14C Southern blot analysis of genomic DNA of ES clones comprising an insertion of the pCAGGS-IgVK1-39 targeting vector. Genomic DNA of four independent clones was digested with BamHI and probed with an internal Neo probe indicating the 5'-border of the targeting vector. All clones comprise a correct, single insertion of the targeting vector.

FIGS. 15A-C: Generation of Rosa26-IgV12-14 KI allele. FIG. 15A Schematic drawing of the pCAGGS-IgVL2-14 targeting vector. FIG. 15B Nucleotide sequence of the pCAGGS-IgVL2-14 targeting vector containing the CAGGS expression insert (SEQ ID NO:101) based on the rearranged germline IGLV2-14/J V lambda region (IGLV2-14/J-Ck). FIG. 15C Targeting strategy.

FIG. 16A displays the binding strength for DRB1 allotypes, while FIG. 16C displays the binding strength for DRB3/4/5, DQ and DP allotypes. The values in the figure represent dissociation constants (Kds) and are plotted on a logarithmic scale in the range 0.01 μM-0.1 μM (very strong binders may have run off the plot). For medium binding peptides, qualitative values are given only, and weak and non-binders are not shown. Values are plotted on the first residue of the peptide in the target sequence (the peptide itself extends by another nine residues). Importantly, only the strongest binding receptor for each peptide is shown: cross-reacting allotypes with lower affinity are not visible in this plot. The strongest binding receptor is indicated by its serotypic name. Finally, any germline-filtered peptides are plotted with a lighter color in the epitope map (in this case, no non-self epitopes were found). FIG. 16B shows the HLA binding promiscuity for every decameric peptide (Y-axis: the number of HLA allotypes recognizing critical epitopes in each of the peptides starting at the indicated residue shown on the X-axis). The promiscuity is measured as the number of allotypes out of the total of 47 for which the peptide is a critical binder. White columns refer to self-peptides, and black columns (absent here) to non-self peptides.

FIG. 18A Targeting strategy. FIG. 18B Schematic drawing of the pIgKappa targeting vector.

FIG. 19A First step of the targeting strategy. FIG. 19B Second step of the targeting strategy.

FIG. 20A pVkP-O12 (VkP-IGKV1-39/J-Ck); FIG. 20B pVkP-O12-del1 (VkP-IGKV1-39/J-Ck-Δ1); FIG. 20C pVkP-O12-del2 (VkP-IGKV1-39/J-Ck-Δ2).

FIG. 21A VkP-O12 (VkP-IGKV1-39/J-Ck); FIG. 21B VkP-O12-del1 (VkP-IGKV1-39/J-Ck-Δ1); FIG. 21C VkP-O12-del2 (VkP-IGKV1-39/J-Ck-Δ2).

FIG. 26A Gating of bone marrow cells. FIG. 26B Histograms of transgene expression with overlay from one WT control.

FIG. 28: Parameters of stability for stable clones containing the germline IGKV1-39 gene.

FIG. 29A-B: Antibody mixtures used for staining of lymphocyte populations. BM=bone marrow, PC=peritoneal cavity, PP=Peyer's patches.

DETAILED DESCRIPTION OF THE INVENTION

EXAMPLES

Figure 1:
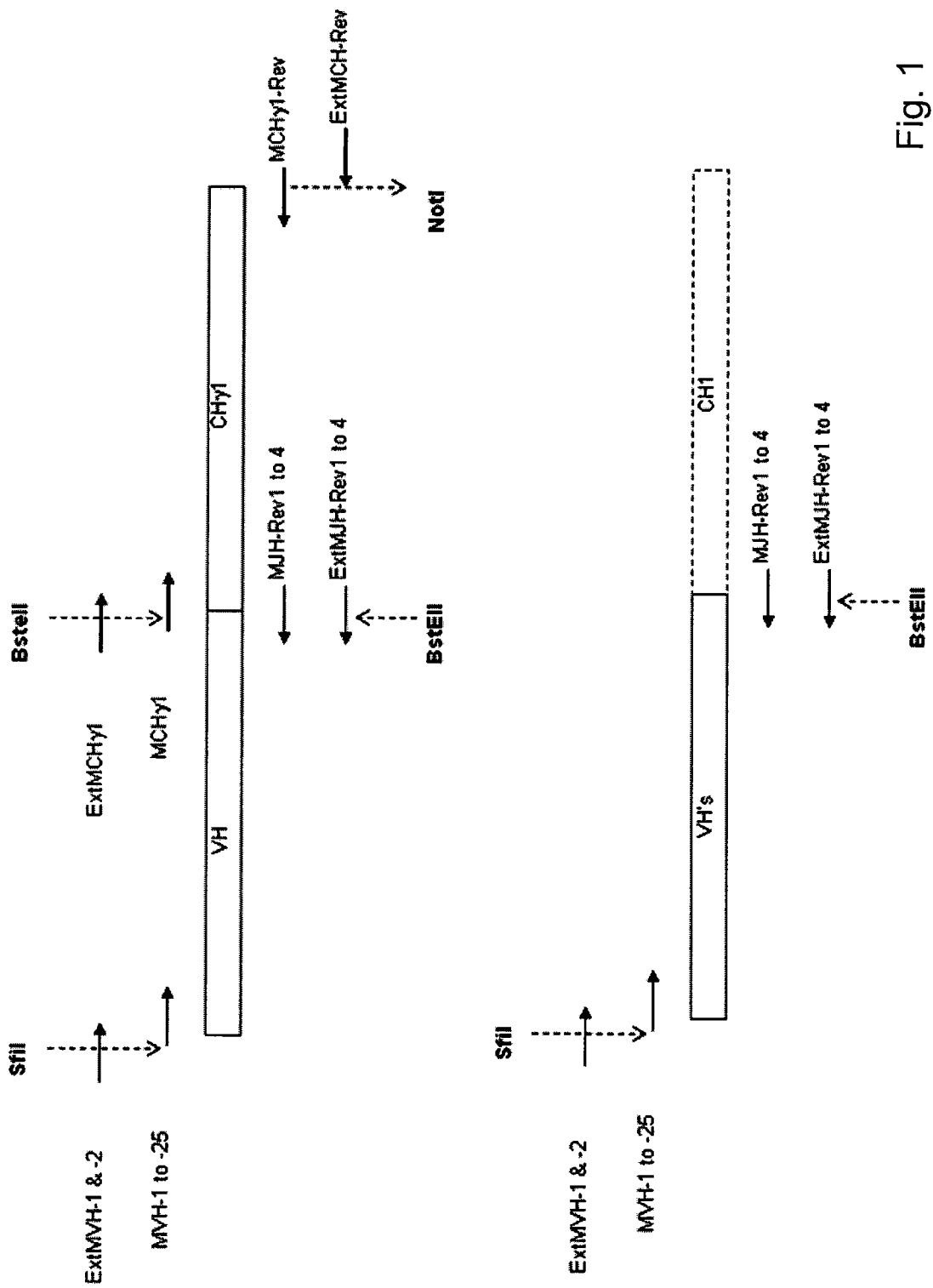
FIG. 1: A topology map of the annealing locations of mouse specific VH primers and the position of required restriction sites that are introduced by overhanging sequences at the 3' end of primers.

Example 1: Human Light Chain V-Gene Clones

This example describes the rationale behind the choice of two human light chain V-genes, one gene of the kappa type and one gene of the lambda type, that are used as a proof of concept for light chain expressing transgenic mice. De Wildt et al. 1999 (de Wildt et al. (1999), *J. Mol. Biol.* 285(3):895) analyzed the expression of human light chains in peripheral IgG-positive B-cells. Based on these data, IGKV1-39 (O12) and IGLV2-14 (2a2) were chosen as light chains as they were well represented in the B-cell repertoire. The J-segment sequence of the light chains has been chosen based upon sequences as presented in GenBank ABA26122 for IGKV1-39 (B. J. Rabquer, S. L. Smithson, A. K. Shriner and M. A. J. Westerink) and GenBank AAF20450 for IGLV2-14 (O. Ignatovich, I. M. Tomlinson, A. V. Popov, M. Bruggemann and G. J. Winter, *J. Mol. Biol.* 294 (2):457-465 (1999)).

All framework segments are converted into germline amino acid sequences to provide the lowest immunogenicity possible in potential clinical applications.

Example 2: Obtaining Mouse Heavy Chain V-Genes that Pair with Human IGKV1-39 Gene Segment to Form Functional Antibody Binding Sites This example describes the identification of mouse heavy chain V-genes that are capable of pairing with a single, rearranged human germline IGKV1-39/J region. A spleen VH repertoire from mice that were immunized with tetanus toxoid was cloned in a phage display Fab vector with a single human IGKV1-39-C kappa light chain and subjected to panning against tetanus toxoid. Clones obtained after a single round of panning were analyzed for their binding specificity. The murine VH genes encoding tetanus toxoid-specific Fab fragments were subjected to sequence analysis to identify unique clones and assign VH, DH and JH utilization.

Many of the protocols described here are standard protocols for the construction of phage display libraries and the panning of phages for binding to an antigen of interest and described in Antibody Phage Display: Methods and Protocols (editor(s): Philippa M. O'Brien and Robert Aitken).

Immunizations

BALB/c mice received one immunization with tetanus toxoid and were boosted after six weeks with tetanus toxoid.

Splenocyte Isolation

Preparation of spleen cell suspension. After dissection, the spleen was washed with PBS and transferred to a 60 mm Petri dish with 20 ml PBS. A syringe capped with 20 ml PBS and a G20 needle was used to repeatedly flush the spleen. After washing the flushed cells with PBS, the cells were carefully brought into suspension using 20 ml PBS and left on a bench for five minutes to separate the splenocytes from the debris and cell clusters. The splenocytes suspension was transferred on top of a Ficoll-Paque™ PLUS-filled tube and processed according to the manufacturer's procedures for lymphocyte isolation (Amersham Biosciences).

RNA Isolation and cDNA Synthesis

After isolation and pelleting of lymphocytes, the cells were suspended in TRIzol LS Reagent (Invitrogen) for the isolation of total RNA according to the accompanying manufacturer's protocol and subjected to reverse transcription reaction using 1 microgram of RNA, Superscript III RT in combination with dT20 according to manufacturer's procedures (Invitrogen).

PCR Amplification of cDNA

The cDNA was amplified in a PCR reaction using primer combinations that allow the amplification of approximately 110 different munne V-genes belonging to 15 VH families (Table 1; RefSeq NG_005838; Thiebe et al. 1999, *European Journal of Immunology* 29:2072-2081). In the first round, primer combinations that bind to the 5' end of the V-genes and 3' end of the J regions were used. In the second round, PCR products that were generated with the MJH-Rev2 primer were amplified in order to introduce modifications in the 3' region to enable efficient cloning of the products. In the last round of amplification, all PCR products were amplified using primers that introduce a SfiI restriction site at the 5' end and a BstEII restriction site at the 3' end (see FIGS. 1 and 2, and Table 1).

Figure 2:
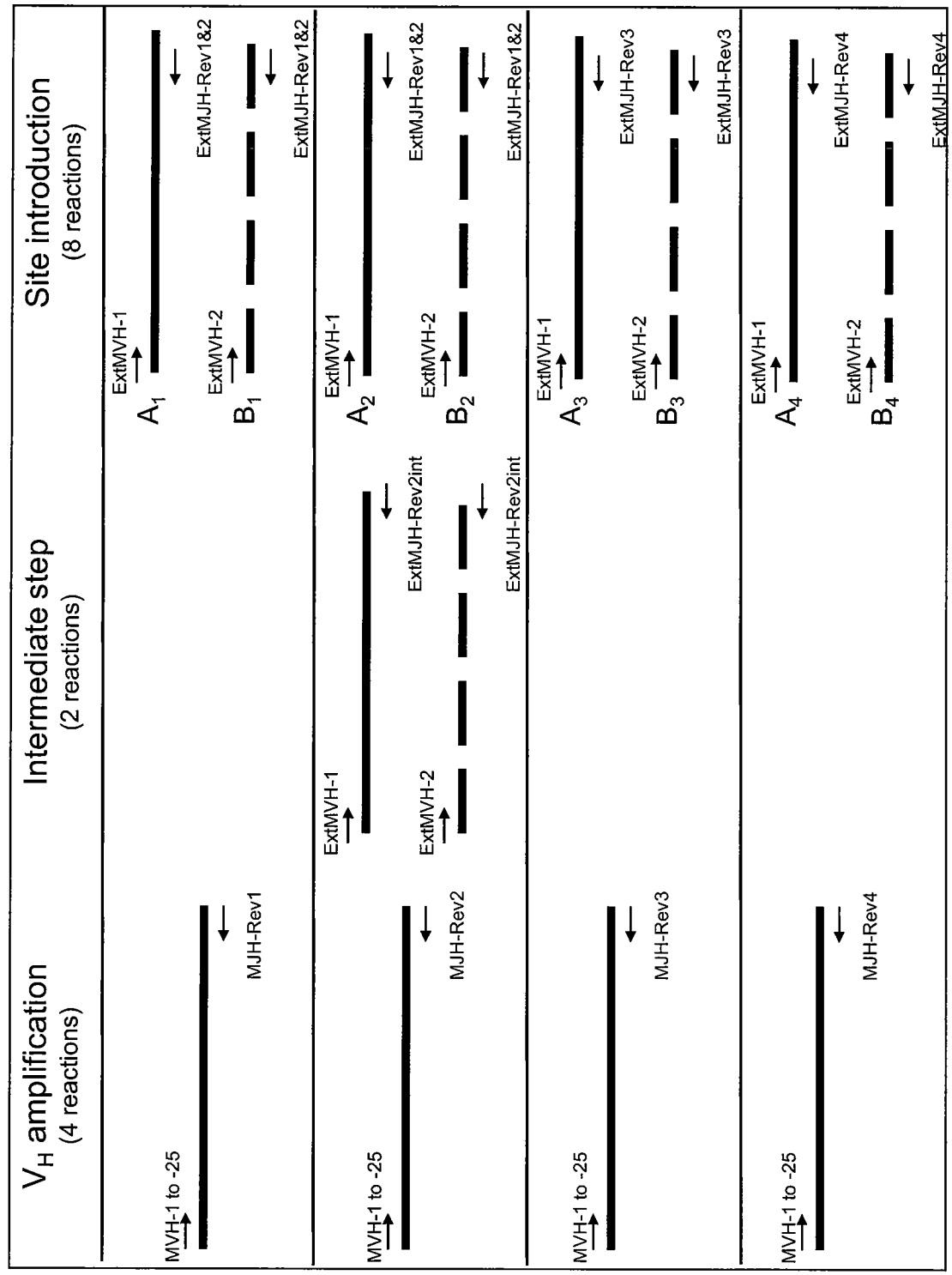
FIG. 2: PCR amplification steps (Amplification, Intermediate and Site introduction). The location and names of the mouse VH amplification primers (and mixtures of primers) are indicated per step.

Reaction conditions for 1st round PCR: four different reactions combining all 25 forward primers (MVH1 to MVH25, Table 1 and FIG. 2) and one reverse primer per reaction (MJH-Rev1, MJH-Rev2, MJH-Rev3 or MJH-Rev4; see Table 1 and FIG. 2). Fifty microliters PCR volumes were composed of 2 microliters cDNA (from RT reactions), 10 microliters 5* Phusion polymerase HF buffer, 40 nM of each of the 25 forward primers (total concentration of 1 micromolar), 1 micromolar reverse primer, 1 microliter 10 mM dNTP stock, 1.25 unit Phusion polymerase and sterile MQ water. The thermocycler program consisted of a touch down program: one cycle 98° C. for 30 seconds, 30 cycles 98° C. for ten seconds, 58° C. decreasing 0.2° C. per cycle ten seconds, 72° C. 20 seconds and one cycle 72° C. for three minutes. The second round PCR program was set up only for the products of the first PCR that contain the MJH-Rev2 primer: two different reactions combining either the ExtMVH-1 or ExtMVH-2 primers (Table 1 and FIG. 2) in combination with the reverse primer ExtMJH-Rev2int (Table 1 and FIG. 2). Fifty microliters PCR volumes were composed of 50 ng PCR product (from first PCR round), 10 microliters 5* Phusion polymerase HF buffer, 500 nM of each forward primer, 1 micromolar reverse primer, 1 microliter 10 mM dNTP stock, 1.25 unit Phusion polymerase and sterile MQ water. The thermocycler program consisted of a touch down program followed by a regular amplification step: one cycle 98° C. for 30 seconds, ten cycles 98° C. for ten seconds, 65° C. decreasing 1.5° C. per cycle ten seconds, 72° C. 20 seconds, ten cycles 98° C. for ten seconds, 55° C. ten seconds, 72° C. 20 seconds and one cycle 72° C. for three minutes. The third round PCR program was setup as described in FIG. 2. Fifty microliters PCR volumes were composed of 50 ng PCR product (from earlier PCR rounds, FIG. 2), 10 microliters 5* Phusion polymerase HF buffer, 1 micromolar forward primer (Table 1 and FIG. 2), 1 micromolar reverse primer, 1 microliter 10 mM dNTP stock, 1.25 unit Phusion polymerase and sterile MQ water. The program consists of a touch down program followed by a regular amplification step: one cycle 98° C. for 30 seconds, ten cycles 98° C. for ten seconds, 65° C. decreasing 1.5° C. per cycle ten seconds, 72° C. 20 seconds, ten cycles 98° C. for ten seconds, 55° C. ten seconds, 72° C. 20 seconds and one cycle 72° C. for three minutes. After PCR amplifications, all PCR products were gel purified using Qiaex II according to the manufacturer's protocols.

Restriction Enzyme Digestions

Figure 3:
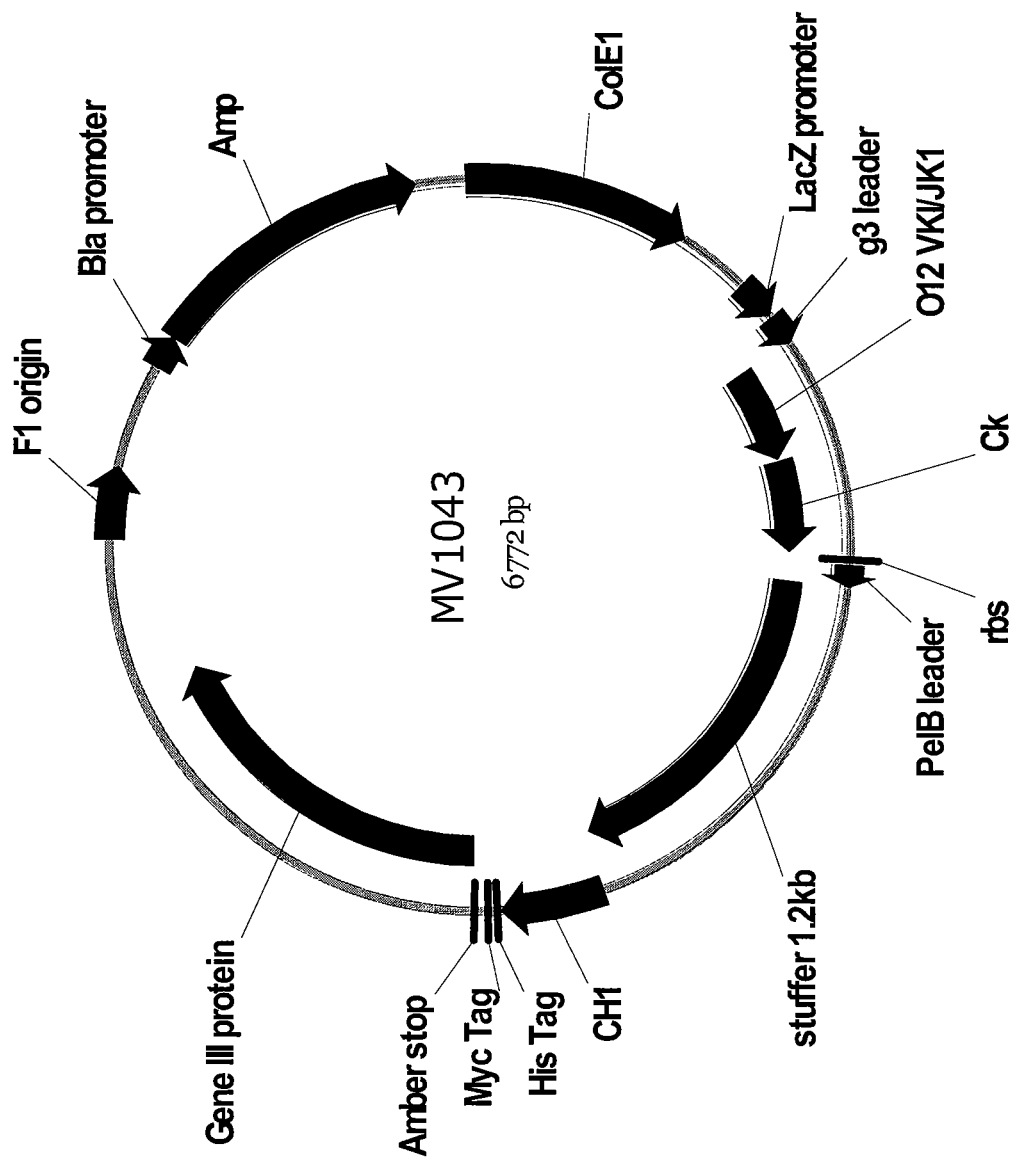
FIG. 3: Topology of the MV1043 vector. This vector is used for the cloning of human or murine VH fragments. O12 (IGKV1-39) is indicated as the VL gene. Products of this vector in combination with helper phages in *E. coli* cells allow the generation of phages that display Fab fragments on the surface of the phage particles as a fusion product to the g3 protein and presence of the vector in the phage as the genetic content (F1 ORI).
Figure 12:
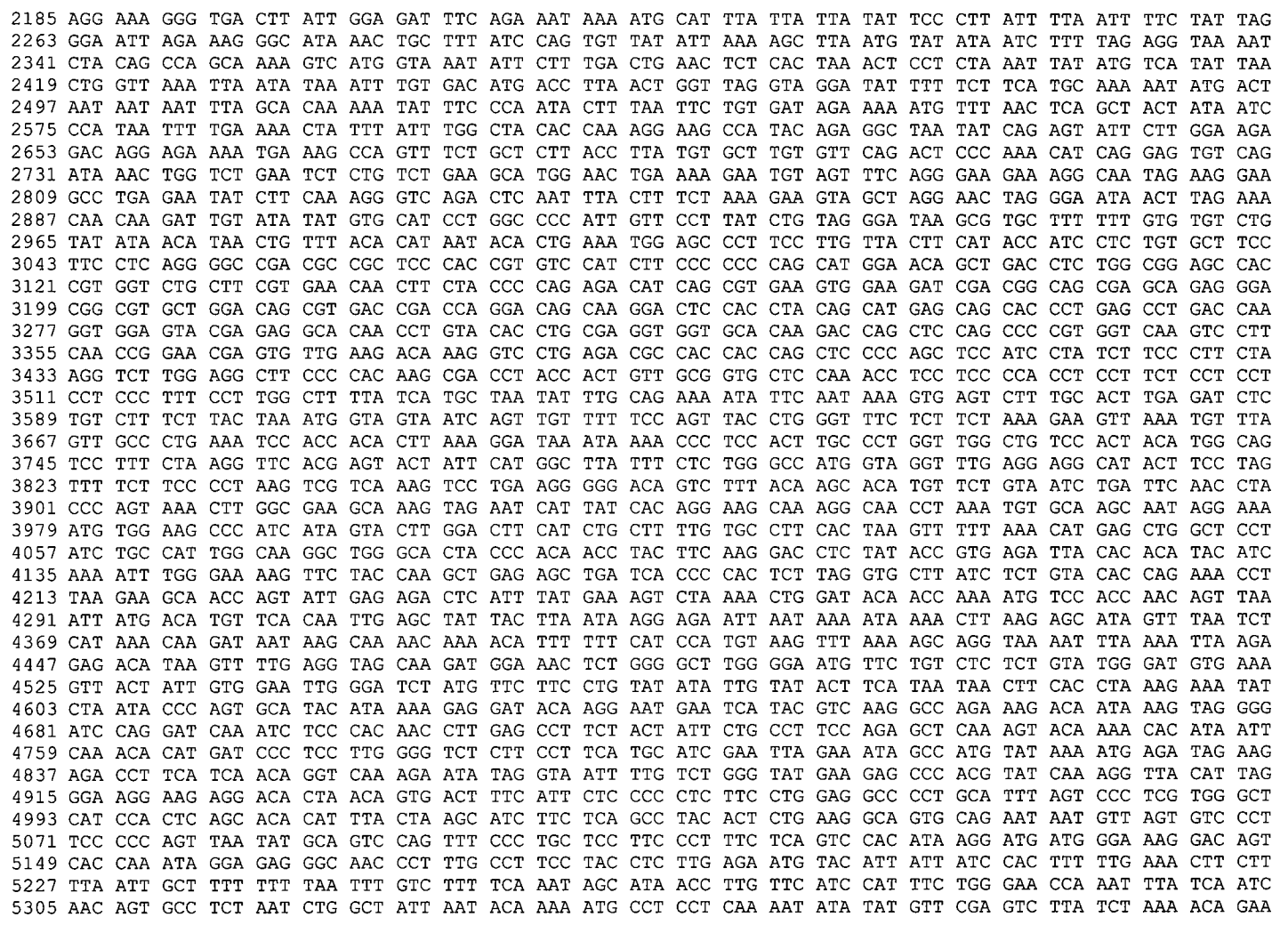
Figure 12:
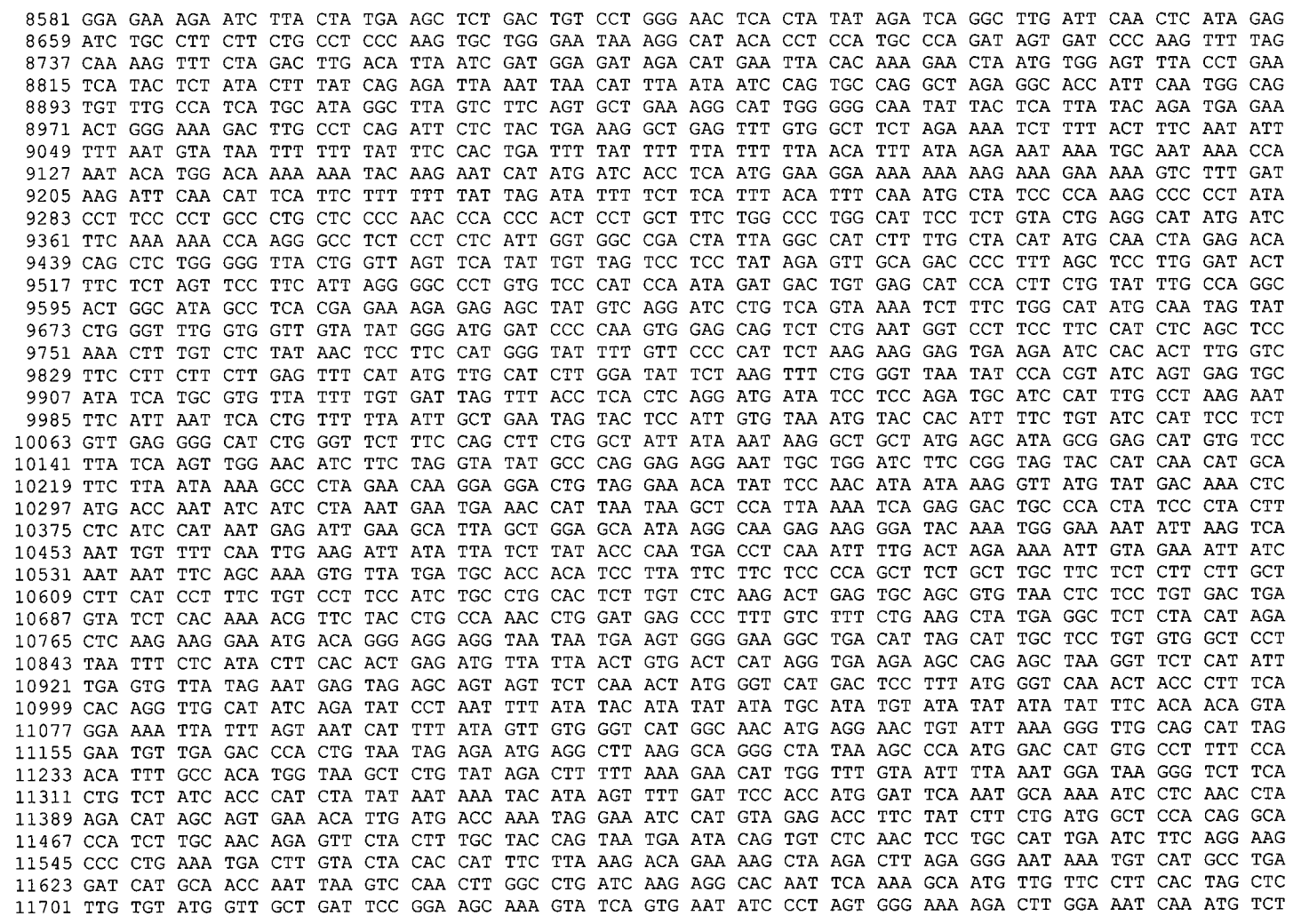

Purified products were digested with BstEII and SfiI in two steps. First 1 microgram of DNA was digested in 100 microliters reactions consisting of 10 microliters of 10* NEB buffer 3 (New England Biolabs), 1 microliter 100* BSA, 12.5 unit BstEII and sterile water for six hours at 60° C. in a stove. The products were purified using Qiaquick PCR Purification kit from Qiagen according to the manual instructions and eluted in 40 microliters water. Next all products were further digested with SfiI in 100 microliters reactions consisting of 10 microliters of 10* NEB buffer 2 (New England Biolabs), 1 microliter 100* BSA, 12.5 unit SfiI and sterile water for 12 hours at 50° C. in a stove. The digested fragments were purified by Qiaquick Gel Extraction kit following gel separation on a 20 cm 1.5% agarose TBE plus ethidium bromide gel at 80 V. 100 micrograms of the acceptor vector (MV1043, FIGS. 3 and 12) was digested with 50 units Eco91I in 600 microliters under standard conditions (Tango buffer) and next purified on a 0.9% agarose gel. After a second digestion step under prescribed conditions with 400 units SfiI in 500 microliters for 12 hours, 100 units BsrGI were added for three hours at 50° C.

Ligations

Each PCR product was ligated separately according to the following scheme: 70 ng digested PCR products, 300 ng digested acceptor vector, 100 units T4 Ligase (NEB), 1* ligase buffer in 30 microliters for 16 hours at 12° C. The ligation reactions were purified with phenol/chloroform/isoamyl alcohol extractions followed by glycogen precipitations (Sigma Aldrich #G1767) according to the manufacturer's protocol and finally dissolved in 25 microliters sterile water.

Transformations and Library Storage

The purified ligation products were transformed by electroporation using 1200 microliters TG1 electrocompetent bacteria (Stratagene #200123) per ligation batch and plated on LB carbenicillin plates containing 4% glucose. Libraries were harvested by scraping the bacteria in 50 ml LB carbenicillin. After centrifugation at 2000 g for 20 minutes at 4° C., the bacterial pellets were resuspended carefully in 2 ml ice cold 2*TY/30% glycerol on ice water and frozen on dry ice/ethanol before storage at −80° C.

Library Amplification

Libraries were grown and harvested according to procedures as described by Kramer et al. 2003 (Kramer et al. (2003), *Nucleic Acids Res.* 31(11):e59) using VCSM13 (Stratagene) as helper phage strain.

Selection of Phages on Coated Immunotubes

Tetanus toxoid was dissolved in PBS in a concentration of 2 µg/ml and coated to MAXISORP™ Nunc-Immuno Tube (Nunc 444474) overnight at 4° C. After discarding the coating solution, the tubes were blocked with 2% skim milk (ELK) in PBS (blocking buffer) for one hour at RT. In parallel, 0.5 ml of the phage library was mixed with 1 ml blocking buffer and incubated for 20 minutes at room temperature. After blocking the phages, the phage solution was added to the tetanus toxoid-coated tubes and incubated for two hours at RT on a slowly rotating platform to allow binding. Next, the tubes were washed ten times with PBS/0.05% TWEEN™-20 detergent followed by phage elution by an incubation with 1 ml 50 mM glycine-HCl pH 2.2 ten minutes at RT on rotating wheel and directly followed by neutralization of the harvested eluent with 0.5 ml 1 M Tris-HCl pH 7.5.

Harvesting Phage Clones

Five ml XL1-Blue MRF (Stratagene) culture at O.D. 0.4 was added to the harvested phage solution and incubated for 30 minutes at 37° C. without shaking to allow infection of the phages. Bacteria were plated on Carbenicillin/Tetracycline 4% glucose 2*TY plates and grown overnight at 37° C.

Phage Production

Phages were grown and processed as described by Kramer et al. 2003 (Kramer et al. 2003, *Nucleic Acids Res.* 31(11):e59) using VCSM13 as helper phage strain.

Phage ELISA

ELISA plates were coated with 100 microliters tetanus toxoid per well at a concentration of 2 micrograms/ml in PBS overnight at 4° C. Plates coated with 100 microliters thyroglobulin at a concentration of 2 micrograms/ml in PBS were used as a negative control. Wells were emptied, dried by tapping on a paper towel, filled completely with PBS-4% skimmed milk (ELK) and incubated for one hour at room temperature to block the wells. After discarding the block solution, phage minipreps pre-mixed with 50 µl blocking solution were added and incubated for one hour at RT. Next five washing steps with PBS-0.05% Tween-20 removed unbound phages. Bound phages were detected by incubating the wells with 100 microliters anti-M13-HRP antibody conjugate (diluted 1/5000 in blocking buffer) for one hour at room temperature. Free antibody was removed by repeating the washing steps as described above, followed by TMB substrate incubation until color development was visible. The reaction was stopped by adding 100 microliters of 2 M $H_2SO_4$ per well and analyzed on an ELISA reader at 450 nm emission wavelength (Table 2). Higher numbers indicate stronger signals and thus higher incidence of specific binding of the phage-Fab complex.

Sequencing

Clones that gave signals at least three times above the background signal (Table 2) were propagated, used for DNA miniprep procedures (see procedures Qiagen miniPrep manual) and subjected to nucleotide sequence analysis. Sequencing was performed according to the Big Dye 1.1 kit accompanying manual (Applied Biosystems) using a reverse primer (CH1_Rev1, Table 1) recognizing a 5' sequence of the CH1 region of the human IgG1 heavy chain (present in the Fab display vector MV1043, FIGS. 3 and 12). Mouse VH sequences of 28 tetanus toxoid binding clones are depicted in Table 3. The results show that the selected murine VH genes belong to different gene families, and different individual members from these gene families are able to pair with the rearranged human IGKV1-39/J VH region to form functional tetanus toxoid-specific antibody binding sites. From the sequence analyses, it was concluded that the murine VH regions utilize a diversity of DH and JH gene segments.

Example 3: Silencing of the Mouse Kappa Light Chain Locus

This example describes the silencing of the mouse endogenous kappa light chain locus. The endogenous kappa locus is modified by homologous recombination in ES cells, followed by the introduction of genetically modified ES cells in mouse embryos to obtain genetically adapted offspring.

Figure 4:
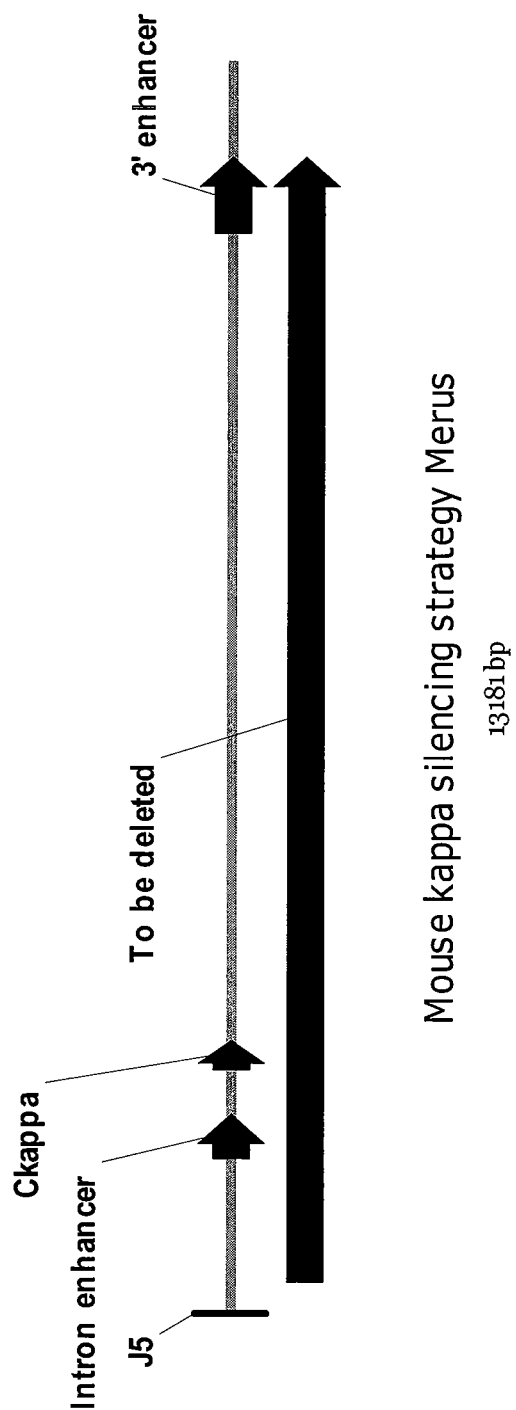
FIG. 4: The topology of the mouse Ckappa locus downstream of the J-segments. Both enhancers and Ckappa region are indicated. The lower arrow indicates the region that is removed in order to silence the locus.
Figure 18A:
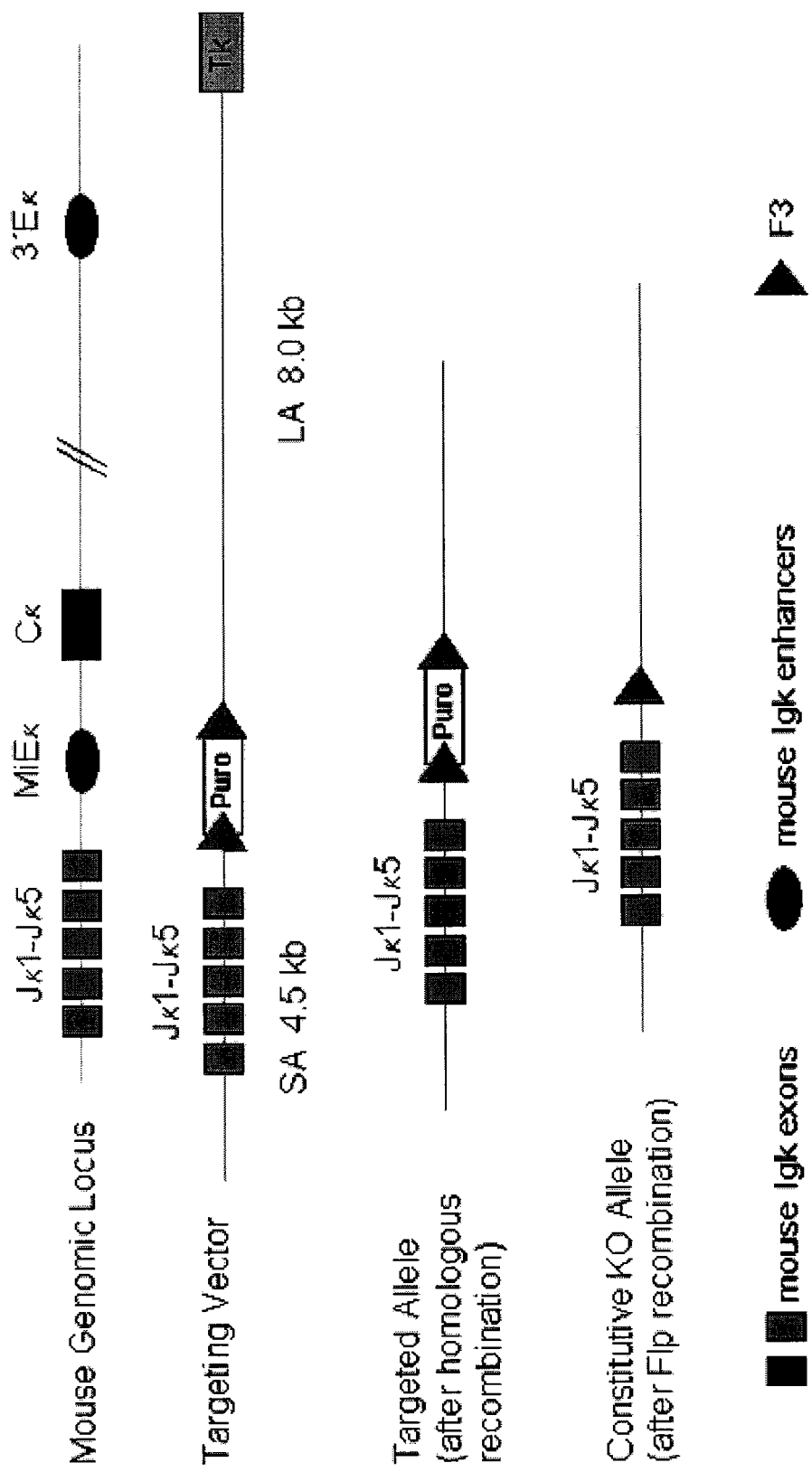
FIGS. 18A-B: Constitutive knock-out (KO) of the Ig kappa locus.
Figure 18B:
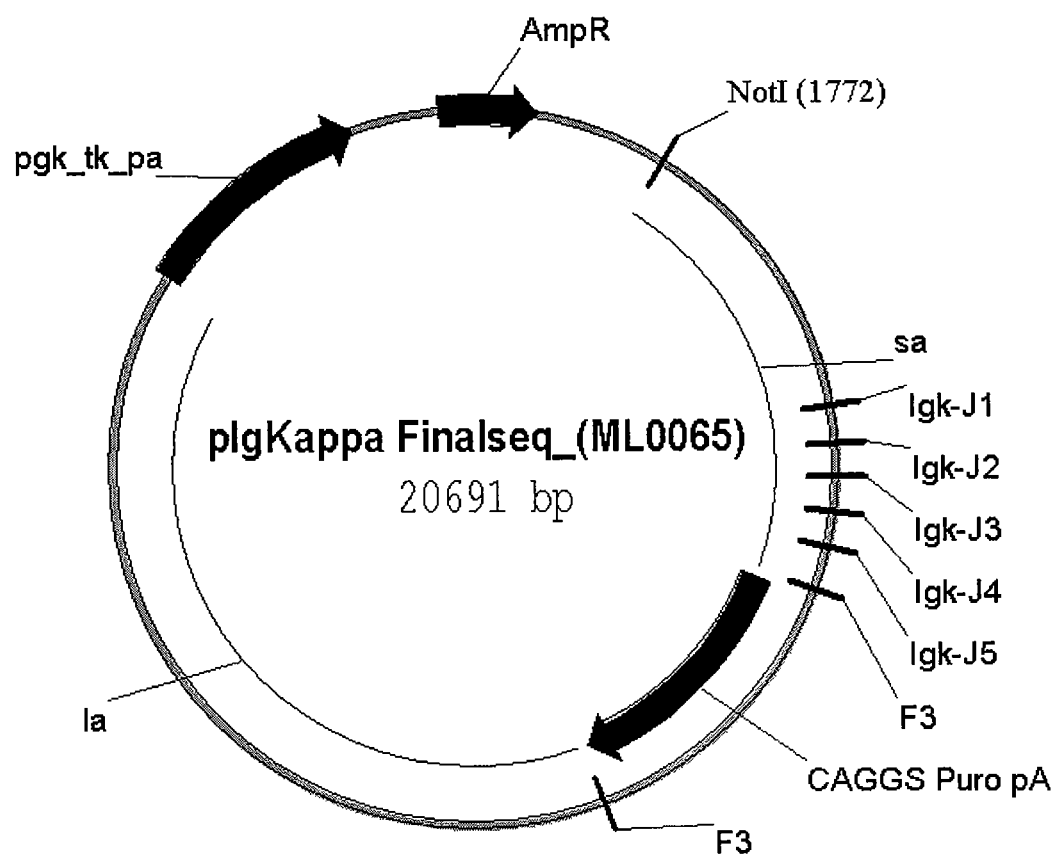

A vector that contains an assembled nucleotide sequence consisting of a part comprising the J-region to 338 bp downstream of the J5 gene segment fused to a sequence ending 3' of the 3' CK enhancer is used for homologous recombination in ES cells. The assembled sequence is used to delete a genomic DNA fragment spanning from 3' of the JK region to just 3' of the 3' CK enhancer. As a consequence of this procedure, the CK constant gene, the 3' enhancer and some intergenic regions are removed (see FIGS. 4 and 18A-B).

Construction of the Targeting Vector

A vector that received 4.5-8 kb flanking arms on the 3' and 5' end fused to the deletion segment was used for targeted homologous recombination in an ES cell line. Both arms were obtained by PCR means ensuring maximum homology. The targeting strategy allows generation of constitutive KO allele. The mouse genomic sequence encompassing the Igk intronic enhancer, Igk constant region and the Igk 3' enhancer was replaced with a PuroR cassette, which was flanked by F3 sites and inserted downstream of the Jk elements. Flp-mediated removal of the selection marker resulted in a constitutive KO allele. The replacement of the Igk MiEk-Igk C-Igk 3'E genomic region (approximately 10 kb) with a F3-Puro cassette (approx. 3 kb) was likely to decrease the efficiency of homologous recombination. Therefore, the arms of homology were extended accordingly and more ES cell colonies were analyzed after transfection in order to identify homologous recombinant clones.

Generation of ES Cells Bearing the Deleted Kappa Fragment

The generation of genetically modified ES cells was essentially performed as described (Seibler et al. (2003), *Nucleic Acids Res.* February 15; 31(4):e12). See also Example 14 for a detailed description.

Generation of ES Mice by Tetraploid Embryo Complementation

The production of mice by tetraploid embryo complementation using genetically modified ES cells was essentially performed as described (Eggan et al., *PNAS* 98:6209-6214; J. Seibler et al. (2003), *Nucleic Acids Res.* February 15; 31(4):e12; Hogan et al. (1994), Summary of mouse development, *Manipulating the Mouse Embryo*, Cold Spring Harbor Laboratory Press, Cold Spring Harbor N.Y., pp. 253-289).

Example 4: Silencing of the Mouse Lambda Light Chain Locus

This example describes the silencing of the mouse endogenous lambda light chain locus. The endogenous lambda locus is modified by homologous recombination in ES cells followed by the introduction of genetically modified ES cells in mouse embryos to obtain genetically adapted offspring.

Two regions of the murine lambda locus that together contain all functional lambda V regions are subject to deletion.

Figure 5:
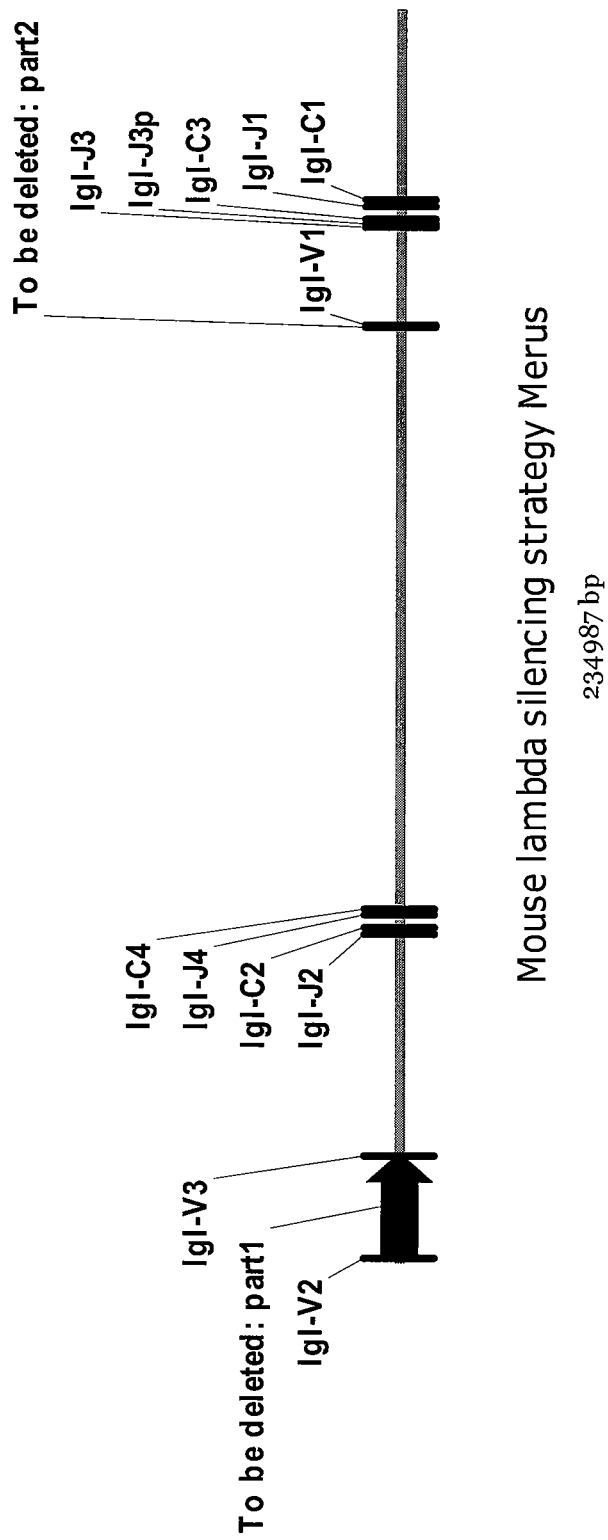
FIG. 5: The topology of the mouse C-lambda locus. All three active V-regions are indicated (Igl-V1, V2 and V3) as are the J-segments (Igl-J1, Igl-J2, Igl-J3, Igl-J4 and the pseudo segment Igl-J3p) and constant regions (Igl-C1, Igl-C2, Igl-C3 and Igl-C4). The regions that are deleted in order to silence the locus are indicated by deletion markers. These deletions include all active V genes (1, 2 and 3) and the intergenic segment between V2 and V3.
Figure 19A:
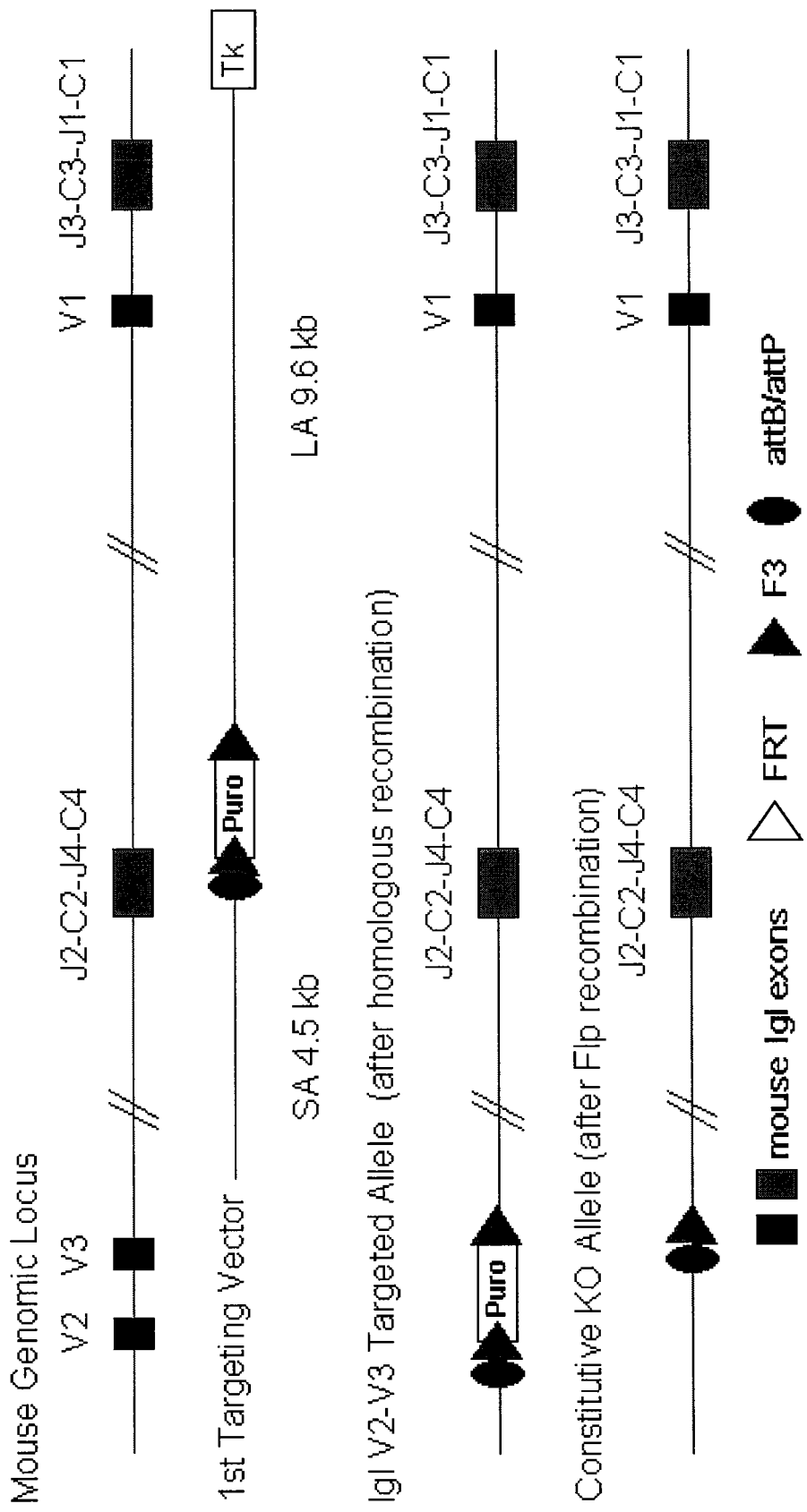
FIGS. 19A-B: Constitutive KO of the Ig lambda locus.
Figure 19B:
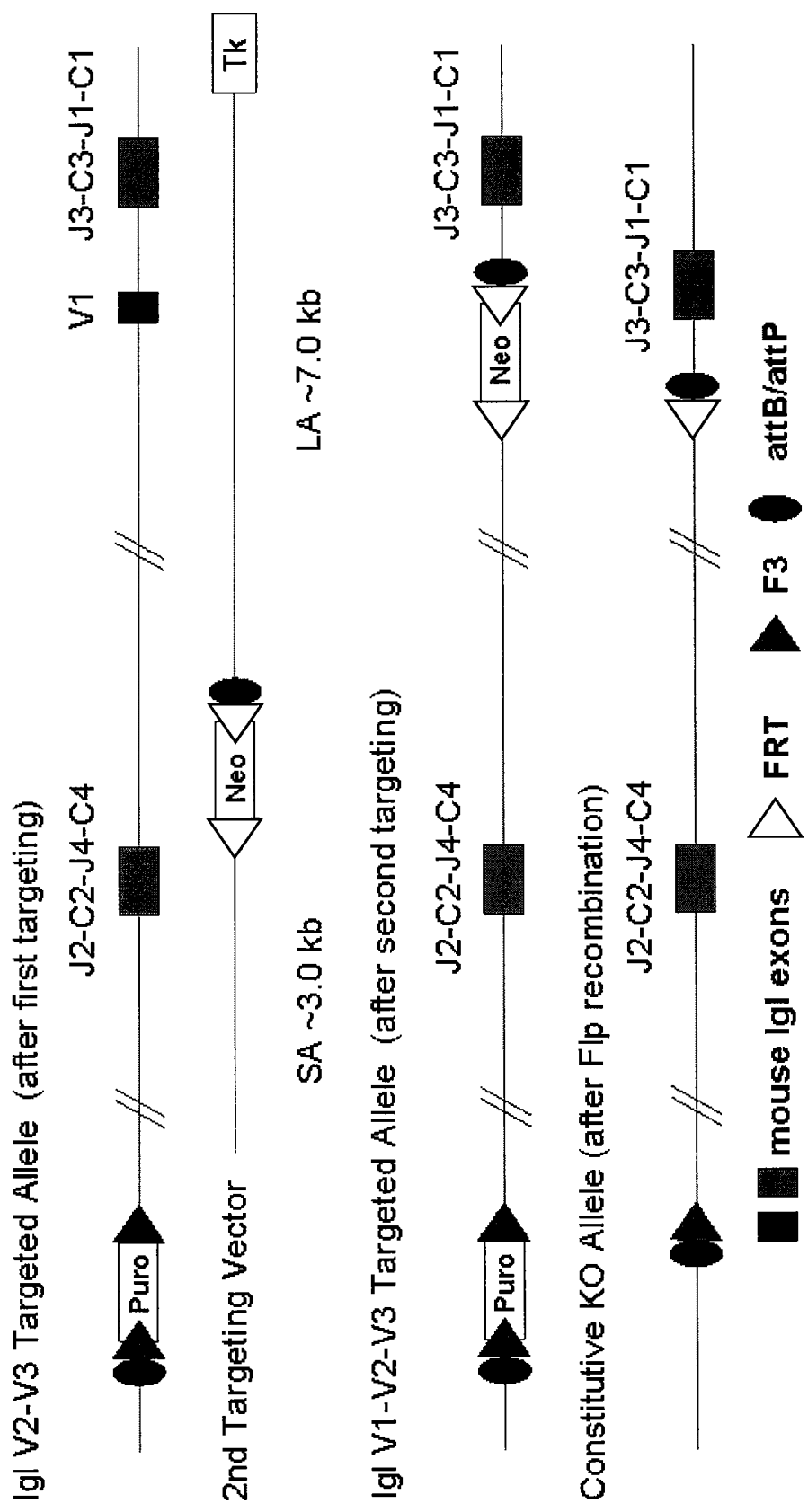

The first region targeted for homologous recombination-based deletion is a region that is located 408 bp upstream of the start site of the IGLV2 gene segment and ends 215 bp downstream of IGLV3 gene segment, including the intergenic sequence stretch between these IGLV gene segments. The second region that is subject to a deletion involves the IGLV1 gene segment consisting of a fragment spanning from 392 bp upstream to 171 bp downstream of the IGLV1 gene segment. As a consequence of these two deletion steps, all functional V-lambda genes segments are deleted, rendering the locus functionally inactive (FIGS. 5 and 19A-B).

Construction of the Targeting Vectors

Vectors that received 3-9.6 kb flanking arms on the 3' and 5' end fused to the deletion segment were used for targeted homologous recombination in an ES cell line. Both arms were obtained by PCR means ensuring maximum homology. In a first step, the mouse genomic sequence encompassing the Igl V2-V3 regions were replaced with a PuroR cassette flanked by F3 sites, which yields a constitutive KO allele after Flp-mediated removal of selection marker (see FIG. 19A). In a second step, the mouse genomic sequence encompassing the Igl V1 region was replaced with a Neo cassette in ES cell clones which already carried a deletion of the Igl V2-V3 regions (see FIG. 19B). The selection marker (NeoR) was flanked by FRT sites. A constitutive KO allele was obtained after Flp-mediated removal of selection markers.

Generation of ES Cells Bearing the Deleted Lambda Fragment

The generation of genetically modified ES cells was essentially performed as described (J. Seibler, B. Zevnik, B. KOter-Luks, S. Andreas, H. Kern, T. Hennek, A. Rode, C. Heimann, N. Faust, G. Kauselmann, M. Schoor, R. Jaenisch, K. Rajewsky, R. Kohn, F. Schwenk (2003), *Nucleic Acids Res.*, February 15; 31(4):e12). See also, Example 14 for a detailed description. To show that both targeting events occurred on the same chromosome several double targeted clones were selected for the in vitro deletion with pCMV C31deltaCpG. The clones were expanded under antibiotic pressure on a mitotically inactivated feeder layer comprised of mouse embryonic fibroblasts in DMEM High Glucose medium containing 20% FCS (PAN) and 1200 μ/mL Leukemia Inhibitory Factor (Millipore ESG 1107). $1\times10^7$ cells from each clone were electroporated with 20 μg of circular pCMV C31deltaCpG at 240 V and 500 μF and plated on four 10 cm dishes each. Two to three days after electroporation, cells were harvested and analyzed by PCR. Primers used were:

```
2005_5:  CCCTTTCCAATCTTTATGGG    (SEQ ID NO: 1)

2005_7:  AGGTGGATTGGTGTCTTTTTCTC (SEQ ID NO: 2)

2005_9:  GTCATGTCGGCGACCCTACGCC  (SEQ ID NO: 3)
```

PCR reactions were performed in mixtures comprising 5 μl PCR Buffer 10× (Invitrogen), 2 μl MgCl$_2$ (50 mM), 1 μl dNTPs (10 mM), 1 μl first primer (5 μM), 1 μl second primer (5 μM), 0.4 μl Taq (5 U/ul, Invitrogen), 37.6 μl H$_2$O, and 2 μl DNA. The program used was 95° C. for five minutes;

followed by 35 cycles of 95° C. for 30 seconds; 60° C. for 30 seconds; 72° C. for 1 minute; followed by 72° C. for ten minutes.

Generation of ES Mice by Tetraploid Embryo Complementation

The production of mice by tetraploid embryo complementation using genetically modified ES cells was essentially performed as described (Eggan et al., *PNAS* 98:6209-6214; J. Seibler, B. Zevnik, B. Klter-Luks, S. Andreas, H. Kern, T. Hennek, A. Rode, C. Heimann, N. Faust, G. Kauselmann, M. Schoor, R. Jaenisch, K. Rajewsky, R. Kihn, and F. Schwenk (2003), *Nucleic Acids Res.*, February 15; 31(4):e12; Hogan et al. (Cold Spring Harbor Laboratory Press, Cold Spring Harbor N.Y.), pp. 253-289).

Example 5: Construction of the CAGGS Expression Insert Based on a Rearranged Human Germline IGKV1-39/J-Ck Gene (IGKV1-39/J-Ck)

Figure 6:
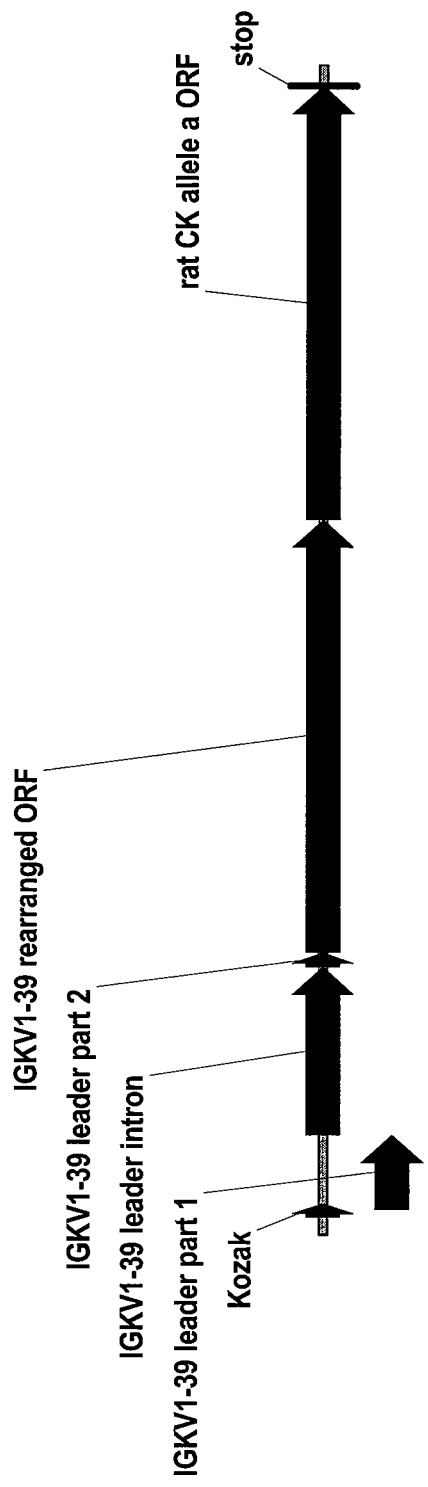
FIG. 6: Construct topology of IGKV1-39/J-Ck with an intron located in the leader open reading frame (ORF).

This example describes the construction of a CAGGS expression cassette incorporating the rearranged human germline IGKV1-39/J region. This insert expression cassette encompasses cloning sites, a Kozak sequence, a leader sequence containing an intron, an open reading frame of the rearranged IGKV1-39 region, a rat CK constant region from allele a and a translational stop sequence (IGKV1-39/J-Ck; FIG. 6). The primary construct consists of naturally occurring sequences and has been analyzed and optimized by removing undesired cis acting elements like internal TATA-boxes, poly adenylation signals, chi-sites, ribosomal entry sites, AT-rich or GC-rich sequence stretches, ARE-, INS- and CRS sequence elements, repeat sequences, RNA secondary structures, (cryptic) splice donor and acceptor sites and splice branch points (GeneArt GmbH). In addition, the codon usage in the open reading frame regions is optimized for expression in mice. The intron sequence is unchanged and thus represents the sequence identical to the coding part of the human IGKV1-39 leader intron.

Figure 13A:
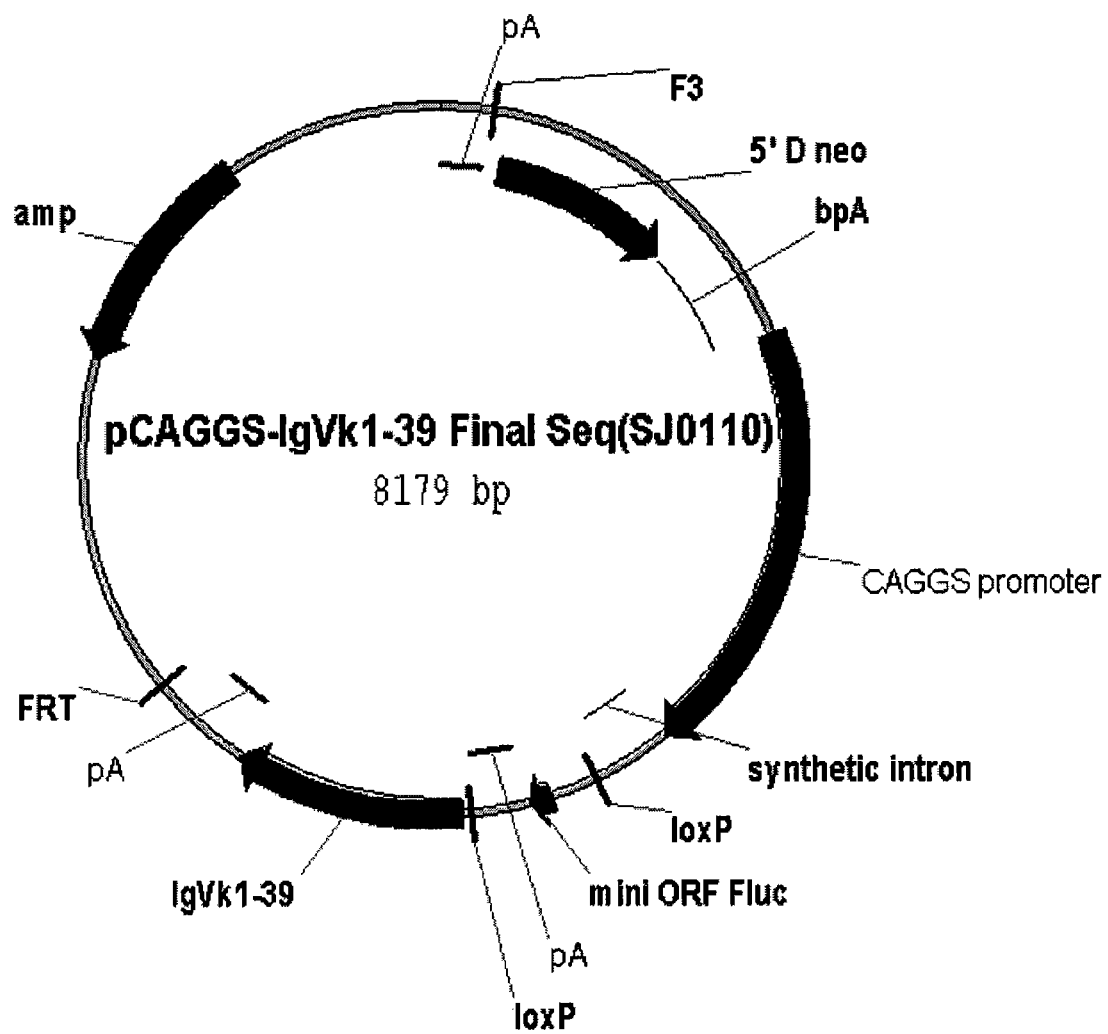
Figure 13C:
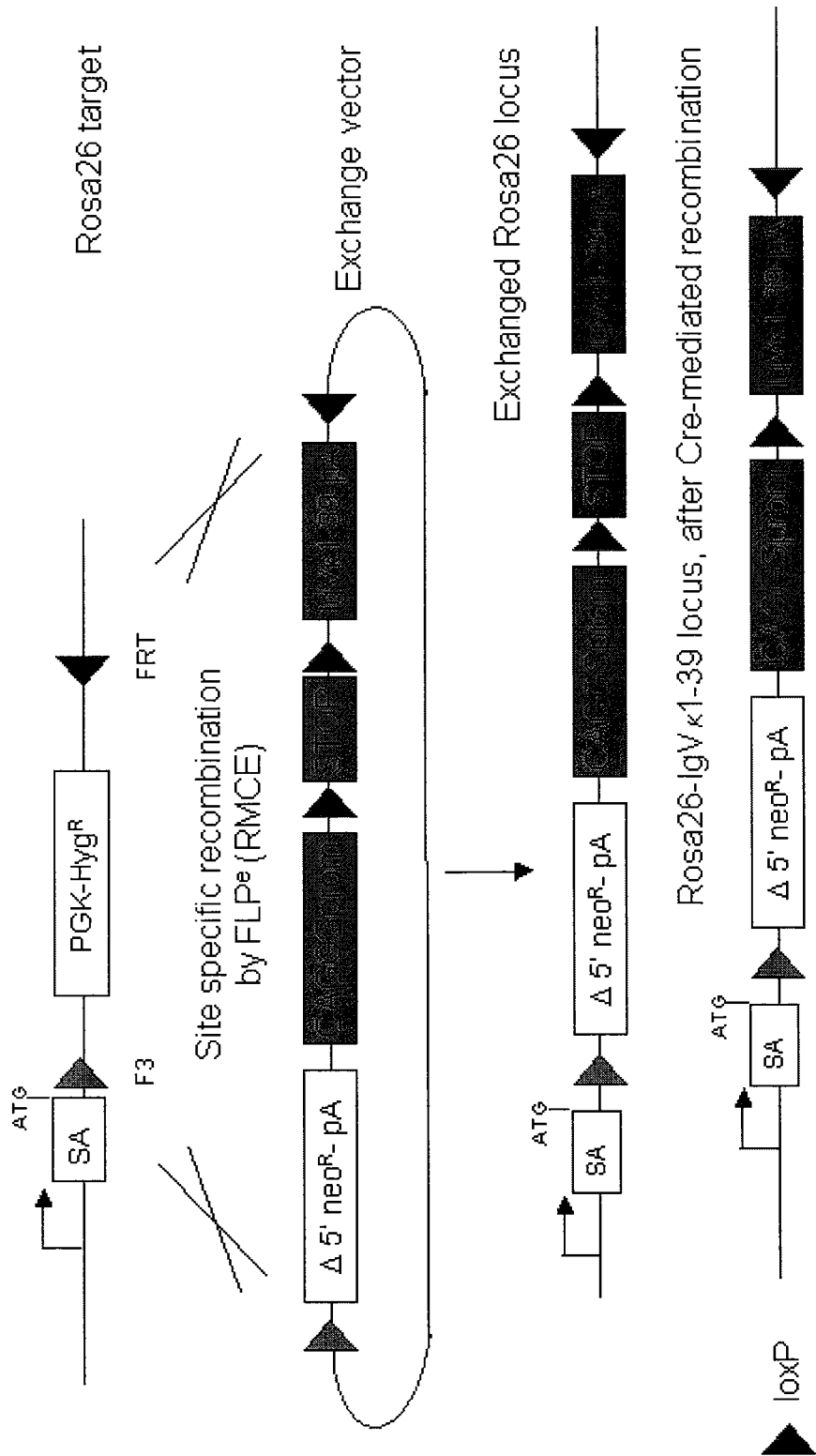

At the 5' end of the expression cassette, a NotI site was introduced and on the 3' site a NheI site. Both sites are used for cloning in the CAGGS expression module. After gene assembly according to methods used by GeneArt, the insert is digested with NotI-NheI and cloned into the expression module containing a CAGGS promoter, a stopper sequence flanked by LoxP sites ("floxed"), a polyadenylation signal sequence and, at the 5' and 3' end, sequences to facilitate homologous recombination into the Rosa26 locus of mouse ES cell lines. Promoter and/or cDNA fragments were amplified by PCR, confirmed by sequencing and/or cloned directly from delivered plasmids into an RMCE exchange vector harboring the indicated features. A schematic drawing and the confirmed sequence of the final targeting vector pCAGGS-IgVK1-39 are shown in FIGS. 13A and 13B. The targeting strategy is depicted in FIG. 13C.

Example 6: CAGGS Expression Insert Based on the Rearranged Germline IGLV2-14/J V Lambda Region (IGLV2-14/J-Ck)

Figure 7:
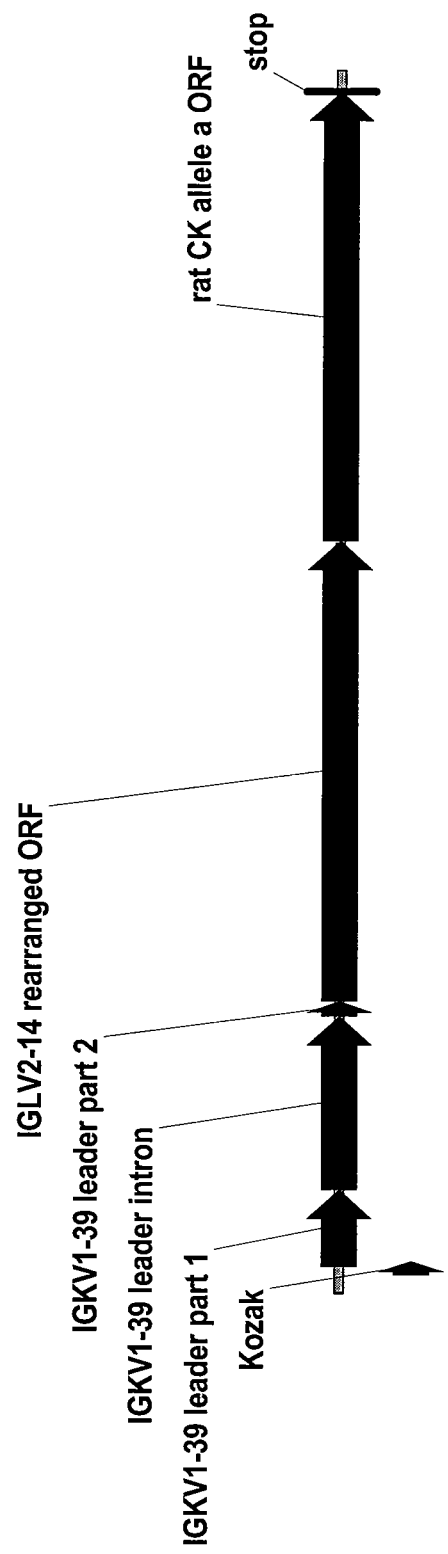
FIG. 7: Construct topology of IGLV2-14/J-Ck with an intron located in the leader open reading frame (ORF).

This example describes the sequence and insertion of an expression cassette incorporating the rearranged germline IGLV2-14/J V lambda region. This insert encompasses cloning sites, a Kozak sequence, a leader sequence containing an intron, an open reading frame of the rearranged IGLV2-14/J region, a rat CK constant region from allele a and a translational stop sequence (IGLV2-14/J-Ck; FIG. 7). The primary construct consists of naturally-occurring sequences and has been analyzed and optimized by removing undesired cis acting elements like: internal TATA-boxes, poly adenylation signals, chi-sites, ribosomal entry sites, AT-rich or GC-rich sequence stretches, ARE-, INS- and CRS sequence elements, repeat sequences, RNA secondary structures, (cryptic) splice donor and acceptor sites and splice branch points (GeneArt GmbH). In addition, the codon usage in the open reading frame regions was optimized for expression in mice. The intron sequence is unchanged and thus represents the sequence identical to the human IGKV1-39 leader intron.

Figure 15A:
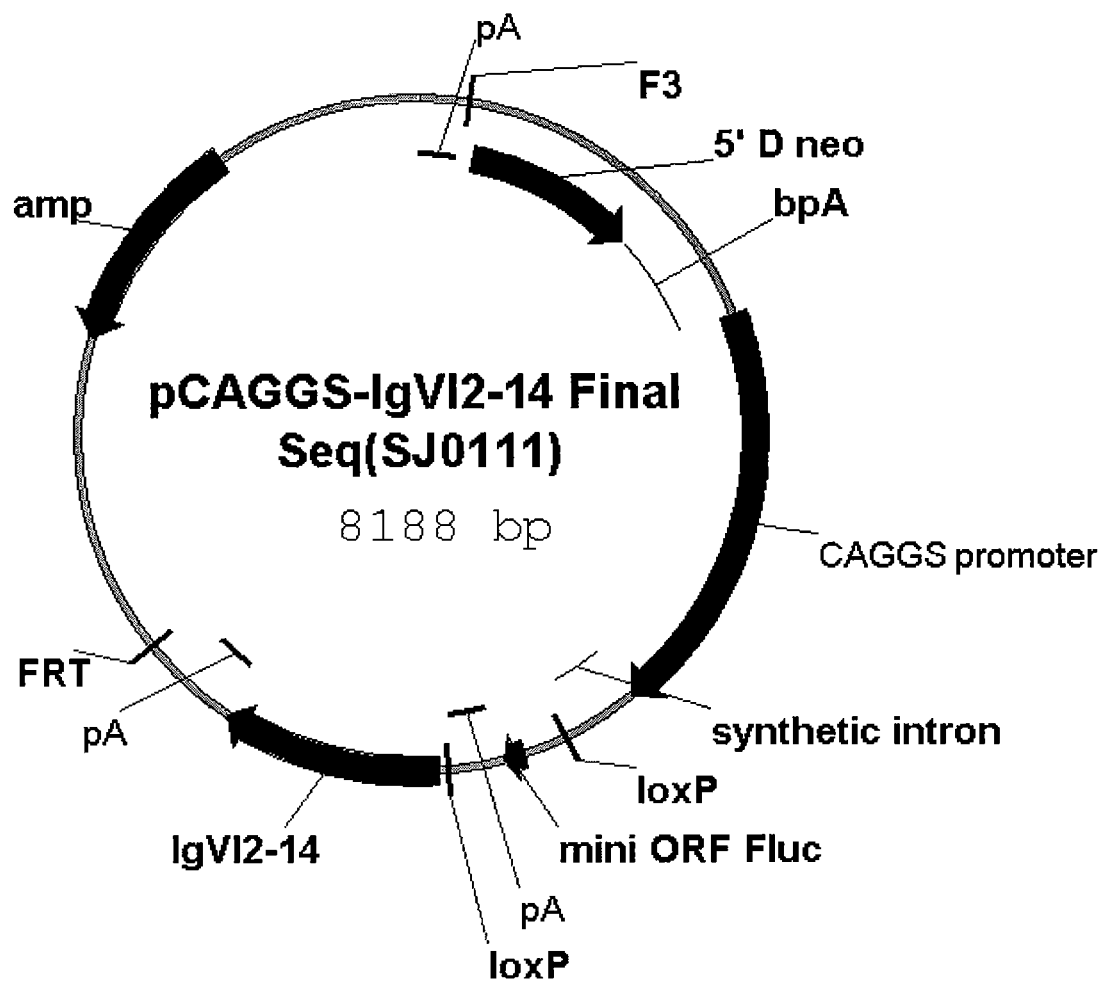
Figure 15C:
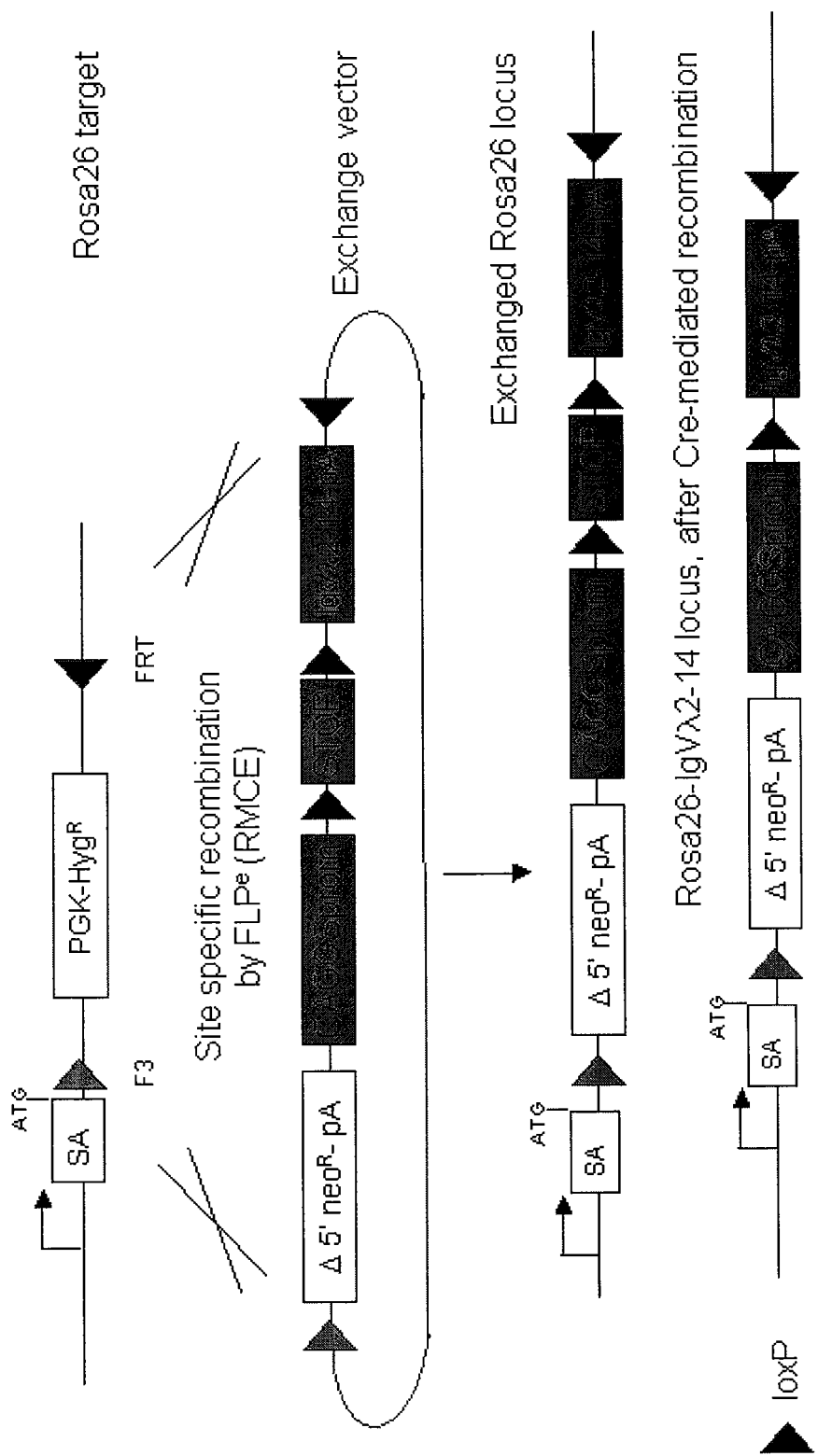
Figure 16A:
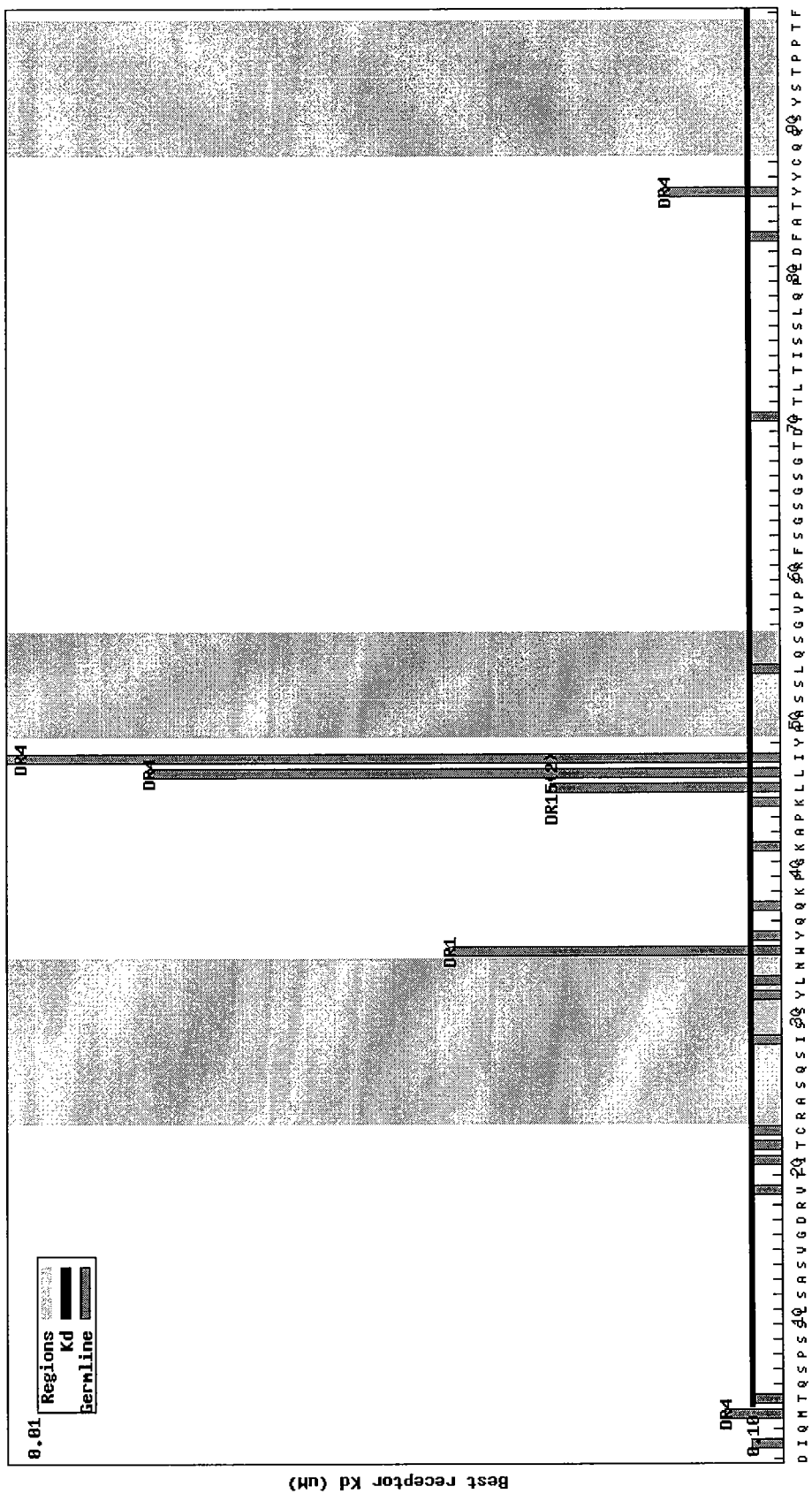
FIGS. 16A-C: Epibase® profile of IGKV1-39 residues 1-107 (SEQ ID NO:85).
Figure 16B:
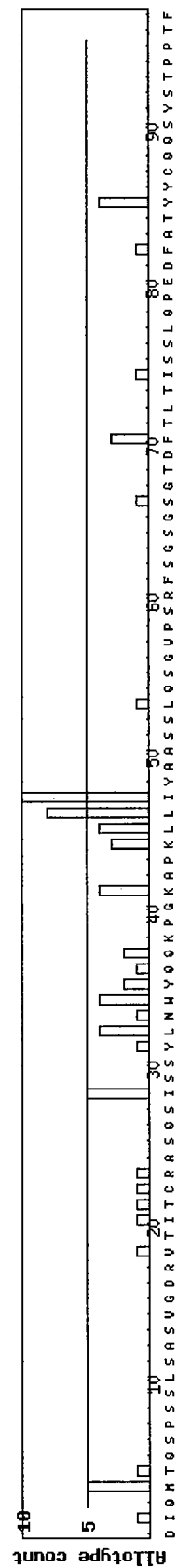
Figure 16C:
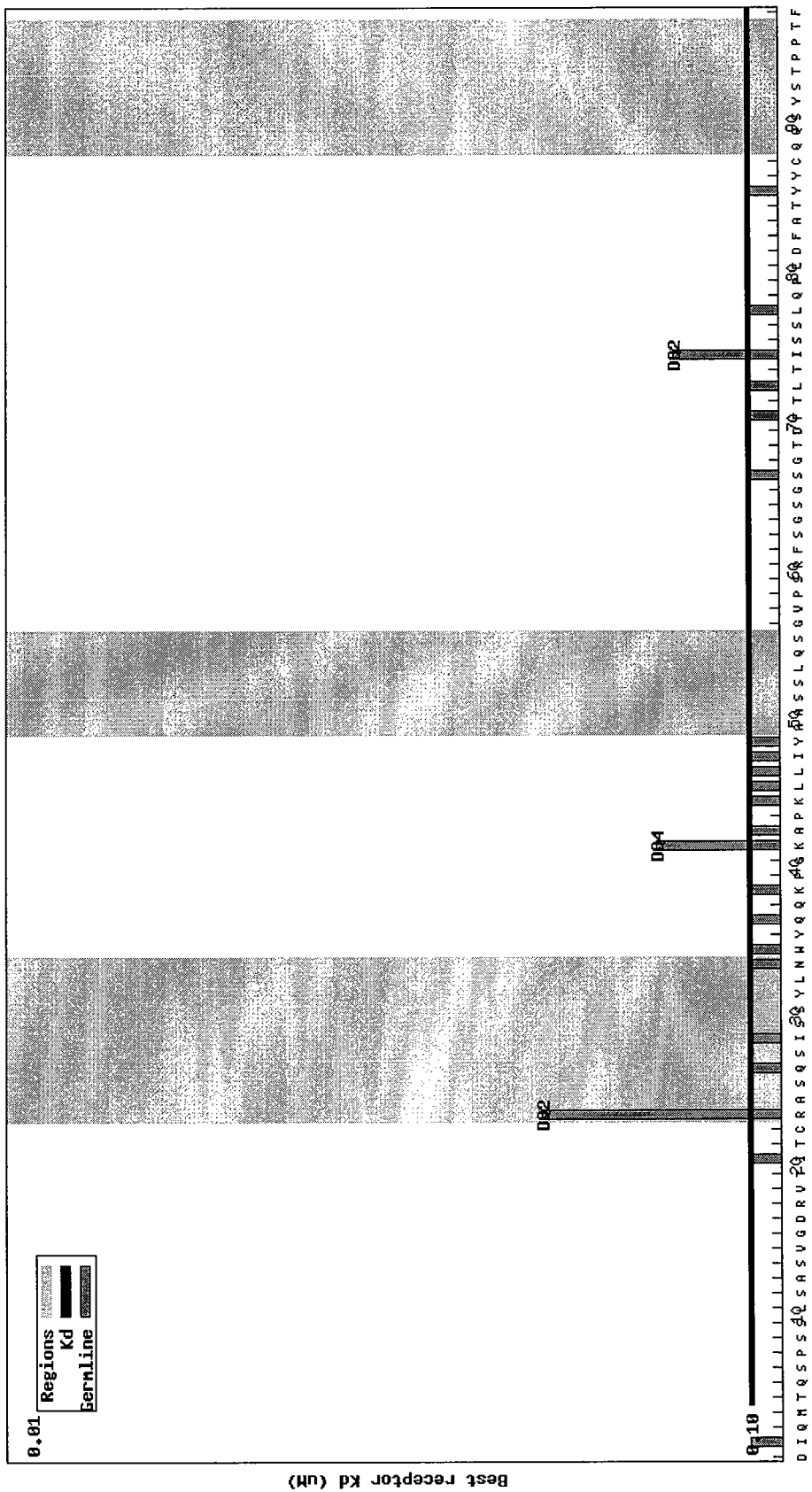
Figure 17:
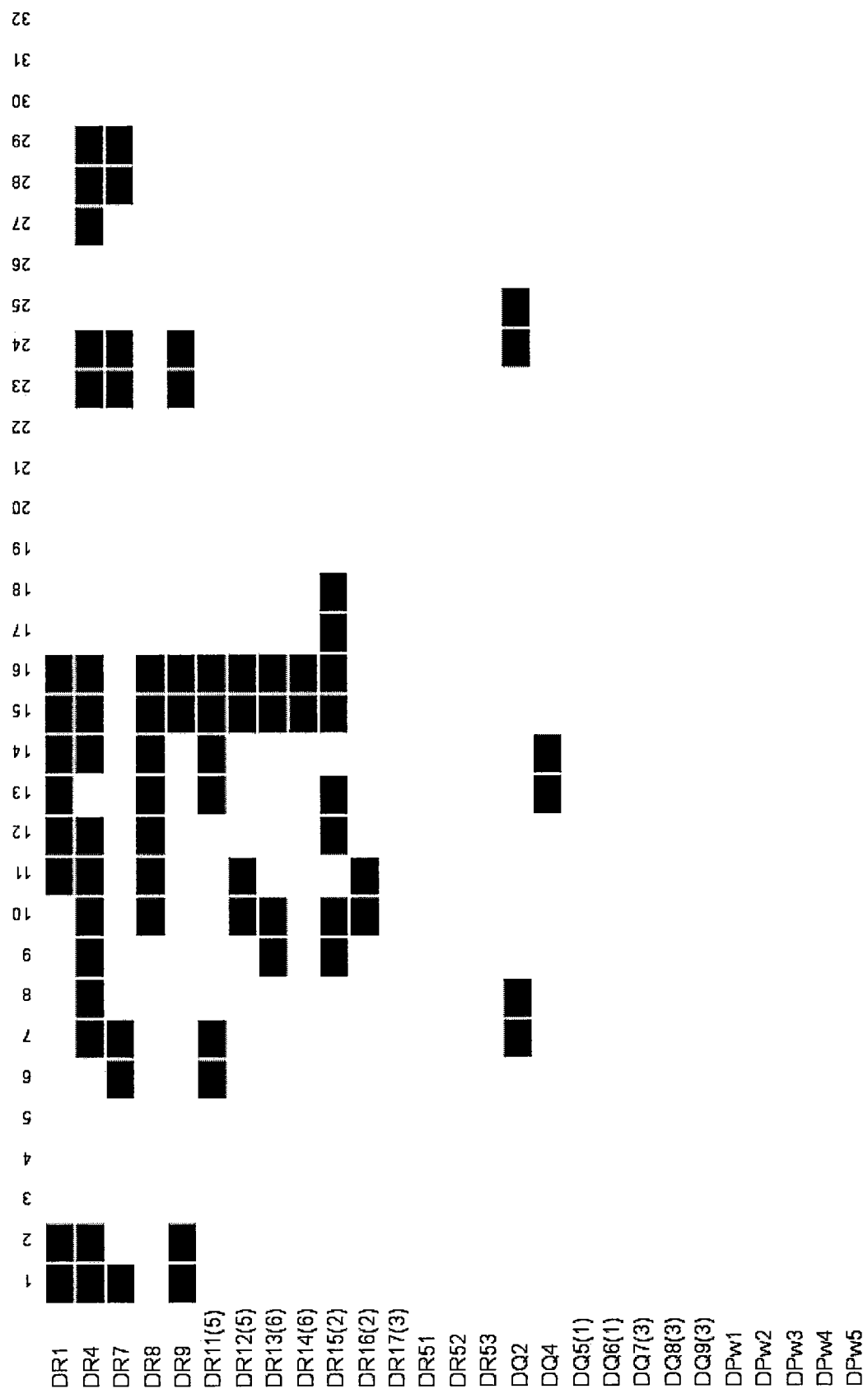
FIG. 17: Epitope map of IGKV-39 showing the presence of peptide binders predicted in the sequence of IGKV1-39 by serotype in the 15-mer format. Each 15-mer is numbered as indicated in the top of the figure. The full sequence of the corresponding 15-mer is listed in Table 7. Black boxes indicate the presence of one or more critical self-epitopes in the 15-mer for the serotype listed on the left. Critical epitopes are operationally defined as strong or medium DRB1 binders and strong DRB3/4/5 or DP or DQ binders.

At the 5' end of the expression cassette, a NotI site was introduced and on the 3' site a NheI site. Both sites are used for cloning in the CAGGS expression module as described by TaconicArtemis. After gene assembly according to methods used by GeneArt, the insert was digested with NotI-NheI and cloned into the expression module containing a CAGGS promoter, a stopper sequence flanked by LoxP sites ("floxed"), a polyadenylation signal sequence and, at the 5' and 3' end, sequences to facilitate homologous recombination into the Rosa26 locus of mouse ES cell lines. To construct the final ROSA26 RMCE targeting vector, promoter and/or cDNA fragments were amplified by PCR. Amplified products were confirmed by sequencing and/or cloned directly from delivered plasmids into an RMCE exchange vector harboring the indicated features. A schematic drawing and the confirmed sequence of the final targeting vector pCAGGS-IgVL2-14 is shown in FIGS. 15A and 15B. The targeting strategy is depicted in FIG. 15C.

Example 7: Expression of IGKV1-39/J-Ck in HEK293 Cell Lines (pSELECT-IGKV1-39/J-Ck)

This example describes a method to verify that the IGKV1-39/J-Ck constructs described in Example 5 enable expression and detection of the IGKV1-39/J-Ck L chain in HEK293 cells. The IGKV1-39/J insert (FIG. 6) was modified at the 5' end by changing the NotI site into a SalI site. This change is required for cloning of the product into the expression cassette plasmid pSELECT-hygro (InvivoGen). The CAGGS expression insert IGKV1-39/J-Ck and pSELECT-hygro were digested with SalI and NheI, ligated and used to transform competent XL1-Blue cells using standard techniques. Colonies were picked and DNA purified using Qiagen Midi-prep columns according to the manufacturer's procedures. The resulting light chain (LC) expressing vector named 0817676_pSELECT_0815426 was used to transfect HEK293 cells with Fugene6 (Roche) according to the manufacturer's protocols. Supernatants were screened for the presence of IGKV1-39/J-Ck light chains by ELISA and western blot using anti-rat-Ck antibodies (Beckton Dickinson #550336 and 553871) and protocols used in the art.

The VH of anti-tetanus toxoid (TT) IgG MG1494 was cloned into IgG expression vector MV1056 using restriction sites SfiI and BstEII. The resulting clone was sequence verified. HEK293T cells were transfected with five different vector combinations as shown in Table 4 (see Example 8 for details of vector 0817678_pSELECT_0815427). Supernatants were harvested and IgG concentrations determined (see Table 4). No IgG could be detected for supernatants A and B containing light chain only as expected (detection antibody recognized Fc part of IgG). IgG concentration in supernatants C and D was comparable to that of positive control supernatant E, indicating correct expression of the light chain constructs.

Binding to TT was analyzed by ELISA to check functionality of the produced antibodies, using hemoglobin as negative control antigen. No TT-specific binding could be detected for supernatants A and B containing light chain only, as expected. TT-specific binding for supernatants C and D was at least as good as for positive control supernatant E, confirming correct expression of the light chain constructs and functional assembly with heavy chain. Antibodies were detected not only using an anti-human IgG secondary antibody, but also an anti-rat Ckappa light chain secondary antibody. The results confirm that the anti-rat Ckappa antibody (BD Pharmingen #553871, clone MRK-1) recognizes the light chain expressed by the pSELECT vectors.

Supernatants were analyzed by non-reducing SDS-PAGE and Western blot (not shown). Detection using an anti-human IgG heavy chain antibody did not show bands for supernatants A and B containing light chain only, as expected. Results for supernatants C and D were comparable to positive control supernatant E, with a band close to the 170 kD marker as expected for intact IgG. Additional lower molecular weight bands were observed as well for supernatants C, D and E, which might represent degradation products, IgG fragments resulting from (partial) reduction and/or irrelevant protein bands due to non-specific binding of the detection antibody.

Detection using an anti-rat Ckappa light chain antibody showed a band close to the 26 kD marker for supernatants A and B, as expected for light chain only. This band was much more intense for A compared to B, indicating that the free IGKV1-39 light chain may be better expressed and/or more stable than the free IGLV2-14 light chain. No bands were detected for control supernatant E as expected, since the expressed IgG contains a human Ckappa light chain. For supernatants C and D, expected bands close to the 170 kD marker were observed; lower molecular weight bands were also observed, but to a lesser extent than above using the anti-human IgG antibody.

In conclusion, transfection of the light chain expression constructs combined with the heavy chain of anti-tetanus toxoid (TT) IgG MG1494 resulted in IgG production comparable to the positive control construct for both the pSELECT kappa and lambda light chain constructs. Both IgG productions yielded ELISA signals in a TT ELISA that were better than or comparable to the control IgG. SDS-PAGE and Western blot analysis confirmed the presence of intact IgG. The tested anti-rat Ckappa antibody worked efficiently in both ELISA and Western blot. Culture supernatant from cells transfected with light chain constructs only did not result in detectable IgG production nor in detectable TT-specific binding, while free light chain was detected on Western blot.

Example 8: Expression of IGLV2-14/J-Ck in HEK293 Cell Lines (pSELECT-IGLV2-14/J-Ck)

This example describes a method to verify that the IGLV2-14/J constructs described in Example 6 enable expression and detection of the IGLV2-14/J-Ck L chain in HEK293 cells. The IGLV2-14/J-Ck insert (FIG. 7) was modified at the 5' end by changing the NotI site into a SalI site. This change is required for cloning of the product into the expression cassette plasmid pSELECT-hygro (InvivoGen). The CAGGS expression insert IGLV2-14/J-Ck and pSELECT-hygro were digested with SalI and NheI ligated and used to transform competentXL1-Blue cells using standard techniques. Colonies were picked and DNA purified using Qiagen Midi-prep columns according to the manufacturer's procedures. The resulting light chain (LC) expressing vector named 0817678_pSELECT_0815427 was used to transfect HEK293 cells with Fugene6 (Roche) according to the manufacturer's protocols. Supernatants were screened for the presence of IGLV2-14/J-Ck light chains by ELISA and western blot using anti-rat-Ck antibodies (Becton Dickinson #550336 and 553871) and protocols used in the art. See Example 7 for details and results.

Example 9: Construction of a VK Promoter-Driven Expression Construct Containing an IGKV1-39/J Insert and Multiple Enhancer Elements Derived from the Murine CK Locus (VkP-IGKV1-39/J-Ck; VkP-O12)

This example describes the construction of an expression cassette that contains relevant elements to enable B-cell and developmental/differentiation stage-specific expression of the rearranged human IGKV1-39 VK region, based on the IGKV1-39 VK promoter region, leader containing an intron, germline V-gene, CDR3, IGKJ segment, mouse intergenic region located between Jk and CK, rat Ck allele a open reading frame, and a mouse intergenic fragment from the 3' end of the mouse CK gene ending just 3' of the 3' CK enhancer.

Optimized open reading frames of the leader, IGKV1-39 rearranged gene, and rat CK allele a gene, as described in Example 5, was used for the construction of the expression cassette. The VK promoter region was obtained by gene synthesis procedures (GeneArt, GmbH) and is almost identical to the sequence of the human IGKV1-39 region between −500 bp and the ATG (start site) of the gene. The only deviation from the natural sequence is the introduction of a GCCACCATGG Kozak sequence (SEQ ID NO:102) at the ATG (start) site in order to promote translation. A genomic fragment from a mouse BAC clone (TaconicArtemis) is used as the basis for the introduction of individual elements. This fragment is identical to the sequence of the mouse VK locus starting with the intron donor site located directly 3' of the JK5 region and ending just 3' of the 3' CK enhancer and covers approximately 12.5 kb.

Figure 8:
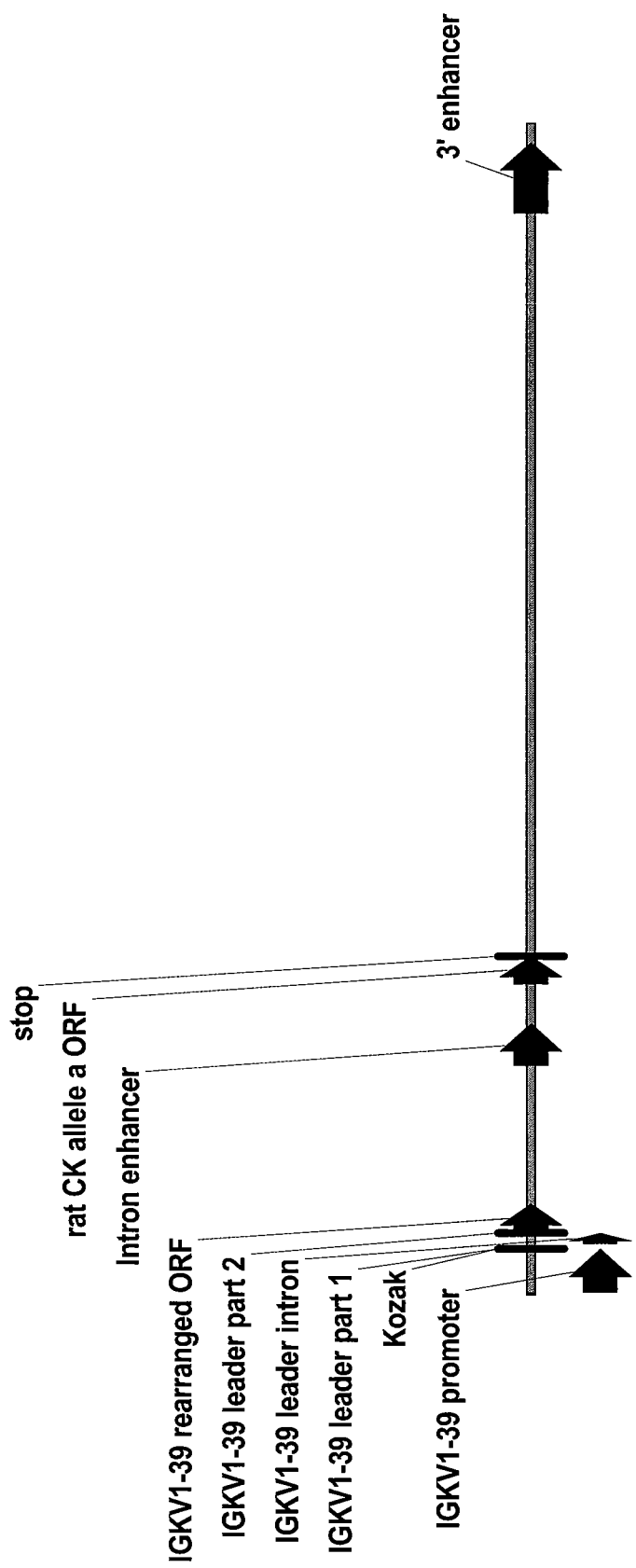
FIG. 8: Construct topology of VkP-IGKV1-39/J-Ck (VkP-O12). The promoter originates from the IGKV1-39 gene and is placed directly in front of the required elements for efficient transcription and translation. Intergenic sequences (including the enhancers) are derived from mice and obtained from BAC clones. The C-kappa sequence codes for the kappa constant region of rat.
Figure 20A:
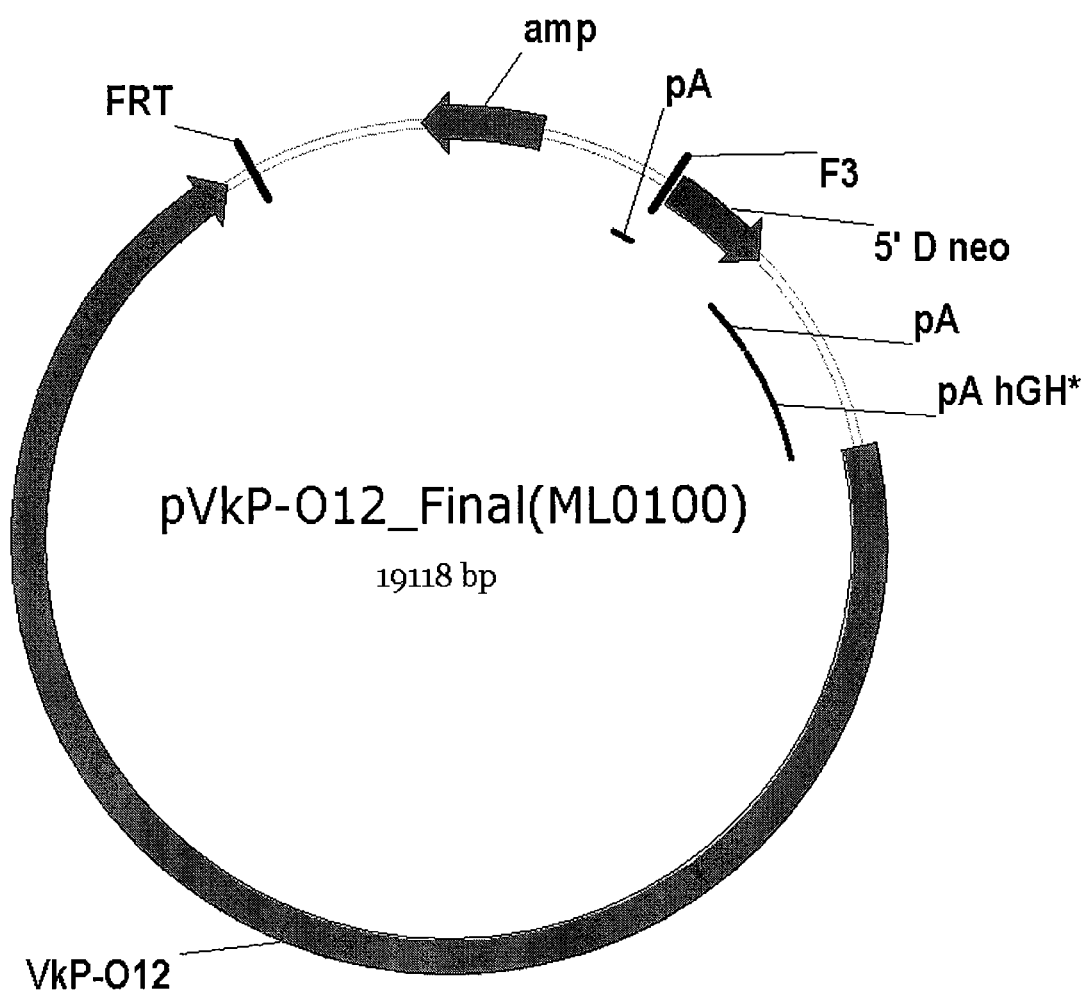
FIGS. 20A-C: Schematic drawing of targeting vectors.
Figure 21A:
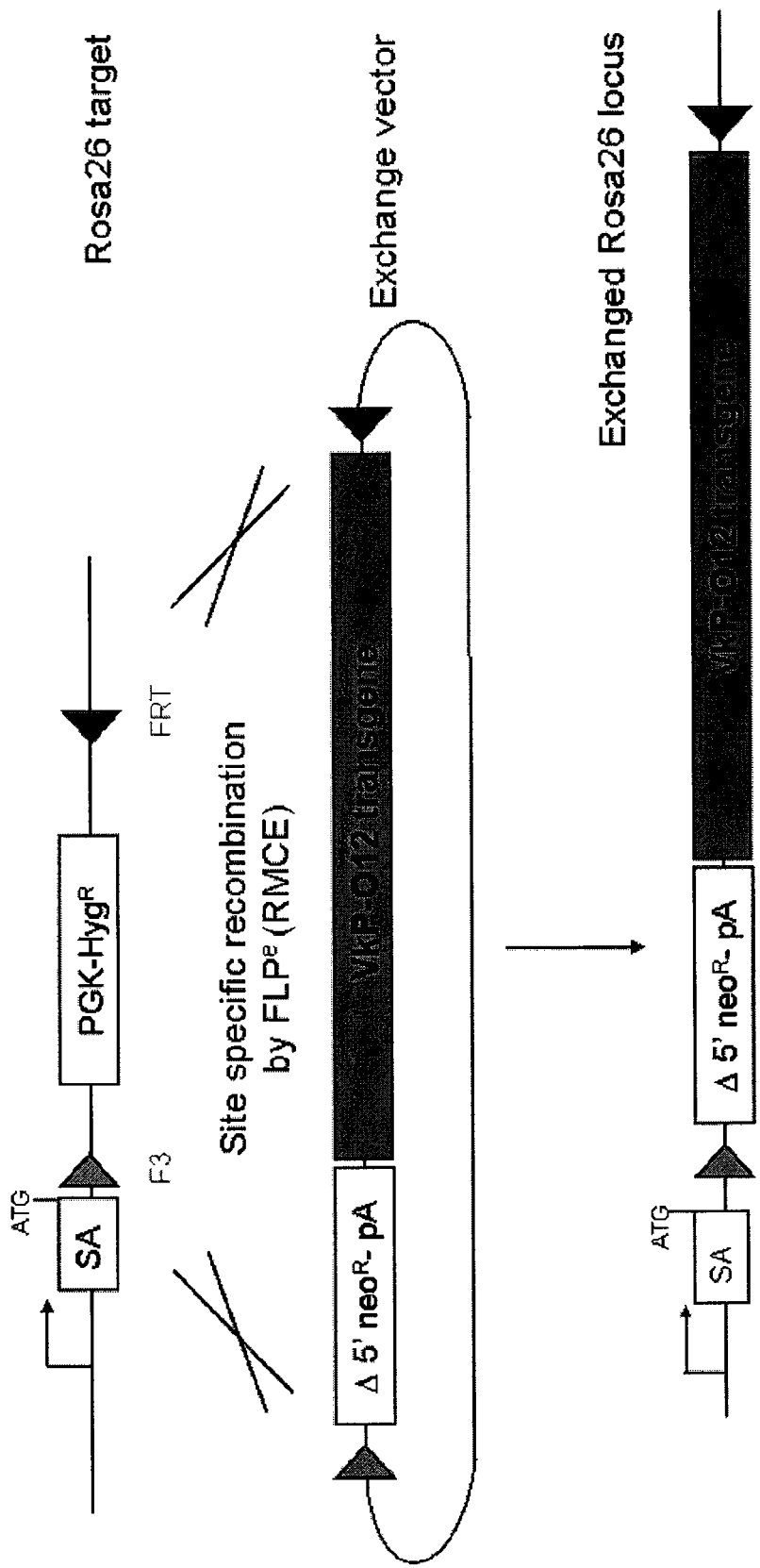
FIGS. 21A-C: Targeting strategies for insertion of transgene into the Rosa26 locus by targeted transgenesis using RMCE.

The final construct contains from 5' to 3' end the following elements: human genomic IGKV1-39 promoter (500 bp), a Kozak sequence, a human IGKV1-39 leader part 1 (optimized), a human IGKV-39 leader intron, a human IGKV1-39 leader part 2 (optimized), a human IGKV1-39 germline gene (optimized), a human J-region (optimized), a mouse intergenic region including the intron enhancer element, a rat (*Rattus norvegicus*) kappa constant region (optimized), and a mouse intergenic region including the 3' kappa enhancer. The elements of this expression cassette are shown in FIG. 8 and named VkP-IGKV1-39/J-Ck (VkP-O12). An outline of the pVkP-O12 vector and the targeting strategy is depicted in FIGS. 20A and 21A. The vector was introduced into ES cells following standard procedures (see Example 14).

Example 10: Construction of a VK Promoter-Driven Expression Construct Containing an IGLV2-14/J Clone and Multiple CK Locus-Derived Enhancer Elements (VkP-IGLVL2-14/J-Ck; VkP-2a2)

Figure 9:
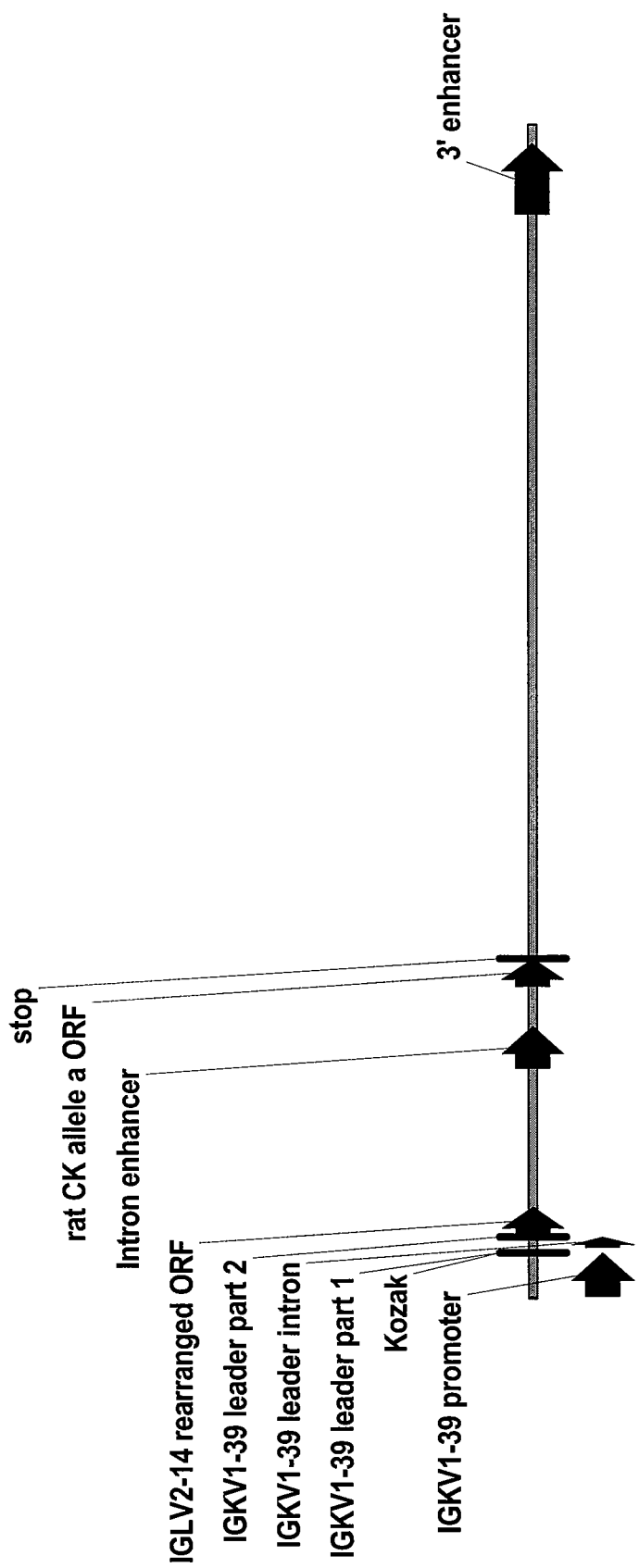
FIG. 9: Construct topology of VkP-IGLV2-14/J-Ck (VkP-2a2). The promoter originates from the IGKV1-39 gene and is placed directly in front of the required elements for efficient transcription and translation. Intergenic sequences (including the enhancers) are derived from mice and obtained from BAC clones. The C-kappa sequence codes for the kappa constant region of rat.

This example describes the same construct as described in Example 9, except that the IGKV1-39 gene and J-region are replaced by the optimized human IGLV2-14 germline gene including a unique V-J region (VkP-IGLV2-14/J-Ck; VkP-2a2; FIG. 9).

Example 11: Construction of a VK Promoter-Driven Expression Construct Containing an IGKV1-39 Clone Lacking the CK Intron Enhancer Element (VkP-IGKV1-39/J-Ck-Δ1; VkP-O12-del1)

Figure 10:
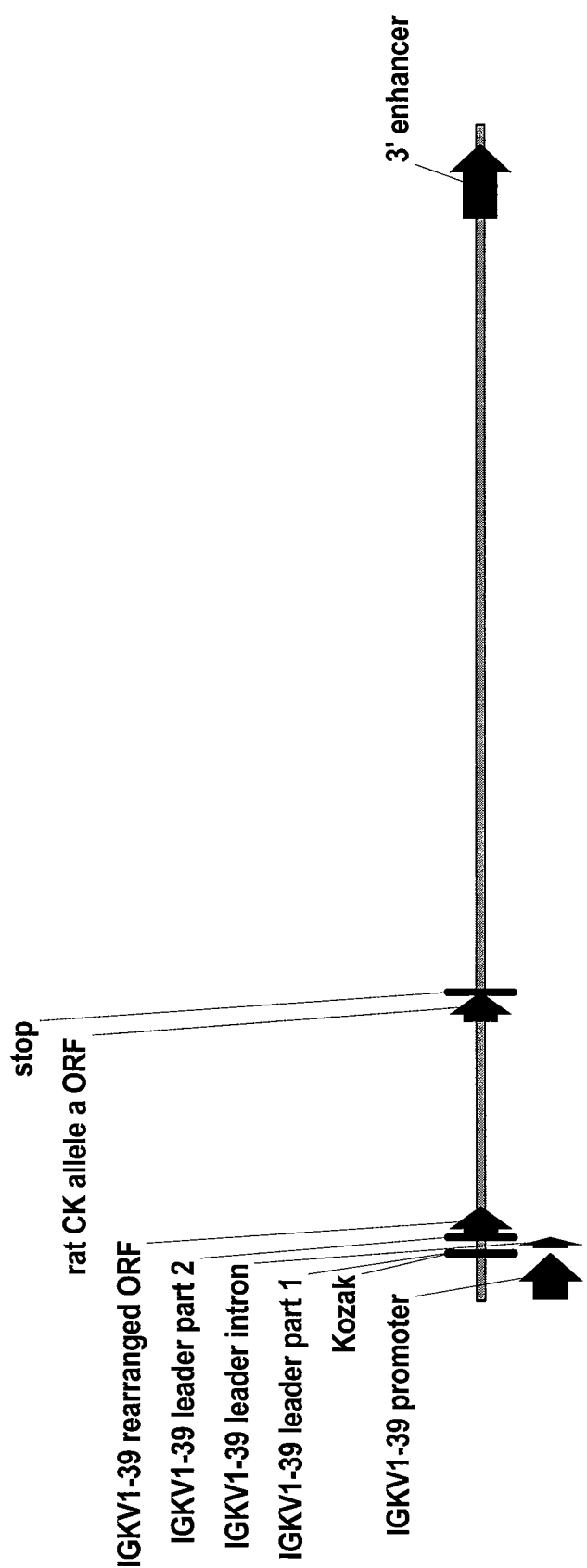
FIG. 10: Construct topology of VkP-IGKV1-39/J-Ck-Δ1 (VkP-O12-del1) is identical to VkP-IGKV1-39/J-Ck from FIG. 9 except that the intron enhancer region is removed.

The construct described in Example 9 was modified by removing the CK intron enhancer element, located in the intergenic region between the human J region and the rat CK region by standard PCR modification and DNA cloning methodologies (GeneArt, GmBH). The resulting expression cassette is shown in FIG. 10 and named VkP-IGKV-39/J-Ck-Δ1 (VkP-O12-del1).

Figure 20B:
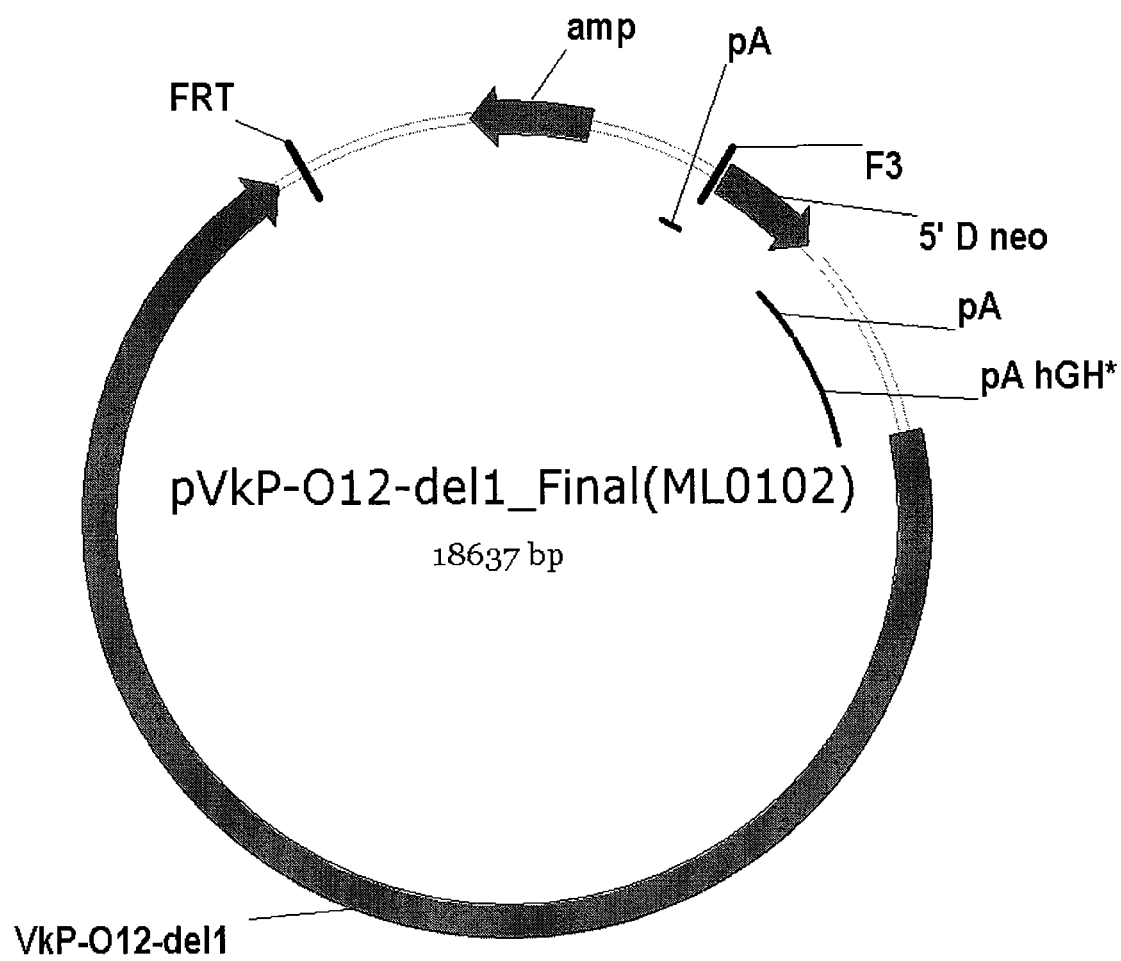
Figure 21B:
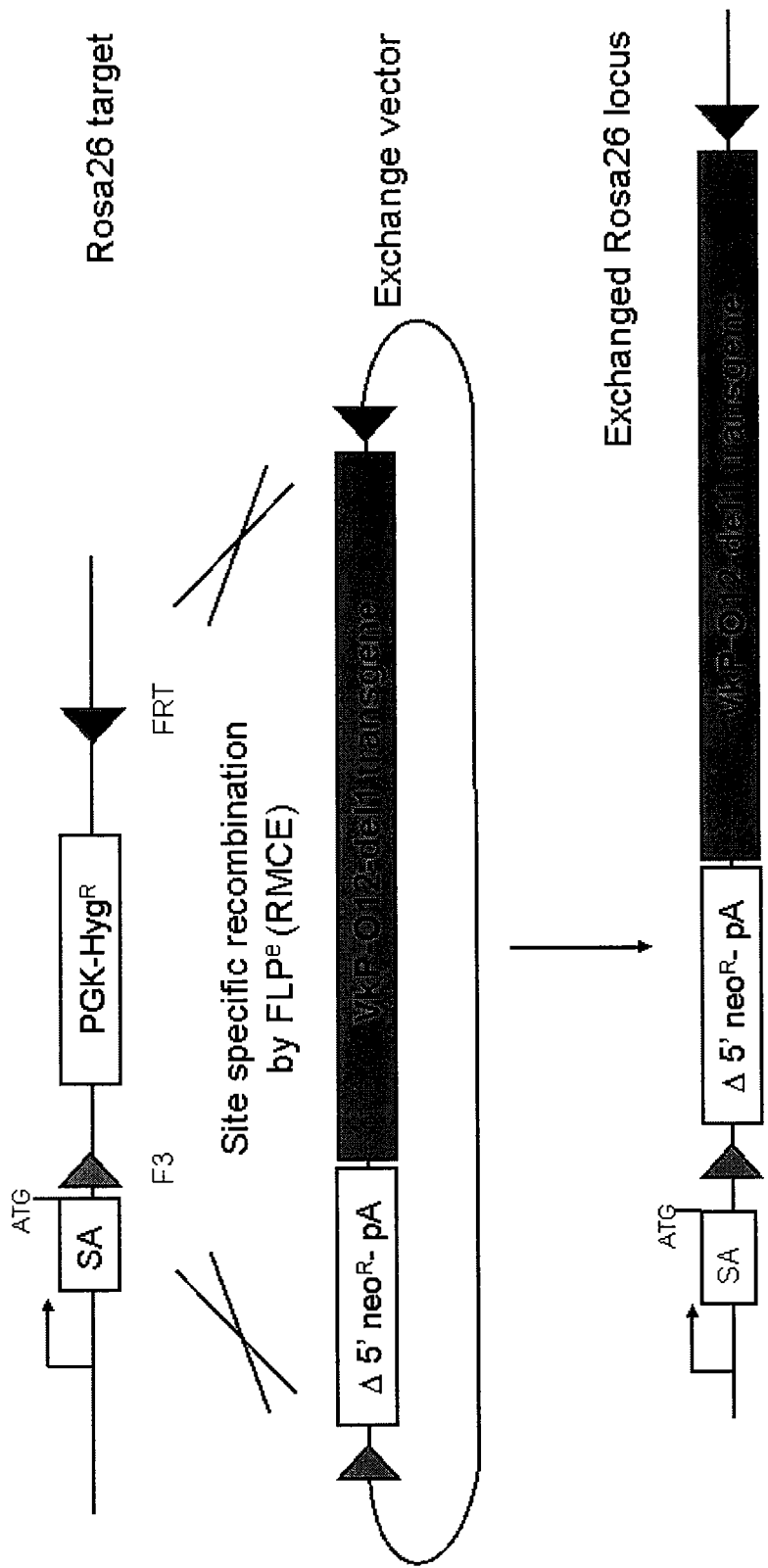

An outline of the pVkP-O12-del1 vector and the targeting strategy is depicted in FIGS. 20B and 21B. The vector was introduced into ES cells following standard procedures (see Example 14).

Example 12: Construction of a VK Promoter-Driven Expression Construct Containing an IGKV1-39 Clone Lacking the CK Intron Enhancer Element and a Truncated 3' CK Enhancer Element (VkP-IGKV1-39/J-Ck-Δ2; VkP-O12-Del2)

Figure 11:
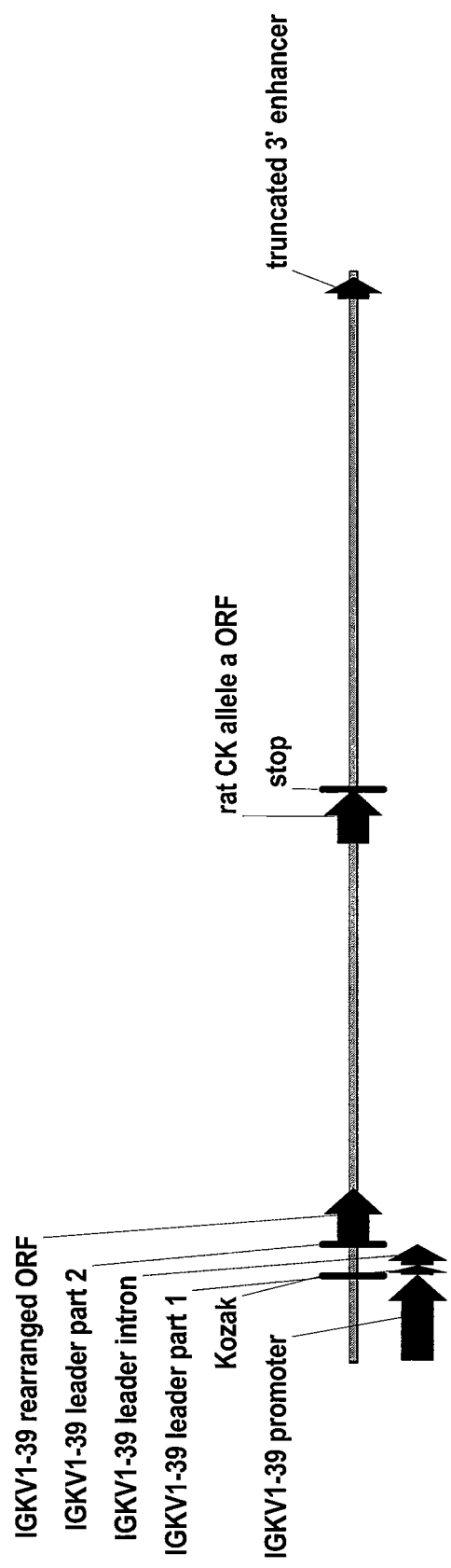
FIG. 11: Construct topology of VkP-IGKV1-39/J-Ck-Δ2 VkP-O12-del2) is identical to VkP-IGKV1-39/J-Ck-Δ1 from FIG. 10 except that a large piece of the intergenic region between the Ck gene and 3' enhancer is deleted. In addition, the 3' enhancer is reduced in size from 809 bp to 125 bp.

The construct described in Example 11 was modified by truncating the 3' CK enhancer element and deleting part of the intergenic region 3' of the rat Ck gene, to remove potential inhibitory elements. This was achieved by removing the intergenic sequence between an EcoRV site (located 3' of the rat Ck gene) and the NcoI site present in the 3' enhancer (5993 bp) and further removing the sequence between the 3' enhancer BstXI site and the BstXI site 3' of the 3' enhancer (474 bp) using standard methods. The resulting expression cassette is shown in FIG. 11 and named VkP-IGKV1-39/J-Ck-Δ2 (VkP-O12-del2).

Figure 20C:
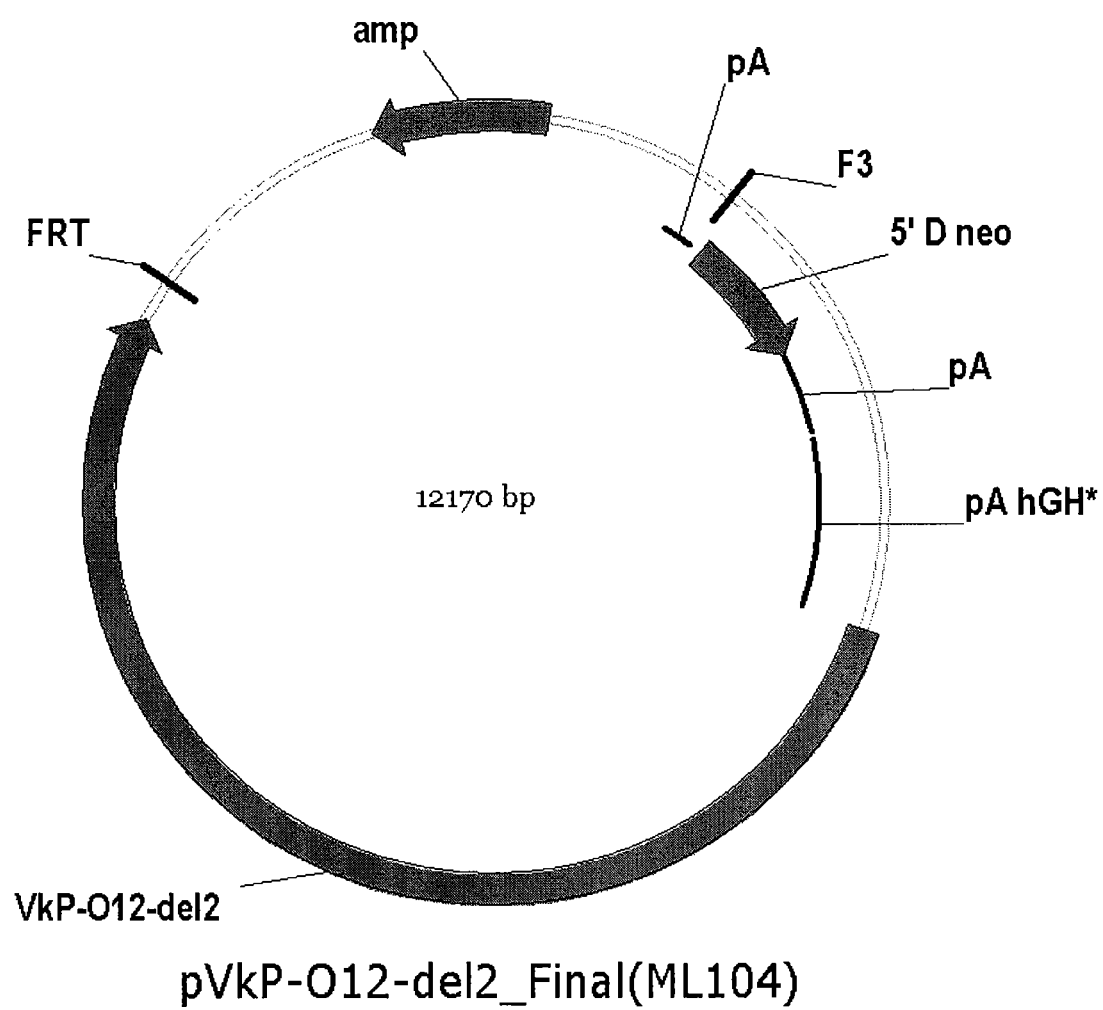
Figure 21C:
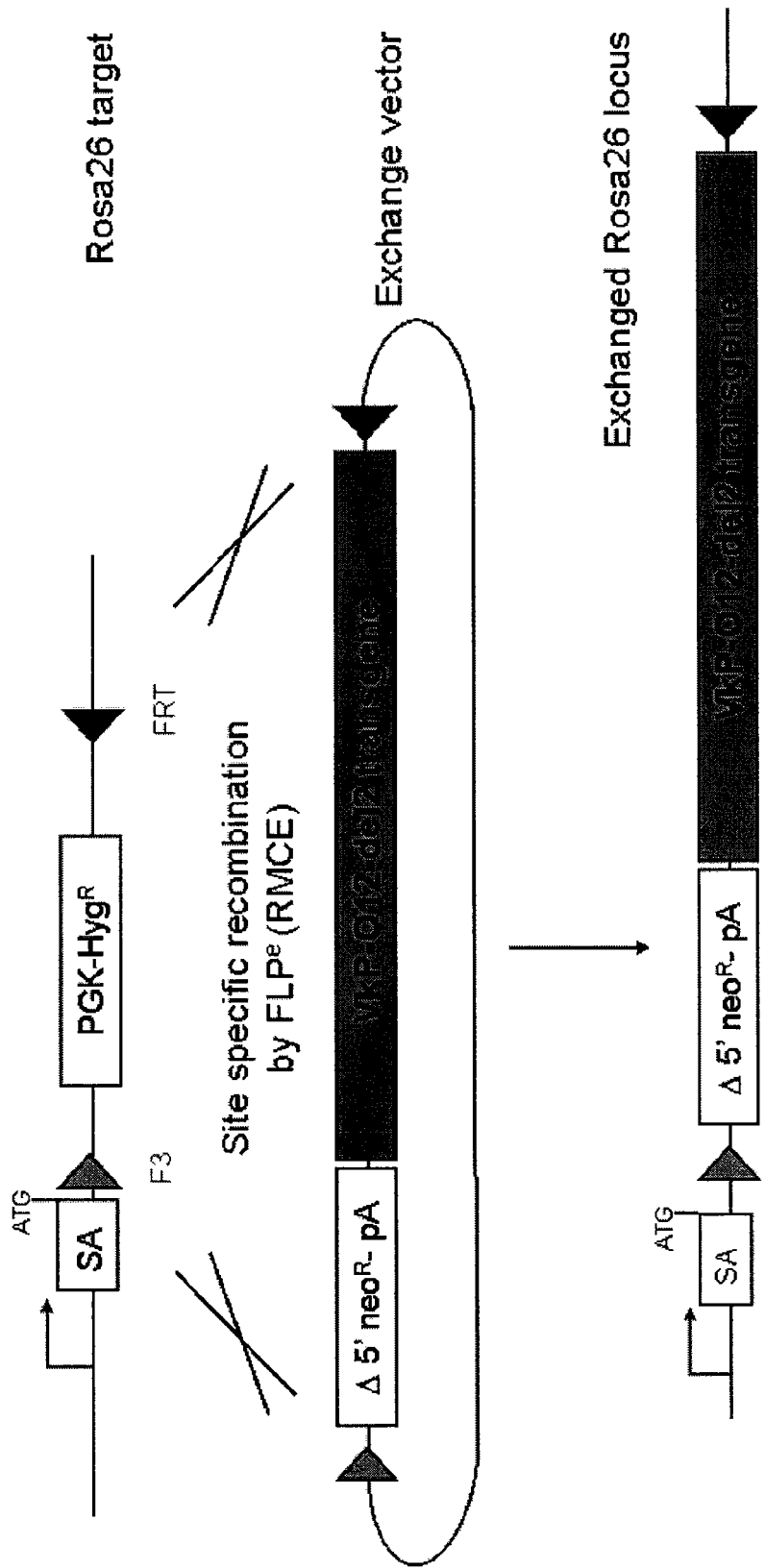

An outline of the pVkP-O12-del2 vector and the targeting strategy is depicted in FIGS. 20C and 21C. The vector was introduced into ES cells following standard procedures (see Example 14).

Example 13: Expression of Vk Constructs in Cell Lines

The constructs described in Examples 9-12 are tested for their ability to produce light chain proteins in the myeloma cell lines MPC11 (ATCC CCL167), B-cell lymphoma WEHI231 (ATCC CRL-1702), the T-cell lymphoma EL4 (ATCC TIB-39) and in HEK293 (ATCC CRL1573). The enhancer and promoter elements in the construct enable expression in the B-cell lines but not in cell lines derived from other tissues. After transfection of the cell lines using purified linearized DNA and Fugene6 (Roche) cells are cultured for transient expression. Cells and supernatant are harvested and subjected to SDS-PAGE analysis followed by western blotting using a specific anti-rat-C-kappa antibody. Supernatants are analyzed in ELISA for secreted L chains using the anti-rat CK antibody (Beckton Dickinson #550336).

Example 14: Generation of Transgenic ES Lines

All constructs as described in Examples 3, 4, 5, 6, 9, 10, 11 and 12 were used to generate individual stable transgenic ES lines by means of homologous recombination. The methods for generation of transgenic ES lines via homologous recombination are known in the field (e.g., Eggan et al., PNAS 98:6209-6214; J. Seibler, B. Zevnik, B. Küter-Luks, S. Andreas, H. Kern, T. Hennek, A. Rode, C. Heimann, N. Faust, G. Kauselmann, M. Schoor, R. Jaenisch, K. Rajewsky, R. Khn, F. Schwenk (2003), Nucleic Acids Res., February 15; 31(4):e12; Hogan et al. (Cold Spring Harbor Laboratory Press, Cold Spring Harbor N.Y.), pp. 253-289).

For all constructs described in Examples 5 and 6, and Examples 9-12, the RMCE ES cell line (derived from mouse strain 129S6B6F1-Gt(ROSA)26Sortm10Arte) was grown on a mitotically inactivated feeder layer comprised of mouse embryonic fibroblasts (MEF) in DMEM High Glucose medium containing 15% FBS (PAN 1302-P220821). Leukemia Inhibitory Factor (Chemicon ESG 1107) was added to the medium at a concentration of 900 U/mL. For manipulation, $2 \times 10^5$ ES-cells were plated on 3.5 cm dishes in 2 ml medium. Directly before transfection, 2 ml fresh medium was added to the cells. Three μl Fugene6 Reagent (Roche; Catalog No. 1 814 443) was mixed with 100 μl serum free medium (OptiMEM I with Glutamax I; Invitrogen; Catalog No. 51985-035) and incubated for five minutes. One hundred μl of the Fugene/OptiMEM solution was added to 2 μg circular vector and 2 μg CAGGS-Flp and incubated for 20 minutes. This transfection complex was added dropwise to the cells and mixed. Fresh medium was added to the cells the following day. From day 2 onwards, the medium was replaced daily with medium containing 250 μg/mL G418 (Geneticin; Invitrogen; Catalog No. 10131-019). Seven days after transfection, single clones were isolated, expanded, and molecular analyzed by Southern blotting according to standard procedures.

Figure 14A:
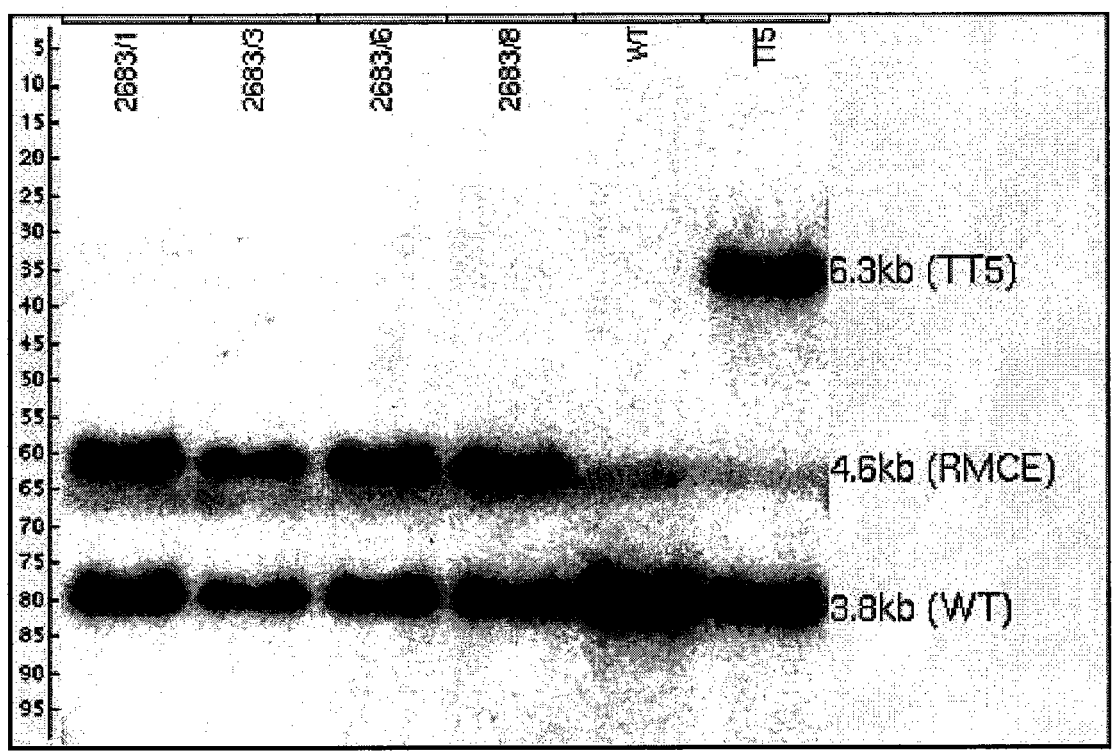
FIGS. 14A-C.
Figure 14B:
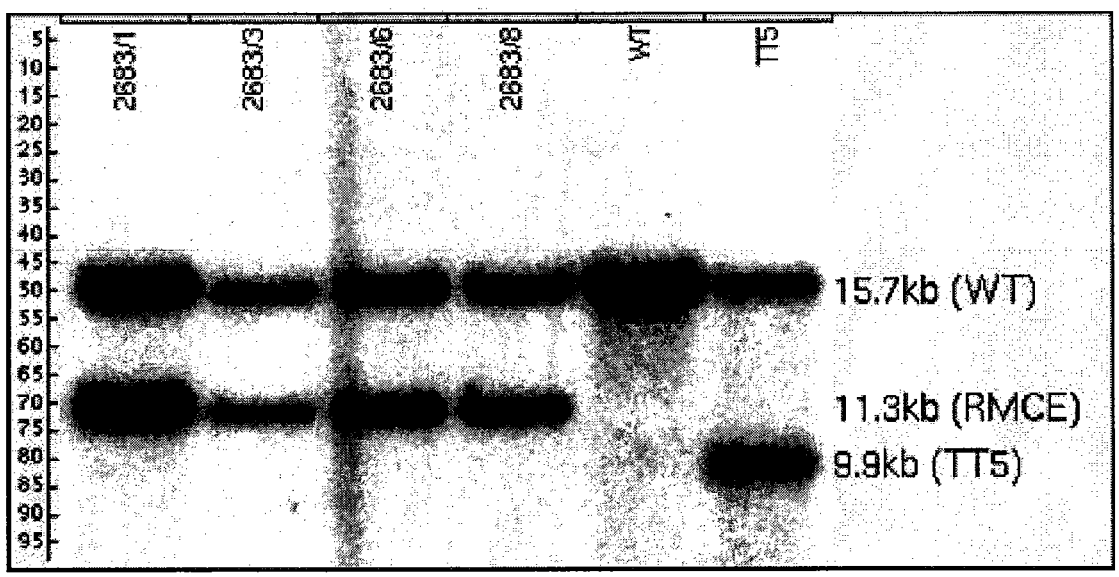
Figure 14C:
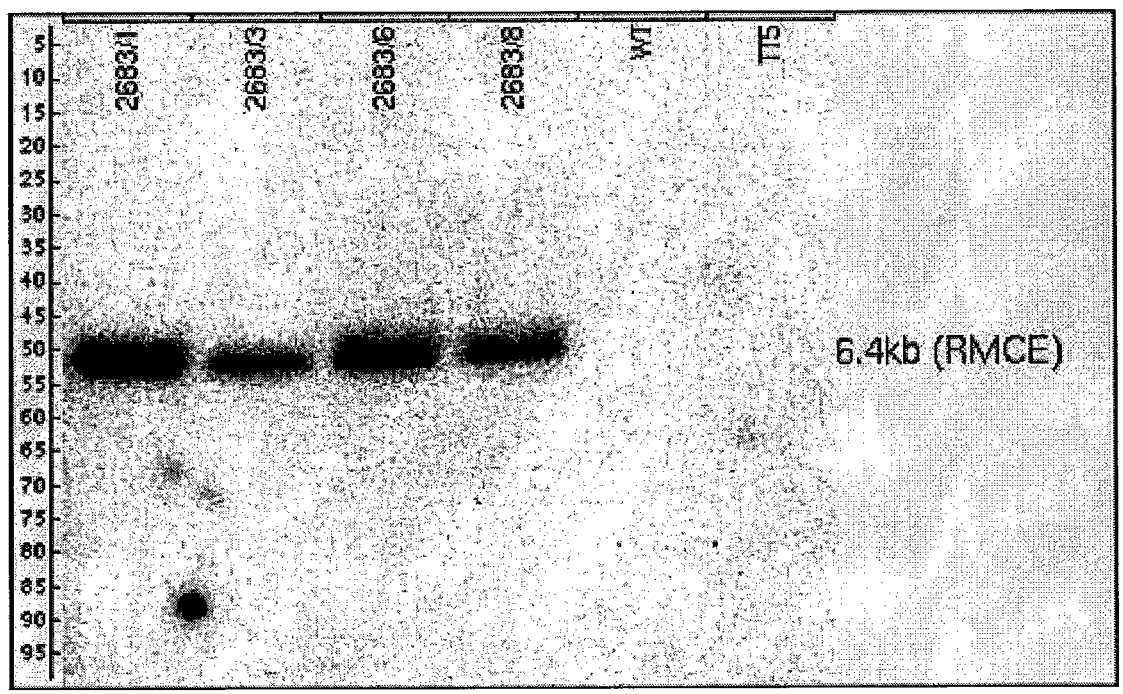

For each construct, analysis of multiple clones by restriction enzyme digestion of genomic DNA of single clones followed by hybridization with 5' probes, 3' probes, and internal probes resulted in clones that comprised a correct, single insertion at the correct position in the Rosa26 locus. An example is provided in FIGS. 14A-C.

Example 15: Generation of Transgenic Mouse Strains

All ES cell lines that were generated and verified for their modifications as described in Example 14 were used to generate stable transgenic mice by means of tetraploid recombination. The methods are known in the field. In general, after administration of hormones, superovulated Balb/c females were mated with Balb/c males. Blastocysts were isolated from the uterus at dpc 3.5. For microinjection, blastocysts were placed in a drop of DMEM with 15% FCS under mineral oil. A flat tip, piezo actuated microinjection-pipette with an internal diameter of 12-15 micrometers was used to inject 10-15 targeted C57BU6 N.tac ES cells into each blastocyst. After recovery, injected blastocysts were transferred to each uterine horn of 2.5 days post coitum, pseudopregnant NMRI females. Chimerism was measured in chimeras (G0) by coat color contribution of ES cells to the Balb/c host (black/white). Highly chimeric mice were bred to strain C57BU6 females. Depending on the project requirements, the C57BU6 mating partners are non-mutant (W) or mutant for the presence of a recombinase gene (Flp-Deleter or Cre-deleter or CreER inducible deleter or combination of Flp-deleter/CreER). Germline transmission was identified by the presence of black, strain C57BU6, offspring (G1).

For example, ESC clone IgVK1-39 2683 8 (see Examples 5 and 14) was injected in a total of 62 blastocysts in three independent experiments. Three litters were obtained with a total of six pups. All pups were chimeric. Three heterozygous offspring pups were obtained that were used for further crossing.

ESC Clone Kappa 2692 A-C10 (see Examples 3 and 14) was injected in a total of 54 blastocysts in three independent experiments. Three litters were obtained with a total of eleven pups, of which ten were chimeric. Eight heterozygous offspring pups were obtained that were used for further crossing.

ESC Clone Kappa 2692 B-C1 (see Examples 3 and 14) was injected in a total of 51 blastocysts in three independent experiments. Two litters were obtained with a total of six pups, of which four were chimeric. Three heterozygous offspring pups were obtained that were used for further crossing.

Example 16: Breeding

This example describes the breeding for obtaining mice that contain transgenic expression cassettes as described Example 14 and knock-out mice in which the endogenous lambda and kappa loci have been silenced. The localization of V-lambda on chromosome 16 and CD19 on chromosome 7 allow standard breeding procedures. The breeding of the co-localized Vκ locus and Rosa26 locus on chromosome 6 with a distance of about 24 cM requires special attention during the screening as only a percentage of the offspring shows crossover in a way that both modifications are brought together on one chromosome.

All four loci have to be combined in a single mouse strain that is homo- or heterozygous for CD19-cre (not described) and modified Rosa26 transgene and homozygous for the other loci. Breeding is performed by standard breeding and screening techniques as appropriate and offered by commercial breeding companies (e.g., TaconicArtemis).

Example 17: Immunizations of Mice

Primary and booster immunization of mice are performed using standard protocols.

To validate the transgenic expression of human rearranged Vκ O12 (IGKV1-39)—rat Cκ light chains (see Examples 5, 14-16) in B cells from CD19-HuVκ1 mice and to assess its impact on VH repertoire size, diversity of VH family usage and V(D)J recombination after immunization, the CD19-HuVκ1 transgenic mice are immunized with tetanus toxin vaccine (TT vaccine) and VH sequence diversity of randomly picked clones from CD19-HuVκ1 mice are compared with TT-immunized wt mice and CD19-Cre HuVk1 negative littermates. Data on the SHM frequency of the human Vκ O12 transgene in the immunized mice are obtained. A diverse collection of at least 40 TT-specific, clonally-unrelated mAbs containing the human Vκ O12 are recovered from CD19-HuVκ1 mice by phage display.

For this, three adult CD19-HuVκ1 mice are vaccinated with TT vaccine using standard immunization procedures. After immunization, serum titers are measured using TT specific ELISA (TT: Statens Serum Institute, Art. no. 2674) and spleen suspensions subjected to cell sorting by the FACS procedure after staining with a rat Cµ-specific monoclonal antibody to isolate transgenic B cells (clone RG7/9.1; BD Pharmingen #553901, Lot #06548). RNA from rat Cκ-positive B cells are extracted and the resulting cDNA material used for library building and SHM analysis.

The standard monoclonal mouse anti-rat Cκ antibody (clone RG7/9.1; BD Pharmingen #553901, Lot #06548) is used in FACS analysis of transgene expressing B cells (Meyer et al. (1996), *Int. Immunol.* 8:1561). The clone RG7/9.1 antibody reacts with a monotypic (common) kappa chain determinant. This anti-rat Cκ antibody (clone RG7/9.1 (BD Pharmingen #553901, Lot #06548) is labeled with R-phycoerythrin (PE) using the LYNX rapid conjugation kit according to the manufacturer's instructions for FACS analysis and sorting. The labeled antibody is firstly tested by flow cytometry for binding to rat Cκ-containing functional light chain proteins produced into transiently transfected HEK-293T cells; the un-conjugated antibody serves as a positive control. Two other antibodies shown to bind to rat Cκ by ELISA and Western-blot (see Example 7) are tested as well by flow cytometry.

Fab-phage display library building is carried out with a set of optimized degenerate PCR primers designed to amplify C57B/6 VH genes; the minimal library size is $10^6$ clones, and minimal insert frequency is 80%. The vector used, MV1043 (FIGS. 3 and 12), contains the human Vκ O12 fused to a human Cκ region. The rat Cκ is therefore exchanged for the human counterpart in the library generation process.

Before selection, VH sequencing of 96 randomly picked clones is performed to validate VH repertoire diversity that is compared to diversity obtained from an unselected library previously generated using the same procedures from BALB/c mice immunized with TT. A library from C57Bl/6 wt mice that are immunized in the same way allows diversity comparison between two preselected libraries sharing the same vaccine and the same genetic background.

Several independent selections are performed on TT coated in immunotubes. Variables that may be included are selections using biotinylated antigens in solution or selections on captured TT. Based on the number and diversity of ELISA-positive clones obtained in the first selections, decisions on additional rounds of selection are made. Clones are considered positive when >3× positive over a negative control clone. Positive clones are analyzed by ELISA against a panel of negative control antigens to verify antigen specificity. The aim is to identify at least 40 unique VH regions, as based on unique CDR3 sequences and $V_H DJ_H$ rearrangements.

Amplification of the cDNA material from rat Cκ-positive sorted B cells is performed with a PCR forward primer specific to the human leader sequence and a PCR reverse primer specific to the rat Cκ sequence, in a region not redundant with the mouse Cκ sequence, as reported in a recent study (Brady et al. (2006), JIM 315:61). Primer combinations and annealing temperatures are firstly tested on cDNA from HEK-293T cells transfected with 0817676_pSELECT_0815426=pSELECT vector with IGKV1-39 DNA cassette (see Example 7).

The amplification products is cloned in pJET-1 vector and after XL-blue transformation, 96 colonies are sequenced for assessing VL SHM frequency by direct comparison to the Vκ O12 (IGKV1-39) germline sequence. The R/S ratio method, as described in our study on human TT-specific antibodies (de Kruif et al. (2009), *J. Mol. Biol.* 387:548) allows discrimination between random mutations and antigen-driven mutations that occurred on VL sequences.

Example 18: Immunofluorescent Analysis of B Cell Populations in Transgenic Mouse Lines This example describes the use of antibodies and flow cytometry to analyze B cell populations in primary (bone marrow) and secondary (spleen, peritoneal) lymphoid organs and blood. Methods and reagents are described in Middendorp et al. (2002), *J. Immunol.* 168:2695; and Middendorp et al. (2004), *J. Immunol.* 172:1371. For analysis of early B cell development in bone marrow, cells were surface stained with combinations of antibodies (Becton Dickinson) specific for B220, CD19, CD25, IgM, IgD, mouse Ckappa, mouse Clambda and rat Ckappa to detect pro-B cells, pre-B cells, large pre-B cells, early and late immature B cells and recirculating B cell populations expressing the transgene on their surface. DAPI staining (Invitrogen) was included to exclude dead cells from the analysis and FC block (Becton Dickinson) to inhibit antibody interaction with Fc receptors on myeloid cells. For analysis of surface transgene expression on B cell populations in peripheral lymphoid organs and blood, cells were stained with combinations of antibodies (Becton Dickinson) specific for B220, CD5, CD19, CD21, CD23, IgM, IgD, mouse Ckappa, mouse Clambda and rat Ckappa. DAPI staining was included to exclude dead cells from the analysis and FC block to inhibit antibody interaction with Fc receptors on myeloid cells. In addition, combinations of antibodies (Becton Dickinson) specific for CD3, CD4, CD11b, CD11c and NK1.1 were included to determine if transgene expression occurred in cell types outside of the B cell compartment.

Three mice heterozygous for the human IGKV1-39/rat Ckappa transgene and heterozygous for the CD19-Cre transgene on a C57BL6 background (HuVk1/CD19-Cre) were analyzed. As controls for the FACS analysis, three littermate mice wild-type for the human IGKV1-39/rat Ckappa transgene and heterozygous for the CD19-Cre transgene on a C57BL6 background (CD19-Cre) and two C57BL6/NTac mice (Wt) were included. All animals were allowed to acclimatize in the animal facility for one week before analysis and all mice were male and six weeks of age. Lymphocytes were isolated from the femurs, spleens, peritoneal cavity and blood of mice using conventional techniques as previously described (Middendorp et al. (2002), *J. Immunol.* 168:2695; and Middendorp et al. (2004), *J. Immunol.* 172:1371). Antibodies were pre-combined as shown in FIG. 29A-B and staining was carried out in 96-well plates. Incubation with the PE-conjugated anti-rat C kappa (described above) was carried out before staining with the rat anti-murine antibodies to avoid non-specific binding. After completion of cell staining, labeled cells were analyzed on a Becton Dickinson LSR II FACS machine and the acquired data analyzed with FlowJo software (v6.4.7).

Transgenic mice were similar in weight, appearance and activity to wild-type mice. No gross anatomical alterations were observed during the harvesting of tissues. No difference was observed in the numbers of B cells in the bone marrow (BM) and spleen (Table 9) or in the numbers of B cells, T cells and myeloid cells in peripheral organs between transgenic and wild-type mice. In addition, the frequency or proportion of the cells in the different lymphocyte developmental pathways was not altered in transgenic mice when compared to wild-type mice. Thus in the double transgenic (HuVk1/CD19-Cre) and transgenic (CD19-Cre) mice lymphoid and most importantly B cell development was indistinguishable from wild-type mice.

Figure 23:
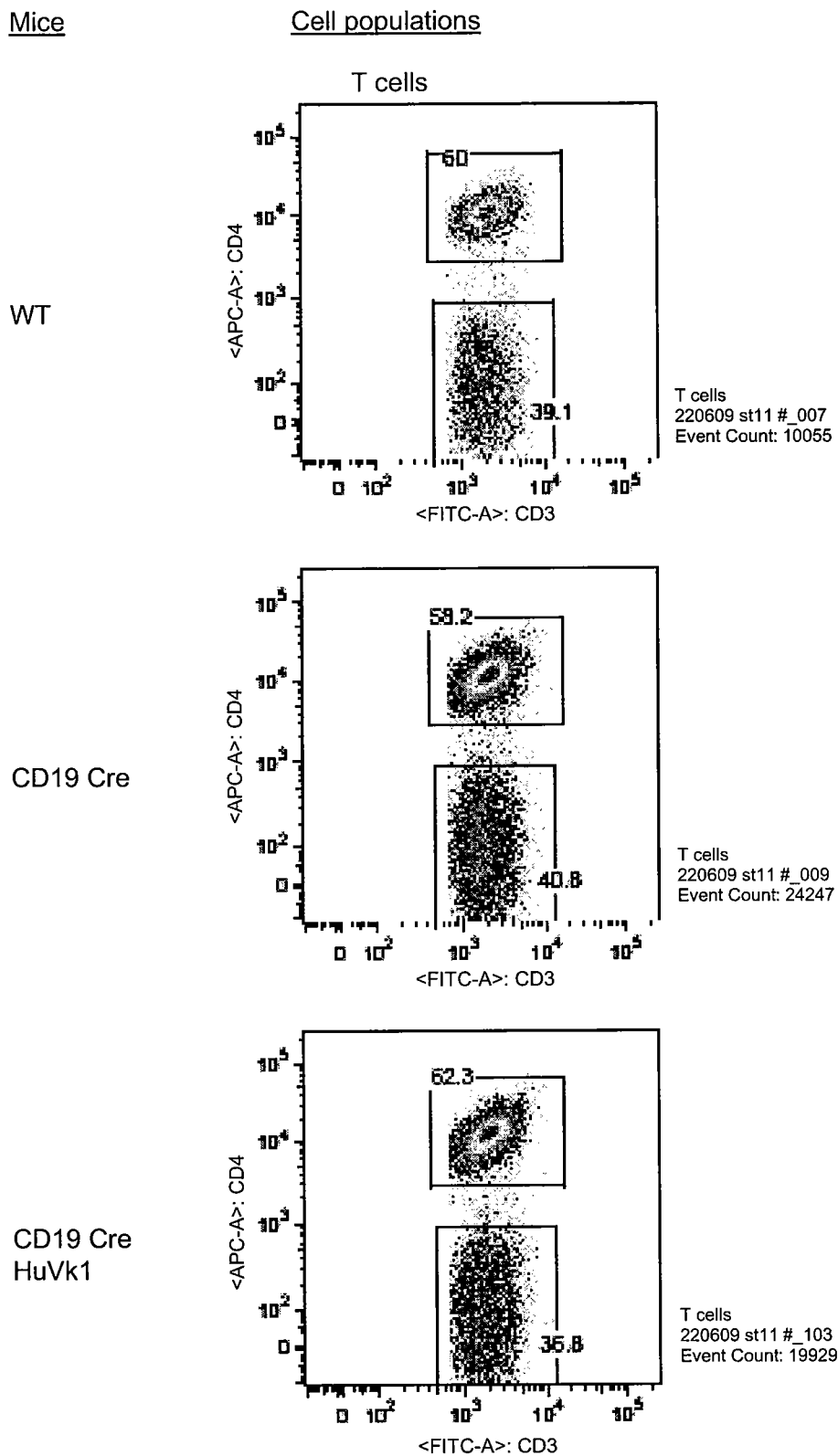
FIG. 23: Lack of transgenic human Vk1 light chain expression in non-B cell populations of the spleen.
Figure 24:
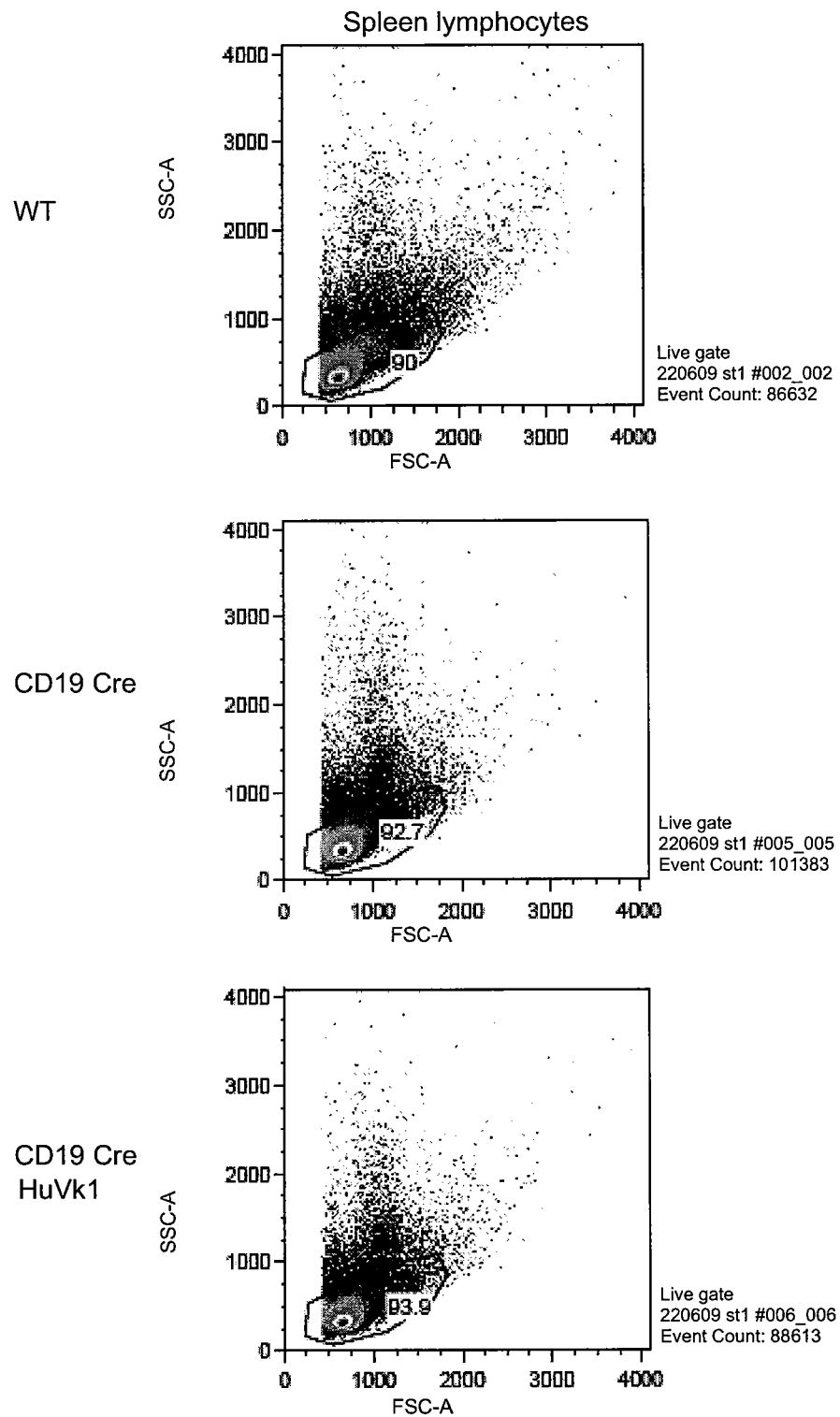
FIG. 24: Transgenic human Vk1 light chain is expressed in all B cell populations of the spleen.
Figure 25:
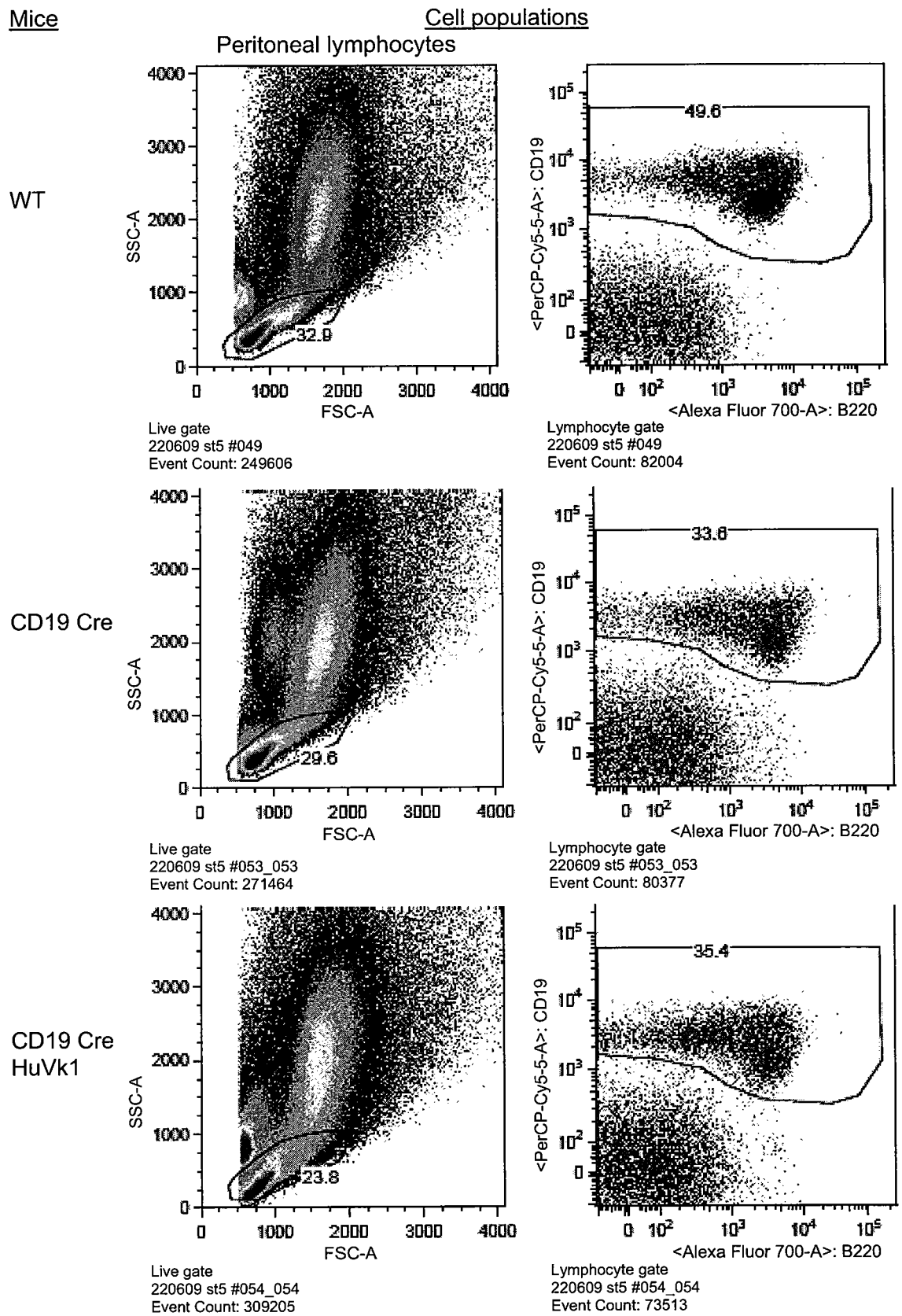
FIG. 25: Transgenic human Vk1 light chain is expressed in B1 cells of the peritoneal cavity.

In the peripheral lymphoid organs, staining with the transgene specific antibody (anti-ratCkappa-PE) was only observed in the B cell populations. T cell, myeloid cell and NK cell populations were all negative for surface expression of the transgene in the spleen (FIG. 23). In contrast, in cells stained with the pan B cell markers B220 and CD19 all cells were shifted to the right in the FACS plot indicating cell surface expression of the transgene (FIG. 24). A similar transgene-specific staining was measured in $CD5^+$ B1 cells of the peritoneum, a developmentally distinct population of B cells (FIG. 25).

Figure 26A:
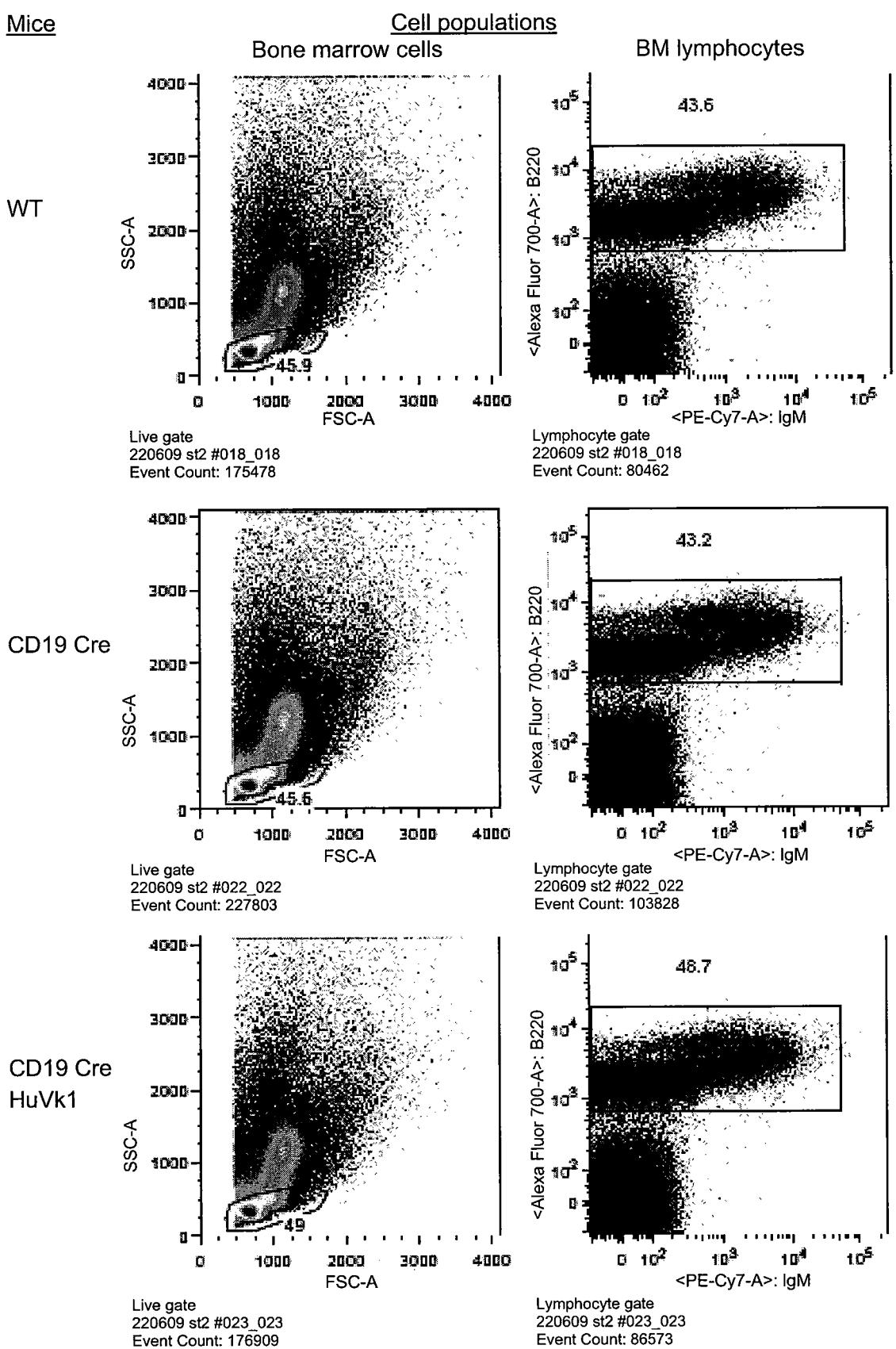
FIGS. 26A-B: Transgenic human Vk1 light chain is not expressed in pro- and pre-B cells but in the immature and recirculating populations B cells in the bone marrow.
Figure 26B:
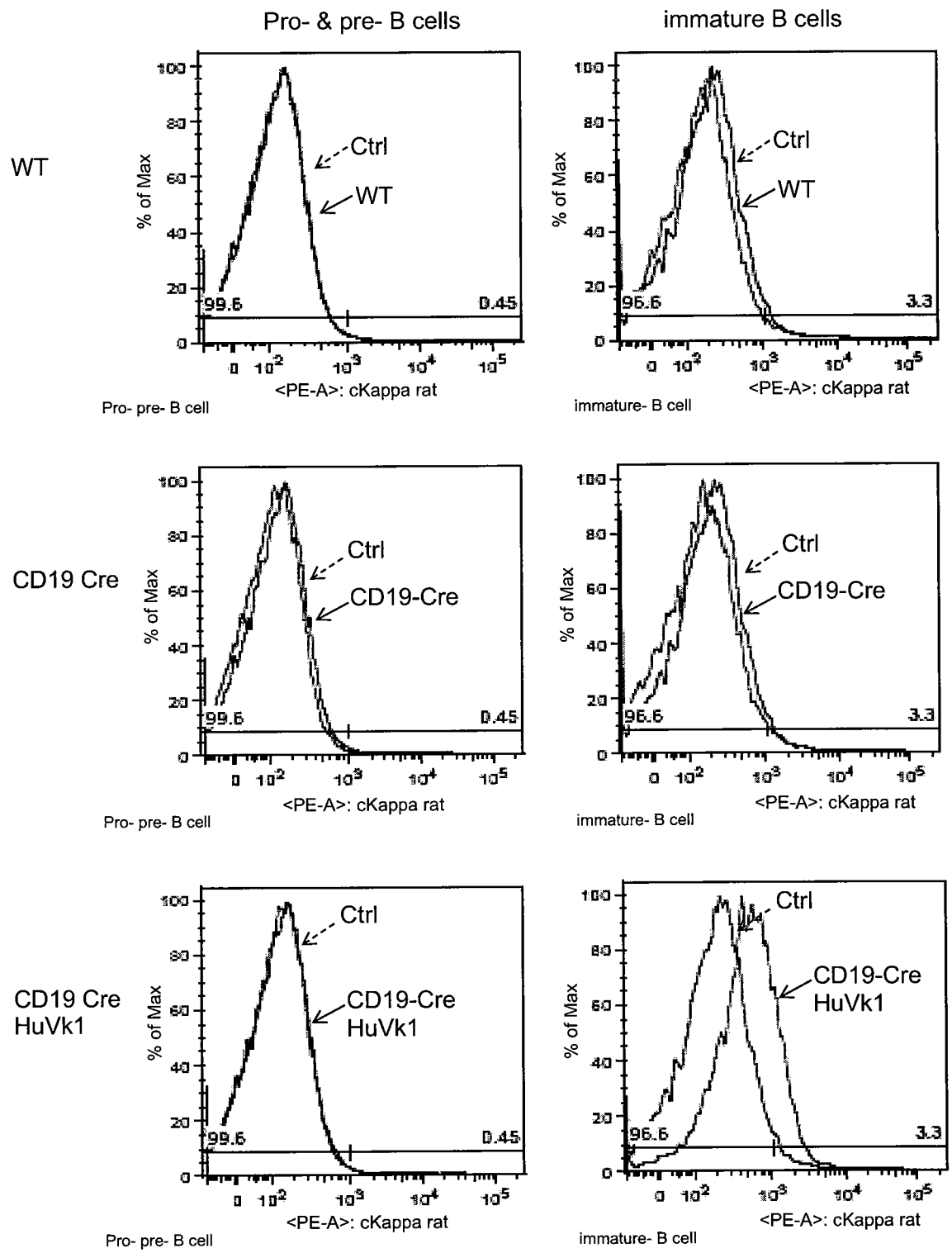
Figure 27:
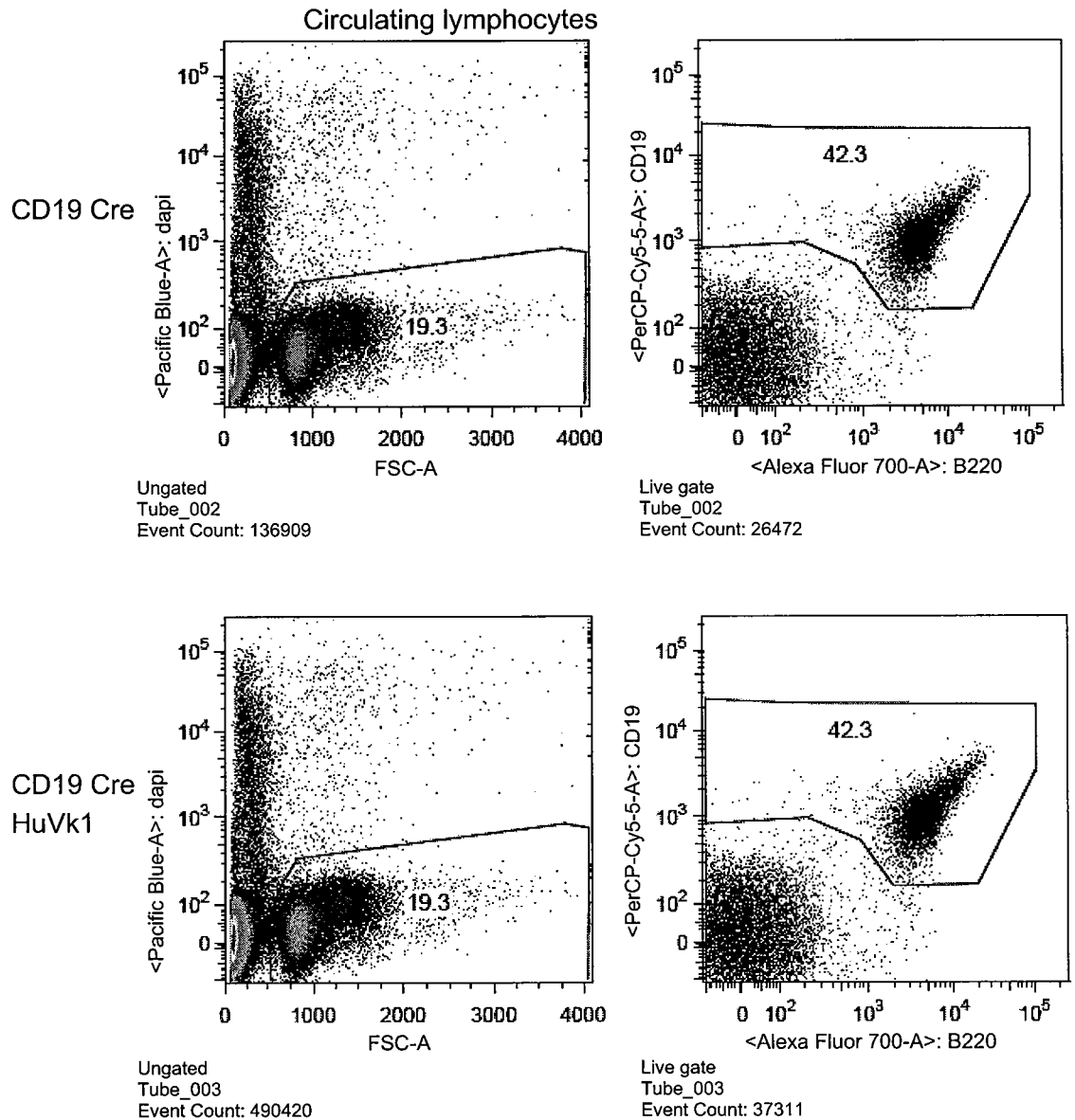
FIG. 27: Transgenic human Vk1 light chain is directly correlated with endogenous light chain and IgM expression in circulating B cells in the blood.

Differentiation of B cells from multilineage precursors to mature B cells occurs in the bone marrow. In the lymphocytes analyzed from the bone marrow, extracellular and transgene expression was not detectable in the earliest B cell progenitors the pro- and pre-B cell consistent with the pattern of normal light chain expression (FIGS. 26A-B). Transgene expression first becomes detectable in immature B cells, the developmental stage at which the germline murine light chain undergoes rearrangement and is expressed at the cell surface in the context of the preselected heavy chain (FIGS. 26A-B). Consistent with the staining in the spleen transgenic light chain expression is also detected on mature recirculating B cells (FIGS. 26A-B). Thus the CD19-Cre driven expression of the transgene is consistent with the normal pattern of light chain expression. The staining with the endogenous light chain-specific antibody is more intense than that of the transgene-specific light chain antibody. This may indicate a higher expression level of the endogenous light chain, a more sensitive staining with the endogenous light chain-specific antibody or a combination of both. Importantly, the intensity of the surface expression of the transgenic light chain is correlated with both endogenous light chain and IgM surface expression as observed in staining of circulating B cells in the blood (FIG. 27).

Thus, overall this analysis demonstrates that expression of the human IGKV1-39/Ckappa transgene is restricted to the B cell compartment and the temporal regulation of its expression is similar to the endogenous kappa and lambda light chains resulting in normal development of all B cell populations. The apparent lower level of expression of the transgene could be explained by the strength of the promoter in comparison to the promoter and enhancers present on endogenous light chain genes or by a delay in transgene expression that gives the endogenous light chains a competitive advantage in pairing with the rearranged heavy chain. This is consistent with the observation that as B cells mature the relative intensity of transgene staining increases compared to the endogenous light chains. In addition, the observation that B cells numbers are normal and that every surface Ig+ B cell co-expresses an endogenous and transgenic light chain supports the conclusion that the IGKV1-39 variable region is capable of pairing with a normal repertoire of different murine heavy chain variable regions. We conclude from this analysis that insertion of the IGKV1-39/rat Ckappa transgene driven by the CD19-Cre activated CAGGS promoter in the Rosa locus facilitates timely and B cell-specific expression of the transgene and that the transgene is capable of pairing with a normal repertoire of murine heavy chains.

Example 19: Epibase® T-Cell Epitope Profile for IGKV1-39

The protein sequence of IGKV1-39 (FIG. 12, human germline IGKV1-39/J Protein) was scanned for the presence of putative HLA class II restricted epitopes, also known as $T_H$-epitopes. For this, Algonomics' Epibase® platform was applied to IGKV1-39. In short, the platform analyzes the HLA binding specificities of all possible 10-mer peptides derived from a target sequence (Desmet et al. (1992), *Nature* 356:539-542; Desmet et al. (1997), *FASEB J.* 11:164-172; Desmet et al. (2002), *Proteins* 48:31-43; Desmet et al. (2005), *Proteins* 58:53-69). Profiling is done at the allotype level for 20 DRB1, 7 DRB3/4/5, 13 DQ and 7 DP, i.e., 47

HLA class II receptors in total (see Table 5). Epibase® calculates a quantitative estimate of the free energy of binding AGbi of a peptide for each of the 47 HLA class II receptors. These data were then further processed as follows:

Free energies were converted into Kd-values through $\Delta G_{bind}$=RT ln(Kd).

Peptides were classified as strong (S), medium (M), weak and non (N) binders.

The following cutoffs were applied:

S: strong binder: Kd<0.1 μM.

M: medium binder: 0.1 μM≤Kd<0.8 μM.

N: weak and non-binder: 0.8 μM≤Kd.

Peptides corresponding to self-peptides were treated separately. The list of self-peptides was taken from 293 antibody germline sequences. They are referred to as "germline-filtered" peptides.

S- and M-peptides are mapped onto the target sequence in so-called epitope maps; S-affinities are plotted quantitatively; M-values are presented qualitatively. As a general overview of the results, Table 6 lists the number of strong and medium binders in the analyzed proteins, for the groups of HLA class II receptors corresponding to the DRB1, DQ, DP and DRB3/4/5 genes. Counting was done separately for strong and medium affinity binders. Peptides binding to multiple allotypes of the same group were counted as one. Values between brackets refer to germline-filtered peptides. In Table 7, the sequence is shown in a format suitable for experimental work. The sequence is broken down in consecutive 15-mers overlapping by 12 residues. For each 15-mer, the promiscuity is listed (the number of allotypes out of a total of 47 for which the 15-mer contains a critical binder), as well as the implied serotypes. The Epibase® profile and epitope maps are shown in FIGS. 16A-C and 17.

It was concluded that IGKV1-39 contains no strong non-self DRB1 binders. Typically, significantly more binders were found for DRB1 than for other HLA genes. This is in agreement with experimental evidence that allotypes belonging to the DRB1 group are more potent peptide binders. Medium strength epitopes for DRB1 allotypes are expected to contribute to the population response, and cannot be disregarded. Again, no non-self DRB1 binders were found in IGKV1-39.

In the humoral response raised against an antigen, the observed $T_H$ cell activation/proliferation is generally interpreted in terms of the DRB1 specificity. However, one cannot ignore the possible contribution of the DRB3/4/5, DQ and DP genes. Given the lower expression levels of these genes as compared to DRB1, the focus was on the class of strong epitopes for DRB3/4/5, DQ and DP. "Critical epitopes" are those epitopes that are strong binders for any DRB1, DRB3/4/5, DQ or DP allotype or are medium binders for DRB1. IGKV1-39 contains no strong or medium non-self binders for DRB3/4/5, DQ, or DP.

A number of peptides are also present in germline sequences (values between brackets in Table 6). Such peptides may very well bind to HLA but they are assumed to be self and, hence, non-immunogenic. In total, six strong and 16 medium germline-filtered DRB1 binders were found in IGKV1-39. Framework region 1 up to framework region 3 is an exact match for germline V-segment VKI 2-1-(1) O12 (VBase), a.k.a. IGKV1-39*01 (IMGT). Framework region 4 is an exact match for germline J-segment JKI (V-base) a.k.a. IGKJ1*01(IMGT). It is hardly surprising that these segments do not contain any non-self epitopes.

Example 20: Production Characteristics of IGKV1-39

Figure 28:
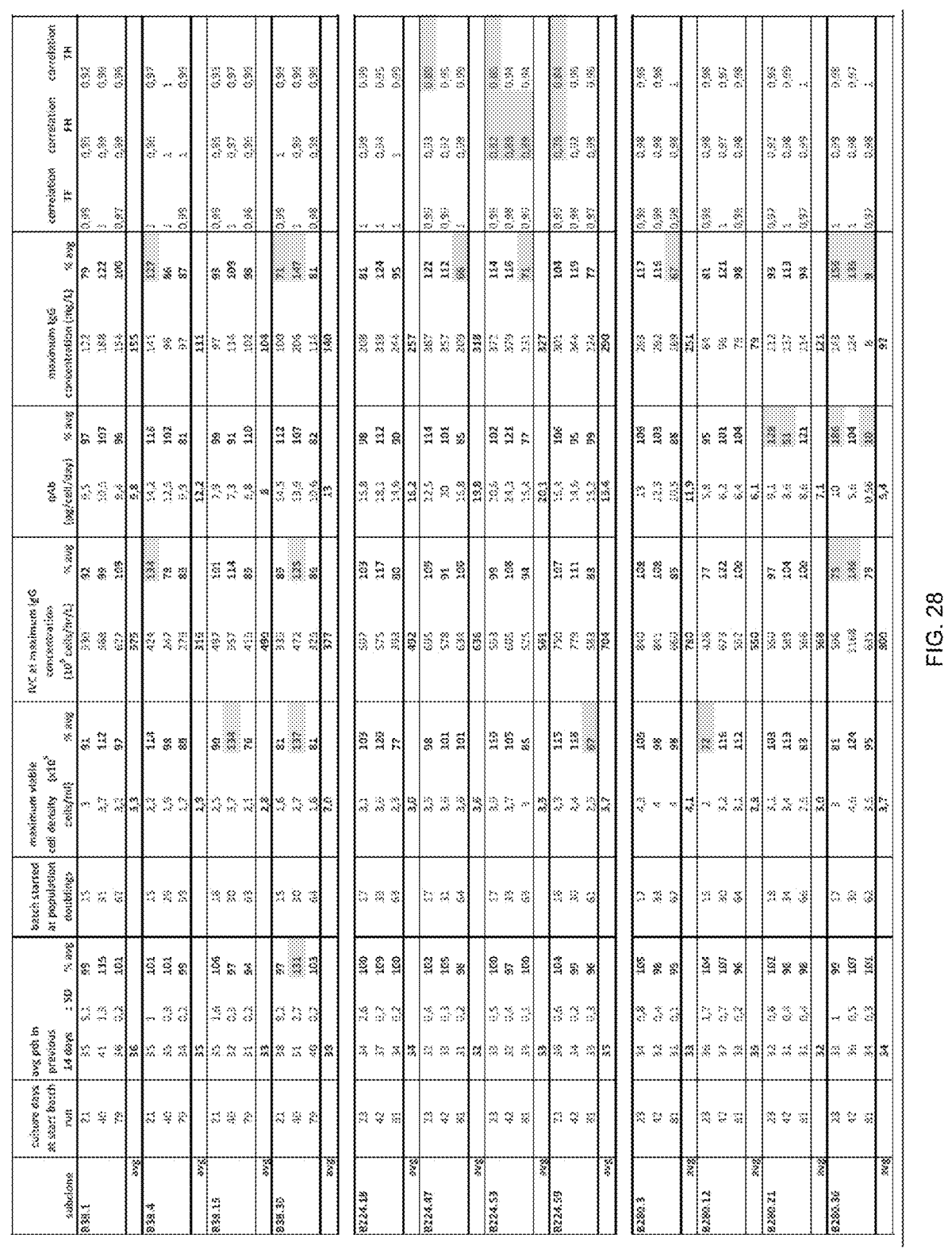

There is a great demand for antibody discovery platforms that yield therapeutic antibodies that are thermodynamically stable and give good expression yields. These characteristics are important in ensuring the stability of the drug substance during production and after injection of the drug product into the patient. In addition good expression yields impact directly on the cost of drug manufacture and thus pricing, patient access and profitability. Virtually all therapeutic antibodies in clinical use today are composed of human IgG1 and kappa constant regions but use different heavy and light chain variable regions that confer specificity. Human variable heavy and light chain domains can be divided into families that have greater than 80% sequence divergence. When rearranged examples of these families in germline configuration are combined and compared for stability and yield it is clear that the gene families are not equal in terms of biophysical properties. In particular $V_H^3$, $V_H1$ and $V_H5$ have favourable stability for the heavy chains and Vk1 and Vk3 have the best stability and yield of light chains. In addition when mutations are introduced as part of the somatic hypermutation process they can interfere with VH/VL pairing. To assess the effect that different light chain genes with different rates of mutation have on the production characteristics of a fixed VH chain, a Fab phage display library was built of light chains (kappa and lambda) from six naïve healthy donors combined with a panel of 44 TT binding heavy chains from immunized donors. After one round of selection TT binding Fab clones were isolated. Several of these shared the same $V_H$ gene as the TT clone PG1433 in combination with different light chains. The Fab light chain fragments were recloned into a kappa expression vector and transfected in combination with DNA encoding the heavy chain of PG1433 into 293 cells and specific IgG production measured by ELISA. As demonstrated in Table 8 the selected clones containing PG1433 VH combined with different light chains had between five- and ten-fold lower protein expression PG1433 VH combined with IGKV1-39. Note that all of the light chains contained amino acid mutations within their coding regions that might disrupt VH paring and reduce production stability. Thus, in addition to reducing the chances of unwanted immunogenicity, it is expected that the use of the light chain IGKV1-39 without mutations contributes to improved production stability and yields of various specificity-contributing $V_H$ genes. Indeed stable clones generated by the transfection of different VH genes all paired with IGKV1-39 are able to be passaged extensively and still retain robust production characteristics as shown in FIG. 28.

Example 21: Generation of Mice Expressing Fully Human VH and VL Regions

Transgenic mice described herein are crossed with mice that already contain a human VH locus. Examples of appropriate mice comprising a human VH locus are disclosed in Taylor et al. (1992), *Nucleic Acids Res.* 20:6287-95; Lonberg et al. (1994), *Nature* 368:856-9; Green et al. (1994), *Nat. Genet.* 7:13-21; Dechiara et al. (2009), *Methods Mol. Biol.* 530:311-24).

After crossing and selecting for mice that are at least heterozygous for the IGKV1-39 transgene and the human VH locus, selected mice are immunized with a target. VH genes are harvested as described hereinabove. This method has the advantage that the VH genes are already fully human and thus do not require humanization.

Example 22: Isolation, Characterization, Oligoclonics Formatting and Production of Antibodies Targeting Human IL6 for Treatment of Chronic Inflammatory Diseases Such as Rheumatoid Arthritis A spleen VH repertoire from transgenic mice that are immunized with human recombinant IL6 is cloned in a phage display Fab vector with a single human IGKV1-39-C kappa light chain (identical to the mouse transgene) and subjected to panning against the immunogen human IL6. Clones that are obtained after two to four rounds of panning are analyzed for their binding specificity. VH genes encoding IL6-specific Fab fragments are subjected to sequence analysis to identify unique clones and assign VH, DH and JH utilization. The Fab fragments are reformatted as IgG1 molecules and transiently expressed. Unique clones are then grouped based on non-competition in binding assays and subjected to affinity and functional analysis. The most potent anti-IL6 IgG1 mAbs are subsequently expressed as combinations of two, three, four or five heavy chains comprising different VH-regions in the Oligoclonics format, together with one IGKV1-39-C-based kappa light chain and tested in vitro for complex formation with IL-6. The Oligoclonics are also tested in vivo for clearance of human IL-6 from mice. An Oligoclonic with the most potent clearance activity is chosen and the murine VH genes humanized according to conventional methods. The humanized IgG1 are transfected into a mammalian cell line to generate a stable clone. An optimal subclone is selected for the generation of a master cell bank and the generation of clinical trial material.

Many of the protocols described here are standard protocols for the construction of phage display libraries and the panning of phages for binding to an antigen of interest and are described, for example, in *Antibody Phage Display: Methods and Protocols* (2002), Editor(s) Philippa M. O'Brien, Robert Aitken, Humana Press, Totowa, N.J., USA.

Immunizations

Transgenic mice receive three immunizations with human IL6 every two weeks using the adjuvant Sigma titerMax according to manufacturer's instructions.

RNA Isolation and cDNA Synthesis

Three days after the last immunization, spleens and lymphnodes from the mice are removed and passed through a 70 micron filter into a tube containing PBS pH 7.4 to generate a single cell suspension. After washing and pelleting of lymphocytes, cells are suspended in TRIzol LS Reagent (Invitrogen) for the isolation of total RNA according to the manufacturer's protocol and subjected to reverse transcription reaction using 1 microgram of RNA, Superscript III RT in combination with dT20 according to manufacturer's procedures (Invitrogen).

The generation of Fab phage display libraries is carried out as described in Example 2.

Selection of Phages on Coated Immunotubes

Human recombinant IL6 is dissolved in PBS in a concentration of 5 µg/ml and coated to MAXISORP™ Nunc-Immuno Tube (Nunc 444474) overnight at 4° C. After discarding the coating solution, the tubes are blocked with 2% skim milk (ELK) in PBS (blocking buffer) for one hour at Room Temperature (RT). In parallel, 0.5 ml of the phage library is mixed with 1 ml blocking buffer and incubated for 20 minutes at room temperature. After blocking the phages, the phage solution is added to the IL6-coated tubes and incubated for two hours at RT on a slowly rotating platform to allow binding. Next, the tubes are washed ten times with PBS/0.05% TWEEN™-20 detergent followed by phage elution by incubating with 1 ml 50 mM glycine-HCl pH 2.2 ten minutes at RT on rotating wheel and directly followed by neutralization of the harvested eluent with 0.5 ml I M Tris-HCl pH 7.5.

Harvesting Phage Clones

A 5 ml XL1-Blue MRF (Stratagene) culture at O.D. 0.4 is added to the harvested phage solution and incubated for 30 minutes at 37° C. without shaking to allow infection of the phages. Bacteria are plated on Carbenicillin/Tetracycline 4% glucose 2*TY plates and grown overnight at 37° C.

Phage Production

Phages are grown and processed as described by Kramer et al. 2003 (Kramer et al. 2003, *NucleicAcids Res.* 31(11): e59) using VCSM13 as helper phage strain.

Phage ELISA

ELISA plates are coated with 100 microliters human recombinant IL6 per well at a concentration of 2.5 micrograms/ml in PBS overnight at 4° C. Plates coated with 100 microliters thyroglobulin at a concentration of 2 micrograms/ml in PBS are used as a negative control. Wells are emptied, dried by tapping on a paper towel, filled completely with PBS-4% skimmed milk (ELK) and incubated for one hour at room temperature to block the wells. After discarding the block solution, phage minipreps pre-mixed with 50 µl blocking solution are added and incubated for one hour at RT. Unbound phages are subsequently removed by five washing steps with PBS-0.05% Tween-20. Bound phages are detected by incubating the wells with 100 microliters anti-M13-HRP antibody conjugate (diluted 1/5000 in blocking buffer) for one hour at room temperature. Free antibody is removed by repeating the washing steps as described above, followed by TMB substrate incubation until color development was visible. The reaction is stopped by adding 100 microliters of 2 M H2SO4 per well and analyzed on an ELISA reader at 450 nm emission wavelength.

Sequencing

Clones that give signals at least three times above the background signal are propagated, used for DNA miniprep procedures (see procedures Qiagen miniPrep manual) and subjected to nucleotide sequence analysis. Sequencing is performed according to the Big Dye 1.1 kit accompanying manual (Applied Biosystems) using a reverse primer (CH1_Rev1, Table 1) recognizing a 5' sequence of the CH1 region of the human IgG1 heavy chain (present in the Fab display vector MV1043, FIGS. 3 and 12). The sequences of the murine VH regions are analyzed for diversity of DH and JH gene segments.

Construction and Expression of Chimeric IgG1

Figure 22:
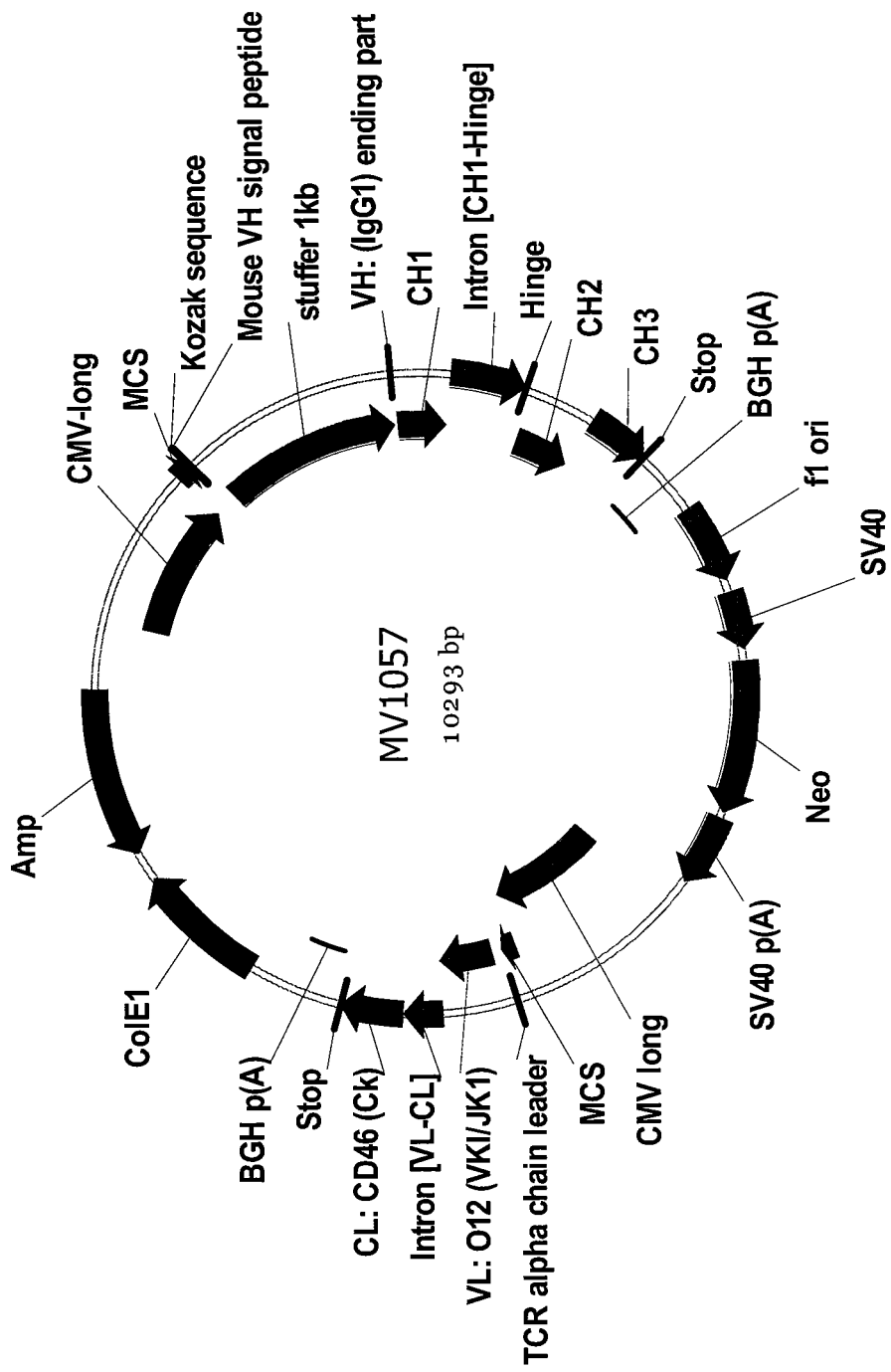
FIG. 22: Topology of the MV1057 vector. Replacing the indicated stuffer fragment with a VH fragment yields an expression vector that can be transfected to eukaryotic cells for the production of IgG1 antibodies with light chains containing an O12 (IGKV1-39) VL gene.

Vector MV1057 (FIGS. 12 and 22) was generated by cloning the transgene (IGKV1-39) L chain fragment into a derivative of vector pcDNA3000Neo (Crucell, Leiden, The Netherlands) that contains the human IgG1- and kappa constant regions. VH regions are cloned into MV1057 and nucleotide sequences for all constructs are verified according to standard techniques. The resulting constructs are transiently expressed in HEK293T cells and supernatants containing chimeric IgG1 are obtained and purified using standard procedures as described before (M. Throsby 2006, *J. Virol.* 80:6982-92).

IgG1 Binding and Competition Analysis

IgG1 antibodies are titrated in ELISA using IL6-coated plates as described above and an anti-human IgG peroxidase conjugate. Competition ELISAs to group antibodies based on epitope recognition are performed by incubating Fab phages together with IgG1 or with commercial antibodies against IL6 (e.g., Abcam cat. no. ab9324) in IL6-coated plates, followed by detection of bound Fab phage using an anti-M13 peroxidase conjugate.

IgG1 Affinity Measurements

The affinities of the antibodies to IL6 are determined with the Quantitative kinetic protocol on the Octet (ForteBio). Antibodies are captured onto an Anti-Human IgG Fc Capture biosensor and exposed to free IL6 and analyzed using proprietary software to calculate the Kd of each antibody.

Functional Activity of IL6 Antibodies

To test the ability of the selected antibodies to inhibit binding between IL6 and IL6 receptor (IL6R), an ELISA based assay is used. Various concentrations of antibody are mixed with a fixed concentration (10 ng/ml) of biotinylated IL6 as described by Naoko et al. 2007, *Can. Res.* 67:817-875. The L6-antibody immune complex is added to immobilized IL6R. The binding of biotinylated IL6 to IL6R is detected with horseradish peroxidase-conjugated streptavidin. The reduction of ELISA signal is a measurement of inhibition. As positive control for inhibition of binding between IL6 and IL6R either anti-IL6R antibody (Abcam cat. no. ab34351; clone B-R6) or anti IL6 antibody (Abcam cat. no. ab9324) is used.

In vitro blocking activity of the selected anti-EL6 antibodies is measured in a proliferation assay using the IL6-dependent cell line 7TDI. Briefly, cells are incubated with different concentrations of human IL6 with or without the anti-EL6 antibody. The available amount of IL6 determines the degree of proliferation. Thus if an added antibody blocks IL6 binding the proliferation readout is reduced compared to a non binding antibody control. Proliferation is measured by the incorporation of 5-bromo-2'-deoxy-uridine (BrdU) into the DNA using the BrdU proliferation kit (Roche cat. no. 11444611001) according to the manufacturer's instructions.

Generation of Anti-IL6 Oligoclonics

The most potent anti-IL6 antibodies are selected from each epitope group. The expression constructs expressing these antibodies are transfected into HEK293T cells in non-competing groups of three in different ratios (1:1:1; 3:1:1; 1:3:1; 1:1:3; 3:3:1; 1:3:3; 3:1:3; 10:1:1; 1:10:1; 1:1:10; 10:10:1; 1:10:10; 10:1:10; 3:10:1; 10:3:1; 1:10:3; 3:1:10; 10:1:3; 1:3:10). Antibody containing supernatants are harvested and purified and characterized as above.

Complex Formation and In Vivo Clearance of Anti-IL6 Oligoclonics

To measure the ability of anti-IL6 Oligoclonics to form immune complexes and to analyze these complexes Size Exclusion Chromatography (SEC) is used according to the approach disclosed by Min-Soo Kim et al. (2007), *JMB* 374:1374-1388, to characterize the immune-complexes formed with different antibodies to TNFα. Different molar ratios of the anti-IL6 Oligoclonics are mixed with human IL6 and incubated for 20 hours at 4° C. or 25° C. The mixture is analyzed on an HPLC system fitted with a size exclusion column; different elution times are correlated to molecular weight using a molecular weight standards.

The ability of antibodies to form complexes with IL6 is correlated with their ability to rapidly clear the cytokine from the circulation in vivo. This is confirmed by measuring the clearance of radiolabelled IL6 from mice. Briefly, female, six- to eight-week-old Balb/c mice are obtained and 18 hours before the experiment, the animals are injected intravenously (IV) via the lateral tail vein with different doses of purified anti-IL6 Oligoclonics. On day 0, the mice are injected IV with 50 microliters of radiolabeled IL-6 (1×10E7 cpm/mL) under the same conditions. Blood samples (approximately 50 microliters) are collected at several time intervals and stored at 4° C. The samples are centrifuged for five minutes at 4000×g and the radioactivity of the serum determined. All pharmacokinetic experiments are performed simultaneously with three animals for each treatment.

Generation of Anti-L6 Oligoclonics Stable Clones and Preclinical Development

A lead anti-IL6 Oligoclonic is selected based on the in vitro and in vivo potency as determined above. The murine VH genes are humanized according to standard methods and combined with the fully human IGKV1-39 light chain in an expression vector as described above. Examples of humanization methods include those based on paradigms such as resurfacing (E. A. Padlan et al. (1991), *Mol. Immunol.* 28:489), superhumanization (P. Tan, D. A., et al. (2002), *J. Immunol.* 169:1119) and human string content optimization (G. A. Lazar et al. (2007), *Mol. Immunol.* 44:1986). The three constructs are transfected into PER.C6 cells at the predetermined optimal ratio (described above) under the selective pressure of G418 according to standard methods. A stable high producing anti-IL6 Oligoclonic clone is selected and a working and qualified master cell bank generated.

TABLE 1

List of primers

| DO- Primer | Sequence |
|---|---|
| 0012 CH1_Rev1 | TGCCAGGGGGAAGACCGATG (SEQ ID NO: 4) |
| 0656 MVH-1 | GCCGGCCATGGCCGAGGTRMAGCTTCAGGAGTCAGGAC (SEQ ID NO: 5) |
| 0657 MVH-2 | GCCGGCCATGGCCGAGGTSCAGCTKCAGCAGTCAGGAC (SEQ ID NO: 6) |
| 0658 MVH-3 | GCCGGCCATGGCCCAGGTGCAGCTGAAGSASTCAGG (SEQ ID NO: 7) |
| 0659 MVH-4 | GCCGGCCATGGCCGAGGTGCAGCTTCAGGAGTCSGGAC (SEQ ID NO: 8) |
| 0660 MVH-5 | GCCGGCCATGGCCGARGTCCAGCTGCAACAGTCYGGAC (SEQ ID NO: 9) |
| 0661 MVH-6 | GCCGGCCATGGCCCAGGTCCAGCTKCAGCAATCTGG (SEQ ID NO: 10) |

TABLE 1-continued

List of primers

| DO- Primer | Sequence |
|---|---|
| 0662 MVH-7 | GCCGGCCATGGCCCAGSTBCAGCTGCAGCAGTCTGG<br>(SEQ ID NO: 11) |
| 0663 MVH-8 | GCCGGCCATGGCCCAGGTYCAGCTGCAGCAGTCTGGRC<br>(SEQ ID NO: 12) |
| 0664 MVH-9 | GCCGGCCATGGCCCAGGTYCAGCTYCAGCAGTCTGG<br>(SEQ ID NO: 13) |
| 0665 MVH-10 | GCCGGCCATGGCCGAGGTCCARCTGCAACAATCTGGACC<br>(SEQ ID NO: 14) |
| 0666 MVH-11 | GCCGGCCATGGCCCAGGTCCACGTGAAGCAGTCTGGG<br>(SEQ ID NO: 15) |
| 0667 MVH-12 | GCCGGCCATGGCCGAGGTGAASSTGGTGGAATCTG<br>(SEQ ID NO: 16) |
| 0668 MVH-13 | GCCGGCCATGGCCGAVGTGAAGYTGGTGGAGTCTG<br>(SEQ ID NO: 17) |
| 0669 MVH-14 | GCCGGCCATGGCCGAGGTGCAGSKGGTGGAGTCTGGGG<br>(SEQ ID NO: 18) |
| 0670 MVH-15 | GCCGGCCATGGCCGAKGTGCAMCTGGTGGAGTCTGGG<br>(SEQ ID NO: 19) |
| 0671 MVH-16 | GCCGGCCATGGCCGAGGTGAAGCTGATGGARTCTGG<br>(SEQ ID NO: 20) |
| 0672 MVH-17 | GCCGGCCATGGCCGAGGTGCARCTTGTTGAGTCTGGTG<br>(SEQ ID NO: 21) |
| 0673 MVH-18 | GCCGGCCATGGCCGARGTRAAGCTTCTCGAGTCTGGA<br>(SEQ ID NO: 22) |
| 0674 MVH-19 | GCCGGCCATGGCCGAAGTGAARSTTGAGGAGTCTGG<br>(SEQ ID NO: 23) |
| 0675 MVH-20 | GCCGGCCATGGCCGAAGTGATGCTGGTGGAGTCTGGG<br>(SEQ ID NO: 24) |
| 0676 MVH-21 | GCCGGCCATGGCCCAGGTTACTCTRAAAGWGTSTGGCC<br>(SEQ ID NO: 25) |
| 0677 MVH-22 | GCCGGCCATGGCCCAGGTCCAACTVCAGCARCCTGG<br>(SEQ ID NO: 26) |
| 0678 MVH-23 | GCCGGCCATGGCCCAGGTYCARCTGCAGCAGTCTG<br>(SEQ ID NO: 27) |
| 0679 MVH-24 | GCCGGCCATGGCCGATGTGAACTTGGAAGTGTCTGG<br>(SEQ ID NO: 28) |
| 0680 MVH-25 | GCCGGCCATGGCCGAGGTGAAGGTCATCGAGTCTGG<br>(SEQ ID NO: 29) |
| 0681 ExtMVH-1 | CAGTCACAGATCCTCGCGAATT*GGCCCA*GCCGGCCATGGCCSANG<br>(SEQ ID NO: 30) |
| 0682 ExtMVH-2 | CAGTCACAGATCCTCGCGAATT*GGCCCAGCCGGCC*ATGGCCSANC<br>(SEQ ID NO: 31) |
| 0683 MJH-Rev1 | GGGGGTGTCGTTTTGGCTGAGGAGAC*GGTGACC*GTGG<br>(SEQ ID NO: 32) |
| 0684 MJH-Rev2 | GGGGGTGTCGTTTTGGCTGAGGAGAC*TGTGAGA*GTGG<br>(SEQ ID NO: 33) |
| 0685 MJH-Rev3 | GGGGGTGTCGTTTTGGCTGCAGAGAC*AGTGACC*AGAG<br>(SEQ ID NO: 34) |
| 0686 MJH-Rev4 | GGGGGTGTCGTTTTGGCTGAGGAGAC*GGTGACT*GAGG<br>(SEQ ID NO: 35) |

TABLE 1-continued

List of primers

| DO- | Primer | Sequence |
|---|---|---|
| 0687 | ExtMJH-Rev1& | GGGGGTGTCGTTTTGGCTGAGGAGAC*GGTGACC*GTGG (SEQ ID NO: 36) |
| 0688 | ExtMJH-Rev2in | GGGGGTGTCGTTTTGGCTGAGGAGAC*GGTGACA*GTGG (SEQ ID NO: 37) |
| 0690 | ExtMJH-Rev3 | GGGGGTGTCGTTTTGGCTGAGGAGAC*GGTGACC*AGAG (SEQ ID NO: 38) |
| 0691 | ExtMJH-Rev4 | GGGGGTGTCGTTTTGGCTGAGGAGAC*GGTGACC*GAGG (SEQ ID NO: 39) |

TABLE 2

Phage ELISA signal levels as measured at 450 nm.

| | 1 | 2 | 3 | 4 | 5 | 6 | 7 | 8 | 9 | 10 | 11 | 12 |
|---|---|---|---|---|---|---|---|---|---|---|---|---|
| TT-coated plate 10/10 washings | | | | | | | | | | | | |
| A | 0.139 | 0.093 | 0.089 | 0.121 | 0.117 | 0.598 | 0.146 | 0.115 | 0.18 | 0.155 | 0.543 | 0.601 |
| B | 0.136 | 0.404 | 0.159 | 0.187 | 0.489 | 0.134 | 0.216 | 0.092 | 0.222 | 0.108 | 0.181 | 0.484 |
| C | 0.197 | 0.526 | 0.09 | 0.213 | 0.395 | 0.155 | 0.108 | 0.12 | 0.183 | 0.136 | 0.092 | 0.866 |
| D | 0.143 | 0.258 | 0.101 | 0.422 | 0.088 | 0.243 | 0.485 | 0.251 | 0.304 | 0.198 | 0.478 | 0.091 |
| E | 0.445 | 0.169 | 0.526 | 0.481 | 0.206 | 0.285 | 0.111 | 0.119 | 0.128 | 0.2 | 0.118 | 0.098 |
| F | 0.237 | 0.291 | 0.594 | 0.139 | 0.206 | 0.565 | 0.543 | 0.091 | 0.136 | 0.227 | 0.228 | 0.099 |
| G | 0.459 | 0.102 | 0.152 | 0.659 | 0.203 | 0.452 | 0.152 | 0.133 | 0.094 | 0.102 | 0.375 | 0.098 |
| H | 0.341 | 0.623 | 0.745 | 0.415 | 0.682 | 0.527 | 0.655 | 0.114 | 0.258 | 0.284 | 0.685 | 0.113 |
| TT-coated plate 15/15 washings | | | | | | | | | | | | |
| A | 0.247 | 0.582 | 0.421 | 0.428 | 0.133 | 0.082 | 0.262 | 0.079 | 0.343 | 0.414 | 0.095 | 0.292 |
| B | 0.065 | 0.364 | 0.073 | 0.042 | 0.049 | 0.071 | 0.046 | 0.103 | 0.078 | 0.057 | 0.048 | 0.155 |
| C | 0.081 | 0.044 | 0.066 | 0.082 | 0.225 | 0.444 | 0.203 | 0.362 | 0.122 | 0.047 | 0.052 | 0.309 |
| D | 0.092 | 0.11 | 0.59 | 0.22 | 0.33 | 0.544 | 0.058 | 0.159 | 0.047 | 0.174 | 0.086 | 0.05 |
| E | 0.469 | 0.577 | 0.206 | 0.304 | 0.13 | 0.749 | 0.431 | 0.062 | 0.167 | 0.049 | 0.056 | 0.049 |
| F | 0.846 | 0.07 | 0.561 | 0.656 | 0.882 | 0.094 | 0.383 | 0.13 | 0.152 | 0.098 | 0.134 | 0.048 |
| G | 0.537 | 0.052 | 0.49 | 0.105 | 0.337 | 0.193 | 0.514 | 0.294 | 0.068 | 0.35 | 0.525 | 0.05 |
| H | 0.061 | 0.306 | 0.157 | 0.853 | 0.054 | 0.534 | 0.102 | 0.235 | 0.441 | 0.412 | 0.565 | 0.061 |
| Thyroglobulin-coated plate 10/10 washings | | | | | | | | | | | | |
| A | 0.047 | 0.051 | 0.045 | 0.043 | 0.051 | 0.044 | 0.046 | 0.042 | 0.047 | 0.048 | 0.049 | 0.05 |
| B | 0.042 | 0.042 | 0.042 | 0.042 | 0.043 | 0.041 | 0.041 | 0.042 | 0.043 | 0.045 | 0.042 | 0.046 |
| C | 0.044 | 0.043 | 0.043 | 0.044 | 0.043 | 0.044 | 0.043 | 0.042 | 0.043 | 0.041 | 0.044 | 0.046 |
| D | 0.045 | 0.044 | 0.044 | 0.044 | 0.045 | 0.046 | 0.045 | 0.056 | 0.045 | 0.049 | 0.048 | 0.73 |
| E | 0.046 | 0.045 | 0.046 | 0.044 | 0.045 | 0.044 | 0.044 | 0.044 | 0.047 | 0.046 | 0.047 | 0.926 |
| F | 0.048 | 0.045 | 0.044 | 0.046 | 0.044 | 0.043 | 0.044 | 0.046 | 0.046 | 0.046 | 0.046 | 0.792 |
| G | 0.051 | 0.048 | 0.045 | 0.045 | 0.044 | 0.043 | 0.048 | 0.045 | 0.048 | 0.051 | 0.045 | 0.053 |
| H | 0.064 | 0.05 | 0.049 | 0.047 | 0.05 | 0.051 | 0.047 | 0.046 | 0.047 | 0.047 | 0.047 | 0.056 |
| Thyroglobulin-coated plate 15/15 washings | | | | | | | | | | | | |
| A | 0.036 | 0.049 | 0.045 | 0.044 | 0.046 | 0.047 | 0.046 | 0.042 | 0.042 | 0.043 | 0.042 | 0.041 |
| B | 0.045 | 0.042 | 0.041 | 0.043 | 0.043 | 0.043 | 0.045 | 0.045 | 0.047 | 0.048 | 0.044 | 0.045 |
| C | 0.049 | 0.047 | 0.047 | 0.046 | 0.046 | 0.046 | 0.045 | 0.047 | 0.046 | 0.045 | 0.045 | 0.052 |
| D | 0.047 | 0.049 | 0.048 | 0.048 | 0.048 | 0.048 | 0.047 | 0.052 | 0.048 | 0.046 | 0.048 | 0.456 |
| E | 0.049 | 0.047 | 0.047 | 0.047 | 0.047 | 0.049 | 0.047 | 0.048 | 0.047 | 0.046 | 0.048 | 0.412 |
| F | 0.05 | 0.047 | 0.046 | 0.046 | 0.046 | 0.046 | 0.046 | 0.046 | 0.046 | 0.047 | 0.048 | 0.528 |
| G | 0.05 | 0.048 | 0.045 | 0.045 | 0.046 | 0.049 | 0.048 | 0.046 | 0.053 | 0.049 | 0.05 | 0.057 |
| H | 0.057 | 0.05 | 0.046 | 0.045 | 0.047 | 0.049 | 0.047 | 0.047 | 0.046 | 0.047 | 0.053 | 0.048 |

TT-coated plates represent plates that were coated with tetanus toxoid. Thyroglobulin-coated plates are used as negative controls. 10/10 and 15/15 indicate the number of wash steps with PBS-Tween during panning procedures. The 10/10 tetanus toxoid and 10/10 thyroglobulin plates and the 15/15 tetanus toxoid and 15/15 thyroglobulin plates are duplicates from each other except for the coating agent. OD values higher than three times the background are assumed specific.

TABLE 3

Protein sequence analysis of ELISA positive tetanus toxoid binders. CDR3 sequence, CDR3 length, VH family members and specific name, JH origin and DH origin of the clones is indicated.

| CDR3/SEQ ID NO: | | CDR3 length | VH | DH | JH | V Gene family |
|---|---|---|---|---|---|---|
| HGAYYTYDEKAWFAY | (SEQ ID NO: 40) | 15 | musIGHV192 | DSP2.11 | JH3 mouse | VH7183 |
| HGAYYTYDEKAWFAY | (SEQ ID NO: 40) | 15 | musIGHV192 | DSP2.11 | JH3 mouse | VH7183 |
| HGAYYTYDEKAWFAY | (SEQ ID NO: 40) | 15 | musIGHV192 | DSP2.11 | JH3 mouse | VH7183 |
| HGAYYTYDEKAWFAY | (SEQ ID NO: 40) | 15 | musIGHV192 | DSP2.11 | JH3 mouse | VH7183 |
| HGAYYTYDEKAWFAY | (SEQ ID NO: 40) | 15 | musIGHV192 | DSP2.11 | JH3 mouse | VH7183 |
| HGAYYTYDEKAWFAY | (SEQ ID NO: 40) | 15 | musIGHV192 | DSP2.11 | JH3 mouse | VH7183 |
| HGAYYTYDEKAWFAY | (SEQ ID NO: 40) | 15 | musIGHV192 | DSP2.11 | JH3 mouse | VH7183 |
| HGAYYTYDEKAWFAY | (SEQ ID NO: 40) | 15 | musIGHV192 | DSP2.11 | JH3 mouse | VH7183 |
| HGAEYTYDEKPWFAY | (SEQ ID NO: 41) | 15 | musIGHV192 | IGHD2-14*01 | JH3 mouse | VH7183 |
| HISYYRYDEEVSFAY | (SEQ ID NO: 42) | 15 | musIGHV192 | IGHD2-14*01 | JH3 mouse | VH7183 |
| HISYYRYDEEVSFAY | (SEQ ID NO: 42) | 15 | musIGHV192 | IGHD2-14*01 | JH3 mouse | VH7183 |
| GWRAFAY | (SEQ ID NO: 43) | 7 | musIGHV131 | DSP2.9 | JH3 mouse | VH7183 |
| GWRAFAY | (SEQ ID NO: 43) | 7 | musIGHV131 | DSP2.9 | JH3 mouse | VH7183 |
| GWRAFAY | (SEQ ID NO: 43) | 7 | musIGHV131 | DSP2.9 | JH3 mouse | VH7183 |
| DRGNYYGMDY | (SEQ ID NO: 44) | 10 | musIGHV178 | DSP2.1 | JH4 mouse | VH7183 |
| LGDYYVDWFFAV | (SEQ ID NO: 45) | 12 | musIGHV165 | DFL16.1 | JH1 mouse | VH7183 |
| NFPAWFAF | (SEQ ID NO: 46) | 8 | musIGHV547 | DST4.3inv | JH3 mouse | VJH558 |
| NFPAWFAY | (SEQ ID NO: 46) | 8 | musIGHV547 | DSP2.1 | JH3 mouse | VJH558 |
| NFPAWFVY | (SEQ ID NO: 46) | 8 | musIGHV547 | DSP2.1 | JH3 mouse | VJH558 |
| SFTPVPFYYGYDWYFDV | (SEQ ID NO: 47) | 17 | musIGHV532 | DSP2.3 | JH1 mouse | VJH558 |
| SFTPVPFYYGYDWYFDV | (SEQ ID NO: 47) | 17 | musIGHV532 | DSP2.3 | JH1 mouse | VJH558 |
| SDYDWYFDV | (SEQ ID NO: 48) | 9 | musIGHV286 | DSP2.2 | JH1 mouse | VJHS558 |
| SDYDWYFDV | (SEQ ID NO: 48) | 9 | musIGHV286 | DSP2.2 | JH1 mouse | VJH558 |
| DSKWAYYFDY | (SEQ ID NO: 49) | 10 | musIGHV532 | DST4.3 | JH2 mouse | VJh558 |
| GDYTGYGMDY | (SEQ ID NO: 50) | 10 | musIGHV125 | DSP2.13 | JH4 mouse | VHSM7 |
| GDYTGYGMDY | (SEQ ID NO: 50) | 10 | musIGHV125 | DSP2.13 | JH4 mouse | VHSM7 |
| GGYDGYWFPY | (SEQ ID NO: 51) | 10 | musIGHV125 | DSP2.9 | JH3 mouse | VHSM7 |

TABLE 4

Vector combinations that were transfected to HEK293T.

| Code | HC vector | LC vector | Combined vector | Prep name | Conc. (μg/ml) |
|---|---|---|---|---|---|
| A | x | 0817676_pSELECT_0815426 (IGKV1-39) | x | PIGKV1-39/P1 | — |
| B | x | 0817678_pSELECT_0815427 (IGLV2-14) | x | PIGLV2-14/P1 | — |
| C | MV1110 | 0817676_pSELECT_0815426 (IGKV1-39) | x | PMV1110/IGKV1-39/P1 | 11.0 |
| D | MV1110 | 0817678_pSELECT_0815427 (IGLV2-14) | x | PMV1110/IGLV2-14/P1 | 15.4 |
| E | x | x | MG1494 | MG1494/P2 | 16.1 |

TABLE 5

HLA allotypes considered in T$_H$-epitope profiling.

| HLA type | Serotype | Population % |
|---|---|---|
| DRB1*0101 | DR1 | 17.4 |
| DRB1*0102 | DR1 | 4.9 |
| DRB1*0301 | DR17(3) | 21.2 |
| DRB1*0401 | DR4 | 11.5 |
| DRB1*0402 | DR4 | 3.1 |
| DRB1*0404 | DR4 | 5.5 |
| DRB1*0405 | DR4 | 2.2 |
| DRB1*0407 | DR4 | <2 |
| DRB1*0701 | DR7 | 23.4 |
| DRB1*0801 | DR8 | 3.3 |
| DRB1*0802 | DR8 | <2 |
| DRB1*0901 | DR9 | <2 |
| DRB1*1101 | DR11(5) | 17 |
| DRB1*1104 | DR11(5) | 5.7 |
| DRB1*1201 | DR12(5) | 3.1 |
| DRB1*1301 | DR13(6) | 15.4 |
| DRB1*1302 | DR13(6) | 10.8 |
| DRB1*1401 | DR14(6) | 4.2 |
| DRB1*1501 | DR15(2) | 13.2 |
| DRB1*1601 | DR16(2) | 5.5 |
| DRB3*0101 | DR52 | 24.6 |
| DRB3*0202 | DR52 | 43 |
| DRB3*0301 | DR52 | 10 |
| DRB4*0101 | DR53 | 25.5 |
| DRB4*0103 | DR53 | 21 |
| DRB5*0101 | DR51 | 15.8 |
| DRB5*0202 | DR51 | 5.7 |
| DQA1*0101/DQB1*0501 | DQ5(1) | 20.5 |
| DQA1*0102/DQB1*0502 | DQ5(1) | 2.6 |
| DQA1*0102/DQB1*0602 | DQ6(1) | 26.5 |
| DQA1*0102/DQB1*0604 | DQ6(1) | 6.7 |
| DQA1*0103/DQB1*0603 | DQ6(1) | 11 |

TABLE 5-continued

HLA allotypes considered in T_H-epitope profiling.

| HLA type | Serotype | Population % |
|---|---|---|
| DQA1*0104/DQB1*0503 | DQ5(1) | 4 |
| DQA1*0201/DQB1*0202 | DQ2 | 20.9 |
| DQA1*0201/DQB1*0303 | DQ9(3) | 7.2 |
| DQA1*0301/DQB1*0301 | DQ7(3) | 12.5 |
| DQA1*0301/DQB1*0302 | DQ8(3) | 18.3 |
| DQA1*0401/DQB1*0402 | DQ4 | 4.5 |
| DQA1*0501/DQB1*0201 | DQ2 | 24.6 |
| DQA1*0501/DQB1*0301 | DQ7(3) | 20.9 |
| DPA1*0103/DPB1*0201 | DPw2 | 19.9 |
| DPA1*0103/DPB1*0401 | DPw4 | 65.1 |
| DPA1*0103/DPB1*0402 | DPw4 | 24.3 |
| DPA1*0201/DPB1*0101 | DPw1 | 6.3 |
| DPA1*0201/DPB1*0301 | DPw3 | <2 |
| DPA1*0201/DPB1*0501 | DPw5 | <2 |
| DPA1*0201/DPB1*0901 | — | 2.4 |

The corresponding serotypes are shown, as well as allotype frequencies in the Caucasian population (Klitz et al. (2003), Tissue Antigens 62: 296-307; Gjertson and Terasake (eds) in: HLA 1997; Gjertson and Terasake (eds) in: HLA 1998; Castelli et al. (2002), J. Immunol. 169: 6928-6934). Frequencies can add up to more than 100% since each individual has two alleles for each gene. If all allele frequencies of a single gene were known, they would add up to slightly less than 200% due to homozygous individuals.

TABLE 6

T_H epitope counts for IGKV1-39.

| | DRB1 | | DRB3/4/5 | | DQ | | DP | |
|---|---|---|---|---|---|---|---|---|
| | Strong | Medium | Strong | Medium | Strong | Medium | Strong | Medium |
| Merus IGKV1-39 | 0 (+6) | 0 (+16) | 0 (+0) | 0 (+5) | 0 (+3) | 0 (+9) | 0 (+0) | 0 (+9) |

Peptides binding to multiple HLAs of the same group (DRB1, DRB3/4/5, DP, DQ) are counted as one. Values between brackets refer to germline-filtered peptides.

TABLE 7

Mapping of Epibase~ predictions for Merus IGKV1-39 in the classical 15-mer peptide format. This table shows the allotype count of critical epitopes (SEQ ID NOs: 52-83) and implicated serotypes for each of the 15-mers spanning the Merus IGKV1-39 sequence.

| 15mer | Start position | 15-mer sequence | Allotype count | Implicated serotypes |
|---|---|---|---|---|
| 1 | 1 | DIQMTQSPSSLSASV | 6 | DR1, DR4, DR7, DR9 |
| 2 | 4 | MTQSPSSLSASVGDR | 5 | DR1, DR4, DR9 |
| 3 | 7 | SPSSLSASVGDRVTI | 0 | |
| 4 | 10 | SLSASVGDRVTITCR | 0 | |
| 5 | 13 | ASVGDRVTITCRASQ | 0 | |
| 6 | 16 | GDRVTITCRASQSIS | 2 | DR11(5), DR7 |
| 7 | 19 | VTITCRASQSISSYL | 4 | DQ2, DR11(5), DR4, DR7 |
| 8 | 22 | TCRASQSISSYLNWY | 2 | DQ2, DR4 |
| 9 | 25 | ASQSISSYLNWYQQK | 5 | DR13(6), DR15(2), DR4 |
| 10 | 28 | SISSYLNWYQQKPGK | 8 | DR12(5), DR13(6), DR15(2), DR16(2), DR4, DR8 |
| 11 | 31 | SYLNWYQQKPGKAPK | 10 | DR1, DR12(5), DR16(2), DR4, DR51, DR8 |
| 12 | 34 | NWYQQKPGKAPKLLI | 9 | DR1, DR15(2), DR4, DR51, DR8 |
| 13 | 37 | QQKPGKAPKLLIYAA | 7 | DQ4, DR1, DR11(5), DR15(2), DR51, DR8 |
| 14 | 40 | PGKAPRLLIYAASSL | 7 | DQ4, DR1, DR11(5), DR4, DR8 |
| 15 | 43 | APKLLIYAASSLQSG | 15 | DR1, DR11(5), DR12(5), DR13(6), DR14(6), DR15(2), DR4, DR51, DR8, DR9 |
| 16 | 46 | LLIYAASSLQSGVPS | 15 | DR1, DR11(5), DR12(5), DR13(6), DR14(6), DR15(2), DR4, DR51, DR8, DR9 |
| 17 | 49 | YAASSLQSGVPSRFS | 1 | DR15(2) |
| 18 | 52 | SSLQSGVPSRFSGSG | 1 | DR15(2) |

TABLE 7-continued

Mapping of Epibase~ predictions for Merus IGKV1-39 in the classical 15-mer peptide format. This table shows the allotype count of critical epitopes (SEQ ID NOs: 52-83) and implicated serotypes for each of the 15-mers spanning the Merus IGKV1-39 sequence.

| 15mer | Start position | 15-mer sequence | Allotype count | Implicated serotypes |
|---|---|---|---|---|
| 19 | 55 | QSGVPSRFSGSGSGT | 0 | |
| 20 | 58 | VPSRFSGSGSGTDFT | 0 | |
| 21 | 61 | RFSGSGSGTDFTLTI | 0 | |
| 22 | 64 | GSGSGTDFTLTISSL | 1 | DR52 |
| 23 | 67 | SGTDFTLTISSLQPE | 4 | DR4, DR52, DR7, DR9 |
| 24 | 70 | SGTDFTLTISSLQPE | 4 | DQ2, DR4, DR7, DR9 |
| 25 | 73 | LTISSLQPEDFATYY | 1 | DQ2 |
| 26 | 76 | SSLQPEDFATYYCQQ | 0 | |
| 27 | 79 | QPEDFATYYCQQSYS | 1 | DR4 |
| 28 | 82 | DFATYYCQQSYSTPP | 5 | DR4, DR51, DR7 |
| 29 | 85 | TYYCQOSYSTPPTFG | 4 | DR4, DR51, DR7 |
| 30 | 88 | CQQSYSTPPTFGQGT | 0 | |
| 31 | 91 | SYSTPPTFGQGTKVE | 0 | |
| 32 | 94 | TPPTFGQGTKVEIK | 0 | |

TABLE 8

The $V_H$ gene from PG1433 paired with various light chain genes with differing rates of amino acid mutation were compared for production levels with the original clone containing the IGKV1-39 gene.

| IgG name | Light chain gene | Number of amino acid mutations | concentration (µg/ml) |
|---|---|---|---|
| PG1433 | 1-39 | 0 | 63, 45.5, 38.6 (avg = 49) |
| PG1631 | 1-12 | 4 | 10.5 |
| PG1632 | 1-27 | 7 | 9.3 |
| PG1634 | 1D-12 | 10 | 10.8 |
| PG1635 | 1D-33 | 6 | 10.2 |
| PG1642 | 1-5 | 8 | 7.1 |
| PG1644 | 1-9 | 3 | 7.8 |
| PG1650 | 1D-39 | 3 | 9.1 |
| PG1652 | 2D-28 | 3 | 7.1 |
| PG1653 | 3-15 | 14 | 7 |
| PG1654 | 3-20 | 2 | 5.2 |
| PG1674 | 1-40 | 7 | 8.2 |
| PG1678 | 2-11 | 2 | 8.1 |
| PG1680 | 2-14 | 15 | 10.8 |
| PG1682 | 3-1 | 13 | 9.9 |
| PG1683 | 6-57 | 6 | 13.9 |

TABLE 9

Numbers of lymphocytes harvested from the bone marrow and spleen of wild-type and transgenic mice

| | *10e6/ml cells | total vol (ml) | total cells *10$^6$ |
|---|---|---|---|
| Bone Marrow | | | |
| Wt | 18.82 | 5.05 | 95.0 |
| Wt | 19.24 | 4.96 | 95.4 |
| CD19-Cre | 23.42 | 5.08 | 119.0 |
| CD19-Cre | 20.58 | 4.82 | 99.2 |
| CD19-Cre | 25.77 | 5.15 | 132.7 |
| CD19-Cre/HuVk1 | 17.71 | 5.06 | 89.6 |
| CD19-Cre/HuVk1 | 12.60 | 5.33 | 67.2 |
| CD19-Cre/HuVk1 | 18.13 | 5.27 | 95.5 |
| Spleen | | | |
| Wt | 41.70 | 5.36 | 223.5 |
| Wt | 37.85 | 4.71 | 178.3 |
| CD19-Cre | 60.19 | 3.77 | 226.9 |
| CD19-Cre | 35.06 | 3.66 | 128.3 |
| CD19-Cre | 80.69 | 4.60 | 371.2 |
| CD19-Cre/HuVk1 | 51.67 | 4.48 | 231.5 |
| CD19-Cre/HuVk1 | 58.80 | 6.24 | 366.9 |
| CD19-Cre/HuVk1 | 24.37 | 6.25 | 152.3 |

What is claimed is:

1. A transgenic mouse immunized with an antigen whose genome comprises a transgene comprising a human immunoglobulin light chain germline V gene segment directly joined to a human immunoglobulin light chain germline J gene segment, so that said joined human V/J gene segments encode a rearranged human immunoglobulin light chain variable region,
   wherein the transgene comprises a murine light chain constant region gene segment or is operatively linked to an endogenous light chain constant region gene segment;
   wherein a regulatory element that contributes to somatic hypermutation of the light chain variable region is lacking; and
   which transgenic mouse contains a repertoire of affinity mature B cells that secrete antibodies that bind said antigen and that have light chains with said rearranged human light chain variable region coupled to a murine light chain constant region, paired with a diversity of immunoglobulin heavy chains.

2. The transgenic mouse of claim 1, wherein said V gene segment is a human germline Vκ gene segment and said J gene segment is a human germline Jκ gene segment, and said murine immunoglobulin light chain constant region is a κ light chain constant region.

3. The transgenic mouse of claim 1, wherein expression of said human immunoglobulin light chain V/J gene segments is under the control of a B cell specific promoter.

4. The transgenic mouse of claim 3, wherein said B cell specific promoter is selected from the group consisting of CD19, CD20, μHC, VpreB1, VpreB2, VpreB3, λ5, Igα, Igβ, κLC, λLC and BSAP (Pax5).

5. A transgenic mouse immunized with an antigen, said mouse comprising in its genome a transgene encoding a rearranged human immunoglobulin light chain variable region, wherein said transgene comprises, in a 5' to 3' direction,
   a promoter selected from the group consisting of CD19, CD20, μHC, VpreB1, VpreB2, VpreB3, λ5, Igα, Igβ, κLC, λLC and BSAP (Pax5),
   a human or mouse leader, and
   a human immunoglobulin light chain germline V gene segment directly joined to a human immunoglobulin light chain germline J gene segment, so that said joined V/J gene segments encode a rearranged human-immunoglobulin light chain variable region,
   wherein the transgene comprises a murine light chain constant region gene segment or is operatively linked to an endogenous light chain constant region gene segment;
   wherein a regulatory element that contributes to somatic hypermutation of the light chain variable region is lacking; and
   which transgenic mouse contains a repertoire of affinity mature B cells that secrete a population of antibodies which bind said antigen comprising said rearranged human light chain variable region coupled to a murine light chain constant region, paired with a diversity of immunoglobulin heavy chains.

6. The transgenic mouse of claim 1, wherein at least one endogenous immunoglobulin light chain locus is functionally silenced.

7. The transgenic mouse of claim 6, wherein the endogenous κ light chain locus is functionally silenced.

8. The transgenic mouse of claim 1, wherein said transgene is located at a locus outside of the endogenous mouse immunoglobulin loci, wherein said locus is resistant to gene silencing.

9. The transgenic mouse of claim 8, wherein said transgene comprises a murine light chain constant region gene segment and is located at a Rosa-locus.

10. The transgenic mouse of claim 2, wherein said human germline Vκ gene segment is IKV1-39.

11. The transgenic mouse of claim 2, wherein said human germline Jκ gene segment is IGKJ1.

12. The transgenic mouse of claim 1, wherein said murine immunoglobulin light chain constant region is a rat constant region.

13. The transgenic mouse of claim 6, wherein the endogenous immunoglobulin light chain locus is disrupted.

14. The transgenic mouse of claim 1, wherein the rearranged human germline V gene segment encodes IGVκ1-39.

* * * * *